(12) United States Patent
Coate et al.

(10) Patent No.: US 9,695,183 B2
(45) Date of Patent: *Jul. 4, 2017

(54) SUBSTITUTED 7-AZABICYCLES AND THEIR USE AS OREXIN RECEPTOR MODULATORS

(71) Applicant: Janssen Pharmaceutica NV, Beerse (BE)

(72) Inventors: Heather R. Coate, San Diego, CA (US); Curt A. Dvorak, Poway, CA (US); Terry P. Lebold, San Diego, CA (US); Cathy Preville, La Jolla, CA (US); Brock T. Shireman, Poway, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/262,882

(22) Filed: Sep. 12, 2016

(65) Prior Publication Data

US 2016/0376280 A1  Dec. 29, 2016

Related U.S. Application Data

(60) Continuation of application No. 14/718,327, filed on May 21, 2015, now Pat. No. 9,475,819, which is a
(Continued)

(51) Int. Cl.
| | |
|---|---|
| A61K 31/5377 | (2006.01) |
| A61K 31/506 | (2006.01) |
| A61K 31/444 | (2006.01) |
| A61K 31/4439 | (2006.01) |
| A61K 31/497 | (2006.01) |
| A61K 31/498 | (2006.01) |
| A61K 31/4709 | (2006.01) |
| A61K 31/501 | (2006.01) |
| A61K 31/4725 | (2006.01) |
| A61K 31/4985 | (2006.01) |
| A61K 31/496 | (2006.01) |
| A61K 31/423 | (2006.01) |
| C07D 487/08 | (2006.01) |

(Continued)

(52) U.S. Cl.
CPC .......... *C07D 487/08* (2013.01); *A61K 31/423* (2013.01); *A61K 31/444* (2013.01); *A61K 31/4439* (2013.01); *A61K 31/4709* (2013.01); *A61K 31/4725* (2013.01); *A61K 31/496* (2013.01); *A61K 31/497* (2013.01); *A61K 31/498* (2013.01); *A61K 31/4985* (2013.01); *A61K 31/501* (2013.01); *A61K 31/506* (2013.01); *A61K 31/5377* (2013.01); *C07D 471/04* (2013.01); *C07D 513/04* (2013.01); *C07D 519/00* (2013.01)

(58) Field of Classification Search
None
See application file for complete search history.

(56) References Cited

U.S. PATENT DOCUMENTS

| 3,674,793 A | 7/1972 | Bailey |
| 8,957,074 B2 | 2/2015 | Brain |

(Continued)

FOREIGN PATENT DOCUMENTS

| WO | WO 02/094790 A1 | 11/2002 |
| WO | WO 2004/069816 A1 | 8/2004 |

(Continued)

OTHER PUBLICATIONS

Aissaoui et al., "N-Glycine-sulfonamides as potent dual orexin 1/orexin 2 receptor antagonists", Bioorganic & Medicinal Chemistry Letters, Nov. 2008, 18, 5729-5733.

(Continued)

*Primary Examiner* — Timothy R Rozof

(57) ABSTRACT

The present invention is directed to compounds of Formula I:

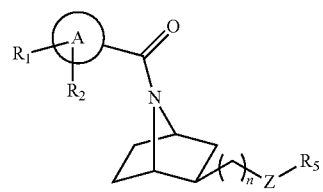

wherein A is phenyl, naphthalenyl, pyridyl, quinolinyl, isoquinolinyl, imidazopyridyl, furanyl, thiazolyl, isoxazolyl, pyrazolyl, imidazothiazolyl, benzimidazolyl, or indazolyl; $R_1$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino; $R_2$ is H, alkyl, alkoxy, hydroxyalkylene, or halo; Z is NH, N-alkyl, or O; $R_5$ is pyridyl, pyrimidinyl, pyrazinyl, pyridazinyl, quinazolinyl, quinoxalinyl, pyrazolyl, benzoxazolyl, imidazopyrazinyl, or triazolopyrazinyl, optionally substituted with a one or two substituents independently selected from the group consisting of alkyl, alkoxy, or halo; and n is 0 or 1. Methods of making the compounds of Formula I are also described. The invention also relates to pharmaceutical compositions comprising compounds of Formula I. Methods of using the compounds of the invention are also within the scope of the invention.

22 Claims, No Drawings

Related U.S. Application Data division of application No. 14/206,764, filed on Mar. 12, 2014, now Pat. No. 9,062,078.

(60) Provisional application No. 61/780,428, filed on Mar. 13, 2013.

(51) Int. Cl.
  C07D 513/04 (2006.01)
  C07D 471/04 (2006.01)
  C07D 519/00 (2006.01)

(56) References Cited

U.S. PATENT DOCUMENTS

| | | |
|---|---|---|
| 8,969,352 B2 | 3/2015 | Gelin et al. |
| 9,062,078 B2 | 6/2015 | Coate et al. |
| 9,309,252 B2 | 4/2016 | Brain |
| 2002/0148272 A1 | 10/2002 | Jroski |
| 2009/0005363 A1 | 1/2009 | Glatthar |
| 2009/0163485 A1 | 6/2009 | Knust et al. |
| 2011/0144150 A1 | 6/2011 | Lampe et al. |
| 2011/0172227 A1 | 7/2011 | Conn et al. |
| 2012/0202783 A1 | 8/2012 | Branstetter et al. |
| 2012/0208812 A1 | 8/2012 | Chai et al. |
| 2014/0275118 A1 | 9/2014 | Gelin |
| 2015/0174129 A1 | 6/2015 | Gelin |
| 2015/0218102 A1 | 8/2015 | Bogdan |
| 2015/0328224 A1 | 11/2015 | Coate et al. |
| 2016/0052939 A1 | 2/2016 | Gelin |
| 2016/0075696 A1 | 3/2016 | Shireman et al. |

FOREIGN PATENT DOCUMENTS

| | | |
|---|---|---|
| WO | WO 2004/074292 A1 | 9/2004 |
| WO | WO 2008/031550 A2 | 3/2008 |
| WO | WO 2008/065626 A2 | 6/2008 |
| WO | WO 2008/081399 A2 | 7/2008 |
| WO | WO 2008/150364 A1 | 12/2008 |
| WO | WO 2009/012275 A1 | 1/2009 |
| WO | WO 2009/012277 A1 | 1/2009 |
| WO | WO 2009/104155 A1 | 8/2009 |
| WO | WO 2009/133522 A1 | 11/2009 |
| WO | WO 2010/009195 A1 | 1/2010 |
| WO | WO 2010/048012 A1 | 4/2010 |
| WO | WO 2010/048016 A1 | 4/2010 |
| WO | WO 2010/063663 A1 | 6/2010 |
| WO | WO 2010/112215 A1 | 10/2010 |
| WO | WO 2010/114958 A1 | 10/2010 |
| WO | WO 2011/050198 A1 | 4/2011 |
| WO | WO 2011/050200 A1 | 4/2011 |
| WO | WO 2011/050202 A1 | 4/2011 |
| WO | WO 2011/053688 A1 | 5/2011 |
| WO | WO 2011/066137 A1 | 6/2011 |
| WO | WO 2011/159657 A1 | 12/2011 |
| WO | WO 2012/089606 A1 | 7/2012 |
| WO | WO 2012/145581 A1 | 10/2012 |
| WO | WO 2013/059222 A1 | 4/2013 |
| WO | WO 2014/066196 A1 | 5/2014 |
| WO | WO 2014/075392 | 5/2014 |
| WO | WO 2014/165070 A1 | 10/2014 |

OTHER PUBLICATIONS

Ammoun et al, "Distinct Recognition of OX1 and OX2 Receptors by Orexin Peptides", Journal of Pharmacology and Experimental Therapeutics, Jan. 2003, 305(2):507-514.

Arendt et al, "Depressive Behavior and Activation of the Orexin/Hypocretin System", Behavioral Neuroscience, Feb. 2013, 127(1):86-94.

Baxter et al., "The First Large-Scale Synthesis of MK-4305: A Dual Orexin Receptor Antagonist for the Treatment of Sleep Disorder", Organic Process Research & Development, Mar. 2011, 15, 367-375.

Bergman et al., "Proline bis-amides as potent dual orexin receptor antagonists", Bioorganic & Medicinal Chemistry Letters, Feb. 2008, 18, 1425-1430.

Betschart et al., "Identification of a Novel Series of Orexin Receptor Antagonists with a Distinct Effect on Sleep Architecture for the Treatment of Insomnia", Journal of Medicinal Chemistry, Oct. 2013, 56, 7590-7607.

Bettica et al., "Phase I studies on the safety, tolerability, pharmacokinetics and pharmacodynamics of SB-649868, a novel dual orexin receptor antagonist", Journal of Psychopharmacology, Aug. 2012, 26(8), 1058-1070.

Bettica et al., "The Orexin Antagonist SB-649868 Promotes and Maintains Sleep in Men with Primary Insomnia", Sleep, Aug. 2012, 35(8), 1097-1104.

Borgland et al, "Orexin A in the VTA is Critical for the Induction of Synaptic Plasticity and Behavioral Sensitization to Cocaine", Neuron, Feb. 2006, 49:589-601.

Brisbare-Roch et al., "Promotion of sleep by targeting the orexin system in rats, dogs and humans", Nature Medicine, Feb. 2007, 13(2), 150-155.

Brundin et al, "Reduced orexin levels in the cerebrospinal fluid of suicidal patients with major depressive disorder", European Neuropsychopharmacology, Jan. 2007, 17:573-579.

Carroll et al, "Synthesis and Muscarinic Receptor Activity of Ester Derivatives of 2-Substituted 2-Azabicyclo[2.2.1]heptan-5-ol and -6-ol", Journal of Medicinal Chemistry, Jun. 1992, 35(12):2184-2191.

Chemelli et al, "Narcolepsy in orexin Knockout Mice: Molecular Genetics of Sleep Regulation", Cell, Aug. 1999, 98:437-451.

Chen et al, "Pressor effects of orexins injected intracisternally and to rostral ventrolateral medulla of anesthetized rats", American Journal of Physiology—Regulatory Integrative comparative Physiology, Mar. 2000, 278:R692-R697.

Chiu, "An improved procedure for the synthesis of chiral2-azabicyclo[2.2.1]heptane", Synthetic Communications, 1996, 26(3):577-584.

Coleman et al., "Design and synthesis of conformationally constrained N,N-disubstituted 1,4-diazepanes as potent orexin receptor antagonists", Bioorganic & Medicinal Chemistry Letters, Apr. 2010, 20, 2311-2315.

Coleman et al., "Discovery of [(2R,5R)-5-{[(5-Fluoropyridin-2-yl)oxy]methyl}-2methylpiperidin-1-yl][5-methyl-2-(pyrimidin-2-yl)phenyl]methanone (MK-6096): A Dual Orexin Receptor Antagonist with Potent Sleep-Promoting Properties", Chem Med Chem, Mar. 2012, 7, 415-424.

Coleman et al., "Discovery of 3,9-diazabicyclo[4.2.1]nonanes as potent dual orexin receptor antagonists with sleep-promoting activity in the rat", Bioorganic & Medicinal Chemistry Letters, Jul. 2010, 20, 4201-4205.

Cox et al., "Conformational analysis of N,N-disubstituted-1,4-diazepane orexin receptor antagonists and implications for receptor binding", Bioorganic & Medicinal Chemistry Letters, Jun. 2009, 19, 2997-3001.

Cox et al., "Discovery of the Dual Orexin Receptor Antagonist [(7R)-4-(5-Chloro-1,3-benzoxazol-2-yl)-7-methyl-1,4-diazepan-1-yl][5-methyl-2-(2H-1,2,3-triazol-2-yl)phenyl]methanone (MK-4305) for the Treatment of Insomnia", Journal of Medicinal Chemistry, Jul. 2010, 53, 5320-5332.

De Lecea et al., "The hypocretins: Hypothalamus-specific peptides with neuroexcitatory activity", Proc. Natl. Acad. Sci., Jan. 1998, 95, 322-327.

De Lecea, Chapter 3, "Hypocretins and the neurobiology of sleep-wake mechanisms", Progress in Brain Research, 2012, vol. 198, A. Shekhar (Ed.), pp. 15-24.

Difabio et al., "Discovery process and pharmacological characterization of a novel dual orexin 1 and orexin 2 receptor antagonist useful for treatment of sleep disorders", Bioorganic & Medicinal Chemistry Letters, Sep. 2011, 21, 5562-5567.

Dugovic et al., "Blockade of Orexin-1 Receptors Attenuates Orexin-2 Receptor Antagonism-Induced Sleep Promotion in the Rat", The Journal of Pharmacology and Experimental Therapeutics, Jul. 2009, 330(1), 142-151.

(56) References Cited

OTHER PUBLICATIONS

Dugovic et al., "Orexin-1 receptor blockade dysregulates REM sleep in the presence of orexin-2 receptor antagonism", Frontiers in Neuroscience, Feb. 2014, vol. 8, Article 29, 1-8.
Fortuyn et al, "Anxiety and mood disorders in narcolepsy: a case-control study", General Hospital Psychiatry, Jan.-Feb. 2010, 32:49-56.
Fujimoto et al., "Discovery of potent, selective, orally active benzoxazepine-based Orexin-2 receptor antagonists", Bioorganic & Medicinal Chemistry Letters, Nov. 2011, 21, 6414-6416.
Fujimoto et al., "Discovery of spiropiperidine-based potent and selective Orexin-2 receptor antagonists", Nov. 2011, 21, 6409-6413.
Gatfield et al., "Orexin Receptor Antagonists: A New Concept in CNS Disorders?", Chem Med Chem, Aug. 2010, 5, 1197-1214.
Girardin et al., "Convergent Kilogram-Scale Synthesis of Dual Orexin Receptor Antagonist", Organic Process Research & Development, Jan. 2013, 17, 61-68.
Gotter et al., "International Union of Basic and Clinical Pharmacology. LXXXVI. Orexin Receptor Function, Nomenclature and Pharmacology", Pharmacological Reviews, Jul. 2012, 64(3), 389-420.
Gotter et al., "Orexin receptors as therapeutic drug targets", Progress in Brain Research, 2012, 198, 163-188.
Gozzi et al., "Functional Magnetic Resonance Imaging Reveals Different Neural Substrates for the Effects of Orexin-1 and Orexin-2 Receptor Antagonists", PLoS One, Jan. 2011, 6(1), e16406, 12 pages.
Hara et al, "Genetic Ablation of Orexin Neurons in Mice Results in Narcolepsy, Hypophagia, and Obesity", Neuron, May 2001, 30:345-354.
Harris et al, "A role for lateral hypothalamic orexin neurons in reward seeking", Nature Sep. 2005, 437:556-559.
Harris et al, "Lateral hypothalamic orexin neurons are critically involved in learning to associate an environment with morphine reward", Behavioural Brain Research, Nov. 2007, 183:43-51.
Hiebabecky et al, "Synthesis of novel azanorbornylpurine derivatives", Tetrahedron, Jan. 2012, 68:1286-1298.
Hirose et al., "N-Acyl 6,7-Dimethoxy-1,2,3,4-tetrahydroisoquinoline: The First Orexin-2 Receptor Selective Nonpeptidic Antagonist", Bioorganic & Medicinal Chemistry Letters, Dec. 2003, 13, 4497-4499.
Hollander et al, "Insular hypocretin transmission regulates nicotine reward", Proceedings of the National Academy of Sciences USA, Dec. 2008, 105(49):19480-19485.
International Patent Application No. PCT/US2014/024293: International Search Report dated May 22, 2014, 2 pages.
Jiang et al., "Disubstituted piperidines as potent orexin (hypocretin) receptor antagonists", Bioorganic & Medicinal Chemistry Letters, Jun. 2012, 22, 3890-3894.
Johnson et al, "A key role for orexin in panic anxiety", Nature Medicine, Sep. 2010, 16(1):111-116.
Johnson et al, "Activation of the Orexin I Receptor is a Critical Component of C02-Medidated Anxiety and Hypertension but not Bradycardia", Neuropsychopharmacology, Mar. 2012, 37:1911-1922.
Johnson et al, Chapter 9, "Orexin, stress, and anxiety/panic states", Progress in Brain Research, 2012, vol. 198, A. Shekhar (Ed.), pp. 133-161.
Kapferer et al, "Electrophilic Bromination of N-Acylated Cyclohex-3-en-1-amines: Synthesis of 7-Azanorbornanes", Helvetica Chimica Acta, Nov. 2004, 87(11):2764-2789.
King, "Bioisosteres, Conformational Restriction, and Pro-drugs—Case History: An Example of a Conformational Restriction Approach", Med. Chem.: Principle and Practice, 1994, 206-208.
Kirchgessner et al, "Orexin Synthesis and Response in the Gut", Neuron, Dec. 1999, 24:941-951.
Kuduk et al., "Synthesis and evaluation of carbon-linked analogs of dual orexin receptor antagonist filorexant", Bioorganic & Medicinal Chemistry Letters, Apr. 2014, 24, 1784-1789.
Kukkonen, "Physiology of the orexinergic/hypocretinergic system: a revisit in 2012", American Journal of Physiology—Cell Physiology, Jan. 2013, 304:C2-C32.
Langmead et al, "Characterisation of the binding of [3H]-SB-674042, a novel non peptide antagonist, to the human orexin-1 receptor", British Journal of Pharmacology, Oct. 2004, 141:340-346.
Larsen et al, "Aza Diels-Aider Reactions in Aqueous Solution: Cyclocondensation of Dienes with Simple Iminium Salts Generated under Mannich Conditions", Journal American Chemistry Society, Mar. 1985, 107:1769-1771.
Lawrence et al, "The orexin system regulates alcohol-seeking in rats", British Journal of Pharmacology, Jul. 2006, 148:752-759.
Lebold et al., "Selective orexin receptor antagonists", Bioorganic & Medicinal Chemistry Letters, Sep. 2013, 23, 4761-4769.
Leroy, "Preparation of 3-Bromopropiolic Esters: Methyl and tert-Butyl 3-Bromopropiolates (2-Propynoic acid, 3-bromo-, methyl and 1,1-dimethylethyl esters)", Organic Syntheses, Shinkai et al (Eds.), 1997, 74:212-216.
Lin et al, "The Sleep Disorder Canine Narcolepsy is Caused by a Mutation in the Hypocretin (Orexin) Receptor 2 Gene", Cell, Aug. 1999, 98:365-376.
Mahler et al, Chapter 7, "Multiple roles for orexin/hypocretin in addiction", Progress in Brain Research (2012) vol. 198, A. Shekhar (Ed.), pp. 79-121.
Malherbe et al, "Biochemical and behavioural characterization of EMPA, a novel high affinity, selective antagonist for the OX2 receptor", British Journal of Pharmacology, Nov. 2009, 156:1326-1341.
Mang et al., "The Dual Orexin Receptor Antagonist Almorexant Induces Sleep and Decreases Orexin-Induced Locomotion by Blocking Orexin 2 Receptors", Sleep, Dec. 2012, 35(12), 1625-1635.
Marcus et al, "Differential Expression of Orexin Receptors 1 and 2 in the Rat Brain", Journal of Comparative Neurology, Jun. 2001, 435:6-25.
McAtee et al., "Novel substituted 4-phenyl-[1,3]dioxanes: potent and selective orexin receptor 2 (OX2R) antagonists", Bioorganic & Medicinal Chemistry Letters, Aug. 2004, 14, 4225-4229.
McElhinny Jr. et al., "Hydrolytic instability of the important orexin 1 receptor antagonist SB-334867: Possible confounding effects on in vivo and in vitro studies", Bioorganic & Medicinal Chemistry Letters, Nov. 2012, 22, 6661-6664.
Mercer et al., "Discovery of 2,5-diarylnicotinamides as selective orexin-2 receptor antagonists (2-SORAs)", Bioorganic & Medicinal Chemistry Letters, Dec. 2013, 23, 6620-6624.
Micheli et al., "2-Methyl-3-furanyl-4H-1,2,4-triazol-3-ylthioamides: A new class of selective orexin 2 antagonists", Bioorganic & Medicinal Chemistry Letters, Nov. 2010, 20, 6405-6407.
Michelson et al., "Safety and efficacy of suvorexant during 1-year treatment of insomnia with subsequent abrupt treatment discontinuation: a phase 3 randomised, double-blind, placebo-controlled trial", The Lancet, May 2014, 13, 461-471.
Mignot et al, "Complex HLA-DR and -DQ Interactions Confer Risk of Narcolepsy-Cataplexy in Three Ethnic Groups", American Journal Human Genetics, Feb. 2001, 68:686-699.
Mignot et al, "Narcolepsy and the HLA System", New England Journal of Medicine, Mar. 2001, 344(9):692.
Nakamura et al, "Orexin-induced hyperlocomotion and stereotypy are mediated by the dopaminergic system", Brain Research, Jun. 2000, 873:181-187.
Nambu et al., "Distribution of orexin neurons in the adult rat brain", Brain Research, May 1999, 827, 243-260.
Narita et al, "Direct Involvement of Orexinergic Systems in the Activation of the Mesolimbic Dopamine Pathway and Related Behaviors Induced by Morphine", Journal of Neuroscience, Jan. 2006, 26(2):398-405.
Oi et al., "Synthesis and Evaluation of Novel Radioligands for Positron Emission Tomography Imaging of the Orexin-2 Receptor", Journal of Medicinal Chemistry, Jul. 2013, 56, 6371-6385.

(56) References Cited

OTHER PUBLICATIONS

Perrey et al., "Diaryl urea analogues of SB-334867 as orexin-1 receptor antagonists", Bioorganic & Medicinal Chemistry Letters, May 2011, 21, 2980-2985.
Perrey et al., "Substituted Tetrahydroisoquinolines as Selective Antagonists for the Orexin 1 Receptor", Journal of Medicinal Chemistry, Sep. 2013, 56, 6901-6916.
Peyron et al, "A mutation in a case of early onset narcolepsy and a generalized absence of hypocretin peptides in human narcoleptic brains", Nature Medicine, Sep. 2000, 6(9):991-997.
Peyron et al, "Neurons Containing Hypocretin (Orexin) Project to Multiple Neuronal Systems", Journal of Neuroscience, Dec. 1998, 18(23):9996-10015.
Piper et al, "The novel brain neuropeptide, orexin-A, modulates the sleep-wake cycle of rats", European Journal of Neuroscience, Feb. 2000, 12:726-730.
Porter et al., "1,3-Biarylureas as Selective Non-peptide Antagonists of the Orexin-1 Receptor", Bioorganic & Medicinal Chemistry Letters, Jul. 2001, 11, 1907-1910.
Renzulli et al., "Disposition and Metabolism of [$^{14}$C]SB-649868, an Orexin 1 and 2 Receptor Antagonist, in Humans", Drug Metabolism and Disposition, 2011, 39(2), 215-227.
Roecker et al., "Discovery of 5"-Chloro-N-[(5,6-dimethoxypyridin-2-yl)methyl]-2,2':5',3"-terpyridine-3'-carboxamide (MK-1064): A Selective Orexin 2 Receptor Antagonist (2-SORA) for the Treatment of Insomnia", Chem Med Chem, Feb. 2014, 9, 311-322.
Sakurai et al, "Orexins and Orexin Receptors: A Family of Hypothalamic Neuropeptides and G Protein-Coupled Receptors that Regulate Feeding Behavior", Cell, Feb. 1998, 92:573-585.
Sakurai, "The neural circuit of orexin (hypocretin): maintaining sleep and wakefulness", Nature Reviews, Mar. 2007, 8, 171-181.
Salomon et al, "Diurnal Variation of Cerebrospinal Fluid Hypocretin-1-(Orexin-A) Levels in Control and Depressed Subjects", Biological Psychiatry, Jul. 2003, 54:96-104.
Samson et al, "Cardiovascular Regulatory Actions of the Hypocretins in Brain", Brain Research, Jun. 1999, 831:248-253.
Sharf et al, "Orexin Mediates the Expression of Precipitated Morphine Withdrawal and Concurrent Activation of the Nucleus Accumbens Shell", Biological Psychiatry, Jan. 2008, 64:175-183.
Shirasaka et al, "Sympathetic and cardiovascular actions of orexins in conscious rats", American Journal of Physiology (Regulatory Integrative Camp. Physiol. 46), Dec. 1999, 277: R1780-R1785.
Shoblock et al, "Selective blockade of the orexin-2 receptor attenuates ethanol self-administration, place preference, and reinstatement", Psychopharmacology, Sep.-Oct. 2011, 215:191-203.
Sifferlen et al., "Discovery of substituted lactams as novel dual orexin receptor antagonists. Synthesis, preliminary structure-activity relationship studies and efforts towards improved metabolic stability and pharmacokinetic properties. Part 1", Bioorganic & Medicinal Chemistry Letters, Feb. 24, 2014, 1201-1208.
Sifferlen et al., "Novel pyrazolo-tetrahydropyridines as potent orexin receptor antagonists", Bioorganic & Medicinal Chemistry Letters, Mar. 2010, 20, 1539-1542.
Sifferlen et al., "Structure-activity relationship studies and sleep-promoting activity of novel 1-chloro-5,6,7,8-tetrahydroimidazo[1,5-a]pyrazine derivatives as dual orexin receptor antagonists. Part 2", Bioorganic & Medicinal Chemistry Letters, Jul. 2013, 23, 3857-3863.
Sifferlen et al., "Synthesis, structure-activity relationship studies, and identification of novel 5,6,7,8-tetrahydroimidazo[1,5-a]pyrazine derivatives as dual orexin receptor antagonists. Part 1", Bioorganic & Medicinal Chemistry Letters, Apr. 2013, 23, 2212-2216.
Singh et al, "Efficient Synthesis of (+)-N-BOC-exo-2-(methoxycarbonyl)-7-Azabicyclo [2.2.1]heptane, A Versatile Intermediate for the Synthesis of Epibatidine and Epiboxidine", Tetrahedron Letters, Sep. 1997, 38(39):6829-6830.
Smart et al., "SB-334867-A: the first selective orexin-1 receptor antagonist", British Journal of Pharmacology, Mar. 2001, 132, 1179-1182.
Stasi et al., "Discovery, synthesis, selectivity modulation and DMPK characterization of 5-azaspiro[2.4]heptanes as potent orexin receptor antagonists", Bioorganic & Medicinal Chemistry Letters, May 2013, 23, 2653-2658.
Steiner et al., "Discovery and Characterization of ACT-335827, an Orally Available, Brain Penetrant Orexin Receptor Type 1 Selective Antagonist", Chem Med Chem, Jun. 2013, 8, 898-903.
Steiner et al., "The brain orexin system and almorexant in fear-conditioned startle reactions in the rat", Psychopharmacology, Oct. 2012, 223, 465-475.
Strawn et al, "Low cerebrospinal fluid and plasma orexin-A (hypocretin-1) concentrations in combat-related posttraumatic stress disorder", Psychoneuroendocrinology, Aug. 2010, 35:1001-1007.
Takahashi et al, "Stimulation of Gastric Acid Secretion by Centrally Administered Orexin-A in Conscious Rats", Biochemical and Biophysical Research Communications, Jan. 1999, 254:623-627.
Trivedi et al, "Distribution of orexin receptor mRNA in the rat brain", FEBS Letters, Oct. 1998, 438:71-75.
Van Den Pol, "Hypothalamic Hypocretin (Orexin): Robust Innervation of the Spinal Cord", Journal of Neuroscience, Apr. 1999, 19(8):3171-3182.
Walker et al, "Design, synthesis, structure-activity relationship, and in vivo activity of azabicyclic aryl amides as α7 nicotinic acetylcholine receptor agonists", Bioorganic & Medicinal Chemistry, Sep. 2006, 14:8219-8248.
Whitman et al., "Discovery of a Potent, CNS-Penetrant Orexin Receptor Antagonist Based on an N,N-Disubstituted-1, 4-diazepane Scaffold that Promotes Sleep in Rats", Chem Med Chem, Jul. 2009, 4, 1069-1074.
Winrow et al., "Discovery and development of orexin receptor antagonists as therapeutics for insomnia", British Journal of Pharmacology, Jan. 2014, 171, 283-293.
Yamanaka et al, "Orexins Activate Histaminergic Neurons via the Orexin 2 Receptor", Biochemical and Biophysical Research Communications, Feb. 2002, 290:1237-1245.

SUBSTITUTED 7-AZABICYCLES AND THEIR USE AS OREXIN RECEPTOR MODULATORS

CROSS REFERENCE TO RELATED APPLICATIONS

This application is a continuation of U.S. patent application Ser. No. 14/718,327, filed May 21, 2015, which is a divisional of U.S. patent application Ser. No. 14/206,764, filed Mar. 12, 2014, now U.S. Pat. No. 9,062,078, which claims the benefit of U.S. Provisional Patent Application No. 61/780,428, filed Mar. 13, 2013, the entire disclosures of which are incorporated herein by reference in their entirety.

TECHNICAL FIELD

The present invention is directed to substituted 7-azabicyclic compounds, pharmaceutical compositions comprising them, methods of making them, and methods of using them for the modulation of the orexin receptor for the treatment of disease states, disorders, and conditions mediated by orexin receptor activity.

BACKGROUND

Orexin/hypocretin signaling is mediated by two receptors and two peptide agonists. The peptides (orexin-A and orexin-B) are cleavage products of the same gene, pre-pro orexin. In the central nervous system, neurons producing pre-pro orexin are found solely in the perifornical nucleus, the dorsal hypothalamus, and the lateral hypothalamus (Peyron et al., 1998, *J. Neurosci.* 18: 9996-10015). Orexigenic cells in these regions project to many areas of the brain, extending rostrally to the olfactory bulbs and caudally to the spinal cord (Van den Pol, 1999, *J. Neurosci.* 19: 3171-3182).

The orexins bind to two high affinity receptors, referred to as orexin-1 and orexin-2 receptors. Orexin-1 and orexin-2 receptors are G-protein-coupled, seven transmembrane receptors that share over 64% amino acid sequence identity with one another. Both receptors are generally excitatory, the common cellular response to orexin-induced receptor activation being increases in intracellular calcium. Homology between the species orthologs is high and there are no known pharmacological differences. Orexin-A and -B are usually considered equal ligands for orexin-2 receptor but orexin-B is thought to be 5- to 100-fold weaker ligand than orexin-A at the orexin-1 receptor (Sakurai et al., 1998, *Cell* 92: 573-585; Ammoun et al., 2003, *J. Pharmacol. Exp. Ther.* 305: 507-514).

Many regions of the brain have fairly selective expression of the orexin-1 or orexin-2 receptors (Marcus et al., 2001, 1 Comp Neurology 435, 6-25; Trivedi et al., 1998, *FEBS Letters*, 438, 71-75). Orexin-1 receptors are selective for the limbic system (bed nucleus of the stria terminalis and amygdala), cingulate cortex and noradrenergic neurons in the locus coeruleus. Conversely, the orexin-2 receptor is almost the exclusive orexin receptor in the histaminergic neurons in the tuberomammilary nucleus which play a critical role in wake promotion; in paraventricular neurons and the parabrachial nucleus. In other brain regions like the dorsal raphe, the ventral tegmental area or the prefontal cortex both receptors are coexpressed.

The broad CNS distribution of cells producing orexin, as well as cells expressing the orexin receptors, suggests involvement of orexin in a number of physiological functions, including feeding and metabolism, regulation of wakefulness and sleep, sympathetic activation and stress response (de Lecea, 2012, *Progress in Brain Research*, 198, 15-24; Kukkonen, 2013, *Am J. Physiol. Cell Physiol.*, 304, C2-C32). Orexin also plays a key role regulating motivation and reward associated with food intake and with drugs of abuse (Mahler et al., 2012, *Progress in Brain Research*, 198, 79-121).

Several lines of evidence indicate that the orexin system is an important modulator of arousal. Rodents administered orexin intracerebroventricularly spend more time awake (Piper et al., 2000, *J. Neurosci.* 12: 726-730. Orexin-mediated effects on arousal have been linked to orexin neuronal projections to histaminergic neurons in the tuberomammillary nucleus (Yamanaka et al., 2002, *Biochem. Biophys. Res. Comm.* 290: 1237-1245). Rodents whose pre-pro orexin gene has been knocked out, or whose orexigenic neurons have been killed, display altered sleep/wake cycles similar to narcolepsy (Chemelli et al., 1999, *Cell* 98: 437-451; Hara et al., 2001, *Neuron* 30: 345-354). Dog models of narcolepsy have been shown to have mutant or non-functional orexin-2 receptors (Lin et al., 1999, *Cell* 98: 365-376). Orexin signaling as a target for sleep-promoting therapies was further validated clinically by findings of attenuated orexin levels and loss of orexinergic neurons in human narcoleptic patients (Mignot et al., 2001, *Am. J. Hum. Genet.* 68: 686-699; Minot & Thorsby, 2001, *New England J. Med.* 344: 692) or, in rare cases, to mutations in the orexin-2 gene (Peyron et al., 2000, *Nature Med.* 6: 991-997). Disorders of the sleep-wake cycle are therefore likely targets for orexin-2 receptor modulator activity. Examples of sleep-wake disorders that may be treated by agonists or other modulators that up-regulate orexin-2 receptor-mediated processes include narcolepsy, jet lag (sleepiness) and sleep disorders secondary to neurological disorders such as depression. Examples of disorders that may be treated by antagonists or other modulators that down-regulate orexin-2 receptor-mediated processes include insomnia, restless leg syndrome, jet lag (wakefulness) and sleep disorders secondary to neurological disorders such as mania, schizophrenia, pain syndromes and the like.

Evidence has accumulated to demonstrate a clear involvement of orexin signaling in reward pathways associated with drug dependence (Mahler et al., 2012, *Progress in Brain Research*, 198, 79-121). Orexinergic neurons send projections to the ventral tegmental area and other brain regions involved in reward processing. Orexin ligands mediate reward behavior, and antagonizing these effects with a selective orexin-1 receptor antagonist in various preclinical model of addiction has suggested that these actions are mediated through orexin-1 receptor. Specifically, a selective orexin-1 antagonist attenuates morphine conditioned place preference and reinstatement (Harris et al., 2005, *Nature*, 437, 556-5599; Narita et al., 2006, *J Neurosci.*, 26, 398-405; Harris et al., 2007, *Behav Brain Res*, 183, 43-51), stress-induced cocaine reinstatement, cocaine-induced behavioral and synaptic plasticity (Borgland et al., 2006, *Neuron*, 49, 589-601), and intake and cue and stress-induced reinstatement of ethanol (Lawrence et al., 2006, *Br J Pharmacol*, 148, 752-759), in addition to attenuating precipitated morphine withdrawal (Sharf et al., 2008, *Biol Psychiatry*, 64, 175-183) and nicotine self-administration (Hollander et al., 2008, *Proc Natl Acad Sci USA.*, 105, 19480-19485). Another recent study has also suggested a role for OX2R (Shoblock et al., 2011, *Psychopharmacology*, 215, 191-203).

Orexin's role in more complex emotional behavior is also emerging (Johnson et al., 2012, *Progress in Brain Research*, 198, 133-161). Changes in orexin levels in patients with panic and posttraumatic stress disorders have been noted as have changes in the prevalence of anxiety behaviors in narcoleptic patients (Johnson et al., 2010, *Nature Medicine,* 16, 111-115; Fortuyn et al., 2010, *General Hospital Psychiatry,* 32, 49-56; Strawn et al., 2010, *Psychoneuroendocrinology,* 35, 1001-1007). Lactate infusion or acute hypercapnia, which causes panic in humans, and are used as an animal model of panic, activates orexin neurons in the perifornical hypothalamus. This activation correlates with anxiety in the social interaction test or open field test. Blocking orexin signaling with either siRNA or selective orexin-1 receptor antagonists attenuates panic-like responses to lactate (Johnson et al., 2010, *Nature Medicine,* 16, 111-115; Johnson et al., 2012, *Neuropsychopharmacology,* 37, 1911, 1922).

Cerebral spinal fluid (CSF) levels of orexin are lower in depressed or suicidal patients, and the level of orexin inversely correlates with illness severity (Brundin et al., 2007, *European Neuropsychopharmacology,* 17, 573-579; Salomon et al., 2003, *Biol Psychiatry,* 54, 96-104). A positive correlation between orexin-1 receptor mRNA in the amygdala and depressive behavior in the forced swim test in mice has been reported (Arendt, 2013, *Behavioral Neuroscience,* 127, 86-94).

The orexin system also interacts with brain dopamine systems. Intracerebroventricular injections of orexin in mice increase locomotor activity, grooming and stereotypy; these behavioral effects are reversed by administration of D2 dopamine receptor antagonists (Nakamura et al., 2000, *Brain Res.* 873: 181-187). Therefore, orexin receptor modulators may be useful to treat various neurological disorders; e.g., agonists or up-regulators to treat catatonia, antagonists or down-regulators to treat Parkinson's disease, Tourette's syndrome, anxiety, delirium and dementias.

Orexins and their receptors have been found in both the myenteric and submucosal plexus of the enteric nervous system, where orexins have been shown to increase motility in vitro (Kirchgessner & Liu, 1999, *Neuron* 24: 941-951) and to stimulate gastric acid secretion in vitro (Takahashi et al., 1999, *Biochem. Biophys. Res. Comm.* 254: 623-627). Orexin effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux.

Body weight may also be affected by orexin-mediated regulation of appetite and metabolism. Some effects of orexin on metabolism and appetite may be mediated in the gut, where, as mentioned, orexins alter gastric motility and gastric acid secretion. Orexin antagonists therefore are likely to be useful in treatment of overweight or obesity and conditions related to overweight or obesity, such as insulin resistance/type II diabetes, hyperlipidemia, gallstones, angina, hypertension, breathlessness, tachycardia, infertility, sleep apnea, back and joint pain, varicose veins and osteoarthritis. Conversely, orexin agonists are likely to be useful in treatment of underweight and related conditions such as hypotension, bradycardia, amenorrhea and related infertility, and eating disorders such as anorexia and bulimia.

Intracerebroventricularly administered orexins have been shown to increase mean arterial pressure and heart rate in freely moving (awake) animals (Samson et al., 1999, *Brain Res.* 831: 248-253; Shirasaka et al., 1999, *Am. J. Physiol.* 277: R1780-R1785) and in urethane-anesthetized animals (Chen et al., 2000, *Am. J. Physiol.* 278: R692-R697), with similar results. Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor modulators, will be of great advantage in the development of therapeutic agents for the treatment of a wide variety of disorders that are mediated through these receptor systems.

SUMMARY

The present invention is directed to compounds of Formula I:

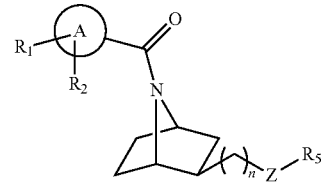

wherein ring A is phenyl, naphthalenyl, pyridyl, quinolinyl, isoquinolinyl, imidazopyridyl, furanyl, thiazolyl, isoxazolyl, pyrazolyl, imidazothiazolyl, benzimidazolyl, or indazolyl; $R_1$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino; $R_2$ is H, alkyl, alkoxy, hydroxyalkylene, or halo; Z is NH, N-alkyl, or O; $R_5$ is pyridyl, pyrimidinyl, pyrazinyl, pyridazinyl, quinazolinyl, quinoxalinyl, pyrazolyl, benzoxazolyl, imidazopyrazinyl, triazolopyrazinyl, optionally substituted with a one or two substituents independently selected from the group consisting of alkyl, alkoxy, or halo; and n is 0 or 1. Enantiomers and diastereomers of the compounds of Formula I are also described, as well as the pharmaceutically acceptable salts.

Methods of making the compounds of Formula I are also described. The invention also relates to pharmaceutical compositions comprising compounds of Formula I. Methods of using the compounds of the invention are also within the scope of the invention.

DETAILED DESCRIPTION OF ILLUSTRATIVE EMBODIMENTS

The invention may be more fully appreciated by reference to the following description, including the following glossary of terms and the concluding examples.

The term "alkyl" refers to a straight- or branched-chain alkyl group having from 1 to 12 carbon atoms in the chain. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups of the invention can be optionally substituted with, for example, one or more halogen atoms. One exemplary substituent is fluoro. Preferred substituted alkyl groups of the invention include trihalogenated alkyl groups such as trifluoromethyl groups.

Alkyl groups of the invention can also refer to "cycloalkyl" moieties. Cycloalkyl refers to monocyclic, non-aromatic hydrocarbon groups having from 3 to 7 carbon atoms. Examples of cycloalkyl groups include, for example, cyclopropyl, cyclobutyl, cyclopentyl, cyclohexyl, 1-methylcyclopropyl, 2-methylcyclopentyl, and the like.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. Alkoxy groups of the inventions can be optionally substituted with, for example, one or more halogen atoms (haloalkoxy). One exemplary substitutent is fluoro. Preferred substituted alkoxy groups of the invention are substituted with one, two, or three halogen atoms, for example, —OCHCF$_2$.

The term "amino" represents NH$_2$. The term "dialkylamino" represents the moiety wherein each H of the amino group is replaced by an alkyl group. These alkyl groups ca be the same or different. Preferred alkyl groups are the C$_{1-6}$alkyl groups. Examples of dialkyl amino groups include dimethylamino, diethylamino, diisopropylamino, and the like. Other examples include methylethylamino, methylisopropylamino, and the like.

The term "aryl ring" represents" a mono- or bi-cyclic aromatic, hydrocarbon ring structure. Aryl rings can have 6 or 10 carbon atoms in the ring.

The term "benzimidazolyl" represents the following moiety:

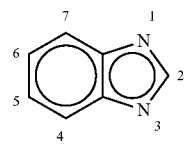

The benzimidazolyl moiety can be attached through any one of the 1-, 2-, 3-, 4-, 5-, 6-, or 7-position atoms.

The term "benzoxazolyl" represents the following moiety:

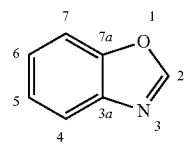

The benoxazolyl moiety can be attached through any one of the 2-, 4-, 5-, 6-, or 7-position carbon atoms.

The term "furanyl" represents the following moiety:

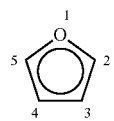

The furanyl moiety can be attached through any one of the 2-, 3-, 4-, or 5-position carbon atoms.

The term "halogen" represents chlorine, fluorine, bromine, or iodine. The term "halo" represents chloro, fluoro, bromo, or iodo.

The term "heteroaryl ring" represents a mono- or bicyclic aromatic ring structure including carbon atoms as well as up to four heteroatoms selected from nitrogen, oxygen, and sulfur. Heteroaryl rings can include a total of 5, 6, 9, or 10 ring atoms.

The term "hydroxyalkylene" represents an alkyl group, terminally substituted with OH. Examples of hydroxyalkylene moieties include —CH$_2$—OH, —CH$_2$CH$_2$—OH, —CH$_2$CH$_2$CH$_2$—OH, and the like.

The term "imidazopyridyl" represents the following moiety:

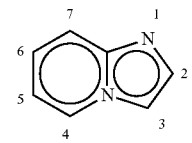

The imidazopyridyl moiety can be attached through any one of the 2-, 3-, 4-, 5-, 6-, or 7-position carbon atoms.

The term "imidazopyrazinyl" represents the following moiety:

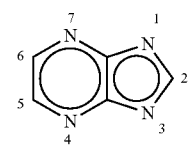

The imidazopyrazinyl moiety can be attached through any one of the 2-, 5-, or 6-position carbon atoms.

The term "imidazothiazolyl" represents the following moiety:

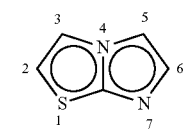

The imidazothiazolyl moiety can be attached through any one of the 2-, 3-, 5-, or 6-position carbon atoms.

The term "indazolyl" represents the following moiety:

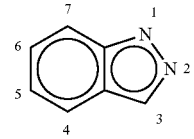

The indazolyl moiety can be attached through any one of the 1-, 3-, 4-, 5-, 6-, or 7-position atoms.

The term "isoquinolinyl" represents the following moiety:

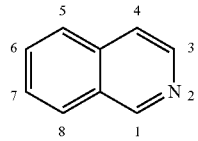

The isoquinolinyl moiety can be attached through any one of the 1-, 3-, 4-, 5-, 6-, 7-, or 8-position carbon atoms.

The term "isoxazolyl" represents the following moiety:

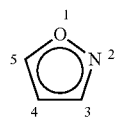

The isoxazolyl moiety can be attached through any one of the 3-, 4-, or 5-position carbon atoms. Isoxazolyl groups of the invention can be optionally substituted with, for example, one or two alkyl groups, for example, one or two methyl groups.

The term "naphthalenyl" represents the following moiety:

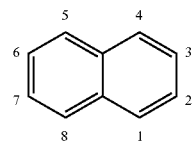

The naphthalenyl moiety can be attached through any one of the 1-, 2-, 3-, 4-, 5-, 6-, 7-, or 8-position carbon atoms.

The term "morpholinyl" represents the following moiety:

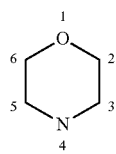

The 4-position nitrogen atom may be substituted with H or alkyl, for example methyl. The 4-position nitrogen can also be protected with a nitrogen protecting group such as a butyl-oxycarbonyl (-Boc). The morpholinyl moiety can be attached through any one of the 2-, 3-, 4-, 5-, or 6-position atoms.

The term "oxazolyl" represents the following moiety:

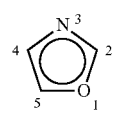

The oxazolyl moiety can be attached through any one of the carbon atoms. Oxazolyl groups of the invention can be optionally substituted, for example, one or two alkyl groups, for example, one or two methyl groups.

The term "oxadiazolyl" represents a 1,2,3-oxadiazole, 1,2,4-oxadiazole, 1,2,5-oxadiazole, or 1,3,4-oxadiazole moiety:

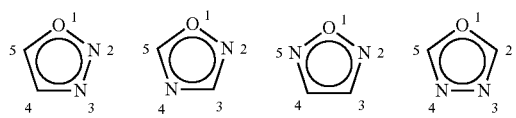

The oxadiazolyl moieties can be attached through any one of the carbon or nitrogen atoms. Within the scope of the invention, "oxadiazolyl" groups can be substituted with an alkyl group, preferably a methyl group.

The term "phenyl" represents the following moiety:

Phenyl groups of the inventions can be optionally substituted with, for example, one or more halogen atoms (halophenyl). Exemplary substituents are fluoro, bromo, and chloro. Preferred substituted phenyl groups of the invention are substituted with one, two, or three halogen atoms.

The term "pyridyl" represents the following moiety:

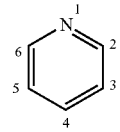

The pyridyl moiety can be attached through any one of the 2-, 3-, 4-, 5-, or 6-position carbon atoms. Pyridyl groups of the invention can be optionally substituted with, for example, one or more alkyl groups, for example, one or two methyl groups.

The term "piperazinyl" represents the following moiety:

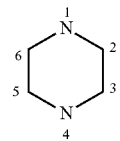

The piperazinyl moiety can be attached through any one of the 1-, 2-, 3-, 4-, 5-, or 6-position atoms. Any one of the nitrogen atoms of the piperazinyl moiety can be substituted with H or alkyl, for example, methyl.

The term "pyrimidinyl" represents the following moiety:

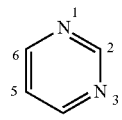

The pyrimidinyl moiety can be attached through any one of the 2-, 4-, 5-, or 6-position carbon atoms. Within the scope of the invention, "pyrimidinyl" groups of the invention can be substituted with halogen, for example fluoro.

The term "pyrazinyl" represents the following moiety:

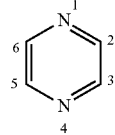

The pyrazinyl moiety can be attached through any one of the 2-, 3-, 5-, or 6-position carbon atoms.

The term "pyridazinyl" represents the following moiety:

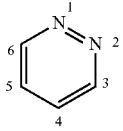

The pyridazinyl moiety can be attached through any one of the 3-, 4-, 5-, or 6-position carbon atoms.

The term "pyrazolyl" represents the following moiety:

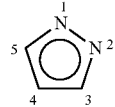

The pyrazolyl moiety can be attached through any one of the 1-, 2-, 3-, 4-, or 5-position carbon atoms. Pyrazolyl groups of the invention can be optionally substituted with, for example, one or two alkyl groups, for example, one or two methyl groups.

The term "pyrrolidinyl" represents the following moiety:

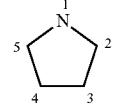

The pyrrolidinyl moiety can be attached through any one of the 1-, 2-, 3-, 4-, or 5-position atoms. When the pyrrolidinyl moiety is not attached through the 1-position nitrogen, the nitrogen can be substituted with H or alkyl, for example methyl.

The term "quinolinyl" represents the following moiety:

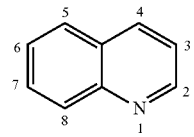

The quinolinyl moiety can be attached through any one of the 2-, 3-, 4-, 5-, 6-, 7-, or 8-position carbon atoms.

The term "quinoxalinyl" represents the following moiety:

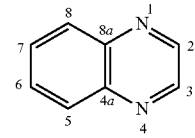

The quinoxalinyl moiety can be attached through any one of the 2-, 3-, 5-, 6-, 7-, or 8-position carbon atoms.

The term "quinazolinyl" represents the following moiety:

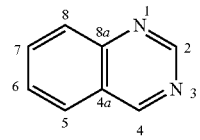

The quinoxalinyl moiety can be attached through any one of the 2-, 4-, 5-, 6-, 7-, or 8-position carbon atoms.

The term "thiazolyl" represents the following moiety:

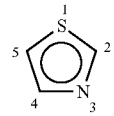

The thiazolyl moiety can be attached through any one of the 2-, 4-, or 5-position carbon atoms.

The term "thiophenyl" represents the following moiety:

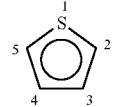

The thiophenyl moiety can be attached through any one of the 2-, 3-, 4-, or 5-position carbon atoms.

The term "triazolopyrazinyl" represents the following moiety:

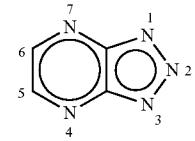

The triazolopyrazinyl moiety can be attached through any one of the 1-, 3-, 4-, 5-, 6-, or 7-position atoms.

The term "triazolyl" represents a 1,2,3-triazole or a 1,2,4-triazole moiety:

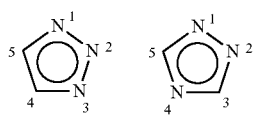

The triazolyl moieties can be attached through any one of their atoms.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present invention," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. Radiolabeled compounds of the invention can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds of the invention, radioactive or not, are intended to be encompassed within the scope of the invention.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The present invention is directed to compounds of Formula I:

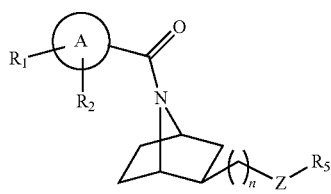

I wherein
ring A is phenyl, naphthalenyl, pyridyl, quinolinyl, isoquinolinyl, imidazopyridyl, furanyl, thiazolyl, isoxazolyl, pyrazolyl, imidazothiazolyl, benzimidazolyl, or indazolyl;
$R_1$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino;
$R_2$ is H, alkyl, alkoxy, hydroxyalkylene, or halo;
Z is NH, N-alkyl, or O;
$R_5$ is pyridyl, pyrimidinyl, pyrazinyl, pyridazinyl, quinazolinyl, quinoxalinyl, pyrazolyl, benzoxazolyl, imidazopyrazinyl, or triazolopyrazinyl, optionally substituted with a one or two substituents independently selected from the group consisting of alkyl, alkoxy, or halo; and
n is 0 or 1.

Enantiomers and diastereomers of the compounds of Formula I are also within the scope of the invention. Also within the scope of the invention are the pharmaceutically acceptable salts of the compounds of Formula I, as well as the pharmaceutically acceptable salts of the enantiomers and diastereomers of the compounds of Formula I.

In preferred embodiments of the invention, Z is NH. In other embodiments, Z is N-alkyl, preferably N—$C_{1-6}$alkyl, with N—$CH_3$ being particularly preferred.

In alternative embodiments, N is O.

In preferred embodiments of the invention, ring A is a heteroaryl ring. Preferably, ring A is furanyl, which can be attached to the compounds of Formula I through any available atom, preferably the 2-position carbon atom. In other embodiments, ring A is thiazolyl, which can be attached to the compounds of Formula I through any available atom, preferably the 4-position carbon atom.

In still other embodiments, ring A is isoxazolyl, which can be attached to the compounds of Formula I through any available atom, preferably the 4-position carbon atom.

In yet other embodiments, ring A is pyrazolyl, which can be attached to the compounds of Formula I through any through any available atom, preferably the 3- or 4-position carbon atoms.

Also preferred are embodiments wherein ring A is imidazothiazolyl, which can be attached to the compounds of Formula I through any available atom, preferably the 5-position carbon atom.

In certain embodiments of the invention, ring A is benzimidazolyl, which can be attached to the compounds of Formula I through any available atom, preferably the 2-position carbon atom.

In other embodiments of the invention, ring A is indazolyl, which can be attached to the compounds of Formula I through any available atom, preferably the 3-position carbon atom.

In yet other embodiments, ring A is imidazopyridyl, which can be attached to the compounds of Formula I through any available atom, preferably the 4-, or 7-position carbon atom In still other embodiments, ring A is quinolinyl, which can be attached to the compounds of Formula I through any available carbon atom, preferably the 5- or 8-position carbon atom.

In other embodiments, ring A is isoquinolinyl, which can be attached to the compounds of Formula I through any available carbon atom, preferably the 4-position carbon atom.

In certain embodiments, ring A is pyridyl, which can be attached to the compounds of Formula I through any available carbon atom, preferably the 2-, 3-, or 4-position carbon atom.

In some embodiments, ring A can be an aryl ring. In certain embodiments, ring A is phenyl. In other embodiments, ring A is naphthalenyl, which can be attached to the compounds of Formula I through any available carbon atom, preferably the 1-position carbon atom.

In preferred embodiments of the invention, $R_1$ is H. In other embodiments, $R_1$ is alkyl, preferably a $C_{1-6}$alkyl, for example, methyl.

In still other embodiments, $R_1$ is alkoxy, preferably a $C_{1-6}$alkoxy such as methoxy or ethoxy. Alternatively, $R_1$ is a substituted alkoxy, preferably substituted with one or more halo such as F, Cl, or Br. One preferred haloalkoxy is difluoromethoxy.

In other embodiments, $R_1$ is hydroxalkylene, for example, hydroxy$C_{1-6}$alkylene such as —$CH_2$—OH or —$CH_2CH_2$—OH. In yet other embodiments, $R_1$ is OH.

In other preferred embodiments, $R_1$ is halo, that is, any one of F, Cl, Br, or I, with F, Cl, or Br being particularly preferred.

In still other embodiments, $R_1$ is phenyl. In some embodiments, the phenyl can be substituted with at least one halo, for example, phenyl substituted with at least one of F, Cl, or Br.

In certain embodiments, $R_1$ is triazolyl, with 1,2,3-triazolyl being preferred. The triazolyl can be attached through any available atom. In preferred embodiments, the 1,2,3-triazolyl is attached through the 2-position nitrogen atom. In other embodiments, the 1,2,3-triazolyl is attached through the 1-position nitrogen atom.

In yet other embodiments, $R_1$ is oxazolyl, which can be attached through any available atom, preferably attached through the 2-position carbon. In some embodiments, the oxazolyl can be substituted with alkyl, for example, a $C_{1-6}$alkyl such as methyl.

In other embodiments, $R_1$ is isoxazolyl, which can be attached through any available atom. In some embodiments, the isoxazolyl can be substituted with alkyl, for example, a $C_{1-6}$alkyl such as methyl.

In still other embodiments, $R_1$ is pyridyl, which can be attached through any available carbon atom. In some embodiments, the pyridyl can be substituted with at least one alkyl, for example, $C_{1-6}$alkyl such as methyl.

In certain embodiments, $R_1$ is pyrimidinyl, which can be attached through any available carbon atom. In other embodiments, $R_1$ is pyrazinyl, which can be attached through any available carbon atom. In yet other embodiments, $R_1$ is pyridazinyl, which can be attached through any available carbon atom.

In other embodiments, $R_1$ is piperazinyl which can be attached through any available atom. In some embodiments, one or both nitrogen atoms of the piperazinyl may be substituted with H or alkyl, for example, $C_{1-6}$alkyl such as methyl.

In still other embodiments, $R_1$ is morpholinyl, which can be attached through any available atom. In some embodiments, the nitrogen of the morpholinyl may be substituted with H or alkyl, for example, $C_{1-6}$alkyl such as methyl.

In yet other embodiments, $R_1$ is pyrrolidinyl, which can be attached through any available atom. In some embodiments, the nitrogen of the pyrrolidinyl may be substituted with H or alkyl, for example, $C_{1-6}$alkyl such as methyl.

In other embodiments, $R_1$ is dialkylamino, for example, dimethylamino, diethylamino, or methylethylamino.

In other embodiments, $R_1$ is pyrazolyl, which can be attached through any available atom. In some embodiments, the pyrazolyl can be substituted with one or two alkyl, for example, $C_{1-6}$alkyl such as methyl.

In yet other embodiments, $R_1$ is oxadiazolyl, which can be a 1,2,3-oxadiazolyl, 1,2,4-oxadiazolyl, 1,2,5-oxadiazolyl, or 1,3,4-oxadiazolyl. Preferably, the oxadiazolyl is 1,2,4-oxadiazolyl. The oxadiazolyl can be attached through any available atom. In some embodiments, the oxadiazolyl can be substituted with alkyl, for example, $C_{1-6}$alkyl such as methyl.

In still other embodiments, $R_1$ is thiophenyl, which can be attached through any available carbon atom.

In preferred embodiments of the invention, $R_2$ is H. In other embodiments, $R_2$ is alkyl, for example, $C_{1-6}$alkyl such as methyl or ethyl. In yet other embodiments, $R_2$ is alkoxy, for example, $C_{1-6}$alkoxy such as methoxy or ethoxy. In other embodiments, $R_2$ is hydroxylalkene, for example, —$CH_2$—OH or $CH_2CH_2$—OH. In still other embodiments, $R_2$ is halo, preferably, any one of F, Cl, or Br.

In exemplary embodiments of the invention, ring A is

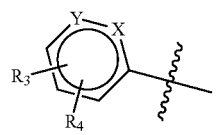

wherein
X is $CR_6$, N, or $NR_6$;
Y is $CR_7$, N, or $NR_7$;
$R_6$ is H, alkyl, alkoxy, OH, halo, triazolyl, oxazolyl, oxadiazolyl, pyridyl, pyrimidinyl, pyrazinyl, pyridazinyl, pyrazolyl, or thiophenyl;
$R_7$ is H, alkyl, alkoxy, or halo;
$R_3$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino;
$R_4$ is H, alkyl, alkoxy, or halo;
or
$R_6$ and $R_7$, together with the atoms to which they are attached, form a 5- or 6-membered heteroaryl ring optionally substituted with alkyl; or
$R_3$ and $R_4$, together with the atoms to which they are attached, form a 6-membered aryl or 6-membered heteroaryl ring; or
$R_7$ and $R_4$, together with the atoms to which they are attached, form a 6-membered aryl or 6-membered heteroaryl ring.

In certain of these embodiments, X is $CR_6$ and Y is $CR_7$.
In other of these embodiments, X is $CR_6$ and Y is N.
In still other of these embodiments, X is N and Y is $CR_7$.
In those embodiments wherein X is $CR_6$, for example those embodiments wherein X is $CR_6$ and Y is $CR_7$ or X is $CR_6$ and Y is N, $R_6$ is H. Alternatively, $R_6$ is alkyl, for example, $C_{1-6}$alkyl such as methyl or ethyl.

In other of these embodiments, $R_6$ is alkoxy, for example, $C_{1-6}$alkoxy such as methoxy or ethoxy.

In still other of these embodiments, $R_6$ is OH.
In yet other of these embodiments, $R_6$ is halo, preferably, any one of F, Cl, or Br.

In those embodiments wherein X is $CR_6$, for example those embodiments wherein X is $CR_6$ and Y is $CR_7$ or X is $CR_6$ and Y is N, $R_6$ is triazolyl with 1,2,3-triazolyl being preferred. The triazolyl can be attached through any available atom. In preferred embodiments, the 1,2,3-triazolyl is attached through the 2-position nitrogen atom. In other embodiments, the 1,2,3-triazolyl is attached through the 1-position nitrogen atom.

In those embodiments wherein X is $CR_6$, for example those embodiments wherein X is $CR_6$ and Y is $CR_7$ or X is $CR_6$ and Y is N, $R_6$ is oxazolyl, which can be attached through any available atom. In some embodiments, the oxazolyl can be substituted with alkyl, for example, $C_{1-6}$alkyl such as methyl.

In those embodiments wherein X is $CR_6$, for example those embodiments wherein X is $CR_6$ and Y is $CR_7$ or X is $CR_6$ and Y is N, $R_6$ is oxadiazolyl, which can be a 1,2,3-oxadiazolyl, 1,2,4-oxadiazolyl, 1,2,5-oxadiazolyl, or 1,3,4-oxadiazolyl. Preferably, the oxadiazolyl is 1,2,4-oxadiazolyl. The oxadiazolyl can be attached through any available atom. In some embodiments, the oxadiazolyl can be substituted with alkyl, for example, $C_{1-6}$alkyl such as methyl.

In those embodiments wherein X is $CR_6$, for example those embodiments wherein X is $CR_6$ and Y is $CR_7$ or X is $CR_6$ and Y is N, $R_6$ is pyrazolyl, which can be attached through any available atom. In some embodiments, the pyrazolyl can be substituted with one or two alkyl, for example, $C_{1-6}$alkyl such as methyl.

In those embodiments wherein X is $CR_6$, for example those embodiments wherein X is $CR_6$ and Y is $CR_7$ or X is $CR_6$ and Y is N, $R_6$ is thiophenyl, which can be attached through any available atom.

In those embodiments wherein X is $CR_6$, for example those embodiments wherein X is $CR_6$ and Y is $CR_7$ or X is $CR_6$ and Y is N, $R_6$ is pyridyl, which can be attached through any available atom. In some embodiments, the pyridyl can be substituted with one or more alkyl, for example, $C_{1-6}$alkyl such as methyl. One exemplary substituted pyridyl is methyl-pyridyl.

In those embodiments wherein X is $CR_6$, for example those embodiments wherein X is $CR_6$ and Y is $CR_7$ or X is $CR_6$ and Y is N, $R_6$ is pyrimidinyl, which can be attached through any available atom. In other embodiments, $R_6$ is pyrazinyl, which can be attached through any available atom. In still other embodiments, $R_6$ is pyridazinyl, which can be attached through any available atom.

In preferred embodiments wherein Y is $CR_7$, for example, those embodiments wherein X is $CR_6$ and Y is $CR_7$ or X is N and Y is $CR_7$, $R_7$ is H. In other embodiments, $R_7$ is alkyl, for example, $C_{1-6}$alkyl such as methyl or ethyl.

In those embodiments wherein Y is $CR_7$, for example, those embodiments wherein X is $CR_6$ and Y is $CR_7$ or X is N and Y is $CR_7$, $R_7$ is alkoxy, for example, $C_{1-6}$alkoxy such as methoxy or ethoxy. In other embodiments, the alkoxy is substituted with, for example, one or more halo. One preferred substituted alkoxy is difluoromethoxy.

In those embodiments wherein Y is $CR_7$, for example, those embodiments wherein X is $CR_6$ and Y is $CR_7$ or X is N and Y is $CR_7$, $R_7$ is halo, preferably one of F, Cl, or Br.

In some embodiments, X is $NR_6$ and Y is $CR_7$.

In other embodiments, X is $CR_6$ and Y is $NR_7$.

In those embodiments wherein X is $NR_6$ and Y is $CR_7$ or X is $CR_6$ and Y is $NR_7$, $R_6$ and $R_7$, together with the atoms to which they are attached, form a 5-membered heteroaryl ring. These 5-membered rings can be optionally substituted with alkyl, for example $C_{1-6}$alkyl such as methyl.

In those embodiments wherein X is $NR_6$ and Y is $CR_7$ or X is $CR_6$ and Y is $NR_7$, $R_6$ and $R_7$, together with the atoms to which they are attached, form a 6-membered heteroaryl ring. These 5-membered rings can be optionally substituted with alkyl, for example $C_{1-6}$alkyl such as methyl.

In those embodiments wherein Y is $CR_7$ or $NR_7$, $R_7$ and $R_4$, together with the atoms to which they are attached, form a 6-membered aryl ring. Alternatively, $R_7$ and $R_4$, together with the atoms to which they are attached, form a 6-membered heteroaryl ring.

In preferred embodiments, $R_3$ is H. In other embodiments, $R_3$ is alkyl, for example, $C_{1-6}$alkyl such as methyl or ethyl.

In other embodiments, $R_3$ is alkoxy, for example, $C_{1-6}$alkoxy such as methoxy or ethoxy. In some embodiments, the alkoxy is substituted with, for example, one or more halo. One preferred substituted alkoxy is difluoromethoxy.

In some embodiments, $R_3$ is hydroxyalkylene, for example, hydroxy$C_{1-6}$alklene such as —$CH_2$—OH and —$CH_2CH_2$—OH. In yet other embodiments, $R_3$ is OH.

In other preferred embodiments, $R_3$ is halo, preferably any one of F, Cl, or Br.

In still other embodiments, $R_3$ is phenyl. In some embodiments, the phenyl can be substituted with one or more halo, for example, phenyl substituted with at least one of F, Cl, or Br.

In certain embodiments, $R_3$ is triazolyl, with 1,2,3-triazolyl being preferred. The triazolyl can be attached through any available atom. In preferred embodiments, the 1,2,3-triazolyl is attached through the 2-position nitrogen atom. In other embodiments, the 1,2,3-triazolyl is attached through the 1-position nitrogen atom.

In yet other embodiments, $R_3$ is oxazolyl, which can be attached through any available atom, preferably attached through the 2-position carbon. In some embodiments, the oxazolyl can be substituted with alkyl, for example, a $C_{1-6}$alkyl such as methyl.

In other embodiments, $R_3$ is isoxazolyl, which can be attached through any available atom. In some embodiments, the isoxazolyl can be substituted with alkyl, for example, a $C_{1-6}$alkyl such as methyl.

In other embodiments, $R_3$ is oxadiazolyl, which can be a 1,2,3-oxadiazolyl, 1,2,4-oxadiazolyl, 1,2,5-oxadiazolyl, or 1,3,4-oxadiazolyl. Preferably, the oxadiazolyl is 1,2,4-oxadiazolyl. The oxadiazolyl can be attached through any available atom. In some embodiments, the oxadiazolyl can be substituted with alkyl, for example, $C_{1-6}$alkyl such as methyl.

In still other embodiments, $R_3$ is pyridyl, which can be attached through any available carbon atom. In some embodiments, the pyridyl can be substituted with one or more alkyl, for example, $C_{1-6}$alkyl such as methyl.

In other embodiments, $R_3$ is pyrazolyl, which can be attached through any available atom. In some embodiments, the pyrazolyl can be substituted with one or two alkyl, for example, $C_{1-6}$alkyl such as methyl.

In certain embodiments, $R_3$ is pyrimidinyl, which can be attached through any available carbon atom. In other embodiments, $R_3$ is pyrazinyl, which can be attached through any available carbon atom. In yet other embodiments, $R_3$ is pyridazinyl, which can be attached through any available carbon atom.

In other embodiments, $R_3$ is piperazinyl which can be attached through any available atom. In some embodiments, one or both nitrogen atoms of the piperazinyl may be substituted with H or alkyl, for example, $C_{1-6}$alkyl such as methyl.

In still other embodiments, $R_3$ is morpholinyl, which can be attached through any available atom. In some embodiments, the nitrogen atom of the morpholinyl may be substituted with H or alkyl, for example, $C_{1-6}$alkyl such as methyl.

In yet other embodiments, $R_3$ is pyrrolidinyl, which can be attached through any available atom. In some embodiments, the nitrogen atom of the pyrrolidinyl may be substituted with H or alkyl, for example, $C_{1-6}$alkyl such as methyl.

In other embodiments, $R_3$ is dialkylamino, for example, dimethylamino, diethylamino, or methylethylamino.

In other embodiments, $R_3$ is pyrazolyl, which can be attached through any available atom. In some embodiments, the pyrazolyl can be substituted with one or two alkyl, for example, $C_{1-6}$alkyl such as methyl.

In still other embodiments, $R_3$ is thiophenyl, which can be attached through any available carbon atom.

In preferred embodiments of the invention, $R_4$ is H. In other embodiments, $R_4$ is alkyl, for example, $C_{1-6}$alkyl such as methyl or ethyl. In still other embodiments, $R_4$ is alkoxy, for example, $C_{1-6}$alkoxy such as methoxy or ethoxy. In yet other embodiments, $R_4$ is halo, preferably, any one of F, Cl, or Br.

In some embodiments, $R_3$ and $R_4$, together with the atoms to which they are attached, form a 6-membered aryl ring.

In other embodiments, $R_3$ and $R_4$, together with the atoms to which they are attached, form a 6-membered heteroarylaryl ring.

In preferred embodiments of the invention, $R_5$ is a heteroaryl ring. According to some embodiments of the invention, $R_5$ is pyridyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is pyrimidinyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is pyrazinyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is pyridazinyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is quinazolinyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is quinoxalinyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is pyrazolyl, which can be attached through any available atom, optionally substituted with a one or two substituents independently selected from the group consisting of alkyl, alkoxy, or halo. In some embodiments, alkyl is trihaloalkyl, for example trifluoromethyl. In some embodiments, the pyrazolyl is methyl-pyrazolyl substituted with trifluoromethyl.

According to some embodiments of the invention, $R_5$ is benzoxazolyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is imidazopyrazinyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is triazolopyrazinyl, which can be attached through any available atom, optionally substituted with a one or two substituents independently selected from the group consisting of alkyl, alkoxy, or halo. In some embodiments, alkyl is trihaloalkyl, for example trifluoromethyl.

In some embodiments of the invention n is 0. In other embodiments, n is 1.

The invention relates to methods of using the compounds described herein to treat subjects diagnosed with or suffering from a disease, disorder, or condition mediated by orexin receptor activity. These methods are accomplished by administering to the subject a compound of the invention.

Diseases, disorders, and conditions mediated by orexin receptor activity include disorders of the sleep-wake cycle, insomnia, restless legs syndrome, jet-lag, disturbed sleep, sleep disorders secondary to neurological disorders, mania, depression, manic depression, schizophrenia, pain syndromes, fibromyalgia, neuropathic pain, catatonia, Parkinson's disease, Tourette's syndrome, anxiety, delirium, dementia, overweight, obesity, or conditions related to overweight or obesity, insulin resistance, type II diabetes, hyperlipidemia, gallstones, angina, hypertension, breathlessness, tachycardia, infertility, sleep apnea, back and joint pain, varicose veins, osteoarthritis, hypertension, tachycardia, arrhythmias, angina pectoris, acute heart failure, ulcers, irritable bowel syndrome, diarrhea gastroesophageal reflux, mood disorders, post-traumatic stress disorder, panic disorders, attention deficit disorders, cognitive deficiencies, or substance abuse.

Compounds of the invention are particularly suited for the treatment of mood disorders, post-traumatic stress disorder, panic disorders, attention deficit disorders, cognitive deficiencies, or substance abuse.

Sleep disorders include, but are not limited to, sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic).

Metabolic disorders include, but are not limited to, overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis.

Neurological disorders include, but are not limited to, Parkinson's disease, Alzheimer's disease, Tourette's Syndrome, catatonia, anxiety, delirium and dementias.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating.

Reactions may also be conducted in sealed pressure vessels above the normal reflux temperature of the solvent.

Scheme 1

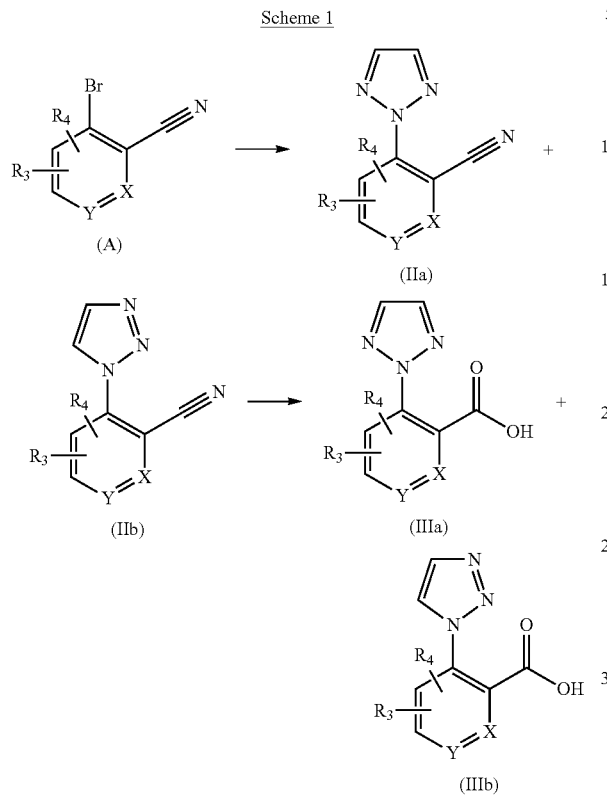

Intermediate compounds of formula (IIIa) and (IIIb) can be prepared as outlined in Scheme 1 from commercially available or synthetically accessible compounds of formula (A) where $R_3$, $R_4$, X and Y are defined in formula (I) as above. Compounds of formula (IIa) and (IIb), are obtained by reacting a compound of formula (A), with commercially available 1,2,3-triazole, in the presence $K_2CO_3$ in DMF or dioxane, at temperatures ranging from about 60° C. to about 100° C. Compounds of formula (IIIa) and (IIIb) are obtained by reacting compounds of formula (II) in the presence of a base such as NaOH in a solvent such as EtOH at temperatures ranging from 80° C. to 100° C. One skilled in the art will recognize that 1,2,3-triazole can exist in two tautomeric forms defined as 2H-[1,2,3]triazole and 1H-[1,2,3]triazole thus accounting for the formation of (IIIa) and (IIIb).

Scheme 2

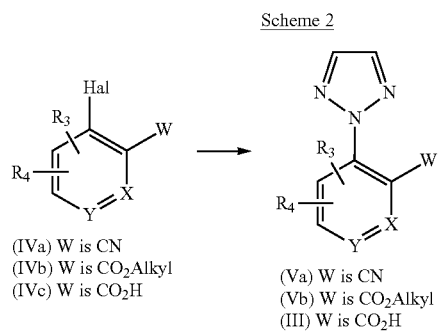

(IVa) W is CN
(IVb) W is $CO_2$Alkyl
(IVc) W is $CO_2$H (Va) W is CN
(Vb) W is $CO_2$Alkyl
(III) W is $CO_2$H

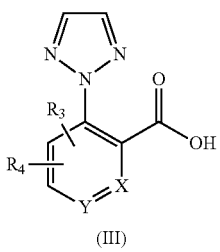

(III)

Intermediate compounds of formula (III) can be prepared as outlined in Scheme 2 from commercially available or synthetically accessible compounds of formula (IVa-c). Compounds of formula (III), (Va) and (Vb) are obtained by reacting compounds of formula (IVa), (IVb) and (IVc) where Hal is —Br, or —I; W is $CO_2H$, $CO_2$Alkyl, or CN and $R_3$ and $R_4$ are —H, halo, —$C_{1-4}$alkyl, —$C_{1-4}$alkoxy and $R_3$ and $R_4$ together with the atoms to which they are attached form a 6-membered aryl or 6 membered heteroaryl ring, with commercially available 1,2,3-triazole, in the presence of, for example, copper(I)iodide, $Cs_2CO_3$ and trans-N,N'-dimethyl-1,2-cyclohexanediamine in, for example, DMF or dioxane, at temperatures ranging from about 60° C. to about 120° C. Compounds of formula (IVc) can be converted to the corresponding esters (Vb) by treatment with, for example, alkyl iodide in the presence of a base such as $K_2CO_3$ in a solvent such as DMF. Compounds of formula (III) are obtained by reacting a compound of formula (Va) and (Vb) in the presence of a base such as NaOH in a solvent such as EtOH at temperatures ranging from about 80° C. to about 100° C. One skilled in the art will recognize that 1,2,3-triazole can exist in two tautomeric forms defined as 2H-[1,2,3]triazole and 1H-[1,2,3]triazole thus compounds of formula (Va), (Vb), and (III) can also exist as the N1 linked variant (structure not shown).

Scheme 3

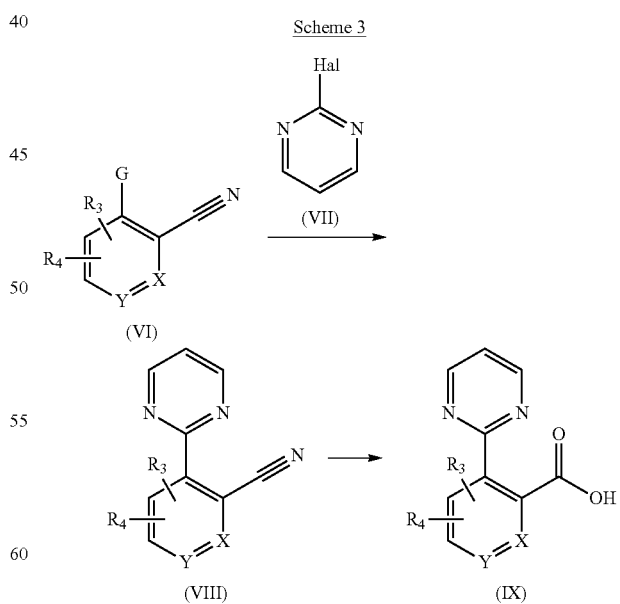

Intermediate compounds of formula (IX) are prepared as outlined in Scheme 3 from commercially available or synthetically accessible compounds of formula (VI) where $R_3$, $R_4$, X, and Y are defined as in formula I above, G is $SnBu_3$ or 4,4,5,5 tetramethyl-1,dioxaboralane and D is Cl, or Br, preferably Br in this case. Compounds of formula (VIII) are obtained by reacting a compound of formula (VI) with commercially available (VII) in the presence of a catalyst such as 1,1'-bis(di-tert-butylphosphino)ferrocene palladium dichloride and a base such as $Na_2CO_3$ in a solvent such as 2-MeTHF or THF at temperatures ranging from about 60° C. to about 90° C. Compounds of formula (IX) are obtained by reacting a compound of formula (VIII) in the presence of a base such as NaOH in a solvent such as MeOH at temperatures ranging from about 80° C. to about 100° C. or acids such as $H_2SO_4$ in solvents such as $H_2O$ at temperatures ranging from about 80 to about 100° C.

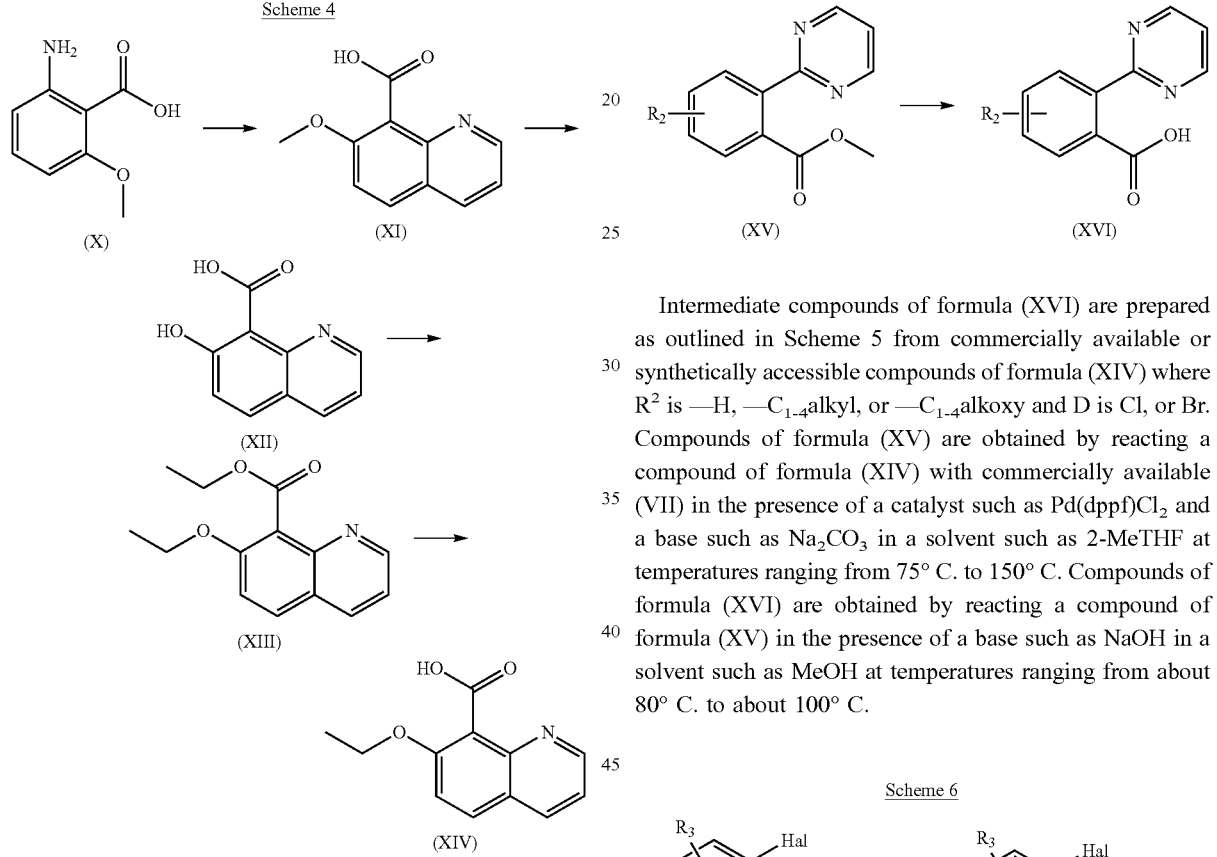

Intermediate compound (XIV) is prepared as outlined in Scheme 4 from commercially available compound (X). Compounds (XI) are obtained by reacting compound (X) with commercially available acrolein in a solvent such as 1,4 dioxane at temperatures of about 200° C. in a microwave reactor. Compound (XII) can be prepared from compound (XI) by treatment with an acid such as HBr in a solvent such as toluene at a temperature of about 90° C. Compound (XIII) can be obtained by treatment of compound (XII) with commercially available iodoethane and a base such as $K_2CO_3$ in a solvent such as DMF at temperatures ranging from about 45° C. to about 65° C. Compound (XIV) is obtained by treating compound (XIII) with a base such as NaOH in a solvent such as MeOH at temperatures ranging from about 80° C. to about 100° C.

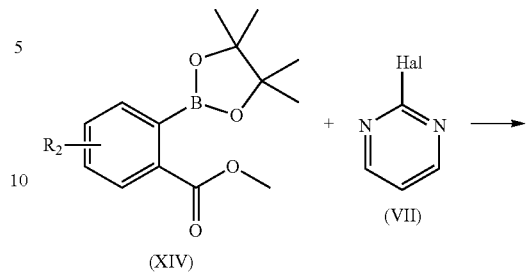

Intermediate compounds of formula (XVI) are prepared as outlined in Scheme 5 from commercially available or synthetically accessible compounds of formula (XIV) where $R^2$ is —H, —$C_{1-4}$alkyl, or —$C_{1-4}$alkoxy and D is Cl, or Br. Compounds of formula (XV) are obtained by reacting a compound of formula (XIV) with commercially available (VII) in the presence of a catalyst such as $Pd(dppf)Cl_2$ and a base such as $Na_2CO_3$ in a solvent such as 2-MeTHF at temperatures ranging from 75° C. to 150° C. Compounds of formula (XVI) are obtained by reacting a compound of formula (XV) in the presence of a base such as NaOH in a solvent such as MeOH at temperatures ranging from about 80° C. to about 100° C.

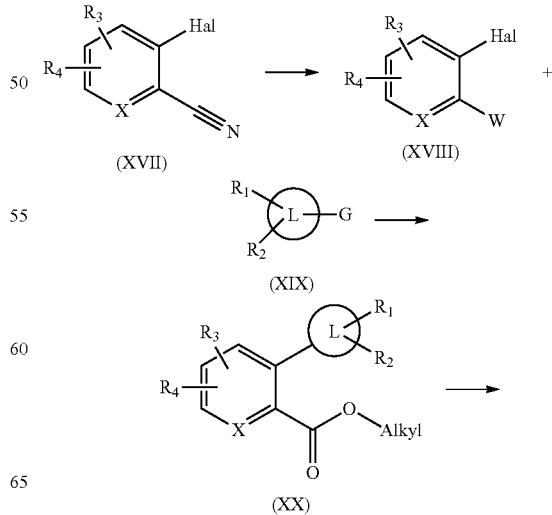

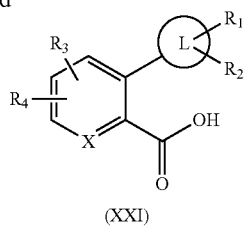

XVIII$_a$ W is CO$_2$H XVIII$_b$ W is CO$_2$Alkyl

Intermediate compounds of formula (XXI) can be prepared as outlined in Scheme 6 from commercially available or synthetically accessible compounds of formula (XVII) where Hal is Br or I; and where R$_3$ and R$_4$ are —H, halo, alkyl, alkoxy. Compounds of formula (XVIIIa) can be converted to the corresponding ester (XVIIIb) by treatment with thionyl chloride in a solvent such as MeOH. Compounds of the formula (XX) are obtained by reacting compounds of formula (XVIIIb) with commercially available compounds of the formula XIX where L is a heterocycle such as pyrazolyl, pyridyl, or oxazolyl; G is SnBu$_3$ or 4,4,5,5 tetramethyl-1,dioxaboralane and R$_1$ and R$_2$ are —H, -alkyl, or -alkoxy in the presence of a catalyst such as Pd(Ph$_3$P)$_4$ and a base such as Na$_2$CO$_3$ in a mixture of solvents such as DME and H$_2$O at temperatures ranging from 100° C. to 150° C. Compounds of formula (XXI) are obtained by reacting a compound of formula (XX) in the presence of a base such as NaOH in a solvent such as MeOH at temperatures ranging from about 80° C. to about 100° C.

about 70° C. Compounds of formula (XXVI) can be obtained from compounds of formula (XXIII) by treatment with bases such as aqueous sodium hydroxide, potassium hydroxide and lithium hydroxide in solvents such as water, methanol or THF. Compounds of formula (XXVI) can also be obtained from compounds of formula (XXV) using procedures described in WO 2004074292.

Scheme 8

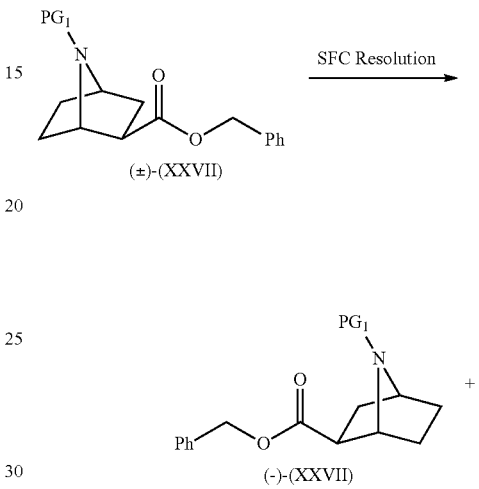

Scheme 7

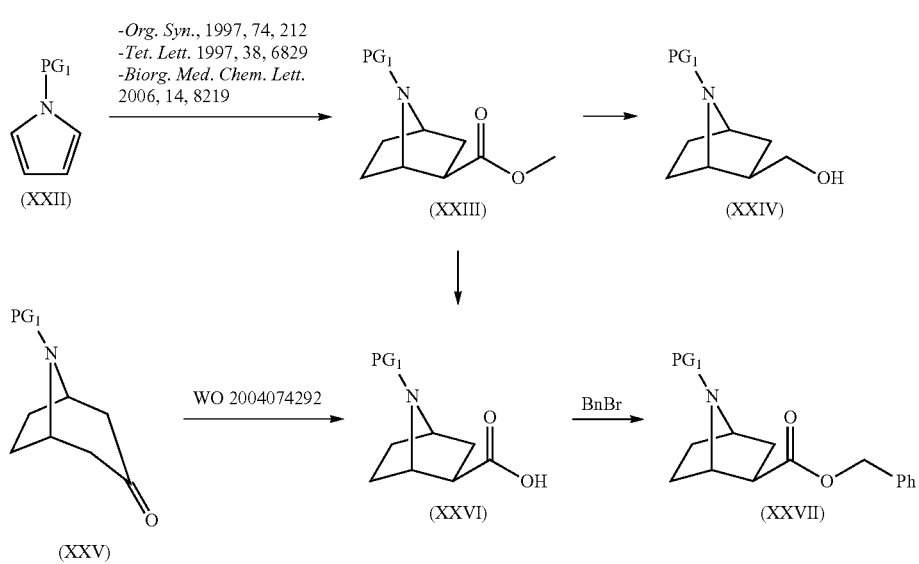

Intermediate compounds of formula (XXIV) and (XXVII) are readily prepared as outlined in Scheme 7 from commercially available or synthetically accessible compounds of formula (XXII) or (XXV). Compounds of formula (XXIII) can be obtained from compounds of formula (XXII) as described in the references listed in Scheme 7. Compounds of formula (XXIV) can be obtained from compounds of formula (XXIII) by treatment with reducing agents such as Dibal-H, LiAlH$_4$ or LiBH$_4$ in solvents such as THF or diethyl ether at temperatures ranging from about 0° C. to -continued

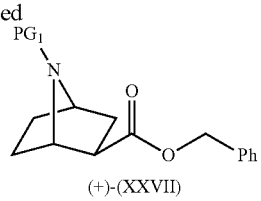

Referring to Scheme 8, where PG$_1$ is a Boc protecting group, compounds of formula (±)-(XXVII) were resolved into individual enantiomers of formula (+)-(XXVII) and (−)-(XXVII) using SFC chromatography on a chiral SFC (CHIRALPAK IC 5 µM 250×20 mm) column using 80% CO$_2$/20% iPrOH as the mobile phase.

Scheme 9

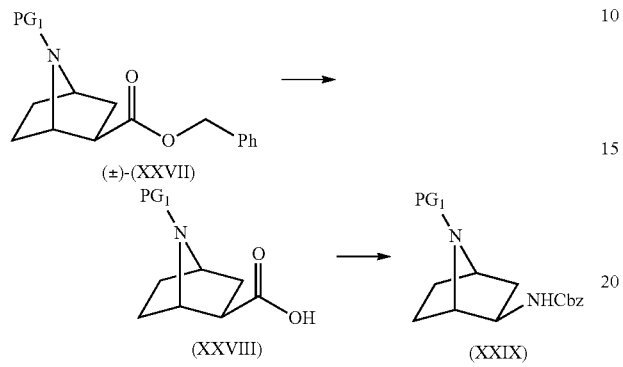

(±)-(XXVII)

(XXVIII)

(XXIX)

Referring to Scheme 9, where PG$_1$ is a Boc protecting group, compounds of formula (XXVIII) are prepared compounds of formula (+)-(XXIX). Compounds of formula (XXVIII) are readily prepared from compounds of formula (+)-(XXVII) by treatment with metal catalyst such as PtO$_2$, Pd/C, or Pd(OH)$_2$ in solvents such as AcOH, MeOH or EtOH under an atmosphere of hydrogen. Compounds of formula (XXIX) are readily prepared from compounds of formula (XXVIII) by reaction with DPPA and TEA in a solvent such as toluene at temperatures ranging from about 0° C. to about 100° C., preferably about 65° C. for a period of about 1 to 8 hours. BnOH is then added to afford a compound of formula (XXIX).

Scheme 10

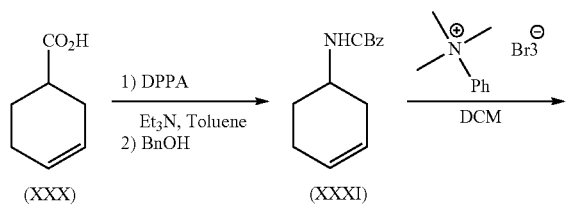

(XXX)    (XXXI)

(XXXII)    (XXXIII)

(XXXIV)    (XXXV)

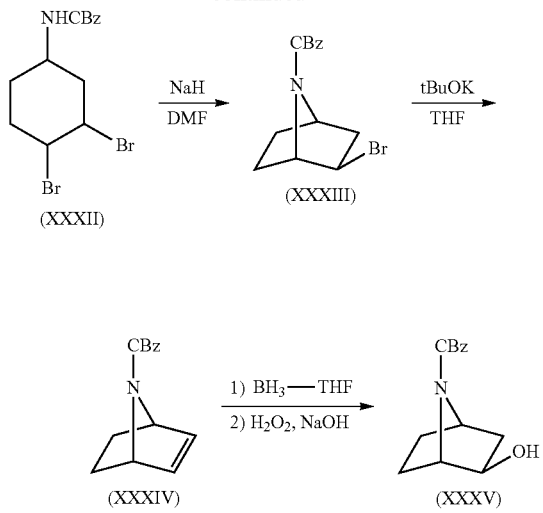

According to Scheme 10, compound (XXXI) is obtained by reaction of compound (XXX) with, for example, DPPA and TEA in a solvent such as toluene at temperatures ranging from about 0° C. to about 100° C., preferably about 65° C. for a period of about 1 to 8 hours, preferably about 4 h. BnOH is then added to afford a compound of formula (XXXI). Compound (XXXII) is obtained from compound (XXXI) by reaction with trimethylphenyl ammonium tribromide at temperatures ranging from about 0° C. to about 23° C., preferably about 0° C. for a period of from 2 to 6 hours, preferably about 4 hours. Compound (XXIII) is obtained from compound (XXXII) by treatment with a base, preferably NaH is a solvent such as DMF. Compound (XXXIV) is obtained from compound (XXXIII) by elimination of HBr with tBuOK in a solvent such as THF in the presence for a period ranging from 2 to 24 hours. Compound (XXXV) is obtained from compound (XXXIV) by hydroboration oxidation by treating the compound (XXXIV) with borane in a solvent such as THF at temperatures ranging from about 0° C. to about 23° C., preferably at about 23° C., for 2 to 12 hours, preferably about 2 hours followed by reaction with, for example, hydrogen peroxide in the presence of a base such as sodium hydroxide.

Scheme 11

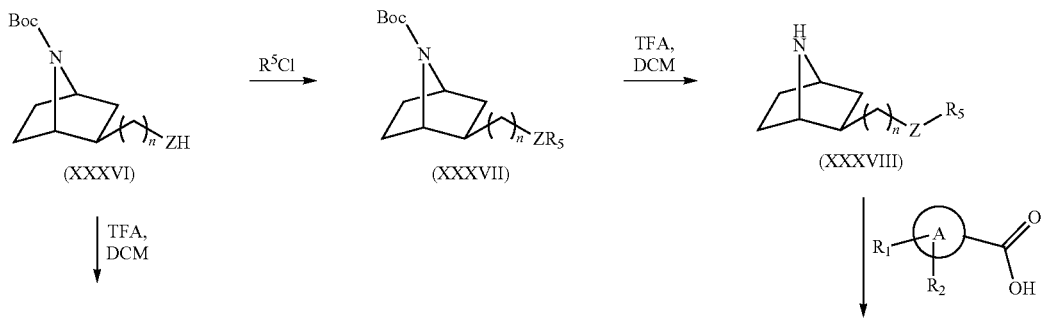

(XXXVI)    (XXXVII)    (XXXVIII)

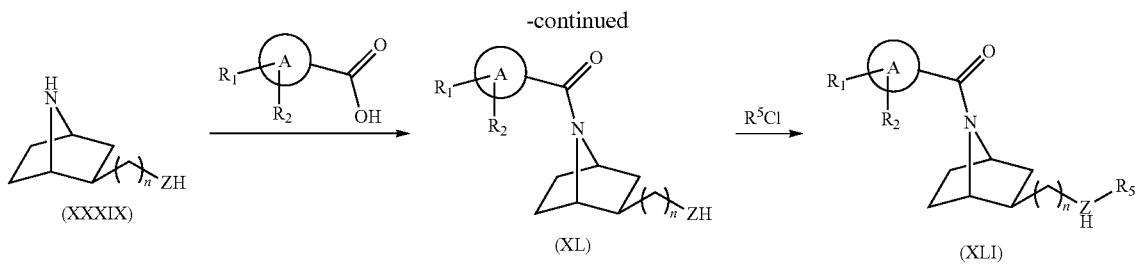

Referring to Scheme 11, one skilled in the art would recognize that compounds of formula (XLI) may be obtained from compounds of formula (XXXVI) by converging pathways. In one sequence, a compound of formula (XXXVII) is obtained by treating a compound of formula (XXXVI) with $R^5Cl$, where $R^5$ is optionally substituted pyridyl, pyrimidyl, pyrazinyl, pyridazinyl, quinazolinyl, quinoxalinyl, pyrazolyl, benzoxazolyl, imidazopyrazinyl, triazolopyrazinyl. Commercially available or synthetically accessible suitably substituted heteroaryl compounds of formula $R^5Cl$ are reacted with compounds of formula (XXXVI), in the presence of a suitably selected tertiary organic or inorganic base such as NaH, $Cs_2CO_3$, $K_2CO_3$, TEA, $iPr_2NEt$ and the like; in a solvent such as DMF, dichloromethane, THF, and the like; at a temperature between room temperature and the reflux temperature of the solvent. In a preferred embodiment the base is NaH and the solvent is DMF. Removal of the tert-butylcarbamate (Boc) in compounds of formula (XXXVII) is accomplished by using methods known to one skilled in the art, such as, HCl, TFA, or p-toluenesulfonic acid, in a solvent such as $CH_3OH$, dioxane, or $CH_2Cl_2$. In a preferred embodiment, a compound of formula (XXXVII) is treated with TFA in DCM or HCl to afford a compound of formula (XXXVIII). A compound of formula (XLI) is obtained by treating a compound of formula (XXXVIII) with $(R^1R^2A)CO_2H$, where $R^1$ is H, alkyl, alkoxy, hydroxyalkylene, OH, halo, phenyl, triazolyl, oxazolyl, isoxazolyl, pyridyl, pyrimidyl, pyrazinyl, pyridazinyl, piperazinyl, pyrazolyl, oxadiazolyl, pyrrolidinyl, thiophenyl, morpholinyl, or dialkylamino and $R_2$ is H, alkyl, alkoxy, or halo. Commercially available or synthetically accessible suitably substituted carboxylic acid compounds of formula $(R^1R^2A)CO_2H$ are combined with compounds of formula (XXXVIII) using under amide coupling methods known to one skilled in the art, such as, CDI, EDCI, HATU, or T3P in a solvent such as THF, DCM, or DMF In a preferred embodiment, a compound of formula (XXXVIII) and $(R^1R^2A)CO_2H$ are treated with EDCI in the presence of HOBT in DMF at ambient temperature to afford a compound of formula (XLI). One skilled in the art would recognize that compounds of formula (XLI) may also be obtained from compounds of formula (XL). Removal of the tert-butylcarbamate (Boc) in compounds of formula (XXXVI) is accomplished by using methods known to one skilled in the art, such as, HCl, TFA, or p-toluenesulfonic acid, in a solvent such as $CH_3OH$, dioxane, or $CH_2Cl_2$. In a preferred embodiment, a compound of formula (XXXVI) is treated with TFA in DCM or HCl to afford a compound of formula (XXXIX). A compound of formula (XL) is obtained by treating a compound of formula (XXXIX) with $(R^1R^2A)CO_2H$. Commercially available or synthetically accessible suitably substituted carboxylic acid compounds of formula $(R^1R^2A)$ $CO_2H$ are combined with compounds of formula (XXXIX) using under amide coupling methods known to one skilled in the art, such as, CDI, EDCI, HATU, or T3P in a solvent such as THF, DCM, or DMF In a preferred embodiment, a compound of formula (XXXIX) and $(R^1R^2A)CO_2H$ are treated with EDCI in the presence of HOBT in DMF at ambient temperature to afford a compound of formula (XL). A compound of formula (XLI) is obtained by treating a compound of formula (XL) with $R^5Cl$. Commercially available or synthetically accessible suitably substituted heteroaryl compounds of formula $R^5Cl$ are reacted with compounds of formula (XL), in the presence of a suitably selected tertiary organic or inorganic base such as NaH, $Cs_2CO_3$, $K_2CO_3$, TEA, $iPr_2NEt$ and the like; in a solvent such as DMF, dichloromethane, THF, and the like; at a temperature between room temperature and the reflux temperature of the solvent. In a preferred embodiment the base is NaH and the solvent is DMF to provide compounds of formula (XLI).

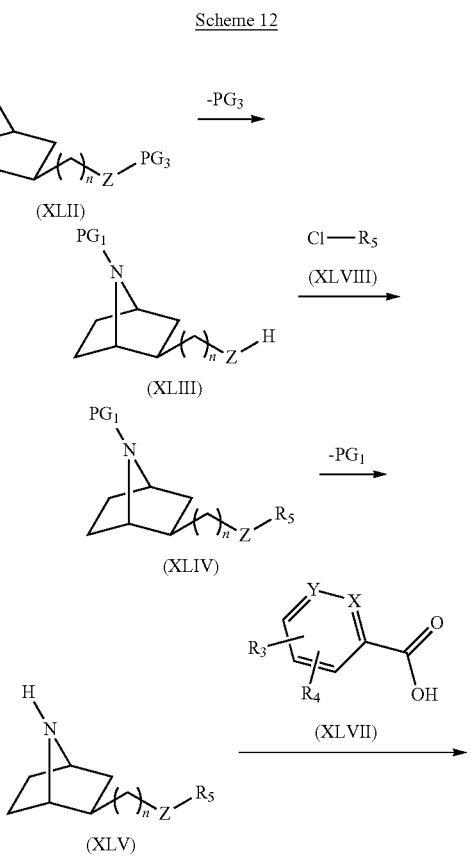

Scheme 12

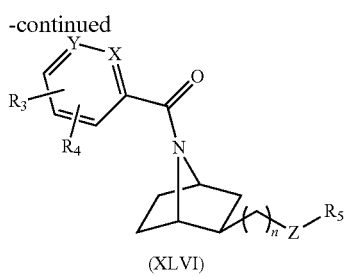

(XLVI)

Where n is 0 and Z is NH

Referring to Scheme 12, compounds of formula (XLVI) were synthesized from compounds of formula (XLII) where $PG_1$ is Boc, $PG_3$ is Cbz, Z is O or NH and n is 0 or 1. $PG_3$ was removed when compound of formula (XLII) was treated with, for example, a Pd catalyst such as 10 wt % Pd/C wet Degussa under an atmosphere of $H_2$ in a solvent such as EtOH to give compound of formula (XLIII). Compounds of formula (XLIV) were obtained from compounds of formula (XLIII) using compounds of formula (XLVIII) in a suitable solvent such as DMSO or DMF in the presence of a base such as $K_2CO_3$ at a temperature of about 70° C. Compounds of formula (XLIV) could also be obtained when compounds of formula (XLIII) and (XLVIII) were treated with a Pd catalyst such as $Pd(OAc)_2$, a ligand such as racemic BINAP, a base such as sodium tert-butoxide in a solvent such as toluene at a temperature of about 70° C. Compound of formula (XLV) were obtained from compounds of formula (XLIV) when treated with an acid such as HCl in a suitable solvent such as EtOAc or DCM at room temperature. Compound of formula (XLVI) were obtained from compounds of formula (XLV) using compounds of formula (XLVII) in a suitable solvent such as DMF or DCM in the presence of a peptide coupling reagent such as HATU or T3P, a base such as DIPEA at a temperature ranging from room temperature to about 45° C.

Scheme 13

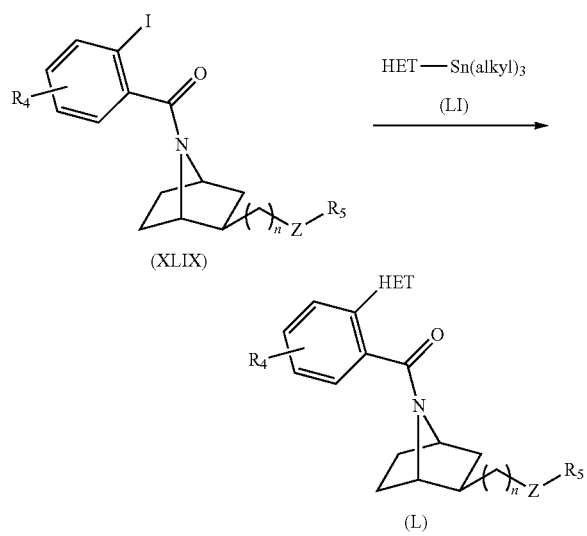

Referring to Scheme 13, compounds of formula (L) were obtained from compound of formula (XLIX) using compounds of formula (LI) in a solvent such as DME in the presence of a Pd catalyst such as $Pd(PPh_3)_4$, an additive or catalyst such as copper iodide at a temperature ranging from about 120° C. to about 150° C.

EXAMPLES

Abbreviations

| Term | Acronym |
|---|---|
| Acetic Acid | HOAc |
| Acetonitrile | ACN |
| Apparent | app |
| Aqueous | aq |
| Atmosphere | atm |
| 2-(1H-9-Azobenzotriazole-1-yl)-1,1,3,3-tetramethylaminium hexafluorophosphate | HATU |
| Benzyl | Bn |
| 2,2'-bis(diphenylphosphino)-1,1'-binaphthalene | BINAP |
| [1,1'-Bis(di-tert-butylphosphino)ferrocene]dichloropalladium(II) | $PdCl_2$(dtbpf) |
| Broad | br |
| tert-Butylcarbamoyl | Boc/Boc |
| Dichloromethane | DCM |
| Diisopropylethylamine | DIPEA |
| 1,2-Dimethoxyethane | DME |
| N,N-Dimethylformamide | DMF |
| Dimethylsulfoxide | DMSO |
| Doublet | d |
| Electrospray ionization | ESI |
| Enantiomeric excess | ee |
| Ethanol | EtOH |
| Ethyl Acetate | EtOAc, or EA |
| Grams | g |
| Hertz | Hz |
| High-pressure liquid chromatography | HPLC |
| Hours | h |
| Liquid chromatography and mass spectrometry | LCMS |
| Mass spectrometry | MS |
| Mass to charge ratio | m/z |
| Methanol | MeOH |
| Microliter | μL |
| Milligrams | mg |
| Milliliter | mL |
| Millimoles | mmol |
| Minute | min |
| Molar | M |
| Multiplet | m |
| Normal | N |
| Nuclear magnetic resonance | NMR |
| Palladium on carbon | Pd/C |
| Palladium hydroxide on carbon | $Pd(OH)_2$/C |
| Parts per million | ppm |
| Phenyl | Ph |
| Propylphosphonic anhydride | $T_3P$ |
| Retention time | $R_t$ |
| Room temperature | rt |
| Quartet | q |
| Singlet | s |
| Supercritical Fluid Chromatography | SFC |
| Temperature | T |
| Thin layer chromatography | TLC |
| Times | X |
| Triethylamine | TEA |
| Trifluoroacetic acid | TFA |
| Triplet | t |

Chemistry:

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$, filtered and concentrated. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Melting point determinations were performed in open capillary tubes on a FP62 or MP50 apparatus (Mettler-Toledo). Melting points were measured with a temperature gradient of 10° C./minute. Maximum temperature was 300° C. The melting point was read from a digital display.

Normal-phase flash column chromatography (FCC) was performed on silica gel ($SiO_2$) using prepackaged cartridges, eluting with the indicated solvents.

Where compounds were purified by "Prep HPLC" the method employed was either:

Preparative reverse-phase high performance liquid chromatography (HPLC) was performed on a Gilson HPLC with an Xterra Prep $RP_{18}$ (5 m, 30×100 mm, or 50×150 mm) column, and a gradient of 10 to 99% acetonitrile/water (20 mM $NH_4OH$) over 12 to 18 min, and a flow rate of 30 mL/min. or Preparative reverse-phase high performance liquid chromatography (HPLC) was performed on a Agilent 1100 Series HPLC with an XBridge C18 column (5 m, 30×100 mm), mobile phase of 5% ACN in 20 mM NH4OH (hold for 2 min) then ramp 5-99% ACN over 15 min, hold at 99% ACN for 5 min. and a flow rate of 40 mL/min. or Preparative reverse-phase high performance liquid chromatography (HPLC) was performed on a Agilent 1100 Series HPLC with an XBridge C18 column (5 m, 50×100 mm), mobile phase of 5% ACN in 20 mM NH4OH (hold for 2 min) then ramp 5-99% ACN over 15 min, hold at 99% ACN for 5 min. and a flow rate of 80 mL/min. or Preparative reverse-phase high performance liquid chromatography (HPLC) was performed on a Gilson HPLC with an Xterra Prep $RP_{18}$ (5 μm, 30×100 mm, or 50×150 mm) column, and a gradient of 10 to 99% acetonitrile/water (20 mM $NH_4OH$) over 12 to 18 min, and a flow rate of 30 mL/min.

Analytical chromatography data was acquired using an Agilent 1100 HPLC, with an Inertsil ODS-3 3 mm 4.6×50 mm column, purchased from GL Sciences (Part #1010L050W046). Samples were run using a gradient profile of 10-99% acetonitrile (ACN) in water, each containing 0.05% trifluoroacetic acid (TFA) over 1.6 minutes, then holding at 99% acetonitrile for 0.3 minutes. Flow rate was 5 mL/min and column temperature was set to 50° C. (Method A).

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Ultra 12.0 (CambridgeSoft Corp., Cambridge, Mass.) or ACD/Name Version 10.01 (Advanced Chemistry Development, Toronto, Ontario, Canada).

Where compounds were purified by "SFC Chromatography" the method employed was either:

On preparative APS 1010 system with autoprep otion from Berger instrument, consisted of two varian SD-1 pumps (walnut creek, CA, USA), one of which was extensively modified to pump $CO_2$, a special pump head heat exchanger, ajulabo FT 401 chiller (labortechnik GmbH, Sellback, Germany), a model SCM 2500 phase separator (berger instruments) with selection valve and set of collection vessels in a Bodan robot. A model Knauer 2500 UV detector with high pressure flow cell (berlin, germany). Sample were applied using a six-port injection valve (Valco, Houston, Tex., USA)) with a 5 ml sample loop and a model YP-300 syringe pump (cavro, san Jose, Calif.). or On a SFC-PICLAB-PREP 200 (PIC SOLUTION, Avignon, France). Modifier was pump with a model K1800 Knauer (Berlin, germany), with 100 ml Pump Head. The $CO_2$ was pump with 2 lewa pumps (Leonberg Germany). Cooling of the pump head and the CO2 line was achieved by a coil alimented by a Huber chiller (Offenburg/Germany). Sample injections were made using 6 switching valves (Valco, Houston, Tex., USA) and a 5 ml sample loop. The system is managed by a PLC automation system.

Intermediates

| Intermediate | Name | Structure | Reference |
| --- | --- | --- | --- |
| A-1 | 2-(2H-1,2,3-trizol-2-yl)benzoic acid | 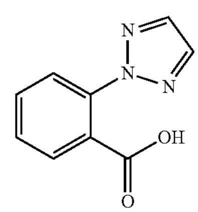 [SMILES: O=C(O)c1ccccc1-n1nccn1] | Prepared according to WO 2011/050198 Intermediate 2. |
| A-2 | 3-fluoro-2-(pyrimidin-2-yl)benzoic acid | 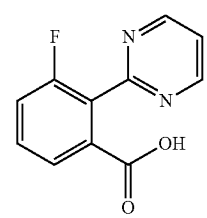 | Prepared according to WO 2011/050198 Intermediate 50. |

-continued

| Intermediate | Name | Structure | Reference |
|---|---|---|---|
| A-3 | 6-methyl-2-(2H-1,2,3-triazol-2-yl)nicotinic acid | 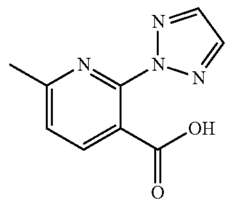 | Prepared according to WO 2011/050198 Intermediate 70 |
| A-4 | 6-methyl-2-(2H-1,2,3-triazol-1-yl)nicotinic acid | 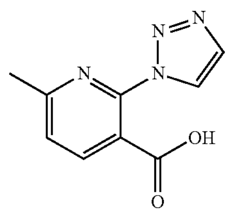 | Prepared according to WO 2011/050198 Intermediate 71 |
| A-5 | 4-methoxy-2-(2H-1,2,3-triazol-2-yl)benzoic acid | 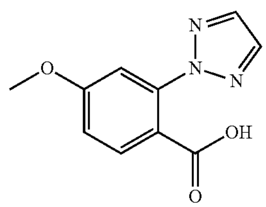 [SMILES: COc1ccc(C(=O)O)c(-n2nccn2)c1] | Prepared according to WO 2011/050198 Intermediate 54 |
| A-6 | 2-fluoro-6-(pyrimidin-2-yl)benzoic acid | 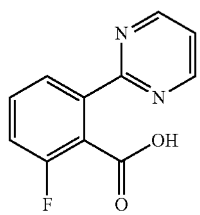 [SMILES: O=C(O)c1c(F)cccc1-c1ncccn1] | Prepared according to WO 2011/050198 Intermediate 14. |
| A-7 | 5-fluoro-2-(pyrimidin-2-yl)benzoic acid. | 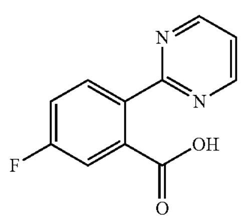 [SMILES: O=C(O)c1cc(F)ccc1-c1ncccn1] | Prepared according to WO 2011/050198 Intermediate 13. |
| A-8 | 3-ethoxy-6-methylpicolinic acid | 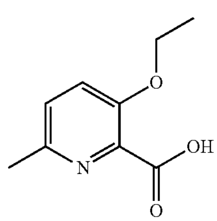 | WO 2010/063663 Description 39 |
| A-9 | 6-methyl-3-(pyrimidin-2-yl)picolinic acid | 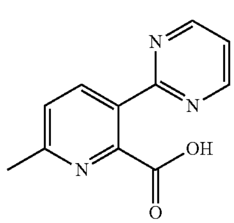 [SMILES: Cc1ccc(-c2ncccn2)c(C(=O)O)n1] | WO 2010/063663 Description 69 |

-continued

| Intermediate | Name | Structure | Reference |
|---|---|---|---|
| A-10 | 5-fluoro-2-(2H-1,2,3-triazol-2-yl)benzoic acid | 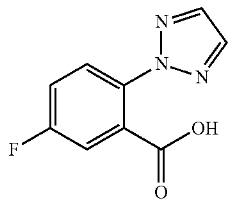 [SMILES: O=C(O)c1cc(F)ccc1-n1nccn1] | Prepared according to WO 2011/050198 Intermediate 1. |
| A-11 | 2-fluoro-6-(2H-1,2,3-triazol-2-yl)benzoic acid | 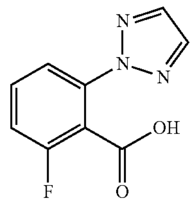 [SMILES: O=C(O)c1c(F)cccc1-n1nccn1] | Prepared according to WO 2011/050198 Intermediate 12. |
| A-12 | 4-fluoro-2-(2H-1,2,3-triazol-2-yl)benzoic acid | 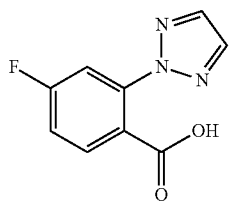 [SMILES: O=C(O)c1ccc(F)cc1-n1nccn1] | Prepared according to WO 2011/050198 Intermediate 4. |
| A-13 | 2-methoxy-6-(2H-1,2,3-triazol-2-yl)benzoic acid | 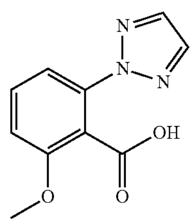 [SMILES: COc1cccc(-n2nccn2)c1C(=O)O] | Prepared analogous to Intermediate A-X using 2-bromo-6-(2H-1,2,3-triazol-2-yl)benzoic acid |
| A-14 | 2-methyl-6-(2H-1,2,3-triazol-2-yl)benzoic acid | 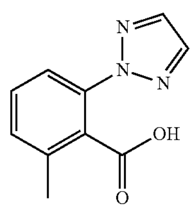 | Prepared according to WO 2011/050198 Intermediate 82. |
| A-15 | 4-methoxy-2-(pyrimidin-2-yl)benzoic acid | 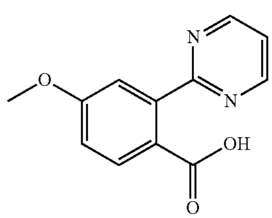 [SMILES: COc1ccc(C(=O)O)c(-c2ncccn2)c1] | Prepared according to WO 2011/050198 Intermediate 88. |
| A-16 | 3-fluoro-2-(2H-1,2,3-triazol-2-yl)benzoic acid | 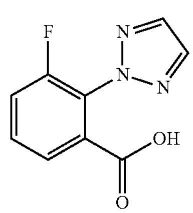 [SMILES: O=C(O)c1cccc(F)c1-n1nccn1] | Prepared according to WO 2011/050198 Intermediate 5. |

| Intermediate | Name | Structure | Reference |
|---|---|---|---|
| A-17 | 3-fluoro-2-(3-methyl-1,2,4-oxadiazol-5-yl)benzoic acid | 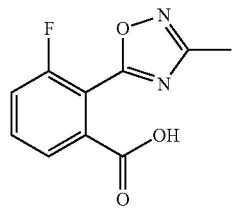 [SMILES: Cc1noc(-c2c(F)cccc2C(=O)O)n1] | Prepared according to WO 2011/050198 Intermediate 63. |
| A-18 | 5-methoxy-2-(2H-1,2,3-triazol-2-yl)benzoic acid | 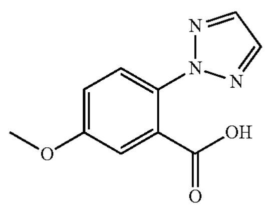 [SMILES: COc1ccc(-n2nccn2)c(C(=O)O)c1] | Prepared according to WO 2011/050198 Intermediate 10 |

Synthesis of 3-fluoro-2-(pyrimidin-2-yl)benzonitrile
(Intermediate in the synthesis of intermediate A-2)

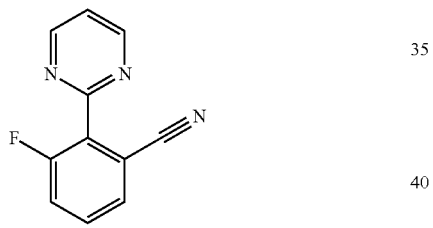

Intermediate A-19:
5-methyl-3-(2H-1,2,3-triazol-2-yl)picolinic acid

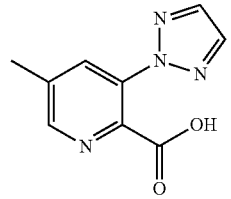

To a solution of 3-fluoro-2-(4,4,5,5-tetramethyl-1,3,2-dioxaborolan-2-yl)benzonitrile (4.98 g, 19.1 mmol) and 2-bromopyridine (3.85 g, 23 mmol) in THF (96 mL) was added $Na_2CO_3$ (6 g, 57.4 mmol) followed by water (43 mL). The reaction mixture was degassed with $N_2$ for 10 minutes. $PdCl_2$(dtbpf) (374 mg, 0.57 mmol) was added and the reaction mixture was stirred at 80° C. for 5 h. The solution was cooled to room temperature and a mixture of EtOAc and water was added. The aqueous was extracted twice with EtOAc and the combined organic layers were dried over MgSO4, filtered and evaporated. The title compound was precipitated by dissolving the residue in a minimum amount of EtOAc and then adding hexanes. The solid was filtered, washed with hexanes and dried to afford the title compound (2.46 g, 64%). MS (ESI) mass calcd. for $C_{11}H_6FN_3$, 199.1; m/z found 200.1 [M+H]$^+$. $^1$H NMR (400 MHz, Chloroform-d) δ 9.02-8.91 (m, 2H), 7.65 (dt, J=7.7, 1.0 Hz, 1H), 7.60-7.52 (m, 1H), 7.51-7.43 (m, 1H), 7.41 (t, J=4.9 Hz, 1H).

Step A: 5-methyl-3-(2H-1,2,3-triazol-2-yl)picolinonitrile. To 3-bromo-5-methylpicolinonitrile (1.5 g, 7.6 mmol) in DMF (19 mL) was added $K_2CO_3$ (1.2 g, 8.4 mmol) and 2H-1,2,3-triazole (440 μL, 7.6 mmol). The mixture was heated to 100° C. for 16 h, cooled to rt and extracted with EtOAc (2×). The combined organics were dried ($Na_2SO_4$) and concentrated. Purification via silica gel chromatography (5-60% EtOAc in hexanes) gave the title compound (490 mg, 35%) $^1$H NMR (500 MHz, $CDCl_3$) 8.58-8.53 (m, 1H), 8.29-8.24 (m, 1H), 7.98 (s, 2H), 2.54 (s, 3H) and 5-methyl-3-(1H-1,2,3-triazol-1-yl)picolinonitrile (387 mg, 27%).

Step B: 5-methyl-3-(2H-1,2,3-triazol-2-yl)picolinate. To a solution of the title compound of Step A (489 mg, 2.6 mmol) in EtOH (7 mL) was added 4 N NaOH (660 μL, 2.6 mmol). The mixture was heated at 100° C. for 24 h. The reaction mixture was concentrated in vacuo to a white solid which was used without further purification in subsequent steps. MS (ESI) mass calcd. for $C_9H_8N_4O_2$, 204.1; m/z found 205.0 [M+H]$^+$.

Intermediate A-20:
5-methyl-3-(1H-1,2,3-triazol-1-yl)picolinic acid

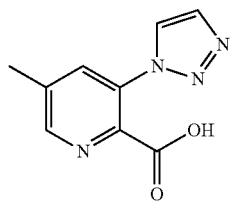

Step A: 5-methyl-3-(1H-1,2,3-triazol-1-yl)picolinonitrile. The title compound was prepared in Intermediate A-19 Step A. $^1$H NMR (500 MHz, CDCl$_3$) 8.65 (dd, J=1.8, 0.9 Hz, 1H), 8.41 (d, J=1.2 Hz, 1H), 8.18-8.15 (m, 1H), 7.95 (d, J=1.2 Hz, 1H), 2.58 (s, 3H).

Step B: 5-methyl-3-(1H-1,2,3-triazol-1-yl)picolinic acid. Prepared analogous to Intermediate A-19 substituting 5-methyl-3-(2H-1,2,3-triazol-2-yl)picolinonitrile with the title compound of Step A. MS (ESI) mass calcd. for C$_9$H$_8$N$_4$O$_2$, 204.1; m/z found 205.0 [M+H]$^+$.

Intermediate A-21:
6-methyl-3-(2H-1,2,3-triazol-2-yl)picolinic acid

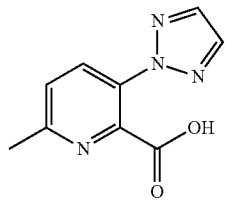

Step A: 6-methyl-3-(2H-1,2,3-triazol-2-yl)picolinonitrile. To 3-bromo-5-methylpicolinonitrile (2.2 g, 11 mmol) in DMF (28 mL) was added K$_2$CO$_3$ (1.7 g, 12 mmol) and 2H-1,2,3-triazole (650 µL, 11 mmol). The mixture was heated to 100° C. for 36 h, cooled to rt and extracted with EtOAc. The combined organics were dried (Na$_2$SO$_4$) and concentrated. Purification via silica gel chromatography (10-100% EtOAc in hexanes) gave the title compound (1 g, 48%).

Step B: 6-methyl-3-(2H-1,2,3-triazol-2-yl)picolinic acid. To a solution of the title compound of Step A (730 mg, 4 mmol) in EtOH (10 mL) was added 4 N NaOH (1 mL, 4 mmol). The mixture was heated at 100° C. for 24 h. The reaction mixture was concentrated in vacuo to a white solid which was used without further purification in subsequent steps.

Intermediate A-22:
3-ethoxyisoquinoline-4-carboxylic acid

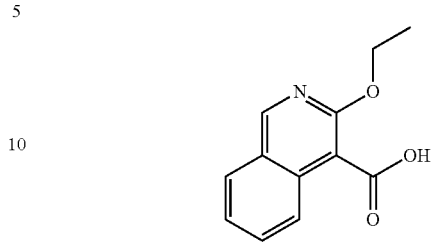

Step A: ethyl 3-hydroxyisoquinoline-4-carboxylate. To a suspension of ethyl 3-aminoisoquinoline-4-carboxylate (583 mg, 2.70 mmol) in 6.8 mL of H$_2$SO$_4$ 5N cooled to 0° C. was added sodium nitrite (223 mg, 3.24 mmol, dissolved in 1 mL of water). The reaction mixture was stirred at 0° C. for 2.5 h and then NaOH$_{(aq)}$ 1N was added until pH=7. The aqueous phase was extracted twice with DCM and the combined organic phases were dried over MgSO$_4$, filtered and evaporated to give the title compound of Step A which was used without further purification in the next step (583 mg, 99%). MS (ESI) mass calcd. for C$_{12}$H$_{11}$NO$_3$, 217.1; m/z found 218.1 [M+H]$^+$.

Step B: ethyl 3-ethoxyisoquinoline-4-carboxylate. To the title compound of Step A (583 mg, 2.68 mmol) in THF (13 mL) was added triphenylphosphine (1.06 g, 4.03 mmol), ethanol (0.24 mL, 4.03 mmol) and DIAD (0.79 mL, 4.03 mmol). The reaction mixture was stirred at room temperature for 16 h and then the solvent was evaporated. The crude was purified via silica gel chromatography (0-30% EtOAc in hexanes) to afford the title compound of Step B (498 mg, 76%). MS (ESI) mass calcd. for C$_{14}$H$_{15}$NO$_3$, 245.1; m/z found 246.1 [M+H]$^+$. $^1$H NMR (500 MHz, Chloroform-d) δ 8.97 (s, 1H), 7.91-7.82 (m, 2H), 7.65-7.60 (m, 1H), 7.42-7.36 (m, 1H), 4.59-4.48 (m, 4H), 1.48-1.39 (m, 6H).

Step C: 3-ethoxyisoquinoline-4-carboxylic acid. The title compound of Step B (492 mg, 2 mmol) dissolved in MeOH (15 mL) was added NaOH$_{(aq)}$ 2M (2.5 mL). The reaction mixture was stirred at 60° C. for 16 h and then NaOH$_{(aq)}$ 4M (2 mL) was added and the mixture was stirred at 70° C. for 4 h. MeOH was evaporated and the aqueous phase was cooled to 0° C. and acidified with the addition of HCl$_{(aq)}$ 6N. The solid was filtered, washed with cold water and dried to afford the title compound (285 mg, 65%). MS (ESI) mass calcd. for C$_{12}$H$_{11}$NO$_3$, 217.1; m/z found 218.1 [M+H]$^+$. $^1$H NMR (400 MHz, DMSO-d6) δ 13.36 (s, 1H), 9.15 (s, 1H), 8.13-8.06 (m, 1H), 7.82-7.70 (m, 2H), 7.54-7.47 (m, 1H), 4.50 (q, J=7.0 Hz, 2H), 1.35 (t, J=7.0 Hz, 3H).

Intermediate A-23: 4-(difluoromethoxy)-2-(2H-1,2,3-triazol-2-yl)benzoic acid

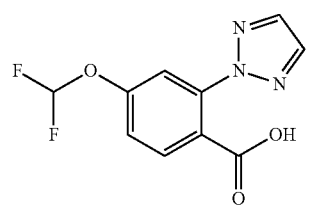 [SMILES: O=C(O)c1ccc(OC(F)F)cc1-n1nccn1]

Prepared analogous to Intermediate A-19 substituting 2-bromo-6-methyl-3-(2H-1,2,3-triazol-2-yl)pyridine with 4-(difluoromethoxy)-2-fluorobenzonitrile.

found 229.1 [M+H]⁺. ¹H NMR (500 MHz, CDCl3) 8.95-8.76 (m, 2H), 7.99-7.75 (m, 1H), 7.50-7.44 (m, 1H), 7.43-7.37 (m, 1H), 7.32-7.24 (m, 1H), 3.64 (s, 3H), 2.15 (s, 3H).

| Intermediate | Name | Structure | Reference |
|---|---|---|---|
| A-24 | 3-methyl-2-(2H-1,2,3-triazol-2-yl)benzoic acid | 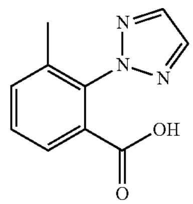 | Prepared according to WO 2011/050198 Intermediate 82 |
| A-25 | 4-fluoro-2-(pyrimidin-2-yl)benzoic acid | 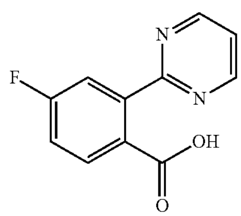 [SMILES: O=C(O)c1ccc(F)cc1-c1ncccn1] | Prepared according to WO 2011/050198 Intermediate 87 |

Intermediate A-26:
3-methyl-2-(pyrimidin-2-yl)benzoic acid

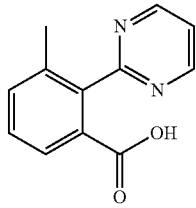 [SMILES: Cc1cccc(C(=O)O)c1-c1ncccn1]

Step A: methyl 3-methyl-2-(pyrimidin-2-yl)benzoate. In a microwave vial was dissolved methyl 3-methyl-2-(4,4,5,5-tetramethyl-1,3,2-dioxaborolan-2-yl)benzoate (619 mg, 2.24 mmol) and 2-chloropyrimidine (314 mg, 2.69 mmol) in 2-MeTHF (10 mL). Na$_2$CO$_3$ (713 mg, 6.73 mmol) was then added followed by water (3.4 mL) and the reaction mixture was degassed with N$_2$ for 45 minutes. Pd(dppf)Cl$_2$ (66 mg, 0.09 mmol) and the reaction mixture was heated at 75° C. for 28 h. More Pd(dppf)Cl$_2$ (33 mg, 0.045 mmol) was added and the reaction mixture was heated at 150° C. for 3.5 h. The mixture was filtered through a pad of celite and rinsed with EtOAc and water. The layers were separated and the aqueous was extracted once with EtOAc. The combined organic layers were dried over MgSO$_4$, filtered and evaporated. The crude was purified via silica gel chromatography (0-50% EtOAc in hexanes) to afford the title compound (116 mg, 23%). MS (ESI) mass calcd. for C$_{13}$H$_{12}$N$_2$O$_2$, 228.1; m/z Step B: 3-methyl-2-(pyrimidin-2-yl)benzoic acid. Prepared analogous to intermediate A-31 step B to give title compound. MS (ESI) mass calcd. for C$_{12}$H$_{10}$N$_2$O$_2$, 214.1; m/z found 215.1 [M+H]⁺.

| Intermediate | Name | Structure | Reference |
|---|---|---|---|
| A-27 | 3-(2H-1,2,3-triazol-2-yl)picolinic acid | 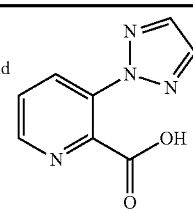 | Prepared according to WO 2011/050198 Intermediate 72 |

Intermediate A-28:
2-methoxy-6-(pyrimidin-2-yl)benzoic acid

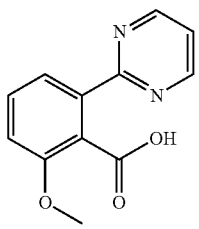 [SMILES: COc1cccc(-c2ncccn2)c1C(=O)O]

Step A: Methyl 2-methoxy-6-(pyrimidin-2-yl)benzoate. In a microwave vial was dissolved methyl 2-methoxy-6-(4,4,5,5-tetramethyl-1,3,2-dioxaborolan-2-yl)benzoate (500 mg, 1.71 mmol), commercially available from Combi- Blocks (CAS #1146214-77-8), and 2-bromopyrimidine (344 mg, 2.05 mmol) in THF (8.5 mL). $Na_2CO_3$ (544 mg, 5.14 mmol) was then added followed by water (4 mL) and the reaction mixture was degassed with $N_2$ for 10 minutes. $PdCl_2$(dtbpf) (45 mg, 0.069 mmol) was then added and the reaction mixture was heated at 80° C. for 4 h. The mixture was cooled to room temperature and water and EtOAc added. The reaction mixture was extracted with EtOAc (3×). The combined organic layers were dried over $Na_2SO_4$, filtered, and concentrated. The crude was purified via silica gel chromatography (0-70% EtOAc in hexanes) to afford the title compound (265 mg, 63%). MS (ESI) mass calcd. for $C_{13}H_{12}N_2O_3$, 244.1; m/z found 245.1 [M+H]$^+$. $^1$H NMR (400 MHz, Chloroform-d) 8.78 (d, J=4.9 Hz, 2H), 7.99 (dd, J=7.9, 0.9 Hz, 1H), 7.49 (t, J=8.1 Hz, 1H), 7.19 (t, J=4.8 Hz, 1H), 7.09 (dd, J=8.3, 0.9 Hz, 1H), 3.90 (s, 3H), 3.89 (s, 3H).

Step B: 2-methoxy-6-(pyrimidin-2-yl)benzoic acid. To a solution of the title compound of Step A (265 mg, 1.09 mmol) in THF (4 mL) was added 2 N NaOH (2 mL). The mixture was heated at 50° C. for 72 h. The reaction mixture was concentrated in vacuo to a white solid which was used without further purification in subsequent steps. MS (ESI) mass calcd. for $C_{12}H_{10}N_2O_3$, 230.1; m/z found 231.1 [M+H]$^+$. $^1$H NMR (500 MHz, DMSO-$d_6$) 12.63 (s, 1H), 8.86 (d, J=4.9 Hz, 2H), 7.77 (dd, J=7.9, 1.0 Hz, 1H), 7.51 (t, J=8.1 Hz, 1H), 7.45 (t, J=4.9 Hz, 1H), 7.25 (dd, J=8.4, 1.0 Hz, 1H), 3.83 (s, 3H).

Intermediate A-29: 7-ethoxyquinoline-8-carboxylic acid

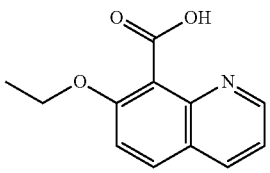 [SMILES: CCOc1ccc2cccnc2c1C(=O)O]

Step A: 7-methoxyquinoline-8-carboxylic acid. In 1 g separate batches a mixture of 2-amino-6methoxybenzoic acid (11 g, 66 mmol) and acrolein (4.8 mL, 72 mmol) in 1,4-dioxane (66 mL) was heated in a microwave reactor for 20 min at 200° C. After combining the reactions, the mixture was concentrated and purified via silica gel chromatography (0-10% MeOH in DCM) to give the title compound (2.8 g, 20%). MS (ESI) mass calcd. for $C_{11}H_{19}NO_3$, 203.1; m/z found 204.0 [M+H]$^+$.

Step B: 7-hydroxyquinoline-8-carboxylic acid. The title compound of Step A (2.9 g, 14.1 mmol) in HBr (14 mL) was heated at 90° C. for 1 h. The mixture was then concentrated washed with PhCH3 and used without further purification in subsequent steps.

Step C: ethyl 7-ethoxyquinoline-8-carboxylate. To the title compound of Step B (800 mg, 3.9 mmol) and $K_2CO_3$ (1.4 g, 10.4 mmol) in DMF (15 mL) was added iodoethane (560 μL, 6.9 mmol). After stirring overnight at rt, the reaction was concentrated and purified via silica gel chromatography (0-30% EtOAc in hexanes) to give the title compound. MS (ESI) mass calcd. for $C_{14}H_{15}NO_3$, 245.1; m/z found 246.0 [M+H]$^+$.

Step D: 7-ethoxyquinoline-8-carboxylic acid. To the title compound of Step C (1.3 g, 5.4 mmol) in THF (22 mL) and $H_2O$ (11 mL) was added LiOH hydrate (675 mg, 16.5 mmol) and MeOH. The mixture was heated at 67° C. for 12 h. Additional LiOH hydrate (675 mg, 16.5 mmol) was added and the heating was continued at 70° C. for 1 days. Additional LiOH hydrate (1.4 g, 33 mmol) was added and the heating was continued at 75° C. for 1 day. The reaction was allowed to cool to rt, acidified to pH=3 with 1N HCl (aq) and concentrated. Purification via prep HPLC gave the title compound (1 g, 84%). MS (ESI) mass calcd. for $C_{12}H_{11}NO_3$, 217.1; m/z found 218.0 [M+H]$^+$.

Intermediate A-30: 2-(1,4-dimethyl-1H-pyrazol-5-yl)-6-methoxybenzoic acid

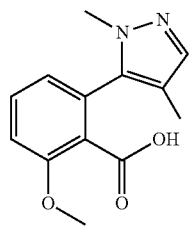 [SMILES: COc1cccc(-c2c(C)cnn2C)c1C(=O)O]

Step A: Ethyl 2-(1,4-dimethyl-1H-pyrazol-5-yl)-6-methoxybenzoate. In a microwave vial was dissolved ethyl 2-bromo-6-methoxybenzoate (500 mg, 1.54 mmol) and 1,4-dimethyl-5-(4,4,5,5-tetramethyl-1,3,2-dioxaborolan-2-yl)-1H-pyrazole (377 mg, 1.70 mmol) in DME (10 mL) and water (2 mL). $Na_2CO_3$ (259 mg, 3.09 mmol) was then added followed by Pd(PPh$_3$)$_4$ (89 mg, 0.077 mmol) and the reaction mixture was degassed with $N_2$ for 10 minutes. The reaction mixture was then heated at 100° C. for 1 h in the microwave. The mixture was cooled to room temperature, filtered through Celite and washed with EtOAc and DCM. The crude solution was concentrated in vacuo and directly purified via silica gel chromatography (10-80% EtOAc in hexanes) to afford the title compound (402 mg, 95%). MS (ESI) mass calcd. for $C_{15}H_{18}N_2O_3$, 274.1; m/z found 275.2 [M+H]$^+$. 1H NMR (400 MHz, Chloroform-d) 7.45 (dd, J=8.4, 7.6 Hz, 1H), 7.29 (s, 1H), 7.04 (dd, J=8.5, 0.9 Hz, 1H), 6.84 (dd, J=7.6, 0.9 Hz, 1H), 4.07 (qd, J=7.2, 1.5 Hz, 2H), 3.90 (s, 3H), 3.61 (s, 3H), 1.86 (s, 3H), 1.01 (t, J=7.1 Hz, 3H).

Step B: 2-(1,4-dimethyl-1H-pyrazol-5-yl)-6-methoxybenzoic acid. Prepared analogous to intermediate A-28 step B to give title compound. MS (ESI) mass calcd. for $C_{13}H_{14}N_2O_3$, 246.1; m/z found 247.2 [M+H]$^+$. $^1$H NMR (500 MHz, DMSO-$d_6$) 7.50 (dd, J=8.5, 7.6 Hz, 1H), 7.25 (s, 1H), 7.21 (dd, J=8.5, 0.9 Hz, 1H), 6.85 (dd, J=7.6, 0.9 Hz, 1H), 3.84 (s, 3H), 3.49 (s, 3H), 1.79 (s, 3H).

Intermediate A-31: 3-methyl-2-(oxazol-2-yl)benzoic acid

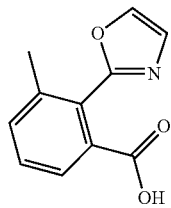

Step A: ethyl 3-methyl-2-(oxazol-2-yl)benzoate. In a microwave vial was dissolved ethyl 2-iodo-3-methylbenzoate (627 mg, 2.16 mmol) and 2-(tributylstannyl)oxazole (0.54 mL, 0.07 mmol) in DME (2.59 mL). The solution was degassed with $N_2$ for 5 minutes then CuI (21 mg, 0.11 mmol) and Pd(PPh$_3$)$_4$ (125 mg, 0.11 mmol) were added. The reaction was purged with $N_2$ and heated at 150° C. for 1 h. The reaction was cooled to rt, filtered through a pad of celite and purified via silica gel chromatography (0-40% EtOAc in hexanes) to give the title compound of step A (333 mg, 67%). MS (ESI) mass calcd. for $C_{13}H_{13}NO_3$, 231.1; m/z found 232.1 [M+H]$^+$. $^1$H NMR (500 MHz, Chloroform-d) 7.89-7.82 (m, 1H), 7.79 (d, J=0.8 Hz, 1H), 7.48-7.43 (m, 2H), 7.30 (d, J=0.9 Hz, 1H), 4.17 (q, J=7.1 Hz, 2H), 2.27 (s, 3H), 1.18 (t, J=7.1 Hz, 3H).

Step B: 3-methyl-2-(oxazol-2-yl)benzoic acid. To the title compound of step A (166 mg, 0.72 mmol) was added MeOH (7.2 mL) and 1M NaOH$_{(aq)}$ (7.2 mL). MeOH was evaporated and then 1 M HCl$_{(aq)}$ was added. To the solution was added DCM and the aqueous was extracted with DCM (3×). The combined organic layers were dried over MgSO$_4$, filtered and evaporated to give the title compound (145 mg). MS (ESI) mass calcd. for $C_{11}H_9NO_3$, 203.1; m/z found 204.1 [M+H]$^+$. $^1$H NMR (400 MHz, DMSO-d$_6$) δ 8.20 (s, 1H), 7.79-7.68 (m, 1H), 7.65-7.49 (m, 2H), 7.35 (s, 1H), 4.34 (s, 1H), 2.20 (s, 3H).

Intermediate A-32:
4-methyl-3-(2H-1,2,3-triazol-2-yl)picolinic acid

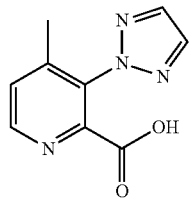

Step A: 4-methyl-3-(2H-1,2,3-triazol-2-yl)picolinonitrile. In a microwave vial was dissolved 2H-1,2,3-triazole (0.22 mL, 3.8 mmol) and CuI (26 mg) in DMF (4 mL). The reaction mixture was degassed with $N_2$ and 3-bromo-4-methylpicolonitrile (300 mg, 1.5 mmol) was added followed by trans-N,N'-dimethyl-1,2-cyclohexanediamine (41 µL, 0.3 mmol) and Cs$_2$CO$_3$ (844 mg, 2.6 mmol). The reaction mixture was heated at 120° C. for 1 h in a microwave reactor. Then H$_2$O was added and the mixture extracted with EtOAc. The combined organic layers were dried (MgSO$_4$). Purification via silica gel chromatography (0-50% EtOAc in heptane) gave the title compound (112 mg, 27%). MS (ESI) mass calcd. for $C_9H_7N_5$, 185.2; m/z found 186 [M+H]$^+$.

Step B: 4-methyl-3-(2H-1,2,3-triazol-2-yl)picolinic acid. Prepared analogous to Intermediate A-19 substituting 5-methyl-3-(2H-1,2,3-triazol-2-yl)picolinonitrile with the title compound of Step A. The reaction mixture was acidified to pH=4 before concentrating. MS (ESI) mass calcd. for $C_{11}H_9NO_3$, 203.1; m/z found 204.1 [M+H]$^+$.

Intermediate A-33:
3-(2H-1,2,3-triazol-2-yl)quinoline-2-carboxylic acid

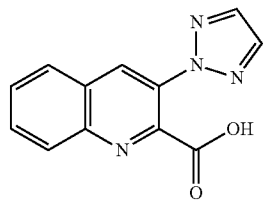 [SMILES: O=C(O)c1nc2ccccc2cc1-n1nccn1]

Step A: ethyl 3-(2H-1,2,3-triazol-2-yl)quinoline-2-carboxylate. Prepared analogous to Intermediate A-40 Step A substituting 2-bromo-4-methylbenzoic acid with ethyl 3-iodoquinoline-2-carboxylate (WO 2011093365) in <10% yield. MS (ESI) mass calcd. for $C_{14}H_{12}N_4O_2$, 268.3; m/z found 269.0 [M+H]$^+$.

Step B: 3-(2H-1,2,3-triazol-2-yl)quinoline-2-carboxylic acid. To the title compound of Step A (134 mg, 0.5 mmol) in MeOH (1 mL) was added aqueous 2M NaOH (1 mL). After 1 h at rt, the reaction was heated to 50° C. for 1 h, cooled to rt, acidified with 1N HCl, concentrated and used in subsequent steps without further purification. MS (ESI) mass calcd. for $C_{12}H_8N_4O_2$, 240.2; m/z found 241.0 [M+H]$^+$.

| Intermediate | Name | Structure | Reference |
| --- | --- | --- | --- |
| A-34 | 5-methyl-2-(pyrimidin-2-yl)benzoic acid | 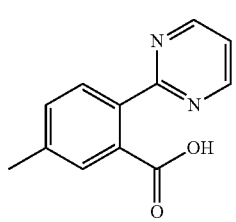 [SMILES: Cc1ccc(-c2ncccn2)c(C(=O)O)c1] | Prepared according to WO 2011/050198 Intermediate 50. |
| A-35 | 2-methyl-6-(pyrimidin-2-yl)benzoic acid | 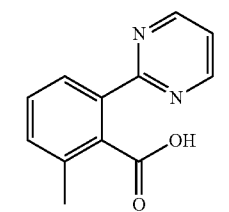 [SMILES: Cc1cccc(-c2ncccn2)c1C(=O)O] | Prepared according to intermediate A-34 or A-2 |

| Intermediate | Name | Structure | Reference |
|---|---|---|---|
| A-36 | 4-methyl-2-(pyrimidin-2-yl)benzoic acid | 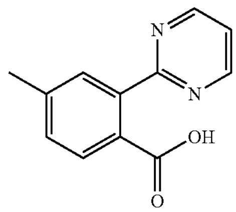 [SMILES: Cc1ccc(C(=O)O)c(-c2ncccn2)c1] | Prepared according to intermediate A-34 or A-2 |
| A-37 | 5-methyl-2-(2H-1,2,3-triazol-2-yl)benzoic acid | 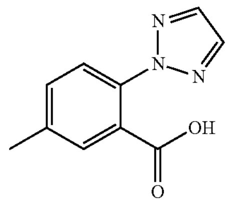 | Prepared according to WO 2011/050198 Intermediate 8. |
| A-38 | 5-chloro-2-(2H-1,2,3-triazol-2-yl)benzoic acid | 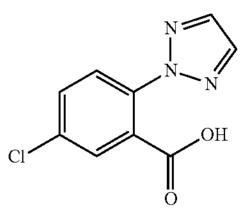 [SMILES: O=C(O)c1cc(Cl)ccc1-n1nccn1] | Prepared according to WO 2011/050198 Intermediate 9. |
| A-39 | 5-fluoro-2-(1H-pyrazol-5-yl)benzoic acid | 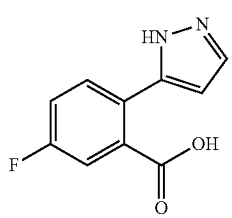 [SMILES: O=C(O)c1cc(F)ccc1-c1ccn[nH]1] | Prepared according to WO 2011/050198 Intermediate 51. |

Intermediate A-40: 4-methyl-2-(2H-1,2,3-triazol-2-yl)benzoic acid

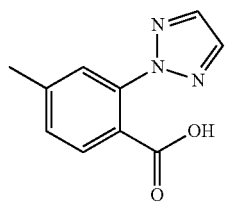

Step A: 4-methyl-2-(2H-1,2,3-triazol-2-yl)benzoic acid and 4-methyl-2-(1H-1,2,3-triazol-1-yl)benzoic acid. In a microwave vial was dissolved 2H-1,2,3-triazole (0.34 mL, 5.81 mmol) and CuI (40 mg, 0.21 mmol) in DMF (5 mL). The reaction mixture was degassed with $N_2$ for 10 minutes and 2-bromo-4-methylbenzoic acid (500 mg, 2.33 mmol) was added followed by trans-N,N'-dimethyl-1,2-cyclohexanediamine (62 μL, 0.40 mmol) and $Cs_2CO_3$ (1.29 g, 3.95 mmol). The reaction mixture was stirred at 100° C. for 20 minutes using a microwave oven before being partitioned between water, $HCl_{(aq)}$ (pH=3) and EtOAc. The organic layer was dried over $MgSO_4$, filtered and evaporated to give the crude product mixture which was used in the next step without any further purification.

Step B: methyl 4-methyl-2-(2H-1,2,3-triazol-2-yl)benzoate. To the title compound of step A (945 mg, 4.65 mmol) in DMF (28 mL) was added K2CO3 (1.3 g, 9.3 mmol) and iodomethane (0.3 mL, 4.7 mmol). The reaction mixture was stirred at room temperature for 16 h under $N_2$. The solvent was evaporated and the residue was dissolved with a saturated solution of $NaHCO_3$. The aqueous phase was extracted with DCM and the organic layer was dried over MgSO4, filtered and evaporated. The crude material was purified via silica gel chromatography (0% to 30% EtOAc/heptane) to afford the title compound (470 mg, 47%).

Step C: Prepared analogous to Intermediate A-31 step B substituting ethyl 3-methyl-2-(oxazol-2-yl)benzoate with the title compound of Step B and used without further purification in subsequent steps.

| Intermediate | Name | Structure | Reference |
|---|---|---|---|
| A-41 | 2-(3-methyl-1,2,4-oxadiazol-5-yl)benzoic acid | 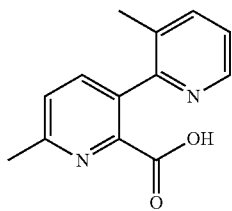 [SMILES: Cc1ccc(-c2ncccc2C)c(C(=O)O)n1] | Prepared analogous to intermediate A-17 |

Intermediate A-42: 3,6'-dimethyl-[2,3'-bipyridine]-2'-carboxylic acid

Step A: 3-bromo-6-methylpicolinic acid. To 3-bromo-6-methylpicolinonitrile (4 g, 20.3 mmol) in EtOH (40 mL) in a sealed tube was added aqueous 4M NaOH (15 mL). The reaction was heated at 90° C. for 24 h. Additional aqueous 4M NaOH was added and heating continued at 90° C. for 24 h. The reaction was cooled to rt, acidified to pH=3 with 1N HCl (aq), concentrated and used without further purification in subsequent steps. MS (ESI) mass calcd. for $C_7H_6BrNO_2$, 216.0; m/z found 218 $[M+H]^+$.

Step B: Methyl 3-bromo-6-methylpicolinate. To the title compound of step A (10.3 g, 20 mmol) in MeOH (50 mL) was added thionyl chloride (4.4 mL, 60 mmol). The reaction was heated at reflux overnight, cooled to rt and concentrated. Purification via silica gel chromatography (0-15% EtOAc in heptane) gave the title compound (1.9 g, 40%). MS (ESI) mass calcd. for $C_8H_8BrNO_2$, 230.1; m/z found 232 $[M+H]^+$.

Step C: 3-methyl-2-(tributylstannyl)pyridine. To 2-bromo-3-methylpyridine (1.3 mL, 11.7 mmol) in THF (35 mL) at −78° C. was added n-BuLi (2.5 M in hexanes, 5.6 mL, 14 mmol). After 30 min, tri-n-butyltin chloride (3.8 mL, 14 mmol) was added. After 1 h at −78° C., the reaction was allowed to warm to rt. EtOAc was added and the reaction mixture was washed with 10% aq KF. The organic layer was dried (MgSO4). Purification via silica gel chromatography (0-15% EtOAc in heptane) gave the title compound (1.2 g, 27%). MS (ESI) mass calcd. for $C_{18}H_{33}NSn$, 382.2; m/z found 384.0 $[M+H]^+$.

Step D: methyl 3,6'-dimethyl-[2,3'-bipyridine]-2'-carboxylate. To the title compound of step B (509 mg, 2.2 mmol) and the title compound of step C (1.1 g, 2.9 mmol) in PhCH3 (6.6 mL) was added Pd(PPh3)4 (225 mg, 0.2 mmol). The reaction was degassed with N2 and heated at 150° C. for 1.5 h using microwave reactor. The reaction was cooled to rt, diluted with H2O and extracted with EtOAc. The organic layer was dried (MgSO4). Purification via silica gel chromatography (0-100% EtOAc in heptane) gave the title compound (101 mg, 18%). MS (ESI) mass calcd. for $C_{14}H_{14}N_2O_2$, 242.3; m/z found 243 $[M+H]^+$.

Step E: 3,6'-dimethyl-[2,3'-bipyridine]-2'-carboxylic acid. Prepared analogous to intermediate A-33 step B substituting ethyl 3-(2H-1,2,3-triazol-2-yl)quinoline-2-carboxylate with the title compound of step D. MS (ESI) mass calcd. for $C_{13}H_{12}N_2O_2$, 228.2; m/z found 229 $[M+H]^+$.

Intermediate A-43: 6-methyl-3-(oxazol-2-yl)picolinic acid

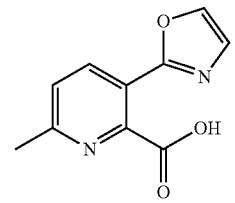

Prepared analogous to Intermediate A-31 substituting ethyl 2-iodo-3-methylbenzoate with methyl 3-iodo-6-methylpicolinate. MS (ESI) mass calcd. for $C_{10}H_8N_2O_3$, 204.2; m/z found 161 $[M-CO2]^+$.

| Intermediate | Name | Structure | Reference |
|---|---|---|---|
| A-44 | 6-methyl-3-(3-methyl-1,2,4-oxadiazol-5-yl)picolinic acid | 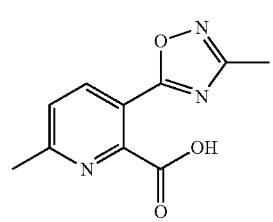 | WO 2010/063663 Description 64 |

-continued

| Intermediate | Name | Structure | Reference |
|---|---|---|---|
| A-45 | 6-methyl-3-(3-methyl-1H-pyrazol-1-yl)picolinic acid | 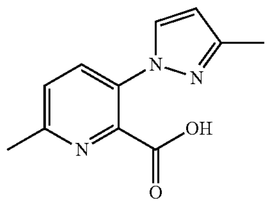 | WO 2010/063663 Description 71 |
| A-46 | 6-methyl-3-(4-methyl-1H-pyrazol-1-yl)picolinic acid | 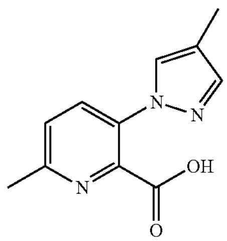 [SMILES: Cc1cnn(-c2ccc(C)nc2C(=O)O)c1] | WO 2010/063663 |
| A-47 | 6-methyl-3-(1H-pyrazol-1-yl)picolinic acid | 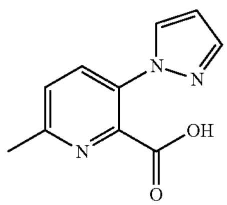 | WO 2010/063663 Description 73 |
| A-48 | 6-methyl-3-(3-methylisoxazol-5-yl)picolinic acid | 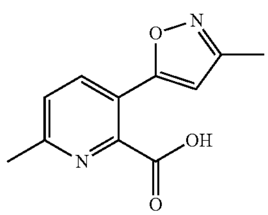 | WO 2010/063663 Description 117 |
| A-49 | 1-methyl-3-phenyl-1H-pyrazole-4-carboxylic acid | 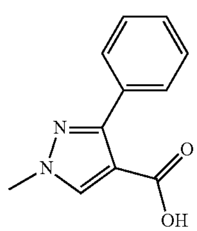 | Purchased |
| A-50 | 1-methyl-4-phenyl-1H-pyrazole-5-carboxylic acid | 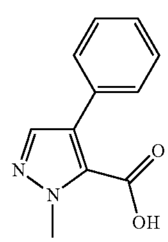 | Purchased |
| A-51 | 1-methyl-5-phenyl-1H-pyrazole-5-carboxylic acid | 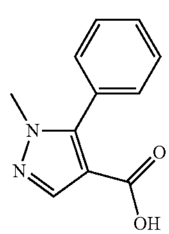 | Purchased |

-continued

| Intermediate | Name | Structure | Reference |
|---|---|---|---|
| A-52 | 5-chloro-3-(2H-1,2,3-triazol-2-yl)picolinic acid | 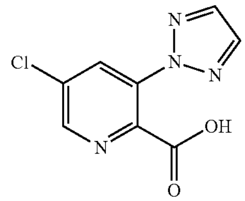 [SMILES: O=C(O)c1ncc(Cl)cc1-n1nccn1] | WO 2012/145581 Intermediate 105 |
| A-53 | 5-methoxy-3-(2H-1,2,3-triazol-2-yl)picolinic acid | 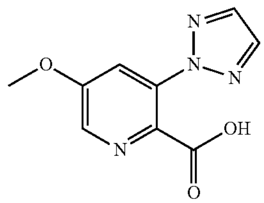 [SMILES: COc1cnc(C(=O)O)c(-n2nccn2)c1] | WO 2012/145581 Intermediate 105 |
| A-54 | 6-methyl-3-(4-methyloxazol-2-yl)picolinic acid | 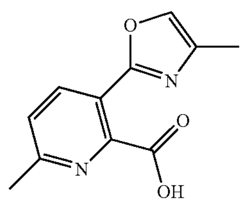 | |

Intermediate B-1: (±)-7-(tert-butoxycarbonyl)-7-azabicyclo[2.2.1]heptane-2-carboxylic acid

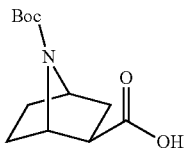 [SMILES: CC(C)(C)OC(=O)N1C2CCC1C(C(=O)O)C2]

Prepared as described in as in WO 2004/074 292 A1. $^1$H NMR (CDCl3): 4.54 (d, J=4.6 Hz, 1H), 4.33-4.24 (m, 1H), 2.61-2.18 (m, 4H), 1.90-1.71 (m, 2H), 1.68-1.57 (m, 1H), 1.56-1.35 (m, 10H).

Intermediates (+)-B-2 and (−)-B-2: (1S,2R,4R)-2-benzyl 7-tert-butyl 7-azabicyclo[2.2.1]heptane-2,7-dicarboxylate

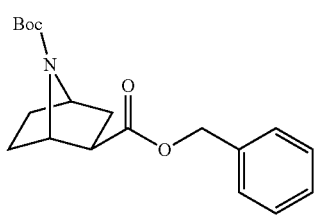 [SMILES: CC(C)(C)OC(=O)N1C2CCC1C(C(=O)OCc1ccccc1)C2]

And (1R,2S,4S)-2-benzyl 7-tert-butyl-7-azabicyclo[2.2.1]heptane-2,7-dicarboxylate

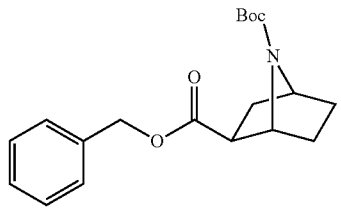 [SMILES: CC(C)(C)OC(=O)N1C2CCC1C(C(=O)OCc1ccccc1)C2]

The title compounds were obtained by chiral SFC (CHIRALPAK IC 5 μM 250×20 mm) resolution of Intermediate B-3 (17 g) using 80% CO$_2$/20% iPrOH as the mobile phase to give (−)-B-3 enantiomer A (7.5 g, 1st eluting enantiomer) and enantiomer (+)-B3 (7.3 g, 2$^{nd}$ eluting enantiomer).

Intermediate (−)-B-2: (−)-2-benzyl 7-tert-butyl-7-azabicyclo[2.2.1]heptane-2,7-dicarboxylate. Enantiomer A, $[\alpha]^D_{25}$−25.2 (c 2.8, CHCl$_3$).

Intermediate (+)-B-2: (+)-2-benzyl 7-tert-butyl-7-azabicyclo[2.2.1]heptane-2,7-dicarboxylate. Enantiomer B, $[\alpha]^D_{25}$+25.0 (c 2.8, CHCl$_3$). $^1$H NMR (CDCl$_3$): 7.39-7.30 (m, 5H), 5.19-5.08 (m, 2H), 4.55 (s, 1H), 4.30 (s, 1H), 2.59 (dd, J=8.9, 5.0 Hz, 1H), 2.36-2.24 (m, 1H), 1.90-1.70 (m, 2H), 1.68-1.57 (m, 1H), 1.52-1.34 (m, 11H).

Intermediate B-3: (1S,2R,4R)-7-(tert-butoxycarbonyl)-7-azabicyclo[2.2.1]heptane-2-carboxylic acid

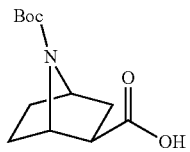 [SMILES: CC(C)(C)OC(=O)N1C2CCC1C(C(=O)O)C2]

To intermediate (+)-B-2 (3.5 g, 10.6 mmol) in EtOH (100 mL) was added 10 wt % Pd/C wet Degussa (750 mg). The reaction was purged with $N_2$ followed by $H_2$, then allowed to proceed under an atmosphere of $H_2$ (balloon). Upon completion, the reaction was filtered and concentrated to give the title compound (2.4 g, 94%) that was used without further purification. $^1$H NMR (CDCl$_3$): 4.62-4.52 (m, 1H), 4.35-4.26 (m, 1H), 2.59 (ddd, J=8.9, 5.0, 1.5 Hz, 1H), 2.29-2.19 (m, 1H), 1.91-1.71 (m, 2H), 1.68-1.58 (m, 1H), 1.54-1.35 (m, 11H).

Intermediate B-4: (1S,2R,4R)-tert-butyl 2-(((benzyloxy)carbonyl)amino)-7-azabicyclo[2.2.1]heptane-7-carboxylate

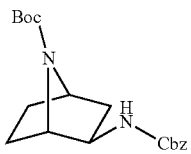 [SMILES: CC(C)(C)OC(=O)N1C2CCC1C(NC(=O)OCc1ccccc1)C2]

To intermediate B-3 (2.4 g, 9.9 mmol) in PhCH$_3$ (32 mL) was added TEA (1.5 mL, 10.9 mmol). After heating in an oil bath to 70° C., DPPA (2.4 mL, 10.9 mmol) in PhCH$_3$ (3 mL) was added. After 1 h, BnOH (1.0 g, 9.5 mmol) was added and the oil bath temperature increased to 90° C. After an additional 18 h, the reaction was cooled to rt, diluted with EtOAc and washed with saturated NaHCO$_3$ (aq). The aqueous layer was extracted with EtOAc (1×). The combined organics were washed with brine and dried (Na$_2$SO$_4$). Purification via silica gel chromatography (10-50% EtOAc in hexanes) gave the title compound (2.8 g, 78%). $^1$H NMR (CDCl$_3$): 7.39-7.28 (m, 5H), 5.20-4.84 (m, 3H), 4.30-4.06 (m, 3H), 3.86-3.68 (m, 1H), 1.93 (dd, J=13.4, 8.1 Hz, 1H), 1.85-1.63 (m, 2H), 1.54-1.29 (m, 11H).

Intermediate B-5: (+)-(1S,2R,4R)-tert-butyl 2-amino-7-azabicyclo[2.2.1]heptane-7-carboxylate

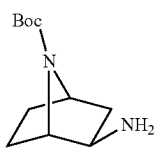

To intermediate B-4 (400 mg, 1.2 mmol) in EtOH (5 mL) was added 10 wt % Pd/C wet Degussa (85 mg). The reaction was purged with $N_2$ followed by $H_2$, then allowed to proceed under an atmosphere of $H_2$ (balloon). Upon completion, the reaction was filtered and concentrated to give the title compound (244 mg, 99%) that was used without further purification. MS (ESI) mass calcd. for $C_{11}H_{20}N_2O_2$, 212.1; m/z found 213.1 [M+H]$^+$. [α]$^D_{25}$+9.8 (c 4.9, CHCl$_3$) $^1$H NMR (CDCl3): 4.25-4.13 (m, 1H), 3.94-3.82 (m, 1H), 2.96 (dd, J=7.8, 3.0 Hz. 1H), 1.85-1.25 (m, 15H).

Intermediate B-6: (±)-tert-butyl 2-amino-7-azabicyclo[2.2.1]heptane-7-carboxylate

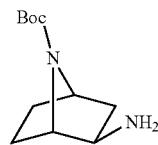 [SMILES: CC(C)(C)OC(=O)N1C2CCC1C(N)C2]

Prepared analogous to intermediate B-5 substituting intermediate B-4 with (±)-7-(tert-butoxycarbonyl)-7-azabicyclo[2.2.1]heptane-2-carboxylic acid (intermediate B-1).

Intermediate B-7: (±)-tert-butyl 2-amino-7-azabicyclo[2.2.1]heptane-7-carboxylate

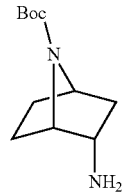

Intermediate B-8: (−)-(1R,2S,4S)-tert-butyl 2-amino-7-azabicyclo[2.2.1]heptane-7-carboxylate

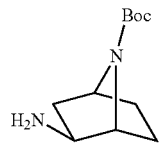 [SMILES: CC(C)(C)OC(=O)N1C2CCC1C(N)C2]

Prepared analogous to intermediate B-5 substituting enantiomer (1S,2R,4R)-2-benzyl 7-tert-butyl 7-azabicyclo[2.2.1]heptane-2,7-dicarboxylate (intermediate (+)-B-2) with enantiomer (1R,2S,4S)-2-benzyl 7-tert-butyl-7-azabicyclo[2.2.1]heptane-2,7-dicarboxylate (intermediate (−)-B-2).

Intermediate B-9: (1S,2R,4R)-tert-butyl 2-(hydroxymethyl)-7-azabicyclo[2.2.1]heptane-7-carboxylate

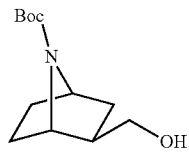 [SMILES: CC(C)(C)OC(=O)N1C2CCC1C(CO)C2]

To intermediate (+)-B-2 (504 mg, 1.5 mmol) in THF (12 mL) at 0° C. was added Dibal-H (1M in THF, 4.6 mL). After 1 h, additional Dibal-H was added. The reaction allowed to warm to rt and quenched with Rochelle's Salt (20 wt %). EtOAc was added and the mixture allowed to stir until 2 clear layers had formed. The aqueous layer was extracted with EtOAc (2×). The combined organics were washed with brine and dried ($Na_2SO_4$). Purification via silica gel chromatography (10-50% EtOAc in hexanes) gave the title compound (171 mg, 49%). MS (ESI) mass calcd. for $C_{12}H_{21}NO_3$, 227.2; m/z found 228.2 [M+H]$^+$, 172.2 [M−55]$^+$. $^1$H NMR (CDCl3): 4.26-4.12 (m, 2H), 3.45-3.32 (m, 2H), 3.00-2.04 (m, 1H). 1.95-1.90 (m, 1H), 1.83-1.73 (m, 2H), 1.53-1.37 (m, 12H), 1.32-1.28 (m, 1H).

Intermediate B-10: (±)-tert-butyl 2-(hydroxymethyl)-7-azabicyclo[2.2.1]heptane-7-carboxylate

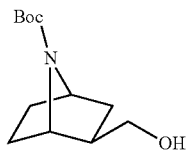 [SMILES: CC(C)(C)OC(=O)N1C2CCC1C(CO)C2]

As in Org. Syn., 1997, 74, 212, Tet. Lett. 1997, 38, 6829 and Biorg. Med. Chem. Lett. 2006, 14, 8219 $^1$H NMR (CDCl$_3$): 4.25-4.13 (m, 2H), 3.47-3.32 (m, 2H), 1.98-1.68 (m, 4H), 1.56-1.26 (m, 13H).

Example 1: (5-fluoro-2-(pyrimidin-2-yl)phenyl)((1S,2R,4R)-2-((pyridin-2-yloxy)methyl)-7-azabicyclo[2.2.1]heptan-7-yl)methanone

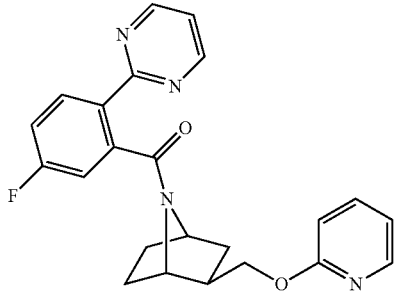 [SMILES: O=C(c1cc(F)ccc1-c1ncccn1)N1C2CCC1C(COc1ccccn1)C2]

Step A: (1S,2R,4R)-tert-butyl 2-((pyridin-2-yloxy)methyl)-7-azabicyclo[2.2.1]heptane-7-carboxylate. To intermediate B-9 (170 mg, 0.75 mmol) in DMF (3 mL) at 0° C. was added NaH (36 mg, 60 wt % in mineral oil, 0.9 mmol). After 30 min, 2-fluoropyridine (102 mg, 1.0 mmol) in DMF (0.5 mL) was added dropwise and the 0° C. ice bath was removed. The flask was then heated to 90° C. in an oil bath. After 2 h, ½ saturated NH$_4$Cl was added and the reaction extracted with EtOAc (2×). The combined organics were washed with brine and dried (Na$_2$SO$_4$). Purification via silica gel chromatography (5-30% EtOAc in hexanes) gave the title compound (172 mg, 76%) as a white solid. MS (ESI) mass calcd. for $C_{17}H_{24}N_2O_3$, 304.2; m/z found 305.1 [M+H]$^+$. $^1$H NMR (CDCl$_3$): 8.13 (dd, J=5.1, 2.0 Hz, 1H), 7.55 (ddd, J=8.7, 7.1, 2.0 Hz, 1H), 6.84 (dd, J=7.0, 5.0 Hz, 1H), 6.73 (d, J=8.3 Hz, 1H), 4.35-4.15 (m, 2H), 4.15-3.99 (m, 2H), 2.26-2.14 (m, 1H), 1.90-1.68 (m, 2H), 1.64-1.55 (m, 1H), 1.54-1.31 (m, 12H).

Step B: (1S,2R,4R)-tert-butyl 2-((pyridin-2-yloxy) methyl)-7-azabicyclo[2.2.1]heptane-7-carboxylate. To the title compound from Step A (130 mg, 0.4 mmol) in EtOAc was added 4M HCl in dioxane. After 3 h, the reaction was concentrated, neutralized with 5% Na$_2$CO$_3$ and extracted with DCM. The combined organics were dried (Na$_2$SO$_4$) to give the title compound from step B as a white solid that was used without further purification. MS (ESI) mass calcd. for $C_{12}H_{16}N_2O$, 204.1; m/z found 205.1 [M+H]$^+$.

Step C: (5-fluoro-2-(pyrimidin-2-yl)phenyl)((1S,2R,4R)-2-((pyridin-2-yloxy)methyl)-7-azabicyclo[2.2.1]heptan-7-yl)methanone. To the title compound of Step B (50 mg, 0.18 mmol) in DMF (1.4 mL) was added DIPEA (0.078 mL, 0.45 mmol), intermediate A-7 (43 mg, 0.2 mmol) and HATU (75 mg, 0.2 mmol). Upon completion of the reaction, purification was performed using Agilent prep method A to give the title compound. MS (ESI) mass calcd. for $C_{23}H_{21}FN_4O_2$, 404.2; m/z found 405.2 [M+H]$^+$. $^1$H NMR (CDCl$_3$): 8.78 (d, J=4.9 Hz, 1H), 8.71 (d, J=4.8 Hz, 1H), 8.26-8.21 (m, 2H), 7.60-7.50 (m, 1H), 7.23-7.00 (m, 3H), 6.90-6.82 (m, 1H), 6.78-6.71 (m, 0.5H), 6.59-6.51 (m, 0.5H), 4.88-4.78 (m, 1H), 4.26-4.09 (m, 1H), 4.09-3.95 (m, 1H), 3.92-3.79 (m, 1H), 2.39-2.18 (m, 1H), 2.04-1.86 (m, 1H), 1.81-1.31 (m, 5H).

Example 2: (±)-(6-methyl-3-(pyrimidin-2-yl)pyridin-2-yl)(2-((pyridin-2-yloxy)methyl)-7-azabicyclo[2.2.1]heptan-7-yl)methanone

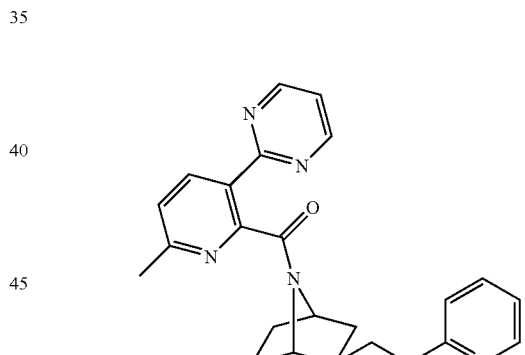

Prepared analogous to Example 1 substituting intermediate B-9 with intermediate B-10, 5-fluoro-2-(pyrimidin-2-yl) benzoic acid with intermediate A-9 and HATU with HBTU to give the title compound. MS (ESI) mass calcd. for $C_{23}H_{23}N_5O_2$, 401.2; m/z found 402.2 [M+H]$^+$. $^1$H NMR (DMSO-D$_6$): 8.92 (d, J=4.9 Hz, 1H), 8.84 (d, J=4.9 Hz, 1H), 8.32 (t, J=8.3 Hz, 1H), 8.24 (dd, J=5.0, 1.4 Hz, 0.5H), 8.15 (dd, J=5.0, 1.5 Hz, 0.5H), 7.76-7.69 (m, 0.5H), 7.69-7.62 (m, 0.5H), 7.52-7.42 (m, 1.5H), 7.34 (d, J=8.1 Hz, 0.5H), 7.05-6.92 (m, 1H), 6.87 (d, J=8.3 Hz, 0.5H), 6.68 (d, J=8.3 Hz, 0.5H), 4.60-4.56 (m, 1H), 4.19 (td, J=10.3, 3.7 Hz, 1H), 4.06 (dt, J=10.4, 5.3 Hz, 1H), 3.86 (t, J=4.0 Hz, 0.5H), 3.77 (d, J=4.1 Hz, 0.5H), 2.56 (s, 1.5H), 2.39-2.15 (m, 1H), 2.06 (s, 1.5H), 1.88-1.33 (m, 6H).

Example 3A: (6-methyl-3-(pyrimidin-2-yl)pyridin-2-yl)((1S*,2R*,4R*)-2-((pyridin-2-yloxy)methyl)-7-azabicyclo[2.2.1]heptan-7-yl)methanone

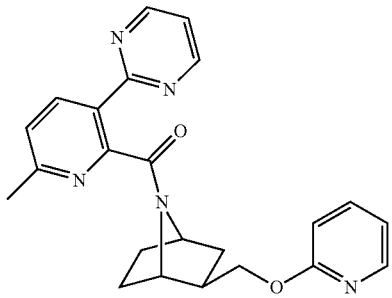 [SMILES: Cc1ccc(-c2ncccn2)c(C(=O)N2C3CCC2C(COc2ccccn2)C3)n1]

And Example 3B: (6-methyl-3-(pyrimidin-2-yl)pyridin-2-yl)((1R*,2S*,4S*)-2-((pyridin-2-yloxy)methyl)-7-azabicyclo[2.2.1]heptan-7-yl)methanone

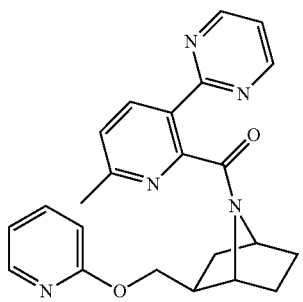 [SMILES: Cc1ccc(-c2ncccn2)c(C(=O)N2C3CCC2C(COc2ccccn2)C3)n1]

The title compounds were obtained by chiral SFC (CHIRALPAK AD-H 5 μM 250×20 mm) resolution of Example 2 (538 mg) using 70% CO$_2$/30% EtOH as the mobile phase to give enantiomer A (230 mg, 1st eluting enantiomer) and enantiomer B (226 mg, 2$^{nd}$ eluting enantiomer). The enantiomeric purity was confirmed by analytical SFC using a CHIRALPAK AD (250×4.6 mm) and a mobile phase of 70% CO$_2$, 30% EtOH containing 0.3% iPrNH$_2$ over 7 minutes. (Example 3A: >98% single enantiomer, 4.00 min retention time; Example 3B>98% single enantiomer, 5.12 min retention time). Example 3A: MS (ESI) mass calcd. for C$_{23}$H$_{23}$N$_5$O$_2$, 401.2; m/z found 402.1 [M+H]$^+$. $^1$H NMR (CDCl$_3$): 8.83 (d, J=4.8 Hz, 0.8H), 8.72 (d, J=4.8 Hz, 1.2H), 8.43-8.37 (m, 1H), 8.19-8.09 (m, 1H), 7.59-7.48 (m, 1H), 7.28 (d, J=8.0 Hz, 0.4H), 7.19-7.16 (m, 1.6H), 6.88-6.81 (m, 1H), 6.76 (dt, J=8.4, 1.0 Hz, 0.4H), 6.57 (dt, J=8.3, 0.9 Hz, 0.6H), 4.92-4.84 (m, 1H), 4.38-4.23 (m, 1H), 4.17 (ddd, J=15.4, 10.3, 5.7 Hz, 1H), 3.97-3.87 (m, 1H), 2.62 (s, 1H), 2.39-2.18 (m, 2.5H), 2.11-1.81 (m, 2H), 1.74 (dd, J=12.3, 8.6 Hz, 0.5H), 1.68-1.36 (m, 4H).

Example 3B: MS (ESI) mass calcd. for C$_{23}$H$_{23}$N$_5$O$_2$, 401.2; m/z found 402.1 [M+H]$^+$.

Example 4: (±)-(6-methyl-3-(2H-1,2,3-triazol-2-yl)pyridin-2-yl)(2-((pyridin-2-yloxy)methyl)-7-azabicyclo[2.2.1]heptan-7-yl)methanone

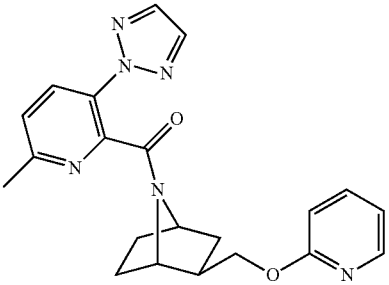 [SMILES: Cc1ccc(-n2nccn2)c(C(=O)N2C3CCC2C(COc2ccccn2)C3)n1]

Prepared analogous to Example 1 substituting intermediate B-9 with intermediate B-10, intermediate A-7 with intermediate A-21 and HATU with HBTU to give the title compound. MS (ESI) mass calcd. for C$_{21}$H$_{22}$N$_6$O$_2$, 390.2; m/z found 391.2 [M+H]$^+$. $^1$H NMR (500 MHz, CDCl$_3$): 8.20-8.07 (m, 2H), 7.84-7.75 (m, 2H), 7.61-7.49 (m, 1H), 7.31 (d, J=8.4 Hz, 0.4H), 7.19 (d, J=8.4 Hz, 0.6H), 6.87-6.83 (m, 1H), 6.76 (dt, J=8.4, 0.9 Hz, 0.4H), 6.57 (dt, J=8.3, 0.9 Hz, 0.6H), 4.91-4.81 (m, 1H), 4.32-4.07 (m, 2H), 3.96-3.84 (m, 1H), 2.62 (s, 1.2H), 2.40-2.17 (m, 2.8H), 2.13-1.94 (m, 1H), 1.94-1.68 (m, 1.8H), 1.68-1.37 (m, 3.2H).

Example 5A: (6-methyl-3-(2H-1,2,3-triazol-2-yl)pyridin-2-yl)((1S,2R,4R)-2-((pyridin-2-yloxy)methyl)-7-azabicyclo[2.2.1]heptan-7-yl)methanone

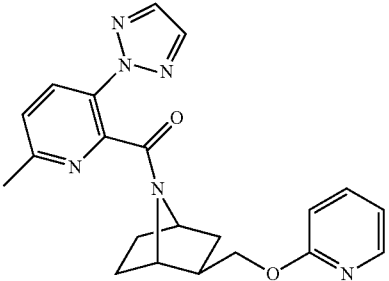 [SMILES: Cc1ccc(-n2nccn2)c(C(=O)N2C3CCC2C(COc2ccccn2)C3)n1]

And Example 5B: (6-methyl-3-(2H-1,2,3-triazol-2-yl)pyridin-2-yl)((1R,2S,4S)-2-((pyridin-2-yloxy)methyl)-7-azabicyclo[2.2.1]heptan-7-yl)methanone

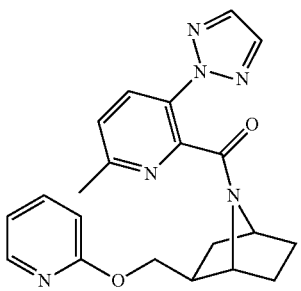 [SMILES: Cc1ccc(-n2nccn2)c(C(=O)N2C3CCC2C(COc2ccccn2)C3)n1]

The title compounds were obtained by chiral SFC (CHIRALPAK AD-H 5 μM 250×20 mm) resolution of Example 4 (555 mg) using 70% CO$_2$/30% EtOH as the mobile phase to give enantiomer A (264 mg, 1st eluting enantiomer) and enantiomer B (248 mg, 2$^{nd}$ eluting enantiomer). The enantiomeric purity was confirmed by analytical SFC using a CHIRALPAK AD (250×4.6 mm) and a mobile phase of 70% CO$_2$, 30% EtOH containing 0.3% iPrNH$_2$ over 7 minutes. (Example 5A: >98% single enantiomer, 2.80 min retention time; Example 5B>98% single enantiomer, 3.90 min retention time). Example 5A: MS (ESI) mass calcd. for C$_{21}$H$_{22}$N$_6$O$_2$, 390.2; m/z found 391.2 [M+H]$^+$. Example 5B: MS (ESI) mass calcd. for C$_{21}$H$_{22}$N$_6$O$_2$, 390.2; m/z found 391.2 [M+H]$^+$.

Example 6: (6-methyl-3-(2H-1,2,3-triazol-2-yl)pyridin-2-yl)((1S,2R,4R)-2-((pyridin-2-yloxy)methyl)-7-azabicyclo[2.2.1]heptan-7-yl)methanone

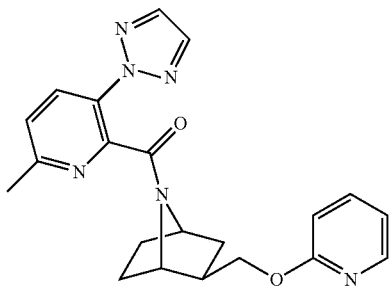 [SMILES: Cc1ccc(-n2nccn2)c(C(=O)N2C3CCC2C(COc2ccccn2)C3)n1]

Prepared analogous to Example 1 substituting intermediate A-7 with intermediate A-21. MS (ESI) mass calcd. for C$_{21}$H$_{22}$N$_6$O$_2$, 390.2; m/z found 391.2 [M+H]$^+$. [α]$_D^{20}$+ 11.4° (c 0.88, CHCl$_3$). $^1$H NMR (CDCl$_3$): 8.19-8.06 (m, 2H), 7.83-7.73 (m, 2H), 7.61-7.48 (m, 1H), 7.30 (d, J=8.4 Hz, 0.4H), 7.19 (d, J=8.4 Hz, 0.6H), 6.89-6.81 (m, 1H), 6.78-6.73 (m, 0.4H), 6.61-6.52 (m, 0.6H), 4.91-4.81 (m, 1H), 4.32-4.08 (m, 2H), 3.96-3.84 (m, 1H), 2.62 (s, 1.2H), 2.39-2.18 (m, 2.8H), 2.11-1.94 (m, 1.5H), 1.94-1.37 (m, 4.5H).

Example 7: (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone

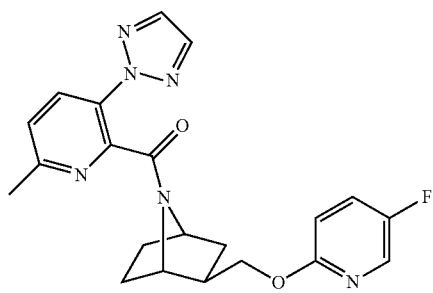 [SMILES: Cc1ccc(-n2nccn2)c(C(=O)N2C3CCC2C(COc2ccc(F)cn2)C3)c1]

Step A Method A: (±)-tert-butyl 2-(((5-fluoropyridin-2-yl)oxy)methyl)-7-azabicyclo[2.2.1]heptane-7-carboxylate. Tri-n-butylphosphine (1.8 mL, 7.8 mmol) was added to intermediate B-10 (830 mg, 3.7 mmol) and 5-fluoropyridin-2(1H)-one (500 mg, 4.4 mmol) in THF (11 mL) under nitrogen bubbling at rt. After 5 min of stirring, DEAD (1.4 mL, 7.1 mmol) was added and the mixture was stirred at 50° C. for 18 hours. The mixture was concentrated and purified silica gel chromatography (0-15% EtOAc in Heptane) to give the title compound of step A (590 mg, 45%) as a white solid.

Step A Method B: (±)-tert-butyl 2-(((5-fluoropyridin-2-yl)oxy)methyl)-7-azabicyclo[2.2.1]heptane-7-carboxylate. Prepared analogous to intermediate B-6 substituting intermediate B-9 with (±)-B-9 and 2-fluropyridine with 2,5-difluoropyridine. MS (ESI) mass calcd. for C$_{17}$H$_{23}$FN$_2$O$_3$, 322.2; m/z found 323.0 [M+H]$^+$. $^1$H NMR (CDCl$_3$): 8.02-7.87 (m, 1H), 7.41-7.27 (m, 1H), 6.70 (dd, J=9.1, 3.6 Hz, 1H), 4.39-4.10 (m, 2H), 4.09-3.89 (m, 2H), 2.25-2.09 (m, 1H), 1.91-1.26 (m, 15H).

Step B: (±)-2-(((5-fluoropyridin-2-yl)oxy)methyl)-7-azabicyclo[2.2.1]heptane. Prepared analogous to Example 1 substituting (±)-tert-butyl-2-((pyridin-2-yloxy)methyl)-7-azabicyclo[2.2.1]heptane-7-carboxylate with the title compound from Step A. $^1$H NMR (CDCl$_3$): 7.96 (d, J=3.1 Hz, 1H), 7.33 (ddd, J=9.0, 7.6, 3.1 Hz, 1H), 6.70 (dd, J=9.0, 3.6 Hz, 1H), 4.09-3.98 (m, 2H), 3.72-3.56 (m, 2H), 2.22-1.99 (m, 3H), 1.72-1.53 (m, 3H), 1.49-1.34 (m, 1H).

Step C: (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone. Prepared analogous to Example 1 substituting 5-fluoro-2-(pyrimidin-2-yl)benzoic acid with 6-methyl-3-(2H-1,2,3-triazol-2-yl)picolinic acid. MS (ESI) mass calcd. for C$_{21}$H$_{21}$FN$_6$O$_2$, 408.2; m/z found 409.2.

Example 8A: ((1S,2R,4R)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone

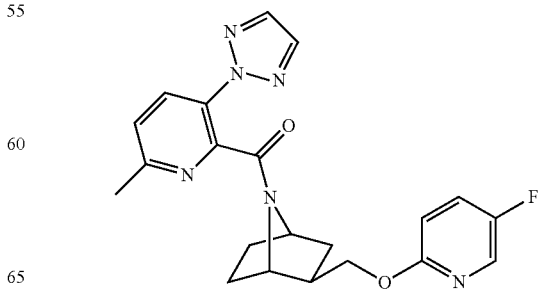

And Example 8B: ((1R,2S,4S)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone

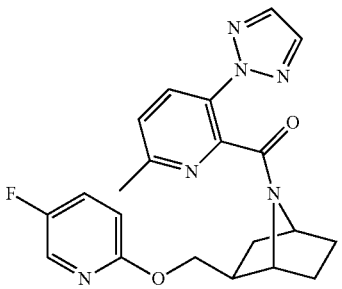

The title compounds were obtained by chiral SFC (CHIRALPAK AD-H 5 µM 250×20 mm) resolution of Example 7 (259 mg) using 70% CO$_2$/30% mixture of EtOH/i-PrOH (50/50 v/v) as the mobile phase to give enantiomer A (72 mg, 1st eluting enantiomer) and enantiomer B (84 mg, 2$^{nd}$ eluting enantiomer). The enantiomeric purity was confirmed by analytical SFC using a CHIRALPAK AD-H (250×4.6 mm) and a mobile phase of 70% CO$_2$, 15% EtOH, 15% iPrOH containing 0.3% iPrNH$_2$ over 7 minutes. (Example 8A: 100% single enantiomer, 3.10 min retention time; Example 8B 100% single enantiomer, 4.58 min retention time). Example 8A: MS (ESI) mass calcd. for C$_{21}$H$_{21}$FN$_6$O$_2$, 408.2; m/z found 409.2 [M+H]$^+$. Example 8B: MS (ESI) mass calcd. for C$_{21}$H$_{21}$FN$_6$O$_2$, 408.2; m/z found 409.2 [M+H]$^+$.

Example 9: (±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone

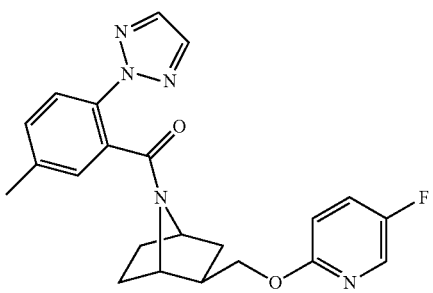 [SMILES: Cc1ccc(-n2nccn2)c(C(=O)N2C3CCC2C(COc2ccc(F)cn2)C3)c1]

Prepared analogous to Example 7 substituting intermediate A-21 with intermediate A-37. MS (ESI) mass calcd. for C$_{22}$H$_{22}$FN$_5$O$_2$, 407.2; m/z found 408.3 [M+H]$^+$. $^1$H NMR (CDCl$_3$): 8.03-7.95 (m, 1H), 7.81-7.70 (m, 3H), 7.38-7.11 (m, 3H), 6.72 (dd, J=9.0, 3.6 Hz, 0.5H), 6.52 (dd, J=9.0, 3.5 Hz, 0.5H), 4.86-4.74 (m, 1H), 4.15-3.68 (m, 3H), 2.46-2.37 (s, 1.6H), 2.32-1.78 (m, 4.4H), 1.72-1.22 (m, 4H).

Example 10A: ((1S,2R,4R)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone

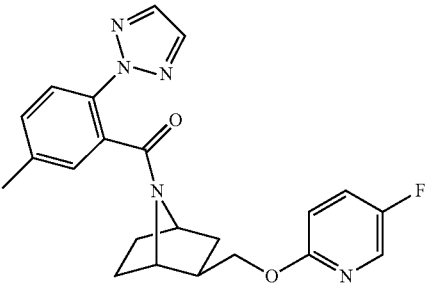

And Example 10B: ((1R,2S,4S)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone

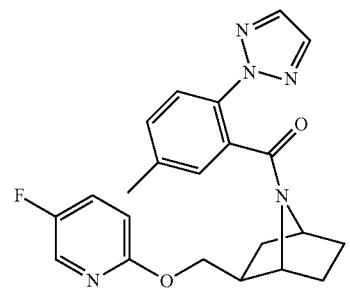 [SMILES: Cc1ccc(-n2nccn2)c(C(=O)N2C3CCC2C(COc2ccc(F)cn2)C3)c1]

The title compounds were obtained by chiral SFC (CHIRALPAK AD-H 5 µM 250×20 mm) resolution of Example 9 (290 mg) using 60% CO$_2$/40% i-PrOH as the mobile phase to give enantiomer A (140 mg, 1st eluting enantiomer) and enantiomer B (134 mg, 2$^{nd}$ eluting enantiomer). The enantiomeric purity was confirmed by analytical SFC using a CHIRALPAK AD-H (250×4.6 mm) and a mobile phase of 60% CO$_2$, 40% iPrOH containing 0.3% iPrNH$_2$ over 7 minutes. (Example 10A: >98% single enantiomer, 2.42 min retention time; Example 10B>98% single enantiomer, 3.20 min retention time).

Example 11: (±)-(2-(((5-fluoropyridin-2-yl)oxy)methyl)-7-azabicyclo[2.2.1]heptan-7-yl)(2-(thiophen-2-yl)phenyl)methanone

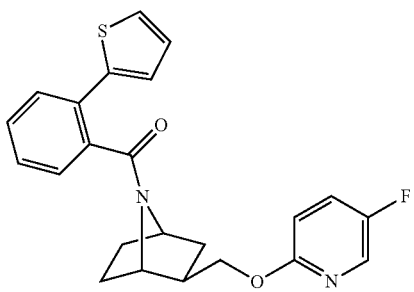 [SMILES: O=C(c1ccccc1-c1cccs1)N1C2CCC1C(COc1ccc(F)cn1)C2]

To (±)-2-(((5-fluoropyridin-2-yl)oxy)methyl)-7-azabicyclo[2.2.1]heptane (35 mg, 0.2 mmol) in DCM (2.5 mL) was added TEA (25 μL, 0.2 mmol)) followed by 2-(thiophen-2-yl)benzoyl chloride (40 mg, 0.2 mmol) in DCM (2.5 mL). After 18 h, the reaction was diluted with DCM and washed with H$_2$O. The aqueous layer was extracted DCM (1×). The combined organics were dried (Na$_2$SO$_4$). Purification via silica gel chromatography (50-100% EtOAc in hexanes) gave the title compound (37 mg, 57%). MS (ESI) mass calcd. for C$_{23}$H$_{21}$FN$_2$O$_2$S, 408.1; m/z found 409.1 [M+H]$^+$.

Example 12A: ((1S*,2R*,4R*)-2-(((5-fluoropyridin-2-yl)oxy)methyl)-7-azabicyclo[2.2.1]heptan-7-yl)(2-(thiophen-2-yl)phenyl)methanone

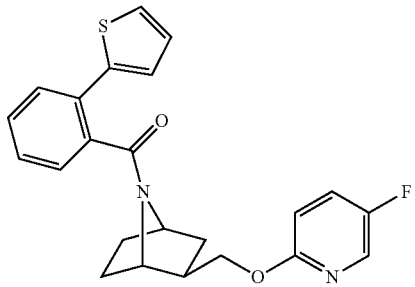 [SMILES: O=C(c1ccccc1-c1cccs1)N1C2CCC1C(COc1ccc(F)cn1)C2]

And Example 12B: ((1R*,2S*,4S*)-2-(((5-fluoropyridin-2-yl)oxy)methyl)-7-azabicyclo[2.2.1]heptan-7-yl)(2-(thiophen-2-yl)phenyl)methanone

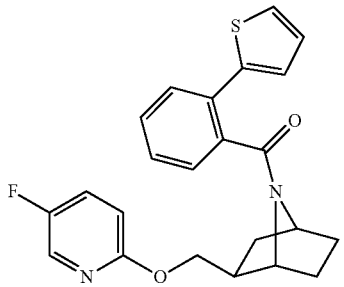 [SMILES: O=C(c1ccccc1-c1cccs1)N1C2CCC1C(COc1ccc(F)cn1)C2]

The title compounds were obtained by chiral SFC (CHIRALPAK AS-H 5 μM 250×20 mm at 40° C.) resolution of Example 11 using 4.2 mL/min MeOH with 0.2% TEA, 37 mL/min CO$_2$ as the mobile phase to give enantiomer A (1st eluting enantiomer) and enantiomer B (2$^{nd}$ eluting enantiomer).

Example 12A: MS (ESI) mass calcd. for C$_{23}$H$_{21}$FN$_2$O$_2$S, 408.2; m/z found 409.2 [M+H]$^+$. $^1$H NMR (CDCl$_3$): 7.97 (dd, J=11.0, 3.0 Hz, 1H), 7.54-7.20 (m, 6.5H), 7.01 (dd, J=5.0, 3.7 Hz, 1.5H), 6.71 (dd, J=9.1, 3.5 Hz, 0.5H), 6.45 (dd, J=9.0, 3.6 Hz, 0.5H), 4.83-4.63 (m, 1H), 4.18-3.38 (m, 3H), 2.70-0.40 (m, 7H).

Example 12B: MS (ESI) mass calcd. for C$_{23}$H$_{21}$FN$_2$O$_2$S, 408.2; m/z found 409.2 [M+H]$^+$. $^1$H NMR (CDCl$_3$): 7.97 (dd, J=11.0, 3.0 Hz, 1H), 7.54-7.20 (m, 6.5H), 7.01 (dd, J=5.0, 3.7 Hz, 1.5H), 6.71 (dd, J=9.1, 3.5 Hz, 0.5H), 6.45 (dd, J=9.0, 3.6 Hz, 0.5H), 4.83-4.63 (m, 1H), 4.18-3.38 (m, 3H), 2.70-0.40 (m, 7H).

Example 13: (±)-(5-methyl-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone

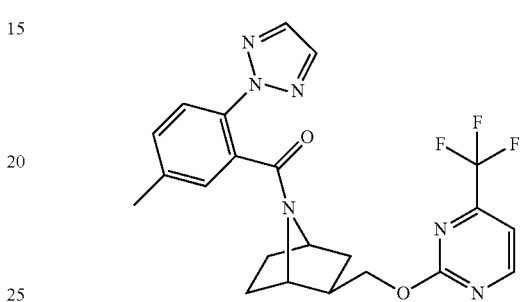

Step A: (±)-7-azabicyclo[2.2.1]heptan-2-ylmethanol hydrochloride. To intermediate B-10 (1.1 g, 4.9 mmol) in MeOH (1 mL) was added 4M HCl in dioxane (3 mL). After 6 h, the reaction was concentrated to give the title compound that was used without further purification.

Step B: ((±)-2-(hydroxymethyl)-7-azabicyclo[2.2.1]heptan-7-yl)(5-methyl-2-(2H-1,2,3-triazol-2-yl)phenyl)methanone. To the title compound of Step A in DMF was added TEA, 5-methyl-2-(2H-1,2,3-triazol-2-yl)benzoic acid and HATU. After 18 h, H$_2$O was added and the mix extracted with EtOAc (2×). The combined organics were washed with brine and dried (Na$_2$SO$_4$). Silica gel chromatography (1-7% 2M NH$_3$/MeOH in DCM) gave the title compound (371 mg, 46%). MS (ESI) mass calcd. for C$_{17}$H$_{20}$N$_4$O$_2$, 312.2; m/z found 313.2 [M+H]$^+$.

Step C: (±)-(5-methyl-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone. To the title compound of step B (33 mg, 0.1 mmol) in THF (2 mL) was added NaOtBu (16 mg, 0.16 mmol). The reaction was then heated at reflux for 15 min and 2-chloro-4-trifluromethyl-pyrimidine (19 mg, 0.16 mmol) was added. The reaction was heated at reflux temperature for 1 h, cooled to rt, diluted with H$_2$O and extracted with DCM (2×). The combined organics were dried (Na$_2$SO$_4$). Purification via silica gel chromatography (0.5-4% 2M NH$_3$/MeOH in DCM gave the title compound (28 mg, 57%). MS (ESI) mass calcd. for C$_{22}$H$_{21}$F$_3$N$_6$O$_2$, 457.2; m/z found 458.2 [M+H]$^+$. $^1$H NMR (CDCl$_3$): 8.82-8.72 (m, 1H), 7.86-7.69 (m, 3H), 7.36-7.10 (m, 3H), 4.85 (m, 1H), 4.47 (t, J=10.1 Hz, 0.5H), 4.20-3.98 (m, 1.5H), 3.90 (d, J=4.7 Hz, 0.5H), 3.78 (t, J=4.5 Hz, 0.5H), 2.51-2.20 (m, 3H), 2.14-1.82 (m, 2H), 1.78-1.17 (m, 5H).

Example 14: (±)-(5-methyl-2-(2H-1,2,3-triazol-2-yl)phenyl)(2-(((5-(trifluoromethyl)pyridin-2-yl)oxy)methyl)-7-azabicyclo[2.2.1]heptan-7-yl)methanone

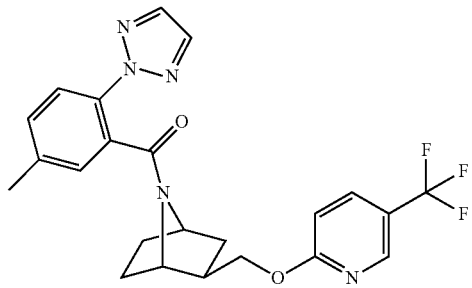 [SMILES: Cc1ccc(-n2nccn2)c(C(=O)N2C3CCC2C(COc2ccc(C(F)(F)F)cn2)C3)c1]

Prepared analogous to Example 13 substituting 2-chloro-4-(trifluoromethyl)pyrimidine with 2-chloro-5-(trifluoromethyl)pyridine. MS (ESI) mass calcd. for $C_{23}H_{22}F_3N_5O_2$, 457.2; m/z found 458.2 [M+H]$^+$.

Example 15: (±)-(5-methyl-2-(2H-1,2,3-triazol-2-yl)phenyl)(2-(((3-(trifluoromethyl)pyridin-2-yl)oxy)methyl)-7-azabicyclo[2.2.1]heptan-7-yl)methanone

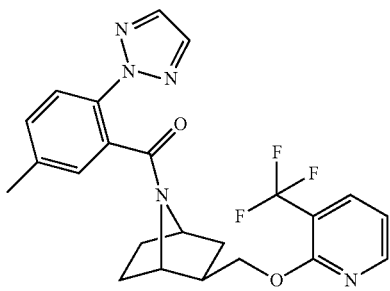 [SMILES: Cc1ccc(-n2nccn2)c(C(=O)N2C3CCC2C(COc2ncccc2C(F)(F)F)C3)c1]

Prepared analogous to Example 13 substituting 2-chloro-4-(trifluoromethyl)pyrimidine with 2-chloro-3-(trifluoromethyl)pyridine. MS (ESI) mass calcd. for $C_{23}H_{22}F_3N_5O_2$, 457.2; m/z found 458.2 [M+H]$^+$. $^1$H NMR (CDCl$_3$): 8.36-8.26 (m, 1H), 7.91-7.69 (m, 4H), 7.36-7.29 (m, 0.5H), 7.25-7.16 (m, 1H), 7.13-7.07 (m, 0.5H), 6.97 (dd, J=7.5, 5.1 Hz, 1H), 4.87-4.70 (m, 1H), 4.53-4.34 (m, 0.5H), 4.25-4.06 (m, 1H), 3.92 (t, J=10.9 Hz, 0.5H), 3.85-3.71 (m, 1H), 2.46-2.40 (m, 1.5H), 2.39-2.19 (m, 1.5H), 2.04-1.79 (m, 3H), 1.72-1.19 (m, 4H).

Example 16: (±)-(5-methyl-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone

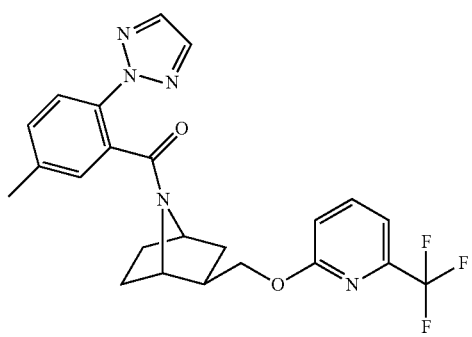 [SMILES: Cc1ccc(-n2nccn2)c(C(=O)N2C3CCC2C(COc2cccc(C(F)(F)F)n2)C3)c1]

Prepared analogous to Example 13 substituting 2-chloro-4-(trifluoromethyl)pyrimidine with 2-chloro-6-(trifluoromethyl)pyridine. MS (ESI) mass calcd. for $C_{23}H_{22}F_3N_5O_2$, 457.2; m/z found 458.2 [M+H]$^+$. $^1$H NMR (CDCl$_3$): 7.87-7.63 (m, 4H), 7.37-7.11 (m, 3H), 6.92 (d, J=8.4 Hz, 0.5H), 6.73 (d, J=8.4 Hz, 0.5H), 4.88-4.75 (m, 1H), 4.20-3.84 (m, 2H), 3.81-3.67 (m, 1H), 2.49-2.36 (s, 2H), 2.34-2.13 (m, 1H), 2.08-1.77 (m, 3H), 1.76-1.10 (m, 4H).

Example 17: (±)-(5-methyl-2-(2H-1,2,3-triazol-2-yl)phenyl)(2-(((4-methylpyridin-2-yl)oxy)methyl)-7-azabicyclo[2.2.1]heptan-7-yl)methanone

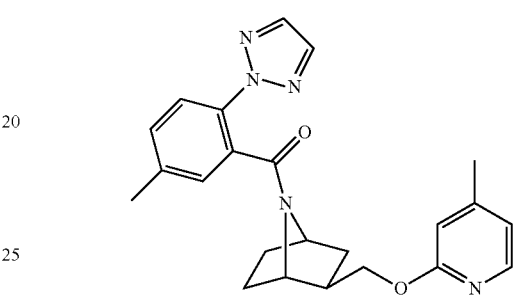

Prepared analogous to Example 13 substituting 2-chloro-4-(trifluoromethyl)pyrimidine with 2-chloro-4-(methyl)pyridine. MS (ESI) mass calcd. for $C_{23}H_{25}N_5O_2$, 403.2; m/z found 404.2 [M+H]$^+$. $^1$H NMR (CDCl$_3$): 8.10-7.91 (m, 1H), 7.87 (d, J=3.7 Hz, 2H), 7.82-7.70 (m, 1H), 7.50-7.42 (m, 1H), 7.34-7.24 (m, 0.5H), 7.16-7.08 (m, 0.5H), 6.90-6.80 (m, 1H), 6.77-6.66 (m, 0.4H), 6.59-6.45 (m, 0.6H), 4.68 (q, J=4.0, 3.3 Hz, 1H), 4.16-3.71 (m, 3H), 2.49-2.18 (m, 5H), 1.94-1.17 (m, 8H).

Example 18: (±)-(5-methyl-2-(2H-1,2,3-triazol-2-yl)phenyl)(2-(((6-methylpyridin-2-yl)oxy)methyl)-7-azabicyclo[2.2.1]heptan-7-yl)methanone

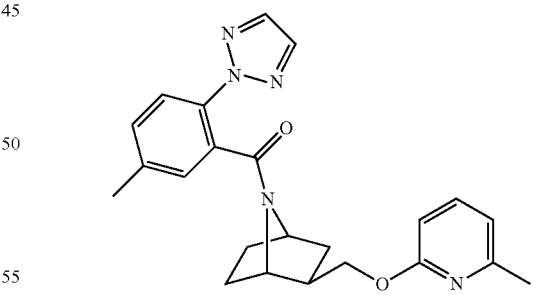

Prepared analogous to Example 13 substituting 2-chloro-4-(trifluoromethyl)pyrimidine with 2-chloro-6-(methyl)pyridine. MS (ESI) mass calcd. for $C_{23}H_{25}N_5O_2$, 403.2; m/z found 404.2 [M+H]$^+$. $^1$H NMR (CDCl$_3$): 7.89 (d, J=1.3 Hz, 2H), 7.82-7.66 (m, 1.5H), 7.61 (dd, J=8.3, 7.3 Hz, 0.5H), 7.43 (ddd, J=8.3, 1.9, 0.9 Hz, 0.5H), 7.35-7.26 (m, 1H), 7.16-7.09 (m, 0.5H), 6.88 (dd, J=16.1, 7.3 Hz, 1H), 6.76 (d, J=8.4 Hz, 0.5H), 6.53 (d, J=8.3 Hz, 0.5H), 4.74-4.64 (m, 1H), 4.24-4.04 (m, 1H), 4.02-3.76 (m, 2H), 2.55-2.21 (m, 5H), 2.05-1.23 (m, 8H).

Example 19: (±)-(5-methyl-2-(2H-1,2,3-triazol-2-yl)phenyl)(2-(((5-methylpyridin-2-yl)oxy)methyl)-7-azabicyclo[2.2.1]heptan-7-yl)methanone

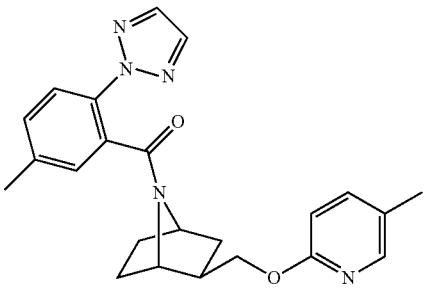

Prepared analogous to Example 13 substituting 2-chloro-4-(trifluoromethyl)pyrimidine with 2-chloro-5-(methyl)pyridine. MS (ESI) mass calcd. for $C_{23}H_{25}N_5O_2$, 403.2; m/z found 404.2 [M+H]$^+$. $^1$H NMR (CDCl$_3$): 8.10-7.58 (m, 4H), 7.43-7.29 (m, 1.5H), 7.26-7.11 (m, 1.5H), 6.66 (d, J=8.4 Hz, 0.5H), 6.45 (d, J=8.4 Hz, 0.5H), 4.86-4.71 (m, 1H), 4.17-3.66 (m, 3H), 2.46-2.38 (s, 1.2H), 2.31-2.14 (m, 3.8H), 2.01-1.79 (m, 2H), 1.71-1.18 (m, 6H).

Example 20: (±)-(2-(((3,6-dimethylpyrazin-2-yl)oxy)methyl)-7-azabicyclo[2.2.1]heptan-7-yl)(5-methyl-2-(2H-1,2,3-triazol-2-yl)phenyl)methanone

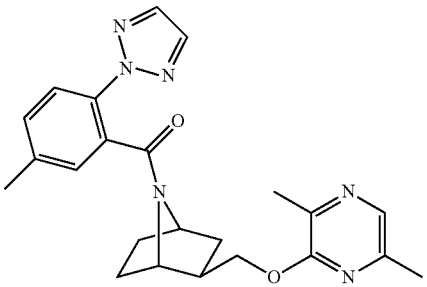

Prepared analogous to Example 13 substituting 2-chloro-4-(trifluoromethyl)pyrimidine with 3-chloro-2,5-dimethylpyrazine. MS (ESI) mass calcd. for $C_{23}H_{26}N_6O_2$, 418.2; m/z found 419.2 [M+H]$^+$. $^1$H NMR (400 MHz, CDCl$_3$) 7.88-7.84 (m, 1H), 7.81-7.72 (m, 2.5H), 7.36-7.12 (m, 2H), 7.11-7.06 (m, 0.5H), 4.86-4.75 (m, 1H), 4.26-4.15 (m, 0.5H), 4.08 (dd, J=11.0, 5.5 Hz, 1H), 3.86-3.71 (m, 1.5H), 2.48-2.34 (m, 6H), 2.34-2.13 (m, 3H), 1.96-1.25 (m, 7H).

Example 21: (±)-(5-methyl-2-(2H-1,2,3-triazol-2-yl)phenyl)(2-(((3-(trifluoromethyl)quinoxalin-2-yl)oxy)methyl)-7-azabicyclo[2.2.1]heptan-7-yl)methanone

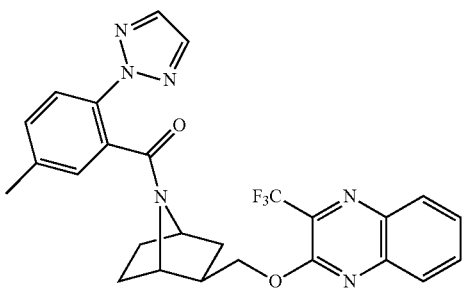 [SMILES: Cc1ccc(-n2nccn2)c(C(=O)N2C3CCC2C(COc2nc4ccccc4nc2C(F)(F)F)C3)c1]

Prepared analogous to Example 13 substituting 2-chloro-4-(trifluoromethyl)pyrimidine with 2-chloro-3-(trifluoromethyl)quinoxaline. MS (ESI) mass calcd. for $C_{26}H_{23}F_3N_6O_2$, 508.2; m/z found 509.2 [M+H]$^+$. $^1$H NMR (CDCl$_3$): 8.16-8.09 (m, 1H), 7.97-7.62 (m, 6H), 7.37-7.23 (m, 1H), 7.19-7.06 (m, 1H), 4.87 (t, J=4.7 Hz, 0.5H), 4.80 (d, J=4.8 Hz, 0.5H), 4.71-4.56 (m, 0.5H), 4.38-4.22 (m, 1H), 4.16-4.01 (m, 0.5H), 3.87-3.73 (m, 1H), 2.49-2.23 (m, 4H), 2.05-1.24 (m, 6H).

Example 22: (±)-(2-(2H-1,2,3-triazol-2-yl)phenyl)(2-(((5-fluoropyridin-2-yl)oxy)methyl)-7-azabicyclo[2.2.1]heptan-7-yl)methanone

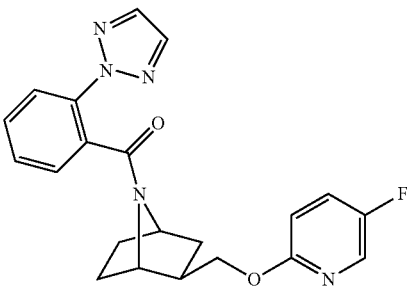 [SMILES: O=C(c1ccccc1-n1nccn1)N1C2CCC1C(COc1ccc(F)cn1)C2]

Prepared analogous to Example 7 substituting intermediate A-21 with intermediate A-1. MS (ESI) mass calcd. for $C_{21}H_{20}FN_5O_2$, 393.2; m/z found 394.2 [M+H]$^+$. $^1$H NMR (400 MHz, MeOD) 8.02-7.78 (m, 4H), 7.62-7.53 (m, 0.5H), 7.49-7.28 (m, 3H), 7.13-7.01 (m, 0.5H), 6.75 (dd, J=9.0, 3.6 Hz, 0.5H), 6.51 (dd, J=9.0, 3.6 Hz, 0.5H), 4.85-4.71 (m, 1H), 4.21-4.03 (m, 1H), 4.02-3.72 (m, 2H), 2.39-2.09 (m, 1H), 2.04-1.16 (m, 6H).

Example 23: (±)-2-(((5-fluoropyridin-2-yl)oxy)methyl)-7-azabicyclo[2.2.1]heptan-7-yl)(quinolin-8-yl)methanone

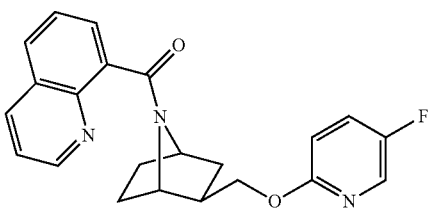 [SMILES: O=C(c1cccc2cccnc12)N1C2CCC1C(COc1ccc(F)cn1)C2]

Prepared analogous to Example 22 substituting intermediate A-1 with quinoline-8-carboxylic acid. MS (ESI) mass calcd. for $C_{22}H_{20}FN_3O_2$, 377.2; m/z found 378.2 [M+H]$^+$. $^1$H NMR (400 MHz, CDCl$_3$): 8.95-8.69 (m, 1H), 8.16 (dd, J=8.3, 1.8 Hz, 0.4H), 8.11-7.81 (m, 2H), 7.81-7.67 (m, 1H), 7.64-7.51 (m, 1H), 7.47-7.09 (m, 2.6H), 6.79 (dd, J=9.0, 3.6 Hz, 0.5H), 6.25 (s, 0.5H), 5.08-4.96 (m, 1H), 4.29 (s, 0.7H), 4.13-3.94 (m, 1.3H), 3.65-3.45 (m, 1H), 2.47-2.02 (m, 2H), 2.02-1.30 (m, 5H).

Example 24: (±)-2-(((5-fluoropyridin-2-yl)oxy)methyl)-7-azabicyclo[2.2.1]heptan-7-yl)(naphthalen-1-yl)methanone

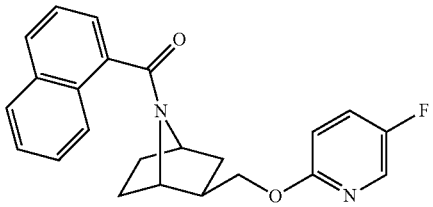 [SMILES: O=C(c1cccc2ccccc12)N1C2CCC1C(COc1ccc(F)cn1)C2]

Prepared analogous to Example 22 substituting intermediate A-1 with 1-naphthoic acid. MS (ESI) mass calcd. for $C_{23}H_{21}FN_2O_2$, 376.2; m/z found 377.2 [M+H]$^+$. $^1$H NMR (400 MHz, CDCl$_3$): 8.10-7.95 (m, 1.5H), 7.92-7.83 (m, 1.5H), 7.81-7.71 (m, 1H), 7.58-7.31 (m, 4H), 7.25-7.13 (m, 1H), 6.77 (dd, J=9.0, 3.6 Hz, 0.5H), 6.36-6.24 (m, 0.5H), 5.04-4.92 (m, 1H), 4.30-4.13 (m, 1H), 4.07-3.84 (m, 1H), 3.81-3.64 (m, 1H), 2.44-2.30 (m, 0.5H), 2.27-2.00 (m, 1.5H), 1.89-1.37 (m, 5H).

Example 25: (±)-2-(((5-fluoropyridin-2-yl)oxy)methyl)-7-azabicyclo[2.2.1]heptan-7-yl)(2-methyl-naphthalen-1-yl)methanone

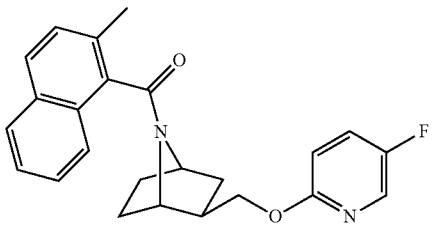 [SMILES: Cc1ccc2ccccc2c1C(=O)N1C2CCC1C(COc1ccc(F)cn1)C2]

Prepared analogous to Example 22 substituting intermediate A-1 with 2-methyl-1-naphthoic acid. $^1$H NMR (CDCl$_3$): 8.06-7.86 (m, 1H), 7.85-7.62 (m, 2.6H), 7.60-7.54 (m, 0.2H), 7.49-7.21 (m, 3.4H), 7.13 (m, 0.8H), 6.77 (ddd, J=12.7, 9.0, 3.6 Hz, 0.6H), 6.43 (dd, J=9.0, 3.6 Hz, 0.2H), 6.03 (dd, J=9.0, 3.6 Hz, 0.2H), 5.11-4.99 (m, 0.9H), 4.38-4.09 (m, 1.2H), 4.08-3.82 (m, 0.7H), 3.69-3.43 (m, 1.2H), 2.58-2.27 (m, 3.5H), 2.23-1.97 (m, 1.5H), 1.92-1.28 (m, 5H).

Example 26: (±)-2-(1H-pyrazol-1-yl)phenyl)(2-(((5-fluoropyridin-2-yl)oxy)methyl)-7-azabicyclo[2.2.1]heptan-7-yl)methanone

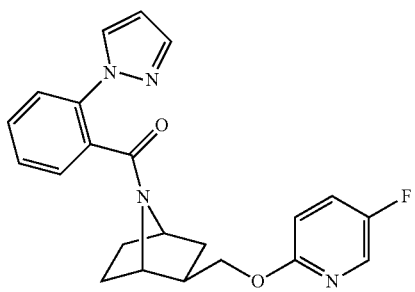 [SMILES: O=C(c1ccccc1-n1cccn1)N1C2CCC1C(COc1ccc(F)cn1)C2]

Prepared analogous to Example 22 substituting intermediate A-1 with 2-(1H-pyrazol-1-yl)benzoic acid. MS (ESI) mass calcd. for $C_{22}H_{21}FN_4O_2$, 392.2; m/z found 393.2 [M+H]$^+$. $^1$H NMR (CDCl$_3$): 7.98 (dd, J=8.3, 3.1 Hz, 1H), 7.91-7.83 (m, 1H), 7.69 (d, J=1.9 Hz, 1H), 7.64-7.23 (m, 4.5H), 6.99 (t, J=7.4 Hz, 0.5H), 6.71 (dd, J=9.0, 3.6 Hz, 0.5H), 6.47-6.34 (m, 1.5H), 4.79-4.63 (m, 1H), 4.03-3.65 (m, 2H), 3.66-3.54 (m, 1H), 2.27-2.03 (m, 1H), 1.86-0.74 (m, 6H).

Example 27: (±)-2-(((5-fluoropyridin-2-yl)oxy)methyl)-7-azabicyclo[2.2.1]heptan-7-yl)(3-phenyl-furan-2-yl)methanone

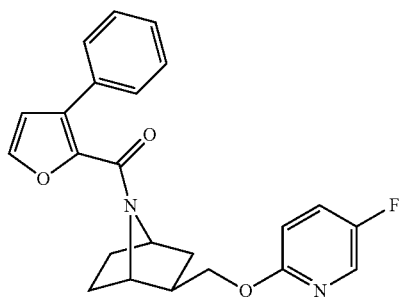 [SMILES: O=C(c1occc1-c1ccccc1)N1C2CCC1C(COc1ccc(F)cn1)C2]

Prepared analogous to Example 22 substituting intermediate A-1 with 3-phenylfuran-2-carboxylic acid. MS (ESI) mass calcd. for $C_{22}H_{21}FN_2O_3$, 392.2; m/z found 393.2 [M+H]$^+$. $^1$H NMR (CDCl$_3$): 8.05-7.82 (m, 1H), 7.59-7.44 (m, 7H), 6.77-6.40 (m, 2H), 4.85-4.61 (m, 1H), 4.45-4.29 (m, 0.5H), 4.24-4.08 (m, 0.5H), 4.06-3.76 (m, 2H), 2.32-2.11 (m, 1H), 2.01-0.83 (m, 6H).

Example 28: (±)-(2-ethoxynaphthalen-1-yl)(2-(((5-fluoropyridin-2-yl)oxy)methyl)-7-azabicyclo[2.2.1]heptan-7-yl)methanone

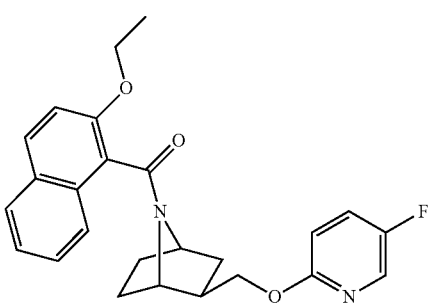 [SMILES: CCOc1ccc2ccccc2c1C(=O)N1C2CCC1C(COc1ccc(F)cn1)C2]

Prepared analogous to Example 22 substituting intermediate A-1 with 2-ethoxy-1-naphthoic acid. MS (ESI) mass calcd. for $C_{25}H_{25}FN_2O_3$, 420.2; m/z found 421.2 [M+H]$^+$. $^1$H NMR (CDCl$_3$): 8.03 (d, J=3.0 Hz, 0.2H), 7.95 (dd, J=8.1, 3.1 Hz, 0.5H), 7.86-7.70 (m, 2.6H), 7.69-7.63 (m, 0.3H), 7.60-7.55 (m, 0.3H), 7.50-7.00 (m, 4.2H), 6.76 (ddd, J=9.3, 6.1, 3.6 Hz, 0.5H), 6.44 (dd, J=9.0, 3.5 Hz, 0.2H), 6.03 (dd, J=9.0, 3.6 Hz, 0.2H), 5.08-4.97 (m, 1H), 4.35-3.92 (m, 3.3H), 3.91-3.76 (m, 0.5H), 3.68-3.52 (m, 1.2H), 2.44-2.27 (m, 0.8H), 2.20-1.93 (m, 2H), 1.85-1.18 (m, 7.2H).

Example 29: (±)-(5-(2-fluorophenyl)-2-methylthi-azol-4-yl)(2-(((5-fluoropyridin-2-yl)oxy)methyl)-7-azabicyclo[2.2.1]heptan-7-yl)methanone

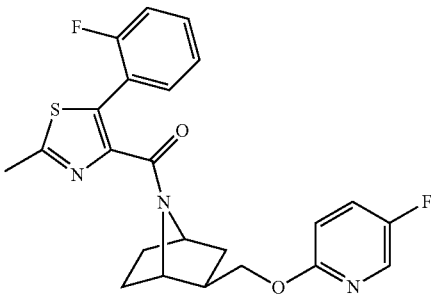 [SMILES: Cc1nc(C(=O)N2C3CCC2C(COc2ccc(F)cn2)C3)c(-c2ccccc2F)s1]

Prepared analogous to Example 22 substituting intermediate A-1 with 5-(2-fluorophenyl)-2-methylthiazole-4-carboxylic acid. MS (ESI) mass calcd. for $C_{23}H_{21}F_2N_3O_2S$, 441.2; m/z found 442.2 [M+H]$^+$. $^1$H NMR (CDCl$_3$): 7.99-7.93 (m, 1H), 7.53-7.44 (m, 1H), 7.36-7.09 (m, 3.5H), 7.04 (ddd, J=9.8, 8.5, 1.2 Hz, 0.5H), 6.66 (ddd, J=15.9, 9.0, 3.6 Hz, 1H), 4.79-4.68 (m, 1H), 4.27-4.21 (m, 0.5H), 4.07 (t, J=4.6 Hz, 0.5H), 3.96-3.73 (m, 2H), 2.74 (s, 1.5H), 2.42 (s, 1.5H), 2.23-2.11 (m, 1H), 1.89-1.57 (m, 2H), 1.54-1.24 (m, 3.5H), 0.92-0.81 (m, 0.5H).

Example 30: (±)-(5-fluoro-2-(2H-1,2,3-triazol-2-yl)phenyl)(2-(((5-fluoropyridin-2-yl)oxy)methyl)-7-azabicyclo[2.2.1]heptan-7-yl)methanone

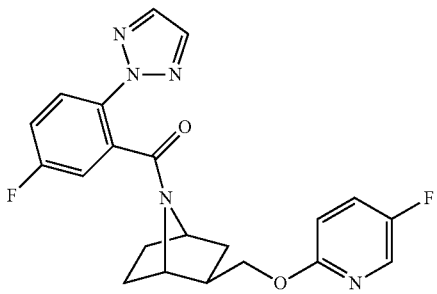 [SMILES: O=C(c1cc(F)ccc1-n1nccn1)N1C2CCC1C(COc1ccc(F)cn1)C2]

Prepared analogous to Example 22 substituting intermediate A-1 with intermediate A-10. MS (ESI) mass calcd. for $C_{21}H_{19}F_2N_5O_2$, 411.2; m/z found 412.2 [M+H]$^+$. $^1$H NMR (CDCl$_3$): 7.98 (dd, J=7.4, 3.0 Hz, 1H), 7.86 (ddd, J=21.7, 8.9, 4.7 Hz, 1H), 7.81-7.75 (m, 1.5H), 7.38-7.03 (m, 3.5H), 6.72 (dd, J=9.0, 3.6 Hz, 0.5H), 6.52 (dd, J=9.0, 3.6 Hz, 0.5H), 4.85-4.75 (m, 1H), 4.17-4.02 (m, 1H), 4.02-3.83 (m, 1H), 3.83-3.75 (m, 1H), 2.34-2.15 (m, 1H), 2.03-1.80 (m, 1H), 1.74-1.20 (m, 5H).

Example 31: (±)-(2-fluoro-6-(pyrimidin-2-yl)phenyl)(2-(((5-fluoropyridin-2-yl)oxy)methyl)-7-azabicyclo[2.2.1]heptan-7-yl)methanone

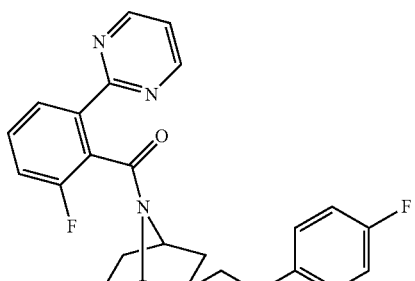

Prepared analogous to Example 22 substituting intermediate A-1 with intermediate A-6. MS (ESI) mass calcd. for $C_{23}H_{20}F_2N_4O_2$, 422.2; m/z found 423.2 [M+H]$^+$. $^1$H NMR (CDCl$_3$): 8.93-8.61 (m, 1.8H), 8.15-7.92 (m, 1.6H), 7.56-7.05 (m, 4.3H), 6.94 (t, J=8.6 Hz, 0.3H), 6.73 (ddd, J=8.9, 5.2, 3.5 Hz, 0.6H), 6.59-6.35 (m, 0.4H), 4.99-4.79 (m, 1H), 4.31 (t, J=9.9 Hz, 0.3H), 4.25-3.63 (m, 2.7H), 2.47-1.11 (m, 7H).

Example 32: (±)-(5-fluoro-2-(pyrimidin-2-yl)phenyl)(2-(((5-fluoropyridin-2-yl)oxy)methyl)-7-azabicyclo[2.2.1]heptan-7-yl)methanone

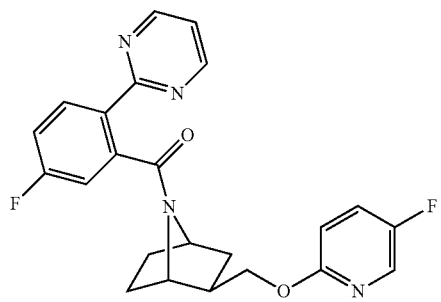 [SMILES: O=C(c1cc(F)ccc1-c1ncccn1)N1C2CCC1C(COc1ccc(F)cn1)C2]

Prepared analogous to Example 22 substituting intermediate A-1 with 5-fluoro-2-(pyrimidin-2-yl)benzoic acid. MS (ESI) mass calcd. for $C_{23}H_{20}F_2N_4O_2$, 422.2; m/z found 423.2 [M+H]$^+$. $^1$H NMR (500 MHz, CDCl$_3$) 8.78 (d, J=4.9 Hz, 1H), 8.72 (d, J=4.8 Hz, 1H), 8.22 (ddd, J=20.6, 8.7, 5.5 Hz, 1H), 8.01-7.93 (m, 1H), 7.37-7.27 (m, 1H), 7.23-7.13 (m, 1.5H), 7.13-6.99 (m, 1.5H), 6.72 (dd, J=9.0, 3.5 Hz, 0.5H), 6.52 (dd, J=9.0, 3.5 Hz, 0.5H), 4.90-4.75 (m, 1H), 4.25-3.91 (m, 2H), 3.91-3.78 (m, 1H), 2.39-2.15 (m, 1H), 2.08-1.13 (m, 6H).

Example 33: (±)-(2-(((5-fluoropyridin-2-yl)oxy)methyl)-7-azabicyclo[2.2.1]heptan-7-yl)(5-methyl-2-(pyrimidin-2-yl)phenyl)methanone

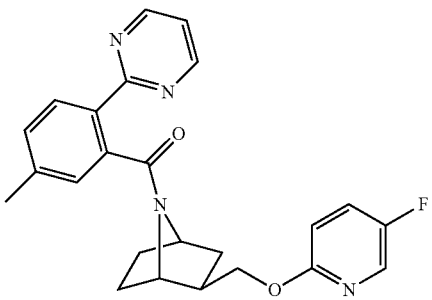 [SMILES: Cc1ccc(-c2ncccn2)c(C(=O)N2C3CCC2C(COc2ccc(F)cn2)C3)c1]

Prepared analogous to Example 22 substituting intermediate A-1 with 5-methyl-2-(pyrimidin-2-yl)benzoic acid. MS (ESI) mass calcd. for $C_{24}H_{23}FN_4O_2$, 418.2; m/z found 419.2 [M+H]$^+$. $^1$H NMR (CDCl$_3$): 8.81-8.68 (m, 2H), 8.09 (dd, J=9.9, 8.0 Hz, 1H), 7.98 (dd, J=8.6, 3.1 Hz, 1H), 7.41-7.24 (m, 1.5H), 7.22-7.16 (m, 1H), 7.16-7.09 (m, 1.5H), 6.73 (dd, J=9.1, 3.6 Hz, 0.5H), 6.52 (dd, J=9.0, 3.6 Hz, 0.5H), 4.88-4.77 (m, 1H), 4.21-4.01 (m, 1H), 4.01-3.89 (m, 1H), 3.88-3.76 (m, 1H), 2.42 (s, 1.6H), 2.35-2.10 (m, 1H), 2.07-1.81 (m, 2.4H), 1.81-1.16 (m, 5H).

Example 34: (±)-(2-(2H-1,2,3-triazol-2-yl)phenyl)(2-((quinoxalin-2-yloxy)methyl)-7-azabicyclo[2.2.1]heptan-7-yl methanone

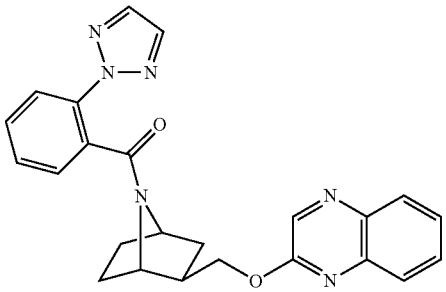 [SMILES: O=C(c1ccccc1-n1nccn1)N1C2CCC1C(COc1cnc3ccccc3n1)C2]

Step A: (±)-2-(-7-azabicyclo[2.2.1]heptan-2-ylmethoxy)quinoxaline. To intermediate B-10 (240 mg, 1.1 mmol) in THF (4 mL) was added NaOtBu (130 mg, 1.4 mmol). The reaction was heated at reflux for 15 min and 2-chloroquinoxaline (207 mg, 1.3 mmol) was added. After 45 min, the reaction was cooled to rt and ½ saturated NH$_4$Cl (aq) was added. The solution was made slightly basic with 5% Na$_2$CO$_3$ (aq) and extracted with DCM (3×). The combined organics were dried (Na$_2$SO$_4$). The resulting compound was treated with TFA in DCM. After the reaction was complete, the reaction was concentrated, neutralized with 5% Na$_2$CO$_3$ and extracted with DCM. The combined organics were dried (Na$_2$SO$_4$). Purification via silica gel chromatography (1-7% (2M NH$_3$ in MeOH)/DCM) gave the title compound (208 mg, 78%). MS (ESI) mass calcd. for C$_{15}$H$_{17}$N$_3$O, 255.1; m/z found 256.2 [M+H]$^+$.

Step B: (±)-(2-(2H-1,2,3-triazol-2-yl)phenyl)(2-((quinoxalin-2-yloxy)methyl)-7-azabicyclo[2.2.1]heptan-7-yl)methanone. Prepared analogous to Example 7 substituting 6-methyl-3-(2H-1,2,3-triazol-2-yl)picolinic acid with intermediate A-1 and (±)-2-(((5-fluoropyridin-2-yl)oxy)methyl)-7-azabicyclo[2.2.1]heptane with the title compound of Step A. MS (ESI) mass calcd. for C$_{24}$H$_{22}$N$_6$O$_2$, 426.2; m/z found 427.2 [M+H]$^+$. $^1$H NMR (CDCl$_3$): 8.49 (s, 0.5H), 8.31-8.21 (s, 0.5H), 8.08-7.98 (m, 1H), 7.95-7.75 (m, 3.4H), 7.75-7.66 (m, 1.1H), 7.65-7.50 (m, 1.7H), 7.50-7.39 (m, 1.1H), 7.36-7.28 (m, 1H), 7.24-7.13 (m, 0.7H), 4.92-4.80 (m, 1H), 4.47-4.28 (m, 1H), 4.22-4.07 (m, 1H), 3.87-3.77 (m, 1H), 2.46-2.23 (m, 1.7H), 2.07-1.83 (m, 1.3H), 1.82-1.29 (m, 4H).

Example 35: (±)-(2-fluoro-6-(2H-1,2,3-triazol-2-yl)phenyl)(2-((quinoxalin-2-yloxy)methyl)-7-azabicyclo[2.2.1]heptan-7-yl)methanone

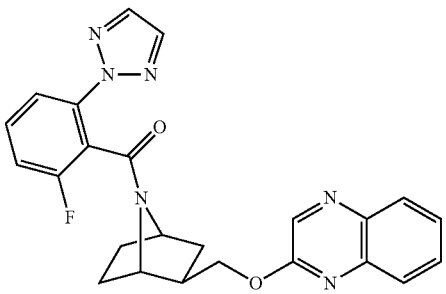 [SMILES: O=C(c1c(F)cccc1-n1nccn1)N1C2CCC1C(COc1cnc3ccccc3n1)C2]

Prepared analogous to Example 34 substituting intermediate A-1 with intermediate A-11. MS (ESI) mass calcd. for C$_{24}$H$_{21}$FN$_6$O$_2$, 444.2; m/z found 445.2 [M+H]. $^1$H NMR (CDCl$_3$): 8.52-8.47 (m, 0.5H), 8.27-8.21 (m, 0.4H), 8.07-7.95 (m, 1H), 7.91-7.09 (m, 7.8H), 6.72-6.63 (m, 0.3H), 4.98-4.87 (m, 1H), 4.63-4.54 (dd, J=10.7, 9.1 Hz, 0.5H), 4.46-4.29 (m, 1H), 4.20-4.04 (m, 0.5H), 3.96-3.76 (m, 1H), 2.51-2.23 (m, 1H), 2.17-1.88 (m, 1H), 1.84-1.19 (m, 5H).

Example 36: (±)-(5-methyl-2-(2H-1,2,3-triazol-2-yl)phenyl)(2-((quinoxalin-2-yloxy)methyl)-7-azabicyclo[2.2.1]heptan-7-yl)methanone

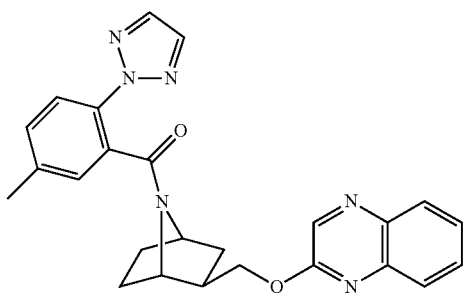 [SMILES: Cc1ccc(-n2nccn2)c(C(=O)N2C3CCC2C(COc2cnc4ccccc4n2)C3)c1]

Prepared analogous to Example 34 substituting intermediate A-1 with intermediate A-37. MS (ESI) mass calcd. for C$_{25}$H$_{24}$N$_6$O$_2$, 440.2; m/z found 441.2 [M+H]$^+$. $^1$H NMR (CDCl$_3$): 8.49 (s, 0.5H), 8.26 (s, 0.5H), 8.03 (ddd, J=8.3, 4.4, 1.4 Hz, 1H), 7.90-7.74 (m, 3H), 7.74-7.65 (m, 1H), 7.59 (dddd, J=8.3, 7.0, 4.8, 1.4 Hz, 1H), 7.33 (ddd, J=8.3, 1.9, 0.9 Hz, 0.6H), 7.29-7.22 (m, 1H), 7.21-7.10 (m, 1.4H), 4.90-4.79 (m, 1H), 4.46-3.98 (m, 2H), 3.91-3.72 (m, 1H), 2.47-2.20 (m, 4H), 2.05-1.22 (m, 6H).

Example 37: (±)-(5-fluoro-2-(2H-1,2,3-triazol-2-yl)phenyl)(2-((quinoxalin-2-yloxy)methyl)-7-azabicyclo[2.2.1]heptan-7-yl)methanone

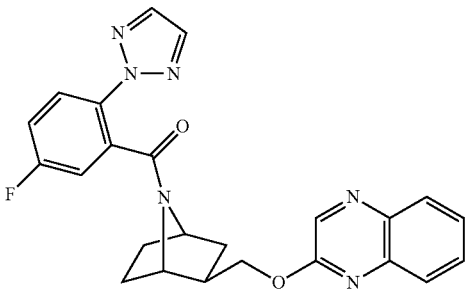 [SMILES: O=C(c1cc(F)ccc1-n1nccn1)N1C2CCC1C(COc1cnc3ccccc3n1)C2]

Prepared analogous to Example 34 substituting intermediate A-1 with intermediate A-10. MS (ESI) mass calcd. for C$_{24}$H$_{21}$FN$_6$O$_2$, 444.2; m/z found 445.2 [M+H]$^+$. $^1$H NMR (CDCl$_3$): 8.55-8.44 (m, 0.5H), 8.36-8.23 (m, 0.5H), 8.08-8.00 (m, 1H), 7.90-7.55 (m, 5H), 7.49-7.09 (m, 3H), 4.91-4.82 (m, 1H), 4.50-4.29 (m, 1H), 4.23-4.07 (m, 1H), 3.82 (dd, J=10.0, 5.0 Hz, 1H), 2.48-2.25 (m, 1H), 2.09-1.88 (m, 1H), 1.82-1.31 (m, 5H).

Example 38: (±)-(5-methyl-2-(pyrimidin-2-yl)phenyl)(2-((quinoxalin-2-yloxy)methyl)-7-azabicyclo[2.2.1]heptan-7-yl)methanone

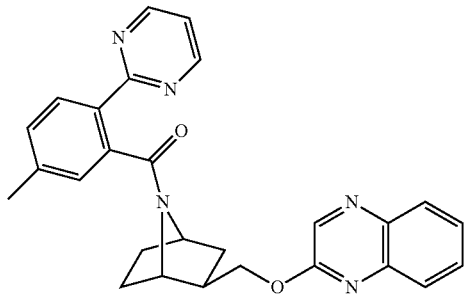 [SMILES: Cc1ccc(-c2ncccn2)c(C(=O)N2C3CCC2C(COc2cnc4ccccc4n2)C3)c1]

Prepared analogous to Example 34 substituting intermediate A-1 with intermediate A-34. MS (ESI) mass calcd. for $C_{27}H_{25}N_5O_2$, 451.2; m/z found 452.2 $[M+H]^+$. $^1$H NMR (CDCl$_3$): 8.87-8.79 (m, 1H), 8.75-8.68 (m, 1H), 8.49 (s, 0.5H), 8.27 (s, 0.5H), 8.14-7.98 (m, 2H), 7.85 (ddd, J=16.5, 8.3, 1.5 Hz, 1H), 7.74-7.66 (m, 1H), 7.64-7.54 (m, 1H), 7.35-7.29 (m, 0.5H), 7.24-7.19 (m, 0.5H), 7.18-7.07 (m, 2H), 4.94-4.83 (m, 1H), 4.52-4.07 (m, 2H), 3.93-3.82 (m, 1H), 2.51-2.20 (m, 2.6H), 2.08-1.83 (m, 1.4H), 1.81-1.12 (m, 6H).

Example 39: (±)-(2-(((4,6-dimethylpyrimidin-2-yl)oxy)methyl)-7-azabicyclo[2.2.1]heptan-7-yl)(5-methyl-2-(2H-1,2,3-triazol-2-yl)phenyl)methanone

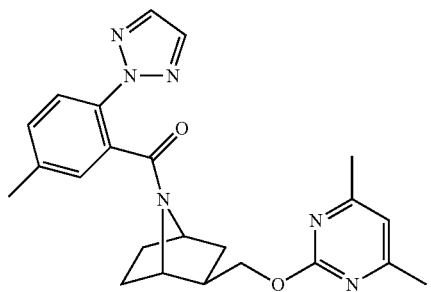

Step A: (±)-2-(((4,6-dimethylpyrimidin-2-yl)oxy)methyl)-7-azabicyclo[2.2.1]heptane. Prepared analogous to Example 34 substituting 2-chloroquinoxaline with 2-chloro-4,6-dimethylpyrimidine. $^1$H NMR (CDCl$_3$): 6.65 (s, 1H), 4.21-3.99 (m, 2H), 3.74-3.56 (m, 2H), 2.39 (s, 6H), 2.14 (ddd, J=9.0, 5.1, 3.7 Hz, 1H), 1.86 (s, 2H), 1.67-1.49 (m, 2H), 1.47-1.30 (m, 2H).
Step B: (±)-(2-(((4,6-dimethylpyrimidin-2-yl)oxy)methyl)-7-azabicyclo[2.2.1]heptan-7-yl)(5-methyl-2-(2H-1,2,3-triazol-2-yl)phenyl)methanone. Prepared analogous to Example 7 substituting 6-methyl-3-(2H-1,2,3-triazol-2-yl)picolinic acid with 5-methyl-2-(2H-1,2,3-triazol-2-yl)benzoic acid and (±)-2-(((5-fluoropyridin-2-yl)oxy)methyl)-7-azabicyclo[2.2.1]heptane with the title compound of Step A. MS (ESI) mass calcd. for $C_{23}H_{26}N_6O_2$, 418.2; m/z found 419.2 $[M+H]^+$. $^1$H NMR (CDCl$_3$): 7.83-7.70 (m, 2.5H), 7.35-7.10 (m, 2.5H), 6.71-6.65 (m, 1H), 4.87-4.72 (m, 1H), 4.34 (dd, J=10.5, 8.8 Hz, 0.5H), 4.14-3.89 (m, 2H), 3.79-3.70 (m, 0.5H), 2.48-2.18 (m, 7.5H), 2.07-1.83 (m, 2.5H), 1.79-1.18 (m, 6H).

Example 40: (±)-2-(((4,6-dimethylpyrimidin-2-yl)oxy)methyl)-7-azabicyclo[2.2.1]heptan-7-yl)(3-methyl-5-phenylisoxazol-4-yl)methanone

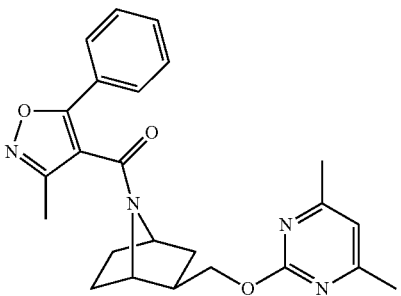 [SMILES: Cc1cc(C)nc(OCC2CC3CCC2N3C(=O)c2c(C)noc2-c2ccccc2)n1]

Prepared analogous to Example 39 substituting 5-methyl-2-(2H-1,2,3-triazol-2-yl)benzoic acid with 3-methyl-5-phenylisoxazole-4-carboxylic acid. MS (ESI) mass calcd. for $C_{24}H_{26}N_4O_3$, 418.2; m/z found 419.2 $[M+H]^+$. $^1$H NMR (CDCl$_3$): 7.67 (m, 2H), 7.50-7.31 (m, 3H), 6.69 (d, J=6.7 Hz, 1H), 4.74 (dd, J=10.8, 5.1 Hz, 1H), 4.17 (dd, J=10.8, 9.2 Hz, 0.5H), 3.85-3.78 (m, 1H), 3.70 (d, J=4.9 Hz, 0.5H), 3.64-3.42 (m, 1H), 2.55 (s, 1.4H), 2.49 (s, 1.6H), 2.43 (s, 3H), 2.39 (s, 3H), 2.29-2.07 (m, 1H), 1.90-1.55 (m, 2H), 1.53-1.06 (m, 3H), 0.76-0.53 (m, 1H).

Example 41: (±)-(2-(((4,6-dimethylpyrimidin-2-yl)oxy)methyl)-7-azabicyclo[2.2.1]heptan-7-yl)(2-ethoxynaphthalen-1-yl)methanone

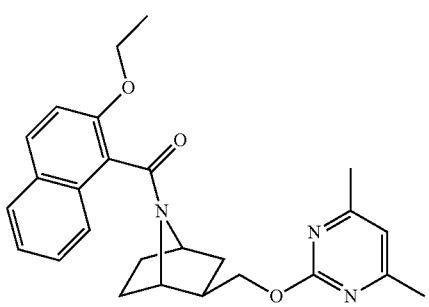 [SMILES: CCOc1ccc2ccccc2c1C(=O)N1C2CCC1C(COc1nc(C)cc(C)n1)C2]

Prepared analogous to Example 39 substituting 5-methyl-2-(2H-1,2,3-triazol-2-yl)benzoic acid with 2-ethoxy-1-naphthoic acid. $^1$H NMR (CDCl$_3$): 7.91-7.70 (m, 2.5H), 7.67-7.54 (m, 0.5H), 7.49-7.38 (m, 0.8H), 7.37-7.28 (m, 0.8H), 7.27-7.16 (m, 0.9H), 7.10-7.02 (m, 0.5H), 6.70 (s, 0.2H), 6.65 (s, 0.5H), 6.53 (s, 0.3H), 5.09-4.95 (m, 1H), 4.56-4.47 (m, 0.5H), 4.28-3.87 (m, 3.3H), 3.79-3.55 (m, 1.2H), 2.46-2.35 (m, 4.5H), 2.28 (s, 1.5H), 2.21-1.95 (m, 2H), 1.85-1.51 (m, 3.5H), 1.51-1.24 (m, 4.5H).

Example 42: (±)-(2-(((4,6-dimethylpyrimidin-2-yl)oxy)methyl)-7-azabicyclo[2.2.1]heptan-7-yl)(2-ethoxyphenyl)methanone)

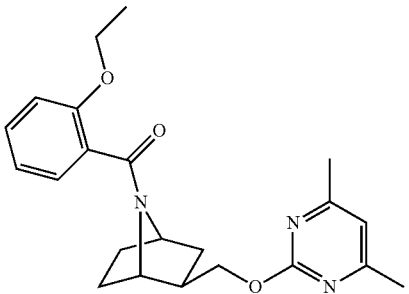 [SMILES: CCOc1ccccc1C(=O)N1C2CCC1C(COc1nc(C)cc(C)n1)C2]

Prepared analogous to Example 39 substituting 5-methyl-2-(2H-1,2,3-triazol-2-yl)benzoic acid with 2-ethoxybenzoic acid. MS (ESI) mass calcd. for $C_{22}H_{27}N_3O_3$, 381.2; m/z found 382.2 [M+H]$^+$. $^1$H NMR (CDCl$_3$): 7.34-7.27 (m, 1H), 7.21-7.12 (m, 1H), 6.98-6.92 (m, 0.5H), 6.89 (d, J=8.2 Hz, 0.5H), 6.78 (d, J=8.3 Hz, 0.5H), 6.72-6.63 (m, 1.5H), 4.89-4.78 (m, 1H), 4.36 (dd, J=10.6, 8.7 Hz, 0.5H), 4.14-3.71 (m, 4.5H), 2.45-2.16 (m, 6.5H), 2.06-1.82 (m, 1.5H), 1.82-1.28 (m, 8H).

Example 43: (±)-(2-(((4,6-dimethylpyrimidin-2-yl)oxy)methyl)-7-azabicyclo[2.2.1]heptan-7-yl)(2-fluoro-6-(pyrimidin-2-yl)phenyl)methanone

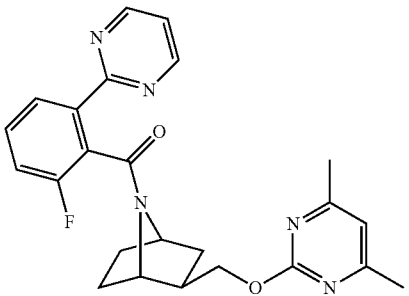 [SMILES: Cc1cc(C)nc(OCC2CC3CCC2N3C(=O)c2c(F)cccc2-c2ncccn2)n1]

Prepared analogous to Example 39 substituting 5-methyl-2-(2H-1,2,3-triazol-2-yl)benzoic acid with 2-fluoro-6-(pyrimidin-2-yl)benzoic acid. MS (ESI) mass calcd. for $C_{24}H_{24}FN_5O_2$, 433.2; m/z found 434.2 [M+H]$^+$. $^1$H NMR (CDCl$_3$): 9.02-8.90 (m, 0.7H), 8.82-8.65 (m, 1.3H), 8.14-7.95 (m, 1H), 7.58-7.31 (m, 1H), 7.31-7.07 (m, 1.7H), 6.97-6.86 (m, 0.3H), 6.75-6.51 (m, 1H), 4.96-4.83 (m, 1H), 4.55 (dd, J=10.3, 9.0 Hz, 0.25H), 4.36 (dd, J=10.6, 8.9 Hz, 0.25H), 4.21-3.78 (m, 2.5H), 2.48-1.17 (m, 13H).

Example 44: (±)-(2-(((4,6-dimethylpyrimidin-2-yl)oxy)methyl)-7-azabicyclo[2.2.1]heptan-7-yl)(5-fluoro-2-(pyrimidin-2-yl)phenyl)methanone

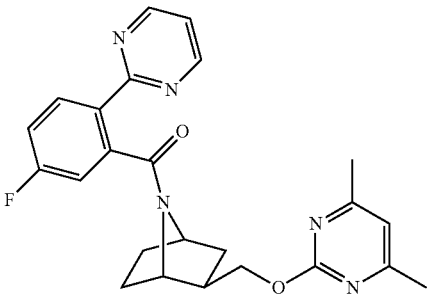 [SMILES: Cc1cc(C)nc(OCC2CC3CCC2N3C(=O)c2cc(F)ccc2-c2ncccn2)n1]

Prepared analogous to Example 39 substituting 5-methyl-2-(2H-1,2,3-triazol-2-yl)benzoic acid with 5-fluoro-2-(pyrimidin-2-yl)benzoic acid. MS (ESI) mass calcd. for $C_{24}H_{24}FN_5O_2$, 433.2; m/z found 434.2 [M+H]$^+$. $^1$H NMR (CDCl$_3$): 8.88-8.78 (m, 1H), 8.72 (d, J=4.8 Hz, 1H), 8.26 (dd, J=8.7, 5.5 Hz, 0.5H), 8.22-8.16 (m, 0.5H), 7.29-7.09 (m, 2H), 7.06-6.97 (m, 1H), 6.68 (s, 1H), 4.88-4.81 (m, 1H), 4.40 (t, J=9.7 Hz, 0.5H), 4.25 (t, J=10.8 Hz, 0.5H), 4.05 (dd, J=10.2, 6.2 Hz, 0.5H), 3.99-3.91 (m, 1H), 3.89-3.80 (m, 0.5H), 2.45-2.21 (m, 7H), 2.05-1.87 (m, 1H), 1.81-1.30 (m, 5H).

Example 45: (±)-(2-(((4,6-dimethylpyrimidin-2-yl)oxy)methyl)-7-azabicyclo[2.2.1]heptan-7-yl)(5-methyl-2-(pyrimidin-2-yl)phenyl)methanone

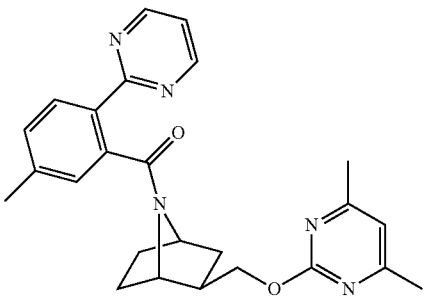

Prepared analogous to Example 39 substituting 5-methyl-2-(2H-1,2,3-triazol-2-yl)benzoic acid with 5-methyl-2-(pyrimidin-2-yl)benzoic acid. MS (ESI) mass calcd. for $C_{25}H_{27}N_5O_2$, 429.2; m/z found 430.2 [M+H]$^+$. $^1$H NMR (CDCl$_3$): 8.83 (d, J=5.0 Hz, 1H), 8.71 (d, J=4.8 Hz, 1H), 8.09 (dd, J=13.6, 8.0 Hz, 1H), 7.33-7.10 (m, 3H), 6.68 (d, J=1.4 Hz, 1H), 4.90-4.79 (m, 1H), 4.41 (dd, J=10.4, 8.8 Hz, 0.5H), 4.20 (t, J=10.6 Hz, 0.5H), 4.07-3.94 (m, 1.5H), 3.80 (t, J=4.7 Hz, 0.5H), 2.49-2.19 (m, 7H), 2.04-1.89 (m, 3H), 1.87-1.47 (m, 4.5H), 1.45-1.29 (m, 1.5H).

Example 46: (±)-(2-(((4,6-dimethylpyrimidin-2-yl)oxy)methyl)-7-azabicyclo[2.2.1]heptan-7-yl)(2-(thiophen-2-yl)phenyl)methanone

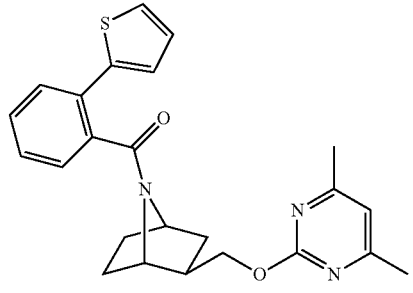 [SMILES: Cc1cc(C)nc(OCC2CC3CCC2N3C(=O)c2ccccc2-c2cccs2)n1]

Prepared analogous to Example 11 substituting (±)-2-(((5-fluoropyridin-2-yl)oxy)methyl)-7-azabicyclo[2.2.1]heptane with (±)-2-(((4,6-dimethylpyrimidin-2-yl)oxy)methyl)-7-azabicyclo[2.2.1]heptane. MS (ESI) mass calcd. for $C_{24}H_{25}N_3O_2S$, 419.2; m/z found 420.2 [M+H]$^+$. $^1$H NMR (400 MHz, CDCl$_3$): 7.55-6.83 (m, 7H), 6.75-6.62 (m, 1H), 4.87-4.62 (m, 1H), 4.09-3.38 (m, 3H), 2.54-2.32 (m, 6H), 2.32-2.03 (m, 1H), 1.97-0.87 (m, 6H).

Example 47: (±)-(6-methyl-3-(2H-1,2,3-triazol-2-yl)pyridin-2-yl)(2-(((5-(trifluoromethyl)pyridin-2-yl)oxy)methyl)-7-azabicyclo[2.2.1]heptan-7-yl)methanone

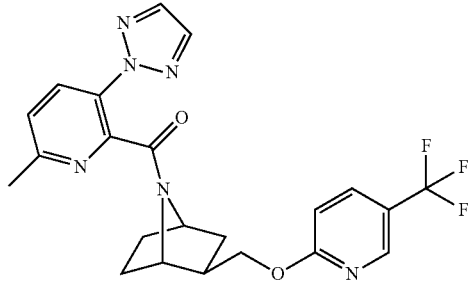 [SMILES: Cc1ccc(-n2nccn2)c(C(=O)N2C3CCC2C(COc2ccc(C(F)(F)F)cn2)C3)n1]

Step A: (±)-2-(((5-(trifluoromethyl)pyridin-2-yl)oxy)methyl)-7-azabicyclo[2.2.1]heptane. Prepared analogous to Example 49 substituting 5-bromo-2-fluoropyridine with 2-fluoro-5-(trifluoromethyl)pyridine. MS (ESI) mass calcd. for $C_{13}H_{15}F_3N_2O$, 272.1; m/z found 273.1, [M+H]$^+$.

Step B: (±)-(6-methyl-3-(2H-1,2,3-triazol-2-yl)pyridin-2-yl)(2-(((5-(trifluoromethyl)pyridin-2-yl)oxy)methyl)-7-azabicyclo[2.2.1]heptan-7-yl)methanone. Prepared analogous to Example 1 substituting 5-fluoro-2-(pyrimidin-2-yl)benzoic acid with 6-methyl-3-(2H-1,2,3-triazol-2-yl)picolinic acid and (1S,2R,4R)-tert-butyl-2-((pyridin-2-yloxy)methyl)-7-azabicyclo[2.2.1]heptane-7-carboxylate with the title compound of Step A. MS (ESI) mass calcd. for $C_{22}H_{21}F_3N_6O_2$, 458.2; m/z found 459.2 [M+H]$^+$. $^1$H NMR (CDCl$_3$): 8.47-8.37 (m, 1H), 8.12 (dd, J=13.2, 8.4 Hz, 1H), 7.85-7.69 (m, 3H), 7.32 (dd, J=8.4, 0.6 Hz, 0.5H), 7.22 (dd, J=8.4, 0.6 Hz, 0.5H), 6.88-6.82 (m, 0.5H), 6.69-6.59 (m, 0.5H), 4.93-4.81 (m, 1H), 4.39-4.18 (m, 2H), 3.94-3.87 (m, 1H), 2.65-2.60 (s, 1.2H), 2.39-2.22 (m, 2.8H), 2.11-1.33 (m, 6H).

Example 48: (±)-(3-ethoxy-6-methylpyridin-2-yl)(2-(((5-(trifluoromethyl)pyridin-2-yl)oxy)methyl)-7-azabicyclo[2.2.1]heptan-7-yl)methanone

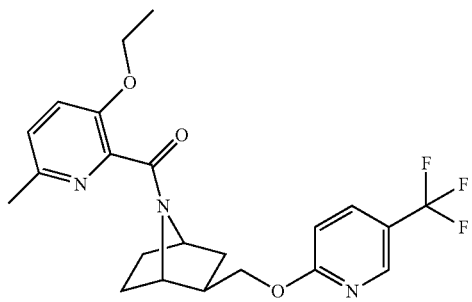 [SMILES: CCOc1ccc(C)nc1C(=O)N1C2CCC1C(COc1ccc(C(F)(F)F)cn1)C2]

Prepared analogous to Example 47 substituting 6-methyl-3-(2H-1,2,3-triazol-2-yl)picolinic acid with 3-ethoxy-6-methylpicolinic acid. MS (ESI) mass calcd. for $C_{22}H_{24}F_3N_3O_3$, 435.2; m/z found 436.2 [M+H]$^+$. $^1$H NMR (CDCl$_3$): 8.43-8.35 (m, 1H), 7.79-7.68 (m, 1H), 7.18-7.07 (m, 1H), 7.07-6.96 (m, 1H), 6.86 (d, J=8.7 Hz, 0.5H), 6.64 (d, J=8.7 Hz, 0.5H), 4.92-4.86 (m, 1H), 4.29-4.20 (m, 1H), 4.19-4.10 (m, 1H), 4.10-3.83 (m, 2H), 3.74 (t, J=3.9 Hz, 1H), 2.52-2.47 (s, 1.5H), 2.41-2.32 (m, 0.5H), 2.28-2.18 (m, 2H), 2.07-1.84 (m, 2H), 1.78-1.63 (m, 1H), 1.62-1.41 (m, 3H), 1.37 (dt, J=11.8, 7.0 Hz, 3H).

Example 49: (±)-(2-(((5-bromopyridin-2-yl)oxy)methyl)-7-azabicyclo[2.2.1]heptan-7-yl)(6-methyl-3-(2H-1,2,3-triazol-2-yl)pyridin-2-yl)methanone

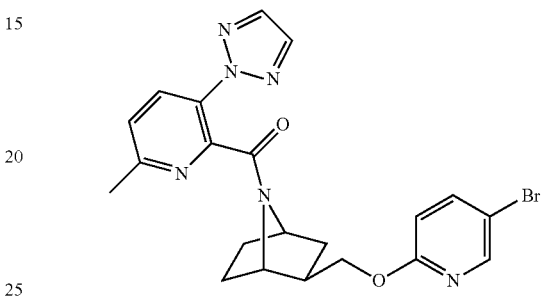

Step A: (±)-2-(((5-bromopyridin-2-yl)oxy)methyl)-7-azabicyclo[2.2.1]heptane. To intermediate B-10 (175 mg, 0.8 mmol) in DMF (3.5 mL) at 0° C. was added NaH (60 wt % in mineral oil, 37 mg, 0.9 mmol). After 30 min, 5-bromo-2-fluoropyridine (190 mg, 1.1 mmol) in DMF (0.5 mL) was added dropwise and the 0° C. ice bath was removed. After 2 h, brine was added and the reaction extracted with EtOAc (2×). The combined organics were washed with brine and dried (Na$_2$SO$_4$) to give a clear oil which was treated with TFA and DCM (1:1, 10 mL). After 2 h, the reaction was concentrated, dissolved in DCM and neutralized with 5% Na$_2$CO$_3$ (aq). The combined organics were extracted with DCM (3×) and dried (Na$_2$SO$_4$) to give the title compound that was used in subsequent reactions without further purification. MS (ESI) mass calcd. for $C_{12}H_{15}BrN_2O$, 282.0; m/z found 283.1, 285.1 [M+H]$^+$. NMR (500 MHz, CDCl$_3$): 8.17 (d, J=2.5 Hz, 1H), 7.63 (dd, J=8.8, 2.5 Hz, 1H), 6.65 (d, J=8.8 Hz, 1H), 4.08-3.99 (m, 2H), 3.65 (t, J=4.5 Hz, 1H), 3.59 (d, J=4.1 Hz, 1H), 2.12-2.06 (m, 1H), 1.87 (s, 1H), 1.68-1.52 (m, 2H), 1.45-1.13 (m, 3H), 0.95-0.76 (m, 1H).

Step B: Prepared analogous to Example 1 substituting 5-fluoro-2-(pyrimidin-2-yl)benzoic acid with 6-methyl-3-(2H-1,2,3-triazol-2-yl)picolinic acid and (1S,2R,4R)-tert-butyl-2-((pyridin-2-yloxy)methyl)-7-azabicyclo[2.2.1]heptane-7-carboxylate with the title compound of Step A. MS (ESI) mass calcd. for $C_{21}H_{21}BrN_6O_2$, 468.1; m/z found 469.1, 471.1 [M+H]$^+$. $^1$H NMR (CDCl$_3$): 8.20 (d, J=2.6 Hz, 0.4H), 8.16 (d, J=2.6 Hz, 0.6H), 8.13 (d, J=8.3 Hz, 0.4H), 8.10 (d, J=8.4 Hz, 0.6H), 7.82-7.77 (m, 2H), 7.64 (dd, J=8.8, 2.6 Hz, 0.4H), 7.60 (dd, J=8.8, 2.6 Hz, 0.6H), 7.33-7.29 (m, 0.4H), 7.22 (d, J=8.4 Hz, 0.6H), 6.69 (d, J=8.8 Hz, 0.4H), 6.50 (d, J=8.8 Hz, 0.6H), 4.84 (dd, J=11.1, 5.2 Hz, 1H), 4.30-4.04 (m, 2H), 3.93-3.85 (m, 1H), 2.62 (s, 1.3H), 2.38-2.17 (m, 2.7H), 2.11-1.95 (m, 1H), 1.94-1.77 (m, 1H), 1.77-1.40 (m, 4H).

Example 50: (±)-(2-(((5-bromopyridin-2-yl)oxy)methyl)-7-azabicyclo[2.2.1]heptan-7-yl)(3-fluoro-2-methoxyphenyl)methanone

Example 52: (±)-(3-fluoro-2-(pyrimidin-2-yl)phenyl)(2-((pyridin-2-yloxy)methyl)-7-azabicyclo[2.2.1]heptan-7-yl)methanone

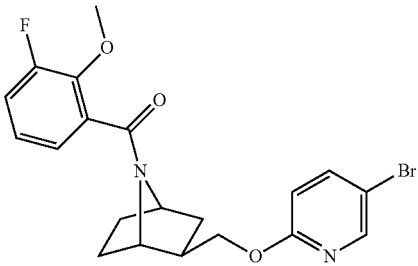 [SMILES: COc1c(F)cccc1C(=O)N1C2CCC1C(COc1ccc(Br)cn1)C2]

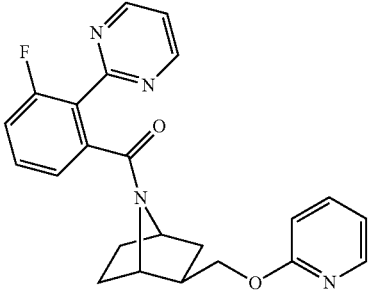

Prepared analogous to Example 49 substituting 6-methyl-3-(2H-1,2,3-triazol-2-yl)picolinic acid with 3-fluoro-2-methoxybenzoic acid. MS (ESI) mass calcd. for $C_{20}H_{20}BrFN_2O_3$, 434.1; m/z found 435.1, 437.1 $[M+H]^+$. $^1$H NMR (CDCl$_3$): 8.19-8.12 (m, 1H), 7.61 (ddd, J=26.6, 8.8, 2.5 Hz, 1H), 7.16-6.98 (m, 2H), 6.96 (dt, J=7.6, 1.3 Hz, 0.5H), 6.85-6.81 (m, 0.5H), 6.69 (dd, J=8.8, 0.8 Hz, 0.5H), 6.46 (d, J=8.7 Hz, 0.5H), 4.88-4.77 (m, 1H), 4.17-4.06 (m, 1H), 4.03-3.86 (m, 4H), 3.81-3.75 (m, 1H), 2.37-2.22 (m, 1H), 2.04-1.40 (m, 6H).

Prepared analogous to Example 1 substituting 5-fluoro-2-(pyrimidin-2-yl)benzoic acid with 3-fluoro-2-(pyrimidin-2-yl)benzoic acid and intermediate B-9 with intermediate B-10. MS (ESI) mass calcd. for $C_{23}H_{21}FN_4O_2$, 404.2; m/z found 405.2 $[M+H]^+$. $^1$H NMR (CDCl$_3$): 8.81 (dd, J=18.0, 4.9 Hz, 2H), 8.20-8.12 (m, 1H), 7.56 (ddd, J=8.3, 7.1, 2.0 Hz, 1H), 7.45 (td, J=8.0, 5.1 Hz, 0.5H), 7.28-7.22 (m, 1.5H), 7.21-7.08 (m, 1.5H), 7.05-6.96 (m, 0.5H), 6.88 (dddd, J=13.2, 7.1, 5.1, 1.0 Hz, 1H), 6.71 (dt, J=8.4, 0.9 Hz, 0.5H), 6.61 (dt, J=8.4, 0.9 Hz, 0.5H), 4.70-4.61 (m, 1H), 4.15-4.07 (m, 1H), 4.06-3.89 (m, 2H), 2.26 (ddt, J=15.3, 8.3, 4.5 Hz, 1H), 1.93-1.27 (m, 6H).

Example 53: (±)-(6-methyl-3-(2H-1,2,3-triazol-2-yl)pyridin-2-yl)(2-((pyridazin-3-yloxy)methyl)-7-azabicyclo[2.2.1]heptan-7-yl)methanone

Example 51: (±)-(2-(((5-bromopyridin-2-yl)oxy)methyl)-7-azabicyclo[2.2.1]heptan-7-yl)(3-ethoxy-6-methylpyridin-2-yl)methanone

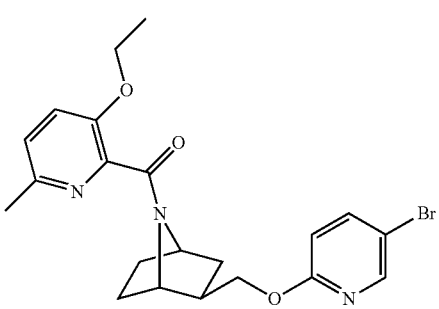 [SMILES: CCOc1ccc(C)nc1C(=O)N1C2CCC1C(COc1ccc(Br)cn1)C2]

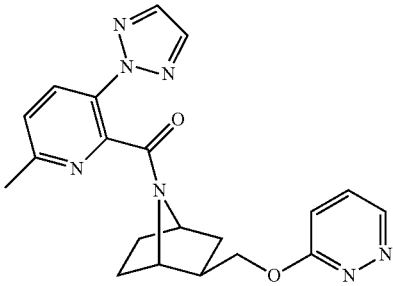 [SMILES: Cc1ccc(-n2nccn2)c(C(=O)N2C3CCC2C(COc2cccnn2)C3)n1]

Prepared analogous to Example 49 substituting 6-methyl-3-(2H-1,2,3-triazol-2-yl)picolinic acid with 3-ethoxy-6-methylpicolinic acid. MS (ESI) mass calcd. for $C_{21}H_{24}BrN_3O_3$, 445.1; m/z found 446.1, 448.1 $[M+H]^+$. $^1$H NMR (CDCl$_3$): 8.17-8.11 (m, 1H), 7.61 (ddd, J=19.5, 8.8, 2.6 Hz, 1H), 7.16-7.06 (m, 1H), 7.05-6.96 (m, 1H), 6.69 (dd, J=8.8, 0.7 Hz, 0.5H), 6.47 (dd, J=8.8, 0.7 Hz, 0.5H), 4.90-4.84 (m, 1H), 4.20-4.10 (m, 1H), 4.09-3.82 (m, 3H), 3.78-3.72 (m, 1H), 2.50 (s, 1.4H), 2.38-2.25 (m, 2.6H), 2.04-1.84 (m, 2H), 1.75-1.40 (m, 4H), 1.60-1.40 (m, 3H), 1.36 (dt, J=7.8, 7.0 Hz, 3H).

Step A: (±)-tert-butyl 2-((pyridazin-3-yloxy)methyl)-7-azabicyclo[2.2.1]heptane-7-carboxylate. To intermediate B-10 (266 mg, 1.2 mmol) in THF (4 mL) at 0 C was added NaH (60 wt % in mineral oil, 70 mg, 1.8 mmol). After 15 min, 3-chloropyridazine (160 mg, 1.4 mmol) was added. The reaction allowed to warm to rt. After 18 h, H$_2$O was added and the mixture extracted with EtOAc. The organic layer was dried. Purification via silica gel chromatography (0-30% EtOAc in heptane) gave the title compound (300 mg, 90%). MS (ESI) mass calcd. for $C_{16}H_{23}N_3O_3$, 305.2; m/z found 306.0 $[M+H]^+$.

Step B: (±)-2-((pyridazin-3-yloxy)methyl)-7-azabicyclo[2.2.1]heptane hydrochloride. To the title compound from step A (300 mg, 1 mmol) in 1,4-dioxane (3 mL) was added 6N HCl in iPrOH (1 mL). The reaction was heated to 70° C. for 3 h, cooled to rt and concentrated to give the title compound that was used without further purification. MS (ESI) mass calcd. for $C_{11}H_{15}N_3O$, 205.1; m/z found 206.0 [M+H]$^+$.

Step C: (±)-(6-methyl-3-(2H-1,2,3-triazol-2-yl)pyridin-2-yl)(2-((pyridazin-3-yloxy)methyl)-7-azabicyclo[2.2.1]heptan-7-yl)methanone. To 6-methyl-3-(2H-1,2,3-triazol-2-yl) picolinic acid (270 mg, 1.3 mmol) in DMF (3 mL) was added DIPEA (630 µL, 3.6 mmol), HBTU (590 mg, 1.5 mmol) and the title compound from step B (250 mg, 1 mmol). After stirring overnight, saturated NaHCO$_3$ (aq) was added and the mixture extracted with EtOAc (3×). The combined organics were dried (MgSO$_4$). Purification by reverse phase chromatography gave material that was triturated with Et$_2$O/pentane to give the title compound (115 mg, 28%) as a beige solid. MS (ESI) mass calcd. for $C_{20}H_{21}N_7O_2$, 391.2; m/z found 392.2 [M+H]$^+$. $^1$H NMR (DMSO-D$_6$): 8.91 (dd, J=8.5, 4.4 Hz, 1H), 8.23-8.04 (m, 3H), 7.69-7.52 (m, 1.5H), 7.41 (d, J=8.4 Hz, 0.5H), 7.28 (d, J=8.9 Hz, 0.5H), 7.10 (d, J=8.9 Hz, 0.5H), 4.60 (t, J=4.8 Hz, 1H), 4.40-4.19 (m, 2H), 3.87 (t, J=4.3 Hz, 0.5H), 3.79 (d, J=4.3 Hz, 0.5H), 2.58 (s, 1.5H), 2.46-2.24 (m, 1H), 2.06 (s, 1.5H), 1.81-1.34 (m, 6H).

Example 54: (±)-(6-methyl-3-(2H-1,2,3-triazol-2-yl) pyridin-2-yl)(2-(((2-methylpyridin-3-yl)oxy) methyl)-7-azabicyclo[2.2.1]heptan-7-yl)methanone

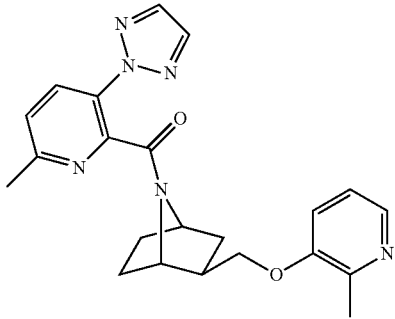 [SMILES: Cc1ccc(-n2nccn2)c(C(=O)N2C3CCC2C(COc2cccnc2C)C3)n1]

Step A: (±)-tert-butyl-2-(((methylsulfonyl)oxy)methyl)-7-azabicyclo[2.2.1]heptane-7-carboxylate. To intermediate B-10 (545 mg, 2.4 mmol) in DCM (12 mL) at 0° C. was added TEA (333 µL, 2.4 mmol) followed by MsCl (190 µL, 2.4 mmol). After 2 h, brine was added and the mixture was extracted with DCM (2×). The combined organics were dried (Na$_2$SO$_4$) to give the title compound (650 mg, 89%) that was used without further purification. MS (ESI) mass calcd. for $C_{12}H_{23}NO_5S$, 305.1; m/z found 249.9 [M−55]$^+$.

Step B: (±)-tert-butyl 2-(((2-methylpyridin-3-yl)oxy) methyl)-7-azabicyclo[2.2.1]heptane-7-carboxylate. To 2-methylpyridin-3-ol in DMF was added KOH. The solution was stirred for 30 min at rt, then the title compound from step A was added and the reaction was heated at 80° C. After 5 h, H$_2$O was added and the mixture extracted with EtOAc. The combined organic layers were dried (MgSO$_4$). Purification via silica gel chromatography (0-7% MeOH in DCM) gave the title compound (201 mg, 90%). MS (ESI) mass calcd. for $C_{18}H_{26}N_2O_3$, 318.2; m/z found 319.0 [M+1]$^+$.

Step C: (±)-2-(((2-methylpyridin-3-yl)oxy)methyl)-7-azabicyclo[2.2.1]heptane. Prepared analogous to example 53 step B substituting (±)-tert-butyl 2-((pyridazin-3-yloxy) methyl)-7-azabicyclo[2.2.1]heptane-7-carboxylate with (±)-tert-butyl 2-(((2-methylpyridin-3-yl)oxy)methyl)-7-azabicyclo[2.2.1]heptane-7-carboxylate. MS (ESI) mass calcd. for $C_{13}H_{18}N_2O$, 218.1; m/z found 219.1 [M+1]$^+$.

Step D: (±)-(6-methyl-3-(2H-1,2,3-triazol-2-yl)pyridin-2-yl)(2-(((2-methylpyridin-3-yl)oxy)methyl)-7-azabicyclo [2.2.1]heptan-7-yl)methanone.

Prepared analogous to example 53 step C substituting (±)-2-((pyridazin-3-yloxy)methyl)-7-azabicyclo[2.2.1]heptane hydrochloride with (±)-2-(((2-methylpyridin-3-yl)oxy) methyl)-7-azabicyclo[2.2.1]heptane. MS (ESI) mass calcd. for $C_{22}H_{24}N_6O_2$, 404.2; m/z found 405.2 [M+H]$^+$. $^1$H NMR (DMSO-D$_6$): 8.22-7.92 (m, 4H), 7.55 (d, J=8.4 Hz, 0.3H), 7.45-7.33 (m, 1H), 7.32-7.10 (m, 1.7H), 4.60-4.57 (m, 1H), 3.92-3.67 (m, 3H), 2.57 (s, 0.9H), 2.42-2.18 (m, 1.9H), 2.08 (s, 2.1H), 1.95 (s, 2.1H), 1.80-1.31 (m, 6H).

Example 55: (±)-(6-methyl-3-(2H-1,2,3-triazol-2-yl) pyridin-2-yl)(2-(((3-methylpyridin-2-yl)oxy) methyl)-7-azabicyclo[2.2.1]heptan-7-yl)methanone

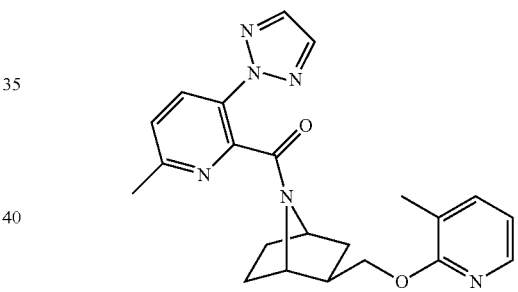

Step A: (±)-tert-butyl 2-(((2-methylpyridin-3-yl)oxy) methyl)-7-azabicyclo[2.2.1]heptane-7-carboxylate. Prepared analogous to Example 7 Step A Method A substituting PBu$_3$ with PPh$_3$, DEAD with DIAD, 5-fluoropyridin-2(1H)-one with 3-methylpyridin-2-ol and performing the reaction at rt. MS (ESI) mass calcd. for $C_{18}H_{26}N_2O_3$, 318.2; m/z found 319.0 [M+H]$^+$.

Step B: (±)-2-(((2-methylpyridin-3-yl)oxy)methyl)-7-azabicyclo[2.2.1]heptane. Prepared analogous to Example 53 Step B substituting (±)-tert-butyl 2-((pyridazin-3-yloxy) methyl)-7-azabicyclo[2.2.1]heptane-7-carboxylate with (±)-tert-butyl 2-(((2-methylpyridin-3-yl)oxy)methyl)-7-azabicyclo[2.2.1]heptane-7-carboxylate. MS (ESI) mass calcd. for $C_{13}H_{18}N_2O$, 218.1; m/z found 219.0 [M+H]$^+$.

Step C: (±)-(6-methyl-3-(2H-1,2,3-triazol-2-yl)pyridin-2-yl)(2-(((3-methylpyridin-2-yl)oxy)methyl)-7-azabicyclo [2.2.1]heptan-7-yl)methanone.

Prepared analogous to Example 53 Step C substituting (±)-2-((pyridazin-3-yloxy)methyl)-7-azabicyclo[2.2.1]heptane hydrochloride with (±)-2-(((2-methylpyridin-3-yl)oxy) methyl)-7-azabicyclo[2.2.1]heptane. MS (ESI) mass calcd. for $C_{22}H_{24}N_6O_2$, 404.2; m/z found 405.2 [M+H]$^+$.

Example 56: (±)-(2-(((1-methyl-1H-pyrazol-5-yl)oxy)methyl)-7-azabicyclo[2.2.1]heptan-7-yl)(6-methyl-3-(2H-1,2,3-triazol-2-yl)pyridin-2-yl)methanone

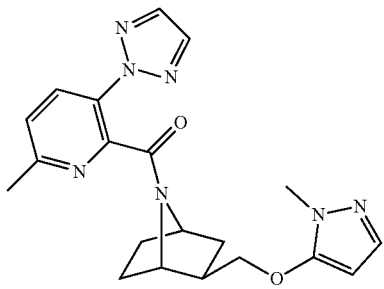 [SMILES: Cc1ccc(-n2nccn2)c(C(=O)N2C3CCC2C(COc2ccnn2C)C3)n1]

Step A: (±)-tert-butyl 2-(((1-methyl-1H-pyrazol-5-yl)oxy)methyl)-7-azabicyclo[2.2.1]heptane-7-carboxylate. Prepared analogous to Example 7 Step A Method A substituting THF with PhCH$_3$ and 5-fluoropyridin-2(1H)-one with 1-methyl-1H-pyrazol-5-ol. MS (ESI) mass calcd. for C$_{16}$H$_{25}$N$_3$O$_3$, 307.2; m/z found 308.0 [M+H]$^+$.

Step B: (±)-2-(((1-methyl-1H-pyrazol-5-yl)oxy)methyl)-7-azabicyclo[2.2.1]heptane. Prepared analogous to Example 53 Step B substituting (±)-tert-butyl 2-((pyridazin-3-yloxy)methyl)-7-azabicyclo[2.2.1]heptane-7-carboxylate the title compound of Step A. MS (ESI) mass calcd. for C$_{11}$H$_{17}$N$_3$O, 207.1; m/z found 208.0 [M+H]$^+$.

Step C: (±)-(2-(((1-methyl-1H-pyrazol-5-yl)oxy)methyl)-7-azabicyclo[2.2.1]heptan-7-yl)(6-methyl-3-(2H-1,2,3-triazol-2-yl)pyridin-2-yl)methanone. Prepared analogous to Example 53 Step C substituting (±)-2-((pyridazin-3-yloxy)methyl)-7-azabicyclo[2.2.1]heptane hydrochloride with the title compound of Step B. MS (ESI) mass calcd. for C$_{20}$H$_{23}$N$_7$O$_2$, 393.2; m/z found 394.2 [M+H]$^+$. $^1$H NMR (DMSO-D$_6$): 8.18-8.05 (m, 3H), 7.56 (d, J=8.4 Hz, 0.4H), 7.49 (d, J=8.4 Hz, 0.6H), 7.23 (d, J=1.7 Hz, 0.4H), 7.19 (d, J=1.7 Hz, 0.6H), 5.70 (d, J=1.8 Hz, 0.4H), 5.59 (d, J=1.8 Hz, 0.6H), 4.59-4.56 (m, 1H), 3.96-3.76 (m, 3H), 3.57 (s, 1.2H), 3.34 (s, 1.8H), 2.58 (s, 1.2H), 2.39-2.17 (m, 2.8H), 1.87-1.27 (m, 6H).

Example 57: (±)-(6-methyl-3-(2H-1,2,3-triazol-2-yl)pyridin-2-yl)(2-((pyridin-4-yloxy)methyl)-7-azabicyclo[2.2.1]heptan-7-yl)methanone

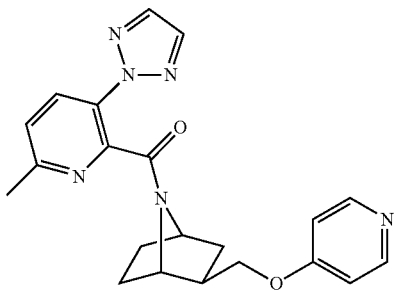 [SMILES: Cc1ccc(-n2nccn2)c(C(=O)N2C3CCC2C(COc2ccncc2)C3)n1]

Prepared analogous to Example 54 substituting 2-methylpyridin-3-ol with pyridin-4-ol. MS (ESI) mass calcd. for C$_{21}$H$_{22}$N$_6$O$_2$, 390.2; m/z found 391.2 [M+H]$^+$. $^1$H NMR (DMSO-D$_6$): 8.41 (d, J=5.5 Hz, 0.8H), 8.36 (d, J=5.5 Hz, 1.2H), 8.20-8.02 (m, 3H), 7.55 (d, J=8.4 Hz, 0.4H), 7.40 (d, J=8.4 Hz, 0.6H), 7.00 (d, J=6.2 Hz, 0.8H), 6.88 (d, J=6.2 Hz, 1.2H), 4.64-4.51 (m, 1H), 4.02-3.78 (m, 2.4H), 3.75 (d, J=4.4 Hz, 0.6H), 2.57 (s, 1.2H), 2.39-2.20 (m, 1H), 2.04 (s, 1.8H), 1.87-1.30 (m, 6H).

Example 58: # (±)-(6-methyl-3-(2H-1,2,3-triazol-2-yl)pyridin-2-yl)(2-((pyridin-3-yloxy)methyl)-7-azabicyclo[2.2.1]heptan-7-yl)methanone

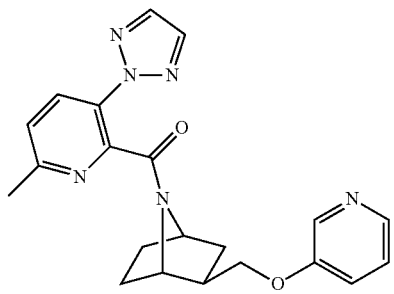 [SMILES: Cc1ccc(-n2nccn2)c(C(=O)N2C3CCC2C(COc2cccnc2)C3)n1]

Prepared analogous to Example 54 substituting 2-methylpyridin-3-ol with pyridin-3-ol. MS (ESI) mass calcd. for C$_{21}$H$_{22}$N$_6$O$_2$, 390.2; m/z found 391.2 [M+H]$^+$. $^1$H NMR (DMSO-D$_6$): 8.33 (d, J=2.7 Hz, 0.4H), 8.21-8.05 (m, 4.6H), 7.55 (d, J=8.4 Hz, 0.4H), 7.46-7.25 (m, 2.6H), 4.58 (t, J=4.8 Hz, 1H), 3.95-3.80 (m, 2.4H), 3.77 (d, J=4.4 Hz, 0.6H), 2.57 (s, 1.2H), 2.38-2.18 (m, 1H), 2.02 (s, 1.8H), 1.85-1.31 (m, 6H).

Example 59: (±)-(6-methyl-3-(2H-1,2,3-triazol-2-yl)pyridin-2-yl)(2-((pyrimidin-2-yloxy)methyl)-7-azabicyclo[2.2.1]heptan-7-yl)methanone

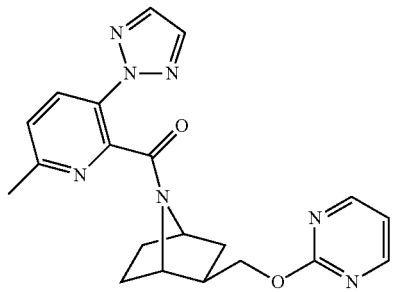 [SMILES: Cc1ccc(-n2nccn2)c(C(=O)N2C3CCC2C(COc2ncccn2)C3)n1]

Prepared analogous to Example 53 substituting 2-chloropyridazine with 2-chloropyrimidine. MS (ESI) mass calcd. for C$_{20}$H$_{21}$N$_7$O$_2$, 391.2; m/z found 392.2 [M+H]$^+$. $^1$H NMR (DMSO-D$_6$): 8.65 (d, J=4.8 Hz, 0.8H), 8.59 (d, J=4.8 Hz, 1.2H), 8.22-8.02 (m, 3H), 7.56 (d, J=8.4 Hz, 0.4H), 7.44 (d, J=8.4 Hz, 0.6H), 7.19-7.13 (m, 1H), 4.59 (t, J=4.5 Hz, 0.6H), 4.55 (d, J=4.4 Hz, 0.4H), 4.24-4.04 (m, 2H), 3.85 (t, J=4.3 Hz, 0.4H), 3.78 (d, J=4.0 Hz, 0.6H), 2.58 (s, 1.2H), 2.39-2.21 (m, 1H), 2.11 (s, 1.8H), 1.86-1.29 (m, 6H).

Example 60: (±)-(6-methyl-3-(2H-1,2,3-triazol-2-yl)pyridin-2-yl)(2-((pyrazin-2-yloxy)methyl)-7-azabicyclo[2.2.1]heptan-7-yl)methanone

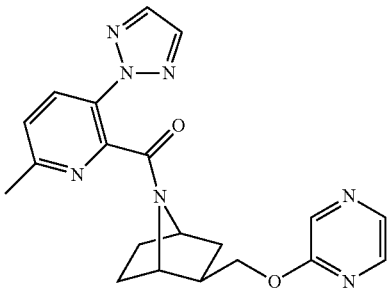 [SMILES: Cc1ccc(-n2nccn2)c(C(=O)N2C3CCC2C(COc2cnccn2)C3)n1]

Prepared analogous to Example 53 substituting 2-chloropyridazine with 2-pyrazine. MS (ESI) mass calcd. for $C_{20}H_{21}N_7O_2$, 391.2; m/z found 392.2 [M+H]$^+$.

Example 61: (±)-(6-methyl-3-(2H-1,2,3-triazol-2-yl)pyridin-2-yl)(2-((pyrimidin-4-yloxy)methyl)-7-azabicyclo[2.2.1]heptan-7-yl)methanone

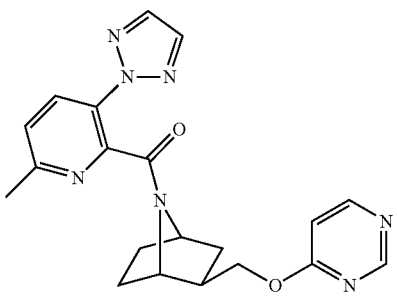 [SMILES: Cc1ccc(-n2nccn2)c(C(=O)N2C3CCC2C(COc2ccncn2)C3)n1]

Prepared analogous to Example 55 substituting 3-methylpyridin-2-ol with pyrimidin-4-ol. MS (ESI) mass calcd. for $C_{20}H_{21}N_7O_2$, 391.2; m/z found 392.2 [M+H]$^+$. The product is present as a mixture of conformers (ratio ca. 50:50) $^1$H NMR (300 MHz, DMSO) 8.84 (s, 0.5H), 8.77 (s, 0.5H), 8.53 (d, J=5.8 Hz, 0.5H), 8.49 (d, J=5.8 Hz, 0.5H), 8.22-8.01 (m, 3H), 7.55 (d, J=8.4 Hz, 0.5H), 7.43 (d, J=8.4 Hz, 0.5H), 7.00 (d, J=5.7 Hz, 0.5H), 6.85 (d, J=5.8 Hz, 0.5H), 4.58 (t, J=3.7 Hz, 0.5H), 4.53 (d, J=4.2 Hz, 0.5H), 4.25-4.04 (m, 2H), 3.85 (t, J=3.7 Hz, 0.5H), 3.75 (d, J=3.9 Hz, 0.5H), 2.57 (s, 1.5H), 2.40-2.16 (m, 1H), 2.12 (s, 1.5H), 1.85-1.31 (m, 6H).

Example 62: (±)-(6-methyl-3-(2H-1,2,3-triazol-2-yl)pyridin-2-yl)(2-(((6-methylpyridin-2-yl)oxy)methyl)-7-azabicyclo[2.2.1]heptan-7-yl)methanone

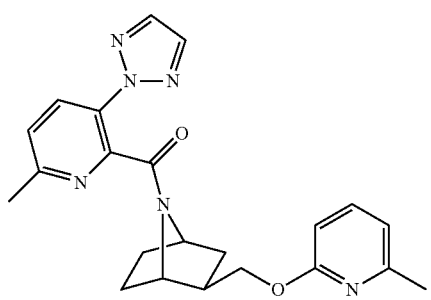

Prepared analogous to Example 55 substituting 3-methylpyridin-2-ol with 6-methylpyridin-2-ol. MS (ESI) mass calcd. for $C_{22}H_{24}N_6O_2$, 404.2; m/z found 405.2 [M+H]$^+$. $^1$H NMR (DMSO-D$_6$): 8.17 (d, J=8.4 Hz, 0.5H), 8.12 (d, J=8.4 Hz, 0.5H), 8.10 (s, 1H), 8.06 (s, 1H), 7.63-7.49 (m, 1.5H), 7.41 (d, J=8.4 Hz, 0.5H), 6.85 (d, J=7.2 Hz, 0.5H), 6.81 (d, J=7.2 Hz, 0.5H), 6.64 (d, J=8.2 Hz, 0.5H), 6.46 (d, J=8.2 Hz, 0.5H), 4.58 (t, J=4.4 Hz, 0.5H), 4.54 (d, J=4.5 Hz, 0.5H), 4.16-3.95 (m, 2H), 3.83 (t, J=4.4 Hz, 0.5H), 3.74 (d, J=4.4 Hz, 0.5H), 2.58 (s, 1.5H), 2.43 (s, 1.5H), 2.37 (s, 1.5H), 2.33-2.14 (m, 1H), 2.11 (s, 1.5H), 1.85-1.31 (m, 6H).

Example 63: (±)-(2-(((5-fluoropyridin-2-yl)oxy)methyl)-7-azabicyclo[2.2.1]heptan-7-yl)(6-methyl-3-(oxazol-2-yl)pyridin-2-yl)methanone

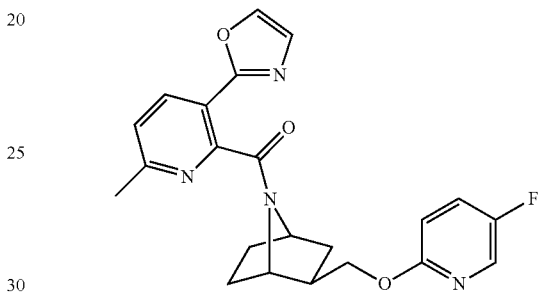

Prepared analogous to Example 7 substituting intermediate A-21 with intermediate A-43. MS (ESI) mass calcd. for $C_{22}H_{21}FN_4O_3$, 408.2; m/z found 409.2 [M+H].

Example 64: (±)-(2-(((5-fluoropyridin-2-yl)oxy)methyl)-7-azabicyclo[2.2.1]heptan-7-yl)(6-methyl-3-(pyrimidin-2-yl)pyridin-2-yl)methanone

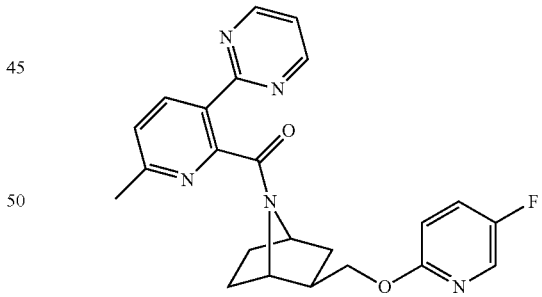

Prepared analogous to Example 7 substituting intermediate A-21 with 6-methyl-3-(pyrimidin-2-yl)picolinic acid. MS (ESI) mass calcd. for $C_{23}H_{22}FN_5O_2$, 419.2; m/z found 420.2 [M+H]$^+$. $^1$H NMR (DMSO-D$_6$): 8.91 (d, J=4.9 Hz, 0.8H), 8.84 (d, J=4.9 Hz, 1.2H), 8.33-8.29 (m, 1H), 8.22 (d, J=3.1 Hz, 0.4H), 8.13 (d, J=3.1 Hz, 0.6H), 7.76-7.59 (m, 1H), 7.53-7.41 (m, 1.4H), 7.35 (d, J=8.1 Hz, 0.6H), 6.94 (dd, J=9.1, 3.6 Hz, 0.4H), 6.75 (dd, J=9.1, 3.6 Hz, 0.6H), 4.59 (t, J=4.1 Hz, 0.6H), 4.56 (d, J=3.8 Hz, 0.4H), 4.16 (dd, J=14.6, 6.2 Hz, 1H), 4.08-3.97 (m, 1H), 3.87 (br s, 0.4H), 3.76 (d, J=3.9 Hz, 0.6H), 2.56 (s, 1.2H), 2.39-2.15 (m, 1H), 2.10 (s, 1.8H), 1.91-1.32 (m, 6H).

Example 65: (±)-(3,6'-dimethyl-[2,3'-bipyridin]-2'-yl)(2-(((5-fluoropyridin-2-yl)oxy)methyl)-7-azabicyclo[2.2.1]heptan-7-yl)methanone

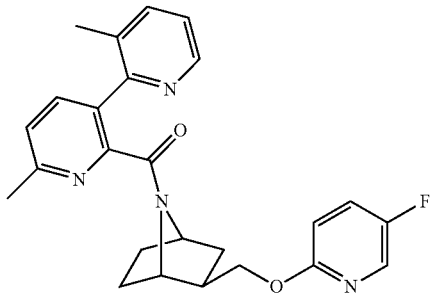 [SMILES: Cc1ccc(-c2ncccc2C)c(C(=O)N2C3CCC2C(COc2ccc(F)cn2)C3)n1]

Prepared analogous to Example 7 substituting intermediate A-21 with 3,6'-dimethyl-[2,3'-bipyridine]-2'-carboxylic acid. MS (ESI) mass calcd. for $C_{25}H_{25}FN_4O_2$, 432.2; m/z found 433.2 [M+H]$^+$. $^1$H NMR (DMSO-D$_6$): 8.33 (t, J=5.1 Hz, 1H), 8.16 (s, 1H), 7.79-7.60 (m, 3H), 7.40 (d, J=7.9 Hz, 0.5H), 7.32-7.23 (m, 1H), 7.20 (dd, J=7.6, 4.8 Hz, 0.5H), 6.85 (dd, J=9.1, 3.6 Hz, 0.5H), 6.80 (dd, J=9.1, 3.6 Hz, 0.5H), 4.39 (brs, 0.5H), 4.35 (d, J=4.1 Hz, 0.5H), 4.19 (t, J=10.3 Hz, 0.5H), 4.04 (dd, J=10.4, 5.2 Hz, 0.5H), 3.90 (d, J=4.8 Hz, 0.5H), 3.85 (t, J=4.0 Hz, 0.5H), 3.75-3.53 (m, 1H), 2.56 (s, 1.5H), 2.22 2.17 (m, 3.5H), 2.11 (s, 1.5H), 1.90-1.81 (m, 0.5H), 1.79-1.17 (m, 6H).

Example 66: (±)-(2-(((5-fluoropyridin-2-yl)oxy)methyl)-7-azabicyclo[2.2.1]heptan-7-yl)(6-methyl-3-(3-methyl-1,2,4-oxadiazol-5-yl)pyridin-2-yl)methanone

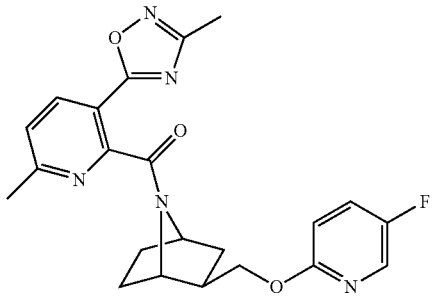 [SMILES: Cc1ccc(-c2nc(C)no2)c(C(=O)N2C3CCC2C(COc2ccc(F)cn2)C3)n1]

Prepared analogous to Example 7 substituting intermediate A-21 with 6-methyl-3-(3-methyl-1,2,4-oxadiazol-5-yl) picolinic acid. MS (ESI) mass calcd. for $C_{22}H_{22}FN_5O_3$, 423.2; m/z found 424.2 [M+H]$^+$. $^1$H NMR (DMSO-D$_6$): 8.33 (d, J=8.1 Hz, 0.4H), 8.28 (d, J=8.1 Hz, 0.6H), 8.14 (d, J=3.1 Hz, 0.4H), 8.10 (d, J=3.1 Hz, 0.6H), 7.76-7.60 (m, 1H), 7.58 (d, J=8.2 Hz, 0.4H), 7.47 (d, J=8.2 Hz, 0.6H), 6.95 (dd, J=3.6, 9.2 Hz, 0.4H), 6.72 (dd, J=3.6, 9.2 Hz, 0.6H), 4.67 (t, J=4.5 Hz, 0.6H), 4.62 (d, J=4.6 Hz, 0.4H), 4.16-3.92 (m, 2H), 3.81 (d, J=4.3 Hz, 0.4H), 3.73 (d, J=4.6 Hz, 0.6H), 2.60 (s, 1.2H), 2.41 (s, 1.2H), 2.38 (s, 1.8H), 2.37-2.19 (m, 1H), 2.18 (s, 1.8H), 1.90-1.30 (m, 6H).

Example 67: (±)-(2-(((5-fluoropyridin-2-yl)oxy)methyl)-7-azabicyclo[2.2.1]heptan-7-yl)(6-methyl-3-(3-methyl-1H-pyrazol-1-yl)pyridin-2-yl)methanone

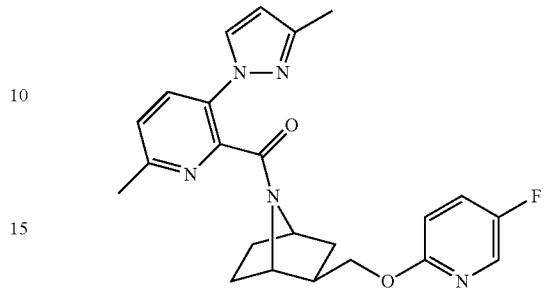

Prepared analogous to Example 7 substituting intermediate A-21 with 6-methyl-3-(3-methyl-1H-pyrazol-1-yl)picolinic acid. MS (ESI) mass calcd. for $C_{23}H_{24}FN_5O_2$, 421.2; m/z found 422.2 [M+H]$^+$. MP=123.2° C.

Example 68: (±)-(2-(((5-fluoropyridin-2-yl)oxy)methyl)-7-azabicyclo[2.2.1]heptan-7-yl)(6-methyl-3-(pyrrolidin-1-yl)pyridin-2-yl)methanone

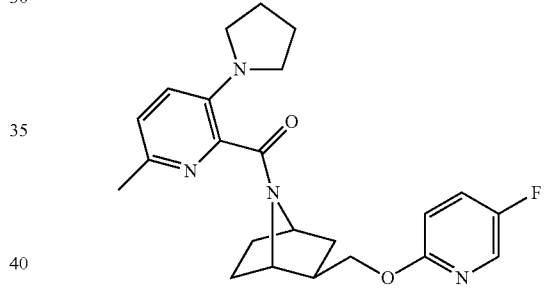

Step A: 6-methyl-3-(pyrrolidin-1-yl)picolinonitrile. To 2-bromo-6-methyl-3-(2H-1,2,3-triazol-2-yl)pyridine (720 mg, 3.7 mmol), pyrrolidine (450 μL, 5.5 mmol), Pd(OAc)$_2$ (25 mg, 11 mol %), XPhos (122 mg, 25 mol %) and Cs$_2$CO$_3$ (2.4 g, 7.3 mmol) in a sealed tube was added PhCH$_3$. The vessel was sealed and heated at 100° C. overnight. After cooling to rt, the reaction was diluted with EtOAc and H$_2$O. The organic layer was dried (MgSO$_4$) and concentrated. Purification via silica gel chromatography (0-50% EtOAc in DCM) gave the title compound (186 mg, 27%).

Step B: 6-methyl-3-(pyrrolidin-1-yl)picolinic acid. To the title compound of Step A (162 mg, 0.9 mmol) in EtOH (2.6 mL) was added 4M KOH (650 μL, 2.6 mmol). The reaction was then heated at 90° C. for 18 h. Additional 4M KOH (1.5 mL, 6 mmol) was added and heating continued overnight. The reaction was then cooled to rt, acidified with 1N HCl (aq), concentrated and used without further purification in the next step.

Step C: (±)-(2-(((5-fluoropyridin-2-yl)oxy)methyl)-7-azabicyclo[2.2.1]heptan-7-yl)(6-methyl-3-(pyrrolidin-1-yl)pyridin-2-yl)methanone Prepared analogous to Example 7 substituting intermediate A-9 with the title compound from Step B. MS (ESI) mass calcd. for $C_{23}H_{27}FN_4O_2$, 410.2; m/z found 411.2 [M+H]$^+$. $^1$H NMR (DMSO-D$_6$): 8.14 (d, J=3.0 Hz, 0.5H), 8.10 (d, J=3.0 Hz, 0.5H), 7.68-7.38 (m, 2H), 6.92

(dd, J=9.1, 3.6 Hz, 0.5H), 6.71 (dd, J=9.1, 3.6 Hz, 0.5H), 4.66 (br s, 0.5H), 4.60 (br s, 0.5H), 4.08-3.01 (m, 7H), 2.45 (s, 1.5H), 2.40-2.01 (m, 2.5H), 1.94-1.30 (m, 10H).

Example 69: # (±)-(2-(((5-fluoropyridin-2-yl)oxy)methyl)-7-azabicyclo[2.2.1]heptan-7-yl)(6-methyl-3-(3-methylisoxazol-5-yl)pyridin-2-yl)methanone

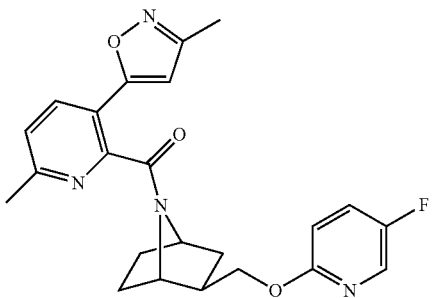 [SMILES: Cc1cc(-c2ccc(C)nc2C(=O)N2C3CCC2C(COc2ccc(F)cn2)C3)on1]

Prepared analogous to Example 7 substituting intermediate A-21 with 6-methyl-3-(3-methylisoxazol-5-yl)picolinic acid. MS (ESI) mass calcd. for $C_{23}H_{23}FN_4O_3$, 422.2; m/z found 423.2 [M+H]$^+$. $^1$H NMR (DMSO-D$_6$): 8.11 (dt, J=10.0, 5.4 Hz, 2H), 7.77-7.55 (m, 1H), 7.50 (d, J=8.2 Hz, 0.4H), 7.38 (d, J=8.2 Hz, 0.6H), 6.94 (dd, J=9.1, 3.6 Hz, 0.4H), 6.70 (dd, J=9.1, 3.6 Hz, 0.6H), 6.62 (d, J=1.6 Hz, 1H), 4.67 (t, J=4.6 Hz, 0.6H), 4.61 (d, J=4.7 Hz, 0.4H), 3.98-3.88 (m, 2H), 3.60 (t, J=4.5 Hz, 0.4H), 3.54 (d, J=3.8 Hz, 0.6H), 2.55 (s, 1.2H), 2.38-2.14 (m, 4H), 2.12 (s, 1.8H), 1.86-1.13 (m, 6H).

Example 70: (±)-(2-(((5-fluoropyridin-2-yl)oxy)methyl)-7-azabicyclo[2.2.1]heptan-7-yl)(6-methyl-3-(1H-pyrazol-1-yl)pyridin-2-yl)methanone

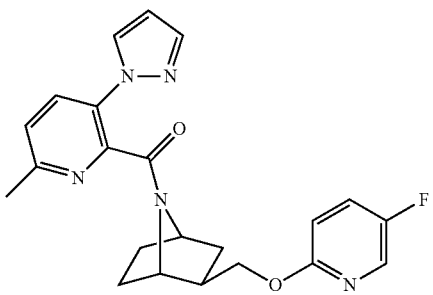 [SMILES: Cc1ccc(-n2cccn2)c(C(=O)N2C3CCC2C(COc2ccc(F)cn2)C3)n1]

Prepared analogous to Example 63 substituting 6-methyl-3-(oxazol-2-yl)picolinic acid with 6-methyl-3-(1H-pyrazol-1-yl)picolinic acid. MS (ESI) mass calcd. for $C_{22}H_{22}FN_5O_2$, 407.2; m/z found 408.2 [M+H]$^+$. $^1$H NMR (DMSO-D$_6$): 8.17 (d, J=3.1 Hz, 0.5H), 8.13 (d, J=3.1 Hz, 0.5H), 8.08 (t, J=2.4 Hz, 1H), 7.95 (t, J=8.5 Hz, 1H), 7.74-7.61 (m, 2H), 7.49 (d, J=8.3 Hz, 0.5H), 7.36 (d, J=8.4 Hz, 0.5H), 6.91 (dd, J=9.1, 3.6 Hz, 0.5H), 6.72 (dd, J=9.1, 3.6 Hz, 0.5H), 6.52-6.49 (m, 0.5H), 6.49-6.46 (m, 0.5H), 4.55 (t, J=4.5 Hz, 0.5H), 4.50 (d, J=4.7 Hz, 0.5H), 3.94 (d, J=7.6 Hz, 2H), 3.67 (t, J=4.2 Hz, 0.5H), 3.59 (d, J=4.5 Hz, 0.5H), 2.54 (s, 1.5H), 2.30-2.11 (m, 1H), 2.07 (s, 1.5H), 1.76-1.14 (m, 6H).

Example 71: (±)-(5-methyl-3-(2H-1,2,3-triazol-2-yl)pyridin-2-yl)(2-((pyridin-2-yloxy)methyl)-7-azabicyclo[2.2.1]heptan-7-yl)methanone

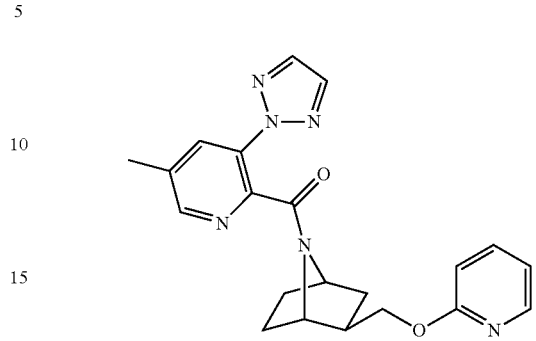

Prepared analogous to Example 2 substituting intermediate A-9 with 5-methyl-3-(2H-1,2,3-triazol-2-yl)picolinic acid. MS (ESI) mass calcd. for $C_{21}H_{22}N_6O_2$, 390.2; m/z found 391.0 [M+H]$^+$. MP=159.7° C.

Example 72: (±)-(4-methyl-3-(2H-1,2,3-triazol-2-yl)pyridin-2-yl)(2-((pyridin-2-yloxy)methyl)-7-azabicyclo[2.2.1]heptan-7-yl)methanone

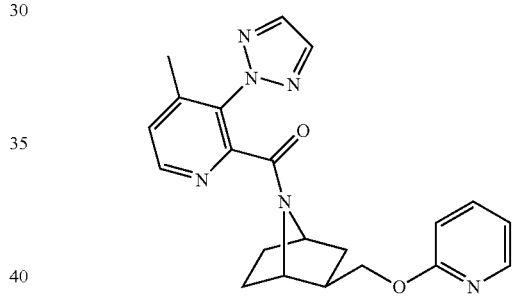

Prepared analogous to Example 2 substituting intermediate A-9 with 4-methyl-3-(2H-1,2,3-triazol-2-yl)picolinic acid. MS (ESI) mass calcd. for $C_{21}H_{22}N_6O_2$, 390.2; m/z found 391.0 [M+H]$^+$. MP=114.5° C.

Example 73: (±)-(3-(dimethylamino)-6-methylpyridin-2-yl)(2-((pyridin-2-yloxy)methyl)-7-azabicyclo[2.2.1]heptan-7-yl)methanone

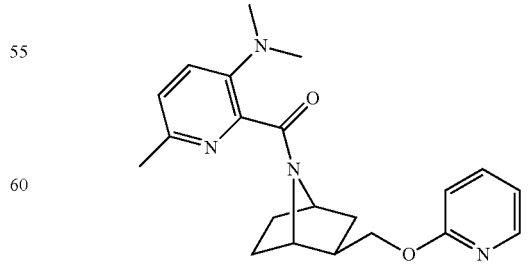

Step A: 3-(dimethylamino)-6-methylpicolinamide. A mixture of 3-bromo-6-methylpicolinonitrile (1 g, 5 mmol) and dimethylamine (2 mL) were heated in a microwave reactor for 2 h at 140° C. The mixture was then concentrated and purified via silica gel chromatography (0-5% MeOH in DCM) to give the title compound (249 mg, 27%). MS (ESI) mass calcd. for $C_9H_{13}N_3O$, 179.1; m/z found 180.0 [M+H].

Step B: 3-(dimethylamino)-6-methylpicolinic acid. To the title compound of Step A (91 mg, 0.5 mmol) in EtOH (1 mL) was added 4M KOH (0.5 µL). The reaction was then heated at 90° C. for 18 h. The reaction was then cooled to rt, acidified with 1N HCl (aq) to pH=3, concentrated and used without further purification in the next step.

Step C: Prepared analogous to Example 2 substituting intermediate A-9 with the title compound of Step B. MS (ESI) mass calcd. for $C_{21}H_{26}N_4O_2$, 366.2; m/z found 367 [M+H]$^+$.

Example 74: (±)-(3-(2H-1,2,3-triazol-2-yl)quinolin-2-yl)(2-((pyridin-2-yloxy)methyl)-7-azabicyclo[2.2.1]heptan-7-yl)methanone

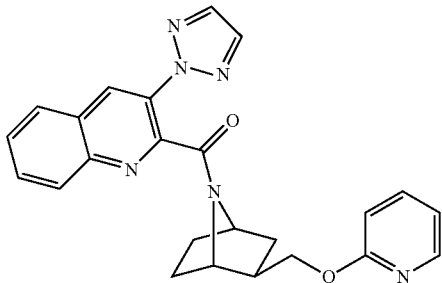 [SMILES: O=C(c1nc2ccccc2cc1-n1nccn1)N1C2CCC1C(COc1ccccn1)C2]

Prepared analogous to Example 2 substituting intermediate A-9 with 3-(2H-1,2,3-triazol-2-yl)quinoline-2-carboxylic acid. MS (ESI) mass calcd. for $C_{24}H_{22}N_6O_2$, 426.2; m/z found 427.2 [M+H]$^+$. $^1$H NMR (DMSO-D$_6$): 8.93 (s, 0.5H), 8.87 (s, 0.5H), 8.26-8.09 (m, 2H), 7.96-7.86 (m, 0.5H), 7.82-7.51 (m, 5H), 7.33 (d, J=8.4 Hz, 0.5H), 7.00 (t, J=6.0 Hz, 1H), 6.87 (d, J=8.3 Hz, 0.5H), 6.52 (d, J=8.3 Hz, 0.5H), 4.70-4.57 (m, 1H), 4.33 (t, J=10.5 Hz, 0.5H), 4.24-4.05 (m, 1.5H), 4.00 (br t, J=3.8 Hz, 0.5H), 3.93 (d, J=3.6 Hz, 0.5H), 2.44-2.20 (m, 1H), 2.01-1.35 (m, 6H).

Example 75: (±)-(7-ethoxyquinolin-8-yl)(2-((pyridin-2-yloxy)methyl)-7-azabicyclo[2.2.1]heptan-7-yl)methanone

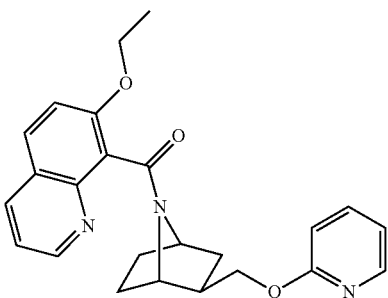 [SMILES: CCOc1ccc2cccnc2c1C(=O)N1C2CCC1C(COc1ccccn1)C2]

Prepared analogous to Example 2 substituting intermediate A-9 with intermediate A-29. MS (ESI) mass calcd. for $C_{24}H_{25}N_3O_3$, 403.2; m/z found 404.2 [M+H]$^+$. $^1$H NMR (DMSO-D$_6$): 9.02-8.54 (m, 1.6H), 8.42 (d, J=7.9 Hz, 0.8H), 8.31-7.83 (m, 2.2H), 7.83-6.75 (m, 3.8H), 6.64-6.46 (m, 0.2H), 6.24 (m, 0.4H), 4.86-4.62 (m, 1.2H), 4.46-4.01 (m, 3.6H), 3.61-3.23 (m, 1.2H), 2.44-2.06 (m, 1H), 2.06-1.15 (m, 9H).

Example 76: (±)-(3,6-dimethylimidazo[1,2-a]pyridin-5-yl)(2-((pyridin-2-yloxy)methyl)-7-azabicyclo[2.2.1]heptan-7-yl)methanone

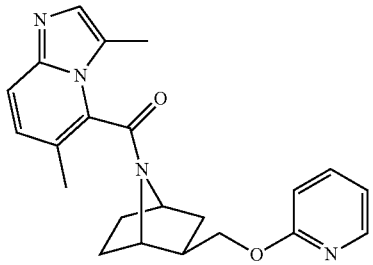 [SMILES: Cc1ccc2ncc(C)n2c1C(=O)N1C2CCC1C(COc1ccccn1)C2]

Step A: 3,6-dimethylimidazo[1,2-a]pyridine-5-carboxylic acid. Prepared analogous to Example 82 substituting chloroacetaldehyde with 2-bromopropanal. MS (ESI) mass calcd. for $C_{10}H_{10}N_2O_2$, 190.1; m/z found 191.0 [M+H]$^+$.

Step B: (±)-(3,6-dimethylimidazo[1,2-a]pyridin-5-yl)(2-((pyridin-2-yloxy)methyl)-7-azabicyclo[2.2.1]heptan-7-yl)methanone. Prepared analogous to Example 2 substituting intermediate A-9 with the title compound of Step A. MS (ESI) mass calcd. for $C_{22}H_{24}N_4O_2$, 376.2; m/z found 377.2 [M+H]$^+$. The product is present as a mixture of conformers (ratio ca. 85:15). $^1$H NMR (300 MHz, DMSO) 8.18 (dd, J=4.5, 1.4 Hz, 0.85H), 7.91 (d, J=5.1 Hz, 0.15H), 7.74 (td, J=7.1, 1.8 Hz, 0.85H), 7.53 (d, J=9.1 Hz, 0.85H), 7.50-7.39 (m, 0.15H), 7.36 (s, 1H), 7.12 (dd, J=6.3 Hz, 1H), 7.06-6.95 (m, 0.85H), 6.88 (d, J=8.4 Hz, 0.85H), 6.72 (d, J=8.6 Hz, 0.15H), 6.62 (d, J=7.4 Hz, 0.15H), 6.46 (d, J=8.5 Hz, 0.15H), 4.77 (d, J=4.4 Hz, 0.85H), 4.72 (d, J=3.6 Hz, 0.15H), 4.25-4.10 (m, 1H), 4.10-3.98 (m, 1H), 3.78 (br s, 0.85H), 3.69 (br s, 0.15H), 2.48-2.38 (m, 1.85H), 2.36 (s, 2H), 2.30 (s, 2H), 2.25-2.21 (m, 0.85H), 2.20-2.16 (m, 0.3H), 1.98-1.32 (m, 6H).

Example 77: (±)-(1-methyl-4-phenyl-1H-pyrazol-3-yl)(2-((pyridin-2-yloxy)methyl)-7-azabicyclo[2.2.1]heptan-7-yl)methanone

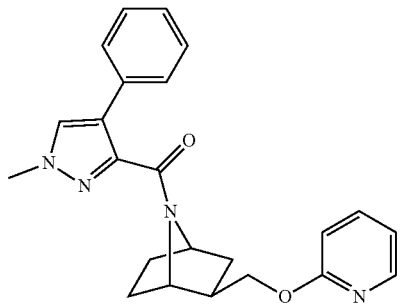 [SMILES: Cn1cc(-c2ccccc2)c(C(=O)N2C3CCC2C(COc2ccccn2)C3)n1]

Prepared analogous to Example 2 substituting intermediate A-9 with 1-methyl-4-phenyl-1H-pyrazole-3-carboxylic acid. MS (ESI) mass calcd. for $C_{23}H_{24}N_4O_2$, 388.2; m/z found 389.2 [M+H]$^+$. $^1$H NMR (DMSO-D$_6$): 8.18 (d, J=3.8

Hz, 0.5H), 8.08 (d, J=3.9 Hz, 0.5H), 8.03 (s, 0.5H), 7.92 (s, 0.5H), 7.76-7.62 (m, 1H), 7.46-7.16 (m, 5H), 7.04-6.90 (m, 1H), 6.84 (d, J=8.3 Hz, 0.5H), 6.71 (d, J=8.3 Hz, 0.5H), 4.60 (t, J=4.6 Hz, 0.5H), 4.56 (d, J=4.7 Hz, 0.5H), 4.15 (br s, 1H), 4.06 (br s, 1H), 3.98-3.83 (m, 2.5H), 3.55 (s, 1.5H), 2.29-2.15 (m, 1H), 1.79-1.22 (m, 6H).

Example 78: (±)-(1-methyl-3-phenyl-1H-pyrazol-4-yl)(2-((pyridin-2-yloxy)methyl)-7-azabicyclo[2.2.1]heptan-7-yl)methanone

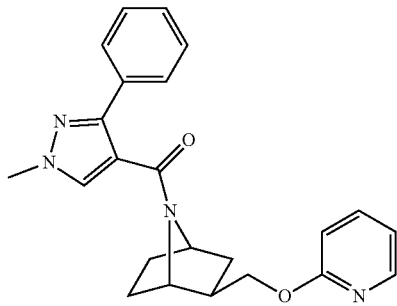 [SMILES: Cn1cc(C(=O)N2C3CCC2C(COc2ccccn2)C3)c(-c2ccccc2)n1]

Prepared analogous to Example 2 substituting intermediate A-9 with 1-methyl-3-phenyl-1H-pyrazole-4-carboxylic acid. MS (ESI) mass calcd. for $C_{23}H_{24}N_4O_2$, 388.2; m/z found 389.2 [M+H]$^+$. $^1$H NMR (DMSO-D$_6$): 8.16 (br s, 1H), 8.09-7.75 (m, 1H), 7.70 (t, J=7.2 Hz, 1H), 7.58 (d, J=7.0 Hz, 2H), 7.47-7.20 (m, 3H), 7.10-6.90 (m, 1H), 6.92-6.52 (br s, 1H), 4.48 (br s, 1H), 4.21-3.44 (m, 6H), 2.17 (br s, 1H), 1.86-1.05 (m, 6H).

Example 79: (±)-((3,7-dimethylimidazo[1,2-a]pyridin-8-yl)(2-((pyridin-2-yloxy)methyl)-7-azabicyclo[2.2.1]heptan-7-yl)methanone

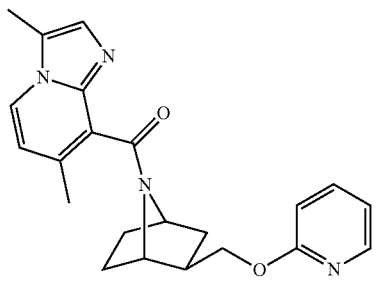 [SMILES: Cc1ccn2c(C)cnc2c1C(=O)N1C2CCC1C(COc1ccccn1)C2]

Step A: Prepared analogous to Example 76 substituting 6-amino-3-methylpicolinic acid with 2-amino-4-methylnicotinic acid.
Step B: (±)-((3,7-dimethylimidazo[1,2-a]pyridin-8-yl)(2-((pyridin-2-yloxy)methyl)-7-azabicyclo[2.2.1]heptan-7-yl)methanone. Prepared analogous to Example 2 substituting intermediate A-9 with 3,7-dimethylimidazo[1,2-a]pyridine-8-carboxylic acid. MS (ESI) mass calcd. for $C_{22}H_{24}N_4O_2$, 376.2; m/z found 377.2 [M+H]$^+$. $^1$H NMR (DMSO-D$_6$): 8.24-8.03 (m, 2H), 7.80-7.68 (m, 0.5H), 7.61 (br s, 0.5H), 7.30 (s, 1H), 7.06-6.27 (m, 3H), 4.70 (t, J=4.3 Hz, 1H), 4.32-3.67 (m, 2H), 3.42 (m, 2H), 2.45 (s, 2H), 2.38-2.02 (m, 4H), 2.02-1.18 (m, 6H).

Example 80: (±)-(7-methylimidazo[1,2-a]pyridin-8-yl)(2-((pyridin-2-yloxy)methyl)-7-azabicyclo[2.2.1]heptan-7-yl)methanone

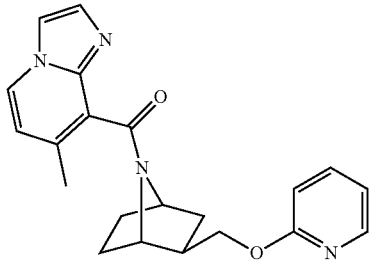 [SMILES: Cc1ccn2ccnc2c1C(=O)N1C2CCC1C(COc1ccccn1)C2]

Step A: 7-methylimidazo[1,2-a]pyridine-8-carboxylic acid. Prepared analogous to Example 82 substituting 6-amino-3-methylpicolinic acid with 2-amino-4-methylnicotinic acid.
Step B: (±)-(7-methylimidazo[1,2-a]pyridin-8-yl)(2-((pyridin-2-yloxy)methyl)-7-azabicyclo[2.2.1]heptan-7-yl)methanone Prepared analogous to Example 2 substituting intermediate A-9 with the title compound of Step A. MS (ESI) mass calcd. for $C_{21}H_{22}N_4O_2$, 362.2; m/z found 363.2 [M+H]$^+$. $^1$H NMR (DMSO-D$_6$): 8.46 (d, J=6.9 Hz, 0.5H), 8.38 (d, J=6.3 Hz, 0.5H), 8.17 (d, J=3.6 Hz, 0.5H), 8.12 (d, J=3.8 Hz, 0.5H), 7.91 (s, 1H), 7.79-7.39 (m, 2H), 7.14-6.70 (m, 2H), 6.70-6.33 (m, 1H), 4.71 (br s, 1H), 4.45-3.66 (m, 2H), 3.63-3.22 (m, 2H), 2.44-2.02 (m, 3H), 2.02-1.08 (m, 6H).

Example 81: (±)-(1-methyl-4-phenyl-1H-pyrazol-5-yl)(2-((pyridin-2-yloxy)methyl)-7-azabicyclo[2.2.1]heptan-7-yl)methanone

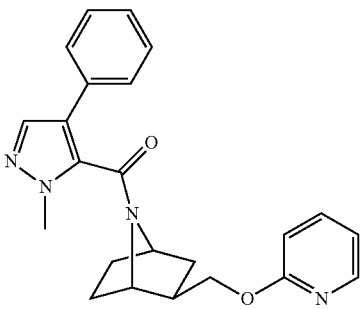 [SMILES: Cn1ncc(-c2ccccc2)c1C(=O)N1C2CCC1C(COc1ccccn1)C2]

Prepared analogous to Example 2 substituting intermediate A-9 with 1-methyl-4-phenyl-1H-pyrazole-5-carboxylic acid. MS (ESI) mass calcd. for $C_{23}H_{24}N_4O_2$, 388.2; m/z found 389.2 [M+H]$^+$. $^1$H NMR (DMSO-D$_6$): 8.19 (d, J=3.8 Hz, 0.6H), 8.09 (d, J=4.0 Hz, 0.4H), 7.79-7.57 (m, 2H), 7.43-7.19 (m, 5H), 7.05-6.91 (m, 1H), 6.84 (d, J=8.3 Hz, 0.6H), 6.62 (d, J=8.3 Hz, 0.4H), 4.62 (t, J=4.5 Hz, 0.4H), 4.57 (d, J=4.5 Hz, 0.6H), 3.96-3.87 (m, 2H), 3.85 (s, 1.8H), 3.79 (s, 1.2H), 3.58 (t, J=4.3 Hz, 0.6H), 3.52 (d, J=4.7 Hz, 0.4H), 2.28-2.02 (m, 1H), 1.76-1.07 (m, 6H).

Example 82: (±)-((6-methylimidazo[1,2-a]pyridin-5-yl)(2-((pyridin-2-yloxy)methyl)-7-azabicyclo[2.2.1]heptan-7-yl)methanone

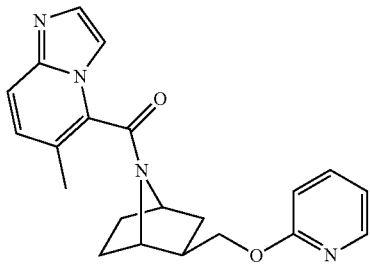 [SMILES: Cc1ccc2nccn2c1C(=O)N1C2CCC1C(COc1ccccn1)C2]

Step A: 6-amino-3-methylpicolinic acid. To methyl 6-amino-3-bromopicolinate (500 mg, 2.2 mmol), tetramethylstannane (900 μL, 6.5 mmol) and LiCl (354 mg, 8.7 mmol) in DMF (6 mL) was added Pd(PPh$_3$)$_4$ (76 mg, 10 mol %). The reaction mixture was heated at 110° C. for 3 h. Additional tetramethylstannane, LiCl and Pd(PPh$_3$)$_4$ were added and heating continued for 6 h. Purification via silica gel chromatography (0-20% MeOH in DCM) gave the title compound.

Step B: 6-methylimidazo[1,2-a]pyridine-5-carboxylic acid. To the title compound of Step A (340 mg, 2.2 mmol) in H$_2$O (7 mL) was added 1M aq. NaOH (2.2 mL, 2.2 mmol) and chloroacetaldehyde (210 μL, 3.4 mmol) and the reaction mixture heated in a microwave reactor at 150° C. for 2 h. Additional 1M aq. NaOH (2.2 mL, 2.2 mmol) and chloroacetaldehyde (210 μL, 3.4 mmol) were added and heating continued at 150° C. for 2 h. The reaction was purified via prep HPLC to give the title compound (282 mg, 72%). MS (ESI) mass calcd. for C$_9$H$_8$N$_2$O$_2$, 176.1; m/z found 177.0 [M+H]$^+$.

Step C: (±)-((6-methylimidazo[1,2-a]pyridin-5-yl)(2-((pyridin-2-yloxy)methyl)-7-azabicyclo[2.2.1]heptan-7-yl)methanone. Prepared analogous to Example 2 substituting intermediate A-9 with 6-methylimidazo[1,2-a]pyridine-5-carboxylic acid. The product is present as a mixture of conformers (ratio ca. 80:20) $^1$H NMR (300 MHz, DMSO) 8.44-8.13 (m, 1.6H), 8.13-7.86 (m, 3H), 7.86-7.41 (m, 1.2H), 6.97 (br d, J=33.5 Hz, 1.6H), 6.68 (br d, J=1.0 Hz, 0.2H), 6.39 (br d, J=1.0 Hz, 0.4H), 4.80 (d, J=16.5 Hz, 1.6H), 4.09-4.06 (m, 0.2H), 3.58 (s, 2H), 3.46-3.30 (m, 0.2H), 2.47-2.07 (m, 4H), 2.07-1.02 (m, 6H).

Example 83: (±)-(3-ethoxyisoquinolin-4-yl)(2-((pyridin-2-yloxy)methyl)-7-azabicyclo[2.2.1]heptan-7-yl)methanone

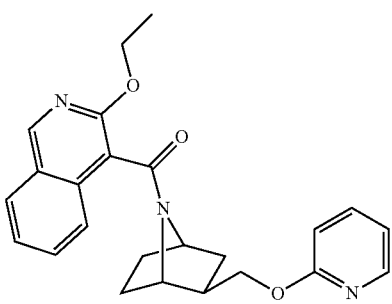 [SMILES: CCOc1ncc2ccccc2c1C(=O)N1C2CCC1C(COc1ccccn1)C2]

Prepared analogous to Example 164 substituting intermediate B-9 with intermediate B-10. MS (ESI) mass calcd. for C$_{24}$H$_{25}$N$_3$O$_3$, 403.2; m/z found 404.2 [M+H]$^+$.

Example 84: (±)-(1-methyl-5-phenyl-1H-pyrazol-4-yl)(-2-((pyridin-2-yloxy)methyl)-7-azabicyclo[2.2.1]heptan-7-yl)methanone

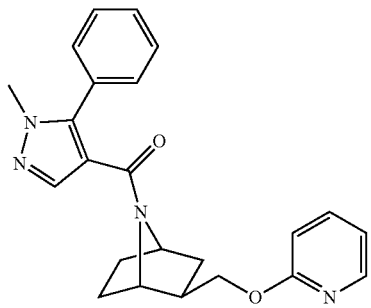 [SMILES: Cn1ncc(C(=O)N2C3CCC2C(COc2ccccn2)C3)c1-c1ccccc1]

Prepared analogous to Example 2 substituting intermediate A-9 with intermediate A-51. MS (ESI) mass calcd. for C$_{23}$H$_{24}$N$_4$O$_2$, 388.2; m/z found 389.2 [M+H]$^+$.

Example 85: (±)-(6-methyl-3-(4-methylpiperazin-1-yl)pyridin-2-yl)(2-((pyridin-2-yloxy)methyl)-7-azabicyclo[2.2.1]heptan-7-yl)methanone

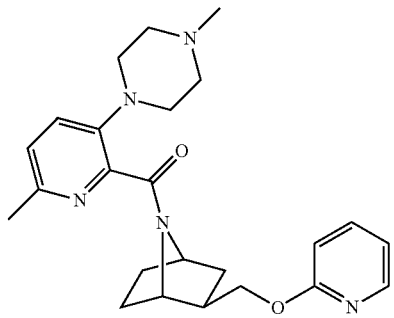 [SMILES: Cc1ccc(N2CCN(C)CC2)c(C(=O)N2C3CCC2C(COc2ccccn2)C3)n1]

Step A: 6-methyl-3-(4-methylpiperazin-1-yl)picolinonitrile. Prepared analogous to Example 68 substituting pyrrolidine with 1-methylpiperazine. MS (ESI) mass calcd. for C$_{12}$H$_{16}$N$_4$, 216.1; m/z found 217.0 [M+H]$^+$.

Step B: 6-methyl-3-(4-methylpiperazin-1-yl)picolinic acid. Prepared analogous to Example 68 substituting 6-methyl-3-(pyrrolidin-1-yl)picolinonitrile with the title compound of Step A. MS (ESI) mass calcd. for C$_{12}$H$_{17}$N$_3$O$_2$, 235.1; m/z found 236.0 [M+H]$^+$.

Step C: Prepared analogous to Example 2 substituting intermediate A-9 with the title compound of Step B. MS (ESI) mass calcd. for C$_{24}$H$_{31}$N$_5$O$_2$, 421.2; m/z found 422.2 [M+H]$^+$. $^1$H NMR (DMSO-D$_6$): 8.19-8.14 (m, 0.5H), 8.12 (dd, J=5.0, 1.5 Hz, 0.5H), 7.78-7.68 (m, 0.5H), 7.68-7.59 (m, 0.5H), 7.52 (d, J=8.4 Hz, 0.5H), 7.37 (d, J=8.4 Hz, 0.5H), 7.23 (d, J=8.4 Hz, 0.5H), 7.07 (d, J=8.3 Hz, 0.5H), 6.97 (ddd, J=12.3, 6.7, 5.4 Hz, 1H), 6.87 (d, J=8.3 Hz, 0.5H), 6.59 (d, J=8.3 Hz, 0.5H), 4.63 (t, J=4.5 Hz, 0.5H), 4.59 (d, J=3.9 Hz, 0.5H), 4.19-3.81 (m, 2H), 3.46 (t, J=3.9 Hz, 0.5H), 3.39

(d, J=4.7 Hz, 0.5H), 3.07-2.92 (m, 2H), 2.92-2.78 (m, 2H), 2.46-2.27 (m, 6H), 2.22-2.05 (m, 3.5H), 1.97 (s, 1.5H), 1.94-1.27 (m, 6H).

Example 86: (±)-(6-methyl-3-(piperazin-1-yl)pyridin-2-yl)(2-((pyridin-2-yloxy)methyl)-7-azabicyclo[2.2.1]heptan-7-yl)methanone

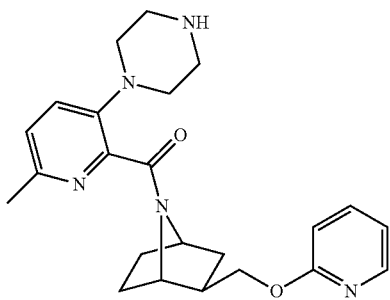 [SMILES: Cc1ccc(N2CCNCC2)c(C(=O)N2C3CCC2C(COc2ccccn2)C3)n1]

Step A: tert-butyl 4-(2-cyano-6-methylpyridin-3-yl)piperazine-1-carboxylate. Prepared analogous to Example 68 substituting pyrrolidine with tert-butyl piperazine-1-carboxylate. MS (ESI) mass calcd. for $C_{16}H_{22}N_4O_2$, 302.2; m/z found 303.0 [M+H]$^+$.

Step B: 3-(4-(tert-butoxycarbonyl)piperazin-1-yl)-6-methylpicolinic acid.

Prepared analogous to Example 68 substituting 6-methyl-3-(pyrrolidin-1-yl)picolinonitrile with the title compound of Step A. MS (ESI) mass calcd. for $C_{16}H_{23}N_3O_4$, 321.2; m/z found 322.0 [M+H]$^+$.

Step C: tert-butyl 4-(6-methyl-2-((±)-2-((pyridin-2-yloxy)methyl)-7-azabicyclo[2.2.1]heptane-7-carbonyl)pyridin-3-yl)piperazine-1-carboxylate. Prepared analogous to example 2 substituting intermediate A-9 with the title compound of Step B.

Step D: (±)-(6-methyl-3-(piperazin-1-yl)pyridin-2-yl)(2-((pyridin-2-yloxy)methyl)-7-azabicyclo[2.2.1]heptan-7-yl) methanone. To the title compound from step C (182 mg, 0.4 mmol) in 1,4-dioxane (1 mL) was added 6N HCl in iPrOH (400 µL). The reaction was heated to 70° C. for 3 h, cooled to rt, concentrated and purified via reverse phase chromatography. The mixture was dissolved with a saturated NaHCO3 (aq) and extracted with DCM (×3). The organic layers were dried over MgSO4 and concentrated. The crude product was triturated with diethyl ether and n-pentane to give the title compound (5 mg, 3%). MS (ESI) mass calcd. for $C_{23}H_{29}N_5O_2$, 407.2; m/z found 408.2 [M+H]$^+$. $^1$H NMR (DMSO-D$_6$): 8.17 (d, J=4.0 Hz, 0.4H), 8.12 (d, J=3.8 Hz, 0.6H), 7.72 (t, J=7.6 Hz, 0.4H), 7.63 (t, J=6.9 Hz, 0.6H), 7.48 (d, J=8.3 Hz, 0.4H), 7.34 (d, J=8.3 Hz, 0.6H), 7.22 (d, J=8.3 Hz, 0.4H), 7.06 (d, J=8.3 Hz, 0.6H), 7.02-6.90 (m, 1H), 6.86 (d, J=8.1 Hz, 0.4H), 6.58 (d, J=8.3 Hz, 0.6H), 4.63-4.60 (m, 1H), 4.14-3.92 (m, 2H), 3.86 (t, J=10.4 Hz, 1H), 2.99-2.65 (m, 8H), 2.39 (s, 1H), 2.34-2.28 (m, 1H), 2.18-2.11 (m, 1H), 1.96-1.88 (m, 2H), 1.86-1.20 (m, 6H).

Example 87: (±)-(6-methyl-3-morpholinopyridin-2-yl)((1S,2R,4R)-2-((pyridin-2-yloxy)methyl)-7-azabicyclo[2.2.1]heptan-7-yl)methanone

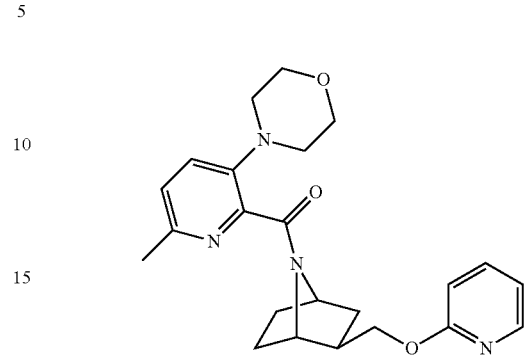

Step A: 6-methyl-3-morpholinopicolinonitrile. Prepared analogous to Example 68 substituting pyrrolidine with morpholine. MS (ESI) mass calcd. for $C_{11}H_{13}N_3O$, 203.1; m/z found 204.0 [M+H]$^+$.

Step B: 6-methyl-3-morpholinopicolinic acid. Prepared analogous to Example 68 substituting 6-methyl-3-(pyrrolidin-1-yl)picolinonitrile with the title compound of Step A. MS (ESI) mass calcd. for $C_{11}H_{14}N_2O_3$, 222.1; m/z found 223.0 [M+H]$^+$.

Step C: Prepared analogous to Example 2 substituting intermediate A-9 with the title compound of Step B. MS (ESI) mass calcd. for $C_{23}H_{28}N_4O_3$, 408.2; m/z found 409.2 [M+H]$^+$.

Example 88: (±)-(7-methoxyquinolin-8-yl)(2-((pyridin-2-yloxy)methyl)-7-azabicyclo[2.2.1]heptan-7-yl)methanone

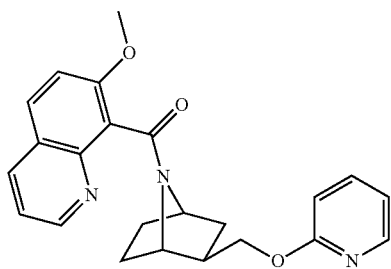 [SMILES: COc1ccc2cccnc2c1C(=O)N1C2CCC1C(COc1ccccn1)C2]

Step A: 7-methoxyquinoline-8-carboxylic acid. In 1 g separate batches a mixture of 2-amino-6-methoxybenzoic acid (1 g, 66 mmol) and acrolein (4.8 mL, 72 mmol) in 1,4-dioxane (66 mL) was heated in a microwave reactor for 20 min at 200° C. After combining the reactions, the mixture was concentrated and purified via silica gel chromatography (0-10% MeOH in DCM) to give the title compound (2.8 g, 20%). MS (ESI) mass calcd. for $C_{11}H_{19}NO_3$, 203.1; m/z found 204.0 [M+H]$^+$.

Step B: Prepared analogous to Example 2 substituting intermediate A-9 with the title compound of Step A. MS (ESI) mass calcd. for $C_{23}H_{23}N_3O_3$, 389.2; m/z found 390.2 [M+H]$^+$.

Example 89: (±)-(2-ethoxynaphthalen-1-yl)(2-((pyridin-2-yloxy)methyl)-7-azabicyclo[2.2.1]heptan-7-yl)methanone

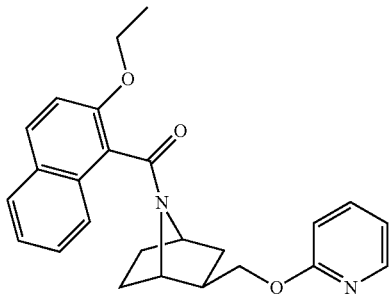 [SMILES: CCOc1ccc2ccccc2c1C(=O)N1C2CCC1C(COc1ccccn1)C2]

Prepared analogous to Example 2 substituting intermediate A-9 with 2-ethoxy-1-naphthoic acid. MS (ESI) mass calcd. for $C_{25}H_{26}N_2O_3$, 402.2; m/z found 403.2 [M+H]$^+$.

Example 90: (±)-(3,6'-dimethyl-[2,3'-bipyridin]-2'-yl)(2-((pyridin-2-yloxy)methyl)-7-azabicyclo[2.2.1]heptan-7-yl)methanone

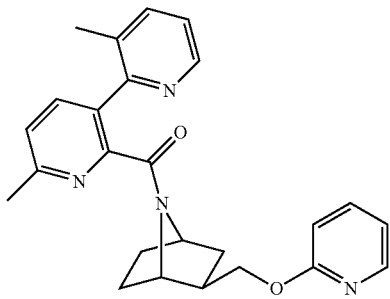 [SMILES: Cc1ccc(-c2ncccc2C)c(C(=O)N2C3CCC2C(COc2ccccn2)C3)n1]

Prepared analogous to Example 2 substituting intermediate A-9 with 3,6'-dimethyl-[2,3'-bipyridine]-2'-carboxylic acid. MS (ESI) mass calcd. for $C_{25}H_{26}N_4O_2$, 414.2; m/z found 415.2 [M+H]$^+$.

Example 91: (±)-(3-(2H-1,2,3-triazol-2-yl)pyridin-2-yl)(2-((pyridin-2-yloxy)methyl)-7-azabicyclo[2.2.1]heptan-7-yl)methanone

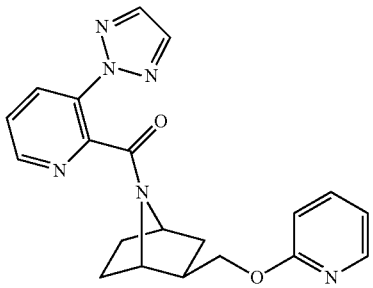 [SMILES: O=C(c1ncccc1-n1nccn1)N1C2CCC1C(COc1ccccn1)C2]

Prepared analogous to Example 2 substituting intermediate A-9 with 3-(2H-1,2,3-triazol-2-yl)picolinic acid. MS (ESI) mass calcd. for $C_{20}H_{20}N_6O_2$, 376.2; m/z found 377.2 [M+H]$^+$. $^1$H NMR (DMSO-D$_6$): 8.70 (d, J=3.6 Hz, 0.5H), 8.40-7.99 (m, 4.5H), 7.82-7.47 (m, 2H), 7.02-6.85 (m, 1H), 6.86 (d, J=8.2 Hz, 0.6H), 6.64 (d, J=8.1 Hz, 0.4H), 4.62-4.65 (m, 1H), 4.20-3.97 (m, 3H), 2.35-2.24 (m, 1H), 2.00-1.09 (m, 6H).

Example 92: (±)-(2-methyl-5-phenylthiazol-4-yl)(2-((pyridin-2-yloxy)methyl)-7-azabicyclo[2.2.1]heptan-7-yl)methanone

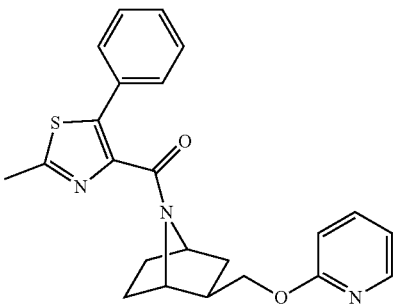 [SMILES: Cc1nc(C(=O)N2C3CCC2C(COc2ccccn2)C3)c(-c2ccccc2)s1]

Prepared analogous to Example 2 substituting intermediate A-9 with 2-methyl-5-phenylthiazole-4-carboxylic acid. MS (ESI) mass calcd. for $C_{23}H_{23}N_3O_2S$, 405.2; m/z found 406.2 [M+H]$^+$. $^1$H NMR (DMSO-D$_6$) 8.18 (dd, J=5.0, 1.4 Hz, 0.5H), 8.10 (dd, J=5.0, 1.4 Hz, 0.5H), 7.77-7.61 (m, 1H), 7.52-7.29 (m, 5H), 7.04-6.89 (m, 1H), 6.82 (d, J=8.3 Hz, 0.5H), 6.69 (d, J=8.3 Hz, 0.5H), 4.57 (t, J=4.5 Hz, 0.5H), 4.52 (d, J=4.7 Hz, 0.5H), 3.90-3.79 (m, 2.5H), 3.69 (t, J=10.6 Hz, 0.5H), 2.69 (s, 1.5H), 2.28 (s, 1.5H), 2.25-2.06 (m, 1H), 1.72-1.04 (m, 6H).

Example 93: (±)-(6-methyl-3-(oxazol-2-yl)pyridin-2-yl)(2-((pyridin-2-yloxy)methyl)-7-azabicyclo[2.2.1]heptan-7-yl)methanone

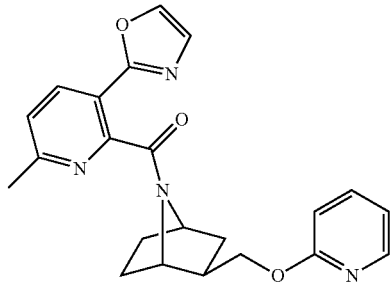 [SMILES: Cc1ccc(-c2ncco2)c(C(=O)N2C3CCC2C(COc2ccccn2)C3)n1]

Prepared analogous to Example 2 substituting intermediate A-9 with intermediate A-43. MS (ESI) mass calcd. for $C_{22}H_{22}N_4O_3$, 390.2; m/z found 391.2 [M+H]$^+$. $^1$H NMR (DMSO-D$_6$): 8.22 (dt, J=14.0, 7.8 Hz, 2.5H), 8.12 (dd, J=5.0, 1.4 Hz, 0.5H), 7.78-7.68 (m, 0.5H), 7.68-7.59 (m, 0.5H), 7.49 (d, J=8.2 Hz, 0.5H), 7.41-7.29 (n, 1.5H), 6.97 (ddd, J=14.7, 6.5, 5.2 Hz, 1H), 6.87 (d, J=8.4 Hz, 0.5H), 6.63 (d, J=8.3 Hz, 0.5H), 4.66 (t, J=4.6 Hz, 0.5H), 4.62 (d, J=4.8 Hz, 0.5H), 4.22-3.93 (m, 2H), 3.70 (t, J=4.4 Hz, 0.5H), 3.61 (d, J=4.0 Hz, 0.5H), 2.55 (s, 1.5H), 2.40-2.14 (m, 1H), 2.08 (s, 1.5H), 1.93-1.23 (m, 6H).

Example 94: (±)-(6-methyl-3-(3-methylisoxazol-5-yl)pyridin-2-yl)(2-((pyridin-2-yloxy)methyl)-7-azabicyclo[2.2.1]heptan-7-yl)methanone

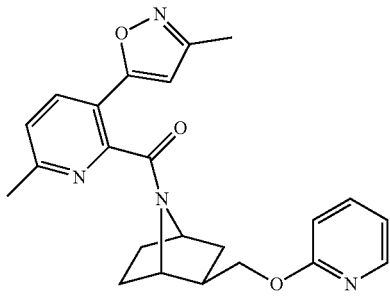 [SMILES: Cc1cc(-c2ccc(C)nc2C(=O)N2C3CCC2C(COc2ccccn2)C3)on1]

Prepared analogous to Example 2 substituting intermediate A-9 with 6-methyl-3-(3-methylisoxazol-5-yl)picolinic acid. MS (ESI) mass calcd. for $C_{23}H_{24}N_4O_3$, 404.2; m/z found 405.0 $[M+H]^+$. $^1$H NMR (DMSO-D$_6$): 8.20-8.02 (m, 2H), 7.73 (t, J=6.9 Hz, 0.4H), 7.65 (t, J=7.7 Hz, 0.6H), 7.50 (d, J=8.1 Hz, 0.4H), 7.37 (d, J=8.2 Hz, 0.6H), 7.03-6.91 (m, 1H), 6.87 (d, J=8.3 Hz, 0.4H), 6.68-6.58 (m, 1.6H), 4.68 (t, J=4.6 Hz, 0.6H), 4.62 (d, J=4.7 Hz, 0.4H), 4.01-3.93 (m, 2H), 3.60 (t, J=4.4 Hz, 0.4H), 3.55 (d, J=3.1 Hz, 0.6H), 2.55 (s, 1.2H), 2.36-2.14 (m, 4H), 2.09 (s, 1.8H), 1.88-1.07 (m, 6H).

Example 95: (±)-(6-methyl-3-(1H-pyrazol-1-yl)pyridin-2-yl)(2-((pyridin-2-yloxy)methyl)-7-azabicyclo[2.2.1]heptan-7-yl)methanone

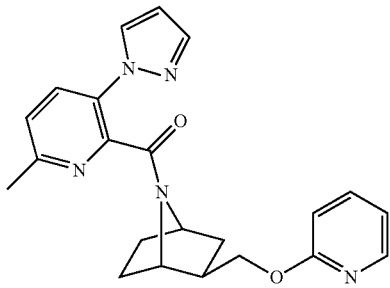 [SMILES: Cc1ccc(-n2cccn2)c(C(=O)N2C3CCC2C(COc2ccccn2)C3)n1]

Prepared analogous to Example 2 substituting intermediate A-9 with 6-methyl-3-(1H-pyrazol-1-yl)picolinic acid. $^1$H NMR (DMSO-D$_6$): 8.19 (dd, J=5.0, 1.4 Hz, 0.5H), 8.14 (dd, J=5.1, 1.5 Hz, 0.5H), 8.08 (t, J=2.9 Hz, 1H), 7.97 (d, J=8.3 Hz, 0.5H), 7.93 (d, J=8.3 Hz, 0.5H), 7.76-7.61 (m, 2H), 7.49 (d, J=8.4 Hz, 0.5H), 7.34 (d, J=8.4 Hz, 0.5H), 6.97 (td, J=7.3, 5.2 Hz, 1H), 6.84 (d, J=8.3 Hz, 0.5H), 6.65 (d, J=8.3 Hz, 0.5H), 6.53-6.48 (m, 0.5H), 6.48-6.43 (m, 0.5H), 4.55 (t, J=4.5 Hz, 0.5H), 4.51 (d, J=4.7 Hz, 0.5H), 4.02-3.93 (m, 2H), 3.67 (t, J=4.1 Hz, 0.5H), 3.60 (d, J=4.5 Hz, 0.5H), 2.54 (s, 1.5H), 2.31-2.11 (m, 1H), 2.04 (s, 1.5H), 1.75-1.16 (m, 6H).

Example 96: (±)-(6-methyl-3-(4-methyl-1H-pyrazol-1-yl)pyridin-2-yl)(2-((pyridin-2-yloxy)methyl)-7-azabicyclo[2.2.1]heptan-7-yl)methanone

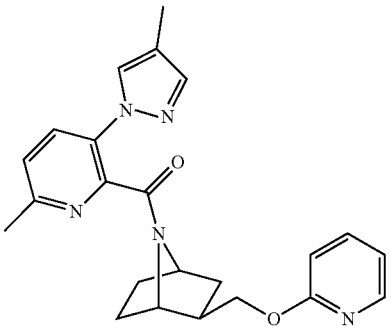 [SMILES: Cc1cnn(-c2ccc(C)nc2C(=O)N2C3CCC2C(COc2ccccn2)C3)c1]

Prepared analogous to Example 2 substituting intermediate A-9 with 6-methyl-3-(4-methyl-1H-pyrazol-1-yl)picolinic acid. MS (ESI) mass calcd. for $C_{23}H_{25}N_5O_2$, 403.2; m/z found 404.2 $[M+H]^+$.

Example 97: (±)-(6-methyl-3-(pyrrolidin-1-yl)pyridin-2-yl)(2-((pyridin-2-yloxy)methyl)-7-azabicyclo[2.2.1]heptan-7-yl)methanone

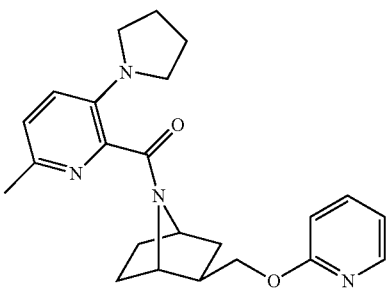 [SMILES: Cc1ccc(N2CCCC2)c(C(=O)N2C3CCC2C(COc2ccccn2)C3)n1]

Prepared analogous to Example 2 substituting intermediate A-9 with 6-methyl-3-(pyrrolidin-1-yl)picolinic acid (Example 68). MS (ESI) mass calcd. for $C_{23}H_{28}N_4O_2$, 392.2; m/z found 393.2 $[M+H]^+$. The product is present as a mixture of conformers (ratio ca. 50:50). $^1$H NMR (300 MHz, DMSO) 8.14 (dd, J=5.1, 1.4 Hz, 0.5H), 8.11 (dd, J=5.1, 1.4 Hz, 0.5H), 7.76-7.59 (m, 1H), 7.06 (q, J=8.6 Hz, 1H), 7.01-6.90 (m, 2H), 6.85 (d, J=8.3 Hz, 0.5H), 6.69 (d, J=8.3 Hz, 0.5H), 4.61 (t, J=4.6 Hz, 0.5H), 4.58 (d, J=4.7 Hz, 0.5H), 4.19-3.91 (m, 2.5H), 3.88 (d, J=4.6 Hz, 0.5H), 3.28-3.11 (m, 3H), 3.10-2.98 (m, 1H), 2.41-2.18 (m, 2.5H), 2.06 (s, 1.5H), 1.95-1.28 (m, 10H).

Example 98: (±)-(3,6'-dimethyl-[2,3'-bipyridin]-2'-yl)(2-(((5-fluoropyrimidin-2-yl)oxy)methyl)-7-azabicyclo[2.2.1]heptan-7-yl)methanone

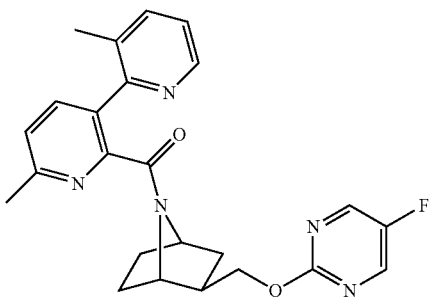

Step A: (±)-tert-butyl 2-(((5-fluoropyrimidin-2-yl)oxy)methyl)-7-azabicyclo[2.2.1]heptane-7-carboxylate. To intermediate B-10 (500 mg, 2.2 mmol) in THF (11 mL) at 0° C. was added NaH (176 mg, 60 wt % in mineral oil, 4.4 mmol). After 15 min, 2-chloro-5-fluoropyrimidine (0.3 mL, 2.4 mmol) was added dropwise and the 0° C. ice bath was removed. After 12 h, H$_2$O was added and the reaction extracted with EtOAc. The combined organics dried (Na$_2$SO$_4$). Purification via silica gel chromatography (5-30% EtOAc in heptane) gave the title compound (490 mg, 69%) as a white solid. MS (ESI) mass calcd. for C$_{16}$H$_{22}$F$_3$N$_3$O$_3$, 323.4; m/z found 224.1 [M−100]$^+$.

Step B: (±)-2-(((5-fluoropyrimidin-2-yl)oxy)methyl)-7-azabicyclo[2.2.1]heptane. To the title compound from step A (474 mg, 1.5 mmol) in 1,4-dioxane (1.5 mL) was added 6N HCl in iPrOH (1.5 mL). The reaction was heated to 40° C. for 1.5 h and concentrated to give the title compound that was used without further purification in subsequent steps. MS (ESI) mass calcd. for C$_{11}$H$_{14}$FN$_3$O, 223.1; m/z found 224.0 [M+H]$^+$.

Step C: (±)-(3,6'-dimethyl-[2,3'-bipyridin]-2'-yl)(2-(((5-fluoropyrimidin-2-yl)oxy)methyl)-7-azabicyclo[2.2.1]heptan-7-yl)methanone. Prepared analogous to example 2 substituting intermediate A-9 with 3,6'-dimethyl-[2,3'-bipyridine]-2'-carboxylic acid and intermediate B-10 with the title compound of Step B. MS (ESI) mass calcd. for C$_{24}$H$_{24}$FN$_5$O$_2$, 433.2; m/z found 434.2 [M+H]$^+$. $^1$H NMR (DMSO-D$_6$): 8.71 (s, 2H), 8.32 (t, J=4.5 Hz, 1H), 7.74 (d, J=7.9 Hz, 1H), 7.66 (t, J=7.3 Hz, 1H), 7.40 (d, J=7.9 Hz, 0.5H), 7.33-7.14 (m, 1.5H), 4.39 (br s, 0.5H), 4.34 (d, J=4.0 Hz, 0.5H), 4.27 (t, J=10.4 Hz, 0.5H), 4.10 (dd, J=5.2, 1.0 Hz, 0.5H), 3.90 (d, J=4.8 Hz, 0.5H), 3.85 (t, J=3.1 Hz, 0.5H), 3.69 (d, J=7.9 Hz, 1H), 2.55 (s, 1.5H), 2.31-2.20 (m, 0.5H), 2.18 (s, 1.5H), 2.16 (s, 1.5H), 2.12 (s, 1.5H), 2.01-1.82 (m, 0.5H), 1.81-1.14 (m, 6H).

Example 99: (±)-(2-(((5-fluoropyrimidin-2-yl)oxy)methyl)-7-azabicyclo[2.2.1]heptan-7-yl)(6-methyl-3-(3-methylisoxazol-5-yl)pyridin-2-yl)methanone

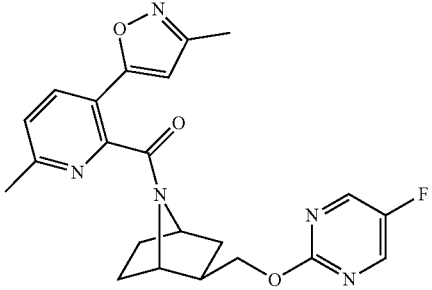 [SMILES: Cc1cc(-c2ccc(C)nc2C(=O)N2C3CCC2C(COc2ncc(F)cn2)C3)on1]

Prepared analogous to example 98 substituting 3,6'-dimethyl-[2,3'-bipyridine]-2'-carboxylic acid with 6-methyl-3-(3-methylisoxazol-5-yl)picolinic acid. MS (ESI) mass calcd. for C$_{22}$H$_{22}$FN$_5$O$_3$, 423.2; m/z found 424.2 [M+H]$^+$. $^1$H NMR (DMSO-D$_6$): 8.71 (s, 1H), 8.66 (s, 1H), 8.12 (d, J=8.1 Hz, 0.4H), 8.09 (d, J=8.2 Hz, 0.6H), 7.50 (d, J=8.2 Hz, 0.4H), 7.40 (d, J=8.2 Hz, 0.6H), 6.64-6.63 (m, 1H), 4.68 (t, J=4.6 Hz, 0.6H), 4.60 (d, J=4.7 Hz, 0.4H), 4.11-3.90 (m, 2H), 3.62 (t, J=4.2 Hz, 0.4H), 3.55 (d, J=4.1 Hz, 0.5H), 2.55 (s, 1.2H), 2.40-2.15 (m, 4H), 2.16 (s, 1.8H), 1.88-1.12 (m, 6H).

Example 100: (±)-(2-(((5-fluoropyrimidin-2-yl)oxy)methyl)-7-azabicyclo[2.2.1]heptan-7-yl)(6-methyl-3-(oxazol-2-yl)pyridin-2-yl)methanone

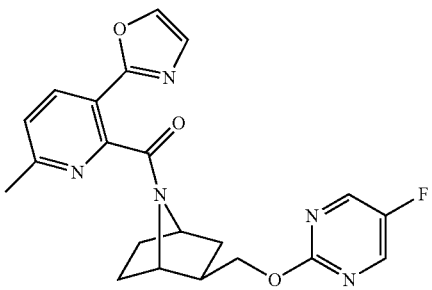 [SMILES: Cc1ccc(-c2ncco2)c(C(=O)N2C3CCC2C(COc2ncc(F)cn2)C3)n1]

Prepared analogous to example 98 substituting 3,6'-dimethyl-[2,3'-bipyridine]-2'-carboxylic acid with intermediate A-43. MS (ESI) mass calcd. for C$_{21}$H$_{20}$FN$_5$O$_3$, 409.2; m/z found 410.2 [M+H]$^+$. $^1$H NMR (DMSO-D$_6$): 8.74 (s, 0.8H), 8.66 (s, 1.2H), 8.31-8.16 (m, 2H), 7.50 (d, J=8.2 Hz, 0.4H), 7.38 (t, J=8.9 Hz, 1.6H), 4.67 (t, J=4.5 Hz, 0.6H), 4.62 (d, J=4.7 Hz, 0.4H), 4.23 (t, J=10.1 Hz, 0.4H), 4.07 (dt, J=10.0, 6.2 Hz, 1.6H), 3.72 (t, J=4.2 Hz, 0.4H), 3.62 (d, J=4.4 Hz, 0.6H), 2.56 (s, 1.2H), 2.43-2.19 (m, 1H), 2.16 (s, 1.8H), 1.93-1.23 (m, 6H).

Example 101: (±)-(2-(((5-fluoropyrimidin-2-yl)oxy)methyl)-7-azabicyclo[2.2.1]heptan-7-yl)(6-methyl-3-(pyrrolidin-1-yl)pyridin-2-yl)methanone

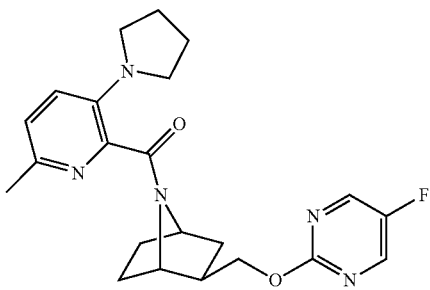 [SMILES: Cc1ccc(N2CCCC2)c(C(=O)N2C3CCC2C(COc2ncc(F)cn2)C3)n1]

Prepared analogous to example 98 substituting 3,6'-dimethyl-[2,3'-bipyridine]-2'-carboxylic acid with 6-methyl-3-(pyrrolidin-1-yl)picolinic acid (example 68). MP=130° C.

Example 102: (±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone

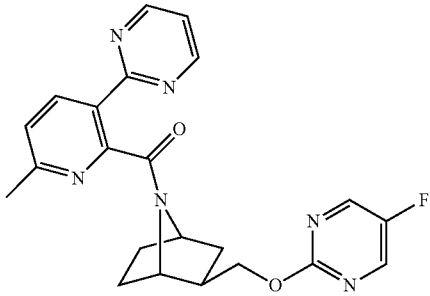 [SMILES: Cc1ccc(-c2ncccn2)c(C(=O)N2C3CCC2C(COc2ncc(F)cn2)C3)n1]

Prepared analogous to example 98 substituting 3,6'-dimethyl-[2,3'-bipyridine]-2'-carboxylic acid with intermediate A-9. MS (ESI) mass calcd. for $C_{22}H_{21}FN_6O_2$, 420.2; m/z found 421.2 [M+H]$^+$. $^1$H NMR (DMSO-D$_6$): 8.93 (d, J=4.9 Hz, 0.8H), 8.88 (d, J=4.9 Hz, 1.2H), 8.79 (s, 0.8H), 8.72 (s, 1.2H), 8.37-8.33 (m, 1H), 7.55-7.47 (m, 1.2H), 7.40 (d, J=8.1 Hz, 0.6H), 4.67-4.61 (br s, 0.6H), 4.59 (d, J=4.0 Hz, 0.4H), 4.33-4.22 (m, 1H), 4.18-4.07 (m, 1H), 3.91 (br s, 0.4H), 3.81 (d, J=3.4 Hz, 0.6H), 2.59 (s, 1.4H), 2.48-2.25 (m, 1H), 2.15 (s, 1.8H), 1.93-1.34 (m, 6H).

Example 103: (±)-(2-(((5-fluoropyrimidin-2-yl)oxy)methyl)-7-azabicyclo[2.2.1]heptan-7-yl)(6-methyl-3-(4-methyl-1H-pyrazol-1-yl)pyridin-2-yl)methanone

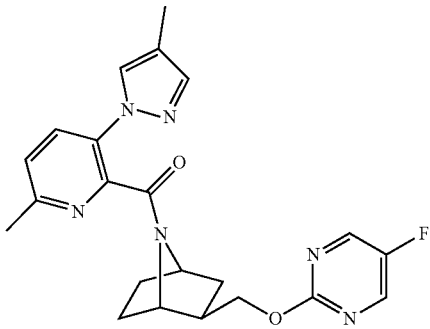 [SMILES: Cc1cnn(-c2ccc(C)nc2C(=O)N2C3CCC2C(COc2ncc(F)cn2)C3)c1]

Prepared analogous to example 98 substituting 3,6'-dimethyl-[2,3'-bipyridine]-2'-carboxylic acid with 6-methyl-3-(4-methyl-1H-pyrazol-1-yl)picolinic acid. MP=151.2° C. $^1$H NMR (DMSO-D$_6$): 8.73 (s, 1H), 8.69 (s, 1H), 7.92 (d, J=5.0 Hz, 0.5H), 7.90 (d, J=5.0 Hz, 0.5H), 7.85 (d, J=2.3 Hz, 1H), 7.51-7.54 (m, 1.5H), 7.35 (d, J=8.4 Hz, 0.5H), 4.57 (t, J=4.5 Hz, 0.5H), 4.51 (d, J=4.7 Hz, 0.5H), 4.08-3.90 (m, 2H), 3.66 (t, J=4.0 Hz, 0.5H), 3.60 (d, J=4.0 Hz, 0.5H), 2.53 (s, 1.5H), 2.35-2.14 (m, 1H), 2.10 (s, 1.5H), 2.07 (s, 1.5H), 2.04 (s, 1.5H), 1.77-1.14 (m, 6H).

Example 104: (±)-(2-(((5-fluoropyrimidin-2-yl)oxy)methyl)-7-azabicyclo[2.2.1]heptan-7-yl)(6-methyl-3-(1H-pyrazol-1-yl)pyridin-2-yl)methanone

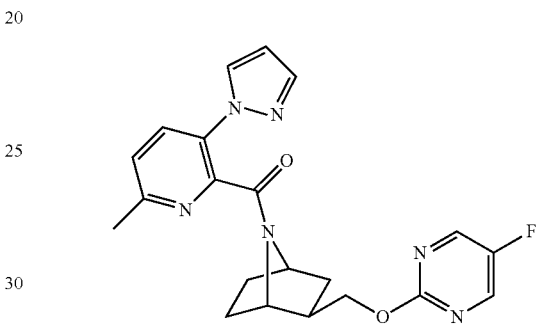

Prepared analogous to example 98 substituting 3,6'-dimethyl-[2,3'-bipyridine]-2'-carboxylic acid with 6-methyl-3-(1H-pyrazol-1-yl)picolinic acid. MS (ESI) mass calcd. for $C_{21}H_{21}FN_6O_2$, 408.2; m/z found 409.2 [M+H]$^+$. MP=119.2° C.

Example 105: (±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone

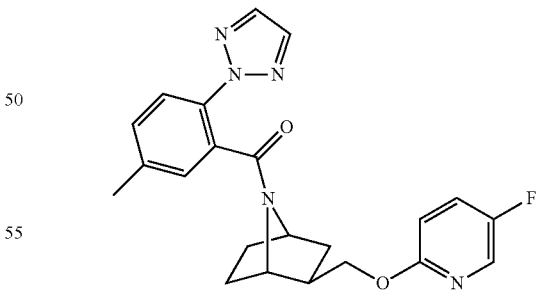

Prepared analogous to Example 7 substituting 6-methyl-3-(2H-1,2,3-triazol-2-yl)picolinic acid with 5-methyl-2-(2H-1,2,3-triazol-2-yl)benzoic acid. (ESI) mass calcd. for $C_{22}H_{22}FN_5O_2$, 407.2; m/z found 408.2 [M+H]$^+$. $^1$H NMR (MeOD): 8.08-7.96 (m, 1H), 7.88 (s, 2H), 7.81-7.73 (m, 1H), 7.56-7.12 (m, 3H), 6.85-6.62 (m, 1H), 4.70-4.67 (m, 1H), 4.25-3.74 (m, 3H), 2.51-1.97 (m, 4H), 1.96-1.31 (m, 6H).

Example 106: (±)-(2,6-dimethoxyphenyl)(2-(((5-fluoropyridin-2-yl)oxy)methyl)-7-azabicyclo[2.2.1]heptan-7-yl)methanone

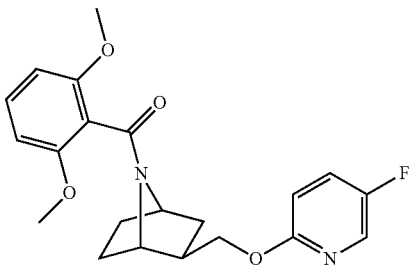 [SMILES: COc1cccc(OC)c1C(=O)N1C2CCC1C(COc1ccc(F)cn1)C2]

Prepared analogous to example 105 substituting 5-methyl-2-(2H-1,2,3-triazol-2-yl)benzoic acid with 2,6-dimethoxybenzoic acid. MS (ESI) mass calcd. for $C_{21}H_{23}FN_2O_4$, 386.2; m/z found 386.9 [M+H]$^+$. $^1$H NMR (MeOD): 8.02-7.93 (m, 1H), 7.57-7.40 (m, 1H), 7.39-7.21 (m, 1H), 6.87-6.63 (m, 2H), 6.62-6.38 (m, 1H), 4.83-4.65 (m, 1H), 4.49-4.07 (m, 1H), 4.07-3.52 (m, 8H), 2.48-2.09 (m, 1H), 2.06-1.07 (m, 6H).

Example 107: (±)-((3-fluoro-2-methoxyphenyl)(2-(((5-fluoropyridin-2-yl)oxy)methyl)-7-azabicyclo[2.2.1]heptan-7-yl)methanone

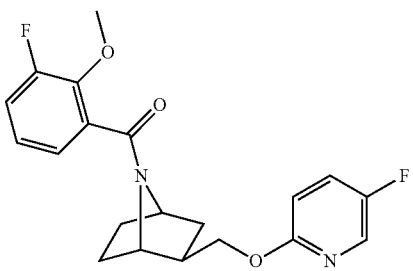 [SMILES: COc1c(F)cccc1C(=O)N1C2CCC1C(COc1ccc(F)cn1)C2]

Prepared analogous to example 105 substituting 5-methyl-2-(2H-1,2,3-triazol-2-yl)benzoic acid with 3-fluoro-2-methoxybenzoic acid. MS (ESI) mass calcd. for $C_{20}H_{20}F_2N_2O_3$, 374.1; m/z found 375.1 [M+H]$^+$. $^1$H NMR (MeOD): 8.01-7.90 (m, 1H), 7.56-7.38 (m, 1H), 7.28-7.06 (m, 2H), 7.02-6.53 (m, 2H), 4.82-4.66 (m, 1H), 4.50-3.73 (m, 6H), 2.85-2.22 (m, 1H), 2.21-1.10 (m, 6H).

Example 108: (±)-(2-(((5-fluoropyridin-2-yl)oxy)methyl)-7-azabicyclo[2.2.1]heptan-7-yl)(2-methoxy-6-(2H-1,2,3-triazol-2-yl)phenyl)methanone

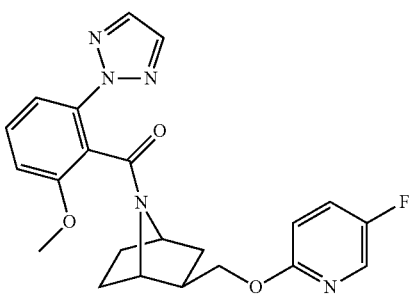 [SMILES: COc1cccc(-n2nccn2)c1C(=O)N1C2CCC1C(COc1ccc(F)cn1)C2]

Prepared analogous to example 105 substituting 5-methyl-2-(2H-1,2,3-triazol-2-yl)benzoic acid with 2-methoxy-6-(2H-1,2,3-triazol-2-yl)benzoic acid. MS (ESI) mass calcd. for $C_{22}H_{22}FN_5O_3$, 423.2; m/z found 424.2 [M+H]$^+$. $^1$H NMR (MeOD): 8.10-7.74 (m, 3H), 7.66-7.41 (m, 3H), 7.25-6.88 (m, 1H), 6.88-6.43 (m, 1H), 4.78-4.64 (m, 1H), 4.51-3.57 (m, 6H), 2.48-0.94 (m, 7H).

Example 109: (±)-(5-fluoro-2-(1H-pyrazol-5-yl)phenyl)(2-(((5-fluoropyridin-2-yl)oxy)methyl)-7-azabicyclo[2.2.1]heptan-7-yl)methanone

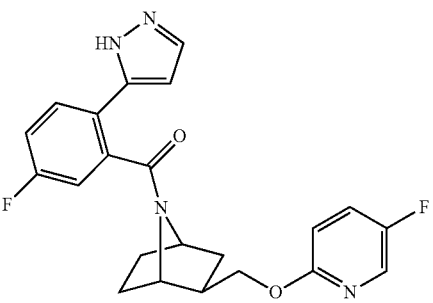 [SMILES: O=C(c1cc(F)ccc1-c1ccn[nH]1)N1C2CCC1C(COc1ccc(F)cn1)C2]

Prepared analogous to example 105 substituting 5-methyl-2-(2H-1,2,3-triazol-2-yl)benzoic acid with 5-fluoro-2-(1H-pyrazol-5-yl)benzoic acid. MS (ESI) mass calcd. for $C_{22}H_{20}F_2N_4O_2$, 410.2; m/z found 411.2 [M+H]$^+$. $^1$H NMR (MeOD): 8.11-7.90 (m, 1H), 7.80-7.59 (m, 2H), 7.58-7.40 (m, 1H), 7.36-6.94 (m, 2H), 6.88-6.47 (m, 2H), 4.78-4.58 (m, 1H), 4.41-3.47 (m, 3H), 2.69-0.60 (m, 8H).

Example 110: (±)-(2-(((5-fluoropyridin-2-yl)oxy)methyl)-7-azabicyclo[2.2.1]heptan-7-yl)(2-methyl-6-(2H-1,2,3-triazol-2-yl)phenyl)methanone

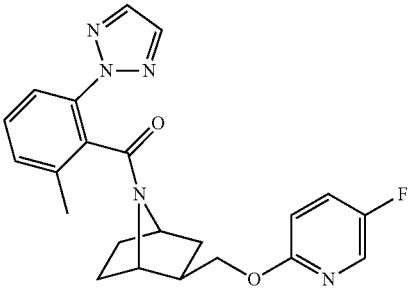

Prepared analogous to example 105 substituting 5-methyl-2-(2H-1,2,3-triazol-2-yl)benzoic acid with 2-methyl-6-(2H-1,2,3-triazol-2-yl)benzoic acid. MS (ESI) mass calcd. for $C_{22}H_{22}FN_5O_2$, 407.2; m/z found 408.2 [M+H]$^+$. $^1$H NMR (MeOD): 8.11-7.62 (m, 4H), 7.59-6.48 (m, 4H), 4.78-4.68 (m, 1H), 4.50-3.37 (m, 3H), 2.80-0.82 (m, 10H).

Example 111: (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone

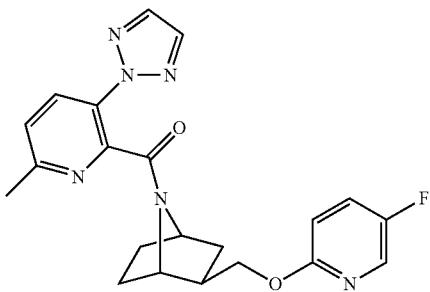 [SMILES: Cc1ccc(-n2nccn2)c(C(=O)N2C3CCC2C(COc2ccc(F)cn2)C3)n1]

Prepared analogous to example 105 substituting 5-methyl-2-(2H-1,2,3-triazol-2-yl)benzoic acid with 6-methyl-3-(2H-1,2,3-triazol-2-yl)picolinic acid. MS (ESI) mass calcd. for $C_{21}H_{21}FN_6O_2$, 408.2; m/z found 409.2 [M+H]$^+$. $^1$H NMR (MeOD): 8.28-8.19 (m, 1H), 8.06-7.88 (m, 3H), 7.57-7.35 (m, 2H), 6.89-6.60 (m, 1H), 4.76-4.73 (m, 1H), 4.32-4.02 (m, 2H), 3.93-3.80 (m, 1H), 2.70-2.20 (m, 4H), 2.05-1.42 (m, 6H).

Example 112: (±)-(5-chloro-3-(2H-1,2,3-triazol-2-yl)pyridin-2-yl)(2-(((5-fluoropyridin-2-yl)oxy)methyl)-7-azabicyclo[2.2.1]heptan-7-yl)methanone

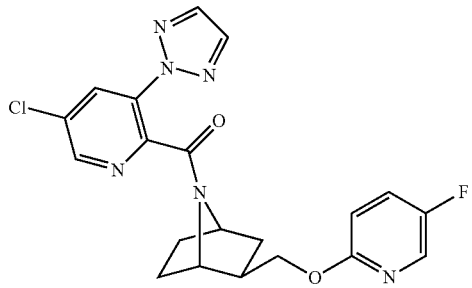 [SMILES: O=C(c1ncc(Cl)cc1-n1nccn1)N1C2CCC1C(COc1ccc(F)cn1)C2]

Prepared analogous to example 105 substituting 5-methyl-2-(2H-1,2,3-triazol-2-yl)benzoic acid with sodium 5-chloro-3-(2H-1,2,3-triazol-2-yl)picolinate. MS (ESI) mass calcd. for $C_{20}H_{18}ClFN_6O_2$, 428.1; m/z found 429.1 [M+H]$^+$. $^1$H NMR (MeOD): 8.74-8.17 (m, 4H), 8.13-7.96 (m, 2H), 7.59-7.46 (m, 1H), 4.90-4.18 (m, 3H), 3.99 (s, 1H), 2.98-2.39 (m, 1H), 2.10-1.19 (m, 6H).

Example 113: (±)-(2-(((5-fluoropyridin-2-yl)oxy)methyl)-7-azabicyclo[2.2.1]heptan-7-yl)(5-methoxy-3-(2H-1,2,3-triazol-2-yl)pyridin-2-yl)methanone

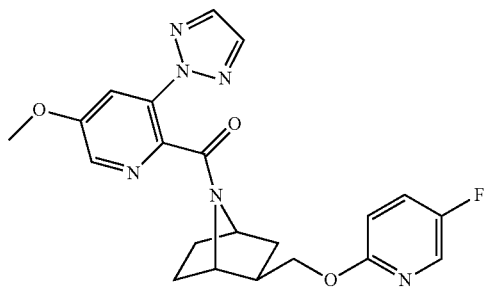 [SMILES: COc1cnc(C(=O)N2C3CCC2C(COc2ccc(F)cn2)C3)c(-n2nccn2)c1]

Prepared analogous to example 105 substituting 5-methyl-2-(2H-1,2,3-triazol-2-yl)benzoic acid with sodium 5-methoxy-3-(2H-1,2,3-triazol-2-yl)picolinate. MS (ESI) mass calcd. for $C_{21}H_{21}FN_6O_3$, 424.2; m/z found 425.1 [M+H]$^+$. $^1$H NMR (MeOD): 8.37-7.79 (m, 5H), 7.56-7.40 (m, 1H), 6.87-6.59 (m, 1H), 4.73 (s, 1H), 4.30-3.82 (m, 6H), 2.48-2.11 (m, 1H), 2.07-1.42 (m, 6H).

Example 114: (±)-(2-(((5-fluoropyridin-2-yl)oxy)methyl)-7-azabicyclo[2.2.1]heptan-7-yl)(5-methoxy-2-(2H-1,2,3-triazol-2-yl)phenyl)methanone

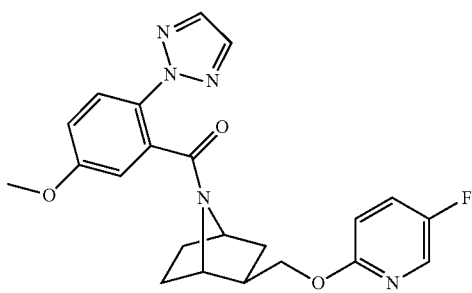 [SMILES: COc1ccc(-n2nccn2)c(C(=O)N2C3CCC2C(COc2ccc(F)cn2)C3)c1]

Prepared analogous to example 105 substituting 5-methyl-2-(2H-1,2,3-triazol-2-yl)benzoic acid with sodium 5-methoxy-2-(2H-1,2,3-triazol-2-yl)benzoate. MS (ESI) mass calcd. for $C_{22}H_{22}FN_5O_3$, 423.2; m/z found 424.2 [M+H]$^+$. $^1$H NMR (MeOD): 8.18-7.68 (m, 4H), 7.58-7.38 (m, 1H), 7.24-6.85 (m, 2H), 6.85-6.57 (m, 1H), 4.78-4.55 (m, 1H), 4.23-3.40 (m, 6H), 2.77-2.18 (m, 1H), 2.13-1.11 (m, 6H).

Example 115: (±)-(2-fluoro-6-(2H-1,2,3-triazol-2-yl)phenyl)(2-(((5-fluoropyridin-2-yl)oxy)methyl)-7-azabicyclo[2.2.1]heptan-7-yl)methanone

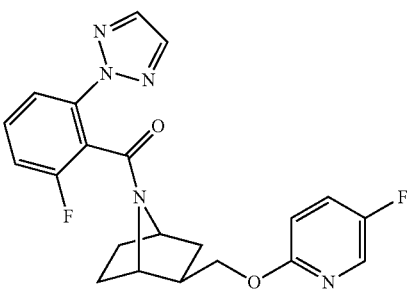 [SMILES: O=C(c1c(F)cccc1-n1nccn1)N1C2CCC1C(COc1ccc(F)cn1)C2]

Prepared analogous to example 105 substituting 5-methyl-2-(2H-1,2,3-triazol-2-yl)benzoic acid with 2-fluoro-6-(2H-1,2,3-triazol-2-yl)benzoic acid. MS (ESI) mass calcd. for $C_{21}H_{19}F_2N_5O_2$, 411.2; m/z found 412.2 [M+H]$^+$. $^1$H NMR (MeOD): 8.11-7.71 (m, 4H), 7.69-7.24 (m, 3H), 6.98-6.43 (m, 1H), 4.83-4.67 (m, 1H), 4.53-3.34 (m, 3H), 2.50-0.96 (m, 7H).

Example 116: (±)-(4-fluoro-2-(2H-1,2,3-triazol-2-yl) phenyl)(2-(((5-fluoropyridin-2-yl)oxy)methyl)-7-azabicyclo[2.2.1]heptan-7-yl)methanone

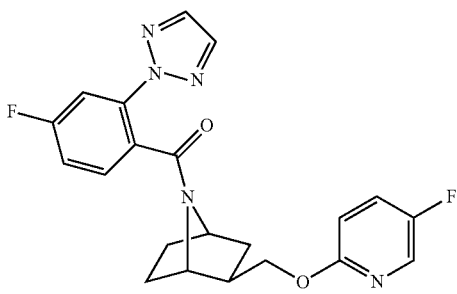 [SMILES: O=C(c1ccc(F)cc1-n1nccn1)N1C2CCC1C(COc1ccc(F)cn1)C2]

Prepared analogous to example 105 substituting 5-methyl-2-(2H-1,2,3-triazol-2-yl)benzoic acid with 4-fluoro-2-(2H-1,2,3-triazol-2-yl)benzoic acid. MS (ESI) mass calcd. for $C_{21}H_{19}F_2N_5O_2$, 411.2; m/z found 412.2 [M+H]$^+$. $^1$H NMR (MeOD): 8.11-7.71 (m, 4H), 7.69-7.24 (m, 3H), 6.98-6.43 (m, 1H), 4.83-4.67 (m, 1H), 4.53-3.34 (m, 3H), 2.50-0.96 (m, 7H).

Example 117: (±)-(3-fluoro-2-(2H-1,2,3-triazol-2-yl) phenyl)(2-(((5-fluoropyridin-2-yl)oxy)methyl)-7-azabicyclo[2.2.1]heptan-7-yl)methanone

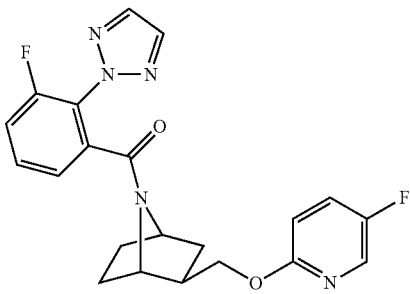 [SMILES: O=C(c1cccc(F)c1-n1nccn1)N1C2CCC1C(COc1ccc(F)cn1)C2]

Prepared analogous to example 105 substituting 5-methyl-2-(2H-1,2,3-triazol-2-yl)benzoic acid with 3-fluoro-2-(2H-1,2,3-triazol-2-yl)benzoic acid. MS (ESI) mass calcd. for $C_{21}H_{19}F_2N_5O_2$, 411.2; m/z found 412.2 [M+H]$^+$. $^1$H NMR (MeOD): 8.14-7.85 (m, 3H), 7.70-7.18 (m, 4H), 6.81-6.65 (m, 1H), 4.67-4.32 (m, 1H), 4.24-3.79 (m, 3H), 2.42-2.24 (m, 1H), 1.97-1.32 (m, 6H).

Example 118: (±)-(3-ethoxy-6-methylpyridin-2-yl) (2-(((5-fluoropyridin-2-yl)oxy)methyl)-7-azabicyclo [2.2.1]heptan-7-yl)methanone

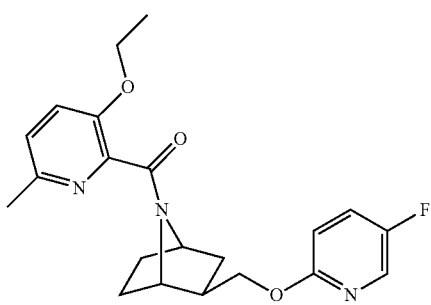 [SMILES: CCOc1ccc(C)nc1C(=O)N1C2CCC1C(COc1ccc(F)cn1)C2]

Prepared analogous to example 105 substituting 5-methyl-2-(2H-1,2,3-triazol-2-yl)benzoic acid with 3-ethoxy-6-methylpicolinic acid. MS (ESI) mass calcd. for $C_{21}H_{24}FN_3O_3$, 385.2; m/z found 385.9 [M+H]$^+$. $^1$H NMR (MeOD): 8.23-7.90 (m, 1H), 7.57-7.11 (m, 3H), 6.87-6.53 (m, 1H), 4.85-4.69 (m, 1H), 4.51-3.56 (m, 5H), 2.84-2.09 (m, 4H), 2.06-1.49 (m, 5H), 1.47-1.05 (m, 4H).

Example 119: (±)-(2-(((5-fluoropyridin-2-yl)oxy) methyl)-7-azabicyclo[2.2.1]heptan-7-yl)(4-methoxy-2-(2H-1,2,3-triazol-2-yl)phenyl)methanone

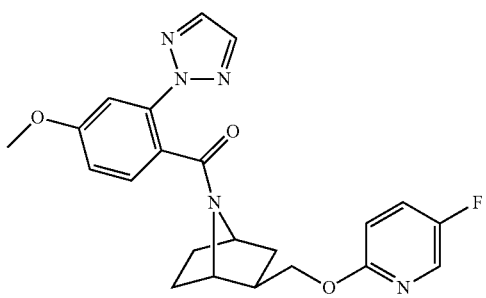

Prepared analogous to example 105 substituting 5-methyl-2-(2H-1,2,3-triazol-2-yl)benzoic acid with 4-methoxy-2-(2H-1,2,3-triazol-2-yl)benzoic acid. MS (ESI) mass calcd. for $C_{22}H_{22}FN_5O_3$, 423.2; m/z found 424.2 [M+H]$^+$. $^1$H NMR (MeOD): 8.12-7.81 (m, 3H), 7.58-7.22 (m, 3H), 7.15-6.57 (m, 2H), 4.75-4.58 (m, 1H), 4.48-3.74 (m, 6H), 2.83-2.08 (m, 1H), 2.02-0.98 (m, 6H).

Example 120: (±)-(5-chloro-2-(2H-1,2,3-triazol-2-yl)phenyl)(2-(((5-fluoropyridin-2-yl)oxy)methyl)-7-azabicyclo[2.2.1]heptan-7-yl)methanone

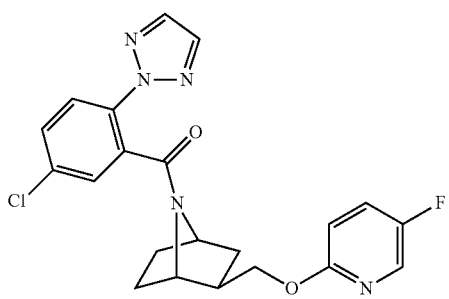 [SMILES: O=C(c1cc(Cl)ccc1-n1nccn1)N1C2CCC1C(COc1ccc(F)cn1)C2]

Prepared analogous to example 105 substituting 5-methyl-2-(2H-1,2,3-triazol-2-yl)benzoic acid with 5-chloro-2-(2H-1,2,3-triazol-2-yl)benzoic acid. MS (ESI) mass calcd. for $C_{21}H_{19}ClFN_5O_3$, 427.2; m/z found 428.2 [M+H]$^+$. $^1$H NMR (MeOD): 8.13-7.77 (m, 4H), 7.70-7.31 (m, 3H), 6.87-6.60 (m, 1H), 4.80-4.60 (m, 1H), 4.51-3.67 (m, 3H), 2.84-2.22 (m, 1H), 2.07-1.11 (m, 6H).

Example 121: (±)-(2-(((5-fluoropyridin-2-yl)oxy)
methyl)-7-azabicyclo[2.2.1]heptan-7-yl)(4-methyl-2-
(2H-1,2,3-triazol-2-yl)phenyl)methanone

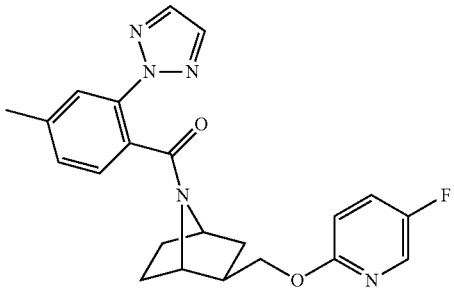 [SMILES: Cc1ccc(C(=O)N2C3CCC2C(COc2ccc(F)cn2)C3)c(-n2nccn2)c1]

Prepared analogous to example 105 substituting
5-methyl-2-(2H-1,2,3-triazol-2-yl)benzoic acid with
4-methyl-2-(2H-1,2,3-triazol-2-yl)benzoic acid. MS (ESI)
mass calcd. for $C_{22}H_{22}FN_5O_2$, 407.2; m/z found 408.2
[M+H]⁺. ¹H NMR (MeOD): 8.10-7.84 (m, 3H), 7.76-7.69
(m, 1H), 7.56-6.87 (m, 3H), 6.87-6.53 (m, 1H), 4.75-4.59
(m, 1H), 4.49-3.65 (m, 3H), 2.80-2.09 (m, 4H), 2.01-1.00
(m, 6H).

Example 122: (±)-(2-(((5-fluoropyridin-2-yl)oxy)
methyl)-7-azabicyclo 2.2.1 heptan-7-yl)(4-methyl-2-
(pyrimidin-2-yl)phenyl)methanone

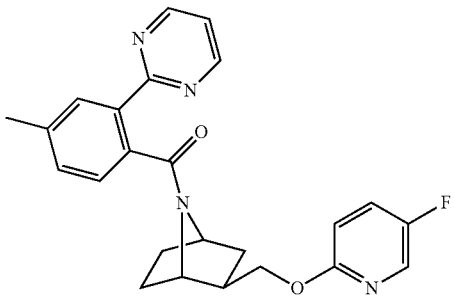 [SMILES: Cc1ccc(C(=O)N2C3CCC2C(COc2ccc(F)cn2)C3)c(-c2ncccn2)c1]

Prepared analogous to example 105 substituting
5-methyl-2-(2H-1,2,3-triazol-2-yl)benzoic acid with
4-methyl-2-(pyrimidin-2-yl)benzoic acid. MS (ESI) mass
calcd. for $C_{24}H_{23}FN_4O_2$, 418.2; m/z found 419.2 [M+H]⁺.
¹H NMR (MeOD): 8.94-8.89 (m, 1H), 8.84-8.81 (m, 1H),
8.08-7.94 (m, 2H), 7.60-7.46 (m, 1H), 7.45-7.33 (m, 2H),
7.22-6.99 (m, 1H), 6.90-6.58 (m, 1H), 4.78-4.62 (m, 1H),
4.52-3.78 (m, 3H), 2.73-2.19 (m, 4H), 2.07-1.05 (m, 6H).

Example 123: (±)-(2-(((5-fluoropyridin-2-yl)oxy)
methyl)-7-azabicyclo[2.2.1]heptan-7-yl)(2-methyl-6-
(pyrimidin-2-yl)phenyl)methanone

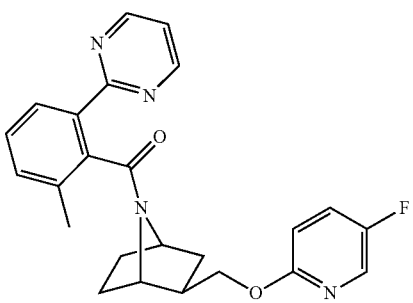 [SMILES: Cc1cccc(-c2ncccn2)c1C(=O)N1C2CCC1C(COc1ccc(F)cn1)C2]

Prepared analogous to example 105 substituting
5-methyl-2-(2H-1,2,3-triazol-2-yl)benzoic acid with
2-methyl-6-(pyrimidin-2-yl)benzoic acid. MS (ESI) mass
calcd. for $C_{24}H_{23}FN_4O_2$, 418.2; m/z found 419.2 [M+H]⁺.
¹H NMR (MeOD): 8.99-8.63 (m, 2H), 8.14-7.70 (m, 2H),
7.61-7.27 (m, 4H), 7.15-6.45 (m, 1H), 4.86-4.65 (m, 1H),
4.55-3.44 (m, 3H), 2.53-2.35 (m, 3H), 2.34-0.78 (m, 7H).

Example 124: (±)-(3-fluoro-2-(pyrimidin-2-yl)phe-
nyl)(-2-(((5-fluoropyridin-2-yl)oxy)methyl)-7-azabi-
cyclo[2.2.1]heptan-7-yl)methanone

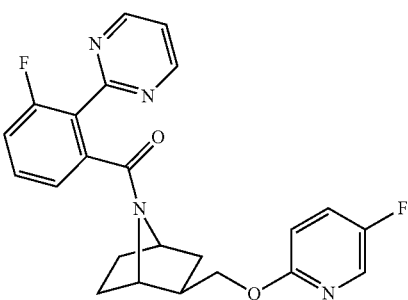 [SMILES: O=C(c1cccc(F)c1-c1ncccn1)N1C2CCC1C(COc1ccc(F)cn1)C2]

Prepared analogous to example 105 substituting
5-methyl-2-(2H-1,2,3-triazol-2-yl)benzoic acid with
3-fluoro-2-(pyrimidin-2-yl)benzoic acid. MS (ESI) mass
calcd. for $C_{23}H_{20}F_2N_4O_2$, 422.2; m/z found 422.8 [M+H]⁺.
¹H NMR (MeOD): 9.03-8.62 (m, 2H), 8.19-7.82 (m, 1H),
7.67-7.11 (m, 5H), 6.85-6.62 (m, 1H), 4.54 (s, 1H), 4.26-
3.76 (m, 3H), 2.33 (s, 1H), 2.01-1.32 (m, 6H).

Example 125: (±)-(2-(((5-fluoropyridin-2-yl)oxy)
methyl)-7-azabicyclo[2.2.1]heptan-7-yl)(3-methyl-2-
(2H-1,2,3-triazol-2-yl)phenyl)methanone

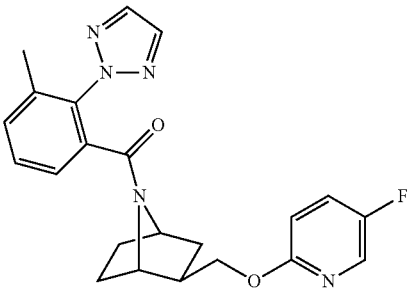 [SMILES: Cc1cccc(C(=O)N2C3CCC2C(COc2ccc(F)cn2)C3)c1-n1nccn1]

Prepared analogous to example 105 substituting
5-methyl-2-(2H-1,2,3-triazol-2-yl)benzoic acid with
3-methyl-2-(2H-1,2,3-triazol-2-yl)benzoic acid. MS (ESI)
mass calcd. for $C_{22}H_{22}FN_5O_2$, 407.2; m/z found 408.2
[M+H]⁺. ¹H NMR (MeOD): 8.05-7.95 (m, 1H), 7.93-7.84
(m, 2H), 7.57-7.05 (m, 4H), 6.81-6.65 (m, 1H), 4.61-3.98
(m, 2H), 3.97-3.75 (m, 2H), 2.38-2.23 (m, 1H), 2.19-2.14
(m, 3H), 1.97-1.32 (m, 6H).

Example 126: (±)-(2-(((5-fluoropyridin-2-yl)oxy)methyl)-7-azabicyclo[2.2.1]heptan-7-yl)(5-(hydroxymethyl)-2-(2H-1,2,3-triazol-2-yl)phenyl)methanone

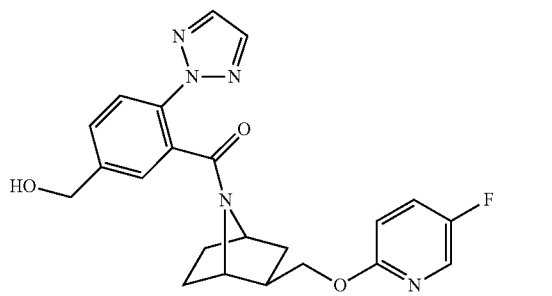 [SMILES: O=C(c1cc(CO)ccc1-n1nccn1)N1C2CCC1C(COc1ccc(F)cn1)C2]

Step A: (±)-(5-bromo-2-(2H-1,2,3-triazol-2-yl)phenyl)(-2-(((5-fluoropyridin-2-yl)oxy)methyl)-7-azabicyclo[2.2.1]heptan-7-yl)methanone. Prepared analogous to example 105 substituting 5-methyl-2-(2H-1,2,3-triazol-2-yl)benzoic acid with 5-bromo-2-(2H-1,2,3-triazol-2-yl)benzoic acid.

Step B: (±)-methyl 3-(-2-(((5-fluoropyridin-2-yl)oxy)methyl)-7-azabicyclo[2.2.1]heptane-7-carbonyl)-4-(2H-1,2,3-triazol-2-yl)benzoate. The title compound of step A (100 mg, 0.2 mmol) and Pd(dppf)Cl$_2$ (35 mg) in MeOH (10 mL) was heated to 120° C. for 24 h in a sealed tube. The reaction was allowed to cool to rt and filtered. The filtrate was concentrated and purified via preparative TLC to give the title compound (20 mg, 21%).

Step C: (±)-(2-(((5-fluoropyridin-2-yl)oxy)methyl)-7-azabicyclo[2.2.1]heptan-7-yl)(5-(hydroxymethyl)-2-(2H-1,2,3-triazol-2-yl)phenyl)methanone. To the title compound of step B (40 mg, 0.1 mmol)) in MeOH (0.2 mL) and THF (6 mL) at 0° C. was added NaBH$_4$ (4 mg, 0.1 mmol). After stirring overnight at rt, the reaction was concentrated and purified directly via silica gel chromatography (EtOAc in petroleum ethers) to give the title compound. MS (ESI) mass calcd. for $C_{21}H_{21}FN_6O_2$, 408.2; m/z found 409.2 [M+H]$^+$. $^1$H NMR (MeOD): 8.07-7.82 (m, 4H), 7.66-7.29 (m, 3H), 6.85-6.60 (m, 1H), 4.70 (d, J=8.7 Hz, 2H), 4.50-3.73 (m, 4H), 2.43-2.20 (m, 1H), 2.04-1.28 (m, 6H).

Example 127: (±)-(2-(3-methyl-1,2,4-oxadiazol-5-yl)phenyl)(2-((pyridin-2-yloxy)methyl)-7-azabicyclo[2.2.1]heptan-7-yl)methanone

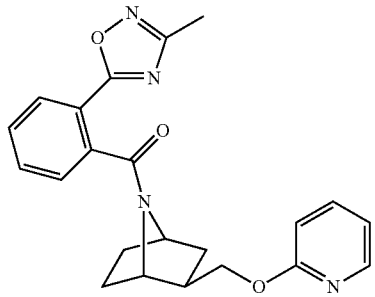 [SMILES: Cc1noc(-c2ccccc2C(=O)N2C3CCC2C(COc2ccccn2)C3)n1]

Prepared analogous to Example 2 substituting intermediate A-9 with 2-(3-methyl-1,2,4-oxadiazol-5-yl)benzoic acid. MS (ESI) mass calcd. for $C_{22}H_{22}N_4O_3$, 390.2; m/z found 391.1 [M+H]$^+$. $^1$H NMR (MeOD): 8.12-8.00 (m, 2H), 7.75-7.58 (m, 2H), 7.55-7.49 (m, 1H), 7.38-7.28 (m, 1H), 6.95-6.91 (m, 1H), 6.85-6.55 (m, 1H), 4.81-4.78 (m, 1H), 4.27-4.14 (m, 1H), 4.01-3.97 (m, 1H), 3.77-3.75 (m, 1H), 2.44-2.26 (m, 4H), 2.10-1.95 (m, 1H), 1.87-1.62 (m, 3H), 1.56-1.46 (m, 2H).

Example 128: (±)-(6-methyl-2-(2H-1,2,3-triazol-2-yl)pyridin-3-yl)(2-((pyridin-2-yloxy)methyl)-7-azabicyclo[2.2.1]heptan-7-yl)methanone

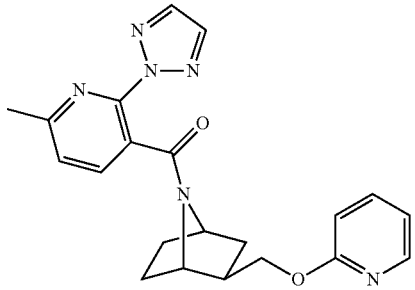 [SMILES: Cc1ccc(C(=O)N2C3CCC2C(COc2ccccn2)C3)c(-n2nccn2)n1]

Prepared analogous to Example 127 substituting 2-(3-methyl-1,2,4-oxadiazol-5-yl)benzoic acid with 6-methyl-2-(2H-1,2,3-triazol-2-yl)nicotinic acid. MS (ESI) mass calcd. for $C_{21}H_{22}N_6O_2$, 390.2; m/z found 391.2 [M+H]$^+$. $^1$H NMR (MeOD): 8.15-8.09 (m, 1H), 7.99 (s, 2H), 7.91-7.71 (m, 1H), 7.69-6.92 (m, 3H), 6.83-6.59 (m, 1H), 4.71-4.68 (m, 1H), 4.22-4.09 (m, 1H), 4.01-3.76 (m, 2H), 2.64-2.52 (m, 3H), 2.43-2.23 (m, 1H), 2.00-1.36 (m, 6H).

Example 129: (±)-(3-fluoro-2-(2H-1,2,3-triazol-2-yl)phenyl)(2-((pyridin-2-yloxy)methyl)-7-azabicyclo[2.2.1]heptan-7-yl)methanone

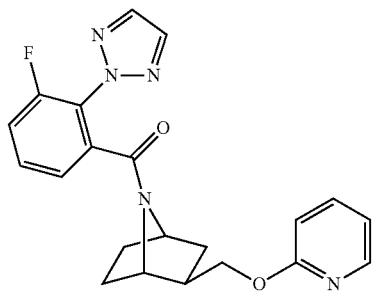 [SMILES: O=C(c1cccc(F)c1-n1nccn1)N1C2CCC1C(COc1ccccn1)C2]

Prepared analogous to Example 127 substituting 2-(3-methyl-1,2,4-oxadiazol-5-yl)benzoic acid with 3-fluoro-2-(2H-1,2,3-triazol-2-yl)benzoic acid. MS (ESI) mass calcd. for $C_{21}H_{20}FN_5O_2$, 393.2; m/z found 394.0 [M+H]$^+$. $^1$H NMR (MeOD): 8.14-8.12 (m, 1H), 7.95-7.93 (m, 2H), 7.69-7.46 (m, 2H), 7.40-7.31 (m, 1H), 7.22-7.12 (m, 1H), 6.99-6.91 (m, 1H), 6.80-6.66 (m, 1H), 4.57-4.56 (m, 1H), 4.04-3.88 (m, 3H), 2.38-2.27 (m, 1H), 1.85-1.43 (m, 6H).

Example 130: (±)-(6-methyl-2-(1H-1,2,3-triazol-1-yl)pyridin-3-yl)(2-((pyridin-2-yloxy)methyl)-7-azabicyclo[2.2.1]heptan-7-yl)methanone

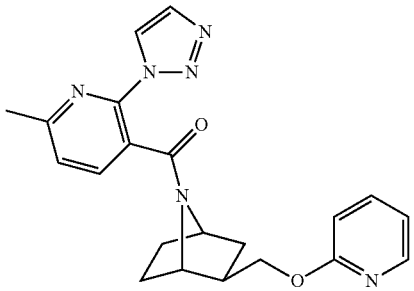 [SMILES: Cc1ccc(C(=O)N2C3CCC2C(COc2ccccn2)C3)c(-n2ccnn2)n1]

Prepared analogous to Example 127 substituting 2-(3-methyl-1,2,4-oxadiazol-5-yl)benzoic acid with 6-methyl-2-(1H-1,2,3-triazol-1-yl)nicotinic acid. MS (ESI) mass calcd. for $C_{21}H_{22}N_6O_2$, 390.2; m/z found 391.2 [M+H]$^+$. $^1$H NMR (MeOD): 8.62-8.61 (m, 1H), 8.12-8.09 (m, 1H), 7.99-7.73 (m, 2H), 7.71-7.62 (m, 1H), 7.50-6.91 (m, 2H), 6.87-6.61 (m, 1H), 4.74-4.71 (m, 1H), 4.17-3.79 (m, 3H), 2.64-2.53 (m, 3H), 2.46-2.26 (m, 1H), 2.06-1.90 (m, 1H), 1.83-1.38 (m, 5H).

Example 131: (±)-(6-methyl-2-(2H-1,2,3-triazol-2-yl)pyridin-3-yl)(2-(((4-(trifluoromethyl)pyrimidin-2-yl)oxy)methyl)-7-azabicyclo[2.2.1]heptan-7-yl)methanone

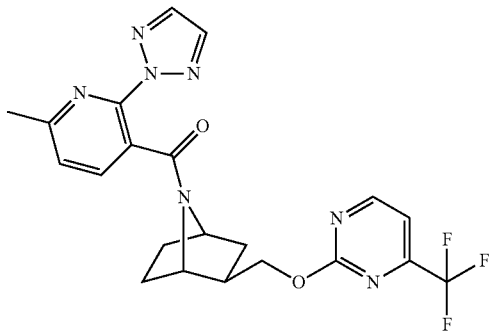 [SMILES: Cc1ccc(C(=O)N2C3CCC2C(COc2nccc(C(F)(F)F)n2)C3)c(-n2nccn2)n1]

Step A: (±)-tert-butyl 2-(((4-(trifluoromethyl)pyrimidin-2-yl)oxy)methyl)-7-azabicyclo[2.2.1]heptane-7-carboxylate. To intermediate B-10 (500 mg, 2.2 mmol) in THF (5 mL) at 0° C. was added NaH (6.6 mmol). After 30 min at rt, 2-chloro-4-(trifluoromethyl)pyrimidine (1.8 g, 9.9 mmol). The flask was then heated to 50° C. in an oil bath. After 3 h, H$_2$O was added and the reaction extracted with EtOAc (2×). Purification via silica gel chromatography (20% EtOAc in petroleum ethers) gave the title compound (752 mg, 92%).

Step B: (±)-2-(((4-(trifluoromethyl)pyrimidin-2-yl)oxy)methyl)-7-azabicyclo[2.2.1]heptane hydrochloride. To the title compound of step A (752 mg, 2 mmol) in MeOH (6 mL) was added HCl.

Step C: (±)-tert-butyl 2-(((4-(trifluoromethyl)pyrimidin-2-yl)oxy)methyl)-7-azabicyclo[2.2.1]heptane-7-carboxylate. Prepared analogous to example 127 substituting 2-(3-methyl-1,2,4-oxadiazol-5-yl)benzoic acid with 6-methyl-2-(2H-1,2,3-triazol-2-yl)nicotinic acid with the title compound of step B. MS (ESI) mass calcd. for $C_{21}H_{20}F_3N_7O_2$, 459.2; m/z found 460.2 [M+H]$^+$. $^1$H NMR (MeOD): 8.89-8.82 (m, 1H), 8.02-7.82 (m, 3H), 7.48-7.14 (m, 2H), 4.75-4.71 (m, 1H), 4.44-4.07 (m, 2H), 3.91-3.84 (m, 1H), 2.64-2.56 (m, 3H), 2.48-2.30 (m, 1H), 2.02-1.43 (m, 6H).

Example 132: (±)-(6-methyl-2-(1H-1,2,3-triazol-1-yl)pyridin-3-yl)(2-(((4-(trifluoromethyl)pyrimidin-2-yl)oxy)methyl)-7-azabicyclo[2.2.1]heptan-7-yl)methanone

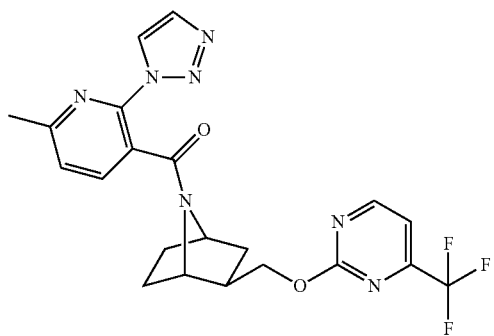

Prepared analogous to Example 131 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{21}H_{20}F_3N_7O_2$, 459.2; m/z found 460.2 [M+H]$^+$. $^1$H NMR (MeOD): 8.86-8.83 (m, 1H), 8.63-8.61 (m, 1H), 8.03-7.84 (m, 2H), 7.49-7.15 (m, 2H), 4.76-4.72 (m, 1H), 4.41-4.31 (m, 1H), 4.27-4.04 (m, 1H), 3.90-3.84 (m, 1H), 2.63-2.54 (m, 3H), 2.47-2.30 (m, 1H), 2.03-1.43 (m, 6H).

Example 133: (±)-(2-(3-methyl-1,2,4-oxadiazol-5-yl)phenyl)(2-(((4-(trifluoromethyl)pyrimidin-2-yl)oxy)methyl)-7-azabicyclo[2.2.1]heptan-7-yl)methanone

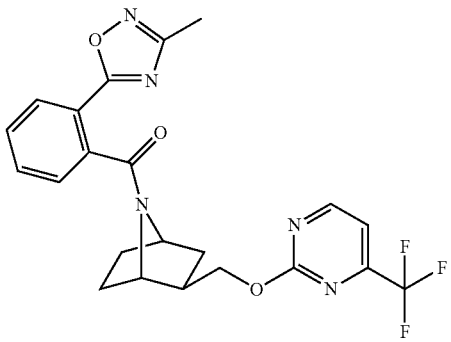 [SMILES: Cc1noc(-c2ccccc2C(=O)N2C3CCC2C(COc2nccc(C(F)(F)F)n2)C3)n1]

Prepared analogous to Example 131 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{22}H_{20}F_3N_5O_2$, 459.2; m/z found 460.2 [M+H]$^+$. $^1$H NMR (MeOD): 8.88-8.80 (m, 1H), 8.08-8.00 (m, 1H), 7.74-7.62 (m, 1H), 7.63-7.51 (m, 1H), 7.48-7.37 (m, 2H), 4.83-4.80 (m, 1H), 4.49-4.33 (m, 1H), 4.23-4.11 (m, 1H), 3.81-3.77 (m, 1H), 2.53-2.36 (m, 4H), 2.07-2.98 (m, 1H), 1.90-1.51 (m, 5H).

Example 134: (±)-(3-fluoro-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone

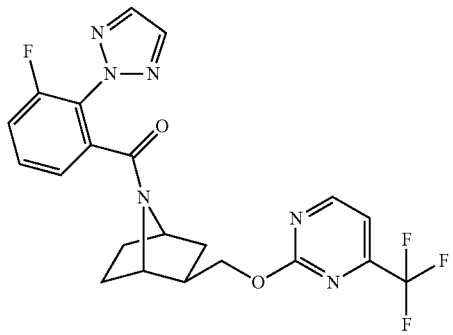 [SMILES: O=C(c1cccc(F)c1-n1nccn1)N1C2CCC1C(COc1nccc(C(F)(F)F)n1)C2]

Prepared analogous to Example 131 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{21}H_{18}F_4N_6O_2$, 462.2; m/z found 463.2 [M+H]$^+$. $^1$H NMR (MeOD): 8.89-8.84 (m, 1H), 7.96-7.94 (m, 2H), 7.69-7.28 (m, 4H), 4.61-4.58 (m, 1H), 4.29-4.06 (m, 2H), 3.97-3.93 (m, 1H), 2.46-2.37 (m, 1H), 1.88-1.40 (m, 6H).

Example 135: (±)-(6-methyl-2-(2H-1,2,3-triazol-2-yl)pyridin-3-yl)(2-(((5-methylpyridin-2-yl)oxy)methyl)-7-azabicyclo[2.2.1]heptan-7-yl)methanone

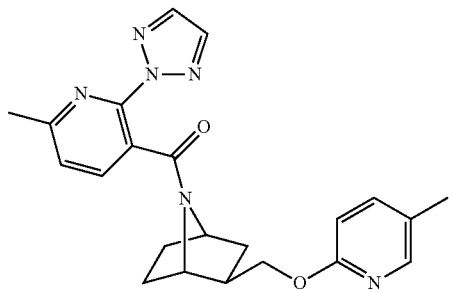

Prepared analogous to Example 131 substituting 2-chloro-4-(trifluoromethyl)pyrimidine with 2-chloro-5-methylpyridine. MS (ESI) mass calcd. for $C_{22}H_{24}N_6O_2$, 404.2; m/z found 405.2 [M+H]$^+$. $^1$H NMR (MeOD): 7.99-7.71 (m, 4H), 7.51-7.00 (m, 2H), 6.73-6.50 (m, 1H), 4.69 (d, J=3.6 Hz, 1H), 4.17-4.04 (m, 1H), 3.96-3.72 (m, 2H), 2.64-2.53 (m, 3H), 2.43-2.20 (m, 4H), 2.03-1.35 (m, 6H).

Example 136: (±)-(6-methyl-2-(1H-1,2,3-triazol-1-yl)pyridin-3-yl)(2-(((5-methylpyridin-2-yl)oxy)methyl)-7-azabicyclo[2.2.1]heptan-7-yl)methanone

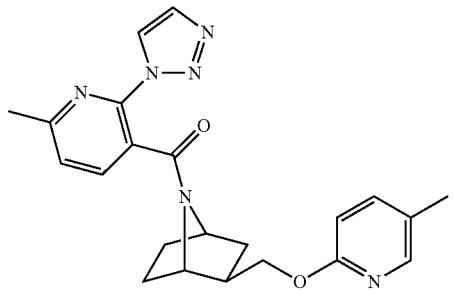

Prepared analogous to Example 135 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{22}H_{24}N_6O_2$, 404.2; m/z found 405.2 [M+H]$^+$. $^1$H NMR (MeOD): 8.62-8.55 (m, 1H), 8.19-7.88 (m, 3H), 7.75-7.47 (m, 2H), 7.05-6.52 (m, 1H), 4.72-4.71 (m, 1H), 4.08-4.02 (m, 1H), 3.98-3.74 (m, 2H), 2.64-2.53 (m, 3H), 2.37-2.24 (m, 4H), 1.96 (brs, 1H), 1.82-1.35 (m, 5H).

Example 137: (±)-(2-(3-methyl-1,2,4-oxadiazol-5-yl)phenyl)(2-(((5-methylpyridin-2-yl)oxy)methyl)-7-azabicyclo[2.2.1]heptan-7-yl)methanone

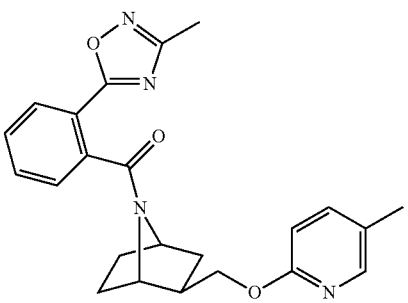 [SMILES: Cc1ccc(OCC2CC3CCC2N3C(=O)c2ccccc2-c2nc(C)no2)nc1]

Prepared analogous to Example 135 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{23}H_{24}N_4O_3$, 404.2; m/z found 405.2 [M+H]$^+$. $^1$H NMR (MeOD): 8.09-8.00 (m, 1H), 7.92-7.88 (m, 1H), 7.75-7.63 (m, 1H), 7.55-7.43 (m, 2H), 7.38-7.29 (m, 1H), 6.76-6.47 (m, 1H), 4.81-4.77 (m, 1H), 4.22-4.09 (m, 1H), 3.95 (d, J=8.1 Hz, 1H), 3.76-3.74 (m, 1H), 2.44-2.20 (m, 7H), 2.07-1.97 (m, 1H), 1.86-1.62 (m, 3H), 1.55-1.42 (m, 2H).

Example 138: (±)-(3-fluoro-2-(2H-1,2,3-triazol-2-yl)phenyl)(2-(((5-methylpyridin-2-yl)oxy)methyl)-7-azabicyclo[2.2.1]heptan-7-yl)methanone

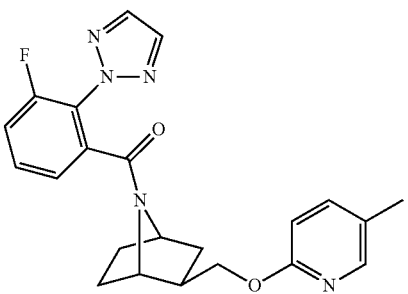 [SMILES: Cc1ccc(OCC2CC3CCC2N3C(=O)c2cccc(F)c2-n2nccn2)nc1]

Prepared analogous to Example 135 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{22}H_{22}FN_5O_2$, 407.2; m/z found 408.2 [M+H]$^+$. $^1$H NMR (MeOD): 7.96-7.93 (m, 3H), 7.69-7.49 (m, 2H), 7.40-7.33 (m, 1H), 7.22-7.13 (m, 1H), 6.71-6.58 (m, 1H), 4.58-4.55 (m, 1H), 4.02-3.83 (m, 3H), 2.37-2.23 (m, 4H), 1.85-1.41 (m, 6H).

Example 139: (±)-(6-methyl-2-(2H-1,2,3-triazol-2-yl)pyridin-3-yl)(2-(((6-methylpyridin-2-yl)oxy)methyl)-7-azabicyclo[2.2.1]heptan-7-yl)methanone

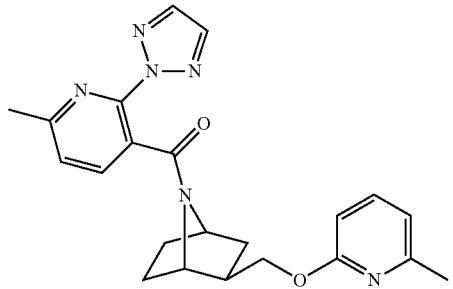

Prepared analogous to Example 135 substituting 2-chloro-4-(trifluoromethyl)pyrimidine with 2-chloro-6-methylpyridine. MS (ESI) mass calcd. for $C_{22}H_{24}N_6O_2$, 404.2; m/z found 405.2 [M+H]$^+$. $^1$H NMR (MeOD): 7.99 (s, 2H), 7.91-7.69 (m, 1H), 7.56-6.77 (m, 3H), 6.60-6.38 (m, 1H), 4.70-4.69 (m, 1H), 4.21-4.05 (m, 1H), 3.98-3.77 (m, 2H), 2.64-2.51 (m, 3H), 2.43-2.20 (m, 4H), 2.03-1.37 (m, 6H).

Example 140: (±)-(6-methyl-2-(1H-1,2,3-triazol-1-yl)pyridin-3-yl)(2-(((6-methylpyridin-2-yl)oxy)methyl)-7-azabicyclo[2.2.1]heptan-7-yl)methanone

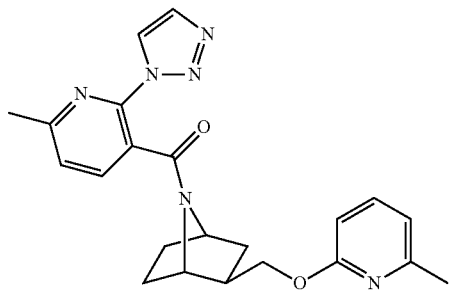

Prepared analogous to Example 139 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{22}H_{24}N_6O_2$, 404.2; m/z found 405.2 [M+H]$^+$. $^1$H NMR (MeOD): 8.34 (d, J=7.1 Hz, 1H), 7.77-7.42 (m, 3H), 7.28-6.35 (m, 3H), 4.82-4.79 (m, 1H), 4.24-3.94 (m, 2H), 3.87-3.81 (m, 1H), 2.63-2.22 (m, 7H), 2.15-1.98 (m, 1H), 1.84-1.34 (m, 5H).

Example 141: (±)-(2-(3-methyl-1,2,4-oxadiazol-5-yl)phenyl)(2-(((6-methylpyridin-2-yl)oxy)methyl)-7-azabicyclo[2.2.1]heptan-7-yl)methanone

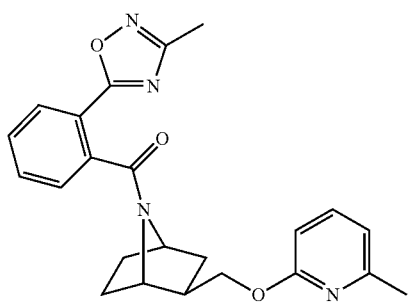 [SMILES: Cc1cccc(OCC2CC3CCC2N3C(=O)c2ccccc2-c2nc(C)no2)n1]

Prepared analogous to Example 139 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{23}H_{24}N_4O_3$, 404.2; m/z found 405.2 [M+H]$^+$. $^1$H NMR (MeOD): 8.10-8.00 (m, 1H), 7.75-7.63 (m, 1H), 7.57-7.47 (m, 2H), 7.37-7.26 (m, 1H), 6.79 (dd, J=7.2, 2.8 Hz, 1H), 6.64-6.35 (m, 1H), 4.81-4.78 (m, 1H), 4.25-4.11 (m, 1H), 3.98-3.95 (m, 1H), 3.79-3.74 (m, 1H), 2.42-2.25 (m, 7H), 2.08-1.95 (m, 1H), 1.86-1.63 (m, 3H), 1.58-1.44 (m, 2H).

Example 142: (±)-(3-fluoro-2-(2H-1,2,3-triazol-2-yl)phenyl)(2-(((6-methylpyridin-2-yl)oxy)methyl)-7-azabicyclo[2.2.1]heptan-7-yl)methanone

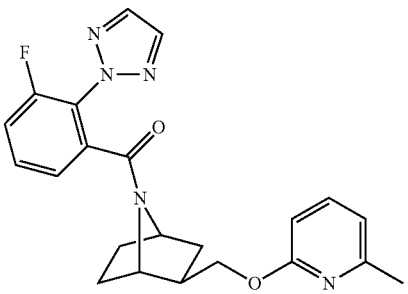 [SMILES: Cc1cccc(OCC2CC3CCC2N3C(=O)c2cccc(F)c2-n2nccn2)n1]

Prepared analogous to Example 139 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{22}H_{22}FN_5O_2$, 407.2; m/z found 408.2 [M+H]$^+$. $^1$H NMR (MeOD): 7.95-7.93 (m, 2H), 7.68-7.47 (m, 2H), 7.40-7.31 (m, 1H), 7.21-7.09 (m, 1H), 6.80 (t, J=8.3 Hz, 1H), 6.58-6.46 (m, 1H), 4.56 (s, 1H), 4.01 (d, J=7.3 Hz, 1H), 3.91 (d, J=7.4 Hz, 2H), 2.43 (d, J=2.5 Hz, 3H), 2.38-2.28 (m, 1H), 1.83-1.45 (m, 6H).

Example 143: (±)-(6-methyl-2-(2H-1,2,3-triazol-2-yl)pyridin-3-yl)(2-(((6-(trifluoromethyl)pyridin-2-yl)oxy)methyl)-7-azabicyclo[2.2.1]heptan-7-yl)methanone

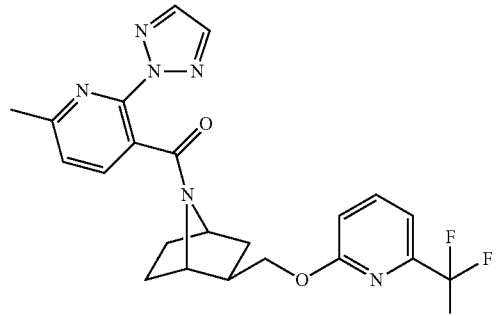

Prepared analogous to Example 131 substituting 2-chloro-4-(trifluoromethyl)pyrimidine with 2-chloro-6-(trifluoromethyl)pyridine. MS (ESI) mass calcd. for $C_{22}H_{21}F_3N_6O_2$, 458.2; m/z found 459.2 [M+H]$^+$. $^1$H NMR (MeOD): 7.91 (s, 1H), 7.84 (s, 1H), 7.73-7.65 (m, 2H), 7.29-7.25 (m, 2H), 6.93-6.69 (m, 1H), 4.85-4.82 (m, 1H), 4.25-4.16 (m, 1H), 3.98-3.96 (m, 1H), 3.79-3.69 (m, 1H), 2.69-2.56 (m, 3H), 2.38-2.16 (m, 1H), 2.05-1.24 (m, 6H).

Example 144: (±)-(6-methyl-2-(1H-1,2,3-triazol-1-yl)pyridin-3-yl)(2-(((6-(trifluoromethyl)pyridin-2-yl)oxy)methyl)-7-azabicyclo[2.2.1]heptan-7-yl)methanone

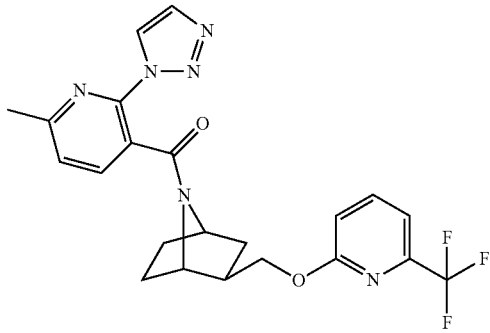

Prepared analogous to Example 143 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{22}H_{21}F_3N_6O_2$, 458.2; m/z found 459.2 [M+H]$^+$. $^1$H NMR (MeOD): 8.61 (t, J=1.1 Hz, 1H), 8.00-7.72 (m, 3H), 7.49-6.83 (m, 3H), 4.75-4.71 (m, 1H), 4.31-4.10 (m, 1H), 4.08-3.95 (m, 1H), 3.89-3.77 (m, 1H), 2.64-2.52 (m, 3H), 2.43-2.27 (m, 1H), 2.06-1.89 (m, 1H), 1.82-1.37 (m, 5H).

Example 145: (±)-(2-(3-methyl-1,2,4-oxadiazol-5-yl)phenyl)(2-(((6-(trifluoromethyl)pyridin-2-yl)oxy)methyl)-7-azabicyclo[2.2.1]heptan-7-yl)methanone

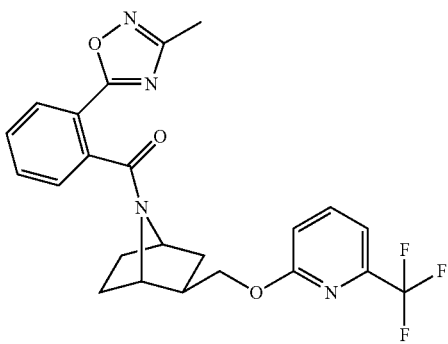 [SMILES: Cc1noc(-c2ccccc2C(=O)N2C3CCC2C(COc2cccc(C(F)(F)F)n2)C3)n1]

Prepared analogous to Example 143 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{23}H_{21}FN_4O_3$, 458.2; m/z found 459.2 [M+H]$^+$. $^1$H NMR (MeOD): 8.10-8.01 (m, 1H), 7.88-7.77 (m, 1H), 7.75-7.63 (m, 1H), 7.54-7.49 (m, 1H), 7.39-7.25 (m, 2H), 7.07-6.78 (m, 1H), 4.82-4.79 (m, 1H), 4.35-4.24 (m, 1H), 4.10-4.07 (m, 1H), 3.78-3.74 (m, 1H), 2.48-2.29 (m, 4H), 2.09-1.96 (m, 1H), 1.88-1.63 (m, 3H), 1.58-1.47 (m, 2H).

Example 146: (±)-(3-fluoro-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone

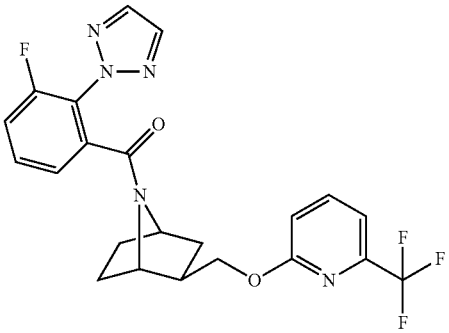 [SMILES: O=C(c1cccc(F)c1-n1nccn1)N1C2CCC1C(COc1cccc(C(F)(F)F)n1)C2]

Prepared analogous to Example 143 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{22}H_{19}F_4N_5O_2$, 461.2; m/z found 462.0 [M+H]$^+$. $^1$H NMR (MeOD): 7.95-7.93 (m, 2H), 7.86-7.80 (m, 1H), 7.68-7.12 (m, 4H), 7.02-6.86 (m, 1H), 4.59-4.56 (m, 1H), 4.10-3.86 (m, 3H), 2.38-2.30 (m, 1H), 1.95-1.45 (m, 6H).

Example 147: (±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone

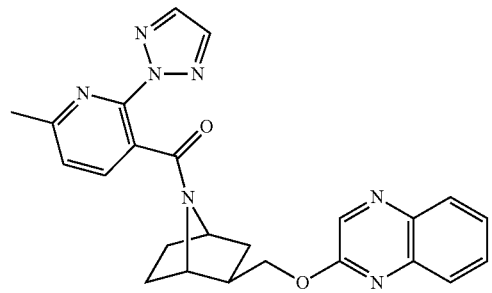 [SMILES: Cc1ccc(C(=O)N2C3CCC2C(COc2cnc4ccccc4n2)C3)c(-n2nccn2)n1]

Prepared analogous to Example 131 substituting 2-chloro-4-(trifluoromethyl)pyrimidine with 2-chloroquinoxaline. MS (ESI) mass calcd. for $C_{24}H_{23}N_7O_2$, 441.2; m/z found 442.2 [M+H]$^+$. $^1$H NMR (MeOD): 8.47-8.04 (m, 2H), 7.98-7.69 (m, 5H), 7.65-7.56 (m, 1H), 7.45-6.73 (m, 1H), 4.77-4.71 (m, 1H), 4.46-4.10 (m, 2H), 3.91-3.79 (m, 1H), 2.64-2.32 (m, 4H), 2.03-1.38 (m, 6H).

Example 148: (±)-(6-methyl-2-(1H-1,2,3-triazol-1-yl)pyridin-3-yl)(2-((quinoxalin-2-yloxy)methyl)-7-azabicyclo[2.2.1]heptan-7-yl)methanone

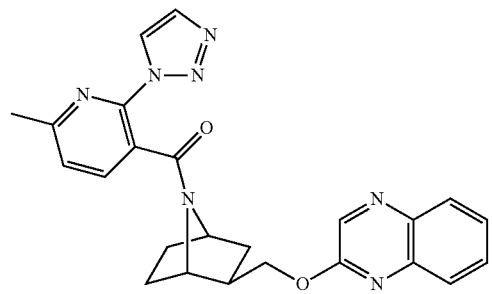 [SMILES: Cc1ccc(C(=O)N2C3CCC2C(COc2cnc4ccccc4n2)C3)c(-n2ccnn2)n1]

Prepared analogous to Example 147 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{24}H_{23}N_7O_2$, 441.2; m/z found 441.2 [M+H]$^+$. $^1$H NMR (MeOD): 8.61-8.59 (m, 1H), 8.46-8.25 (m, 1H), 8.04-7.55 (m, 6H), 7.48-6.74 (m, 1H), 4.78-4.74 (m, 1H), 4.43-4.30 (m, 1H), 4.21-4.18 (m, 1H), 3.92-3.82 (m, 1H), 2.63-2.34 (m, 4H), 2.08-1.89 (m, 1H), 1.88-1.39 (m, 5H).

Example 149: (±)-(2-(3-methyl-1,2,4-oxadiazol-5-yl)phenyl)(2-((quinoxalin-2-yloxy)methyl)-7-azabicyclo[2.2.1]heptan-7-yl)methanone

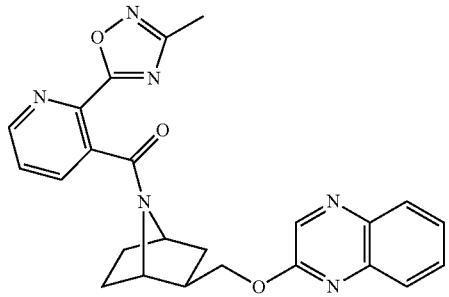 [SMILES: Cc1noc(-c2ncccc2C(=O)N2C3CCC2C(COc2cnc4ccccc4n2)C3)n1]

Prepared analogous to Example 147 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{25}H_{23}N_5O_3$, 441.2; m/z found 442.2 [M+H]$^+$. $^1$H NMR (MeOD): 8.48-8.20 (m, 1H), 8.08-7.91 (m, 2H), 7.83-7.12 (m, 6H), 4.86-4.81 (m, 1H), 4.50-4.36 (m, 1H), 4.26-4.18 (m, 1H), 3.80-3.77 (m, 1H), 2.55-2.34 (m, 4H), 2.09-1.97 (m, 1H), 1.91-1.64 (m, 3H), 1.61-1.50 (m, 2H).

Example 150: (±)-(3-fluoro-2-(2H-1,2,3-triazol-2-yl)phenyl)(2-((quinoxalin-2-yloxy)methyl)-7-azabicyclo[2.2.1]heptan-7-yl)methanone

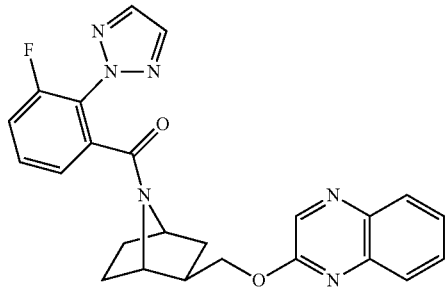 [SMILES: O=C(c1cccc(F)c1-n1nccn1)N1C2CCC1C(COc1cnc3ccccc3n1)C2]

Prepared analogous to Example 147 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{24}H_{21}FN_6O_2$, 444.2; m/z found 445.1 [M+H]$^+$. $^1$H NMR (MeOD): 8.47-8.33 (m, 1H), 8.01-7.60 (m, 6H), 7.54-6.92 (m, 3H), 4.65-4.60 (m, 1H), 4.31-4.13 (m, 2H), 3.96-3.95 (m, 1H), 2.52-2.40 (m, 1H), 1.96-1.44 (m, 6H).

Example 151: (±)-(2-(((4,6-dimethylpyrimidin-2-yl)oxy)methyl)-7-azabicyclo[2.2.1]heptan-7-yl)(6-methyl-2-(2H-1,2,3-triazol-2-yl)pyridin-3-yl)methanone

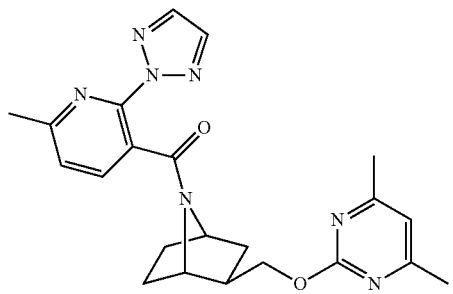

Prepared analogous to Example 131 substituting 2-chloro-4-(trifluoromethyl)pyrimidine with 2-chloro-4,6-dimethylpyrimidine. MS (ESI) mass calcd. for $C_{22}H_{25}N_7O_2$, 419.2; m/z found 420.2 [M+H]$^+$. $^1$H NMR (MeOD): 8.02-7.99 (m, 2H), 7.94-7.46 (m, 1H), 7.48-7.10 (m, 1H), 6.87 (s, 1H), 4.72-4.71 (m, 1H), 4.38-3.97 (m, 2H), 3.89-3.84 (m, 1H), 2.65-2.17 (m, 10H), 1.98-1.37 (m, 6H).

Example 152: (±)-(2-(((4,6-dimethylpyrimidin-2-yl)oxy)methyl)-7-azabicyclo[2.2.1]heptan-7-yl)(6-methyl-2-(1H-1,2,3-triazol-1-yl)pyridin-3-yl)methanone

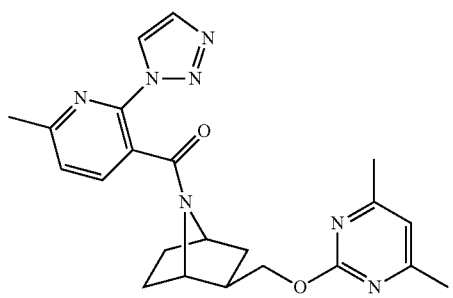

Prepared analogous to Example 151 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{22}H_{25}N_7O_2$, 419.2; m/z found 420.2 [M+H]$^+$. $^1$H NMR (MeOD): 8.62-8.61 (m, 1H), 7.98-7.78 (m, 2H), 7.50-7.11 (m, 1H), 6.86 (d, J=9.7 Hz, 1H), 4.75-4.71 (m, 1H), 4.25-4.23 (m, 1H), 4.16-3.84 (m, 2H), 2.64-2.55 (m, 3H), 2.46-2.25 (m, 7H), 2.06-1.88 (m, 1H), 1.85-1.39 (m, 5H).

Example 153: (±)-(2-(((4,6-dimethylpyrimidin-2-yl)oxy)methyl)-7-azabicyclo[2.2.1]heptan-7-yl)(2-(3-methyl-1,2,4-oxadiazol-5-yl)phenyl)methanone

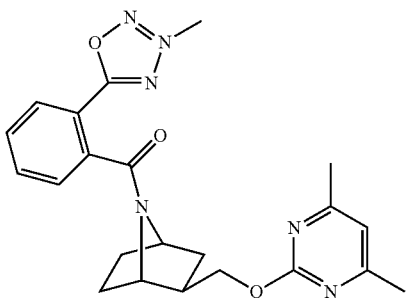

Prepared analogous to Example 151 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{23}H_{25}N_5O_3$, 419.2; m/z found 420.2 [M+H]$^+$. $^1$H NMR (MeOD): 8.10-8.01 (m, 1H), 7.76-7.64 (m, 1H), 7.58-7.51 (m, 1H), 7.42-7.36 (m, 1H), 6.86 (s, 1H), 4.83-4.80 (m, 1H), 4.42-4.22 (m, 1H), 4.13-4.00 (m, 1H), 3.83-3.76 (m, 1H), 2.49-2.28 (m, 10H), 2.08-1.98 (m, 1H), 1.89-1.65 (m, 3H), 1.58-1.48 (m, 2H).

Example 154: (±)-(2-(((4,6-dimethylpyrimidin-2-yl)oxy)methyl)-7-azabicyclo[2.2.1]heptan-7-yl)(3-fluoro-2-(2H-1,2,3-triazol-2-yl)phenyl)methanone

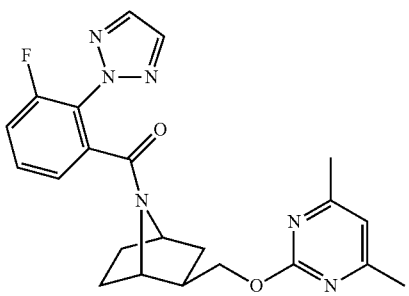 [SMILES: Cc1cc(C)nc(OCC2CC3CCC2N3C(=O)c2cccc(F)c2-n2nccn2)n1]

Prepared analogous to Example 151 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{22}H_{23}FN_6O_2$, 422.2; m/z found 423.1 [M+H]$^+$. $^1$H NMR (MeOD): 7.96-7.95 (m, 2H), 7.69-7.22 (m, 3H), 6.87 (d, J=5.8 Hz, 1H), 4.58-4.56 (m, 1H), 4.19-3.89 (m, 3H), 2.42-2.34 (m, 7H), 1.90-1.37 (m, 6H).

Example 155: (±)-(2-ethoxy-4-methylpyridin-3-yl)(2-((pyridin-2-yloxy)methyl)-7-azabicyclo[2.2.1]heptan-7-yl)methanone

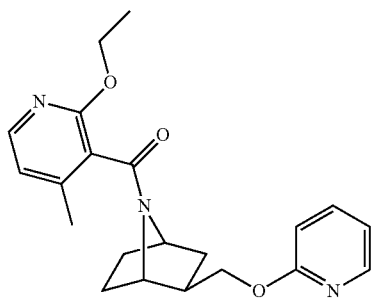 [SMILES: CCOc1nccc(C)c1C(=O)N1C2CCC1C(COc1ccccn1)C2]

Prepared analogous to Example 1 substituting intermediate B-9 with B-10 and 5-fluoro-2-(pyrimidin-2-yl)benzoic acid with 2-ethoxy-4-methylnicotinic acid. MS (ESI) mass calcd. for $C_{21}H_{25}N_3O_3$, 367.2; m/z found 368.3 [M+H]$^+$. $^1$H NMR (CDCl$_3$): 8.13-8.05 (m, 1H), 7.99-7.87 (m, 1H), 7.58-7.46 (m, 1H), 6.87-6.79 (m, 1H), 6.76-6.67 (m, 1H), 6.55-6.49 (m, 1H), 4.92-4.84 (m, 1H), 4.43-3.64 (m, 5H), 2.43-1.22 (m, 13H).

Example 156: (±)-(6-methylimidazo[2,1-b]thiazol-5-yl)(2-((pyridin-2-yloxy)methyl)-7-azabicyclo[2.2.1]heptan-7-yl)methanone

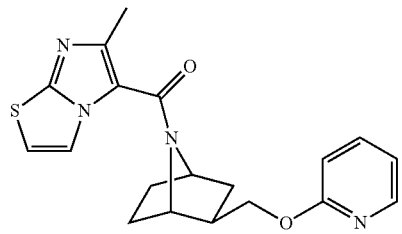 [SMILES: Cc1nc2sccn2c1C(=O)N1C2CCC1C(COc1ccccn1)C2]

Prepared analogous to Example 1 substituting intermediate B-9 with B-10 and 5-fluoro-2-(pyrimidin-2-yl)benzoic acid with 6-methylimidazo[2,1-b]thiazole-5-carboxylic acid. $^1$H NMR (CDCl$_3$): 8.05-7.98 (m, 1H), 7.79 (d, J=4.5 Hz, 1H), 7.54-7.47 (m, 1H), 6.84-6.78 (m, 1H), 6.76 (d, J=4.5 Hz, 1H), 6.62 (d, J=8.4 Hz, 1H), 4.54-4.35 (m, 2H), 4.11-4.03 (m, 1H), 4.02-3.88 (m, 1H), 2.46 (s, 3H), 2.39-2.28 (m, 1H), 2.07-1.97 (m, 1H), 1.80-1.70 (m, 2H), 1.65-1.52 (m, 3H).

Example 157: (±)-(5-bromo-2-ethoxypyridin-3-yl)(2-((pyridin-2-yloxy)methyl)-7-azabicyclo[2.2.1]heptan-7-yl)methanone

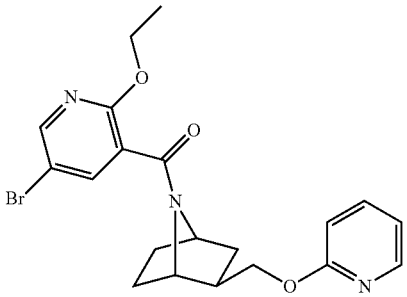 [SMILES: CCOc1ncc(Br)cc1C(=O)N1C2CCC1C(COc1ccccn1)C2]

Prepared analogous to Example 1 substituting intermediate B-9 with B-10 and 5-fluoro-2-(pyrimidin-2-yl)benzoic acid with 5-bromo-2-ethoxynicotinic acid. MS (ESI) mass calcd. for $C_{20}H_{22}BrN_3O_3$, 431.1; m/z found 432.2 [M+H]$^+$. $^1$H NMR (CDCl$_3$): 8.33-8.07 (m, 2H), 7.74 (d, J=2.5 Hz, 0.5H), 7.61 (d, J=2.5 Hz, 0.5H), 7.59-7.49 (m, 1H), 6.89-6.81 (m, 1H), 6.75 (d, J=8.3 Hz, 0.5H), 6.55 (d, J=8.4 Hz, 0.5H), 4.86-4.80 (m, 1H), 4.48-3.78 (m, 5H), 2.43-2.33 (m, 0.5H), 2.32-2.23 (m, 0.5H), 2.03-1.39 (m, 6H), 1.37-1.29 (m, 3H).

Example 158: (±)-(2-ethoxy-6-methylpyridin-3-yl)(2-((pyridin-2-yloxy)methyl)-7-azabicyclo[2.2.1]heptan-7-yl)methanone

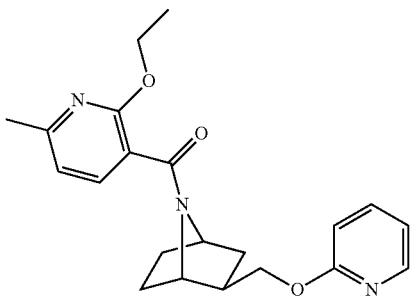 [SMILES: CCOc1nc(C)ccc1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 2-ethoxy-6-methylnicotinic acid. MS (ESI) mass calcd. for $C_{21}H_{25}N_3O_3$, 367.2; m/z found 368.3 [M+H]$^+$. $^1$H NMR (CDCl$_3$): 8.14-8.08 (m, 1H), 7.57-7.47 (m, 1.5H), 7.38 (d, J=7.4 Hz, 0.5H), 6.86-6.82 (m, 1H), 6.74 (d, J=8.3 Hz, 0.5H), 6.72 (d, J=7.4 Hz, 0.5H), 6.51 (d, J=8.3 Hz, 0.5H), 6.46 (d, J=7.4 Hz, 0.5H), 4.84-4.79 (m, 1H), 4.44-4.34 (m, 1.5H), 4.27-4.09 (m, 1.5H), 4.06-4.01 (m, 0.5H), 3.92-3.80 (m, 1.5H), 2.43 (s, 1.5H), 2.38-2.32 (m, 2H), 2.26-2.20 (m, 0.5H), 2.01-1.40 (m, 6H), 1.36-1.28 (m, 3H).

Example 159: (±)-(7-hydroxyquinolin-8-yl)(2-((pyridin-2-yloxy)methyl)-7-azabicyclo[2.2.1]heptan-7-yl)methanone

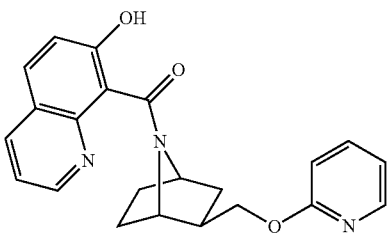 [SMILES: O=C(c1c(O)ccc2cccnc12)N1C2CCC1C(COc1ccccn1)C2]

Prepared analogous to Example 1 substituting intermediate B-9 with intermediate B-10 and 5-fluoro-2-(pyrimidin-2-yl)benzoic acid with 7-hydroxyquinoline-8-carboxylic acid (intermediate A-29 step B). MS (ESI) mass calcd. for $C_{22}H_{21}N_3O_3$, 375.2; m/z found 376.3 [M+H]$^+$. $^1$H NMR (CDCl$_3$): 8.88-8.66 (m, 1H), 8.19-7.93 (m, 2H), 7.80-7.41 (m, 2H), 7.26-6.25 (series of m, 4H), 5.10-4.87 (m, 1H), 4.34-3.60 (m, 3H), 2.51-1.00 (series of m, 7H).

Example 160: (±)-(2-ethoxy-5-phenylpyridin-3-yl)(2-((pyridin-2-yloxy)methyl)-7-azabicyclo[2.2.1]heptan-7-1)methanone

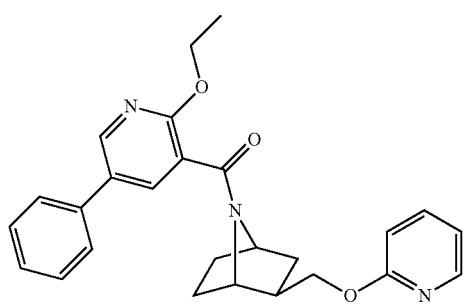 [SMILES: CCOc1ncc(-c2ccccc2)cc1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 2-ethoxy-5-phenylnicotinic acid. MS (ESI) mass calcd. for $C_{26}H_{27}N_3O_3$, 429.2; m/z found 430.2 [M+H]$^+$. $^1$H NMR (CDCl$_3$): 8.40 and 8.30 (2d, J=2.5 Hz, 1H), 8.15-8.12 and 7.98-7.94 (2m, 1H), 7.87 and 7.74 (2d, J=2.5 Hz, 1H), 7.59-7.28 (m, 6H), 6.88-6.83 and 6.72-6.68 (2m, 1H), 6.76 and 6.47 (2d, J=8.3 Hz, 1H), 4.89-4.84 (m, 1H), 4.34-3.84 (series of m, 5H), 2.43-2.34 and 2.32-2.23 (m, 1H), 2.06-1.45 (series of m, 6H), 1.42-1.32 (m, 3H).

Example 161: (±)-(4-bromo-2-ethoxypyridin-3-yl)(2-((pyridin-2-yloxy)methyl)-7-azabicyclo[2.2.1]heptan-7-yl)methanone

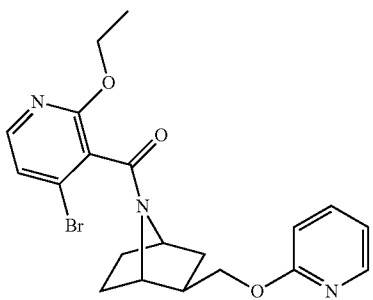 [SMILES: CCOc1nccc(Br)c1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 4-bromo-2-ethoxynicotinic acid. MS (ESI) mass calcd. for $C_{20}H_{22}BrN_3O_3$, 431.1; m/z found 432.2 [M+H]$^+$. $^1$H NMR (CDCl$_3$): 8.15-8.08 (m, 1H), 7.96-7.87 (m, 1H), 7.60-7.49 (m, 1H), 7.11-6.92 (series of m, 1H), 6.88-6.82 (m, 1H), 6.78-6.52 (series of m, 1H), 4.94-4.87 (m, 1H), 4.47-3.67 (series of m, 5H), 2.45-1.41 (series of m, 7H), 1.38-1.27 (m, 3H).

Example 162: (±)-(2-chloro-4-ethoxypyridin-3-yl)(2-((pyridin-2-yloxy)methyl)-7-azabicyclo[2.2.1]heptan-7-yl)methanone

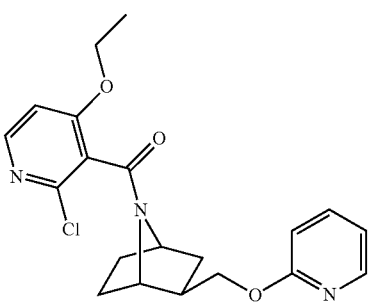 [SMILES: CCOc1ccnc(Cl)c1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 2-chloro-4-ethoxynicotinic acid. MS (ESI) mass calcd. for $C_{20}H_{22}ClN_3O_3$, 387.1; m/z found 388.3 [M+H]$^+$. $^1$H NMR (CDCl$_3$): 8.27-8.17 (m, 1H), 8.15-8.07 (m, 1H), 7.60-7.48 (m, 1H), 6.88-6.82 (m, 1H), 6.80-6.73 (m, 1H), 6.58-6.49 (m, 1H), 4.93-4.87 (m, 1H), 4.27-4.02 (m, 3H), 3.92-3.58 (series of m, 2H), 2.44-1.35 (series of m, 10OH).

Example 163: (±)-(2,4-diethoxypyridin-3-yl)(2-((pyridin-2-yloxy)methyl)-7-azabicyclo[2.2.1]heptan-7-yl)methanone

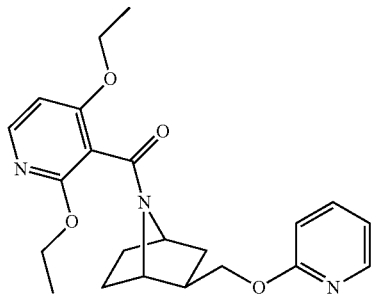 [SMILES: CCOc1ccnc(OCC)c1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 2,4-diethoxynicotinic acid. MS (ESI) mass calcd. for $C_{22}H_{27}BrN_3O_4$, 397.2; m/z found 398.2 [M+H]$^+$. $^1$H NMR (CDCl$_3$): 8.15-8.07 (m, 1H), 8.03-7.94 (m, 1H), 7.60-7.46 (m, 1H), 6.87-6.80 (m, 1H), 6.77-6.73 (m, 0.5H), 6.56-6.45 (m, 1H), 6.30-6.27 (m, 0.5H) 4.88-4.83 (m, 1H), 4.50-3.51 (series of m, 7H), 2.40-1.15 (series of m, 13H).

Example 164: (3-ethoxyisoquinolin-4-yl)((1S,2R,4R)-2-((pyridin-2-yloxy)methyl)-7-azabicyclo[2.2.1]heptan-7-yl)methanone

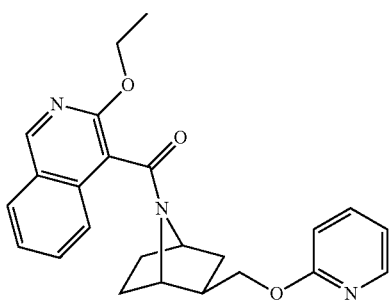

Prepared analogous to Example 1 substituting 5-fluoro-2-(pyrimidin-2-yl)benzoic acid with intermediate A-22. MS (ESI) mass calcd. for $C_{24}H_{25}N_3O_3$, 403.2; m/z found 404.2 [M+H]$^+$. $^1$H NMR (400 MHz, CDCl$_3$) 8.97-8.89 (m, 0.7H), 8.87-8.81 (m, 0.3H), 8.22-8.07 (m, 0.7H), 7.95-7.85 (m, 1H), 7.82 (dq, J=8.6, 0.9 Hz, 0.2H), 7.78-7.69 (m, 0.6H), 7.69-7.47 (m, 2H), 7.43-7.28 (m, 1.2H), 7.10 (ddd, J=8.0, 6.8, 1.0 Hz, 0.3H), 6.93-6.68 (m, 1.5H), 6.52-6.46 (m, 0.2H), 6.16-6.09 (m, 0.3H), 5.02 (td, J=9.5, 4.6 Hz, 1H), 4.65-3.99 (m, 3.5H), 3.92 (dd, J=10.5, 5.6 Hz, 0.25H), 3.74-3.58 (m, 1.25H), 2.52-2.29 (m, 0.5H), 2.27-1.93 (m, 2H), 1.86-0.78 (m, 7.5H).

Example 165: (±)-(2-ethoxyphenyl)(2-(((5-fluoropyridin-2-yl)oxy)methyl)-7-azabicyclo[2.2.1]heptan-7-yl)methanone

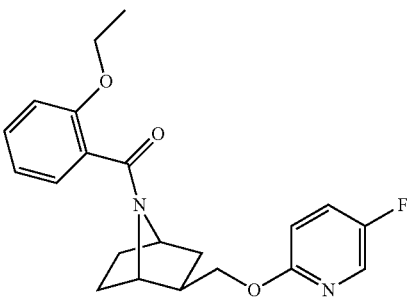 [SMILES: CCOc1ccccc1C(=O)N1C2CCC1C(COc1ccc(F)cn1)C2]

Prepared analogous to Example 7 substituting 6-methyl-3-(2H-1,2,3-triazol-2-yl)picolinic acid with 2-ethoxybenzoic acid. $^1$H NMR (400 MHz, CDCl$_3$): 7.95 (dd, J=7.3, 3.1 Hz, 1H), 7.37-7.18 (m, 2.5H), 7.14 (dd, J=7.4, 1.7 Hz, 0.5H), 6.95 (td, J=7.5, 0.9 Hz, 0.5H), 6.90 (dd, J=8.4, 1.0 Hz, 0.5H), 6.83-6.68 (m, 1.5H), 6.47 (dd, J=9.0, 3.6 Hz, 0.5H), 4.88-4.80 (m, 1H), 4.17-3.72 (m, 5H), 2.40-2.28 (m, 0.5H), 2.26-2.14 (m, 0.5H), 2.07-1.85 (m, 2H), 1.83-1.17 (m, 7H).

Example 166: (±)-(5-fluoro-2-(2H-1,2,3-triazol-2-yl)phenyl)(2-((quinoxalin-2-yloxy)methyl)-7-azabicyclo[2.2.1]heptan-7-yl)methanone

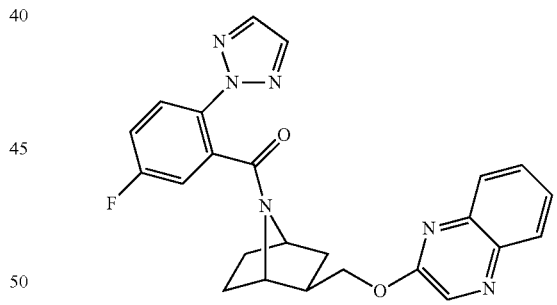

Prepared analogous to Example 2 substituting 6-methyl-3-(2H-1,2,3-triazol-2-yl)picolinic acid with intermediate A-10 and 2-fluoropyridine with 2-chloroquinoxaline. MS (ESI) mass calcd. for $C_{24}H_{21}FN_6O_2$, 444.2; m/z found 445.2 [M+H]$^+$. $^1$H NMR (400 MHz, CDCl$_3$): 8.49 (s, 0.4H), 8.30 (s, 0.4H), 8.04 (ddd, J=8.2, 6.9, 1.5 Hz, 1H), 7.90-7.76 (m, 2.5H), 7.75-7.66 (m, 1.5H), 7.65-7.55 (m, 1.5H), 7.44 (dd, J=8.5, 5.8 Hz, 0.5H), 7.32 (dd, J=8.5, 5.8 Hz, 0.5H), 7.29-7.22 (m, 0.2H), 7.21-7.10 (m, 1H), 6.49 (s, 0.5H), 4.93-4.84 (m, 1H), 4.52-4.30 (m, 1H), 4.23-4.07 (m, 1H), 3.87-3.78 (m, 1H), 2.48-2.25 (m, 1.8H), 2.10-1.88 (m, 1.2H), 1.83-1.31 (m, 4H).

Example 167: (±)-5-methyl-2-(2H-1,2,3-triazol-2-yl)phenyl)(2-(((5-methylpyridin-2-yl)oxy)methyl)-7-azabicyclo[2.2.1]heptan-7-yl)methanone

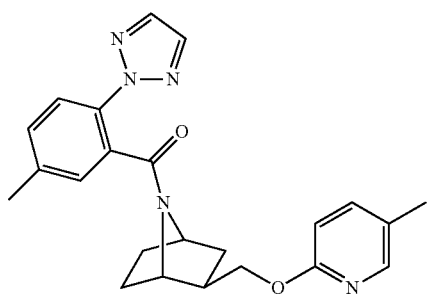

Prepared analogous to Example 13 substituting 2-chloro-4-trfluoromethylpyrimidine with 2-fluoro-5-methylpyridine. MS (ESI) mass calcd. for C$_{23}$H$_{25}$N$_5$O$_2$, 403.2; m/z found 404.2 [M+H]$^+$. $^1$H NMR (400 MHz, CDCl$_3$): 7.99-7.92 (m, 1H), 7.81-7.68 (m, 2.5H), 7.42-7.29 (m, 1.5H), 7.26-7.21 (m, 0.5H), 7.21-7.10 (m, 1H), 6.66 (d, J=8.4 Hz, 0.5H), 6.45 (d, J=8.4 Hz, 0.5H), 4.85-4.73 (m, 1H), 4.16-3.68 (m, 3H), 2.42 (s, 1.3H), 2.34-2.14 (m, 3.7H), 2.02-1.79 (m, 2.5H), 1.72-1.21 (m, 5.5H).

Example 168: (±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone

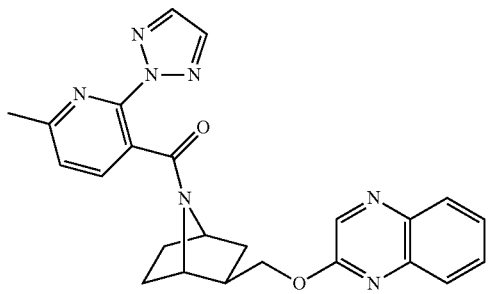

Prepared analogous to Example 1 substituting intermediate B-9 with intermediate B-10, 2-fluoropyridine with 2-chloroquinoxaline and 5-fluoro-2-(pyrimidin-2-yl)benzoic acid with intermediate A-3 to give the title compound. MS (ESI) mass calcd. for C$_{24}$H$_{23}$N$_7$O$_2$, 441.2; m/z found 442.2 [M+H]$^+$. $^1$H NMR CD$_3$OD: 8.47-8.04 (m, 2H), 7.98-7.69 (m, 5H), 7.65-7.56 (m, 1H), 7.45-6.73 (m, 1H), 4.77-4.71 (m, 1H), 4.46-4.10 (m, 2H), 3.91-3.79 (m, 1H), 2.64-2.32 (m, 4H), 2.03-1.38 (m, 6H).

Example 169: (±)-(5-fluoro-2-(2H-1,2,3-triazol-2-yl)phenyl)(2-((pyridin-2-ylamino)methyl)-7-azabicyclo[2.2.1]heptan-7-yl)methanone

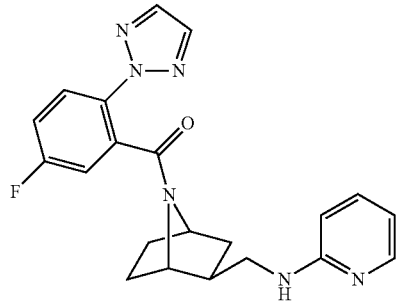 [SMILES: O=C(c1cc(F)ccc1-n1nccn1)N1C2CCC1C(CNc1ccccn1)C2]

Prepared analogous to example 170 substituting 2-chloro-4,6-dimethylpyrimidine with 2-fluoropyridine. MS (ESI) mass calcd. for C$_{21}$H$_{21}$FN$_6$O, 392.2; m/z found 393.1 [M+H]$^+$. 1H NMR (CD3OD): 8.02-7.83 (m, 4H), 7.47-7.23 (m, 3H), 6.59-6.38 (m, 2H), 4.73-4.55 (m, 1H), 3.87-3.70 (m, 1H), 3.24-2.80 (m, 2H), 2.27-2.03 (m, 1H), 1.97-1.34 (m, 6H).

Example 170: (±)-(2-(((4,6-dimethylpyrimidin-2-yl)amino)methyl)-7-azabicyclo[2.2.1]heptan-7-yl)(5-fluoro-2-(2H-1,2,3-triazol-2-yl)phenyl)methanone

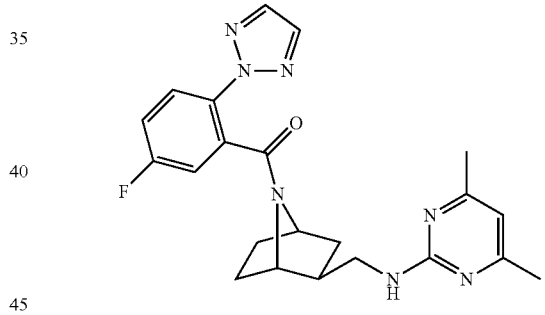

Step A: (±)-tert-butyl 2-(((methylsulfonyl)oxy)methyl)-7-azabicyclo[2.2.1]heptane-7-carboxylate. To intermediate B-10 (2.6 g, 11.5 mmol) and TEA (1.7 g, 17.2 mmol) in DCM (15 mL) at 0° C. was added MsCl (1.6 g, 13.7 mmol) dropwise over 10m. This ice bath was removed and the reaction was allowed to proceed at rt for 12 h and H2O was added. The layers were separated and the organic layer was washed with brine and dried (Na2SO4). Purification via silica gel chromatography (15% EtOAc in petroleum ethers) gave the title compound (3.5 g).

Step B: (±)-tert-butyl 2-(azidomethyl)-7-azabicyclo[2.2.1]heptane-7-carboxylate. To the title compound of step A (3.4 g, 11.1 mmol) in DMF (15 mL) was added sodium azide (2.1 g, 33.4 mmol). The mixture was heated at 100° C. overnight, cooled to rt, poured into H$_2$O and extracted with DCM. The combined organics were washed with brine and dried (Na$_2$SO$_4$). Purification via silica gel chromatography (10% EtOAc in petroleum ethers) gave the title compound (2.6 g).

Step C: (±)-2-(azidomethyl)-7-azabicyclo[2.2.1]heptane. To the title compound of step B in DCM was added TFA.

After 3 h at rt, the reaction mixture was concentrated to give the title compound (1.7 g) as the TFA salt.

Step D: (±)-2-(azidomethyl)-7-azabicyclo[2.2.1]heptan-7-yl)(5-fluoro-2-(2H-1,2,3-triazol-2-yl)phenyl)methanone. Prepared analogous to example 22 substituting 2-(2H-1,2,3-triazol-2-yl)benzoic acid with 5-fluoro-2-(2H-1,2,3-triazol-2-yl)benzoic acid and using the title compound of step C.

Step E: 2-(aminomethyl)-7-azabicyclo[2.2.1]heptan-7-yl)(5-fluoro-2-(2H-1,2,3-triazol-2-yl)phenyl)methanone. The title compound of step D in MeOH was hydrogenated under an atmosphere of hydrogen in the presence of 10 wt % Pd/C for 4 h. The catalyst was removed by filtration. Purification via silica gel chromatography (7% MeOH in DCM) gave the title compound.

Step F: (±)-(2-(((4,6-dimethylpyrimidin-2-yl)amino)methyl)-7-azabicyclo[2.2.1]heptan-7-yl)(5-fluoro-2-(2H-1,2,3-triazol-2-yl)phenyl)methanone. To the title compound of step E (30 mg) in NMP (3 mL) was added 2-chloro-4,6-dimethylpyrimidine (16 mg) and $Cs_2CO_3$ (43 mg). The reaction was heated to 180° C. for 2 h. After cooling to rt, $H_2O$ was added and the mixture extracted with EtOAc. Purification via prep-HPLC gave the title compound. MS (ESI) mass calcd. for $C_{22}H_{24}FN_7O$, 421.2; m/z found 422.2 $[M+H]^+$. $^1H$ NMR (CD3OD) 7.90-7.73 (m, 3H), 7.34-7.14 (m, 2H), 6.31-6.26 (m, 1H), 4.62-4.41 (m, 1H), 3.74-3.57 (m, 1H), 3.46-3.22 (m, 1H), 3.18-2.93 (m, 1H), 2.40-1.91 (m, 7H), 1.85-1.20 (m, 6H).

Example 171: (±)-(5-fluoro-2-(2H-1,2,3-triazol-2-yl)phenyl)(2-(((4-(trifluoromethyl)pyrimidin-2-yl)amino)methyl)-7-azabicyclo[2.2.1]heptan-7-yl)methanone

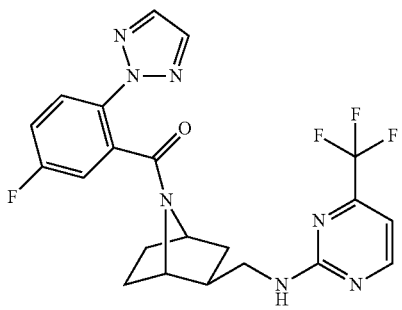 [SMILES: O=C(c1cc(F)ccc1-n1nccn1)N1C2CCC1C(CNc1nccc(C(F)(F)F)n1)C2]

Prepared analogous to example 170 substituting 2-chloro-4,6-dimethylpyrimidine with 2-chloro-4-(trifluoromethyl)pyrimidine. MS (ESI) mass calcd. for $C_{21}H_{19}F_4N_7O$, 461.2; m/z found 462.1 $[M+H]^+$. 1H NMR (CD3OD): 8.51 (s, 1H), 7.99-7.83 (m, 3H), 7.46-7.16 (m, 2H), 6.88 (d, J=4.9 Hz, 1H), 4.74-4.53 (m, 1H), 3.87-3.66 (m, 1H), 3.34 (s, 1H), 3.30-3.02 (m, 1H), 2.33-2.08 (m, 1H), 1.97-1.32 (m, 6H).

Example 172: (±)-(5-fluoro-2-(2H-1,2,3-triazol-2-yl)phenyl)(2-(((6-(trifluoromethyl)pyridin-2-yl)amino)methyl)-7-azabicyclo[2.2.1]heptan-7-yl)methanone

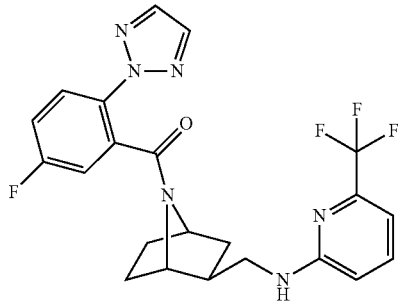 [SMILES: O=C(c1cc(F)ccc1-n1nccn1)N1C2CCC1C(CNc1cccc(C(F)(F)F)n1)C2]

Prepared analogous to example 170 substituting 2-chloro-4,6-dimethylpyrimidine with 2-chloro-6-(trifluoromethyl)pyridine. MS (ESI) mass calcd. for $C_{22}H_{20}F_4N_6O$, 460.2; m/z found 461.2 $[M+H]^+$. 1H NMR (CD3OD): 8.07-7.84 (m, 3H), 7.60-7.22 (m, 3H), 6.90 (d, J=7.2 Hz, 1H), 6.74-6.58 (m, 1H), 4.77-4.58 (m, 1H), 3.90-3.72 (m, 1H), 3.30-3.05 (m, 2H), 2.37-2.12 (m, 1H), 1.99-1.37 (m, 6H).

Example 173: (±)-(3-fluoro-2-methoxyphenyl)(2-(((5-fluoropyridin-2-yl)oxy)methyl)-7-azabicyclo[2.2.1]heptan-7-yl)methanone

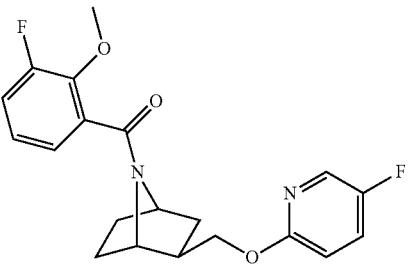 [SMILES: COc1c(F)cccc1C(=O)N1C2CCC1C(COc1ccc(F)cn1)C2]

Prepared analogous to Example 7 substituting 6-methyl-3-(2H-1,2,3-triazol-2-yl)picolinic acid with 3-fluoro-2-methoxybenzoic acid. MS (ESI) mass calcd. for $C_{20}H_{20}F_2N_2O_3$, 374.1; m/z found 375.1 $[M+H]^+$. 1H NMR (CD3OD): 8.01-7.90 (m, 1H), 7.56-7.38 (m, 1H), 7.28-7.06 (m, 2H), 7.02-6.53 (m, 2H), 4.82-4.66 (m, 1H), 4.50-3.73 (m, 6H), 2.85-2.22 (m, 1H), 2.21-1.10 (m, 6H).

Example 174: (±)-(5-fluoro-2-(2H-1,2,3-triazol-2-yl)phenyl)(2-((quinoxalin-2-ylamino)methyl)-7-azabicyclo[2.2.1]heptan-7-yl)methanone

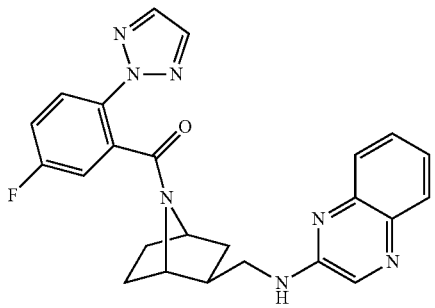 [SMILES: O=C(c1cc(F)ccc1-n1nccn1)N1C2CCC1C(CNc1cnc3ccccc3n1)C2]

Prepared analogous to example 170 substituting 2-chloro-4,6-dimethylpyrimidine with 2-chloroquinoxaline. MS (ESI) mass calcd. for $C_{24}H_{22}FN_7O$, 443.2; m/z found 444.2 [M+H]$^+$.

Example 175: (±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone

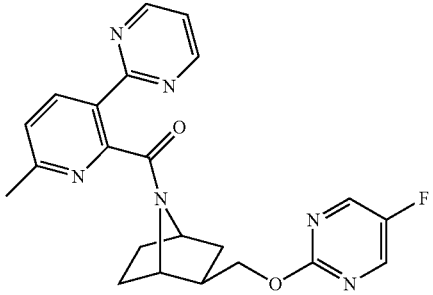 [SMILES: Cc1ccc(-c2ncccn2)c(C(=O)N2C3CCC2C(COc2ncc(F)cn2)C3)n1]

Prepared analogous to example 98 substituting 3,6'-dimethyl-[2,3'-bipyridine]-2'-carboxylic acid with intermediate A-9. MS (ESI) mass calcd. for $C_{22}H_{21}FN_6O_2$, 420.2; m/z found 421 [M+H]$^+$.

Example 176: (±)-(6-methyl-3-(2H-1,2,3-triazol-2-yl)pyridin-2-yl)(2-(((3-methylpyridin-2-yl)oxy)methyl)-7-azabicyclo[2.2.1]heptan-7-yl)methanone

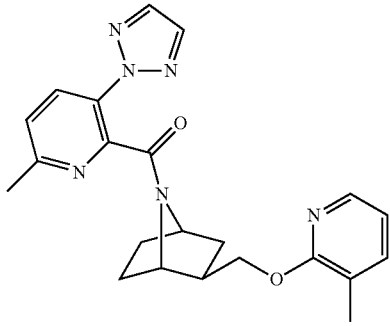 [SMILES: Cc1ccc(-n2nccn2)c(C(=O)N2C3CCC2C(COc2ncccc2C)C3)n1]

Prepared analogous to example 7 substituting 5-fluoropyridin-2(1H)-one with 3-methylpyridin-2-ol. MS (ESI) mass calcd. for $C_{22}H_{24}N_6O_2$, 404.2; m/z found 405 [M+H]

Example 177: (±)-(2-(((5-fluoropyridin-2-yl)oxy)methyl)-7-azabicyclo[2.2.1]heptan-7-yl)(6-methyl-3-(4-methyloxazol-2-yl)pyridin-2-yl)methanone

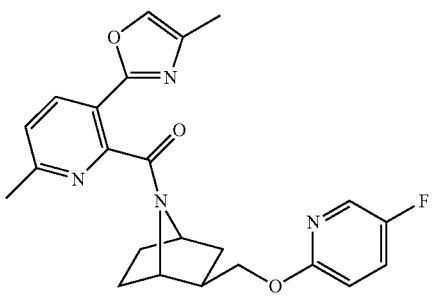

Prepared analogous to Example 7 substituting 6-methyl-3-(2H-1,2,3-triazol-2-yl)picolinic acid with intermediate A-54. MS (ESI) mass calcd. for $C_{23}H_{23}FN_4O_3$, 422.2; m/z found 423 [M+H]$^+$.

Example 178: (6-methyl-3-(4-methyloxazol-2-yl)pyridin-2-yl)((1S,2R,4R)-2-((pyridin-2-yloxy)methyl)-7-azabicyclo[2.2.1]heptan-7-yl)methanone

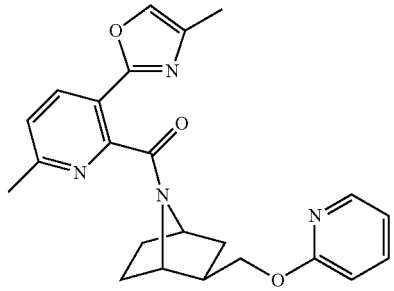 [SMILES: Cc1coc(-c2ccc(C)nc2C(=O)N2C3CCC2C(COc2ccccn2)C3)n1]

Prepared analogous to Example 1 substituting intermediate A-7 with intermediate A-54. MS (ESI) mass calcd. for $C_{23}H_{24}N_4O_3$, 404.2; m/z found 405 [M+H]$^+$.

Example 179: ((1S,2R,4R)-2-(((5-fluoropyrimidin-2-yl)oxy)methyl)-7-azabicyclo[2.2.1]heptan-7-yl)(6-methyl-3-(4-methyloxazol-2-yl)pyridin-2-yl)methanone

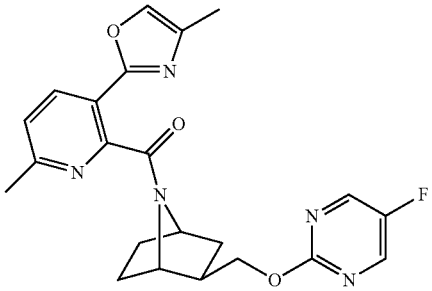 [SMILES: Cc1coc(-c2ccc(C)nc2C(=O)N2C3CCC2C(COc2ncc(F)cn2)C3)n1]

Prepared analogous to Example 98 substituting intermediate 3,6'-dimethyl-[2,3'-bipyridine]-2'-carboxylic acid with intermediate A-54. MS (ESI) mass calcd. for $C_{22}H_{22}FN_5O_3$, 423.2; m/z found 424 [M+H]$^+$.

Example 180: (±)-(5-methyl-2-(2H-1,2,3-triazol-2-yl)phenyl)(2-(((6-methyl-2-(trifluoromethyl)pyrimidin-4-yl)oxy)methyl)-7-azabicyclo[2.2.1]heptan-7-yl)methanone

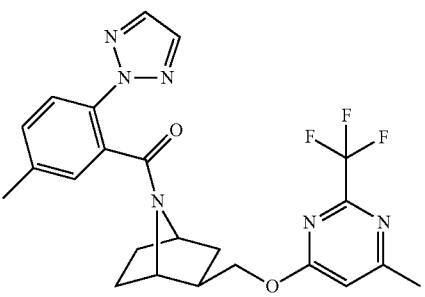

Prepared analogous to Example 13 substituting 2-chloro-4-(trifluoromethyl)pyrimidine with 4-chloro-6-methyl-2-(trifluoromethyl)pyrimidine. MS (ESI) mass calcd. for $C_{23}H_{23}F_3N_6O_2$, 472.2; m/z found 473.2 [M+H]$^+$. $^1$H NMR (CDCl$_3$): 7.88-7.72 (m, 3H), 7.38-7.12 (m, 2H), 6.74-6.70 (s, 0.6H), 6.55-6.50 (s, 0.4H), 4.89-4.75 (m, 1H), 4.30-3.87 (m, 2H), 3.85-3.46 (m, 1H), 2.56-2.49 (m, 3H), 2.46-2.39 (s, 2H), 2.32-1.80 (m, 3H), 1.74-1.11 (m, 5H).

Example 181: (2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

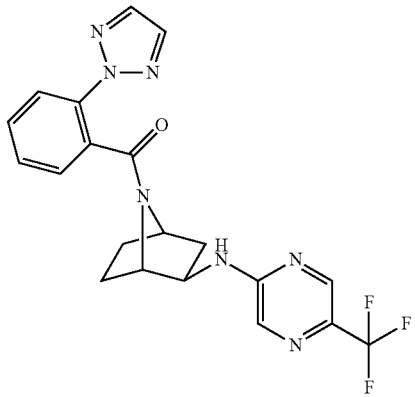 [SMILES: O=C(c1ccccc1-n1nccn1)N1C2CCC1C(Nc1cnc(C(F)(F)F)cn1)C2]

Step A: (1S,2R,4R)-tert-butyl 2-((5-(trifluoromethyl)pyrazin-2-yl)amino)-7-azabicyclo[2.2.1]heptane-7-carboxylate. To intermediate B-5 (1.6 g, 7.3 mmol) and K$_2$CO$_3$ (1.5 g, 10 mmol) in DMF (11 mL) was added 2-chloro-5-(trifluoromethyl)pyrazine (1.1 mL, 8.8 mmol). After heating at 70° C. for 2 h, the mixture was cooled to rt, diluted with EtOAc and H$_2$O. The aqueous layer was extracted with EtOAc (3×). The combined organics were washed with 4% (aq) and dried (MgSO$_4$). Purification via silica gel chromatography (0-40% EtOAc in hexanes) gave the title compound (1.8 g, 67%). MS (ESI) mass calcd. for $C_{16}H_{21}F_3N_4O_2$, 358.2; m/z found 359.2 [M+H]$^+$. $^1$H NMR (CDCl3): 8.32 (s, 1H), 7.86-7.82 (m, 1H), 5.33 (s, 1H), 4.38-4.15 (m, 2H), 4.10-3.96 (m, 1H), 2.14-1.98 (m, 1H), 1.93-1.67 (m, 2H), 1.61-1.36 (m, 12H).

Step B: (1S,2R,4R)—N-(5-(trifluoromethyl)pyrazin-2-yl)-7-azabicyclo[2.2.1]heptan-2-amine. To the title compound of step A (200 mg, 0.6 mmol) in EtOAc (1 mL) was added 4M HCl in dioxane (3 mL). After 2 h, the reaction was concentrated, neutralized with 5% Na$_2$CO$_3$ (aq) and extracted with DCM (2×). The combined organics were dried (Na$_2$SO$_4$) to give the title compound of step B that was used without further purification. MS (ESI) mass calcd. for $C_{11}H_{13}F_3N_4$, 258.1; m/z found 259.1 [M+H]$^+$.

Step C: (2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone. To the title compound of step B (140 mg, 0.5 mmol) and intermediate A-1 (113 mg, 0.6 mmol) in DMF (4 mL) was added DIPEA (230 μL, 1.4 mmol) and HATU (155 mg, 0.6 mmol). Upon completion of the reaction, purification was performed using Agilent prep method X to give the title compound (172 mg, 74%). MS (ESI) mass calcd. for $C_{20}H_{18}F_3N_7O$, 429.2; m/z found 430 [M+H]$^+$. $^1$H NMR (CDCl3): 8.32 (s, 0.3H), 8.17 (s, 0.7H), 7.99-7.89 (m, 1.5H), 7.88-7.77 (m, 1.5H), 7.62-7.30 (m, 4H), 6.24-6.15 (m, 0.3H), 4.86 (s, 0.7H), 4.76 (d, J=5.4 Hz, 0.3H), 4.45-4.23 (m, 1H), 4.08-3.90 (m, 1H), 2.23-1.34 (m, 6H).

Example 182: (±)-((2-(2H-1,2,3-triazol-2-yl)phenyl)(2-((5-(trifluoromethyl)pyrazin-2-yl)amino)-7-azabicyclo[2.2.1]heptan-7-yl)methanone

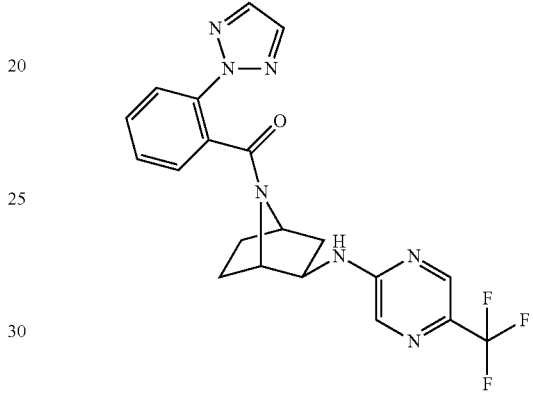

Step A: (±)-tert-butyl 2-((5-(trifluoromethyl)pyrazin-2-yl)amino)-7-azabicyclo[2.2.1]heptane-7-carboxylate. Prepared analogous to Example 181 step A substituting intermediate B-5 with intermediate B-6.

Step B: (±)-N-(5-(trifluoromethyl)pyrazin-2-yl)-7-azabicyclo[2.2.1]heptan-2-amine. Prepared analogous to Example 181 step B substituting (1S,2R,4R)-tert-butyl 2-((5-(trifluoromethyl)pyrazin-2-yl)amino)-7-azabicyclo[2.2.1]heptane-7-carboxylate with (±)-tert-butyl 2-((5-(trifluoromethyl)pyrazin-2-yl)amino)-7-azabicyclo[2.2.1]heptane-7-carboxylate.

Step C: (±)-((2-(2H-1,2,3-triazol-2-yl)phenyl)(2-((5-(trifluoromethyl)pyrazin-2-yl)amino)-7-azabicyclo[2.2.1]heptan-7-yl)methanone.

To 2-(2H-1,2,3-triazol-2-yl)benzoic acid (125 mg, 0.6 mmol) and DMF (4 mL) was added (i-Pr)$_2$NEt (0.23 mL, 1.3 mmol) and HBTU (155 mg, 0.6 mmol). After 10 min, the title compound from step B (146 mg. 0.4 mmol) was added. After stirring overnight at rt, saturated NaHCO$_3$ (aq.) was added and the mixture extracted with EtOAc (3×). The combined organics were dried (MgSO$_4$) and concentrated. Purification via preparative HPLC gave the title compound (89 mg, 47%) as a beige solid. MS (ESI) mass calcd. for $C_{20}H_{18}F_3N_7O$, 429.2; m/z found 430 [M+H]$^+$. $^1$H NMR (DMSO-D$_6$): 8.47 (s, 0.3H), 8.24 (s, 0.7H), 8.14-8.05 (m, 2.2H), 8.02 (s, 0.7H), 7.85 (d, J=7.2 Hz, 1.3H), 7.72-7.55 (m, 1.7H), 7.49-7.34 (m, 1.4H), 7.13 (t, J=7.4 Hz, 0.7H), 4.58 (t, J=4.3 Hz, 0.7H), 4.44 (d, J=4.7 Hz, 0.3H), 4.04-3.93 (m, 0.3H), 3.82 (t, J=4.1 Hz, 0.3H), 3.79-3.70 (m, 0.7H), 3.54 (d, J=4.8 Hz, 0.7H), 2.07-1.90 (m, 1H), 1.85-1.07 (m, 5H).

Example 183a: (2-(2H-1,2,3-triazol-2-yl)phenyl)
((1S,2R,4R)-2-((5-(trifluoromethyl)pyrazin-2-yl)
amino)-7-azabicyclo[2.2.1]heptan-7-yl)methanone Example 184: (±)-(5-methyl-3-(2H-1,2,3-triazol-2-
yl)pyridin-2-yl)(2-((5-(trifluoromethyl)pyrazin-2-yl)
amino)-7-azabicyclo[2.2.1]heptan-7-yl)methanone

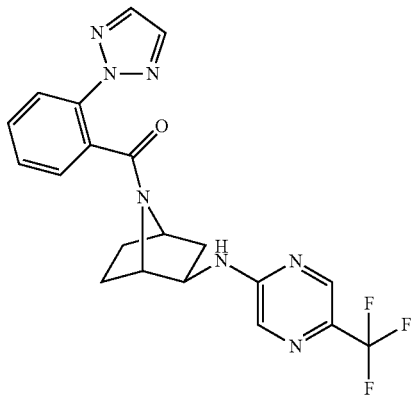 [SMILES: O=C(c1ccccc1-n1nccn1)N1C2CCC1C(Nc1cnc(C(F)(F)F)cn1)C2]

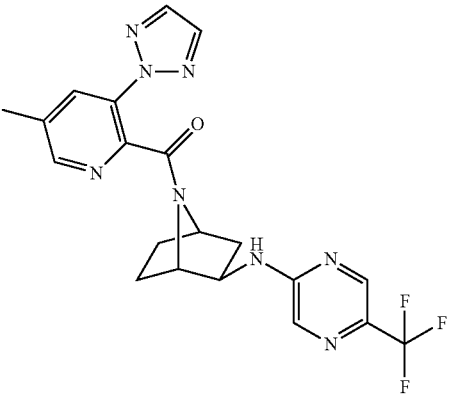

And Example 183b: (2-(2H-1,2,3-triazol-2-yl)phenyl)((1R,2S,4S)-2-((5-(trifluoromethyl)pyrazin-2-yl)amino)-7-azabicyclo[2.2.1]heptan-7-yl)methanone Prepared analogous to Example 182 substituting intermediate A-1 with intermediate A-19 and HBTU with HATU. MS (ESI) mass calcd. for $C_{20}H_{19}F_3N_8O$, 444.2; m/z found 445.1 $[M+H]^+$.

Example 185: (±)-(5-methyl-3-(1H-1,2,3-triazol-1-
yl)pyridin-2-yl)(2-((5-(trifluoromethyl)pyrazin-2-yl)
amino)-7-azabicyclo[2.2.1]heptan-7-yl)methanone

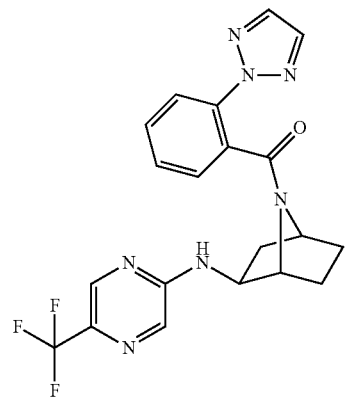 [SMILES: O=C(c1ccccc1-n1nccn1)N1C2CCC1C(Nc1cnc(C(F)(F)F)cn1)C2]

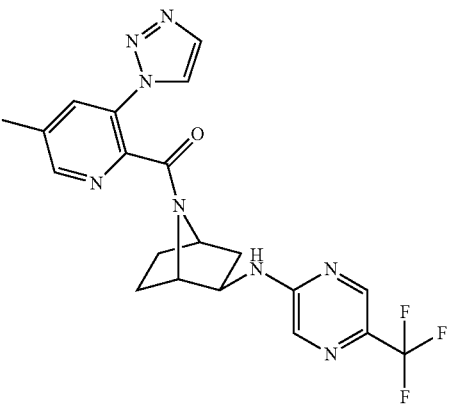 [SMILES: Cc1cnc(C(=O)N2C3CCC2C(Nc2cnc(C(F)(F)F)cn2)C3)c(-n2ccnn2)c1]

The title compounds were obtained by chiral SFC (CHIRALPAK OD-H 5 µM 250×20 mm) resolution of Example 182 (81 mg) using 70% $CO_2$/30% EtOH as the mobile phase to give enantiomer A (37 mg, 1st eluting enantiomer, example 183a) and enantiomer B (38 mg, $2^{nd}$ eluting enantiomer, example 183b). Example 183a: >98% single enantiomer, 2.45 min retention time; Example 183b>98% single enantiomer, 3.33 min retention time.

Example 183a: Enantiomer A: MS (ESI) mass calcd. for $C_{20}H_{18}F_3N_7O$, 429.2; m/z found 430 $[M+H]^+$.

Example 183b: Enantiomer B: MS (ESI) mass calcd. for $C_{20}H_{18}F_3N_7O$, 429.2; m/z found 430 $[M+H]^+$.

Prepared analogous to Example 184 substituting intermediate A-19 with intermediate A-20. MS (ESI) mass calcd. for $C_{20}H_{19}F_3N_8O$, 444.2; m/z found 445.1 $[M+H]^+$. HPLC $R_t$=1.13.

Example 186: (±)-(6-methyl-3-(2H-1,2,3-triazol-2-yl)pyridin-2-yl)(2-((5-(trifluoromethyl)pyrazin-2-yl)amino)-7-azabicyclo[2.2.1]heptan-7-yl)methanone

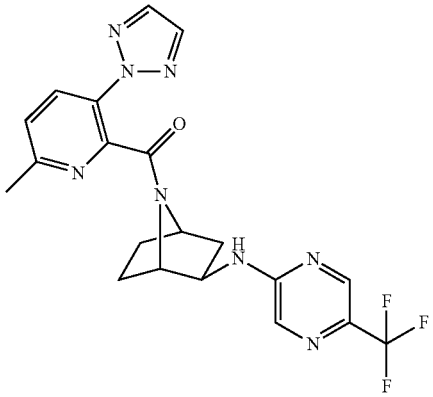 [SMILES: Cc1ccc(-n2nccn2)c(C(=O)N2C3CCC2C(Nc2cnc(C(F)(F)F)cn2)C3)n1]

Prepared analogous to Example 184 substituting intermediate A-19 with intermediate A-21. MS (ESI) mass calcd. for C$_{20}$H$_{19}$F$_3$N$_8$O, 444.2; m/z found 445.1 [M+H]$^+$. $^1$H NMR (CDCl$_3$): 8.36-8.32 (s, 0.2H), 8.27-8.23 (s, 0.8H), 8.22-8.18 (d, J=8.4 Hz, 0.2H), 8.13-8.08 (d, J=8.3 Hz, 0.8H), 7.93-7.84 (m, 2H), 7.79-7.75 (m, 0.8H), 7.40-7.36 (d, J=8.4 Hz, 0.2H), 7.36-7.31 (d, J=8.4 Hz, 0.8H), 7.26-7.22 (m, 0.2H), 6.26-6.19 (d, J=8.5 Hz, 0.2H), 4.96-4.86 (t, J=4.8 Hz, 0.8H), 4.83-4.75 (d, J=5.4 Hz, 0.2H), 4.36-4.19 (m, 1H), 4.13-3.92 (d, J=5.0 Hz, 1H), 2.69-2.56 (m, 3H), 2.29-2.14 (dd, J=13.1, 7.5 Hz, 1H), 2.14-1.87 (m, 2H), 1.81-1.78 (m, 1H), 1.63-1.56 (m, 2H).

Example 187: (±)-(6-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone

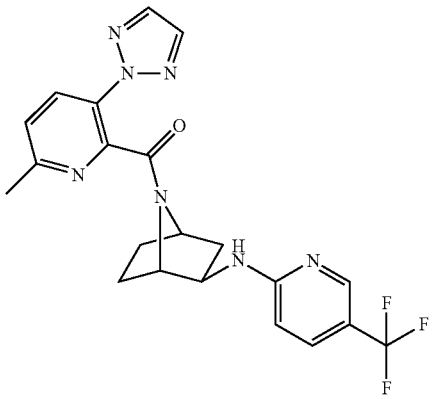

Step A: (±)-tert-butyl 2-((5-(trifluoromethyl)pyridin-2-yl)amino)-7-azabicyclo[2.2.1]heptane-7-carboxylate. To intermediate B-6 (150 mg, 0.7 mmol) in DMSO (10 mL) was added DIPEA (244 µL, 1.4 mmol) and 2-chloro-5-(trifluoromethyl)pyridine (170 µL, 1.4 mmol). After heating at 100° C. for 4 h, the mixture was cooled to rt and saturated NaHCO$_3$ (aq) was added. The mixture was extracted with DCM (3×). The combined organics were washed with brine and dried (MgSO$_4$). Purification via silica gel chromatography (0-13% EtOAc in heptanes) gave the title compound. MS (ESI) mass calcd. for C$_{17}$H$_{22}$F$_3$N$_7$O$_2$, 357.2; m/z found 358.0 [M+H]$^+$.

Step B: (±)-N-(5-(trifluoromethyl)pyridin-2-yl)-7-azabicyclo[2.2.1]heptan-2-amine hydrochloride. To the title compound from step A (262 mg, 0.7 mmol) in 1,4-dioxane (10 mL) was added 6N HCl in iPrOH (700 µL). The reaction was heated to 70° C. for 2 h, cooled to rt, concentrated and used without further purification in subsequent steps.

Step C: (±)-(6-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone.

Prepared analogous to Example 182 substituting intermediate A-1 with intermediate A-21 and (±)-N-(5-(trifluoromethyl)pyrazin-2-yl)-7-azabicyclo[2.2.1]heptan-2-amine with the title compound of step B. MP=193.9° C. $^1$H NMR (DMSO-D$_6$): 8.38 (s, 0.3H), 8.24-8.16 (m, 1H), 8.15-8.11 (m, 2H), 8.05 (d, J=8.3 Hz, 0.7H), 7.69 (dd, J=8.9, 2.3 Hz, 0.3H), 7.63 (dd, J=8.9, 2.4 Hz, 0.7H), 7.57 (d, J=8.4 Hz, 0.3H), 7.37 (d, J=8.4 Hz, 0.7H), 7.33 (d, J=5.8 Hz, 0.7H), 7.14 (d, J=4.5 Hz, 0.3H), 6.75 (d, J=8.9 Hz, 0.3H), 6.61 (d, J=8.9 Hz, 0.7H), 4.60 (t, J=4.5 Hz, 0.7H), 4.51 (d, J=4.8 Hz, 0.3H), 3.99-3.90 (m, 0.6H), 3.89-3.77 (m, 1.4H), 2.60 (s, 0.9H), 2.23 (s, 2.1H), 1.99 (dd, J=12.6, 7.6 Hz, 1H), 1.83-1.21 (m, 5H).

Example 188: (±)-(5-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone

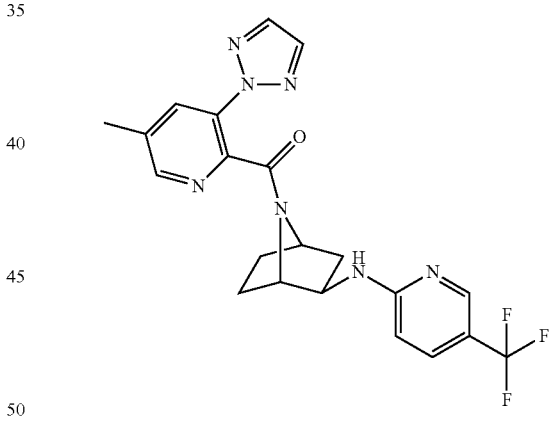

Prepared analogous to Example 187 substituting intermediate A-21 with intermediate A-19. MS (ESI) mass calcd. for C$_{21}$H$_{20}$F$_3$N$_7$O, 443.2; m/z found 444.1 [M+H]$^+$. $^1$H NMR (CDCl$_3$): 8.49-8.44 (dd, J=1.9, 0.9 Hz, 0.2H), 8.41-8.32 (m, 1H), 8.28-8.21 (m, 0.8H), 8.18-8.11 (m, 0.2H), 8.06-7.98 (m, 0.8H), 7.94-7.86 (m, 2H), 7.60-7.53 (dd, J=8.8, 2.4 Hz, 0.2H), 7.45-7.35 (dd, J=8.9, 2.4 Hz, 0.8H), 6.71-6.59 (d, J=8.7 Hz, 0.8H), 6.45-6.37 (d, J=8.8 Hz, 0.2H), 6.27-6.17 (d, J=8.8 Hz, 0.8H), 5.82-5.72 (m, 0.2H), 4.95-4.84 (t, J=4.6 Hz, 0.8H), 4.82-4.74 (d, J=5.2 Hz, 0.2H), 4.36-4.18 (m, 1H), 4.08-3.97 (m, 1H), 2.51-2.47 (s, 0.7H), 2.45-2.41 (m, 2.3H), 2.22-2.14 (dd, J=13.0, 7.7 Hz, 0.8H), 2.11-1.90 (m, 2.2H), 1.82-1.40 (m, 3H).

Example 189: (±)-(6-methyl-2-(2H-1,2,3-triazol-2-yl)pyridin-3-yl)(2-((5-(trifluoromethyl)pyridin-2-yl)amino)-7-azabicyclo[2.2.1]heptan-7-yl)methanone

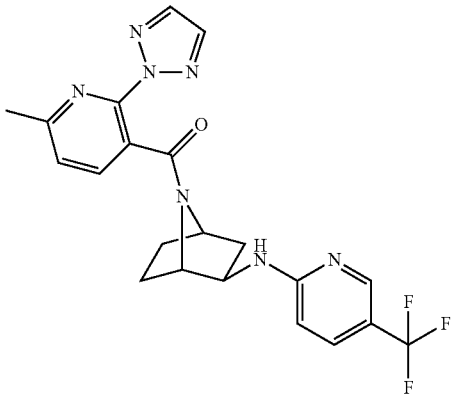

Prepared analogous to Example 187 substituting intermediate A-21 with intermediate A-3. MS (ESI) mass calcd. for $C_{21}H_{20}F_3N_7O$, 443.2; m/z found 444.1 [M+H]$^+$. $^1$H NMR (CDCl$_3$): 8.40-8.33 (s, 0.4H), 8.26-8.19 (d, J=2.0 Hz, 0.6H), 7.98-7.88 (m, 2H), 7.78-7.71 (d, J=7.7 Hz, 0.4H), 7.64-7.55 (m, 1H), 7.41-7.27 (m, 1.6H), 7.20-7.08 (m, 0.7H), 6.43-6.35 (d, J=8.8 Hz, 0.3H), 6.13-6.01 (d, J=8.7 Hz, 0.7H), 5.74-5.56 (m, 0.3H), 4.90-4.81 (m, 0.7H), 4.78-4.71 (d, J=5.3 Hz, 0.3H), 4.38-4.14 (m, 1H), 3.99-3.85 (m, 1H), 2.78-2.55 (m, 3H), 2.24-2.10 (dd, J=13.2, 7.9 Hz, 1H), 2.08-1.39 (m, 5H).

Example 190: (±)-(6-methyl-2-(1H-1,2,3-triazol-1-yl)pyridin-3-yl)(2-((5-(trifluoromethyl)pyridin-2-yl)amino)-7-azabicyclo[2.2.1]heptan-7-yl)methanone

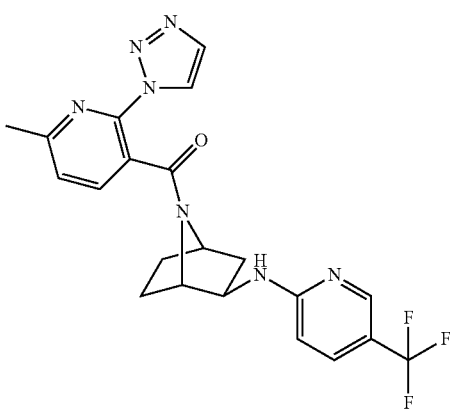 [SMILES: Cc1ccc(C(=O)N2C3CCC2C(Nc2ccc(C(F)(F)F)cn2)C3)c(-n2ccnn2)n1]

Prepared analogous to Example 187 substituting intermediate A-21 with intermediate A-4. MS (ESI) mass calcd. for $C_{21}H_{20}F_3N_7O$, 443.2; m/z found 444.1 [M+H]$^+$. $^1$H NMR (CDCl$_3$): 8.50-8.46 (m, 0.6H), 8.37-8.34 (d, J=1.2 Hz, 0.4H), 8.34-8.31 (s, 0.6H), 8.24-8.17 (s, 0.4H), 7.90-7.84 (m, 1H), 7.75-7.69 (d, J=7.7 Hz, 0.6H), 7.65-7.60 (d, J=7.8 Hz, 0.4H), 7.55-7.47 (dd, J=8.7, 2.4 Hz, 0.7H), 7.36-7.27 (m, 1.3H), 7.22-7.14 (m, 0.4H), 6.94-6.83 (d, J=8.7 Hz, 0.6H), 6.29-6.11 (d, J=8.9 Hz, 1H), 4.91-4.74 (m, 1H), 4.55-4.28 (m, 1H), 4.04-3.90 (m, 1H), 2.66-2.62 (s, 1.9H), 2.59-2.55 (s, 1.1H), 2.23-2.15 (dd, J=13.1, 8.1 Hz, 0.5H), 2.06-1.79 (m, 2.5H), 1.77-1.68 (m, 1H), 1.55-1.47 (m, 2H).

Example 191: (±)-(4-methoxy-2-(2H-1,2,3-triazol-2-yl)phenyl)(2-((5-(trifluoromethyl)pyridin-2-yl)amino)-7-azabicyclo[2.2.1]heptan-7-yl)methanone

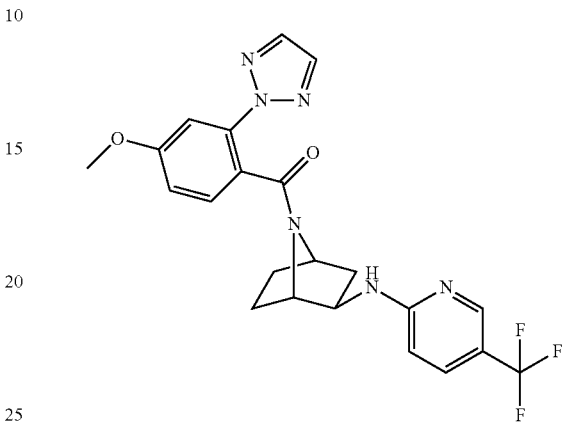

Prepared analogous to Example 187 substituting intermediate A-21 with intermediate A-5. MS (ESI) mass calcd. for $C_{22}H_{21}F_3N_6O_2$, 458.2; m/z found 459.1 [M+H]$^+$. $^1$H NMR (CDCl$_3$): 8.38-8.32 (s, 0.3H), 8.26-8.19 (s, 0.7H), 7.93-7.87 (s, 1.3H), 7.87-7.80 (s, 0.7H), 7.60-7.53 (m, 0.4H), 7.49-7.43 (d, J=2.5 Hz, 0.4H), 7.40-7.26 (m, 2.7H), 7.00-6.93 (dd, J=8.5, 2.5 Hz, 0.4H), 6.90-6.80 (d, J=8.4 Hz, 0.7H), 6.43-6.35 (d, J=8.7 Hz, 0.4H), 6.12-6.04 (d, J=8.8 Hz, 0.7H), 5.77-5.67 (m, 0.3H), 4.84-4.79 (m, 0.7H), 4.74-4.68 (m, 0.3H), 4.36-4.15 (m, 1H), 4.02-3.95 (m, 1H), 3.94-3.87 (s, 1H), 3.87-3.81 (s, 2H), 2.20-2.11 (dd, J=13.0, 8.0 Hz, 0.7H), 2.07-1.99 (dd, J=12.9, 7.6 Hz, 0.3H), 1.99-1.83 (s, 2H), 1.79-1.34 (m, 3H).

Example 192: (±)-(3-fluoro-2-(pyrimidin-2-yl)phenyl)(2-((5-(trifluoromethyl)pyridin-2-yl)amino)-7-azabicyclo[2.2.1]heptan-7-yl)methanone

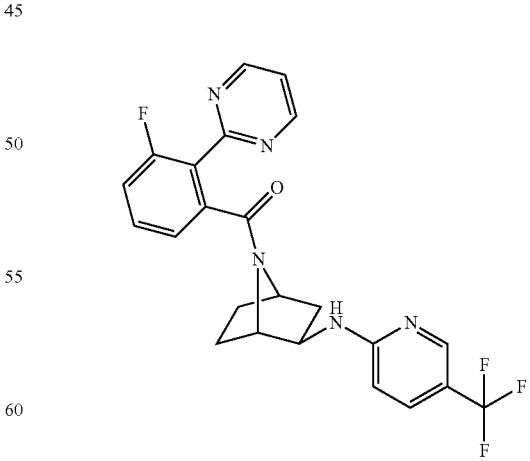

Prepared analogous to Example 187 substituting intermediate A-21 with intermediate A-6. MS (ESI) mass calcd. for $C_{23}H_{19}F_4N_5O$, 457.2; m/z found 458.1 [M+H]$^+$. $^1$H NMR (CDCl$_3$): 8.91-8.76 (m, 2H), 8.36-8.18 (m, 1H), 7.68-7.52

(m, 1H), 7.40-7.27 (m, 3H), 7.24-7.14 (m, 2H), 6.29-6.15 (m, 1H), 4.78-4.66 (t, J=4.9 Hz, 1H), 4.44-4.30 (m, 1H), 4.16-4.02 (d, J=5.0 Hz, 1H), 2.19-2.11 (dd, J=12.9, 8.2 Hz, 1H), 2.08-1.97 (m, 1H), 1.97-1.85 (m, 1H), 1.77-1.60 (m, 2H), 1.54-1.49 (m, 1H).

Example 193: (±)-((3-fluoro-2-methoxyphenyl)(2-((5-(trifluoromethyl)pyridin-2-yl)amino)-7-azabicyclo[2.2.1]heptan-7-yl)methanone

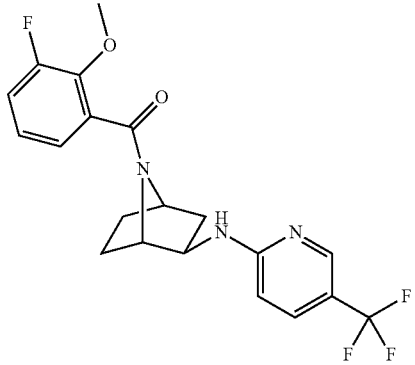 [SMILES: COc1c(F)cccc1C(=O)N1C2CCC1C(Nc1ccc(C(F)(F)F)cn1)C2]

Prepared analogous to Example 187 substituting intermediate A-21 with 3-fluoro-2-methoxybenzoic acid. MS (ESI) mass calcd. for $C_{20}H_{19}F_4N_3O_2$, 409.1; m/z found 410.4 [M+H]$^+$. $^1$H NMR (MeOD): 8.39 (s, 0.3H), 8.18 (s, 0.7H), 7.69 (dd, J=8.9, 2.3 Hz, 0.3H), 7.60 (dd, J=8.9, 2.4 Hz, 0.7H), 7.36 (ddd, J=11.7, 7.6, 2.1 Hz, 0.3H), 7.30-7.05 (m, 2.3H), 7.01 (d, J=7.6 Hz, 0.7H), 6.85-6.73 (m, 0.7H), 6.68 (d, J=8.8 Hz, 0.3H), 6.59 (d, J=8.9 Hz, 0.7H), 4.66 (br s, 0.7H), 4.54 (d, J=4.8 Hz, 0.3H), 4.00-3.90 (m, 0.3H), 3.89-3.77 (m, 3.7H), 3.75 (t, J=4.3 Hz, 0.3H), 3.64 (br s, 0.7H), 2.08-1.91 (m, 1H), 1.80-1.37 (m, 5H).

Example 194: (±)-(3-ethoxy-6-methylpyridin-2-yl)(2-((5-(trifluoromethyl)pyridin-2-yl)amino)-7-azabicyclo[2.2.1]heptan-7-yl)methanone

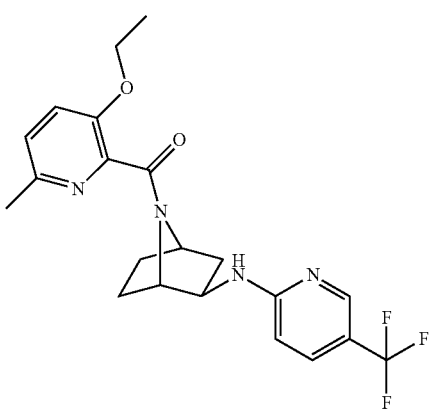 [SMILES: CCOc1ccc(C)nc1C(=O)N1C2CCC1C(Nc1ccc(C(F)(F)F)cn1)C2]

Prepared analogous to Example 187 substituting intermediate A-21 with intermediate A-8. MP=147° C. $^1$H NMR (DMSO-D$_6$): 8.38 (s, 0.3H), 8.16 (s, 0.7H), 7.68 (dd, J=8.9, 2.3 Hz, 0.3H), 7.59 (dd, J=8.9, 2.4 Hz, 0.7H), 7.46 (d, J=8.6 Hz, 0.3H), 7.36-7.18 (m, 2H), 7.05 (d, J=8.6 Hz, 0.7H), 6.71 (d, J=8.9 Hz, 0.3H), 6.57 (d, J=8.9 Hz, 0.7H), 4.65 (br s, 0.7H), 4.55 (d, J=2.8 Hz, 0.3H), 4.13-3.84 (m, 2.3H), 3.83-3.72 (m, 0.7H), 3.67 (d, J=3.5 Hz, 1H), 2.41 (s, 0.9H), 2.16 (s, 2.1H), 2.04-1.91 (m, 1H), 1.80-1.37 (m, 5H), 1.31-1.19 (m, 3H).

Example 195: (±)-(6-methyl-3-(pyrimidin-2-yl)pyridin-2-yl)(2-((5-(trifluoromethyl)pyridin-2-yl)amino)-7-azabicyclo[2.2.1]heptan-7-yl)methanone

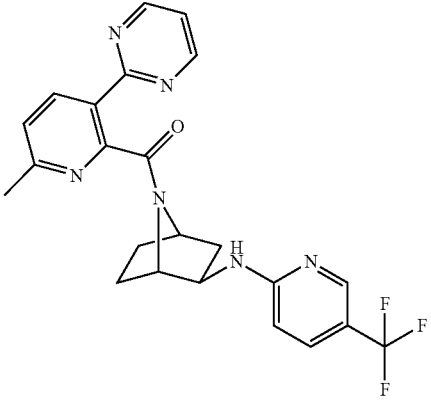 [SMILES: Cc1ccc(-c2ncccn2)c(C(=O)N2C3CCC2C(Nc2ccc(C(F)(F)F)cn2)C3)n1]

Prepared analogous to Example 187 substituting intermediate A-21 with intermediate A-9. MS (ESI) mass calcd. for $C_{23}H_{21}F_3N_6O$, 454.2; m/z found 455 [M+H]$^+$. $^1$H NMR (DMSO-D$_6$): 8.95-8.81 (m, 2H), 8.37 (s, 0.3H), 8.32 (d, J=8.0 Hz, 0.3H), 8.25-8.13 (m, 1.4H), 7.68 (dd, J=8.8, 2.1 Hz, 0.3H), 7.60 (dd, J=8.9, 2.2 Hz, 0.7H), 7.52-7.39 (m, 2H), 7.30 (d, J=8.1 Hz, 0.7H), 7.25 (d, J=3.7 Hz, 0.3H), 6.75 (d, J=8.8 Hz, 0.3H), 6.54 (d, J=8.9 Hz, 0.7H), 4.61 (t, J=4.2 Hz, 0.7H), 4.51 (d, J=4.2 Hz, 0.3H), 4.01-3.82 (m, 2H), 2.58 (s, 0.9H), 2.24 (s, 2.1H), 2.07-1.95 (m, 1H), 1.86-1.32 (m, 5H).

Example 196: (±)-(2-(2H-1,2,3-triazol-2-yl)phenyl)(2-((5-(trifluoromethyl)pyridin-2-yl)amino)-7-azabicyclo[2.2.1]heptan-7-yl)methanone

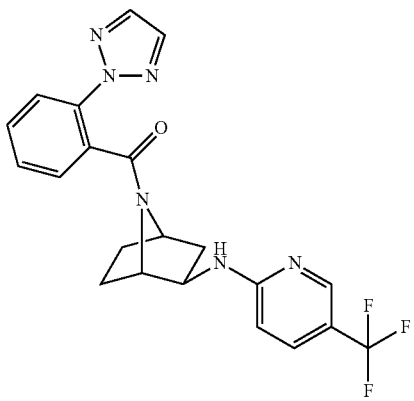 [SMILES: O=C(c1ccccc1-n1nccn1)N1C2CCC1C(Nc1ccc(C(F)(F)F)cn1)C2]

Prepared analogous to Example 187 substituting intermediate A-21 with intermediate A-1. MS (ESI) mass calcd. for $C_{21}H_{19}F_3N_6O$, 428.2; m/z found 409.2 [M+H]$^+$. $^1$H NMR (MeOD): 8.38 (s, 0.3H), 8.16 (s, 0.7H), 8.08 (s, 2H), 7.85 (d, J=7.2 Hz, 0.3H), 7.74-7.53 (m, 3H), 7.46-7.35 (m, 1.3H), 7.31 (d, J=6.1 Hz, 0.7H), 7.14 (t, J=7.5 Hz, 0.7H), 6.68 (d, J=8.9 Hz, 0.3H), 6.62 (d, J=8.9 Hz, 0.7H), 4.57 (t, J=4.5 Hz, 0.7H), 4.41 (d, J=4.8 Hz, 0.3H), 4.04-3.95 (m, 0.3H), 3.88-3.76 (m, 1H), 3.55 (br s, 0.7H), 1.97 (dd, J=12.7, 8.0 Hz, 1H), 1.79-1.23 (m, 5H).

Example 197: (±)-(2-((4,6-dimethylpyrimidin-2-yl)amino)-7-azabicyclo[2.2.1]heptan-7-yl)(5-fluoro-2-2H-1,2,3-triazol-2-yl)phenyl)methanone

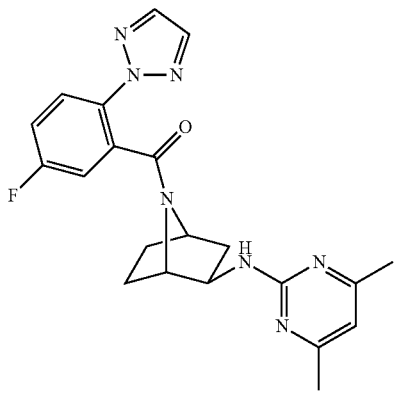 [SMILES: Cc1cc(C)nc(NC2CC3CCC2N3C(=O)c2cc(F)ccc2-n2nccn2)n1]

Step A: (±)-tert-butyl 2-((4,6-dimethylpyrimidin-2-yl)amino)-7-azabicyclo[2.2.1]heptane-7-carboxylate. To a microwave vial was weighed intermediate B-6 (210 mg, 1 mmol), 2-chloro-4,6-dimethylpyrimidine (212 mg, 1.5 mmol), sodium tert-butoxide (142 mg, 1.5 mmol), Pd(dba)$_2$ (28 mg, 5 mol %), Ctc-Q-Phos (44 mg, 10 mol). The vial was capped, evacuated and refilled with N$_2$ (2×). Then PhCH$_3$ (1 mL) was added and the reaction was heated at 125° C. for 4 h. The reaction allowed to cool to rt, applied directly purified via silica gel chromatography 1-7% 2M NH3/MeOH in DCM to give P1 (125 mg, 40%). MS (ESI) mass calcd. for C$_{17}$H$_{26}$N$_4$O$_2$, 318.2; m/z found 319.3 [M+H]$^+$. $^1$H NMR (CDCl$_3$): 6.31 (s, 1H), 5.18-4.94 (m, 1H), 4.35-4.13 (m, 2H), 4.08 (td, J=7.9, 3.2 Hz, 1H), 2.27 (s, 6H), 1.97 (dd, J=12.9, 7.8 Hz, 1H), 1.82-1.62 (m, 2H), 1.62-1.30 (m, 12H).

Step B: (±)-N-(4,6-dimethylpyrimidin-2-yl)-7-azabicyclo[2.2.1]heptan-2-amine. To the title compound of step A (125 mg, 0.4 mmol) in DCM (3 mL) was added TFA (3 mL). After starting material was consumed, the reaction was concentrated, neutralized with 5% Na$_2$CO$_3$ and extracted with DCM. The combined organics were dried (Na$_2$SO$_4$) to give the title compound that was used in subsequent reactions without further purification. MS (ESI) mass calcd. for C$_{12}$H$_{18}$N$_4$, 218.2; m/z found 219.2 [M+H]$^+$.

Step C: (±)-(2-((4,6-dimethylpyrimidin-2-yl)amino)-7-azabicyclo[2.2.1]heptan-7-yl)(5-fluoro-2-(2H-1,2,3-triazol-2-yl)phenyl)methanone. Prepared analogous to Example 181 substituting intermediate A-1 with intermediate A-10 and (1 S,2R,4R)—N-(5-(trifluoromethyl)pyrazin-2-yl)-7-azabicyclo[2.2.1]heptan-2-amine with the title compound of step B. MS (ESI) mass calcd. for C$_{21}$H$_{22}$FN$_7$O, 407.2; m/z found 408.2 [M+H]$^+$. $^1$H NMR (CDCl$_3$): 8.23-7.67 (m, 2.5H), 7.54-6.93 (m, 2.5H), 6.40-6.19 (m, 1H), 4.89-4.65 (m, 1H), 4.41-3.66 (m, 2H), 2.39-1.34 (m, 12H).

Example 198: (±)-(2-((4,6-dimethylpyrimidin-2-yl)amino)-7-azabicyclo[2.2.1]heptan-7-yl)(2-fluoro-6-(2H-1,2,3-triazol-2-yl)phenyl)methanone

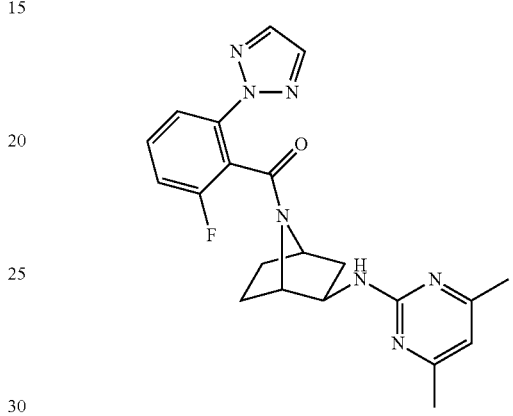

Prepared analogous to Example 197 substituting intermediate A-10 with intermediate A-11. MS (ESI) mass calcd. for C$_{21}$H$_{22}$FN$_7$O, 407.2; m/z found 408.2 [M+H]$^+$.

Example 199: (±)-(2-((4,6-dimethylpyrimidin-2-yl)amino)-7-azabicyclo[2.2.1]heptan-7-yl)(4-fluoro-2-(2H-1,2,3-triazol-2-yl)phenyl)methanone

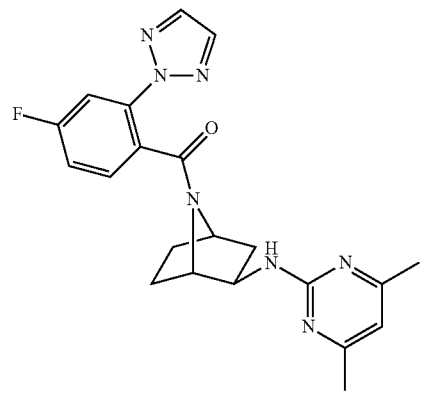 [SMILES: Cc1cc(C)nc(NC2CC3CCC2N3C(=O)c2ccc(F)cc2-n2nccn2)n1]

Prepared analogous to Example 197 substituting intermediate A-10 with intermediate A-12. MS (ESI) mass calcd. for C$_{21}$H$_{22}$FN$_7$O, 407.2; m/z found 408.2 [M+H]$^+$. $^1$H NMR (MeOD): 8.23-7.33 (m, 4H), 7.22-6.75 (m, 1H), 6.42-6.21 (m, 1H), 4.91-4.73 (m, 1H), 4.44-4.01 (m, 1H), 3.97-3.71 (m, 1H), 2.41-1.30 (m, 12H).

Example 200: (±)-(2-((4,6-dimethylpyrimidin-2-yl)amino)-7-azabicyclo[2.2.1]heptan-7-yl)(6-methyl-3-(pyrimidin-2-yl)pyridin-2-yl)methanone

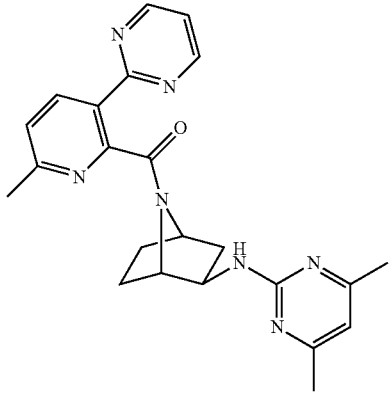

Prepared analogous to Example 187 substituting 2-chloro-5-(trifluoromethyl)pyridine with 2-chloro-4,6-dimethylpyrimidine and intermediate A-21 with intermediate A-9. MS (ESI) mass calcd. for $C_{23}H_{25}N_7O$, 415.2; m/z found 416 [M+H]$^+$. $^1$H NMR (DMSO-D$_6$): 9.05 (d, J=4.9 Hz, 0.6H), 8.90 (d, J=4.9 Hz, 1.4H), 8.37 (d, J=8.1 Hz, 0.3H), 8.28 (d, J=8.0 Hz, 0.7H), 7.57-7.45 (m, 1.3H), 7.41 (d, J=8.1 Hz, 0.7H), 7.09 (d, J=7.8 Hz, 0.7H), 6.46 (s, 0.3H), 6.43-6.29 (m, 1H), 4.62 (br s, 0.7H), 4.51 (d, J=4.4 Hz, 0.3H), 4.15-3.97 (m, 1H), 3.97-3.92 (m, 0.3H), 3.89 (d, J=3.7 Hz, 0.7H), 2.59 (s, 0.9H), 2.50 (s, 2.1H), 2.26 (s, 1.8H), 2.14 (s, 4.2H), 2.05 (dd, J=12.5, 7.6 Hz, 1H), 1.99-1.37 (m, 5H).

Example 201: (±)-(2-((4,6-dimethylpyrimidin-2-yl)amino)-7-azabicyclo[2.2.1]heptan-7-yl)(6-methyl-3-(2H-1,2,3-triazol-2-yl)pyridin-2-yl)methanone

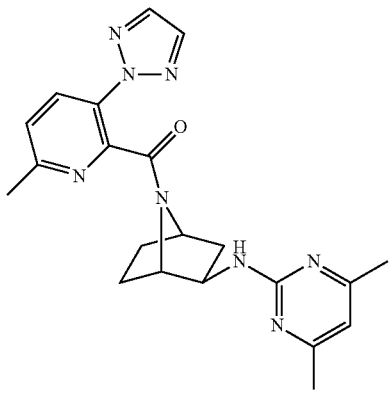

Prepared analogous to Example 200 substituting intermediate A-9 with intermediate A-21. MP=171.9° C. 1H NMR (DMSO-D$_6$): 8.28-8.17 (m, 1.2H), 8.17-8.09 (m, 1.8H), 7.57 (d, J=8.4 Hz, 0.4H), 7.46 (d, J=8.4 Hz, 0.6H), 6.89 (d, J=7.0 Hz, 0.6H), 6.46 (s, 0.4H), 6.42 (d, J=7.5 Hz, 0.4H), 6.35 (s, 0.6H), 4.59 (t, J=4.2 Hz, 0.6H), 4.50 (d, J=4.9 Hz, 0.4H), 4.08 (td, J=7.8, 3.0 Hz, 0.4H), 4.00-3.86 (m, 1.6H), 2.60 (s, 1.2H), 2.45 (s, 1.8H), 2.26 (s, 2.4H), 2.15 (s, 3.6H), 1.97 (ddd, J=16.3, 12.6, 7.9 Hz, 1H), 1.83-1.35 (m, 5H).

Example 202: (±)-(2-(2H-1,2,3-triazol-2-yl)phenyl)(2-((4,6-dimethylpyrimidin-2-yl)amino)-7-azabicyclo[2.2.1]heptan-7-yl)methanone

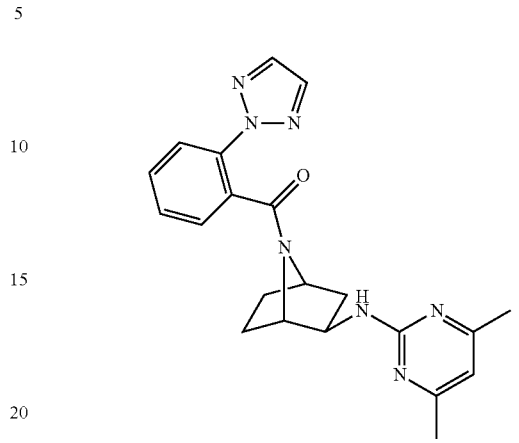

Prepared analogous to Example 200 substituting intermediate A-9 with intermediate A-1. MP=154.2° C. 1H NMR (DMSO-D$_6$): 8.12 (s, 1H), 8.07 (s, 1H), 7.85 (d, J=7.7 Hz, 0.5H), 7.77 (d, J=6.8 Hz, 0.5H), 7.72-7.61 (m, 1H), 7.58 (dd, J=10.7, 4.2 Hz, 0.5H), 7.49-7.39 (m, 1H), 7.15 (t, J=7.5 Hz, 0.5H), 6.99 (d, J=6.1 Hz, 0.5H), 6.87 (br s, 0.5H), 6.43 (s, 0.5H), 6.33 (s, 0.5H), 4.51 (t, J=4.1 Hz, 0.5H), 4.37 (d, J=3.9 Hz, 0.5H), 4.12-3.97 (m, 0.5H), 3.88-3.72 (m, 1H), 3.68 (d, J=4.4 Hz, 0.5H), 2.24 (s, 3H), 2.15 (s, 3H), 1.97-1.21 (m, 6H).

Example 203: (±)-(2-((4,6-dimethylpyrimidin-2-yl)amino)-7-azabicyclo[2.2.1]heptan-7-yl)(3-ethoxy-6-methylpyridin-2-yl)methanone

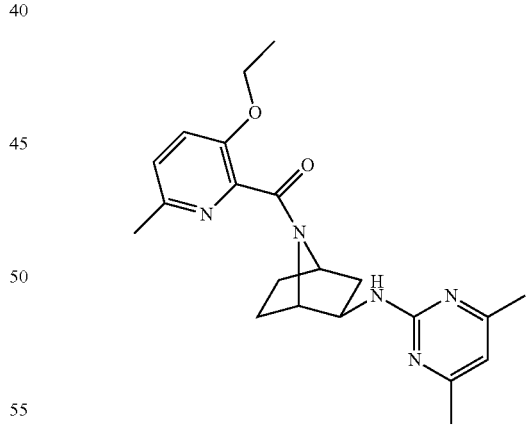

Prepared analogous to Example 200 substituting intermediate A-9 with intermediate A-8. MS (ESI) mass calcd. for $C_{21}H_{27}N_5O_2$, 381.2; m/z found 382.5 [M+H]$^+$. MP=137.8° C. $^1$H NMR (DMSO-D$_6$): 7.20-7.01 (m, 2H), 6.45 (d, J=8.5 Hz, 0.7H), 6.31 (s, 0.3H), 6.24 (s, 0.7H), 5.31 (d, J=8.6 Hz, 0.3H), 4.91 (t, J=4.5 Hz, 0.7H), 4.80 (d, J=5.1 Hz, 0.3H), 4.32-4.14 (m, 1.7H), 4.14-3.98 (m, 1.3H), 3.80 (t, J=4.7 Hz, 0.3H), 3.75 (d, J=4.6 Hz, 0.7H), 2.53 (s, 2.1H), 2.49 (s, 0.9H), 2.26 (s, 1.8H), 2.22 (s, 4.2H), 2.20-2.08 (m, 1H), 2.05-1.49 (m, 5H), 1.48-1.40 (m, 3H).

Example 204: (±)-(2-(2H-1,2,3-triazol-2-yl)phenyl)(2-(quinoxalin-2-ylamino)-7-azabicyclo[2.2.1]heptan-7-yl)methanone

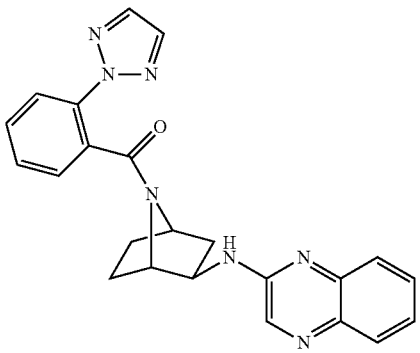 [SMILES: O=C(c1ccccc1-n1nccn1)N1C2CCC1C(Nc1cnc3ccccc3n1)C2]

Step A: (±)-tert-butyl 2-(quinoxalin-2-ylamino)-7-azabicyclo[2.2.1]heptane-7-carboxylate. To intermediate B-6 (500 mg, 2.4 mmol) in dry DMA (7 mL) was added K$_2$CO$_3$ (650 mg, 4.7 mmol) and 2-chloroquinoxaline (580 mg, 3.5 mmol). After heating at 80° C. for 48 h, the mixture was cooled to rt and saturated NaHCO$_3$ (aq) was added. The mixture was extracted with EtOAc (3×). The combined organics were washed with brine and dried (MgSO$_4$). Purification via silica gel chromatography (0-25% EtOAc in heptanes) gave the title compound. MS (ESI) mass calcd. for C$_{19}$H$_{24}$N$_4$O$_2$, 340.2; m/z found 341.0 [M+H]$^+$.

Step B: N-((±)-7-azabicyclo[2.2.1]heptan-2-yl)quinoxalin-2-amine hydrochloride. To the title compound from step A (343 mg, 1 mmol) in 1,4-dioxane (10 mL) was added 6N HCl in iPrOH (1 mL). The reaction was heated to 70° C. for 2 h, cooled to rt, concentrated and used without further purification in subsequent steps.

Step C: (±)-(2-(2H-1,2,3-triazol-2-yl)phenyl)(2-(quinoxalin-2-ylamino)-7-azabicyclo[2.2.1]heptan-7-yl)methanone. Prepared analogous to Example 187 substituting intermediate A-21 with intermediate A-1 and (±)-N-(5-(trifluoromethyl)pyridin-2-yl)-7-azabicyclo[2.2.1]heptan-2-amine hydrochloride with the title compound from step B. MS (ESI) mass calcd. for C$_{23}$H$_{21}$N7O, 411.2; m/z found 412 [M+H]$^+$. $^1$H NMR (DMSO-D$_6$): 8.38 (s, 0.3H), 8.31 (s, 0.7H), 8.08 (s, 2H), 7.88-7.73 (m, 1.3H), 7.72-7.20 (m, 7H), 7.14-7.04 (m, 0.7H), 4.60 (t, J=4.4 Hz, 0.7H), 4.54 (d, J=4.7 Hz, 0.3H), 4.15-4.03 (m, 0.3H), 3.97-3.87 (m, 0.7H), 3.82 (t, J=3.9 Hz, 0.3H), 3.65 (d, J=3.2 Hz, 0.7H), 2.12-1.96 (m, 1H), 1.84-1.28 (m, 5H).

Example 205: (±)-(6-methyl-3-(2H-1,2,3-triazol-2-yl)pyridin-2-yl)(2-(quinoxalin-2-ylamino)-7-azabicyclo[2.2.1]heptan-7-yl)methanone

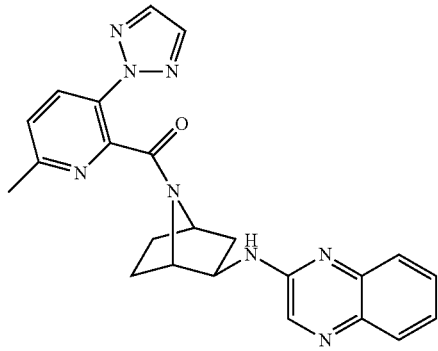 [SMILES: Cc1ccc(-n2nccn2)c(C(=O)N2C3CCC2C(Nc2cnc4ccccc4n2)C3)n1]

Prepared analogous to Example 204 substituting with intermediate A-1 with intermediate A-21. MP=260.8° C. $^1$H NMR (DMSO-D$_6$): 8.44 (s, 0.3H), 8.32 (s, 0.7H), 8.19 (d, J=8.4 Hz, 0.3H), 8.13 (s, 2H), 7.96 (d, J=8.3 Hz, 0.7H), 7.83-7.72 (m, 1H), 7.68-7.27 (m, 4.3H), 7.19 (d, J=8.4 Hz, 0.7H), 4.64 (br s, 1H), 4.06-3.86 (m, 2H), 2.61 (s, 0.9H), 2.09 (s, 2.1H), 2.06-1.99 (m, 1H), 1.88-1.62 (m, 2H), 1.62-1.38 (m, 3H).

Example 206: (±)-(3-fluoro-2-methoxyphenyl)(2-(quinoxalin-2-ylamino)-7-azabicyclo[2.2.1]heptan-7-yl)methanone

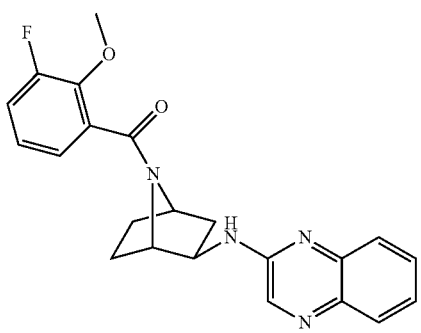 [SMILES: COc1c(F)cccc1C(=O)N1C2CCC1C(Nc1cnc3ccccc3n1)C2]

Prepared analogous to Example 204 substituting intermediate A-1 with 3-fluoro-2-methoxybenzoic acid. MP=179.2° C. $^1$H NMR (DMSO-D$_6$): 8.38 (s, 0.3H), 8.27 (s, 0.7H), 7.80 (d, J=8.0 Hz, 0.3H), 7.73 (d, J=8.0 Hz, 0.7H), 7.65-7.52 (m, 1.4H), 7.52-7.28 (m, 2.7H), 7.28-7.15 (m, 0.7H), 7.09 (d, J=7.6 Hz, 0.7H), 6.96 (ddd, J=11.7, 8.2, 1.4 Hz, 0.7H), 6.75 (td, J=7.9, 4.8 Hz, 0.7H), 4.75-4.63 (m, 1H), 4.11-4.01 (m, 0.4H), 3.99-3.90 (m, 0.7H), 3.86 (br s, 0.9H), 3.83-3.73 (m, 2.1H), 2.06 (dt, J=16.7, 8.4 Hz, 1H), 1.87-1.45 (m, 6H).

Example 207: (±)-(3-ethoxy-6-methylpyridin-2-yl)(2-(quinoxalin-2-ylamino)-7-azabicyclo[2.2.1]heptan-7-yl)methanone

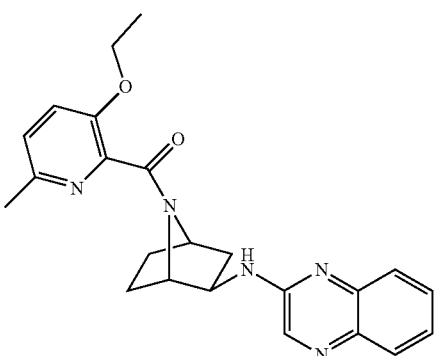

Prepared analogous to Example 204 substituting with intermediate A-1 with intermediate A-8. MS (ESI) mass calcd. for C$_{23}$H$_{25}$N$_5$O$_2$, 403.2; m/z found 404 [M+H]$^+$. MP=184.9 C. $^1$H NMR (DMSO-D$_6$): 8.41 (s, 0.3H), 8.26 (s, 0.7H), 7.79 (d, J=8.1 Hz, 0.3H), 7.72 (d, J=8.0 Hz, 0.7H), 7.64-7.53 (m, 1.7H), 7.50-7.22 (m, 2.9H), 7.18 (d, J=8.6 Hz, 0.7H), 6.86 (d, J=8.6 Hz, 0.7H), 4.68 (br s, 1H), 4.12-3.83

(m, 3H), 3.79 (d, J=4.1 Hz, 0.7H), 3.71 (br s, 0.3H), 2.41 (s, 0.9H), 2.11-1.96 (m, 3.1H), 1.89-1.42 (m, 5H), 1.25 (t, J=6.9 Hz, 3H).

Example 208: (±)-(6-methyl-3-(pyrimidin-2-yl)pyridin-2-yl)(2-(quinoxalin-2-ylamino)-7-azabicyclo[2.2.1]heptan-7-yl)methanone

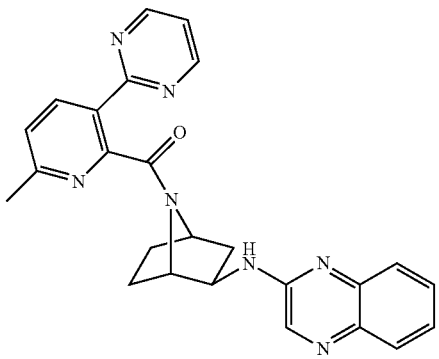 [SMILES: Cc1ccc(-c2ncccn2)c(C(=O)N2C3CCC2C(Nc2cnc4ccccc4n2)C3)n1]

Prepared analogous to Example 204 substituting with intermediate A-1 with intermediate A-9. MS (ESI) mass calcd. for $C_{25}H_{23}N_7O$, 437.2; m/z found 438 [M+H]$^+$. $^1$H NMR (DMSO-D$_6$): 8.93-8.82 (m, 2H), 8.46 (s, 0.3H), 8.33 (d, J=8.1 Hz, 0.3H), 8.27 (s, 0.7H), 8.14 (d, J=8.0 Hz, 0.7H), 7.81-7.26 (m, 6.3H), 7.17 (d, J=8.1 Hz, 0.7H), 4.66 (br s, 1H), 4.06-3.94 (m, 2H), 2.60 (s, 0.9H), 2.13-2.01 (m, 3.1H), 1.92-1.36 (m, 5H).

Example 209: (±)-(2-(2H-1,2,3-triazol-2-yl)phenyl)(2-((6-(trifluoromethyl)pyridin-2-yl)amino)-7-azabicyclo[2.2.1]heptan-7-yl)methanone

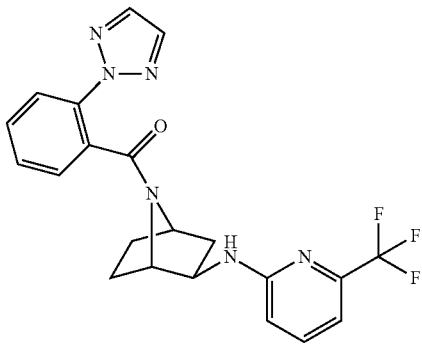 [SMILES: O=C(c1ccccc1-n1nccn1)N1C2CCC1C(Nc1cccc(C(F)(F)F)n1)C2]

Step A: (±)-tert-butyl-2-((6-(trifluoromethyl)pyridin-2-yl)amino)-7-azabicyclo[2.2.1]heptane-7-carboxylate. To 2-chloro-6-(trifluoromethyl)pyridine (113 mg, 0.6 mmol) in THF (3 mL) was added sodium tert-butoxide (120 mg, 1.2 mmol), Xanphos (26 mg, 7 mol %) and Pd$_2$(dba)$_3$ (23 mg, 4 mol %) at rt while N$_2$ was bubbled through the solution. After 10 minutes, intermediate B-6 (132 mg, 0.6 mmol) was added. The reaction mixture was heated at 90° C. for 3 h. After allowing to cool to rt, saturated NaHCO$_3$ (aq) the mixture extracted with EtOAc (2×). The combined organics were dried (MgSO$_4$). Purification via silica gel chromatography (0-7% EtOAc in heptane) gave the title compound. MS (ESI) mass calcd. for $C_{17}H_{22}F_3N_3O_2$, 357.2; m/z found 358.4 [M+H]$^+$.

Step B: (±)-N-(6-(trifluoromethyl)pyridin-2-yl)-7-azabicyclo[2.2.1]heptan-2-amine hydrochloride. Prepared analogous to Example 204 substituting (±)-tert-butyl 2-(quinoxalin-2-ylamino)-7-azabicyclo[2.2.1]heptane-7-carboxylate with the title compound of step A.

Step C: (±)-tert-butyl-2-((6-(trifluoromethyl)pyridin-2-yl)amino)-7-azabicyclo[2.2.1]heptane-7-carboxylate. Prepared analogous to Example 204 substituting N-((±)-7-azabicyclo[2.2.1]heptan-2-yl)quinoxalin-2-amine hydrochloride with the title compound of step B. MS (ESI) mass calcd. for $C_{21}H_{19}F_3N_6O$, 428.2; m/z found 429. [M+H]$^+$. MP=96.8° C. $^1$H NMR (DMSO-D$_6$): 8.07 (s, 2H), 7.85 (d, J=7.9 Hz, 0.3H), 7.74-7.51 (m, 2.7H), 7.46-7.36 (m, 1.3H), 7.17-6.94 (m, 2H), 6.86 (d, J=7.2 Hz, 0.7H), 6.82 (d, J=8.6 Hz, 0.3H), 6.74 (d, J=8.4 Hz, 0.7H), 4.55 (t, J=4.5 Hz, 0.7H), 4.41 (d, J=4.6 Hz, 0.3H), 3.94-3.84 (m, 0.3H), 3.84-3.71 (m, 1H), 3.61 (d, J=4.6 Hz, 0.7H), 1.96 (dd, J=12.6, 8.0 Hz, 1H), 1.80-1.21 (m, 5H).

Example 210: (±)-((2-(2H-1,2,3-triazol-2-yl)phenyl)(2-((4-(trifluoromethyl)pyridin-2-yl)amino)-7-azabicyclo[2.2.1]heptan-7-yl)methanone

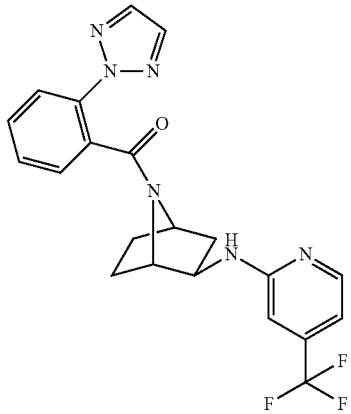 [SMILES: O=C(c1ccccc1-n1nccn1)N1C2CCC1C(Nc1cc(C(F)(F)F)ccn1)C2]

Prepared analogous to Example 209 substituting 2-chloro-6-(trifluoromethyl)pyridine with 2-chloro-4-(trifluoromethyl)pyridine. MP=153.5° C. MS (ESI) mass calcd. for $C_{21}H_{19}F_3N_6O$, 428.2; m/z found 429 [M+H]$^+$. $^1$H NMR (DMSO-D$_6$): 8.27 (d, J=5.3 Hz, 0.3H), 8.12-7.99 (m, 2.7H), 7.85 (d, J=7.9 Hz, 0.3H), 7.72-7.54 (m, 1.6H), 7.50-7.33 (m, 1.4H), 7.13-6.92 (m, 2H), 6.82 (d, J=12.6 Hz, 0.3H), 6.78 (s, 0.7H), 6.67 (d, J=5.3 Hz, 0.7H), 4.56 (t, J=4.5 Hz, 0.7H), 4.41 (d, J=4.6 Hz, 0.3H), 4.04-3.93 (m, 0.3H), 3.86-3.72 (m, 1H), 3.52 (br s, 0.7H), 1.96 (dd, J=12.6, 8.0 Hz, 1H), 1.78-1.17 (m, 5H).

Example 211: (±)-(2-(2H-1,2,3-triazol-2-yl)phenyl)(2-((5-chloropyridin-2-yl)amino)-7-azabicyclo[2.2.1]heptan-7-yl)methanone

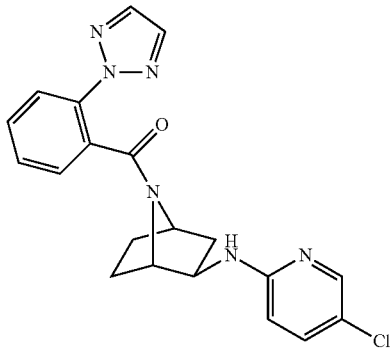 [SMILES: O=C(c1ccccc1-n1nccn1)N1C2CCC1C(Nc1ccc(Cl)cn1)C2]

Prepared analogous to Example 209 substituting 2-chloro-6-(trifluoromethyl)pyridine with 5-chloro-2-iodopyridine. MS (ESI) mass calcd. for $C_{20}H_{19}ClN_6O$, 394.1; m/z found 395 [M+H]⁺. MP=157.0° C. ¹H NMR (DMSO-D₆): 8.14-7.99 (m, 2.3H), 7.87-7.79 (m, 1H), 7.71-7.52 (m, 1.7H), 7.52-7.36 (m, 2.6H), 7.23-7.11 (m, 0.7H), 6.80 (d, J=6.4 Hz, 0.7H), 6.58 (d, J=9.0 Hz, 0.3H), 6.52 (d, J=8.9 Hz, 0.7H), 4.53 (t, J=4.6 Hz, 0.7H), 4.37 (d, J=4.6 Hz, 0.3H), 3.92-3.82 (m, 0.3H), 3.81-3.68 (m, 1H), 3.52 (d, J=4.3 Hz, 0.7H), 1.94 (dd, J=12.5, 8.1 Hz, 1H), 1.73-1.22 (m, 5H).

Example 212: (±)-(2-(2H-1,2,3-triazol-2-yl)phenyl) (2-((6-(trifluoromethyl)pyridazin-3-yl)amino)-7-azabicyclo[2.2.1]heptan-7-yl)methanone

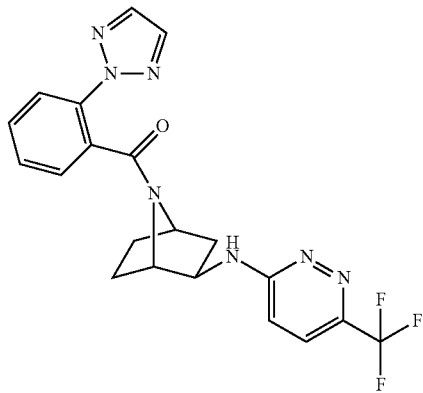 [SMILES: O=C(c1ccccc1-n1nccn1)N1C2CCC1C(Nc1ccc(C(F)(F)F)nn1)C2]

Prepared analogous to Example 209 substituting 2-chloro-6-(trifluoromethyl)pyridine with 3-chloro-6-(trifluoromethyl)pyridazine. MP=134.0° C. MS (ESI) mass calcd. for $C_{20}H_{18}F_3N_7O$, 429.2; m/z found 430 [M+H]⁺. ¹H NMR (DMSO-D₆): 8.08 (s, 1.4H), 8.07 (s, 0.6H), 7.85 (d, J=7.8 Hz, 0.3H), 7.77-7.46 (m, 3.6H), 7.44-7.31 (m, 1.4H), 7.20-7.09 (m, 0.7H), 7.06 (d, J=9.4 Hz, 0.3H), 6.98 (d, J=9.3 Hz, 0.7H), 4.59 (t, J=4.4 Hz, 0.7H), 4.48 (d, J=4.7 Hz, 0.3H), 3.97-3.87 (m, 0.7H), 3.81 (t, J=4.0 Hz, 0.3H), 3.58-3.56 (m, 1H), 2.01 (dd, J=12.9, 8.0 Hz, 1H), 1.82-1.18 (m, 5H).

Example 213: (±)-(2-(2H-1,2,3-triazol-2-yl)phenyl) (2-((5-methoxypyridin-2-yl)amino)-7-azabicyclo [2.2.1]heptan-7-yl)methanone

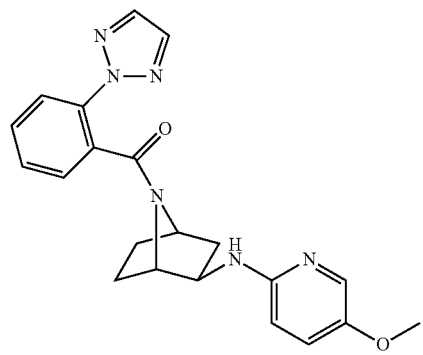 [SMILES: COc1ccc(NC2CC3CCC2N3C(=O)c2ccccc2-n2nccn2)nc1]

Prepared analogous to Example 209 substituting 2-chloro-6-(trifluoromethyl)pyridine with 2-chloro-5-methoxypyridine. MS (ESI) mass calcd. for $C_{21}H_{22}N_6O_2$, 390.2; m/z found 391 [M+H]⁺. MP=174.0° C. ¹H NMR (DMSO-D₆): 8.31 (s, 0.3H), 8.13-8.02 (m, 2H), 7.84 (d, J=8.0 Hz, 0.3H), 7.79 (d, J=3.0 Hz, 0.3H), 7.71-7.61 (m, 1.3H), 7.60-7.53 (m, 1H), 7.50-7.37 (m, 1.4H), 7.22-7.04 (m, 1.7H), 6.52 (d, J=9.0 Hz, 0.3H), 6.46 (d, J=9.0 Hz, 0.7H), 6.21 (d, J=6.9 Hz, 0.7H), 4.52 (t, J=4.5 Hz, 0.7H), 4.37 (d, J=4.5 Hz, 0.2H), 3.90-3.79 (m, 0.3H), 3.79-3.68 (m, 1.9H), 3.64 (s, 2.1H), 3.57 (d, J=4.0 Hz, 0.7H), 1.98-1.84 (m, 1H), 1.76-1.21 (m, 5H).

Example 214: (±)-(2-(2H-1,2,3-triazol-2-yl)phenyl) (2-((5-methylpyridin-2-yl)amino)-7-azabicyclo [2.2.1]heptan-7-yl)methanone

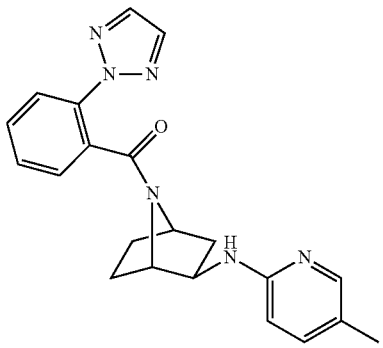 [SMILES: Cc1ccc(NC2CC3CCC2N3C(=O)c2ccccc2-n2nccn2)nc1]

Prepared analogous to Example 209 substituting 2-chloro-6-(trifluoromethyl)pyridine with 2-chloro-5-methylpyridine. MS (ESI) mass calcd. for $C_{21}H_{22}N_6O$, 374.2; m/z found 375.2 [M+H]⁺. ¹H NMR (DMSO-D₆): 8.32 (s, 0.7H), 8.09 (s, 0.6H), 8.07 (s, 1.4H), 7.89-7.80 (m, 0.6H), 7.72-7.53 (m, 2.1H), 7.52-7.37 (m, 1.3H), 7.27 (dd, J=8.5, 2.2 Hz, 0.3H), 7.23-7.11 (m, 1.3H), 6.47 (d, J=8.5 Hz, 0.3H), 6.41 (d, J=8.2 Hz, 0.7H), 6.35 (d, J=6.9 Hz, 0.7H), 4.53 (t, J=4.5 Hz, 0.7H), 4.37 (d, J=4.4 Hz, 0.3H), 3.95-3.84 (m, 0.3H), 3.84-3.70 (m, 1H), 3.56 (d, J=4.3 Hz, 0.7H), 2.12 (s, 0.9H), 2.04 (s, 2.1H), 1.99-1.86 (m, 1H), 1.78-1.24 (m, 5H).

Example 215: (±)-(2-(2H-1,2,3-triazol-2-yl)phenyl) (2-(pyridin-2-ylamino)-7-azabicyclo[2.2.1]heptan-7-yl)methanone

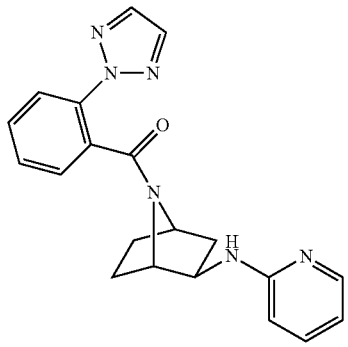 [SMILES: O=C(c1ccccc1-n1nccn1)N1C2CCC1C(Nc1ccccn1)C2]

Prepared analogous to Example 209 substituting 2-chloro-6-(trifluoromethyl)pyridine with 2-iodopyridine. MS (ESI) mass calcd. for $C_{20}H_{20}N_6O$, 360.2; m/z found 361

[M+H]⁺. MP=167.9° C. ¹H NMR (DMSO-D₆): 8.12-8.00 (m, 2.3H), 7.88-7.79 (m, 1H), 7.73-7.53 (m, 1.5H), 7.50-7.28 (m, 2.5H), 7.13 (t, J=7.4 Hz, 0.7H), 6.63-6.37 (m, 3H), 4.54 (t, J=4.5 Hz, 0.7H), 4.39 (d, J=4.4 Hz, 0.3H), 3.92 (td, J=7.5, 3.2 Hz, 0.3H), 3.86-3.73 (m, 1H), 3.58 (d, J=4.3 Hz, 0.7H), 2.02-1.86 (m, 1H), 1.78-1.23 (m, 5H).

Example 216: (±)-(2-(2H-1,2,3-triazol-2-yl)phenyl) (2-((5-chlorobenzo[d]oxazol-2-yl)amino)-7-azabicyclo[2.2.1]heptan-7-yl)methanone

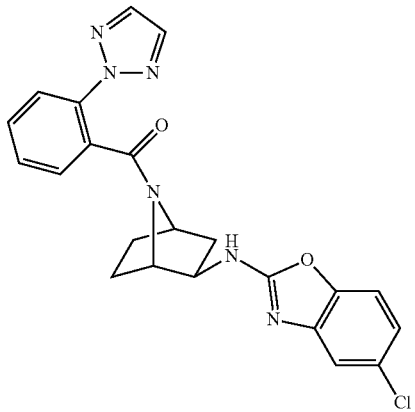 [SMILES: O=C(c1ccccc1-n1nccn1)N1C2CCC1C(Nc1nc3cc(Cl)ccc3o1)C2]

Step A: (±)-tert-butyl 2-((5-chlorobenzo[d]oxazol-2-yl)amino)-7-azabicyclo[2.2.1]heptane-7-carboxylate. To intermediate B-6 (116 mg, 0.6 mmol) in 1,4-dioxane (3 mL) was added DIPEA (190 μL, 1.1 mmol) and 5-chloro-2-(methylsulfinyl)benzo[d]oxazole (235 mg, 1.1 mmol). After heating at 80° C. for 4 h, the mixture was cooled to rt and saturated NaHCO₃ (aq) was added. The aqueous layer was extracted with EtOAc (3×). The combined organics were dried (MgSO₄). Purification via silica gel chromatography (0-10% EtOAc in hexanes) gave the title compound (130 mg, 66%). MS (ESI) mass calcd. for C₁₈H₂₂ClN₃O₃, 363.1; m/z found 364.0 [M+H]⁺.

Step B: N-((±)-7-azabicyclo[2.2.1]heptan-2-yl)-5-chlorobenzo[d]oxazol-2-amine hydrochloride. Prepared analogous to Example 209 substituting (±)-tert-butyl-2-((6-(trifluoromethyl)pyridin-2-yl)amino)-7-azabicyclo[2.2.1] heptane-7-carboxylate with the title compound of step A. MS (ESI) mass calcd. for C₁₃H₁₄ClN₃O, 263.1; m/z found 264.0 [M+H]⁺.

Step C: (±)-(2-(2H-1,2,3-triazol-2-yl)phenyl)(2-((5-chlorobenzo[d]oxazol-2-yl)amino)-7-azabicyclo[2.2.1]heptan-7-yl)methanone. Prepared analogous to Example 209 substituting (±)-N-(6-(trifluoromethyl)pyridin-2-yl)-7-azabicyclo[2.2.1]heptan-2-amine hydrochloride with the title compound of step B. MS (ESI) mass calcd. for C₂₂H₁₉ClN₆O₂, 434.1; m/z found 435 [M+H]⁺. ¹H NMR (DMSO-D₆): 8.20 (d, J=5.6 Hz, 1H), 8.13-8.05 (m, 2H), 7.85 (d, J=7.4 Hz, 0.3H), 7.76 (d, J=7.3 Hz, 0.3H), 7.72-7.55 (m, 1.3H), 7.53-7.44 (m, 0.7H), 7.44-7.29 (m, 2H), 7.24 (d, J=2.1 Hz, 0.7H), 7.16-7.08 (m, 0.7H), 7.08-6.98 (m, 1H), 4.66-4.47 (m, 1H), 3.97-3.86 (m, 0.3H), 3.82 (t, J=3.9 Hz, 0.3H), 3.79-3.66 (m, 1.4H), 2.07-1.92 (m, 1H), 1.88-1.22 (m, 5H).

Example 217: (±)-(2-((5-bromopyridin-2-yl)amino)-7-azabicyclo[2.2.1]heptan-7-yl)(6-methyl-3-(pyrimidin-2-yl)pyridin-2-yl)methanone

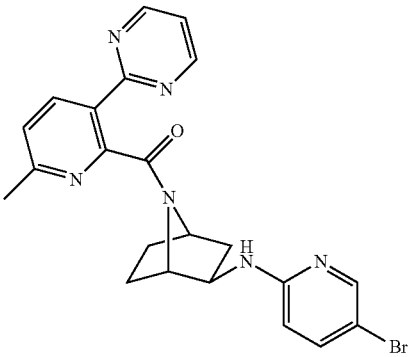 [SMILES: Cc1ccc(-c2ncccn2)c(C(=O)N2C3CCC2C(Nc2ccc(Br)cn2)C3)n1]

Prepared analogous to Example 209 substituting 2-chloro-6-(trifluoromethyl)pyridine with 5-bromo-2-iodopyridine and intermediate A-1 with intermediate A-9. MS (ESI) mass calcd. for C₂₂H₂₁BrN₆O, 464.1; m/z found 466 [M+H]⁺. MP=221.8° C. ¹H NMR (DMSO-D₆): 8.96-8.78 (m, 2H), 8.32 (d, J=8.0 Hz, 0.3H), 8.19 (d, J=8.0 Hz, 0.7H), 8.10 (d, J=2.4 Hz, 0.3H), 7.93 (d, J=2.4 Hz, 0.7H), 7.56 (dd, J=8.9, 2.5 Hz, 0.3H), 7.51-7.39 (m, 2H), 7.33 (d, J=8.1 Hz, 0.7H), 6.93 (d, J=7.1 Hz, 0.7H), 6.66 (d, J=5.6 Hz, 0.3H), 6.61 (d, J=9.0 Hz, 0.3H), 6.36 (d, J=8.9 Hz, 0.7H), 4.59 (t, J=4.1 Hz, 0.7H), 4.47 (d, J=4.3 Hz, 0.3H), 3.96-3.75 (m, 2H), 2.58 (s, 0.9H), 2.31 (s, 2.1H), 2.07-1.91 (m, 1H), 1.88-1.30 (m, 5H).

Example 218: (±)-(2-((5-bromopyridin-2-yl)amino)-7-azabicyclo[2.2.1]heptan-7-yl)(3-fluoro-2-methoxyphenyl)methanone

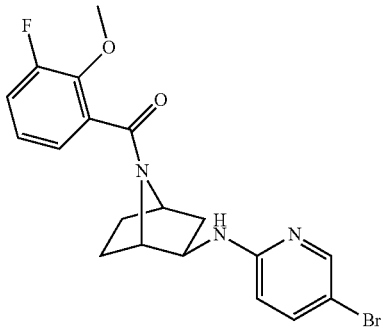 [SMILES: COc1c(F)cccc1C(=O)N1C2CCC1C(Nc1ccc(Br)cn1)C2]

Prepared analogous to Example 217 substituting intermediate A-9 with 3-fluoro-2-methoxybenzoic acid. MS (ESI) mass calcd. for C₁₉H₁₉BrFN₃O₂, 419.1; m/z found 420.1 [M+H]⁺. MP=175.2° C. ¹H NMR (DMSO-D₆): 8.10 (d, J=2.4 Hz, 0.3H), 7.90 (d, J=2.4 Hz, 0.7H), 7.56 (dd, J=8.9, 2.5 Hz, 0.3H), 7.47 (dd, J=8.9, 2.5 Hz, 0.7H), 7.34 (ddd, J=11.7, 7.5, 2.3 Hz, 0.3H), 7.24-7.08 (m, 1.3H), 7.02 (d, J=7.6 Hz, 0.7H), 6.87-6.66 (m, 1.7H), 6.54 (d, J=8.9 Hz, 0.3H), 6.46 (d, J=8.9 Hz, 0.7H), 4.63 (br s, 0.7H), 4.50 (d, J=4.8 Hz, 0.3H), 3.88-3.68 (m, 4.3H), 3.58 (d, J=2.9 Hz, 0.7H), 2.05-1.87 (m, 1H), 1.78-1.20 (m, 5H).

Example 219: (±)-(2-((5-bromopyridin-2-yl)amino)-7-azabicyclo[2.2.1]heptan-7-yl)(3-ethoxy-6-methyl-pyridin-2-yl)methanone

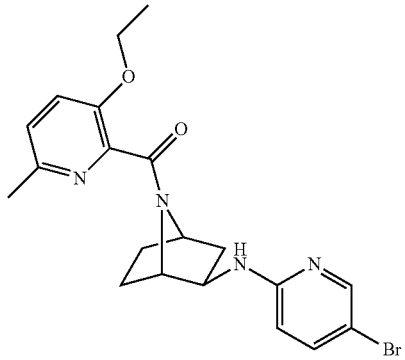 [SMILES: CCOc1ccc(C)nc1C(=O)N1C2CCC1C(Nc1ccc(Br)cn1)C2]

Prepared analogous to Example 217 substituting intermediate A-9 with intermediate A-8. MS (ESI) mass calcd. for $C_{20}H_{23}BrN_4O_2$, 430.1; m/z found 431.1 [M+H]$^+$. MP=134.5° C. $^1$H NMR (DMSO-D$_6$): 8.10 (d, J=2.4 Hz, 0.3H), 7.88 (d, J=2.4 Hz, 0.7H), 7.55 (dd, J=8.9, 2.5 Hz, 0.3H), 7.50-7.41 (m, 1H), 7.30 (d, J=8.6 Hz, 0.7H), 7.24 (d, J=8.6 Hz, 0.3H), 7.08 (d, J=8.6 Hz, 0.7H), 6.76 (d, J=5.7 Hz, 0.7H), 6.63 (d, J=5.3 Hz, 0.3H), 6.57 (d, J=8.9 Hz, 0.3H), 6.43 (d, J=8.9 Hz, 0.7H), 4.62 (br s, 0.7H), 4.51 (d, J=2.8 Hz, 0.3H), 4.13-3.88 (m, 2H), 3.83-3.73 (m, 0.3H), 3.72-3.61 (m, 1H), 3.59 (d, J=3.5 Hz, 0.7H), 2.39 (s, 0.9H), 2.21 (s, 2.1H), 2.02-1.85 (m, 1H), 1.75-1.33 (m, 5H), 1.25 (td, J=6.9, 3.6 Hz, 3H).

Example 220: (±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone

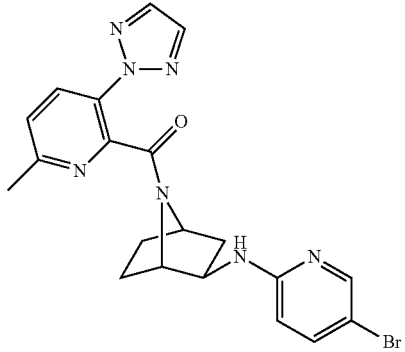 [SMILES: Cc1ccc(-n2nccn2)c(C(=O)N2C3CCC2C(Nc2ccc(Br)cn2)C3)n1]

Prepared analogous to Example 217 substituting intermediate A-9 with intermediate A-21. MS (ESI) mass calcd. for $C_{20}H_{20}BrN_7O$, 453.1; m/z found 454.1 [M+H]$^+$. MP=214.9° C. $^1$H NMR (DMSO-D$_6$): 8.18 (d, J=8.4 Hz, 0.3H), 8.14-8.09 (m, 2.3H), 8.05 (d, J=8.4 Hz, 0.7H), 7.93 (d, J=2.4 Hz, 0.7H), 7.62-7.53 (m, 0.6H), 7.50 (dd, J=8.9, 2.5 Hz, 0.7H), 7.40 (d, J=8.4 Hz, 0.7H), 6.76 (d, J=6.3 Hz, 0.7H), 6.61 (d, J=8.9 Hz, 0.3H), 6.52 (d, J=5.7 Hz, 0.3H), 6.45 (d, J=8.9 Hz, 0.7H), 4.58 (t, J=4.5 Hz, 0.7H), 4.47 (d, J=4.8 Hz, 0.3H), 3.91 (t, J=4.3 Hz, 0.3H), 3.88-3.68 (m, 1.7H), 2.60 (s, 0.9H), 2.31 (s, 2.1H), 2.03-1.90 (m, 1H), 1.81-1.29 (m, 5H).

Example 221: (±)-(2-(2H-1,2,3-triazol-2-yl)phenyl)(2-((5-(trifluoromethyl)pyrimidin-2-yl)amino)-7-azabicyclo[2.2.1]heptan-7-yl)methanone

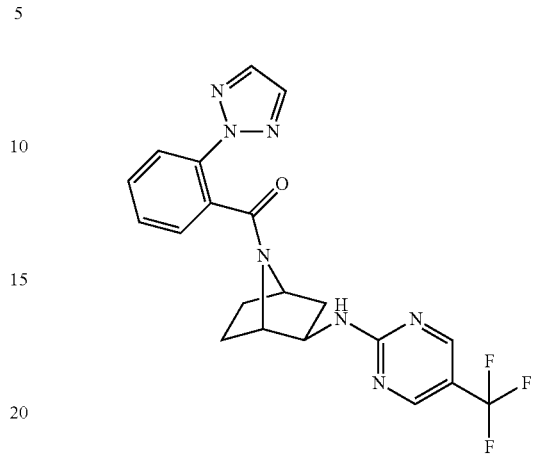

Prepared analogous to Example 220 substituting intermediate A-21 with intermediate A-1. MP=167.1° C. $^1$H NMR (DMSO-D$_6$): 8.75 (s, 0.4H), 8.70 (s, 0.4H), 8.66 (s, 0.6H), 8.53 (s, 0.6H), 8.12-8.03 (m, 2.6H), 7.86 (d, J=7.3 Hz, 0.4H), 7.80 (d, J=7.2 Hz, 0.4H), 7.72-7.54 (m, 1.6H), 7.48-7.34 (m, 1.4H), 7.16 (t, J=7.4 Hz, 0.6H), 4.56 (br s, 0.6H), 4.41 (d, J=4.3 Hz, 0.4H), 4.08 (dd, J=11.1, 6.8 Hz, 0.4H), 3.90-3.75 (m, 1H), 3.61 (d, J=4.3 Hz, 0.6H), 2.01-1.27 (m, 6H).

Example 222: (±)-(3-fluoro-2-methoxyphenyl)(2-((5-(trifluoromethyl)pyrimidin-2-yl)amino)-7-azabicyclo[2.2.1]heptan-7-yl)methanone

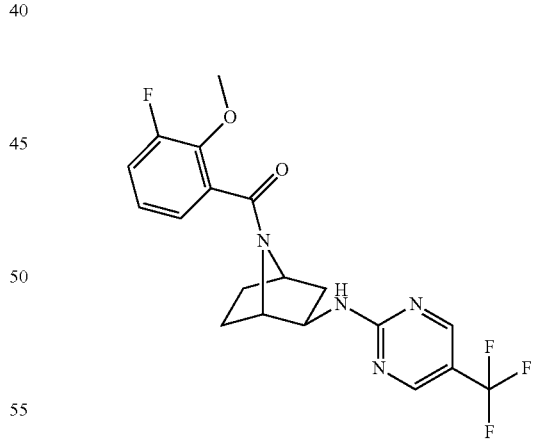

Prepared analogous to Example 221 substituting intermediate A-1 with 3-fluoro-2-methoxybenzoic acid. $^1$H NMR (DMSO-D$_6$): 8.72 (br d, J=22.6 Hz, 0.8H), 8.58 (br d, J=24.1 Hz, 1.2H), 8.12 (br d, J=5.6 Hz, 0.4H), 7.99 (br d, J=5.0 Hz, 0.6H), 7.45-7.23 (m, 0.8H), 7.26-7.06 (m, 1.2H), 6.97 (d, J=7.5 Hz, 0.6H), 6.90-6.72 (m, 0.6H), 4.65 (br s, 0.6H), 4.53 (d, J=4.8 Hz, 0.4H), 3.97 (dd, J=11.4, 6.0 Hz, 0.4H), 3.84 (s, 1.2H), 3.93-3.71 (m, 1H), 3.78 (s, 1.8H), 3.69 (br d, J=2.9 Hz, 0.6H), 2.06-1.35 (m, 6H)

Example 223: (±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone

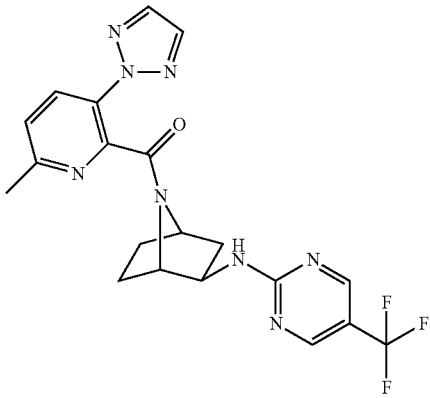

Prepared analogous to Example 221 substituting intermediate A-1 with intermediate A-21. $^1$H NMR (DMSO-D$_6$): 8.74 (br d, J=12.1 Hz, 0.4H), 8.63 (br d, J=13.2 Hz, 1.2H), 8.26-8.01 (m, 3.4H), 7.61 (dd, J=21.8, 7.4 Hz, 0.4H), 7.43 (d, J=8.4 Hz, 0.6H), 4.61 (br s, 0.6H), 4.55 (d, J=5.0 Hz, 0.4H), 4.11-4.01 (m, 0.4H), 4.02-3.93 (m, 1H), 3.88 (dd, J=10.1, 6.1 Hz, 0.6H), 3.22-3.06 (m, 1H), 2.60 (s, 1H), 2.30 (s, 2H), 2.06-1.34 (n, 6H).

Example 224: (±)-(3-ethoxy-6-methylpyridin-2-yl)(2-((5-(trifluoromethyl)pyrimidin-2-yl)amino)-7-azabicyclo[2.2.1]heptan-7-yl)methanone

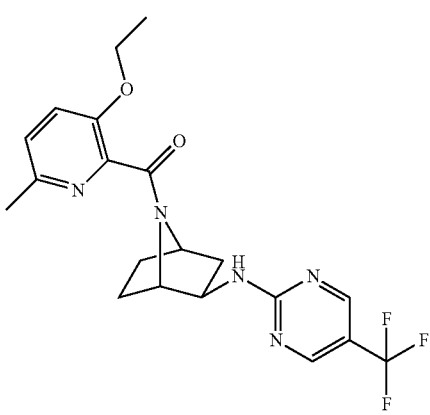

Prepared analogous to Example 221 substituting intermediate A-1 with intermediate A-8. $^1$H NMR (DMSO-D$_6$): 8.79 (br d, J=22.9 Hz, 0.6H), 8.65 (br d, J=17.4 Hz, 1.4H), 8.21 (d, J=5.3 Hz, 0.7H), 7.92 (d, J=5.2 Hz, 0.3H), 7.52 (d, J=8.6 Hz, 0.3H), 7.42 (d, J=8.6 Hz, 0.7H), 7.32 (d, J=8.6 Hz, 0.3H), 7.18 (d, J=8.6 Hz, 0.7H), 4.71 (br s, 0.7H), 4.64 (br d, J=4.7 Hz, 0.3H), 4.23-3.93 (m, 2.5H), 3.93-3.78 (m, 1.4H), 3.78-3.55 (m, 1.7H), 3.31-3.07 (m, 1.4H), 2.47 (s, 1H), 2.31 (s, 2H), 2.06-1.40 (m, 6H).

Example 225: (±)-(6-methyl-3-(pyrimidin-2-yl)pyridin-2-yl)(2-((5-(trifluoromethyl)pyrimidin-2-yl)amino)-7-azabicyclo[2.2.1]heptan-7-yl)methanone

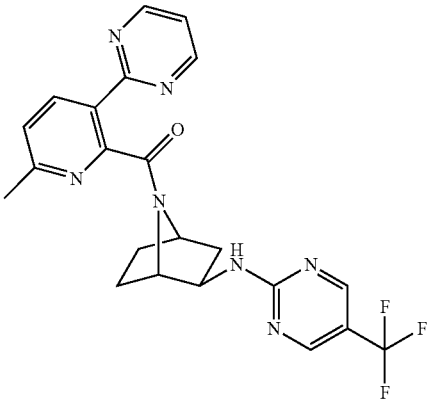 [SMILES: Cc1ccc(-c2ncccn2)c(C(=O)N2C3CCC2C(Nc2ncc(C(F)(F)F)cn2)C3)n1]

Prepared analogous to Example 221 substituting intermediate A-1 with intermediate A-9. MP=203° C. MS (ESI) mass calcd. for C$_{22}$H$_{20}$F$_3$N$_7$O, 455.2; m/z found 427.5 [M+H]$^+$. $^1$H NMR (DMSO-D$_6$): 8.94 (d, J=4.9 Hz, 0.4H), 8.89 (d, J=4.9 Hz, 1.6H), 8.77 (s, 0.2H), 8.71 (s, 0.2H), 8.61 (s, 1.4H), 8.36 (d, J=8.1 Hz, 0.2H), 8.24 (d, J=7.9 Hz, 1.8H), 7.72 (d, J=6.0 Hz, 0.2H), 7.54-7.44 (m, 1.2H), 7.38 (d, J=8.1 Hz, 0.8H), 4.64 (br s, 0.8H), 4.58 (d, J=4.6 Hz, 0.2H), 4.06-3.90 (m, 2H), 2.60 (s, 0.6H), 2.35 (s, 2.4H), 2.11-1.73 (m, 4H), 1.62-1.35 (m, 2H).

Example 226: (±)-(3-fluoro-2-methoxyphenyl)(2-((5-(trifluoromethyl)pyrimidin-2-yl)amino)-7-azabicyclo[2.2.1]heptan-7-yl)methanone

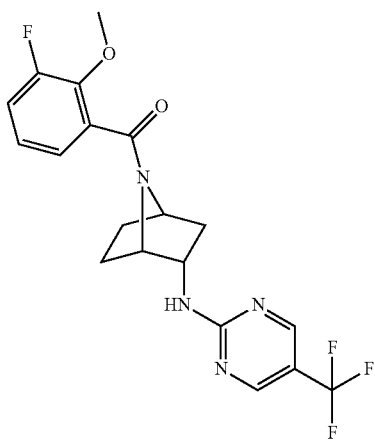 [SMILES: COc1c(F)cccc1C(=O)N1C2CCC1C(Nc1ncc(C(F)(F)F)cn1)C2]

Prepare analogous to Example 222 substituting intermediate B-6 with intermediate B-7. MS (ESI) mass calcd. for C$_{19}$H$_{18}$F$_4$N$_4$O$_2$, 410.2; m/z found 411.3 [M+H]$^+$. $^1$H NMR (DMSO-D$_6$): 8.75 (s, 0.5H), 8.68 (s, 0.5H), 8.61 (s, 0.5H), 8.57 (s, 0.5H), 8.52 (d, J=6.3 Hz, 0.5H), 8.44 (d, J=6.3 Hz, 0.5H), 7.44-7.29 (m, 1H), 7.23-7.08 (m, 2H), 4.82 (t, J=3.9 Hz, 0.5H), 4.58 (t, J=4.5 Hz, 0.5H), 4.34-4.12 (m, 1H), 3.94-3.81 (m, 3.5H), 3.68 (t, J=4.2 Hz, 0.5H), 2.31-2.11 (m, 1H), 1.93-1.40 (m, 5H).

Example 227: (±)-(3-ethoxy-6-methylpyridin-2-yl)(2-((5-(trifluoromethyl)pyrimidin-2-yl)amino)-7-azabicyclo[2.2.1]heptan-7-yl)methanone

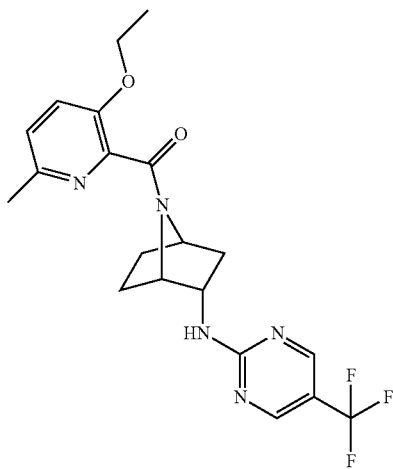 [SMILES: CCOc1ccc(C)nc1C(=O)N1C2CCC1C(Nc1ncc(C(F)(F)F)cn1)C2]

Prepare analogous to Example 224 substituting intermediate B-6 with intermediate B-7. MP=79.7° C. MS (ESI) mass calcd. for $C_{20}H_{22}F_3N_5O_2$, 421.2; m/z found 422.4 [M+H]$^+$. $^1$H NMR (DMSO-D$_6$): 8.76 (s, 0.5H), 8.68 (s, 0.5H), 8.61 (s, 0.5H), 8.56 (s, 0.5H), 8.52 (d, J=6.4 Hz, 0.5H), 8.44 (d, J=6.6 Hz, 0.5H), 7.48 (d, J=3.2 Hz, 0.5H), 7.45 (d, J=3.2 Hz, 0.5H), 7.28 (d, J=3.3 Hz, 0.5H), 7.25 (d, J=3.3 Hz, 0.5H), 4.83 (t, J=4.2 Hz, 0.5H), 4.59 (t, J=4.3 Hz, 0.5H), 4.40-4.29 (m, 0.5H), 4.28-4.19 (m, 0.5H), 4.16-4.01 (m, 2H), 3.79 (t, J=4.4 Hz, 0.5H), 3.61 (t, J=4.6 Hz, 0.5H), 2.41 (s, 1.5H), 2.40 (s, 1.5H), 2.30-2.09 (m, 1H), 1.93-1.41 (m, 5H), 1.34-1.23 (m, 3H).

Example 228: (±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone

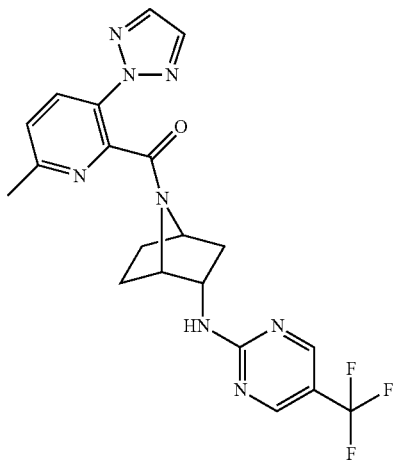 [SMILES: Cc1ccc(-n2nccn2)c(C(=O)N2C3CCC2C(Nc2ncc(C(F)(F)F)cn2)C3)n1]

Prepare analogous to Example 223 substituting intermediate B-6 with intermediate B-7. MS (ESI) mass calcd. for $C_{20}H_{19}F_3N_8O$, 444.2; m/z found 445.4 [M+H]$^+$. MP=89.1° C. $^1$H NMR (DMSO-D$_6$): 8.77 (s, 0.6H), 8.68 (s, 0.6H), 8.61 (s, 0.4H), 8.55 (s, 0.4H), 8.51 (d, J=6.3 Hz, 0.6H), 8.44 (d, J=6.3 Hz, 0.4H), 8.24-8.16 (m, 1H), 8.13 (s, 1H), 8.12 (s, 1H), 7.63-7.52 (m, 1H), 4.81 (t, J=4.2 Hz, 0.6H), 4.55 (t, J=4.2 Hz, 0.4H), 4.40-4.21 (m, 1H), 4.06 (t, J=4.4 Hz, 0.4H), 3.79 (t, J=4.4 Hz, 0.6H), 2.61 (s, 1.2H), 2.58 (s, 1.8H), 2.34-2.20 (m, 0.6H), 2.19-2.03 (m, 0.6H), 1.94-1.50 (m, 4.2H), 1.44 (dd, J=12.3, 4.6 Hz, 0.6H).

Example 229: (±)-(3-ethoxy-6-methylpyridin-2-yl)(2-(quinoxalin-2-ylamino)-7-azabicyclo[2.2.1]heptan-7-yl)methanone

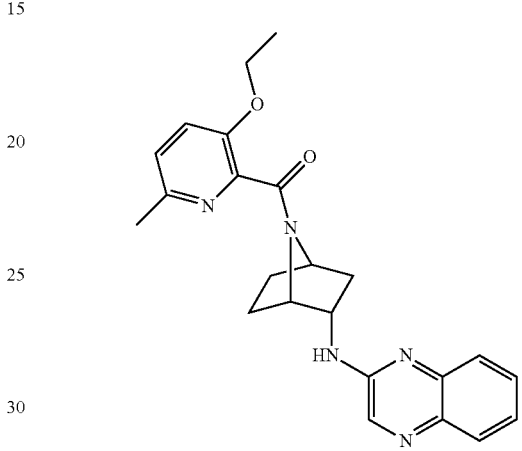

Prepare analogous to Example 207 substituting intermediate B-6 with intermediate B-7. MS (ESI) mass calcd. for $C_{23}H_{25}N_5O_2$, 403.2; m/z found 404.5 [M+H]$^+$. MP=115.1° C. $^1$H NMR (DMSO-D$_6$): 8.37 (s, 0.5H), 8.30 (s, 0.5H), 7.97 (t, J=5.4 Hz, 1H), 7.80 (d, J=7.4 Hz, 0.5H), 7.75 (d, J=7.1 Hz, 0.5H), 7.69-7.44 (m, 2.5H), 7.43-7.23 (m, 2.5H), 4.99 (t, J=4.4 Hz, 0.5H), 4.63 (t, J=4.6 Hz, 0.5H), 4.48-4.27 (m, 1H), 4.26-4.13 (m, 2H), 3.96 (t, J=4.4 Hz, 0.5H), 3.64 (t, J=4.6 Hz, 0.5H), 2.44 (s, 1.5H), 2.41 (s, 1.5H), 2.39-2.26 (m, 1H), 1.98-1.37 (m, 5H), 1.36-1.28 (m, 3H).

Example 230: (±)-(6-methyl-3-(2H-1,2,3-triazol-2-yl)pyridin-2-yl)(2-(quinoxalin-2-ylamino)-7-azabicyclo[2.2.1]heptan-7-yl)methanone

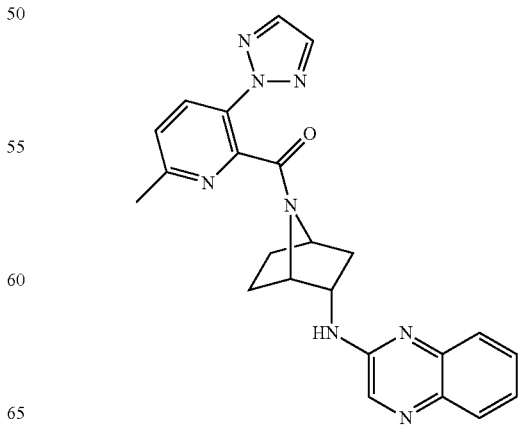

Prepare analogous to Example 205 substituting intermediate B-6 with intermediate B-7. MS (ESI) mass calcd. for $C_{23}H_{22}N8O$, 426.2; m/z found 427.5 [M+H]$^+$. MP=152.3° C. $^1$H NMR (DMSO-D$_6$): 8.37 (s, 0.5H), 8.28-8.20 (m, 2H), 8.16-8.13 (m, 2H), 7.95 (dd, J=5.6, 3.6 Hz, 1H), 7.79 (d, J=8.1 Hz, 0.5H), 7.74 (d, J=8.1 Hz, 0.5H), 7.70-7.48 (m, 2.5H), 7.41-7.23 (m, 1.5H), 4.98 (t, J=4.2 Hz, 0.5H), 4.60 (t, J=4.6 Hz, 0.5H), 4.36-4.24 (m, 1H), 4.19 (t, J=4.5 Hz, 0.5H), 3.81 (t, J=4.6 Hz, 0.5H), 2.67 (s, 1.5H), 2.60 (s, 1.5H), 2.43-2.17 (m, 1H), 1.97-1.25 (m, 5H).

Example 231: (±)-(3-fluoro-2-methoxyphenyl)(2-(quinoxalin-2-ylamino)-7-azabicyclo[2.2.1]heptan-7-yl)methanone

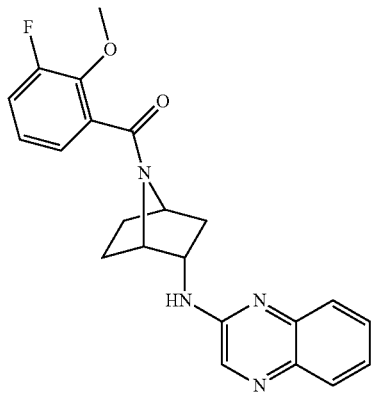 [SMILES: COc1c(F)cccc1C(=O)N1C2CCC1C(Nc1cnc3ccccc3n1)C2]

Prepare analogous to Example 206 substituting intermediate B-6 with intermediate B-7. $^1$H NMR (DMSO-D$_6$): 8.36 (s, 0.5H), 8.29 (s, 0.5H), 8.08-7.95 (m, 1H), 7.85-7.69 (m, 1H), 7.69-7.49 (m, 1.5H), 7.49-7.27 (m, 2H), 7.27-7.12 (m, 2.5H), 5.00 (t, J=4.2 Hz, 0.5H), 4.62 (t, J=4.2 Hz, 0.5H), 4.43-4.17 (m, 1H), 4.11 (t, J=4.3 Hz, 0.5H), 3.95 (s, 1.5H), 3.88 (s, 1.5H), 3.72 (t, J=4.5 Hz, 0.5H), 2.45-2.25 (m, 1H), 1.99-1.46 (m, 4H), 1.46-1.28 (m, 1H).

Example 232: (±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone

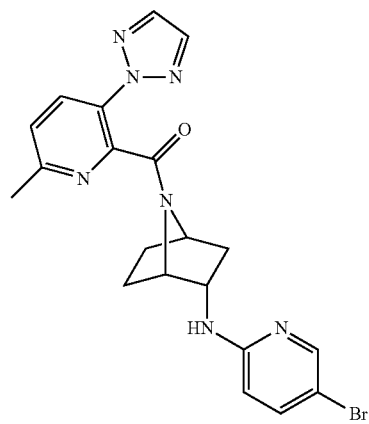 [SMILES: Cc1ccc(-n2nccn2)c(C(=O)N2C3CCC2C(Nc2ccc(Br)cn2)C3)n1]

Prepare analogous to Example 220 substituting intermediate B-6 with intermediate B-7. MP=196.0° C. $^1$H NMR (DMSO-D$_6$): 8.25-8.16 (m, 1H), 8.16-8.10 (m, 2.6H), 7.90 (d, J=2.4 Hz, 0.4H), 7.63-7.53 (m, 1.6H), 7.50 (dd, J=8.9, 2.5 Hz, 0.4H), 7.19 (d, J=6.0 Hz, 0.6H), 7.12 (d, J=6.1 Hz, 0.4H), 6.54 (d, J=8.9 Hz, 0.6H), 6.44 (d, J=8.9 Hz, 0.4H), 4.81 (t, J=4.2 Hz, 0.6H), 4.54 (t, J=4.2 Hz, 0.4H), 4.23-4.07 (m, 1H), 4.04 (t, J=4.5 Hz, 0.4H), 3.75 (t, J=4.5 Hz, 0.6H), 2.61 (s, 1.2H), 2.58 (s, 1.8H), 2.36-2.05 (m, 1H), 1.92-1.41 (m, 4H), 1.30 (dd, J=12.4, 4.4 Hz, 0.4H), 1.18 (dd, J=12.2, 4.6 Hz, 0.6H).

Example 233: (±)-(2-((5-bromopyridin-2-yl)amino)-7-azabicyclo[2.2.1]heptan-7-yl)(3-ethoxy-6-methyl-pyridin-2-yl)methanone

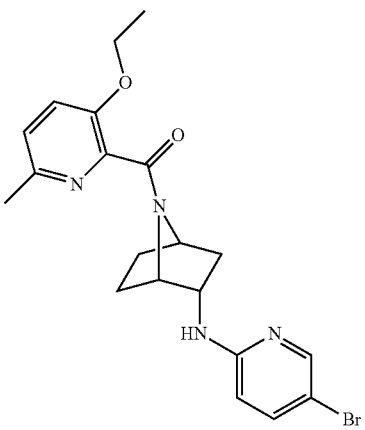 [SMILES: CCOc1ccc(C)nc1C(=O)N1C2CCC1C(Nc1ccc(Br)cn1)C2]

Prepare analogous to Example 219 substituting intermediate B-6 with intermediate B-7. MP=176.1° C. H $^1$H NMR (DMSO-D$_6$): 8.11 (d, J=2.4 Hz, 0.5H), 7.91 (d, J=2.4 Hz, 0.5H), 7.61-7.43 (m, 2H), 7.33-7.20 (m, 1.5H), 7.15 (d, J=6.1 Hz, 0.5H), 6.55 (d, J=8.9 Hz, 0.5H), 6.46 (d, J=8.9 Hz, 0.5H), 4.83 (t, J=4.3 Hz, 0.5H), 4.57 (t, J=4.6 Hz, 0.5H), 4.20 (d, J=5.5 Hz, 0.5H), 4.09 (dq, J=10.2, 6.9 Hz, 2.5H), 3.79 (t, J=4.3 Hz, 0.5H), 3.58 (t, J=4.6 Hz, 0.5H), 2.41 (s, 1.5H), 2.40 (s, 1.5H), 2.32-2.14 (m, 1H), 1.93-1.45 (m, 4H), 1.36-1.17 (m, 4H).

Example 234: (±)-(2-((5-bromopyridin-2-yl)amino)-7-azabicyclo[2.2.1]heptan-7-yl)(3-fluoro-2-methoxyphenyl)methanone

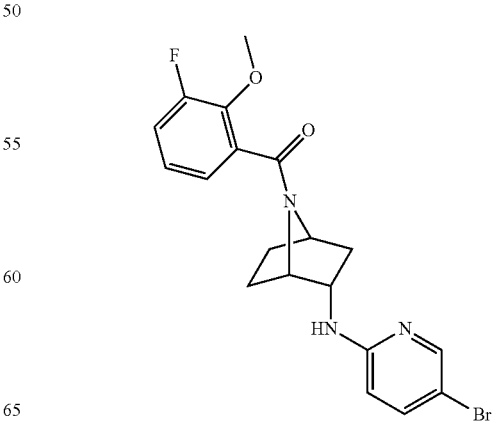

Prepare analogous to Example 217 substituting intermediate B-6 with intermediate B-7. MP=144.5° C. ¹H NMR (DMSO-D₆): 8.11 (d, J=2.4 Hz, 0.6H), 7.91 (d, J=2.4 Hz, 0.4H), 7.56 (dd, J=8.9, 2.5 Hz, 0.6H), 7.50 (dd, J=8.9, 2.5 Hz, 0.4H), 7.43-7.30 (m, 1H), 7.27-7.05 (m, 3H), 6.54 (d, J=8.9 Hz, 0.6H), 6.46 (d, J=8.9 Hz, 0.4H), 4.83 (t, J=4.3 Hz, 0.6H), 4.57 (t, J=4.7 Hz, 0.4H), 4.21-3.99 (m, 1H), 3.95-3.81 (m, 3.4H), 3.66 (t, J=4.7 Hz, 0.6H), 2.36-2.14 (m, 1H), 1.94-1.43 (m, 4H), 1.36-1.14 (m, 1H).

Example 235: (±)-((2-(2H-1,2,3-triazol-2-yl)phenyl)(2-((4-(trifluoromethyl)pyridin-2-yl)amino)-7-azabicyclo[2.2.1]heptan-7-yl)methanone

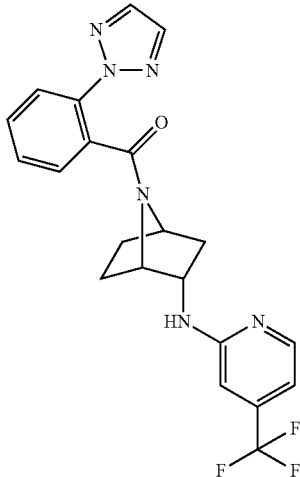 [SMILES: O=C(c1ccccc1-n1nccn1)N1C2CCC1C(Nc1cc(C(F)(F)F)ccn1)C2]

Prepare analogous to Example 210 substituting intermediate B-6 with intermediate B-7. MS (ESI) mass calcd. for C₂₁H₁₉F₃N₆O, 428.2; m/z found 429 [M+H]⁺. MP=274.2° C. ¹H NMR (DMSO-D₆): 8.27 (d, J=5.2 Hz, 0.5H), 8.13-8.01 (m, 2.5H), 7.89-7.80 (m, 1H), 7.73-7.61 (m, 1H), 7.61-7.51 (m, 2H), 7.44 (d, J=6.1 Hz, 0.5H), 7.38 (d, J=5.9 Hz, 0.5H), 6.83-6.75 (m, 1H), 6.73-6.63 (m, 1H), 4.78 (t, J=3.9 Hz, 0.5H), 4.50 (t, J=4.6 Hz, 0.5H), 4.27-4.04 (m, 1H), 3.96 (t, J=4.1 Hz, 0.5H), 3.64 (t, J=4.1 Hz, 0.5H), 2.40-2.21 (m, 0.5H), 2.17-1.99 (m, 0.5H), 1.88-1.32 (m, 4H), 1.27 (dd, J=12.3, 4.3 Hz, 0.5H), 1.12 (dd, J=12.2, 4.5 Hz, 0.5H).

Example 236: (±)-(2-((5-fluoropyridin-2-yl)amino)-7-azabicyclo[2.2.1]heptan-7-yl)(6-methyl-3-(2H-1,2,3-triazol-2-yl)pyridin-2-yl)methanone

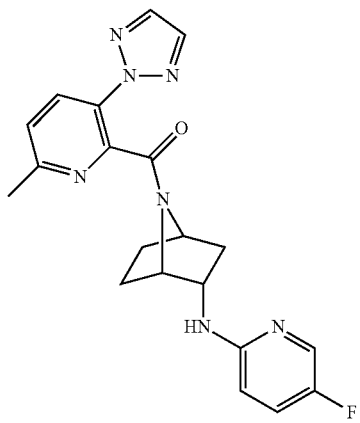 [SMILES: Cc1ccc(-n2nccn2)c(C(=O)N2C3CCC2C(Nc2ccc(F)cn2)C3)n1]

Prepared analogous to Example 209 substituting 2-chloro-6-(trifluoromethyl)pyridine with 5-fluoro-2-iodopyridine and intermediate A-1 with A-21. MP=100.1° C. MS (ESI) mass calcd. for C₂₀H₂₀FN₇O, 393.2; m/z found 394.2 [M+H]⁺. ¹H NMR (DMSO-D₆): 8.24-8.15 (m, 1H), 8.12 (s, 1.2H) 8.11 (s, 0.8H), 8.00 (d, J=2.9 Hz, 0.6H), 7.80 (d, J=2.8 Hz, 0.4H), 7.63-7.51 (m, 1H), 7.43-7.26 (m, 1H), 6.94 (d, J=5.9 Hz, 0.6H), 6.87 (d, J=6.0 Hz, 0.4H), 6.55 (dd, J=9.1, 3.6 Hz, 0.6H), 6.45 (dd, J=9.1, 3.7 Hz, 0.4H), 4.81 (t, J=4.2 Hz, 0.6H), 4.52 (t, J=4.6 Hz, 0.4H), 4.19-3.99 (m, 1.4H), 3.73 (t, J=4.6 Hz, 0.6H), 2.60 (s, 1.2H), 2.58 (s, 1.8H), 2.35-2.20 (m, 0.6H), 2.19-2.05 (m, 0.4H), 1.96-1.38 (m, 4H), 1.27 (dd, J=12.5, 4.2 Hz, 0.6H), 1.15 (dd, J=12.2, 4.8 Hz, 0.4H).

Example 237: (±)-(3-fluoro-2-methoxyphenyl)(2-((5-fluoropyridin-2-yl)amino)-7-azabicyclo[2.2.1]heptan-7-yl)methanone

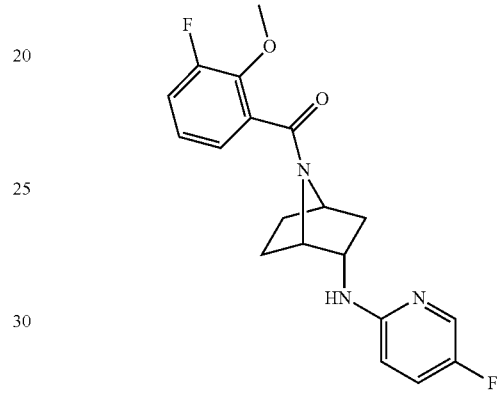

Prepared analogous to Example 209 substituting 2-chloro-6-(trifluoromethyl)pyridine with 5-fluoro-2-iodopyridine and intermediate A-1 with 3-fluoro-2-methoxybenzoic acid. MS (ESI) mass calcd. for C₁₉H₁₉F₂N₃O₂, 359.1; m/z found 360.2 [M+H]⁺. MP=134.7° C. ¹H NMR (DMSO-D₆): 8.00 (d, J=2.9 Hz, 0.5H), 7.80 (d, J=2.9 Hz, 0.5H), 7.45-7.26 (m, 2H), 7.24-7.06 (m, 2H), 6.96 (d, J=6.0 Hz, 0.5H), 6.89 (d, J=5.8 Hz, 0.5H), 6.56 (dd, J=9.1, 3.6 Hz, 0.5H), 6.48 (dd, J=9.2, 3.6 Hz, 0.5H), 4.83 (t, J=4.3 Hz, 0.5H), 4.56 (t, J=4.7 Hz, 0.5H), 4.18-3.98 (m, 1H), 3.95-3.81 (m, 3.5H), 3.64 (t, J=4.6 Hz, 0.5H), 2.35-2.14 (m, 1H), 1.96-1.43 (m, 4H), 1.30-1.13 (m, 1H).

Example 238: (3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

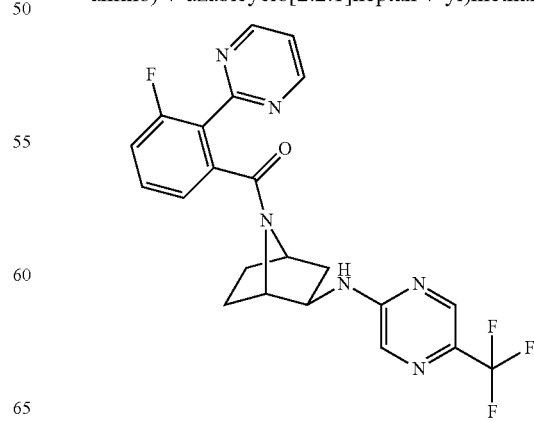

Step A: (1S,2R,4R)—N-(5-(trifluoromethyl)pyrazin-2-yl)-7-azabicyclo[2.2.1]heptan-2-amine hydrochloride. To the intermediate of Example 181 Step A (100 mg, 0.3 mmol) in DCM (3 mL) was added 4M HCl in dioxane (0.8 mL). The reaction was allowed to proceed overnight then concentrated neutralized with 5% $Na_2CO_3$ (aq) and extracted with DCM (2×). The combined organics were dried ($Na_2SO_4$) to give the title compound of step A that was used without further purification.

Step B: (3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone. To the title compound of step A (1.44 g, 5.6 mmol) in DCM (56 mL) was added DIPEA (1.25 mL, 7.3 mmol) and intermediate A-2 (1.43 g, 6.1 mmol). Then T3P (50% solution in DMF, 10 mL, 17 mmol) was added dropwise and the reaction heated at 45° C. for 16 h. After allowing to cool to rt, DCM was added and the mixture washed with $H_2O$ then saturated $NaHCO_3$ (aq). The combined aq layers were extracted with DCM. The combined organic layers were dried ($Na_2SO_4$). Purification via silica gel chromatography (10-100% EtOAc in hexanes) gave the title compound (2 g, 78%). MS (ESI) mass calcd. for $C_{22}H_{18}F_4N_6O$, 458.2; m/z found 459.1 $[M+H]^+$. $^1$H NMR ($CDCl_3$) 8.91-8.73 (m, 2H), 8.35-8.22 (m, 1H), 8.19 (s, 1H), 7.66 (s, 1H), 7.44-7.13 (m, 4H), 4.79-4.68 (m, 1H), 4.46-4.35 (m, 1H), 4.12-4.03 (m, 1H), 2.22-2.00 (m, 2H), 1.99-1.84 (m, 1H), 1.79-1.45 (m, 3H).

Example 239: (2-ethoxynaphthalen-1-yl)((1S,2R,4R)-2-((5-(trifluoromethyl)pyrazin-2-yl)amino)-7-azabicyclo[2.2.1]heptan-7-yl)methanone

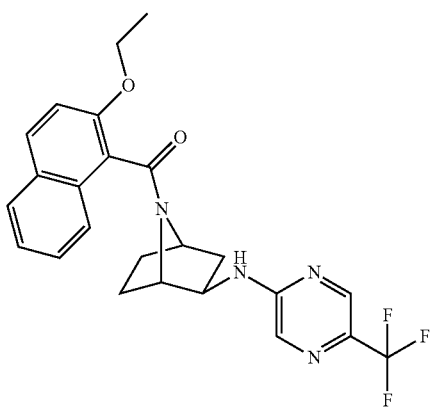

Prepared analogous to Example 181 substituting intermediate A-1 with 2-ethoxy-1-naphthoic acid. MS (ESI) mass calcd. for $C_{24}H_{23}F_3N_4O_2$, 456.2; m/z found 457.2 $[M+H]^+$. $^1$H NMR ($CDCl_3$): 8.39-8.31 (m, 0.3H), 8.18 (s, 0.5H), 8.08-7.98 (m, 0.3H), 7.96-7.67 (m, 3.6H), 7.57-7.32 (m, 2H), 7.31-7.16 (m, 1.3H), 7.10-7.04 (m, 0.2H), 6.34 (d, J=9.1 Hz, 0.5H), 5.90-5.75 (m, 0.3H), 5.17-4.95 (m, 1H), 4.70 (d, J=7.1 Hz, 0.2H), 4.49-4.07 (m, 2.7H), 3.90 (td, J=7.4, 2.9 Hz, 0.2H), 3.77-3.65 (m, 0.3H), 3.62-3.56 (m, 0.2H), 3.39 (d, J=5.1 Hz, 0.4H), 2.30-1.94 (m, 2H), 1.81-1.47 (m, 5H), 1.47-1.33 (m, 2H).

Example 240: isoquinolin-4-yl((1S,2R,4R)-2-((5-(trifluoromethyl)pyrazin-2-yl)amino)-7-azabicyclo[2.2.1]heptan-7-yl)methanone

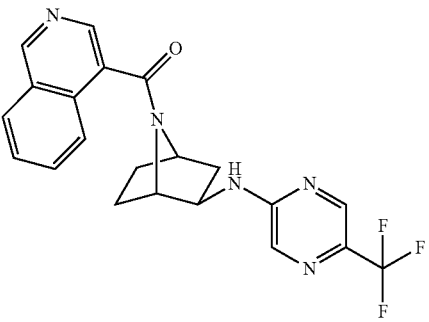 [SMILES: O=C(c1cncc2ccccc12)N1C2CCC1C(Nc1cnc(C(F)(F)F)cn1)C2]

Prepared analogous to Example 181 substituting intermediate A-1 with isoquinoline-4-carboxylic acid. MS (ESI) mass calcd. for $C_{21}H_{18}F_3N_5O$, 413.2; m/z found 414.2 $[M+H]^+$. $^1$H NMR ($CDCl_3$): 9.31 (s, 0.5H), 9.13 (s, 0.5H), 8.68-8.49 (m, 1H), 8.40-7.53 (m, 5.5H), 7.42 (s, 0.5H), 6.20 (s, 0.5H), 4.99 (s, 1.5H), 4.21 (s, 0.5H), 4.06-3.77 (m, 1.5H), 2.27-1.43 (m, 6H).

Example 241: (4-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

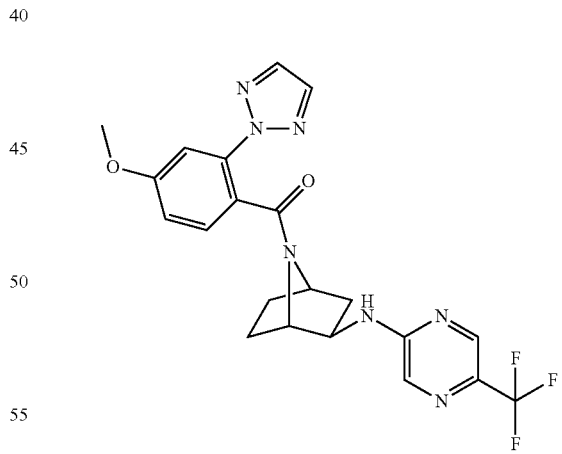

Prepared analogous to Example 181 substituting intermediate A-1 with intermediate A-5. MS (ESI) mass calcd. for $C_{21}H_{20}F_3N_7O_2$, 459.2; m/z found 460.3 $[M+H]^+$. $^1$H NMR ($CDCl_3$): 8.31 (s, 0.3H), 8.18 (s, 0.7H), 7.91 (s, 1.5H), 7.87-7.77 (m, 1H), 7.54 (s, 0.8H), 7.48-7.39 (m, 0.7H), 7.35-7.28 (m, 1.7H), 6.97 (dd, J=8.5, 2.5 Hz, 0.3H), 6.87 (d, J=8.3 Hz, 0.7H), 6.29 (s, 0.3H), 4.85-4.79 (m, 0.7H), 4.75-4.70 (m, 0.3H), 4.40-4.22 (m, 1H), 4.09-4.03 (m, 0.3H), 3.99 (s, 0.7H), 3.94-3.83 (m, 3H), 2.19-1.41 (m, 6H).

Example 242: (2-methoxy-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone Example 244: (5-(4-fluorophenyl)-2-methylthiazol-4-yl)((1S,2R,4R)-2-((5-(trifluoromethyl)pyrazin-2-yl)amino)-7-azabicyclo[2.2.1]heptan-7-yl)methanone

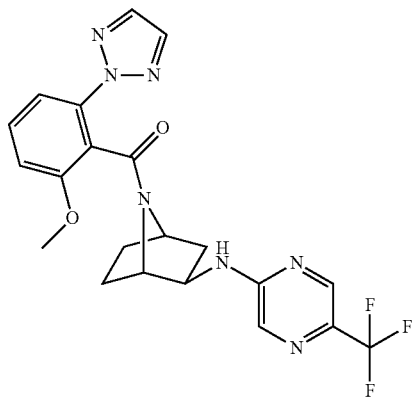 [SMILES: COc1cccc(-n2nccn2)c1C(=O)N1C2CCC1C(Nc1cnc(C(F)(F)F)cn1)C2]

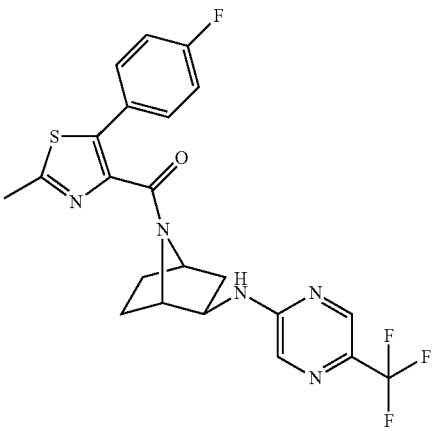

Prepared analogous to Example 181 substituting intermediate A-1 with intermediate A-13. MS (ESI) mass calcd. for $C_{21}H_{20}F_3N_7O_2$, 459.2; m/z found 460.3 [M+H]$^+$. $^1$H NMR (CDCl$_3$): 8.37-8.30 (m, 0.3H), 8.25-8.17 (m, 0.7H), 7.97-7.85 (m, 1.5H), 7.84-7.74 (m, 0.8H), 7.65-7.56 (m, 0.4H), 7.55-7.37 (m, 2.7H), 7.05-6.94 (m, 1H), 6.17-5.98 (m, 0.2H), 5.90-5.66 (m, 0.4H), 5.02-4.86 (m, 0.7H), 4.86-4.71 (m, 0.3H), 4.45-4.18 (m, 0.8H), 4.05 (s, 0.7H), 3.97-3.75 (m, 3.3H), 3.62-3.57 (m, 0.2H), 2.25-1.29 (m, 6H).

Prepared analogous to Example 181 substituting intermediate A-1 with 5-(4-fluorophenyl)-2-methylthiazole-4-carboxylic acid. MS (ESI) mass calcd. for $C_{22}H_{19}F_4N_5OS$, 477.2; m/z found 478.1 [M+H]$^+$. $^1$H NMR (CDCl$_3$): 8.32-8.20 (m, 1H), 7.95-7.84 (m, 1H), 7.56-7.40 (m, 2H), 7.15-7.04 (m, 2H), 6.97-6.77 (m, 0.8H), 6.01-5.88 (m, 0.2H), 4.85 (t, J=4.5 Hz, 1H), 4.21-3.90 (m, 2H), 2.80-2.56 (m, 3H), 2.19-1.95 (m, 1.7H), 1.93-1.31 (m, 4.3H).

Example 243: (5-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone Example 245: (3-methyl-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

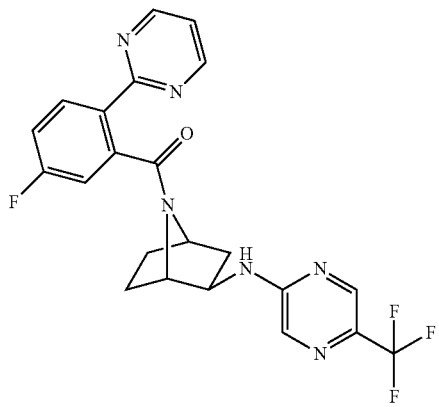 [SMILES: O=C(c1cc(F)ccc1-c1ncccn1)N1C2CCC1C(Nc1cnc(C(F)(F)F)cn1)C2]

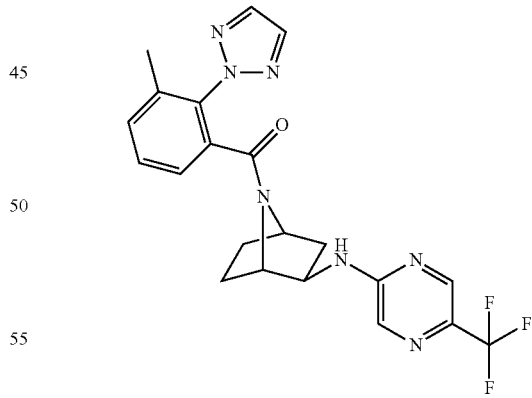

Prepared analogous to Example 181 substituting intermediate A-1 with intermediate A-7. MS (ESI) mass calcd. for $C_{22}H_{18}F_4N_6O$, 458.2; m/z found 459.3 [M+H]$^+$. $^1$H NMR (CDCl$_3$): 8.88-8.79 (m, 1.7H), 8.77-8.69 (m, 0.3H), 8.36-8.14 (m, 1.8H), 8.01 (dd, J=8.6, 5.4 Hz, 1H), 7.81 (s, 0.2H), 7.42-7.30-7.02 (m, 3.8H), 6.26 (d, J=7.8 Hz, 0.2H), 4.90-4.81 (m, 0.8H), 4.74 (d, J=5.2 Hz, 0.2H), 4.42 (s, 0.8H), 4.27 (s, 0.2H), 4.12-3.96 (m, 1H), 2.29-1.39 (m, 6H).

Prepared analogous to Example 181 substituting intermediate A-1 with intermediate A-24. MS (ESI) mass calcd. for $C_{21}H_{20}F_3N_7O$, 443.2; m/z found 444.3 [M+H]$^+$. $^1$H NMR (CDCl$_3$): 8.29-8.23 (m, 0.2H), 8.21-8.15 (m, 0.8H), 7.95-7.88 (m, 1.6H), 7.84-7.74 (m, 1.3H), 7.62-7.39 (m, 1.2H), 7.37-7.19 (m, 2.7H), 5.81 (s, 0.2H), 4.79-4.65 (m, 0.8H), 4.61-4.51 (m, 0.2H), 4.38-3.90 (m, 2H), 2.19 (s, 3H), 2.14-1.42 (m, 6H).

Example 246: (3-ethoxyisoquinolin-4-yl)((1S,2R,4R)-2-((5-(trifluoromethyl)pyrazin-2-yl)amino)-7-azabicyclo[2.2.1]heptan-7-yl)methanone

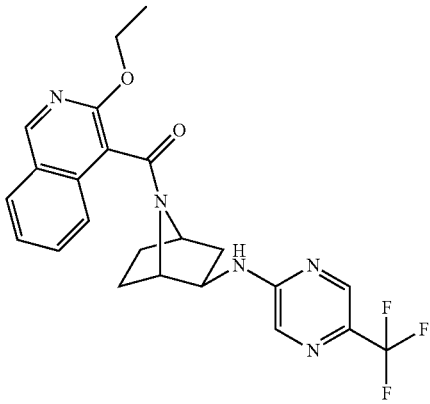 [SMILES: CCOc1ncc2ccccc2c1C(=O)N1C2CCC1C(Nc1cnc(C(F)(F)F)cn1)C2]

Prepared analogous to Example 181 substituting intermediate A-1 with intermediate A-22. MS (ESI) mass calcd. for C$_{23}$H$_{22}$F$_3$N$_5$O$_2$, 457.2; m/z found 458.3 [M+H]$^+$. $^1$H NMR (CDCl$_3$): 9.01-8.92 (m, 0.8H), 8.82 (s, 0.2H), 8.35 (s, 0.5H), 8.22 (s, 0.3H), 8.05 (s, 0.1H), 8.00-7.85 (m, 1.6H), 7.84-7.71 (m, 1H), 7.71-7.54 (m, 1.2H), 7.50-7.39 (m, 0.8H), 7.39-7.31 (m, 0.4H), 7.18 (s, 0.3H), 6.11 (s, 0.1H), 5.95 (d, J=8.8 Hz, 0.3H), 5.83 (d, J=8.0 Hz, 0.4H), 5.15-5.06 (m, 0.3H), 5.06-4.94 (m, 0.7H), 4.92-4.72 (m, 0.5H), 4.68-4.41 (m, 1.5H), 4.40-4.30 (m, 0.3H), 4.24-4.07 (m, 0.4H), 3.89-3.81 (m, 0.2H), 3.81-3.67 (m, 0.7H), 3.51 (d, J=5.1 Hz, 0.3H), 2.30-1.95 (m, 2.5H), 1.91-1.21 (m, 6.5H).

Example 247: (6-methyl-2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone

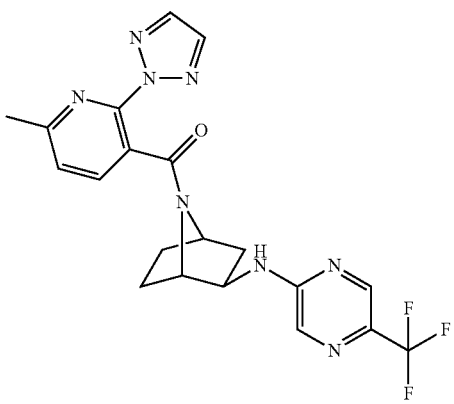

Prepared analogous to Example 181 substituting intermediate A-1 with intermediate A-3. MS (ESI) mass calcd. for C$_{20}$H$_{19}$F$_3$N$_8$O, 444.2; m/z found 445.2 [M+H]$^+$. $^1$H NMR (CDCl$_3$): 8.32 (s, 0.4H), 8.18 (s, 0.6H), 7.96 (s, 1.3H), 7.88 (d, J=4.6 Hz, 1.1H), 7.79 (d, J=7.7 Hz, 0.5H), 7.73-7.52 (m, 1.5H), 7.35-7.27 (m, 0.5H), 7.18 (s, 0.7H), 6.28 (s, 0.4H), 4.89-4.70 (m, 1H), 4.42-4.19 (m, 1H), 4.03-3.81 (m, 1H), 2.76-2.56 (m, 3H), 2.26-1.40 (m, 6H).

Example 248: (6-methyl-2-(1H-1,2,3-triazol-1-yl)pyridin-3-yl)((1S,2R,4R)-2-((5-(trifluoromethyl)pyrazin-2-yl)amino)-7-azabicyclo[2.2.1]heptan-7-yl)methanone

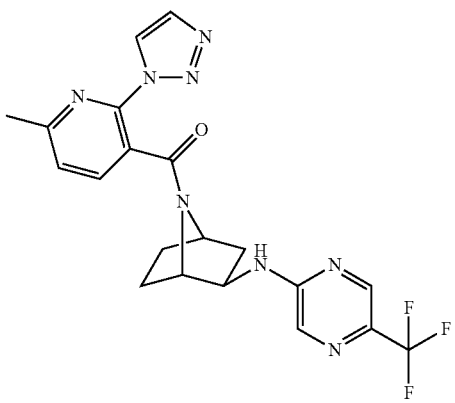

Prepared analogous to Example 181 substituting intermediate A-1 with intermediate A-4. MS (ESI) mass calcd. for C$_{20}$H$_{19}$F$_3$N$_8$O, 444.2; m/z found 445.2 [M+H]$^+$. $^1$H NMR (CDCl$_3$): 8.51-8.35 (m, 1.6H), 8.29 (s, 0.7H), 8.17 (s, 0.3H), 7.92-7.80 (m, 1H), 7.76-7.60 (m, 1.3H), 7.35-7.18 (m, 1.4H), 6.81-6.61 (m, 0.7H), 4.95-4.85 (m, 0.3H), 4.84-4.75 (m, 0.7H), 4.49-4.32 (m, 1H), 4.07 (t, J=4.4 Hz, 0.7H), 3.93 (s, 0.3H), 2.70-2.54 (m, 3H), 2.22 (dd, J=13.1, 8.0 Hz, 0.4H), 2.14-1.46 (m, 5.6H).

Example 249: (4-methoxy-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

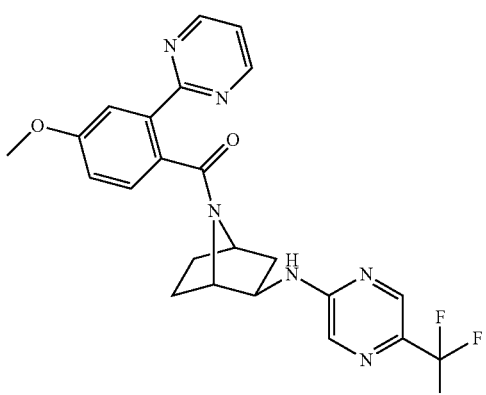

Prepared analogous to Example 181 substituting intermediate A-1 with intermediate A-15. MS (ESI) mass calcd. for C$_{23}$H$_{21}$F$_3$N$_6$O$_2$, 470.2; m/z found 471.2 [M+H]$^+$. $^1$H NMR (CDCl$_3$): 8.89-8.69 (m, 2H), 8.38-8.12 (m, 2H), 7.81-7.74 (m, 0.1H), 7.70-7.62 (m, 0.1H), 7.49-7.28 (m, 3.8H), 6.91 (dd, J=8.4, 2.6 Hz, 0.9H), 6.48-6.39 (m, 0.1H), 4.85-4.77 (m, 0.9H), 4.73-4.67 (m, 0.1H), 4.48-4.34 (m, 0.9H), 4.24 (s, 0.1H), 4.09 (d, J=5.0 Hz, 1H), 3.94-3.79 (m, 3H), 2.18 (dd, J=13.0, 8.1 Hz, 1H), 2.13-1.37 (m, 5H).

Example 250: (1H-benzo[d]imidazol-2-yl)((1S,2R,4R)-2-((5-(trifluoromethyl)pyrazin-2-yl)amino)-7-azabicyclo[2.2.1]heptan-7-yl)methanone

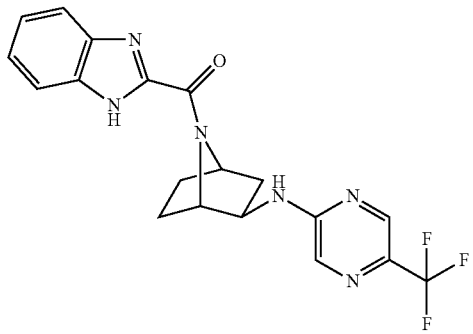

Prepared analogous to Example 181 substituting intermediate A-1 with 1H-benzo[d]imidazole-2-carboxylic acid. MS (ESI) mass calcd. for $C_{19}H_{17}F_3N_6O$, 402.1; m/z found 403.2 [M+H]$^+$. $^1$H NMR (CDCl$_3$): 8.35-7.61 (m, 3.5H), 7.40-7.13 (m, 3.5H), 6.26-5.75 (m, 1H), 5.06-4.63 (m, 1.5H), 4.27-3.95 (m, 1.5H), 2.86-2.47 (m, 1H), 2.33-1.45 (m, 5H).

Example 251: (1-methyl-1H-benzo[d]imidazol-2-yl)((1S,2R,4R)-2-((5-(trifluoromethyl)pyrazin-2-yl)amino)-7-azabicyclo[2.2.1]heptan-7-yl)methanone

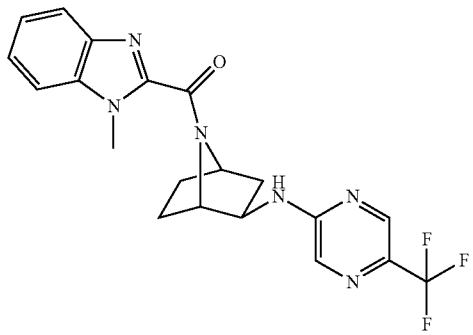 [SMILES: Cn1c(C(=O)N2C3CCC2C(Nc2cnc(C(F)(F)F)cn2)C3)nc2ccccc21]

Prepared analogous to Example 181 substituting intermediate A-1 with 1-methyl-1H-benzo[d]imidazole-2-carboxylic acid. MS (ESI) mass calcd. for $C_{20}H_{19}F_3N_6O$, 416.2; m/z found 417.2 [M+H]$^+$.

Example 252: (3-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

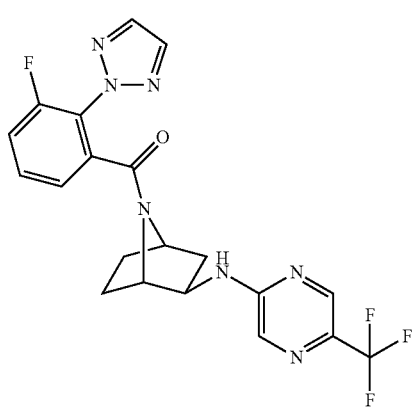 [SMILES: O=C(c1cccc(F)c1-n1nccn1)N1C2CCC1C(Nc1cnc(C(F)(F)F)cn1)C2]

Prepared analogous to Example 181 substituting intermediate A-1 with intermediate A-16. MS (ESI) mass calcd. for $C_{20}H_{17}F_4N_7O$, 447.1; m/z found 448.3 [M+H]$^+$. $^1$H NMR (CDCl$_3$): 8.30 (s, 0.3H), 8.19 (s, 0.7H), 7.96-7.75 (m, 2.8H), 7.58-7.49 (m, 0.3H), 7.45-7.11 (m, 3.7H), 5.83 (s, 0.2H), 4.80-4.58 (m, 1H), 4.38-4.25 (m, 0.8H), 4.24-4.13 (m, 0.2H), 4.13-4.04 (m, 0.2H), 3.97 (d, J=4.9 Hz, 0.8H), 2.22-2.07 (m, 1H), 2.07-1.40 (m, 5H).

Example 253: (4-(difluoromethoxy)-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

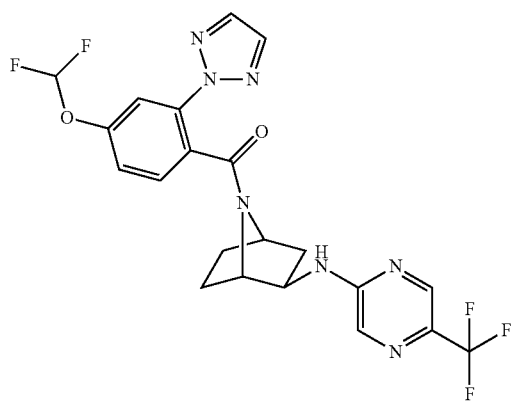 [SMILES: O=C(c1ccc(OC(F)F)cc1-n1nccn1)N1C2CCC1C(Nc1cnc(C(F)(F)F)cn1)C2]

Prepared analogous to Example 181 substituting intermediate A-1 with intermediate A-23. MS (ESI) mass calcd. for $C_{21}H_{18}F_5N_7O_2$, 495.1; m/z found 496.3 [M+H]$^+$. $^1$H NMR (CDCl$_3$): 8.32 (s, 0.3H), 8.19 (s, 0.7H), 7.98-7.81 (m, 2.4H), 7.77 (d, J=2.3 Hz, 0.4H), 7.61 (d, J=2.4 Hz, 0.7H), 7.58-7.45 (m, 1H), 7.39 (d, J=8.4 Hz, 0.7H), 7.21 (dd, J=8.4, 2.4 Hz, 0.5H), 7.18-7.00 (m, 0.9H), 6.59 (td, J=72.6, 31.4 Hz, 1H), 6.33-6.16 (m, 0.4H), 4.92-4.70 (m, 1H), 4.43-4.19 (m, 1H), 4.09-3.83 (m, 1H), 2.30-1.44 (m, 6H).

Example 254: (3-fluoro-2-(3-methyl-1,2,4-oxadiazol-5-yl)phenyl)((1S,2R,4R)-2-((5-(trifluoromethyl)pyrazin-2-yl)amino)-7-azabicyclo[2.2.1]heptan-7-yl)methanone

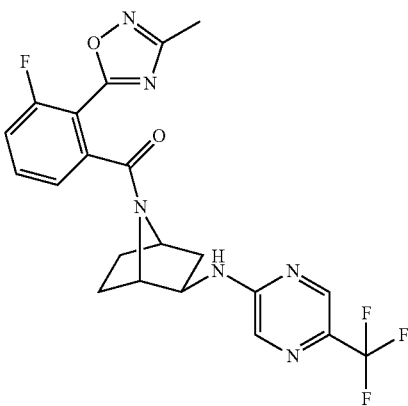 [SMILES: Cc1noc(-c2c(F)cccc2C(=O)N2C3CCC2C(Nc2cnc(C(F)(F)F)cn2)C3)n1]

Prepared analogous to Example 181 substituting intermediate A-1 with intermediate A-17. MS (ESI) mass calcd. for $C_{21}H_{18}F_4N_6O_2$, 462.1; m/z found 463.3 [M+H]. $^1$H NMR (CDCl$_3$): 8.31 (s, 0.3H), 8.18 (s, 0.7H), 8.09 (s, 0.3H), 7.75-7.68 (m, 0.7H), 7.63 (td, J=8.0, 5.0 Hz, 0.3H), 7.49 (td, J=7.9, 5.1 Hz, 0.7H), 7.44-7.13 (m, 2.6H), 5.79 (d, J=8.0 Hz, 0.4H), 4.88-4.67 (m, 1H), 4.40-4.22 (m, 1H), 4.10-3.88 (m, 1H), 2.52 (s, 3H), 2.28-1.54 (m, 6H).

Example 255: (5-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

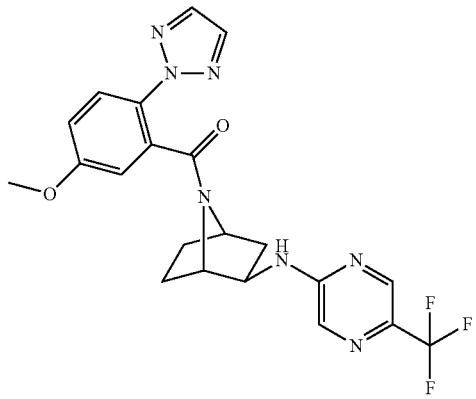 [SMILES: COc1ccc(-n2nccn2)c(C(=O)N2C3CCC2C(Nc2cnc(C(F)(F)F)cn2)C3)c1]

Prepared analogous to Example 181 substituting intermediate A-1 with intermediate A-18. MS (ESI) mass calcd. for $C_{21}H_{20}F_3N_7O_2$, 459.2; m/z found 460.3 [M+H]$^+$. $^1$H NMR (CDCl$_3$): 8.32 (s, 0.3H), 8.19 (s, 0.7H), 7.96-7.76 (m, 2.5H), 7.74-7.63 (m, 1H), 7.56 (s, 1H), 7.07 (dd, J=8.9, 2.9 Hz, 0.4H), 7.03-6.92 (m, 1H), 6.87 (d, J=2.9 Hz, 0.8H), 6.17-6.05 (m, 0.3H), 4.89-4.70 (m, 1H), 4.43-4.19 (m, 1H), 4.10-3.94 (m, 1H), 3.92-3.75 (m, 3H), 2.25-1.43 (m, 6H).

Example 256: (5-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

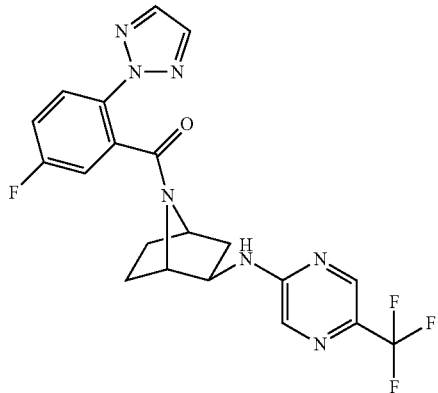 [SMILES: O=C(c1cc(F)ccc1-n1nccn1)N1C2CCC1C(Nc1cnc(C(F)(F)F)cn1)C2]

Prepared analogous to Example 181 substituting intermediate A-1 with intermediate A-10. MS (ESI) mass calcd. for $C_{20}H_{17}F_4N_7O$, 447.2; m/z found 448.3 [M+H]$^+$. $^1$H NMR (CDCl$_3$): 8.32 (s, 0.3H), 8.20 (s, 0.7H), 8.02-7.87 (m, 1.5H), 7.88-7.71 (m, 1.5H), 7.54 (s, 0.7H), 7.38-7.00 (m, 3H), 6.32-6.08 (m, 0.3H), 4.92-4.68 (m, 1H), 4.46-4.20 (m, 1H), 4.12-3.88 (m, 1H), 2.28-1.39 (m, 6H).

Example 257: (4-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

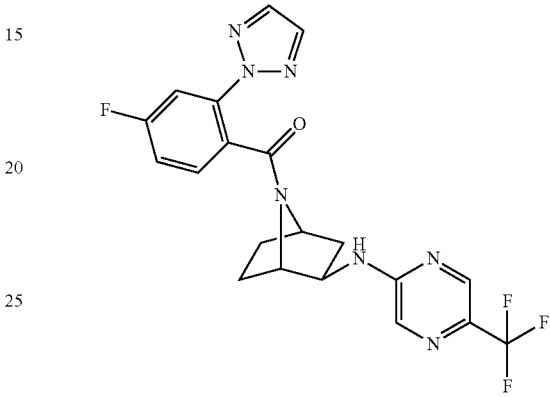

Prepared analogous to Example 181 substituting intermediate A-1 with intermediate A-12. MS (ESI) mass calcd. for $C_{20}H_{17}F_4N_7O$, 447.2; m/z found 448.3 [M+H]$^+$. $^1$H NMR (CDCl$_3$): 8.33 (s, 0.3H), 8.20 (s, 0.7H), 8.01-7.79 (m, 2.4H), 7.73 (dd, J=9.4, 2.6 Hz, 0.4H), 7.63-7.44 (m, 1.7H), 7.38 (dd, J=8.5, 5.7 Hz, 0.7H), 7.21-6.94 (m, 1.4H), 6.20 (d, J=8.5 Hz, 0.4H), 4.91-4.73 (m, 1H), 4.46-4.17 (m, 1H), 4.09-3.85 (m, 1H), 2.25-1.44 (m, 6H).

Example 258: (2-fluoro-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

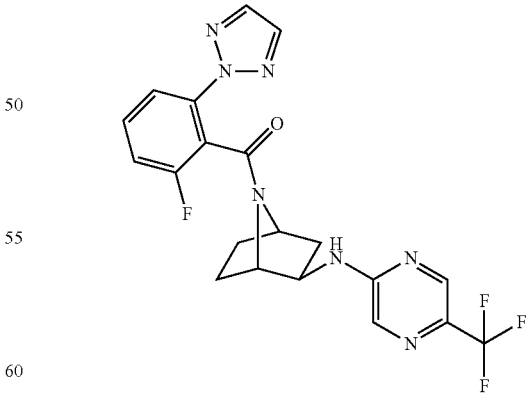

Prepared analogous to Example 181 substituting intermediate A-1 with intermediate A-11. MS (ESI) mass calcd. for $C_{20}H_{17}F_4N_7O$, 447.2; m/z found 448.3 [M+H]$^+$. $^1$H NMR (CDCl$_3$): 8.41-8.29 (m, 0.3H), 8.20 (s, 0.7H), 8.01-7.60 (m, 3H), 7.60-7.11 (m, 3.2H), 7.03-6.89 (m, 0.2H), 6.20-6.06

(m, 0.2H), 5.45-5.34 (m, 0.2H), 5.16-5.04 (m, 0.2H), 4.99-4.75 (m, 1H), 4.49-4.16 (m, 1H), 4.13-4.00 (m, 0.3H), 3.88 (d, J=5.2 Hz, 0.5H), 3.69 (d, J=5.1 Hz, 0.2H), 2.33-1.36 (m, 6H).

Example 259: (6-methylimidazo[2,1-b]thiazol-5-yl)((1S,2R,4R)-2-((5-(trifluoromethyl)pyrazin-2-yl)amino)-7-azabicyclo[2.2.1]heptan-7-yl)methanone

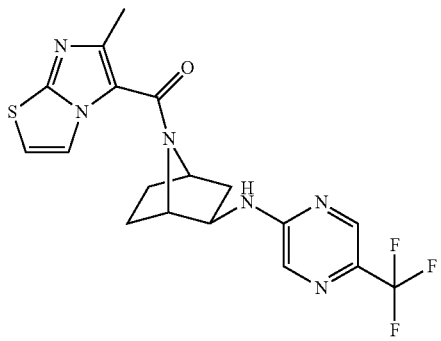 [SMILES: Cc1nc2sccn2c1C(=O)N1C2CCC1C(Nc1cnc(C(F)(F)F)cn1)C2]

Prepared analogous to Example 181 substituting 2 intermediate A-1 with 6-methylimidazo[2,1-b]thiazole-5-carboxylic acid. MS (ESI) mass calcd. for $C_{18}H_{17}F_3N_6OS$, 422.2; m/z found 423.2 [M+H]$^+$. $^1$H NMR (CDCl$_3$): 8.26 (s, 1H), 7.91-7.75 (m, 2H), 6.96-6.80 (m, 1H), 5.91 (s, 1H), 4.58 (d, J=5.0 Hz, 1H), 4.42 (t, J=4.8 Hz, 1H), 4.21-4.05 (m, 1H), 2.49 (s, 3H), 2.25 (dd, J=13.2, 7.5 Hz, 1H), 2.10-1.88 (m, 2H), 1.73-1.54 (m, 3H).

Example 260: (3-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone

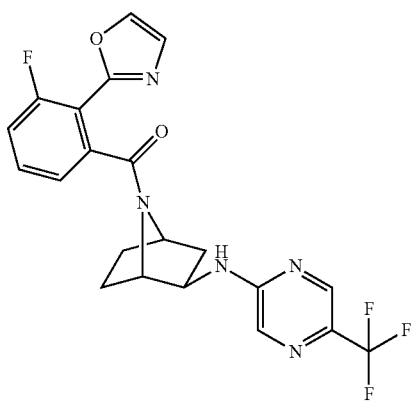 [SMILES: O=C(c1cccc(F)c1-c1ncco1)N1C2CCC1C(Nc1cnc(C(F)(F)F)cn1)C2]

Step A: (3-fluoro-2-iodophenyl)((1S,2R,4R)-2-((5-(trifluoromethyl)pyrazin-2-yl)amino)-7-azabicyclo[2.2.1]heptan-7-yl)methanone. Prepared analogous to Example 238 substituting intermediate A-2 with 3-fluoro-2-iodobenzoic acid. MS (ESI) mass calcd. for $C_{18}H_{15}F_4IN_4O$, 506.0; m/z found 507.2 [M+H]$^+$. $^1$H NMR (CDCl$_3$): 8.27-8.14 (m, 1H), 8.10-7.81 (m, 1H), 7.48-7.32 (m, 0.5H), 7.23-6.83 (m, 2.5H), 6.66-5.98 (m, 1H), 4.94-4.69 (m, 1H), 4.31-4.14 (m, 0.5H), 4.08-3.90 (m, 0.5H), 3.90-3.75 (m, 0.5H), 3.72-3.44 (m, 0.5H), 2.27-1.41 (m, 6H).

Step B: (3-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone. The title compound of step A (35 mg) and 2-(tributylstannyl)oxazole (17 µL) were dissolved in DME (1 mL). The solution was degassed with N$_2$ as CuI (1 mg) and Pd(PPh$_3$)$_4$ (4 mg) was added. The reaction was heated at 120° C. for 3 h. Additional CuI and Pd(PPh$_3$)$_4$ and the reaction purged with N$_2$. Heating was continued overnight. The reaction was cooled to rt, filtered through a pad of celite and purified via prep HPLC to give the title compound (12 mg, 39%). MS (ESI) mass calcd. for $C_{21}H_{17}F_4N_5O_2$, 447.1; m/z found 448.3 [M+H]$^+$. $^1$H NMR (CDCl$_3$): 8.34 (s, 1H), 8.16 (s, 1H), 7.98-7.78 (m, 1H), 7.69 (s, 0.8H), 7.60-7.06 (m, 4H), 6.80-6.61 (m, 0.2H), 4.92-4.66 (m, 1H), 4.46-4.23 (m, 1H), 4.06-3.80 (m, 1H), 2.36-1.51 (m, 6H).

Example 261: (2-((4,6-dimethylpyrimidin-2-yl)amino)-7-azabicyclo[2.2.1]heptan-7-yl)(3-fluoro-2-methoxyphenyl)methanone

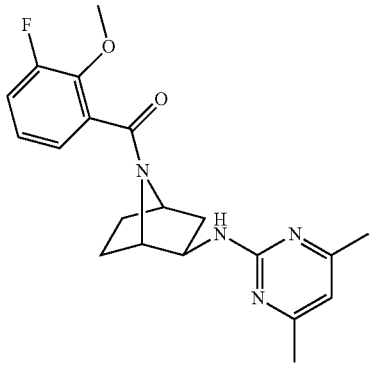 [SMILES: COc1c(F)cccc1C(=O)N1C2CCC1C(Nc1nc(C)cc(C)n1)C2]

Example 262: (3-fluoro-2-(pyridazin-3-yl)phenyl)((1S,2R,4R)-2-((5-(trifluoromethyl)pyrazin-2-yl)amino)-7-azabicyclo[2.2.1]heptan-7-yl)methanone

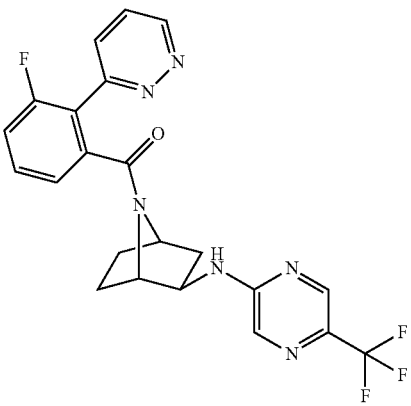 [SMILES: O=C(c1cccc(F)c1-c1cccnn1)N1C2CCC1C(Nc1cnc(C(F)(F)F)cn1)C2]

Prepared analogous to Example 260 substituting 2-(tributylstannyl)oxazole with 3-(tributylstannyl)pyridazine. MS (ESI) mass calcd. for $C_{22}H_{18}F_4N_6O$, 458.1; m/z found 459.1 [M+H]$^+$. $^1$H NMR (500 MHz, Chloroform-d) 9.25-9.14 (m, 1H), 8.50 (s, 0.5H), 8.28 (s, 0.8H), 8.17 (s, 0.5H), 7.97-7.80

(m, 1.5H), 7.72-7.59 (m, 1H), 7.55-7.41 (m, 1H), 7.34-7.18 (m, 2.2H), 6.96 (d, J=8.1 Hz, 0.5H), 4.79-4.72 (m, 0.55H), 4.71-4.64 (m, 0.45H), 4.53-4.43 (m, 0.6H), 4.38-4.28 (m, 0.45H), 4.18 (s, 0.4H), 4.13-4.05 (m, 0.55H), 2.30-1.47 (m, 6H).

Example 263: (3-methyl-2-(pyridazin-3-yl)phenyl)((1S,2R,4R)-2-((5-(trifluoromethyl)pyrazin-2-yl)amino)-7-azabicyclo[2.2.1]heptan-7-yl)methanone

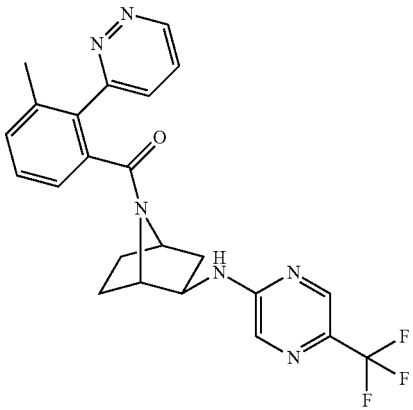 [SMILES: Cc1cccc(C(=O)N2C3CCC2C(Nc2cnc(C(F)(F)F)cn2)C3)c1-c1cccnn1]

Step A: (2-iodo-3-methylphenyl)((1S,2R,4R)-2-((5-(trifluoromethyl)pyrazin-2-yl)amino)-7-azabicyclo[2.2.1]heptan-7-yl)methanone. Prepared analogous to Example 238 substituting intermediate A-2 with 2-iodo-3-methylbenzoic acid. MS (ESI) mass calcd. for $C_{19}H_{18}F_3IN_4O$, 502.0; m/z found 503.0 [M+H]$^+$. $^1$H NMR (400 MHz, Chloroform-d) 8.26-8.03 (m, 1.4H), 7.88-6.60 (m, 4.6H), 4.93-4.58 (m, 1H), 4.32-4.15 (m, 0.4H), 3.92 (s, 0.4H), 3.86-3.76 (m, 0.6H), 3.57 (s, 0.6H), 2.51 (s, 1.4H), 2.40 (s, 1.6H), 2.21-0.66 (m, 6H).

Step B: (3-methyl-2-(pyridazin-3-yl)phenyl)((1S,2R,4R)-2-((5-(trifluoromethyl)pyrazin-2-yl)amino)-7-azabicyclo[2.2.1]heptan-7-yl)methanone. Prepared analogous to Example 260 Step B substituting 2-(tributylstannyl)oxazole with 3-(tributylstannyl)pyridazine. MS (ESI) mass calcd. for $C_{23}H_{21}F_3N_6O$, 454.2; m/z found 455.2 [M+H]$^+$. $^1$H NMR (400 MHz, Chloroform-d) 9.22 (dd, J=4.9, 1.7 Hz, 0.25H), 9.19 (dd, J=4.8, 1.8 Hz, 0.75H), 8.57 (s, 0.75H), 8.27 (s, 0.25H), 8.21 (s, 0.25H), 8.16 (s, 0.75H), 7.97 (s, 0.75H), 7.72-7.56 (m, 2H), 7.44-7.27 (m, 2.25H), 7.25-7.19 (m, 0.75H), 6.40 (d, J=8.0 Hz, 0.25H), 4.68-4.62 (m, 0.75H), 4.59-4.54 (m, 0.25H), 4.39 (ddd, J=9.3, 8.1, 3.9 Hz, 0.75H), 4.28-4.15 (m, 0.5H), 4.08-4.03 (m, 0.75H), 2.32 (s, 0.75H), 2.21 (s, 2.25H), 2.18-1.42 (m, 6H).

Example 264 (3-fluoro-2-(pyridazin-4-yl)phenyl)((1S,2R,4R)-2-((5-(trifluoromethyl)pyrazin-2-yl)amino)-7-azabicyclo[2.2.1]heptan-7-yl)methanone

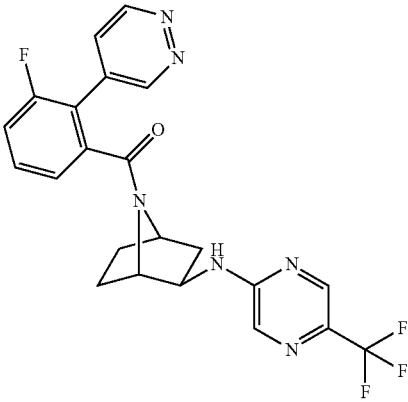 [SMILES: O=C(c1cccc(F)c1-c1ccnnc1)N1C2CCC1C(Nc1cnc(C(F)(F)F)cn1)C2]

Prepared analogous to Example 260 substituting 2-(tributylstannyl)oxazole with 4-(tributylstannyl)pyridazine. MS (ESI) mass calcd. for $C_{22}H_{18}F_4N_6O$, 458.1; m/z found 459.2 [M+H]$^+$. $^1$H NMR (400 MHz, Chloroform-d) 9.38-9.20 (m, 2H), 8.28 (s, 0.6H), 8.19 (s, 0.4H), 8.00 (s, 0.6H), 7.94 (s, 0.4H), 7.71-7.63 (m, 0.6H), 7.62-7.50 (m, 1H), 7.40-7.29 (m, 1H), 7.24-7.08 (m, 1.4H), 5.24 (s, 0.4H), 4.80 (s, 0.6H), 4.67 (s, 0.4H), 4.61 (d, J=5.3 Hz, 0.6H), 4.02-3.92 (m, 0.6H), 3.85-3.75 (m, 0.4H), 3.70-3.59 (m, 1H), 1.90-2.07 (m, 1H), 1.84-0.79 (m, 5H).

Example 265 (3-fluoro-2-(pyrazin-2-yl)phenyl)((1S,2R,4R)-2-((5-(trifluoromethyl)pyrazin-2-yl)amino)-7-azabicyclo[2.2.1]heptan-7-yl)methanone

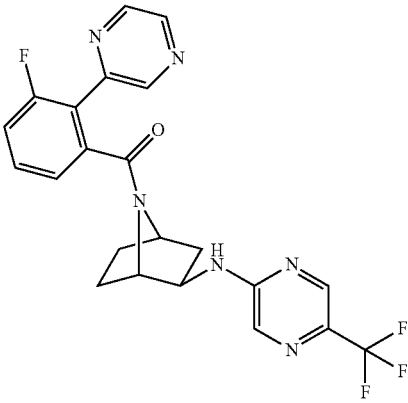 [SMILES: O=C(c1cccc(F)c1-c1cnccn1)N1C2CCC1C(Nc1cnc(C(F)(F)F)cn1)C2]

Prepared analogous to Example 260 substituting 2-(tributylstannyl)oxazole with 2-(tributylstannyl)pyrazine. MS (ESI) mass calcd. for $C_{22}H_{18}F_4N_6O$, 458.1; m/z found 459.2 [M+H]$^+$. $^1$H NMR (400 MHz, Chloroform-d) 8.99-8.94 (m, 1H), 8.69 (d, J=2.6 Hz, 1H), 8.58-8.51 (m, 1H), 8.19 (s, 1H), 8.03 (s, 1H), 7.57 (s, 1H), 7.44-7.37 (m, 1H), 7.25-7.20 (m, 2H), 4.80-4.74 (m, 1H), 4.40 (td, J=8.6, 3.6 Hz, 1H), 4.05 (d, J=5.1 Hz, 1H), 2.24-2.16 (m, 1H), 1.78-1.67 (m, 2H), 1.62-1.51 (m, 2H), 1.41-1.29 (m, 1H).

Example 266 (3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone

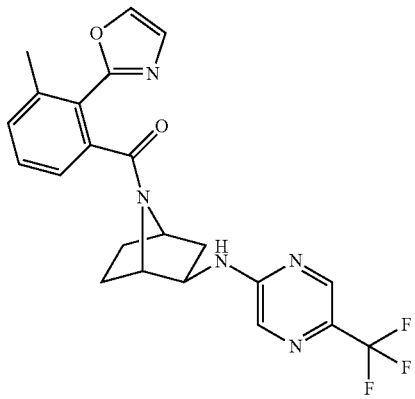 [SMILES: Cc1cccc(C(=O)N2C3CCC2C(Nc2cnc(C(F)(F)F)cn2)C3)c1-c1ncco1]

Prepared analogous to Example 263 substituting 3-(tributylstannyl)pyridazine with 2-(tributylstannyl)oxazole. MS (ESI) mass calcd. for $C_{22}H_{20}F_3N_5O_2$, 443.2; m/z found 444.2 [M+H]$^+$. $^1$H NMR (500 MHz, Chloroform-d) 8.57 (s, 1H), 8.14 (s, 1H), 7.88 (d, J=0.9 Hz, 1H), 7.79 (d, J=1.4 Hz, 1H), 7.33-7.23 (m, 3H), 7.20-7.14 (m, 1H), 4.82-4.75 (m, 1H), 4.29 (td, J=8.5, 3.7 Hz, 1H), 3.94 (d, J=4.9 Hz, 1H), 2.28 (s, 3H), 2.16-1.45 (m, 6H).

Example 267 (4-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

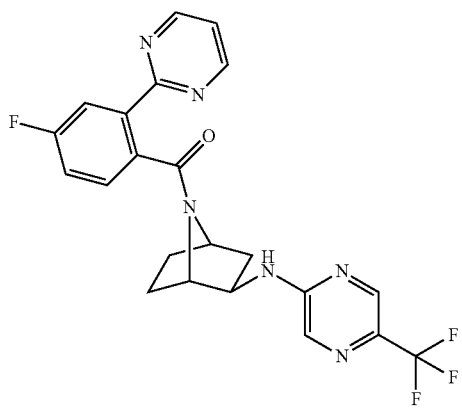

Prepared analogous to Example 238 substituting intermediate A-2 with intermediate A-25. MS (ESI) mass calcd. for: $C_{22}H_{18}F_4N_6O$, 458.1; m/z found 459.2 [M+H]$^+$. $^1$H NMR (500 MHz, Chloroform-d) 8.89-8.81 (m, 1.7H), 8.80-8.73 (m, 0.3H), 8.33-7.87 (m, 2H), 7.80 (s, 0.2H), 7.74-7.66 (m, 0.8H), 7.56-7.31 (m, 2.8H), 7.21-7.14 (m, 0.2H), 7.14-7.06 (m, 0.8H), 6.58 (s, 0.2H), 4.88-4.78 (m, 0.8H), 4.72 (d, J=5.2 Hz, 0.2H), 4.40 (s, 0.8H), 4.26 (s, 0.2H), 4.10-3.97 (m, 1H), 2.27-1.39 (m, 6H).

Example 268 (3-fluoro-2-(pyridin-4-yl)phenyl)((1S,2R,4R)-2-((5-(trifluoromethyl)pyrazin-2-yl)amino)-7-azabicyclo[2.2.1]heptan-7-yl)methanone

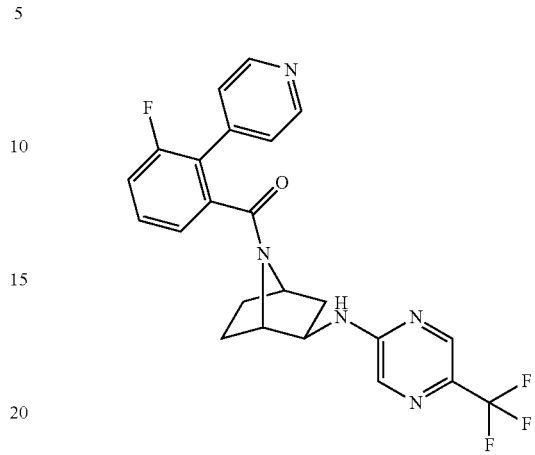

Prepared analogous to Example 260 substituting 2-(tributylstannyl)oxazole with 4-(tributylstannyl)pyridine. MS (ESI) mass calcd. for: $C_{23}H_{19}F_4N_5O$, 457.2; m/z found 458.2 [M+H]$^+$. $^1$H NMR (500 MHz, Chloroform-d) 8.78-8.61 (m, 2H), 8.28 (s, 0.6H), 8.15 (s, 0.4H), 7.87 (s, 1H), 7.72-7.28 (m, 4.2H), 7.23-7.02 (m, 1.4H), 5.49 (s, 0.4H), 4.67-4.60 (m, 0.4H), 4.56 (d, J=5.3 Hz, 0.6H), 3.99-3.89 (m, 0.6H), 3.82-3.72 (m, 0.4H), 3.65-3.58 (m, 0.6H), 3.56 (d, J=5.4 Hz, 0.4H), 2.00-0.80 (m, 6H).

Example 269 (3-fluoro-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone

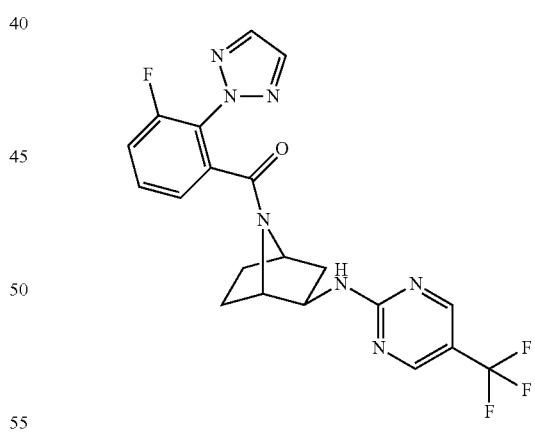

Step A: (1S,2R,4R)-tert-butyl 2-((5-(trifluoromethyl)pyrimidin-2-yl)amino)-7-azabicyclo[2.2.1]heptane-7-carboxylate. To intermediate B-5 (250 mg, 1.2 mmol) and $K_2CO_3$ (244 mg, 1.8 mmol) in DMF (1.7 mL) was added 2-chloro-5-(trifluoromethyl)pyrimidine (258 mg, 1.4 mmol). After heating at 70° C. for 17 h, the mixture was cooled to rt, diluted with EtOAc and $H_2O$. The aqueous layer was extracted with EtOAc (3×). The combined organics were washed with 4% $MgSO_4$ (aq) and dried ($MgSO_4$). Purification via silica gel chromatography (0-30% EtOAc in hexanes) gave the title compound (356 mg, 84%). MS (ESI)

mass calcd. for $C_{16}H_{21}F_3N_4O_2$, 358.2; m/z found 359.2 [M+H]$^+$. $^1$H NMR (500 MHz, Chloroform-d) 8.58-8.37 (m, 2H), 5.70 (s, 1H), 4.30 (s, 1H), 1.78-1.68 (m, 1H), 4.25-4.17 (m, 1H), 1.89-1.79 (m, 1H), 4.12-4.03 (m, 1H), 2.03 (dd, J=13.1, 7.8 Hz, 1H), 1.63-1.37 (m, 12H).

Step B: (1S,2R,4R)—N-(5-(trifluoromethyl)pyrimidin-2-yl)-7-azabicyclo[2.2.1]heptan-2-amine. To the title compound of step A (355 mg, 1 mmol) in DCM (9.7 mL) was added 4M HCl in dioxane (1.2 mL). The reaction was allowed to proceed overnight then concentrated and neutralized with 5% $Na_2CO_3$ (aq) and extracted with DCM (2×). The combined organics were dried ($Na_2SO_4$) to give the title compound of step B that was used without further purification.

Step C: (3-fluoro-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone. To the title compound of step B (25 mg, 0.1 mmol) in DCM (1 mL) was added DIPEA (22 μL, 0.13 mmol) and intermediate A-16 (22 mg, 0.1 mmol). Then T3P (50% solution in DMF, 0.17 mL, 0.29 mmol) was added dropwise and the reaction heated at 45° C. for 12 h. After allowing to cool to rt, DCM was added and the mixture washed with $H_2O$ then saturated $NaHCO_3$ (aq). The combined aq layers were extracted with DCM. The combined organic layers were dried ($Na_2SO_4$). Purification was performed using Agilent prep method X to give the title compound (35 mg, 80%). MS (ESI) mass calcd. for: $C_{20}H_{17}F_4N_7O$, 447.1; m/z found 448.2 [M+H]$^+$. $^1$H NMR (400 MHz, Chloroform-d) 8.50 (s, 0.9H), 8.41 (s, 1.1H), 8.09 (s, 0.9H), 7.95 (s, 1.1H), 7.56-7.47 (m, 0.5H), 7.44-7.32 (m, 1H), 7.33-7.23 (m, 1.5H), 7.20-7.14 (m, 0.5H), 6.18 (d, J=8.6 Hz, 0.5H), 4.83-4.74 (m, 0.5H), 4.67 (d, J=5.2 Hz, 0.5H), 4.34-4.19 (m, 1H), 4.11-4.04 (m, 0.5H), 3.99 (d, J=4.8 Hz, 0.5H), 2.21-1.44 (m, 6H).

Example 270 ((1S,2R,4R)-2-((3-bromoimidazo[1,2-a]pyrazin-8-yl)amino)-7-azabicyclo[2.2.1]heptan-7-yl)(3-fluoro-2-(pyrimidin-2-yl)phenyl)methanone

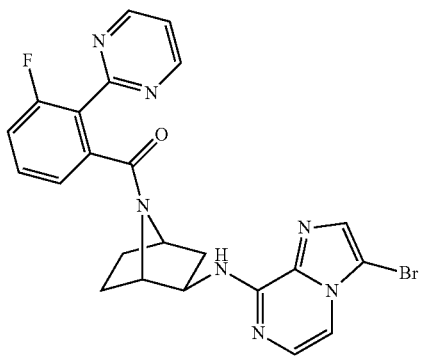 [SMILES: O=C(c1cccc(F)c1-c1ncccn1)N1C2CCC1C(Nc1nccn3c(Br)cnc13)C2]

Step A: (1S,2R,4R)-tert-butyl 2-((3-bromoimidazo[1,2-a]pyrazin-8-yl)amino)-7-azabicyclo[2.2.1]heptane-7-carboxylate. Prepared analogous to Example 269 step A substituting 2-chloro-5-(trifluoromethyl)pyrimidine with 3-bromo-8-chloroimidazo[1,2-a]pyrazine. MS (ESI) mass calcd. for: $C_{17}H_{22}BrN_5O_2$, 407.1; m/z found 408.1 [M+H]$^+$. $^1$H NMR (500 MHz, Chloroform-d) 7.45 (s, 1H), 7.43 (d, J=4.7 Hz, 1H), 7.40 (d, J=4.7 Hz, 1H), 6.15 (s, 1H), 4.37-4.27 (m, 2H), 4.27-4.21 (m, 1H), 2.08 (dd, J=13.0, 7.8 Hz, 1H), 1.90-1.33 (m, 14H).

Step B: N-((1S,2R,4R)-7-azabicyclo[2.2.1]heptan-2-yl)-3-bromoimidazo[1,2-a]pyrazin-8-amine. Prepared analogous to Example 269 step B using title compound of step A.

Step C: ((1S,2R,4R)-2-((3-bromoimidazo[1,2-a]pyrazin-8-yl)amino)-7-azabicyclo[2.2.1]heptan-7-yl)(3-fluoro-2-(pyrimidin-2-yl)phenyl)methanone. Prepared analogous to Example 269 step C substituting intermediate A-16 with intermediate A-2. MS (ESI) mass calcd. for: $C_{23}H_{19}BrFN_7O$, 507.1; m/z found 508.1 [M+H]$^+$. $^1$H NMR (400 MHz, Chloroform-d) 8.92 (d, J=4.9 Hz, 0.7H), 8.88 (d, J=4.9 Hz, 1.3H), 7.53-7.03 (m, 7.6H), 5.82 (d, J=7.6 Hz, 0.4H), 4.81-4.75 (m, 0.6H), 4.71 (d, J=5.1 Hz, 0.4H), 4.47-4.37 (m, 0.6H), 4.31-4.22 (m, 0.4H), 4.13-4.07 (m, 0.6H), 4.06-3.99 (m, 0.4H), 2.26-1.36 (m, 6H).

Example 271 (3-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone

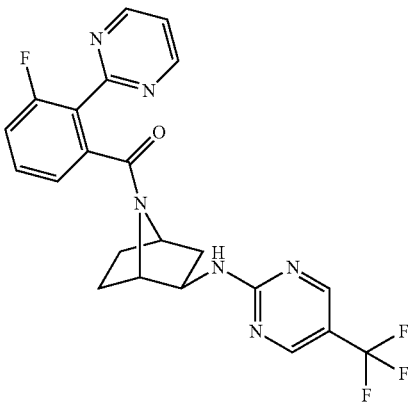

Prepared analogous to Example 269 substituting intermediate A-16 with intermediate A-2. MS (ESI) mass calcd. for: $C_{22}H_{18}F_4N_6O$, 458.1; m/z found 459.2 [M+H]$^+$. $^1$H NMR (400 MHz, Chloroform-d) 8.90 (d, J=5.0 Hz, 2H), 8.49 (s, 1H), 8.44-8.31 (m, 2H), 7.43-7.32 (m, 2H), 7.26-7.14 (m, 2H), 4.80-4.75 (m, 1H), 4.45-4.37 (m, 1H), 4.09 (d, J=5.0 Hz, 1H), 2.22 (dd, J=12.9, 8.0 Hz, 1H), 2.11-1.51 (m, 5H).

Example 272 (3-methyl-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone

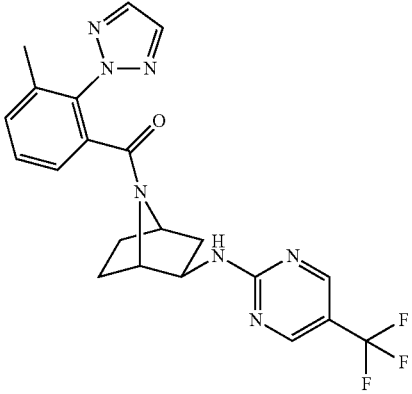

Prepared analogous to Example 269 substituting intermediate A-16 with intermediate A-24. MS (ESI) mass calcd. for: $C_{21}H_{20}F_3N_7O$, 443.2; m/z found 444.2 [M+H]. $^1$H NMR (400 MHz, Chloroform-d) 8.49 (s, 0.8H), 8.41 (s, 1.2H), 8.02 (s, 0.8H), 7.91 (s, 1.2H), 7.47-7.39 (m, 1H), 7.38-7.28 (m, 2H), 7.23-7.16 (m, 0.6H), 5.98 (d, J=8.4 Hz, 0.4H), 4.77-4.68 (m, 0.6H), 4.60 (d, J=5.1 Hz, 0.4H), 4.29-4.17 (m, 1H), 4.11-4.03 (m, 0.4H), 3.99 (d, J=5.0 Hz, 0.6H), 2.27 (s, 1.3H), 2.24 (s, 1.7H), 2.18-1.41 (m, 6H).

Example 273 (3-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

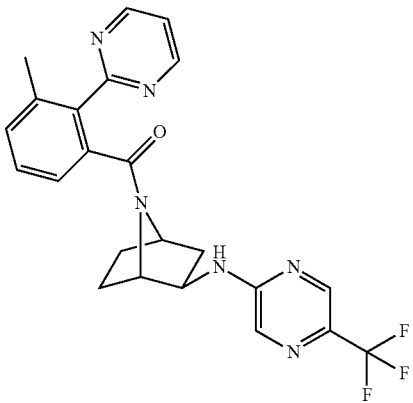 [SMILES: Cc1cccc(C(=O)N2C3CCC2C(Nc2cnc(C(F)(F)F)cn2)C3)c1-c1ncccn1]

Prepared analogous to Example 238 substituting intermediate A-2 with intermediate A-26. MS (ESI) mass calcd. for: $C_{23}H_{21}F_3N_6O$, 454.2; m/z found 455.1 [M+H]$^+$. $^1$H NMR (400 MHz, Chloroform-d) 8.85 (d, J=5.0 Hz, 2H), 8.50 (d, J=9.2 Hz, 1H), 8.17 (s, 1H), 7.66 (d, J=1.3 Hz, 1H), 7.37 (t, J=5.0 Hz, 1H), 7.31-7.18 (m, 3H), 4.73-4.67 (m, 1H), 4.35 (td, J=8.7, 3.7 Hz, 1H), 4.14-4.09 (m, 1H), 2.29 (s, 3H), 2.19-1.45 (m, 6H).

Example 274 (3-fluoro-2-(pyrimidin-2-yl)phenyl)((1S,2R,4R)-2-((3-(trifluoromethyl)-[1,2,4]triazolo[4,3-a]pyrazin-8-yl)amino)-7-azabicyclo[2.2.1]heptan-7-yl)methanone

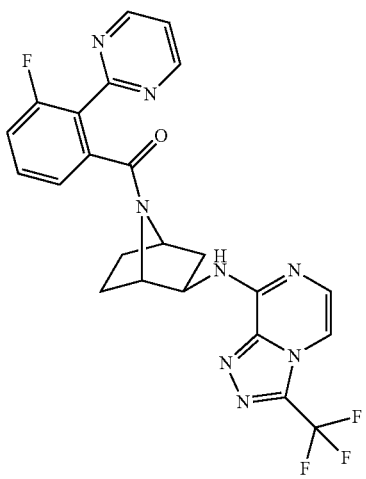 [SMILES: O=C(c1cccc(F)c1-c1ncccn1)N1C2CCC1C(Nc1nccn3c(C(F)(F)F)nnc13)C2]

Step A: (1S,2R,4R)-tert-butyl 2-((3-(trifluoromethyl)-[1,2,4]triazolo[4,3-a]pyrazin-8-yl)amino)-7-azabicyclo[2.2.1]heptane-7-carboxylate. Prepared analogous to Example 269 step A substituting 2-chloro-5-(trifluoromethyl)pyrimidine with 8-chloro-3-(trifluoromethyl)-[1,2,4]triazolo[4,3-a]pyrazine. MS (ESI) mass calcd. for: $C_{17}H_{21}F_3N_6O_2$, 398.2; m/z found 399.2 [M+H]$^+$. $^1$H NMR (500 MHz, Chloroform-d) 7.51-7.48 (m, 1H), 7.48-7.45 (m, 1H), 6.58 (d, J=7.6 Hz, 1H), 4.41-4.25 (m, 3H), 1.94-1.83 (m, 1H), 2.12 (dd, J=13.1, 7.8 Hz, 1H), 1.83-1.70 (m, 2H), 1.59-1.52 (m, 1H), 1.50-1.41 (m, 10H).

Step B: N-((1S,2R,4R)-7-azabicyclo[2.2.1]heptan-2-yl)-3-(trifluoromethyl)-[1,2,4]triazolo[4,3-a]pyrazin-8-amine. Prepared analogous to Example 269 step B using title compound of step A.

Step C: (3-fluoro-2-(pyrimidin-2-yl)phenyl)((1S,2R,4R)-2-((3-(trifluoromethyl)-[1,2,4]triazolo[4,3-a]pyrazin-8-yl)amino)-7-azabicyclo[2.2.1]heptan-7-yl)methanone. Prepared analogous to Example 269 step C substituting intermediate A-16 with intermediate A-2. MS (ESI) mass calcd. for: $C_{23}H_{18}F_4N_8O$, 498.2; m/z found 499.2 [M+H]$^+$. $^1$H NMR (400 MHz, Chloroform-d) 8.99 (d, J=4.9 Hz, 0.6H), 8.95 (d, J=5.0 Hz, 1.4H), 8.72 (s, 0.7H), 7.55-7.28 (m, 4.6H), 7.21-7.10 (m, 1.4H), 6.18 (d, J=7.5 Hz, 0.3H), 4.88-4.80 (m, 0.7H), 4.75 (d, J=5.1 Hz, 0.3H), 4.67 (s, 0.7H), 4.33 (s, 0.3H), 4.16-4.06 (m, 1H), 2.27 (dd, J=12.7, 8.2 Hz, 0.7H), 2.11 (dd, J=13.0, 8.1 Hz, 0.3H), 2.04-1.41 (m, 5H).

Example 275 methyl 5-(((1S,2R,4R)-7-(3-fluoro-2-(pyrimidin-2-yl)benzoyl)-7-azabicyclo[2.2.1]heptan-2-yl)amino)pyrazine-2-carboxylate

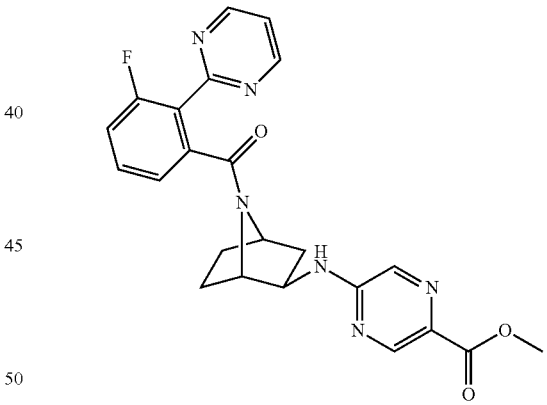

Step A: (1S,2R,4R)-tert-butyl 2-((5-(methoxycarbonyl)pyrazin-2-yl)amino)-7-azabicyclo[2.2.1]heptane-7-carboxylate. Prepared analogous to Example 269 step A substituting 2-chloro-5-(trifluoromethyl)pyrimidine with methyl 5-chloropyrazine-2-carboxylate. MS (ESI) mass calcd. for: $C_{17}H_{24}N_4O_4$, 348.2; m/z found 349.2 [M+H]$^+$. $^1$H NMR (400 MHz, Chloroform-d) 8.77 (d, J=1.4 Hz, 1H), 7.88 (d, J=1.4 Hz, 1H), 5.55 (s, 1H), 4.34-4.27 (m, 1H), 4.25-4.18 (m, 1H), 4.12-4.06 (m, 1H), 3.95 (s, 3H), 2.12-2.05 (m, 1H), 1.92-1.72 (m, 2H), 1.63-1.38 (m, 12H).

Step B: methyl 5-((1S,2R,4R)-7-azabicyclo[2.2.1]heptan-2-ylamino)pyrazine-2-carboxylate. Prepared analogous to Example 269 step B using title compound of step A.

Step C: methyl 5-(((1S,2R,4R)-7-(3-fluoro-2-(pyrimidin-2-yl)benzoyl)-7-azabicyclo[2.2.1]heptan-2-yl)amino)pyrazine-2-carboxylate. Prepared analogous to Example 269 step C substituting intermediate A-16 with intermediate A-2. MS (ESI) mass calcd. for: $C_{23}H_{21}FN_6O_3$, 448.2; m/z found 449.2 [M+H]$^+$. $^1$H NMR (500 MHz, Chloroform-d) 8.87 (d, J=4.9 Hz, 2H), 8.65 (s, 1H), 8.37 (d, J=9.4 Hz, 1H), 7.67 (s, 1H), 7.42-7.34 (m, 2H), 7.24-7.17 (m, 2H), 4.77-4.70 (m, 1H), 4.48-4.39 (m, 1H), 4.07 (d, J=5.1 Hz, 1H), 3.90 (s, 3H), 2.18 (dd, J=13.0, 8.1 Hz, 1H), 2.11-2.00 (m, 1H), 1.97-1.62 (m, 3H), 1.58-1.48 (m, 1H).

Example 276 (2-iodo-3-methylphenyl)((1S,2R,4R)-2-((5-(trifluoromethyl)pyrimidin-2-yl)amino)-7-azabicyclo[2.2.1]heptan-7-yl)methanone

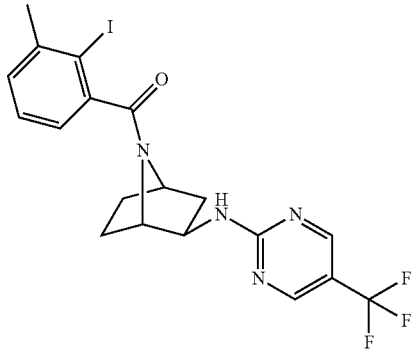 [SMILES: Cc1cccc(C(=O)N2C3CCC2C(Nc2ncc(C(F)(F)F)cn2)C3)c1I]

Prepared analogous to Example 269 substituting intermediate A-16 with 2-iodo-3-methylbenzoic acid. MS (ESI) mass calcd. for: $C_{19}H_{18}F_3IN_4O$, 502.0; m/z found 503.0 [M+H]$^+$. $^1$H NMR (400 MHz, Chloroform-d) 8.59-8.30 (m, 2H), 7.32-7.22 (m, 1.4H), 7.19-6.96 (m, 1H), 6.93-6.83 (m, 0.6H), 6.02 (s, 0.5H), 5.54 (s, 0.5H), 5.01-4.91 (m, 0.5H), 4.84 (d, J=5.1 Hz, 0.5H), 4.28 (s, 0.5H), 4.02 (s, 0.5H), 3.84-3.66 (m, 1H), 2.50 (s, 1.5H), 2.43 (s, 1.5H), 2.24-1.39 (m, 6H).

Example 277 (3-fluoro-2-iodophenyl)((1S,2R,4R)-2-((5-(trifluoromethyl)pyrimidin-2-yl)amino)-7-azabicyclo[2.2.1]heptan-7-yl)methanone

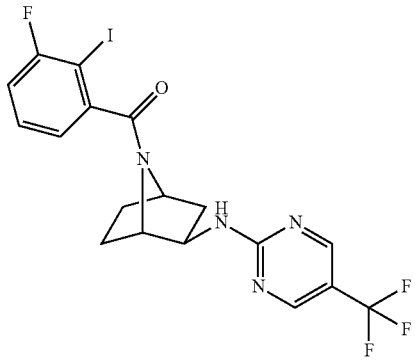 [SMILES: O=C(c1cccc(F)c1I)N1C2CCC1C(Nc1ncc(C(F)(F)F)cn1)C2]

Prepared analogous to Example 269 substituting intermediate A-16 with 3-fluoro-2-iodobenzoic acid. MS (ESI) mass calcd. for: $C_{18}H_{15}F_4IN_4O$, 506.0; m/z found 507.0 [M+H]$^+$. $^1$H NMR (400 MHz, Chloroform-d) 8.57-8.33 (m, 2H), 7.42-7.32 (m, 0.5H), 7.16-7.02 (m, 1.5H), 6.99-6.88 (m, 1H), 5.99 (d, J=7.6 Hz, 0.5H), 5.55 (s, 0.5H), 5.00-4.91 (m, 0.5H), 4.85 (d, J=5.3 Hz, 0.5H), 4.32-4.24 (m, 0.5H), 4.05-3.97 (m, 0.5H), 3.81-3.71 (m, 1H), 2.22-1.93 (m, 2H), 1.91-1.43 (m, 4H).

Example 278 (3-fluoro-2-(pyrimidin-2-yl)phenyl)((1S,2R,4R)-2-((5-methylpyrazin-2-yl)amino)-7-azabicyclo[2.2.1]heptan-7-yl)methanone

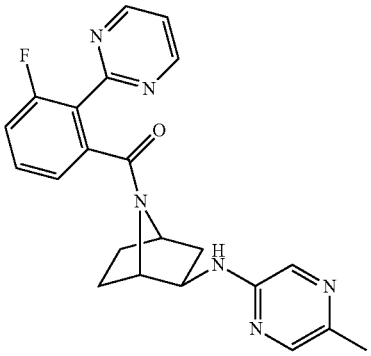 [SMILES: Cc1cnc(NC2CC3CCC2N3C(=O)c2cccc(F)c2-c2ncccn2)cn1]

Step A: (1S,2R,4R)-tert-butyl 2-((5-methylpyrazin-2-yl)amino)-7-azabicyclo[2.2.1]heptane-7-carboxylate. Prepared analogous to Example 279 step A substituting 2-chloro-5-(trifluoromethyl)pyridine with 2-chloro-5-methylpyrazine. MS (ESI) mass calcd. for: $C_{16}H_{24}N_4O_2$, 304.2; m/z found 305.2 [M+H]$^+$. $^1$H NMR (400 MHz, Chloroform-d) 7.86 (s, 1H), 7.78 (d, J=1.5 Hz, 1H), 4.71 (s, 1H), 4.28 (s, 1H), 4.19 (d, J=4.9 Hz, 1H), 3.95-3.85 (m, 1H), 2.38 (s, 3H), 2.11-1.96 (m, 1H), 1.89-1.66 (m, 2H), 1.58-1.33 (m, 12H).

Step B: (1S,2R,4R)—N-(5-methylpyrazin-2-yl)-7-azabicyclo[2.2.1]heptan-2-amine. Prepared analogous to Example 279 step B using title compound of step A.

Step C: (3-fluoro-2-(pyrimidin-2-yl)phenyl)((1S,2R,4R)-2-((5-methylpyrazin-2-yl)amino)-7-azabicyclo[2.2.1]heptan-7-yl)methanone. Prepared analogous to Example 279 step C. MS (ESI) mass calcd. for: $C_{22}H_{21}FN_6O$, 404.2; m/z found 405.2 [M+H]$^+$. $^1$H NMR (500 MHz, Chloroform-d) 8.87 (d, J=5.0 Hz, 2H), 7.74 (s, 1H), 7.60 (s, 1H), 7.41-7.30 (m, 3H), 7.23-7.12 (m, 2H), 4.76-4.68 (m, 1H), 4.30-4.17 (m, 1H), 4.08-4.01 (m, 1H), 2.30 (s, 3H), 2.15 (dd, J=12.9, 8.1 Hz, 1H), 2.07-1.95 (m, 1H), 1.95-1.84 (m, 1H), 1.74-1.46 (m, 3H).

Example 279 (3-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone

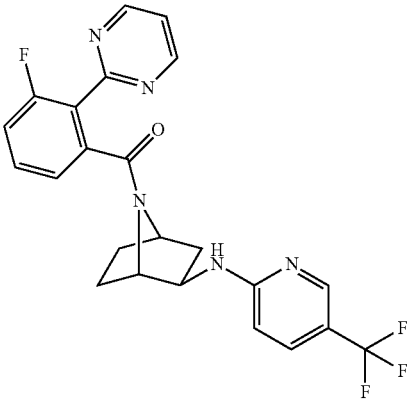

Step A: (1S,2R,4R)-tert-butyl 2-((5-(trifluoromethyl)pyridin-2-yl)amino)-7-azabicyclo[2.2.1]heptane-7-carboxylate. In a microwave vial, toluene (8.3 mL) was degassed with $N_2$ for 10 minutes then Pd(OAc)$_2$ (22 mg, 0.03 mmol) and racemic BINAP (21 mg, 0.03 mmol) were added and the solution was degassed with $N_2$ for 5 minutes. Then intermediate B-5, 2-chloro-5-(trifluoromethyl)pyridine (150 mg, 0.83 mmol) and sodium tert-butoxide (115 mg, 1.16 mmol) were added and the reaction mixture was stirred at 70° C. After 15 h the reaction mixture was filtered through a pad of celite and solvent was evaporated. Purification via silica gel chromatography (0-40% EtOAc in hexanes) gave the title compound of step A (192 mg, 65%). MS (ESI) mass calcd. for: $C_{17}H_{22}F_3N_3O_2$, 357.2; m/z found 358.2 [M+H]$^+$. $^1$H NMR (500 MHz, Chloroform-d) 8.33 (s, 1H), 7.61-7.49 (m, 1H), 6.35 (d, J=8.8 Hz, 1H), 5.06 (s, 1H), 4.29 (s, 1H), 4.20 (s, 1H), 4.03-3.91 (m, 1H), 2.04 (dd, J=13.0, 7.6 Hz, 1H), 1.89-1.79 (m, 1H), 1.79-1.71 (m, 1H), 1.59-1.37 (m, 12H).

Step B: (1S,2R,4R)—N-(5-(trifluoromethyl)pyridin-2-yl)-7-azabicyclo[2.2.1]heptan-2-amine. To the title compound of step A (319 mg, 0.89 mmol) in DCM (8.7 mL) was added 4M HCl in dioxane (1.1 mL). The reaction was allowed to proceed overnight then concentrated and neutralized with 5% Na$_2$CO$_3$ (aq) and extracted with DCM (2×). The combined organics were dried (Na$_2$SO$_4$) to give the title compound of step B that was used without further purification.

Step C: (3-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone. To the title compound of step B (100 mg, 0.39 mmol) in DCM (3.9 mL) was added DIPEA (87 μL, 0.51 mmol) and intermediate A-2 (100 mg, 0.43 mmol). Then T3P (50% solution in DMF, 0.7 mL, 1.16 mmol) was added dropwise and the reaction heated at 45° C. for 12 h. After allowing to cool to rt, DCM was added and the mixture washed with H$_2$O then saturated NaHCO$_3$ (aq). The combined aq layers were extracted with DCM. The combined organic layers were dried (Na$_2$SO$_4$). Purification was performed using Agilent prep method X to give the title compound (61 mg, 34%). MS (ESI) mass calcd. for: $C_{23}H_{19}F_4N_5O$, 457.2; m/z found 458.2 [M+H]$^+$. $^1$H NMR (400 MHz, Chloroform-d) 8.88 (d, J=4.9 Hz, 2H), 8.22 (s, 1H), 7.67 (d, J=9.3 Hz, 1H), 7.43-7.28 (m, 3H), 7.24-7.12 (m, 2H), 6.19 (d, J=8.8 Hz, 1H), 4.76-4.68 (m, 1H), 4.43-4.32 (m, 1H), 4.08 (d, J=5.0 Hz, 1H), 2.16 (dd, J=12.9, 8.1 Hz, 1H), 2.08-1.83 (m, 2H), 1.77-1.38 (m, 3H).

Example 280 (4-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone Prepared analogous to Example 279 substituting intermediate A-2 with intermediate A-25. MS (ESI) mass calcd. for: $C_{23}H_{19}F_4N_5O$, 457.2; m/z found 458.2 [M+H]$^+$. $^1$H NMR (400 MHz, Chloroform-d) 8.89-8.76 (m, 2H), 8.36 (s, 0.2H), 8.26-8.19 (m, 0.8H), 8.05-7.91 (m, 0.4H), 7.70 (dd, J=9.3, 2.7 Hz, 0.6H), 7.60-7.53 (m, 0.3H), 7.48-7.40 (m, 0.3H), 7.40-7.28 (m, 2.6H), 7.25-6.99 (m, 1.6H), 6.36 (d, J=8.7 Hz, 0.2H), 5.96 (d, J=8.8 Hz, 0.8H), 5.70 (s, 0.2H), 4.87-4.80 (m, 0.8H), 4.73 (d, J=5.3 Hz, 0.2H), 4.38 (s, 0.8H), 4.17 (s, 0.2H), 4.06-4.00 (m, 0.8H), 4.00-3.94 (m, 0.2H), 2.21 (dd, J=12.9, 8.0 Hz, 0.8H), 2.12-1.35 (m, 5.2H).

Example 281 (3-methyl-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone

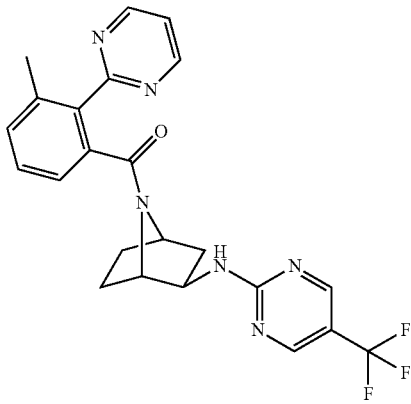

Prepared analogous to Example 269 substituting intermediate A-16 with intermediate A-26. MS (ESI) mass calcd. for: $C_{23}H_{21}F_3N_6O$, 454.2; m/z found 455.3 [M+H]$^+$. $^1$H NMR (500 MHz, Chloroform-d) 8.89-8.85 (m, 2H), 8.70 (s, 1H), 8.44-8.32 (m, 2H), 7.34-7.23 (m, 3H), 7.21-7.15 (m, 1H), 4.77-4.68 (m, 1H), 4.43-4.33 (m, 1H), 4.11 (d, J=5.1 Hz, 1H), 2.36 (s, 3H), 2.19 (dd, J=12.8, 7.9 Hz, 1H), 2.09-1.99 (m, 1H), 1.94-1.85 (m, 1H), 1.72-1.48 (m, 3H).

Example 282 (3-fluoro-2-(pyrimidin-2-yl)phenyl)((1S,2R,4R)-2-(methyl(5-(trifluoromethyl)pyrazin-2-yl)amino)-7-azabicyclo[2.2.1]heptan-7-yl)methanone

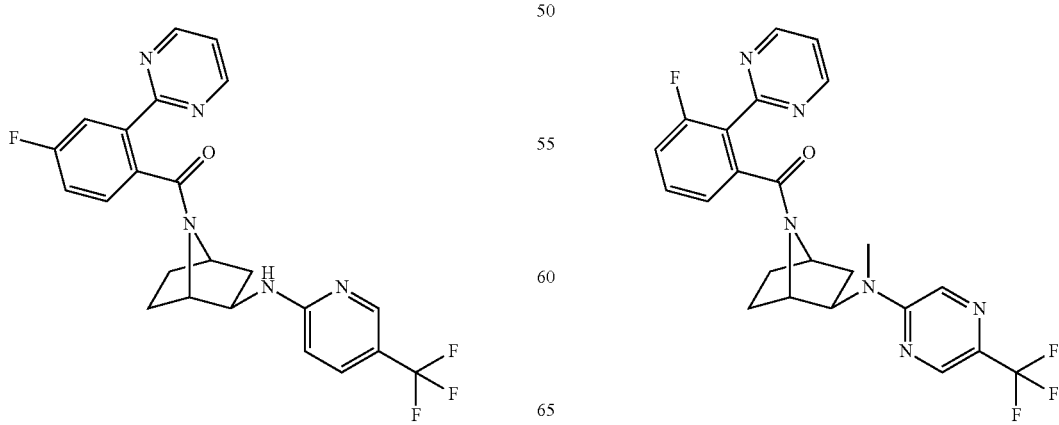

The title compound of Example 238 (63 mg, 0.14 mmol) was dissolved in DMF (1.4 mL) and then sodium tert-butoxide (15 mg, 0.15 mmol) followed by iodomethane (9 μL, 0.14 mmol) were added. After 15 h at room temperature the reaction mixture was diluted with EtOAc and water was added. The aqueous phase was extracted twice with EtOAc and the combined organic phases were dried over MgSO$_4$, filtered and evaporated. Purification was performed using Agilent prep method X to give the title compound (40 mg, 62%). MS (ESI) mass calcd. for: $C_{23}H_{20}F_4N_6O$, 472.2; m/z found 473.2 [M+H]$^+$. $^1$H NMR (500 MHz, Chloroform-d) 8.81 (d, J=4.9 Hz, 2H), 8.35 (s, 1H), 8.02 (s, 1H), 7.55-7.46 (m, 1H), 7.34-7.20 (m, 3H), 4.81-4.73 (m, 1H), 4.67 (d, J=4.3 Hz, 1H), 4.17-4.08 (m, 1H), 3.05 (s, 3H), 2.12 (dd, J=12.8, 8.3 Hz, 1H), 1.98-1.44 (m, 5H).

Example 283 (3-methyl-2-(oxazol-2-yl)phenyl)((1S, 2R,4R)-2-((5-(trifluoromethyl)pyrimidin-2-yl) amino)-7-azabicyclo[2.2.1]heptan-7-yl)methanone

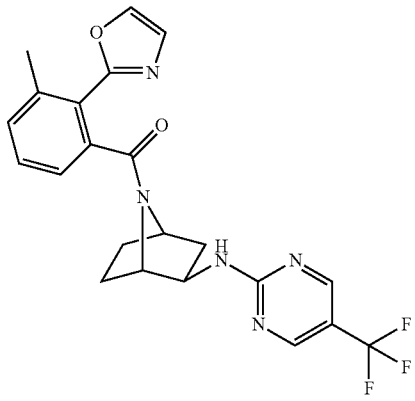 [SMILES: Cc1cccc(C(=O)N2C3CCC2C(Nc2ncc(C(F)(F)F)cn2)C3)c1-c1ncco1]

Prepared analogous to Example 269 substituting intermediate A-16 with intermediate A-31. MS (ESI) mass calcd. for: $C_{22}H_{20}F_3N_5O_2$, 443.2; m/z found 444.1 [M+H]$^+$. $^1$H NMR (400 MHz, Chloroform-d) 8.48 (s, 1H), 8.35 (s, 1H), 7.88-7.78 (m, 1H), 7.68 (s, 0.4H), 7.44-7.21 (m, 3.6H), 7.15 (dd, J=6.6, 2.2 Hz, 0.6H), 7.06-6.97 (m, 0.4H), 4.84-4.78 (m, 0.6H), 4.73-4.67 (m, 0.4H), 4.33 (td, J=8.4, 3.0 Hz, 0.4H), 4.24 (td, J=8.2, 3.7 Hz, 0.6H), 4.04-3.98 (m, 0.4H), 3.97-3.89 (m, 0.6H), 2.47 (s, 1.7H), 2.37 (s, 1.3H), 2.19-1.41 (m, 6H).

Example 284 (3-fluoro-2-(oxazol-2-yl)phenyl)((1S, 2R,4R)-2-((5-(trifluoromethyl)pyrimidin-2-yl) amino)-7-azabicyclo[2.2.1]heptan-7-yl)methanone

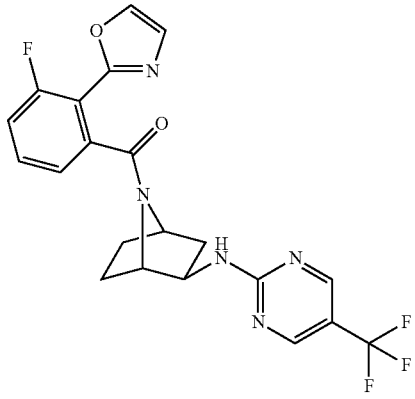

In a microwave vial was dissolved the title compound of Example 277 (30 mg, 0.06 mmol) and 2-(tributylstannyl) oxazole (15 μL, 0.07 mmol) in DME (1 mL). The solution was degassed with N$_2$ for 5 minutes then CuI (1 mg, 0.0045 mmol) and Pd(PPh$_3$)$_4$ (5 mg, 0.0045 mmol) were added. The reaction was purged with N$_2$ and heated at 145° C. for 3 h. The reaction was cooled to rt, filtered through a pad of celite and purified via prep HPLC to give the title compound (19 mg, 72%). MS (ESI) mass calcd. for: $C_{21}H_{17}F_4N_5O_2$, 447.1; m/z found 448.1 [M+H]$^+$. $^1$H NMR (500 MHz, Chloroform-d) 8.49 (s, 1H), 8.36 (s, 0.8H), 7.85 (s, 0.8H), 7.76 (s, 0.4H), 7.62-7.45 (m, 1H), 7.43-7.33 (m, 1H), 7.32-7.23 (m, 2H), 7.23-7.09 (m, 1H), 4.91-4.85 (m, 0.4H), 4.78 (d, J=5.4 Hz, 0.6H), 4.42 (td, J=8.6, 2.8 Hz, 0.6H), 4.28 (td, J=8.2, 3.6 Hz, 0.4H), 4.00-3.95 (m, 0.6H), 3.89 (d, J=4.4 Hz, 0.4H), 2.23-1.44 (m, 6H).

Example 285 (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone

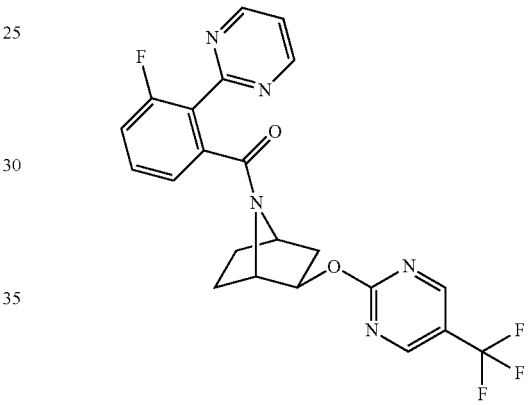

Step A: (±)-tert-butyl 2-((5-(trifluoromethyl)pyrimidin-2-yl)oxy)-7-azabicyclo[2.2.1]heptane-7-carboxylate: To (±)-tert-butyl 2-hydroxy-7-azabicyclo[2.2.1]heptane-7-carboxylate (exo) (52 mg, 0.25 mol) in DMF (5 mL) was added 60 wt % NaH (20 mg, 0.5 mmol) in one portion. The reaction was heated at 80° C. for 5 min, then 2-chloro-5-(trifluoromethyl)pyrimidine (89.7 mg, 0.49 mmol) was added. After heating at 80° C. for 2 hours, water was added and the mixture extracted with DCM (3×). The combined organics were dried (Na$_2$SO$_4$) and concentrated. Purification via silica gel chromatography (0-50% EtOAc in hexanes) gave the title compound (20 mg, 23%). MS (ESI) mass calcd. for: $C_{16}H_{20}F_3N_3O_3$, 359.4; m/z found 260.1 [M-Boc]$^+$.

Step B: (±)-(3-fluoro-2-(pyrimidin-2-yl)phenyl)(2-((5-(trifluoromethyl)pyrimidin-2-yl)oxy)-7-azabicyclo[2.2.1] heptan-7-yl)methanone: To (±)-tert-butyl 2-((5-(trifluoromethyl)pyrimidin-2-yl)oxy)-7-azabicyclo[2.2.1]heptane-7-carboxylate (20 mg, 0.06 mmol0 in DCM (2 mL) was added 2 mL (2M HCl in Et$_2$O) and stirred at rt for 3 h. The reaction mixture was concentrated and placed under high vacuum for 1 h. To the intermediate in DCM (2 mL) was added carboxylic acid (A-2) (13.3 mg, 0.06 mmol), HOBt (13.7 mg, 0.101 mmol), EDCI (19.4 mg, 0.101 mmol) and DIEPA (26 μL, 0.15 mmol). After stirring at rt for 2 h, saturated NaHCO$_3$ (aq.) was added and the mixture was extracted with DCM (3×). The combined organics were dried (Na$_2$SO$_4$), and concentrated. Purification via silica gel chromatography (0-100% EtOAc in hexanes) gave the title compound (9 mg, 38%). MS (ESI) mass calcd. for: $C_{22}H_{17}F_4N_5O_2$, 459.1; m/z found 460.1 [M+H]$^+$. $^1$H NMR (500 MHz, Chloroform-d) 8.88 (d, J=4.9 Hz, 1H), 8.81 (d, J=4.9 Hz, 1H), 8.74 (d, J=12.6 Hz, 2H), 7.63-7.27 (m, 3H), 7.14 (t, J=8.9 Hz, 1H), 4.99 (dt, J=8.3, 4.8 Hz, 1H), 4.87-4.66 (m, 1H), 4.16-3.97 (m, 1H), 2.07 (d, J=4.3 Hz, 1H), 1.91 (d, J=32.9 Hz, 1H), 1.85-1.68 (m, 2H), 1.66-1.60 (m, 1H), 1.51 (dd, J=7.9, 4.8 Hz, 1H).

Example 286 (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone

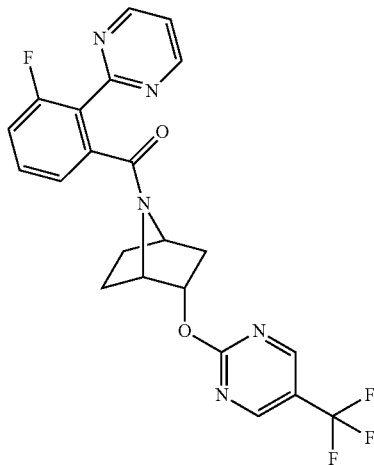 [SMILES: O=C(c1cccc(F)c1-c1ncccn1)N1C2CCC1C(Oc1ncc(C(F)(F)F)cn1)C2]

Step A: (±)-tert-butyl 2-((5-(trifluoromethyl)pyrimidin-2-yl)oxy)-7-azabicyclo[2.2.1]heptane-7-carboxylate: To (±)-tert-butyl 2-hydroxy-7-azabicyclo[2.2.1]heptane-7-carboxylate (endo) (150 mg, 0.703 mol) in DMF (8 mL) was added 60 wt % NaH (56.3 mg, 1.41 mmol) in one portion. The reaction was heated at 80° C. for 5 min, then 2-chloro-5-(trifluoromethyl)pyrimidine (257 mg, 1.4 mmol) was added. After heating at 80° C. for 2 hours, water was added and the mixture extracted with DCM (3×). The combined organics were dried (Na$_2$SO$_4$) and concentrated. Purification via silica gel chromatography (0-50% EtOAc in hexanes) gave the title compound (130 mg, 51%). MS (ESI) mass calcd. for: $C_{16}H_{20}F_3N_3O_3$, 359.4; m/z found 260.1 [M-Boc]$^+$. $^1$H NMR (400 MHz, Chloroform-d) 8.82-8.71 (m, 2H), 5.28 (d, J=10.0 Hz, 1H), 4.59 (s, 1H), 4.25 (s, 1H), 2.43 (dddd, J=13.1, 10.1, 5.2, 2.8 Hz, 1H), 2.18-2.04 (m, 1H), 1.85 (dd, J=7.8, 3.8 Hz, 1H), 1.69 (s, 1H), 1.59 (s, 2H), 1.47 (s, 9H).

Step B: (3-fluoro-2-(pyrimidin-2-yl)phenyl)((1R,2S,4S)-2-((5-(trifluoromethyl)pyrimidin-2-yl)oxy)-7-azabicyclo[2.2.1]heptan-7-yl)methanone: To (±)-tert-butyl 2-((5-(trifluoromethyl)pyrimidin-2-yl)oxy)-7-azabicyclo[2.2.1]heptane-7-carboxylate (143 mg, 0.398 mmol) in DCM (3 mL) was added 2M HCl in Et$_2$O (3 mL). After 3 h at rt the reaction mixture was concentrated and placed under high vacuum for 1 h. To the intermediate in DCM (3 mL) was added carboxylic acid (A-2) (95.5 mg, 0.438 mmol), HOBt (88.9 mg, 0.658 mmol0, EDCI (126.1 mg, 0.658 mmol) and DIEPA (170 μL, 0.987 mmol). After stirring at rt for 2 h, saturated NaHCO$_3$ (aq.) was added and the mixture was extracted with DCM (3×). The combined organics were dried (Na$_2$SO$_4$), and concentrated. Purification via silica gel chromatography (0-100% EtOAc in hexanes) gave the title compound (78.6 mg, 47%). MS (ESI) mass calcd. for: $C_{22}H_{17}F_4N_5O_2$, 459.1; m/z found 460.1 [M+H]$^+$. $^1$H NMR (400 MHz, Chloroform-d) δ 8.85 (t, J=5.2 Hz, 2H), 8.76 (d, J=12.3 Hz, 2H), 7.47 (dd, J=8.5, 5.4 Hz, 1H), 7.29 (td, J=5.4, 4.9, 4.3 Hz, 3H), 5.58-5.40 (m, 1H), 5.30 (s, 1H), 5.09-4.92 (m, 1H), 4.67 (s, 1H), 4.34 (s, 1H), 4.02 (s, 1H), 2.61-2.39 (m, 1H), 2.32-2.08 (m, 1H), 1.90 (d, J=13.7 Hz, 1H).

Example 287 (3-ethoxy-6-methylpyridin-2-yl)((1S,2R,4R)-2-((5-(trifluoromethyl)pyrazin-2-yl)amino)-7-azabicyclo[2.2.1]heptan-7-yl)methanone

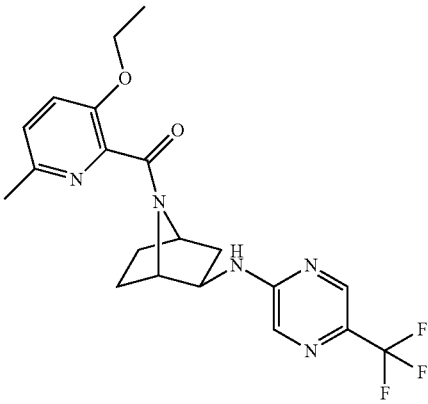 [SMILES: CCOc1ccc(C)nc1C(=O)N1C2CCC1C(Nc1cnc(C(F)(F)F)cn1)C2]

Prepared analogous to Example 238 substituting intermediate A-2 with intermediate A-8. MS (ESI) mass calcd. for: $C_{20}H_{22}F_3N_5O_2$, 421.2; m/z found 422.2 [M+H]$^+$. $^1$H NMR (400 MHz, Chloroform-d) 8.31 (s, 0.2H), 8.24 (s, 0.8H), 8.01-7.81 (m, 1.8H), 7.25-7.09 (m, 2H), 6.15 (d, J=8.0 Hz, 0.2H), 5.01-4.93 (m, 0.8H), 4.87-4.80 (m, 0.2H), 4.32-4.24 (m, 0.2H), 4.18-4.02 (m, 2.8H), 3.95 (d, J=4.6 Hz, 0.8H), 3.88-3.82 (m, 0.2H), 2.55-2.46 (m, 3H), 2.26-1.23 (m, 9H).

Example 288 (3-(2H-1,2,3-triazol-2-yl)pyridin-2-yl)((1S,2R,4R)-2-((5-(trifluoromethyl)pyrazin-2-yl)amino)-7-azabicyclo[2.2.1]heptan-7-yl)methanone

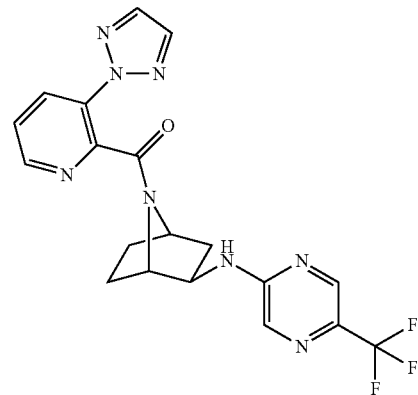 [SMILES: O=C(c1ncccc1-n1nccn1)N1C2CCC1C(Nc1cnc(C(F)(F)F)cn1)C2]

Prepared analogous to Example 238 substituting intermediate A-2 with intermediate A-27. MS (ESI) mass calcd. for: $C_{19}H_{17}F_3N_8O$, 430.1; m/z found 431.2 [M+H]$^+$. $^1$H NMR (400 MHz, Chloroform-d) 8.65 (dd, J=4.7, 1.5 Hz, 0.2H), 8.55 (dd, J=4.8, 1.5 Hz, 0.8H), 8.39-8.32 (m, 0.4H), 8.29-8.18 (m, 1.6H), 7.97-7.86 (m, 2.2H), 7.70 (s, 0.8H), 7.56 (dd, J=8.3, 4.7 Hz, 0.2H), 7.50 (dd, J=8.3, 4.7 Hz, 0.8H), 7.15 (d, J=8.6 Hz, 0.8H), 6.12 (d, J=8.6 Hz, 0.2H), 4.97-4.89 (m, 0.8H), 4.82 (d, J=5.2 Hz, 0.2H), 4.29 (td, J=7.9, 2.8 Hz, 1H), 4.12-4.07 (m, 0.2H), 4.04 (d, J=5.0 Hz, 0.8H), 2.27-1.43 (m, 6H).

Example 289 (2-methoxy-6-(pyrimidin-2-yl)phenyl)((1S,2R,4R)-2-((5-(trifluoromethyl)pyrazin-2-yl)amino)-7-azabicyclo[2.2.1]heptan-7-yl)methanone

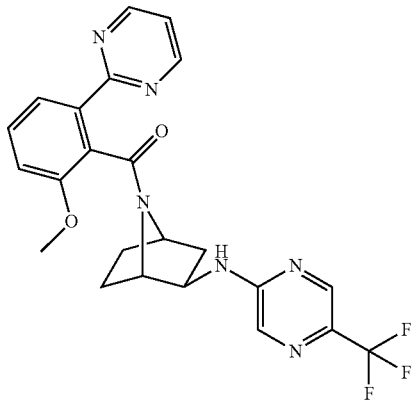 [SMILES: COc1cccc(-c2ncccn2)c1C(=O)N1C2CCC1C(Nc1cnc(C(F)(F)F)cn1)C2]

Prepared analogous to Example 238 substituting intermediate A-2 with intermediate A-28. MS (ESI) mass calcd. for: C$_{23}$H$_{21}$F$_3$N$_6$O$_2$, 470.2; m/z found 471.2[M+H]$^+$. $^1$H NMR (400 MHz, Chloroform-d) 8.89-8.71 (m, 2H), 8.53-8.14 (m, 1.5H), 7.99-7.76 (m, 0.5H), 7.60-7.29 (m, 3.7H), 7.23-6.99 (m, 1H), 6.08 (d, J=8.9 Hz, 0.2H), 5.78 (d, J=8.5 Hz, 0.1H), 5.00-4.78 (m, 1H), 4.46-4.35 (m, 1H), 4.07 (s, 0.5H), 3.91-3.79 (m, 3.5H), 2.32-1.24 (m, 6H).

Example 290 (2-fluoro-6-(pyrimidin-2-yl)phenyl)((1S,2R,4R)-2-((5-(trifluoromethyl)pyrazin-2-yl)amino)-7-azabicyclo[2.2.1]heptan-7-yl)methanone

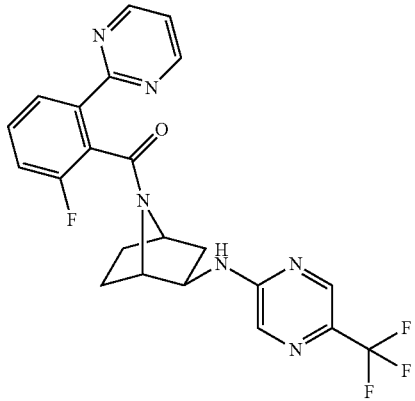 [SMILES: O=C(c1c(F)cccc1-c1ncccn1)N1C2CCC1C(Nc1cnc(C(F)(F)F)cn1)C2]

Prepared analogous to Example 238 substituting intermediate A-2 with intermediate A-6. MS (ESI) mass calcd. for: C$_{22}$H$_{18}$F$_4$N$_6$O, 458.1; m/z found 459.2 [M+H]$^+$. $^1$H NMR (400 MHz, Chloroform-d) 8.89-8.72 (m, 2H), 8.38-8.16 (m, 2H), 7.78 (dd, J=7.8, 1.1 Hz, 1H), 7.55-7.44 (m, 1H), 7.43-7.35 (m, 1H), 7.34-7.14 (m, 2H), 4.93-4.85 (m, 1H), 4.50-4.39 (m, 1H), 3.98-3.88 (m, 1H), 2.31-1.11 (m, 6H).

Example 291 (7-ethoxyquinolin-8-yl)((1S,2R,4R)-2-((5-(trifluoromethyl)pyrazin-2-yl)amino)-7-azabicyclo[2.2.1]heptan-7-yl)methanone

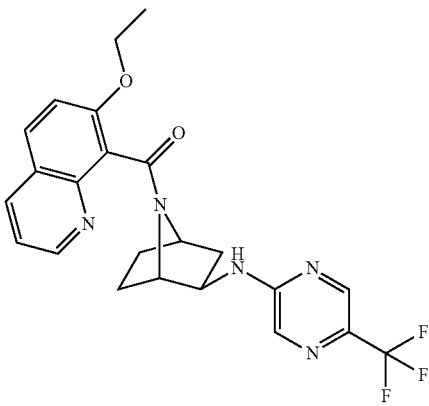 [SMILES: CCOc1ccc2cccnc2c1C(=O)N1C2CCC1C(Nc1cnc(C(F)(F)F)cn1)C2]

Prepared analogous to Example 238 substituting intermediate A-2 with intermediate A-29. MS (ESI) mass calcd. for: C$_{23}$H$_{22}$F$_3$N$_5$O$_2$, 457.2 m/z found 458.2 [M+H]$^+$.

Example 292 (2-(1,4-dimethyl-1H-pyrazol-5-yl)-6-methoxyphenyl)((1 S,2R,4R)-2-((5-(trifluoromethyl)pyrazin-2-yl)amino)-7-azabicyclo[2.2.1]heptan-7-yl)methanone

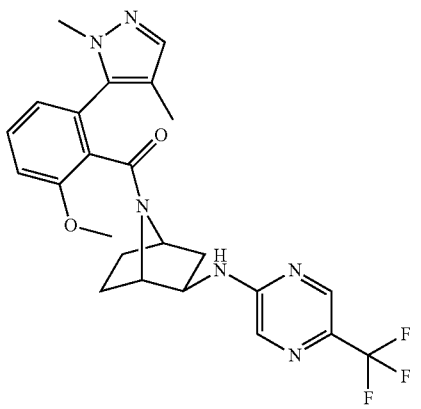 [SMILES: COc1cccc(-c2c(C)cnn2C)c1C(=O)N1C2CCC1C(Nc1cnc(C(F)(F)F)cn1)C2]

Prepared analogous to Example 238 substituting intermediate A-2 with intermediate A-30. MS (ESI) mass calcd. for: C$_{24}$H$_{25}$F$_3$N$_6$O$_2$, 486.2 m/z found 487.2 [M+H]$^+$.

Example 293 (3-methyl-2-(pyridin-2-yl)phenyl)((1S,2R,4R)-2-((5-(trifluoromethyl)pyrimidin-2-yl)amino)-7-azabicyclo[2.2.1]heptan-7-yl)methanone

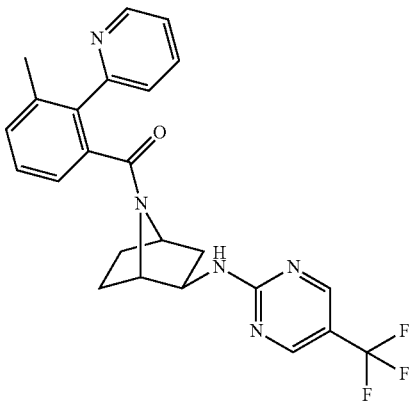 [SMILES: Cc1cccc(C(=O)N2C3CCC2C(Nc2ncc(C(F)(F)F)cn2)C3)c1-c1ccccn1]

Prepared analogous to Example 284 substituting title compound of Example 277 with title compound of Example 276 and 2-(tributylstannyl)oxazole with 2-(tributylstannyl)pyridine. MS (ESI) mass calcd. for: $C_{24}H_{22}F_3N_5O$, 453.2 m/z found 454.2 [M+H]$^+$. $^1$H NMR (400 MHz, Chloroform-d) 8.72-8.66 (m, 1H), 8.45 (s, 0.5H), 8.39 (s, 1.5H), 7.86-7.75 (m, 1H), 7.52-7.44 (m, 1H), 7.38-7.20 (m, 4.2H), 7.18-7.12 (m, 0.8H), 4.72-4.65 (m, 0.8H), 4.49-4.45 (m, 0.2H), 4.32 (s, 0.8H), 4.03-3.95 (m, 1H), 3.88-3.83 (m, 0.2H), 2.26 (s, 2.2H), 2.23 (s, 0.8H), 2.16 (dd, J=12.8, 7.9 Hz, 0.8H), 1.98-1.08 (m, 5.2H).

Example 294 (3-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone

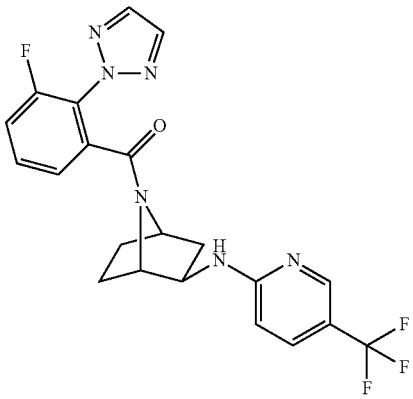

Prepared analogous to Example 279 substituting intermediate A-2 with intermediate A-16. MS (ESI) mass calcd. for: $C_{21}H_{18}F_4N_6O$, 446.1 m/z found 447.2 [M+H]$^+$. $^1$H NMR (500 MHz, Chloroform-d) 8.33 (s, 0.2H), 8.23 (s, 0.8H), 7.96 (s, 1.55H), 7.91 (s, 0.45H), 7.57-7.48 (m, 0.4H), 7.44-7.29 (m, 2H), 7.30-7.21 (m, 0.8H), 7.21-7.13 (m, 0.8H), 6.72 (s, 0.6H), 6.36-6.25 (m, 1H), 5.34 (s, 0.2H), 4.78-4.69 (m, 0.8H), 4.61 (d, J=5.2 Hz, 0.2H), 4.28 (s, 0.8H), 4.12 (s, 0.2H), 4.05-3.95 (m, 1H), 2.17-1.41 (m, 6H).

Example 295 (3-methyl-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone

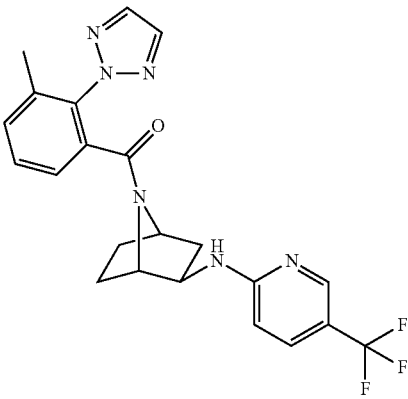 [SMILES: Cc1cccc(C(=O)N2C3CCC2C(Nc2ccc(C(F)(F)F)cn2)C3)c1-n1nccn1]

Prepared analogous to Example 279 substituting intermediate A-2 with intermediate A-24. MS (ESI) mass calcd. for: $C_{22}H_{21}F_3N_6O$, 442.1 m/z found 443.2 [M+H]$^+$. $^1$H NMR (500 MHz, Chloroform-d) 8.32 (s, 0.2H), 8.23 (s, 0.8H), 7.90 (s, 1.55H), 7.85 (s, 0.45H), 7.57-7.25 (m, 3.2H), 7.24-7.15 (m, 0.8H), 6.93 (s, 0.8H), 6.38-6.27 (m, 1H), 5.22 (s, 0.2H), 4.74-4.65 (m, 0.8H), 4.55 (d, J=4.7 Hz, 0.2H), 4.28 (s, 0.8H), 4.09 (s, 0.2H), 4.03-3.95 (m, 1H), 2.20 (s, 3H), 2.13-1.38 (m, 6H).

Example 296 (3-methyl-2-(oxazol-2-yl)phenyl)((1S,2R,4R)-2-((5-(trifluoromethyl)pyridin-2-yl)amino)-7-azabicyclo[2.2.1]heptan-7-yl)methanone

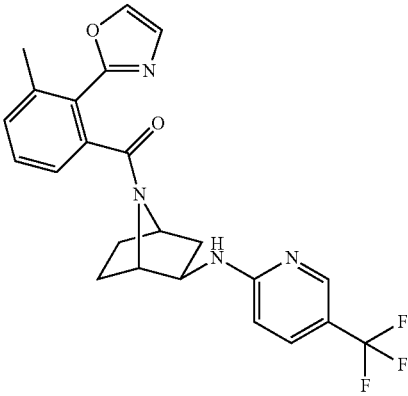

Prepared analogous to Example 279 substituting intermediate A-2 with intermediate A-31. MS (ESI) mass calcd. for: $C_{23}H_{21}F_3N_4O_2$, 442.2 m/z found 443.2 [M+H]$^+$. $^1$H NMR (500 MHz, Chloroform-d) 8.19 (s, 1H), 7.91-7.80 (m, 2H), 7.32-7.21 (m, 4H), 7.19-7.13 (m, 1H), 6.32 (d, J=8.8 Hz, 1H), 4.79-4.72 (m, 1H), 4.36-4.28 (m, 1H), 3.93 (d, J=4.6 Hz, 1H), 2.29 (s, 3H), 2.10 (dd, J=12.9, 8.1 Hz, 1H), 2.00-1.85 (m, 2H), 1.76-1.64 (m, 2H), 1.55-1.46 (m, 1H).

Example 297 (3-fluoro-2-(pyrimidin-2-yl)phenyl)((1R,2S,4S)-2-((5-(trifluoromethyl)pyrazin-2-yl)amino)-7-azabicyclo[2.2.1]heptan-7-yl)methanone

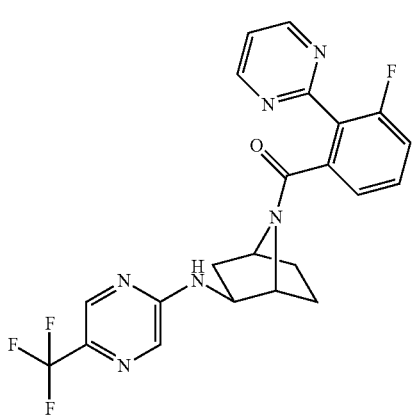 [SMILES: O=C(c1cccc(F)c1-c1ncccn1)N1C2CCC1C(Nc1cnc(C(F)(F)F)cn1)C2]

Prepared analogous to Example 238 substituting intermediate B-5 with intermediate B-8. MS (ESI) mass calcd. for $C_{22}H_{18}F_4N_6O$, 458.2; m/z found 459.1 $[M+H]^+$. $^1H$ NMR (500 MHz, Chloroform-d) 8.91-8.84 (m, 2H), 8.27 (s, 1H), 8.19 (s, 1H), 7.65 (d, J=1.4 Hz, 1H), 7.44-7.34 (m, 2H), 7.24-7.16 (m, 2H), 4.77-4.68 (m, 1H), 4.43-4.33 (m, 1H), 4.07 (d, J=5.1 Hz, 1H), 2.16 (dd, J=13.0, 8.2 Hz, 1H), 2.10-1.99 (m, 1H), 1.98-1.86 (m, 1H), 1.78-1.65 (m, 2H), 1.58-1.48 (m, 1H).

Example 298: (3-fluoro-2-(oxazol-2-yl)phenyl)((1S,2R,4R)-2-((5-(trifluoromethyl)pyridin-2-yl)amino)-7-azabicyclo[2.2.1]heptan-7-yl)methanone

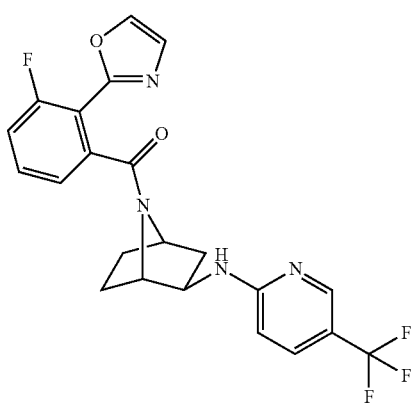 [SMILES: O=C(c1cccc(F)c1-c1ncco1)N1C2CCC1C(Nc1ccc(C(F)(F)F)cn1)C2]

Example 299: (3-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone

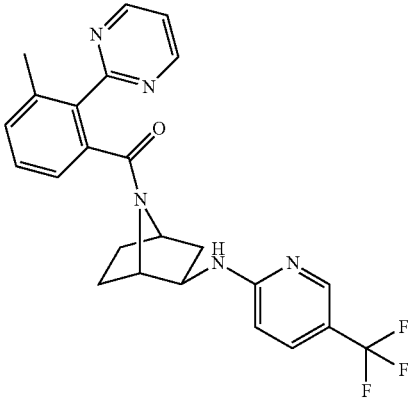 [SMILES: Cc1cccc(C(=O)N2C3CCC2C(Nc2ccc(C(F)(F)F)cn2)C3)c1-c1ncccn1]

Example 300: (3-chloro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

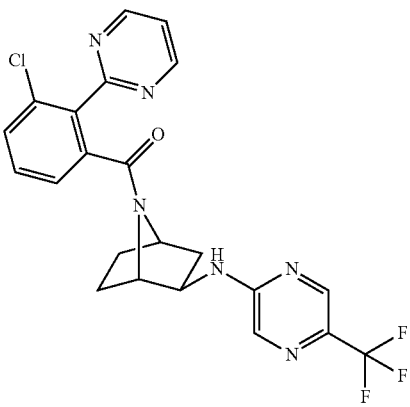 [SMILES: O=C(c1cccc(Cl)c1-c1ncccn1)N1C2CCC1C(Nc1cnc(C(F)(F)F)cn1)C2]

Example 301: ((1S,2R,4R)-2-((5-bromopyridin-2-yl)amino)-7-azabicyclo[2.2.1]heptan-7-yl)(3-fluoro-2-(oxazol-2-yl)phenyl)methanone

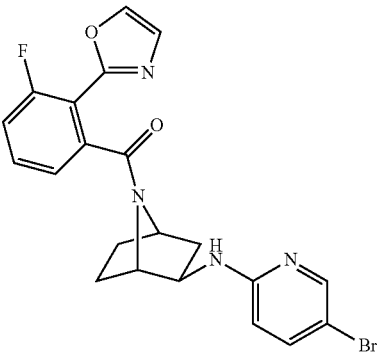

Example 302: ((1S,2R,4R)-2-((5-bromopyridin-2-yl)amino)-7-azabicyclo[2.2.1]heptan-7-yl)(3-methyl-2-(oxazol-2-yl)phenyl)methanone

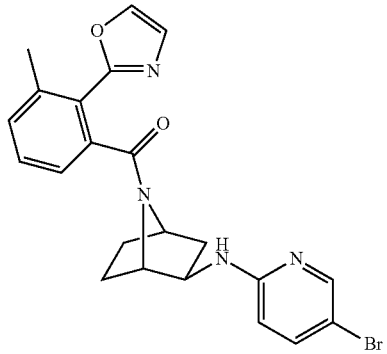

Example 303: ((1S,2R,4R)-2-((5-bromopyridin-2-yl)amino)-7-azabicyclo[2.2.1]heptan-7-yl)(3-fluoro-2-(pyrimidin-2-yl)phenyl)methanone

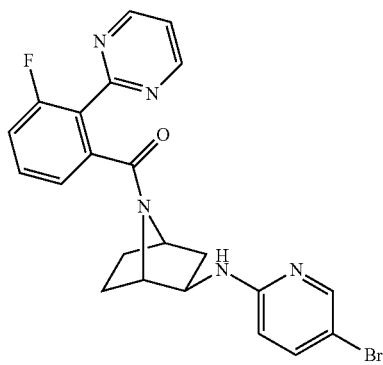

Example 304: ((1S,2R,4R)-2-((5-bromopyridin-2-yl)amino)-7-azabicyclo[2.2.1]heptan-7-yl)(3-methyl-2-(pyrimidin-2-yl)phenyl)methanone

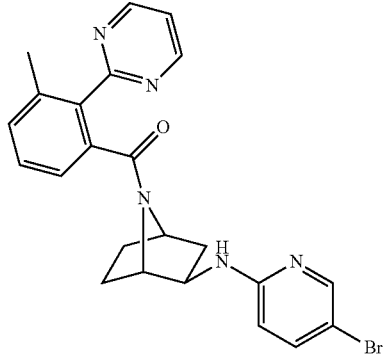 [SMILES: Cc1cccc(C(=O)N2C3CCC2C(Nc2ccc(Br)cn2)C3)c1-c1ncccn1]

Example 305: ((1S,2R,4R)-2-((5-bromopyridin-2-yl)amino)-7-azabicyclo[2.2.1]heptan-7-yl)(3-fluoro-2-(2H-1,2,3-triazol-2-yl)phenyl)methanone

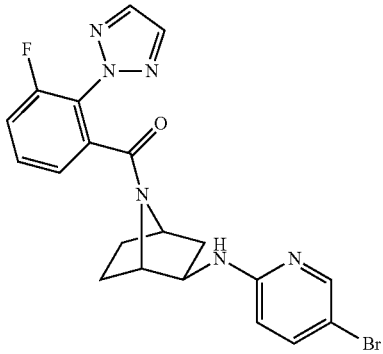

Example 306: ((1S,2R,4R)-2-((5-bromopyridin-2-yl)amino)-7-azabicyclo[2.2.1]heptan-7-yl)(3-methyl-2-(2H-1,2,3-triazol-2-yl)phenyl)methanone

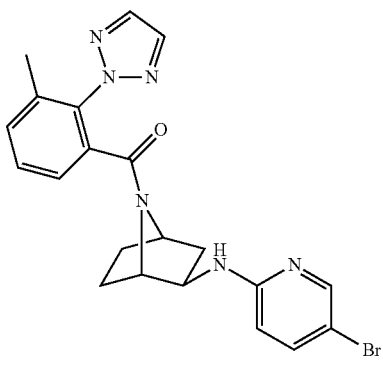

Example 307: ((1S,2R,4R)-2-((5-bromopyrazin-2-yl)amino)-7-azabicyclo[2.2.1]heptan-7-yl)(3-fluoro-2-(oxazol-2-yl)phenyl)methanone

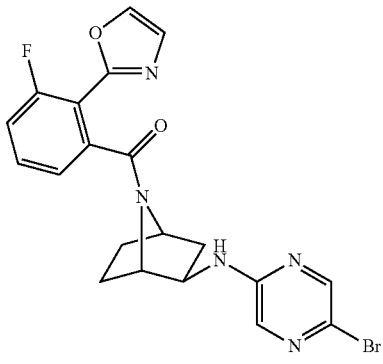

Example 308: ((1S,2R,4R)-2-((5-bromopyrazin-2-yl)amino)-7-azabicyclo[2.2.1]heptan-7-yl)(3-methyl-2-(oxazol-2-yl)phenyl)methanone

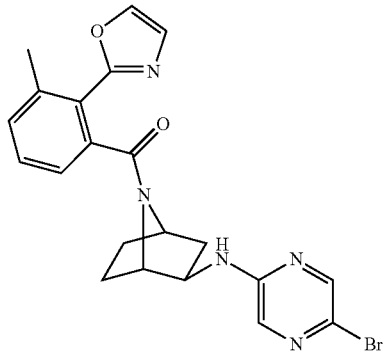 [SMILES: Cc1cccc(C(=O)N2C3CCC2C(Nc2cnc(Br)cn2)C3)c1-c1ncco1]

Example 309: ((1S,2R,4R)-2-((5-bromopyrazin-2-yl)amino)-7-azabicyclo[2.2.1]heptan-7-yl)(3-fluoro-2-(pyrimidin-2-yl)phenyl)methanone

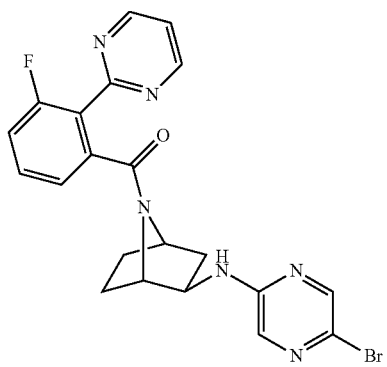 [SMILES: O=C(c1cccc(F)c1-c1ncccn1)N1C2CCC1C(Nc1cnc(Br)cn1)C2]

Example 310: ((1S,2R,4R)-2-((5-bromopyrazin-2-yl)amino)-7-azabicyclo[2.2.1]heptan-7-yl)(3-methyl-2-(pyrimidin-2-yl)phenyl)methanone

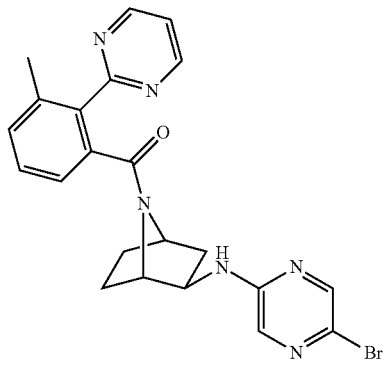 [SMILES: Cc1cccc(C(=O)N2C3CCC2C(Nc2cnc(Br)cn2)C3)c1-c1ncccn1]

Example 311: ((1S,2R,4R)-2-((5-bromopyrazin-2-yl)amino)-7-azabicyclo[2.2.1]heptan-7-yl)(3-methyl-2-(2H-1,2,3-triazol-2-yl)phenyl)methanone

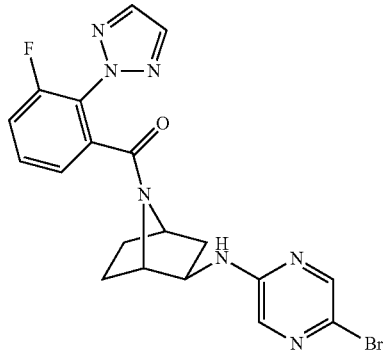

Example 312: ((1S,2R,4R)-2-((5-bromopyrimidin-2-yl)amino)-7-azabicyclo[2.2.1]heptan-7-yl)(3-fluoro-2-(oxazol-2-yl)phenyl)methanone

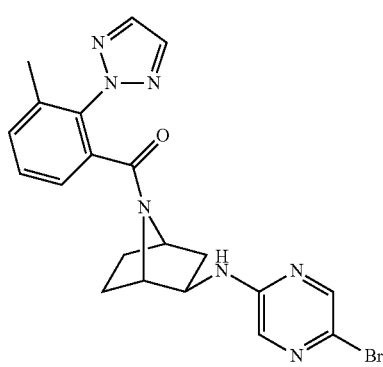 [SMILES: Cc1cccc(C(=O)N2C3CCC2C(Nc2cnc(Br)cn2)C3)c1-n1nccn1]

Example 313: ((1S,2R,4R)-2-((5-bromopyrimidin-2-yl)amino)-7-azabicyclo[2.2.1]heptan-7-yl)(3-fluoro-2-(oxazol-2-yl)phenyl)methanone

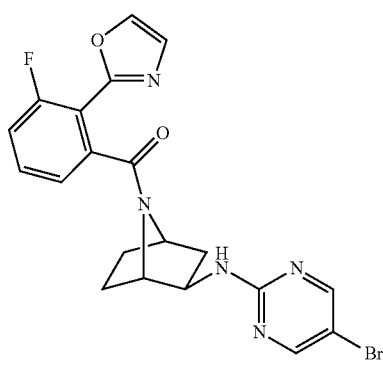 [SMILES: O=C(c1cccc(F)c1-c1ncco1)N1C2CCC1C(Nc1ncc(Br)cn1)C2]

Example 314: ((1S,2R,4R)-2-((5-bromopyrimidin-2-yl)amino)-7-azabicyclo[2.2.1]heptan-7-yl)(3-methyl-2-(oxazol-2-yl)phenyl)methanone

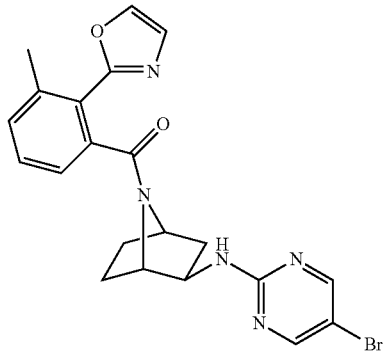 [SMILES: Cc1cccc(C(=O)N2C3CCC2C(Nc2ncc(Br)cn2)C3)c1-c1ncco1]

Example 315: ((1S,2R,4R)-2-((5-bromopyrimidin-2-yl)amino)-7-azabicyclo[2.2.1]heptan-7-yl)(3-fluoro-2-(pyrimidin-2-yl)phenyl)methanone

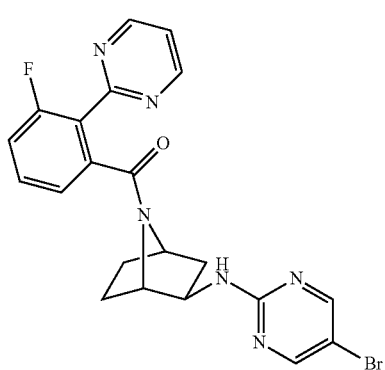

Example 316: ((1S,2R,4R)-2-((5-bromopyrimidin-2-yl)amino)-7-azabicyclo[2.2.1]heptan-7-yl)(3-methyl-2-(pyrimidin-2-yl)phenyl)methanone

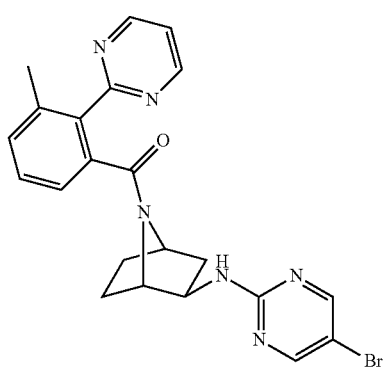 [SMILES: Cc1cccc(C(=O)N2C3CCC2C(Nc2ncc(Br)cn2)C3)c1-c1ncccn1]

Example 317: ((1S,2R,4R)-2-((5-bromopyrimidin-2-yl)amino)-7-azabicyclo[2.2.1]heptan-7-yl)(3-fluoro-2-(2H-1,2,3-triazol-2-yl)phenyl)methanone

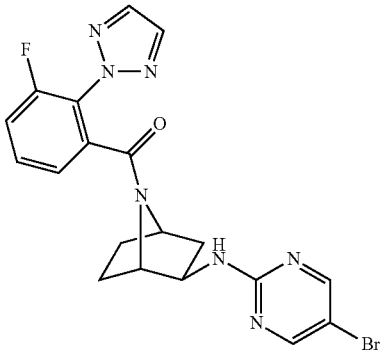 [SMILES: Cc1cccc(C(=O)N2C3CCC2C(Nc2ncc(Br)cn2)C3)c1-n1nccn1]

Example 318: ((1S,2R,4R)-2-((5-bromopyrimidin-2-yl)amino)-7-azabicyclo[2.2.1]heptan-7-yl)(3-methyl-2-(2H-1,2,3-triazol-2-yl)phenyl)methanone

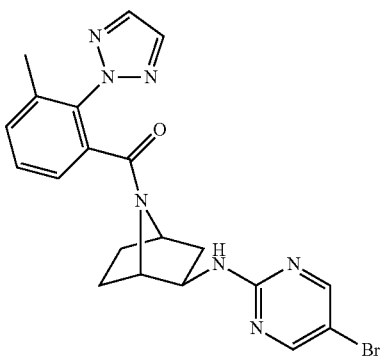

Example 319: (3-methyl-2-(pyridin-2-yl)phenyl)((1S,2R,4R)-2-((5-(trifluoromethyl)pyridin-2-yl)amino)-7-azabicyclo[2.2.1]heptan-7-yl)methanone

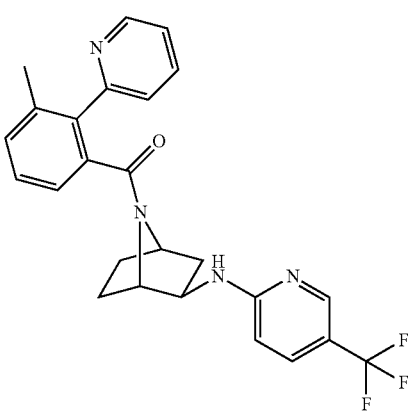 [SMILES: O=C(c1cccc(F)c1-c1ccccn1)N1C2CCC1C(Nc1ccc(C(F)(F)F)cn1)C2]

Example 320: (3-fluoro-2-(pyridin-2-yl)phenyl)((1S, 2R,4R)-2-((5-(trifluoromethyl)pyridin-2-yl)amino)-7-azabicyclo[2.2.1]heptan-7-yl)methanone

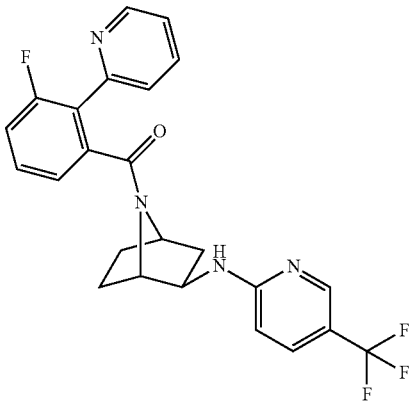

Example 321: (3-fluoro-2-(pyridin-2-yl)phenyl)((1S, 2R,4R)-2-((5-(trifluoromethyl)pyrimidin-2-yl)amino)-7-azabicyclo[2.2.1]heptan-7-yl)methanone

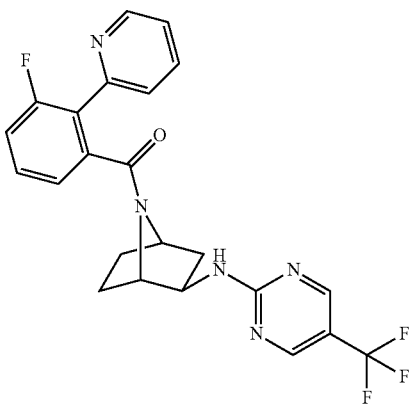

Example 322: (3-methyl-2-(pyridin-2-yl)phenyl)((1S,2R,4R)-2-((5-(trifluoromethyl)pyrazin-2-yl)amino)-7-azabicyclo[2.2.1]heptan-7-yl)methanone

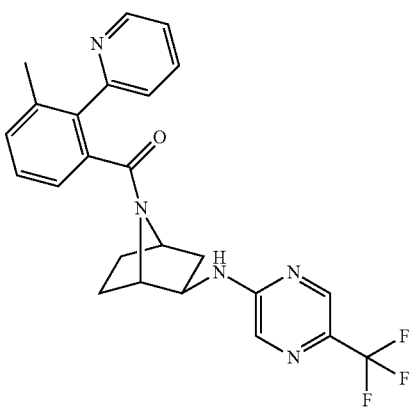

Example 323: (3-fluoro-2-(pyridin-2-yl)phenyl)((2S)-2-((5-(trifluoromethyl)pyrazin-2-yl)amino)-7-azabicyclo[2.2.1]heptan-7-yl)methanone

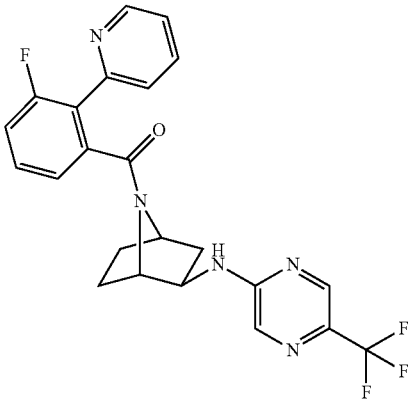 [SMILES: Cc1cccc(C(=O)N2C3CCC2C(Nc2cnc(C(F)(F)F)cn2)C3)c1-c1ccccn1]

Example 324: (3-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone

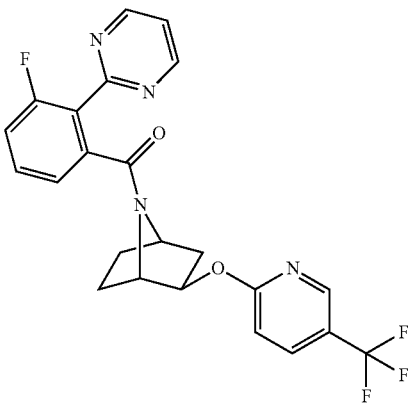 [SMILES: O=C(c1cccc(F)c1-c1ncccn1)N1C2CCC1C(Oc1ccc(C(F)(F)F)cn1)C2]

Example 325: (2-methoxy-6-(pyrimidin-2-yl)phenyl)((1S,2R,4R)-2-((5-(trifluoromethyl)pyridin-2-yl)oxy)-7-azabicyclo[2.2.1]heptan-7-yl)methanone

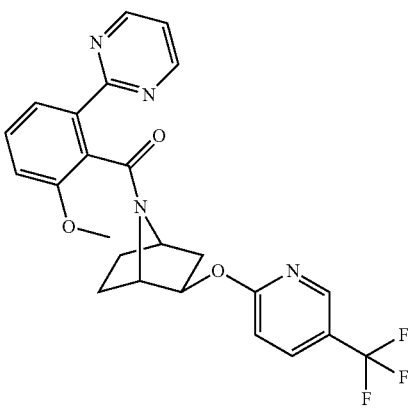 [SMILES: COc1cccc(-c2ncccn2)c1C(=O)N1C2CCC1C(Oc1ccc(C(F)(F)F)cn1)C2]

Example 326: (5-fluoro-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

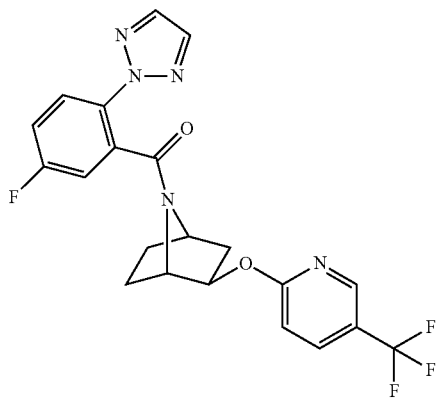 [SMILES: O=C(c1cc(F)ccc1-n1nccn1)N1C2CCC1C(Oc1ccc(C(F)(F)F)cn1)C2]

Example 327: (4-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

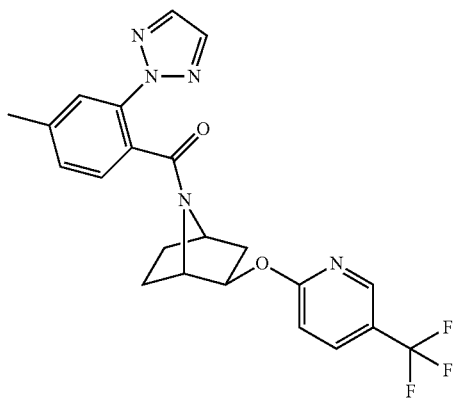

Example 328: (3-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

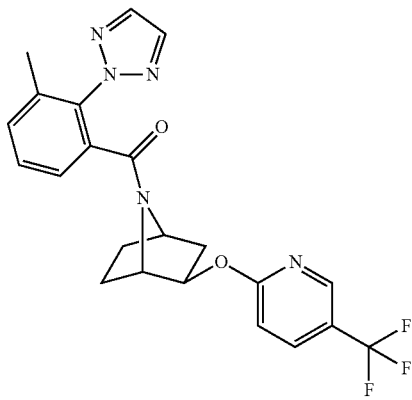 [SMILES: Cc1cccc(C(=O)N2C3CCC2C(Oc2ccc(C(F)(F)F)cn2)C3)c1-n1nccn1]

Example 329: (5-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone

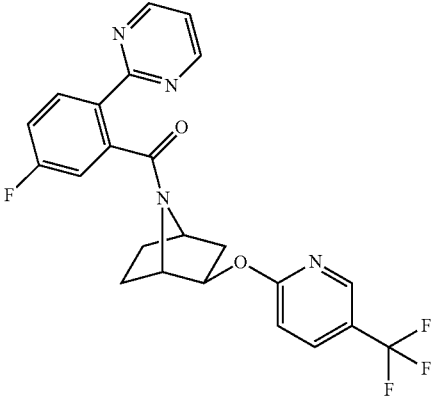 [SMILES: O=C(c1cc(F)ccc1-c1ncccn1)N1C2CCC1C(Oc1ccc(C(F)(F)F)cn1)C2]

Example 330: (2-fluoro-6-(pyrimidin-2-yl)phenyl)((1S,2R,4R)-2-((5-(trifluoromethyl)pyridin-2-yl)oxy)-7-azabicyclo[2.2.1]heptan-7-yl)methanone

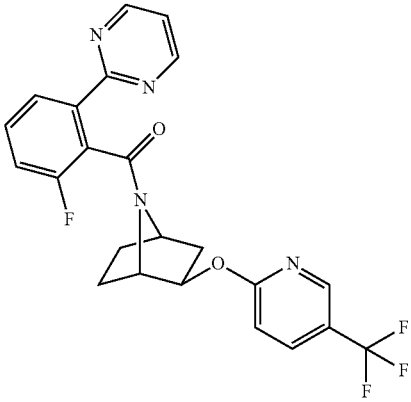

Example 331: (2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

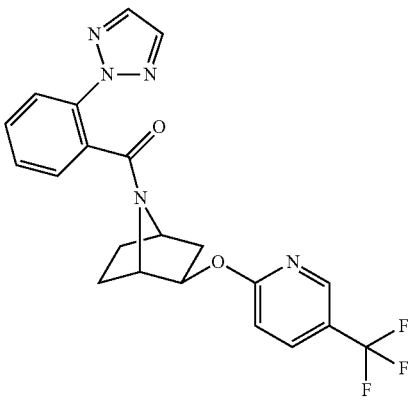 [SMILES: O=C(c1ccccc1-n1nccn1)N1C2CCC1C(Oc1ccc(C(F)(F)F)cn1)C2]

Example 332: (6-methyl-3-(2H-1,2,3-triazol-2-yl)pyridin-2-yl)((1S,2R,4R)-2-((5-(trifluoromethyl)pyridin-2-yl)oxy)-7-azabicyclo[2.2.1]heptan-7-yl)methanone

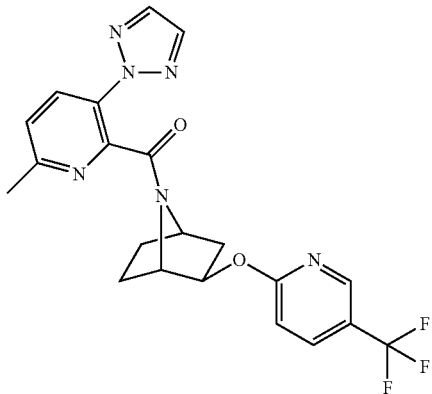

Example 333: (3-methyl-2-(oxazol-2-yl)phenyl)((1S,2R,4R)-2-((5-(trifluoromethyl)pyridin-2-yl)oxy)-7-azabicyclo[2.2.1]heptan-7-yl)methanone

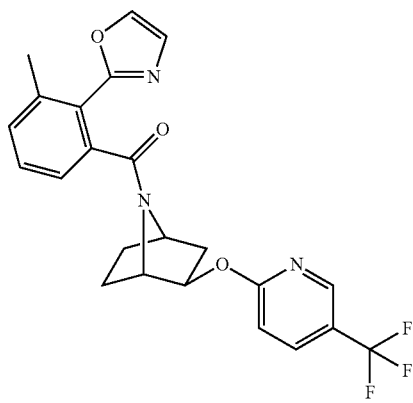 [SMILES: Cc1cccc(C(=O)N2C3CCC2C(Oc2ccc(C(F)(F)F)cn2)C3)c1-c1ncco1]

Example 334: (3-methyl-2-(pyridin-2-yl)phenyl)((1S,2R,4R)-2-((5-(trifluoromethyl)pyridin-2-yl)oxy)-7-azabicyclo[2.2.1]heptan-7-yl)methanone

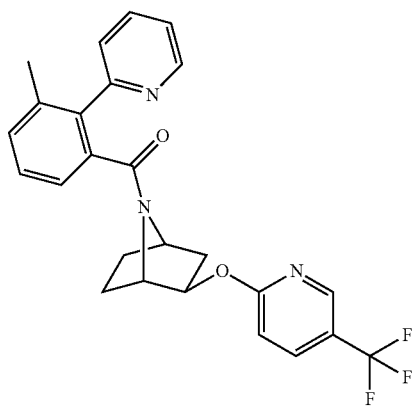 [SMILES: Cc1cccc(C(=O)N2C3CCC2C(Oc2ccc(C(F)(F)F)cn2)C3)c1-c1ccccn1]

Example 335: (2-(5-fluoropyrimidin-2-yl)phenyl)((1S,2R,4R)-2-((5-(trifluoromethyl)pyridin-2-yl)oxy)-7-azabicyclo[2.2.1]heptan-7-yl)methanone

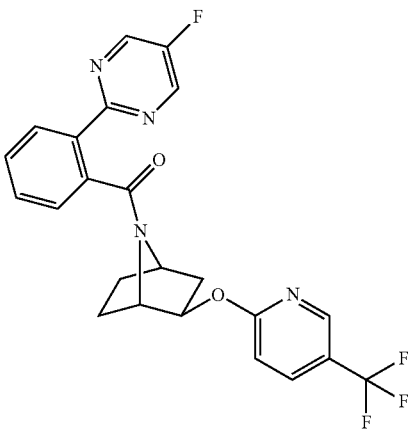 [SMILES: O=C(c1ccccc1-c1ncc(F)cn1)N1C2CCC1C(Oc1ccc(C(F)(F)F)cn1)C2]

Example 336: (2-fluoro-6-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

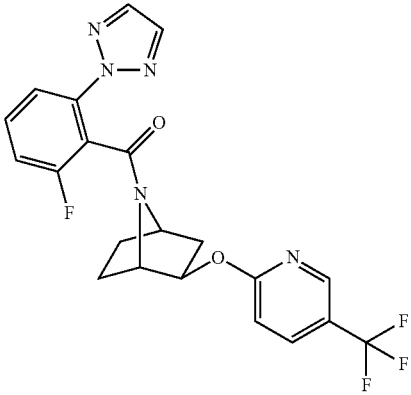

Example 337: (5-methyl-3-(2H-1,2,3-triazol-2-yl)pyridin-2-yl)((1 S,2R,4R)-2-((5-(trifluoromethyl)pyridin-2-yl)oxy)-7-azabicyclo[2.2.1]heptan-7-yl)methanone

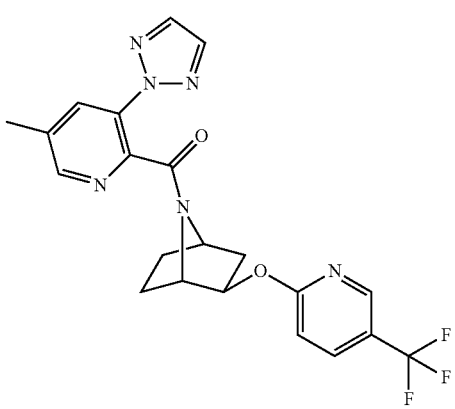

Example 338: (2-bromo-3-fluorophenyl)((1S,2R,4R)-2-((5-(trifluoromethyl)pyridin-2-yl)oxy)-7-azabicyclo[2.2.1]heptan-7-yl)methanone

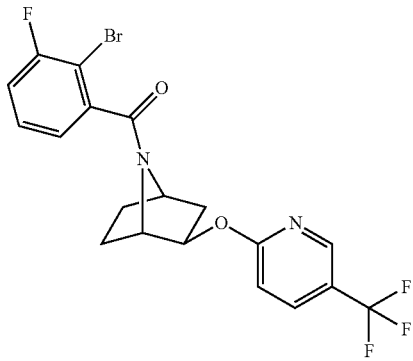 [SMILES: O=C(c1cccc(F)c1Br)N1C2CCC1C(Oc1ccc(C(F)(F)F)cn1)C2]

Example 339: (3-fluoro-2-(pyrimidin-2-yl)phenyl)((1S,2R,4R)-2-((5-(trifluoromethyl)pyrazin-2-yl)oxy)-7-azabicyclo[2.2.1]heptan-7-yl)methanone

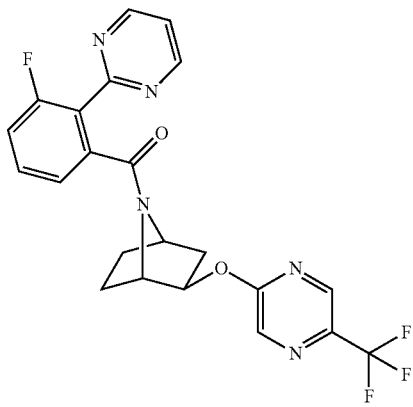 [SMILES: O=C(c1cccc(F)c1-c1ncccn1)N1C2CCC1C(Oc1cnc(C(F)(F)F)cn1)C2]

Example 340: (2-methoxy-6-(pyrimidin-2-yl)phenyl)((1S,2R,4R)-2-((5-(trifluoromethyl)pyrazin-2-yl)oxy)-7-azabicyclo[2.2.1]heptan-7-yl)methanone

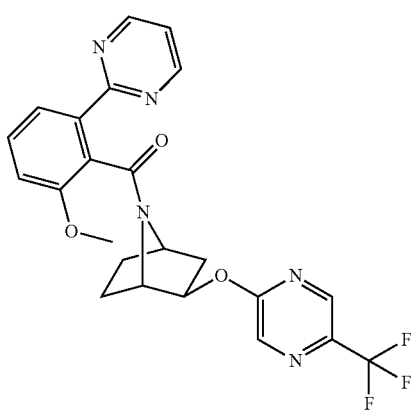 [SMILES: COc1cccc(-c2ncccn2)c1C(=O)N1C2CCC1C(Oc1cnc(C(F)(F)F)cn1)C2]

Example 341: (5-fluoro-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone

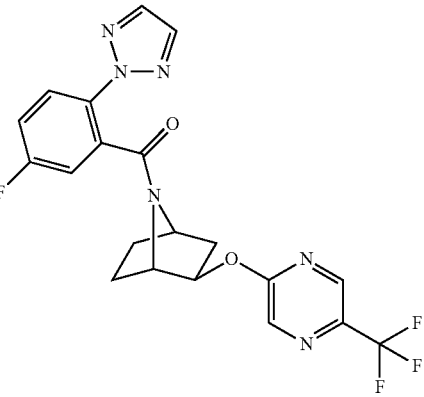

Example 342: (4-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone

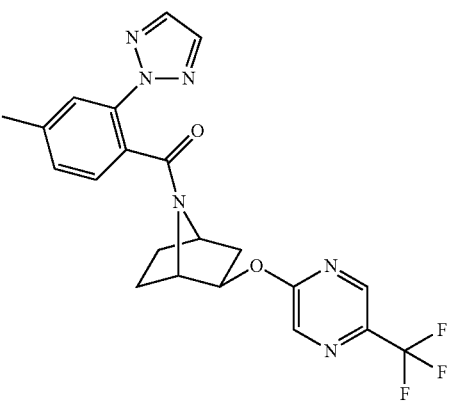

Example 343: (3-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone

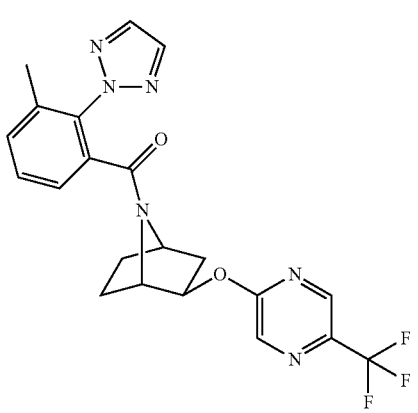 [SMILES: Cc1cccc(C(=O)N2C3CCC2C(Oc2cnc(C(F)(F)F)cn2)C3)c1-n1nccn1]

Example 344: (5-fluoro-2-(pyrimidin-2-yl)phenyl)
((1S,2R,4R)-2-((5-(trifluoromethyl)pyrazin-2-yl)
oxy)-7-azabicyclo[2.2.1]heptan-7-yl)methanone

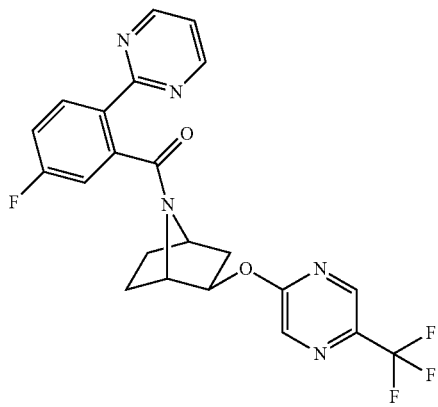 [SMILES: O=C(c1cc(F)ccc1-c1ncccn1)N1C2CCC1C(Oc1cnc(C(F)(F)F)cn1)C2]

Example 345: (2-fluoro-6-(pyrimidin-2-yl)phenyl)
((1S,2R,4R)-2-((5-(trifluoromethyl)pyrazin-2-yl)
oxy)-7-azabicyclo[2.2.1]heptan-7-yl)methanone

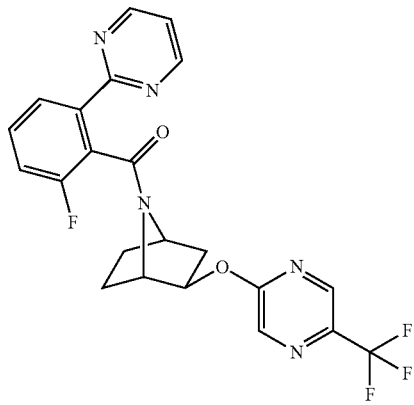 [SMILES: O=C(c1c(F)cccc1-c1ncccn1)N1C2CCC1C(Oc1cnc(C(F)(F)F)cn1)C2]

Example 346: (2-(2H-1,2,3-triazol-2-yl)phenyl)((1S,
2R,4R)-2-((5-(trifluoromethyl)pyrazin-2-yl)oxy)-7-
azabicyclo[2.2.1]heptan-7-yl)methanone

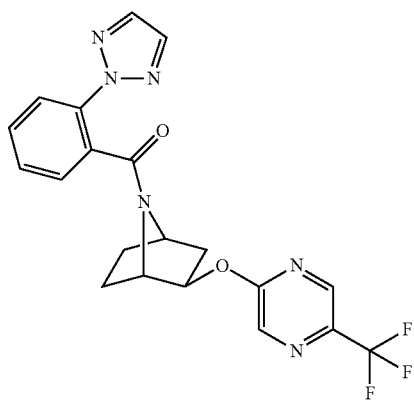 [SMILES: O=C(c1ccccc1-n1nccn1)N1C2CCC1C(Oc1cnc(C(F)(F)F)cn1)C2]

Example 347: (6-methyl-3-(2H-1,2,3-triazol-2-yl)
pyridin-2-yl)((1S,2R,4R)-2-((5-(trifluoromethyl)
pyrazin-2-yl)oxy)-7-azabicyclo[2.2.1]heptan-7-yl)
methanone

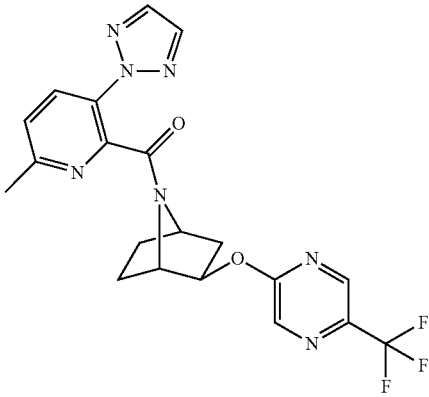

Example 348: (3-methyl-2-(oxazol-2-yl)phenyl)
((1S,2R,4R)-2-((5-(trifluoromethyl)pyrazin-2-yl)
oxy)-7-azabicyclo[2.2.1]heptan-7-yl)methanone

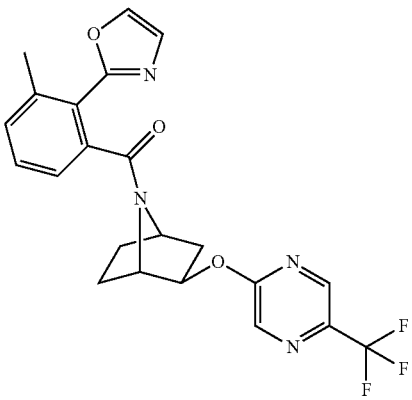 [SMILES: Cc1cccc(C(=O)N2C3CCC2C(Oc2cnc(C(F)(F)F)cn2)C3)c1-c1ncco1]

Example 349: (3-methyl-2-(pyridin-2-yl)phenyl)
((1S,2R,4R)-2-((5-(trifluoromethyl)pyrazin-2-yl)
oxy)-7-azabicyclo[2.2.1]heptan-7-yl)methanone

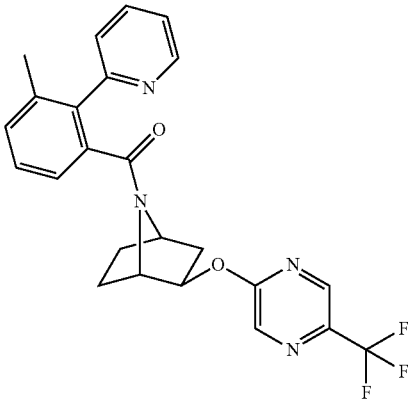 [SMILES: Cc1cccc(C(=O)N2C3CCC2C(Oc2cnc(C(F)(F)F)cn2)C3)c1-c1ccccn1]

Example 350: (2-(5-fluoropyrimidin-2-yl)phenyl)
((1S,2R,4R)-2-((5-(trifluoromethyl)pyrazin-2-yl)
oxy)-7-azabicyclo[2.2.1]heptan-7-yl)methanone

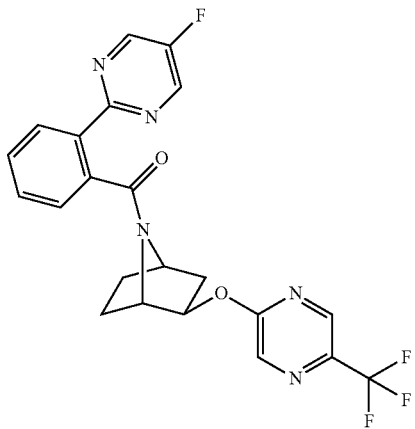 [SMILES: O=C(c1ccccc1-c1ncc(F)cn1)N1C2CCC1C(Oc1cnc(C(F)(F)F)cn1)C2]

Example 351: (2-fluoro-6-(2H-1,2,3-triazol-2-yl)
phenyl)((1S,2R,4R)-2-((5-(trifluoromethyl)pyrazin-
2-yl)oxy)-7-azabicyclo[2.2.1]heptan-7-yl)methanone

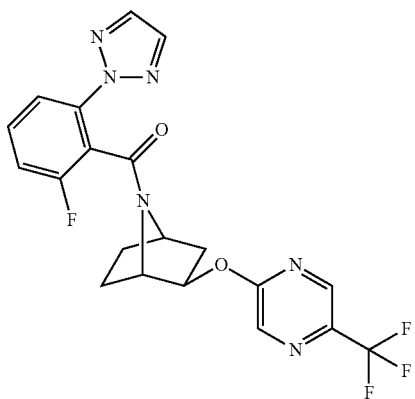 [SMILES: O=C(c1c(F)cccc1-n1nccn1)N1C2CCC1C(Oc1cnc(C(F)(F)F)cn1)C2]

Example 352: (5-methyl-3-(2H-1,2,3-triazol-2-yl)
pyridin-2-yl)((1S,2R,4R)-2-((5-(trifluoromethyl)
pyrazin-2-yl)oxy)-7-azabicyclo[2.2.1]heptan-7-yl)
methanone

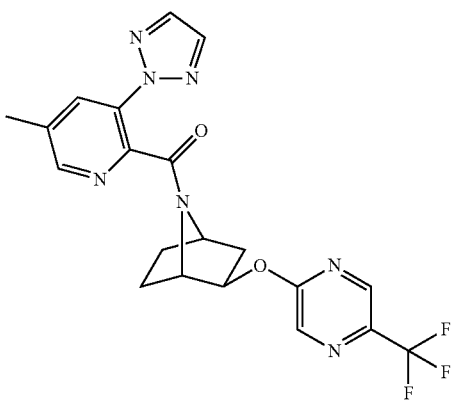 [SMILES: Cc1cnc(C(=O)N2C3CCC2C(Oc2cnc(C(F)(F)F)cn2)C3)c(-n2nccn2)c1]

Example 353: (2-bromo-3-fluorophenyl)((1S,2R,
4R)-2-((5-(trifluoromethyl)pyrazin-2-yl)oxy)-7-
azabicyclo[2.2.1]heptan-7-yl)methanone

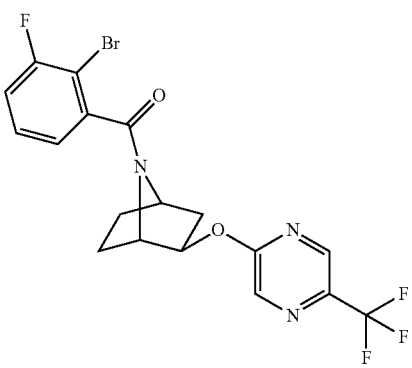 [SMILES: O=C(c1cccc(F)c1Br)N1C2CCC1C(Oc1cnc(C(F)(F)F)cn1)C2]

Example 354: (2-methoxy-6-(pyrimidin-2-yl)phe-
nyl)((1S,2R,4R)-2-((5-(trifluoromethyl)pyrimidin-
2-yl)oxy)-7-azabicyclo[2.2.1]heptan-7-yl)methanone

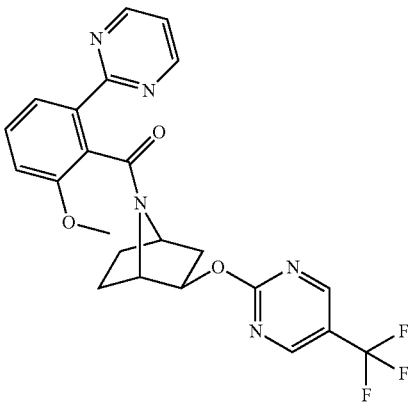

Example 355: (5-fluoro-2-(2H-1,2,3-triazol-2-yl)
phenyl)((1S,2R,4R)-2-((5-(trifluoromethyl)pyrimi-
din-2-yl)oxy)-7-azabicyclo[2.2.1]heptan-7-yl)metha-
none

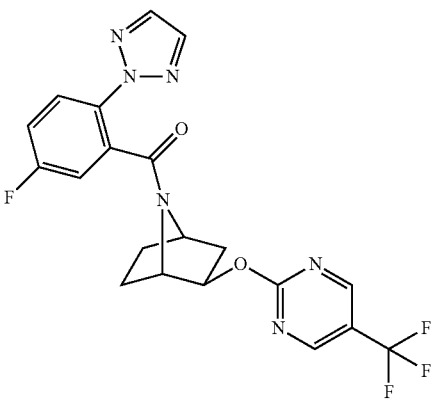

Example 356: (4-methyl-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone

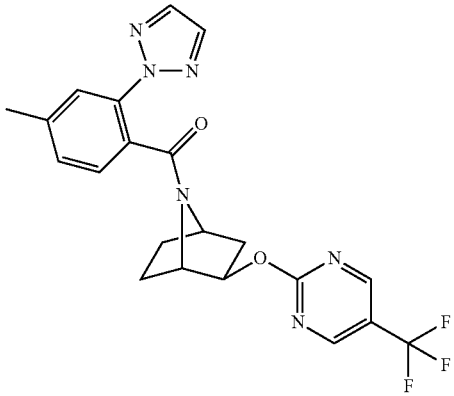

Example 357: (3-methyl-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone

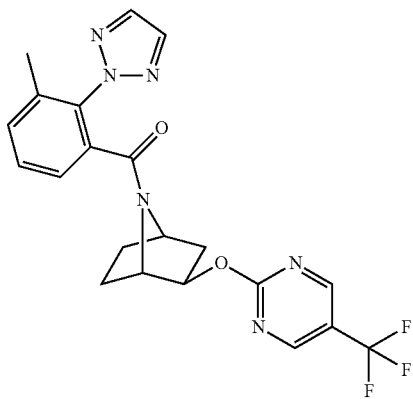

Example 358: (5-fluoro-2-(pyrimidin-2-yl)phenyl)((1S,2R,4R)-2-((5-(trifluoromethyl)pyrimidin-2-yl)oxy)-7-azabicyclo[2.2.1]heptan-7-yl)methanone

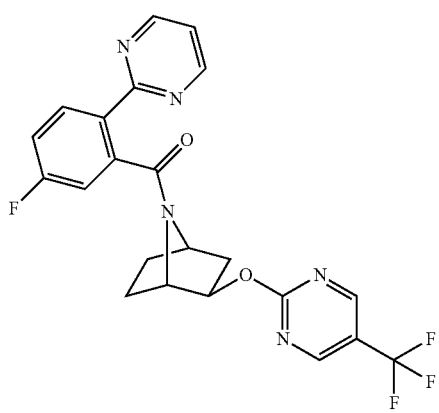

Example 359: (2-fluoro-6-(pyrimidin-2-yl)phenyl)((1S,2R,4R)-2-((5-(trifluoromethyl)pyrimidin-2-yl)oxy)-7-azabicyclo[2.2.1]heptan-7-yl)methanone

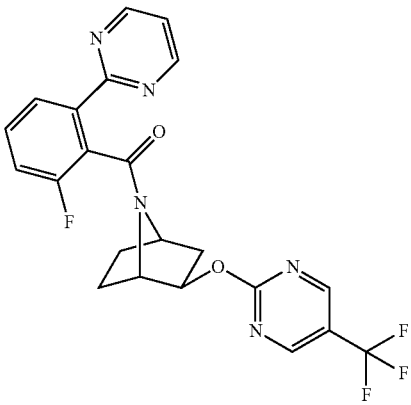

Example 360: (2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone

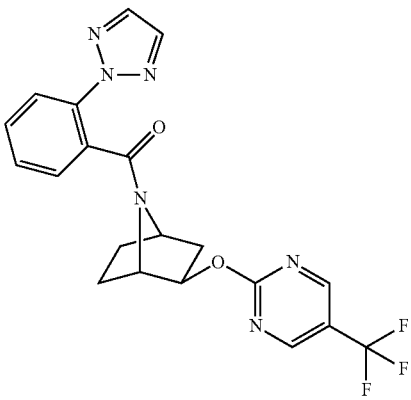

Example 361: (6-methyl-3-(2H-1,2,3-triazol-2-yl)pyridin-2-yl)((1S,2R,4R)-2-((5-(trifluoromethyl)pyrimidin-2-yl)oxy)-7-azabicyclo[2.2.1]heptan-7-yl)methanone

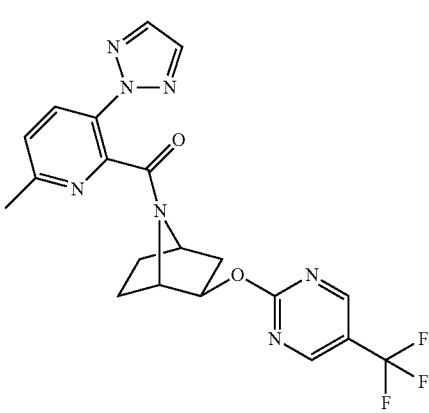 [SMILES: Cc1ccc(-n2nccn2)c(C(=O)N2C3CCC2C(Oc2ncc(C(F)(F)F)cn2)C3)n1]

Example 362: (3-methyl-2-(oxazol-2-yl)phenyl)
((1S,2R,4R)-2-((5-(trifluoromethyl)pyrimidin-2-yl)
oxy)-7-azabicyclo[2.2.1]heptan-7-yl)methanone

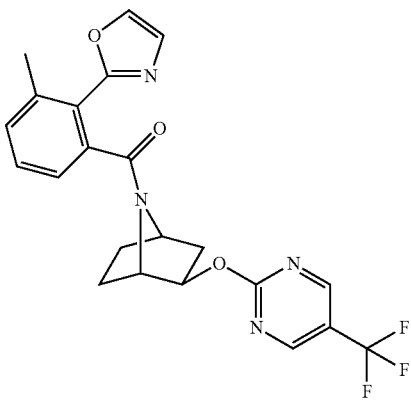

Example 363: (3-methyl-2-(pyridin-2-yl)phenyl)
((1S,2R,4R)-2-((5-(trifluoromethyl)pyrimidin-2-yl)
oxy)-7-azabicyclo[2.2.1]heptan-7-yl)methanone

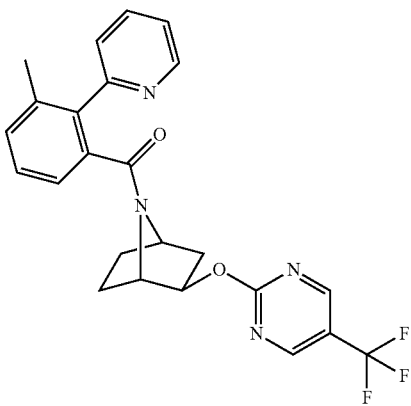

Example 364: (2-(5-fluoropyrimidin-2-yl)phenyl)
((1S,2R,4R)-2-((5-(trifluoromethyl)pyrimidin-2-yl)
oxy)-7-azabicyclo[2.2.1]heptan-7-yl)methanone

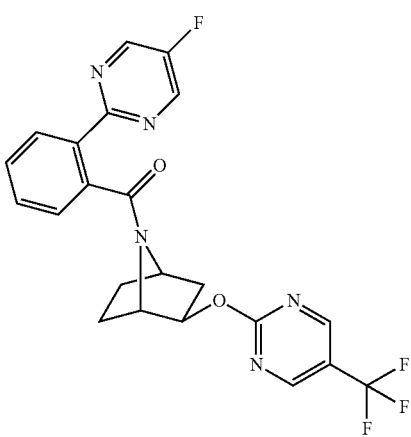

Example 365: (2-fluoro-6-(2H-1,2,3-triazol-2-yl)
phenyl)((1S,2R,4R)-2-((5-(trifluoromethyl)pyrimidin-2-yl)oxy)-7-azabicyclo[2.2.1]heptan-7-yl)methanone

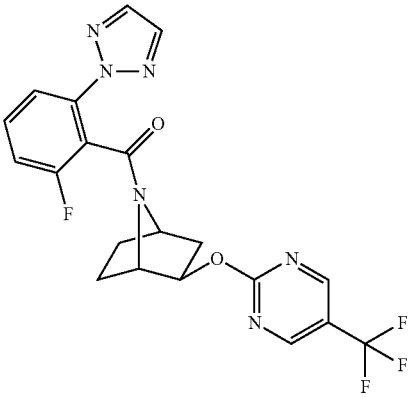

Example 366: (5-methyl-3-(2H-1,2,3-triazol-2-yl)
pyridin-2-yl)((1S,2R,4R)-2-((5-(trifluoromethyl)
pyrimidin-2-yl)oxy)-7-azabicyclo[2.2.1]heptan-7-yl)
methanone

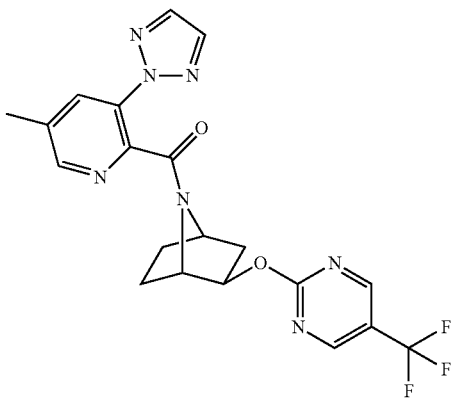 [SMILES: Cc1cnc(C(=O)N2C3CCC2C(Oc2ncc(C(F)(F)F)cn2)C3)c(-n2nccn2)c1]

Example 367: (2-bromo-3-fluorophenyl)((1S,2R,
4R)-2-((5-(trifluoromethyl)pyrimidin-2-yl)oxy)-7-
azabicyclo[2.2.1]heptan-7-yl)methanone

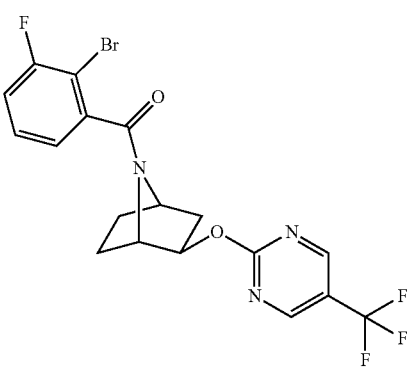

Assays

The in vitro affinity of the compounds of the invention for the rat/human orexin 1 and human orexin 2 receptors was determined by competitive radioligand binding using [3H](1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone)(Langmead et al., 2004) and [3H]EMPA (n-ethyl-2[96-methoxy-pyridin-3-yl)-(toluene-2-sulfonyl)-amino]-N-pyridin-3-ylmethyl acetamide), respectively (Langmead et al., 2004, British Journal of Pharmacology 141:340-346; Malherbe et al., 2004, British Journal of Pharmacology 156:1326-41).

The in vitro functional antagonism of the compounds on the human orexin 1 and orexin 2 receptors was determined using fluorometric imaging plate reader (FLIPR) based calcium assays.

Rat and Human Orexin 1 Receptor Radioligand Binding Studies

Human Embryonic Kidney 293 cells (HEK293) stably expressing rat orexin 1 receptor (Genebank accession number NM_001525) or Chinese ovary cells (CHO) stably expressing human orexin 1 receptor (Genebank accession number NM_001526) were grown to confluency in DMEM (Hyclone, cat # SH30022), 10% FBS, 1× Pen/Strep, 1× sodium pyruvate, 10 mM HEPES, 600 µg/mL G418 and DMEM/$F_{12}$ (Gibco, Cat #11039), 10% FBS, 1× Pen/Strep, 600 µg/mL G418 media, respectively on 150 cm2 tissue culture plates, washed with 5 mM EDTA in PBS (HyClone Dulbecco's Phosphate Buffered Saline 1× with Calcium and Magnesium, Cat # SH30264.01, hereafter referred to simply as PBS) and scraped into 50 ml tubes. After centrifugation (2K×G, 5 min at 4° C.), the supernatant was aspirated and the pellets frozen and stored at −800 C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec prior to addition to the reactions. Competition binding experiments in 96 well polypropylene plates were performed using [3H]-SB674042 (Moraveck Corporation, specific activity=35.3 Ci/mmol), diluted to a 10 nM concentration in PBS (4 nM final). Compounds were solubilized in 100% DMSO (Acros Organics, Cat. #61042-1000) and tested over a range of 7 concentrations (from 0.1 nM to 10 µM). The final concentration of DMSO in the reactions is equal to or less than 0.1%. Total and nonspecific binding was determined in the absence and presence of 10 µM almorexant. The total volume of each reaction is 200 µL (20 µL of diluted compounds, 80 µL of [$^3$H]-(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) diluted in PBS and 100 µL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

$IC_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as Ki=$IC_{50}$/(1+C/Kd), where C is concentration of radioligand and Kd=4 nM for rat orexin 1 receptor and 6 nM for human orexin 1 receptor.

Human Orexin 2 Receptor Radioligand Binding Studies

HEK293 stably expressing human orexin 2 receptor (Genebank accession number NM_001526) were grown to confluency in DMEM (Hyclone, cat # SH30022), 10% FBS, 1× Pen/Strep, 1× NaPyruvate, 10 mM HEPES, 600 g/ml G418 media on 150 cm² tissue culture plates, washed with 5 mM EDTA in PBS (HyClone Dulbecco's Phosphate Buffered Saline 1× with Calcium and Magnesium, Cat # SH30264.01, hereafter referred to simply as PBS) and scraped into 50 ml tubes. After centrifugation (2K xG, 5 min at 40° C.), the supernatant was aspirated and the pellets frozen and stored at −800° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec just prior to addition to the reactions. Competition binding experiments in 96 well polypropylene plates were performed using [3H]-EMPA (Moraveck Corporation, specific activity=29.6 Ci/mmol), diluted to a 5 nM concentration in PBS (2 nM final concentration). Compounds were solubilized in 100% DMSO (Acros Organics, Cat. #61042-1000) and tested over a range of 7 concentration (from 0.1 nM to 10 µM). The final concentration of DMSO in the reactions is equal to or less than 0.1%. Total and nonspecific binding was determined in the absence and presence of 10 µM almorexant. The total volume of each reaction is 200 µL (20 µL of diluted compounds, 80 µL of [3H]-EMPA diluted in PBS and 100 µL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

$IC_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as Ki=$IC_{50}$/(1+C/Kd), where C is concentration of radioligand and Kd=2 nM.

Human Orexin 1 Receptor Ca2+ Mobilization Assay

CHO cells stably transfected with the human orexin 1 receptor (Genebank accession number NM_001526) were grown to confluency in DMEM/F12, 10% FBS, 1× penstrep, 400 g/ml G418. Cells were seeded on to 384-well Packard viewplates at a density of 10,000 cells/well and incubated overnight at 370 C, 5% $CO_2$. The cells were dye-loaded with BD Calcium Assay kit (BD, cat #640178) in HBSS (Gibco, cat#14025-092) with 2.5 mM probenecid and incubated at 37° C., 5% CO2 for 45 min. Cells were pre-incubated with compounds (diluted in DMEM/F-12) for 15-30 minutes before agonist (orexin A, 10 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent pKB values using a modified Cheng-Prusoff correction. Apparent pKB=−log $IC_{50}$/1+[conc agonist/$EC_{50}$]. Data are expressed as mean±S.E.M.

Human Orexin 2 Receptor Ca2+ Mobilization Assay

PFSK-1 cells endogenously expressing the human orexin 2 receptor were grown to confluency in RPMI1640 (Hyclone, cat#30027.02), 10% FBS, 1× pen-strep. Cells were seeded on to 384-well Packard viewplates at a density of 5,000 cells/well and incubated overnight at 370 C, 5% $CO_2$. The cells were dye-loaded with BD Calcium Assay kit (BD, cat #640178) in HBSS (Gibco, cat#14025-092) with 2.5 mM probenecid and incubated at 37° C., 5% CO2 for 45 min. Cells were pre-incubated with compounds (diluted in DMEM/F-12) for 15-30 minutes before agonist (orexin B, 100 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent pKB values using a modified Cheng-Prusoff correction. Apparent pKB=$-\log IC_{50}/1+$[conc agonist/EC50]. Data are expressed as mean±S.E.M.

Preferred compounds of the invention are set forth in the table below. Orexin receptor activity of certain compounds of the invention is also set forth in the below table.

| Ex. No. | Compound | rOX1 $K_i$ (nm) | hOX1 $K_i$ (nm) | hOX2 $K_i$ (nm) | Compound Name |
|---|---|---|---|---|---|
| 1 | | | 25 | 41 | 276 | (5-fluoro-2-(pyrimidin-2-yl)phenyl)((1S,2R,4R)-2-((pyridin-2-yloxy)methyl)-7-azabicyclo[2.2.1]heptan-7-yl)methanone |
| 2 | | | 31 | 23 | 500 | (±)-(6-methyl-3-(pyrimidin-2-yl)pyridin-2-yl)(2-((pyridin-2-yloxy)methyl)-7-azabicyclo[2.2.1]heptan-7-yl)methanone |
| 3A | | | 24 | 19 | 268 | (6-methyl-3-(pyrimidin-2-yl)pyridin-2-yl)((1S*,2R*,4R*)-2-((pyridin-2-yloxy)methyl)-7-azabicyclo[2.2.1]heptan-7-yl)methanone |
| 3B | | | | >10000 | >10000 | (6-methyl-3-(pyrimidin-2-yl)pyridin-2-yl)((1R*,2S*,4S*)-2-((pyridin-2-yloxy)methyl)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 4 | | 36 | 41 | 927 | (±)-(6-methyl-3-(2H-1,2,3-triazol-2-yl)pyridin-2-yl)(2-((pyridin-2-yloxy)methyl)-7-azabicyclo[2.2.1]heptan-7-yl)methanone |
| 5A | | 14 | 15 | 428 | (6-methyl-3-(2H-1,2,3-triazol-2-yl)pyridin-2-yl)((1S,2R,4R)-2-((pyridin-2-yloxy)methyl)-7-azabicyclo[2.2.1]heptan-7-yl)methanone |
| 5B | | >10000 | | >10000 | (6-methyl-3-(2H-1,2,3-triazol-2-yl)pyridin-2-yl)((1R,2S,4S)-2-((pyridin-2-yloxy)methyl)-7-azabicyclo[2.2.1]heptan-7-yl)methanone |
| 6 | | 14 | 15 | 428 | (6-methyl-3-(2H-1,2,3-triazol-2-yl)pyridin-2-yl)((1S,2R,4R)-2-((pyridin-2-yloxy)methyl)-7-azabicyclo[2.2.1]heptan-7-yl)methanone |
| 7 | | 19 | 19 | 198 | (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 8A | | 9 | 14 | 94 | ((1S,2R,4R)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 8B | | >10000 | | >10000 | ((1R,2S,4S)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 9 | | | 9 | 57 | (±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone |
| 10A | | 4 | 3 | 32 | ((1S,2R,4R)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone |
| 10B | | 3937 | 3200 | 5148 | ((1R,2S,4S)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 11 | | | 10 | 12 | (±)-(2-(((5-fluoropyridin-2-yl)oxy)methyl)-7-azabicyclo[2.2.1]heptan-7-yl)(2-(thiophen-2-yl)phenyl)methanone |
| 12A | | | 177 | 339 | ((1S*,2R*,4R*)-2-(((5-fluoropyridin-2-yl)oxy)methyl)-7-azabicyclo[2.2.1]heptan-7-yl)(2-(thiophen-2-yl)phenyl)methanone |
| 12B | | | 3 | 5 | ((1R*,2S*,4S*)-2-(((5-fluoropyridin-2-yl)oxy)methyl)-7-azabicyclo[2.2.1]heptan-7-yl)(2-(thiophen-2-yl)phenyl)methanone |
| 13 | | | 118 | 109 | (±)-(5-methyl-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone |
| 14 | | | 50 | 71 | (±)-(5-methyl-2-(2H-1,2,3-triazol-2-yl)phenyl)(2-(((5-(trifluoromethyl)pyridin-2-yl)oxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 15 | | | 56 | 120 | (±)-(5-methyl-2-(2H-1,2,3-triazol-2-yl)phenyl)(2-(((3-(trifluoromethyl)pyridin-2-yl)oxy)methyl)-7-azabicyclo[2.2.1]heptan-7-yl)methanone |
| 16 | | | 20 | 42 | (±)-(5-methyl-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone |
| 17 | | | 41 | 69 | (±)-(5-methyl-2-(2H-1,2,3-triazol-2-yl)phenyl)(2-(((4-methylpyridin-2-yl)oxy)methyl)-7-azabicyclo[2.2.1]heptan-7-yl)methanone |
| 18 | | | 12 | 44 | (±)-(5-methyl-2-(2H-1,2,3-triazol-2-yl)phenyl)(2-(((6-methylpyridin-2-yl)oxy)methyl)-7-azabicyclo[2.2.1]heptan-7-yl)methanone |
| 19 | | | 12 | 44 | (±)-(5-methyl-2-(2H-1,2,3-triazol-2-yl)phenyl)(2-(((5-methylpyridin-2-yl)oxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 20 | | | 270 | 364 | (±)-(2-(((3,6-dimethylpyrazin-2-yl)oxy)methyl)-7-azabicyclo[2.2.1]heptan-7-yl)(5-methyl-2-(2H-1,2,3-triazol-2-yl)phenyl)methanone |
| 21 | | | 300 | 487 | (±)-(5-methyl-2-(2H-1,2,3-triazol-2-yl)phenyl)(2-(((3-(trifluoromethyl)quinoxalin-2-yl)oxy)methyl)-7-azabicyclo[2.2.1]heptan-7-yl)methanone |
| 22 | | | 47 | 50 | (±)-(2-(2H-1,2,3-triazol-2-yl)phenyl)(2-(((5-fluoropyridin-2-yl)oxy)methyl)-7-azabicyclo[2.2.1]heptan-7-yl)methanone |
| 23 | | | 322 | 1500 | (±)-2-(((5-fluoropyridin-2-yl)oxy)methyl)-7-azabicyclo[2.2.1]heptan-7-yl)(quinolin-8-yl)methanone |
| 24 | | | 122 | 164 | (±)-2-(((5-fluoropyridin-2-yl)oxy)methyl)-7-azabicyclo[2.2.1]heptan-7-yl)(naphthalen-1-yl)methanone |
| 25 | | | 74 | 160 | (±)-2-(((5-fluoropyridin-2-yl)oxy)methyl)-7-azabicyclo[2.2.1]heptan-7-yl)(2-methylnaphthalen-1-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 26 | | | 117 | 394 | (±)-2-(1H-pyrazol-1-yl)phenyl)(2-(((5-fluoropyridin-2-yl)oxy)methyl)-7-azabicyclo[2.2.1]heptan-7-yl)methanone |
| 27 | | | 677 | 380 | (±)-2-(((5-fluoropyridin-2-yl)oxy)methyl)-7-azabicyclo[2.2.1]heptan-7-yl)(3-phenylfuran-2-yl)methanone |
| 28 | | | 14 | 11 | (±)-(2-ethoxynaphthalen-1-yl)(2-(((5-fluoropyridin-2-yl)oxy)methyl)-7-azabicyclo[2.2.1]heptan-7-yl)methanone |
| 29 | | | 11 | 60 | (±)-(5-(2-fluorophenyl)-2-methylthiazol-4-yl)(2-(((5-fluoropyridin-2-yl)oxy)methyl)-7-azabicyclo[2.2.1]heptan-7-yl)methanone |
| 30 | | | 47 | 149 | (±)-(5-fluoro-2-(2H-1,2,3-triazol-2-yl)phenyl)(2-(((5-fluoropyridin-2-yl)oxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 31 | | | 33 | 122 | (±)-(2-fluoro-6-(pyrimidin-2-yl)phenyl)(2-(((5-fluoropyridin-2-yl)oxy)methyl)-7-azabicyclo[2.2.1]heptan-7-yl)methanone |
| 32 | | | 21 | 123 | (±)-(5-fluoro-2-(pyrimidin-2-yl)phenyl)(2-(((5-fluoropyridin-2-yl)oxy)methyl)-7-azabicyclo[2.2.1]heptan-7-yl)methanone |
| 33 | | 15 | 9 | 39 | (±)-(2-(((5-fluoropyridin-2-yl)oxy)methyl)-7-azabicyclo[2.2.1]heptan-7-yl)(5-methyl-2-(pyrimidin-2-yl)phenyl)methanone |
| 34 | | | 60 | 467 | (±)-(2-(2H-1,2,3-triazol-2-yl)phenyl)(2-((quinoxalin-2-yloxy)methyl)-7-azabicyclo[2.2.1]heptan-7-yl)methanone |
| 35 | | 69 | 58 | 693 | (±)-(2-fluoro-6-(2H-1,2,3-triazol-2-yl)phenyl)(2-((quinoxalin-2-yloxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 36 | | | 70 | 107 | (±)-(5-methyl-2-(2H-1,2,3-triazol-2-yl)phenyl)(2-((quinoxalin-2-yloxy)methyl)-7-azabicyclo[2.2.1]heptan-7-yl)methanone |
| 37 | | | 300 | 487 | (±)-(5-fluoro-2-(2H-1,2,3-triazol-2-yl)phenyl)(2-((quinoxalin-2-yloxy)methyl)-7-azabicyclo[2.2.1]heptan-7-yl)methanone |
| 38 | | | 120 | 383 | (±)-(5-methyl-2-(pyrimidin-2-yl)phenyl)(2-((quinoxalin-2-yloxy)methyl)-7-azabicyclo[2.2.1]heptan-7-yl)methanone |
| 39 | | | 29 | 27 | (±)-(2-(((4,6-dimethylpyrimidin-2-yl)oxy)methyl)-7-azabicyclo[2.2.1]heptan-7-yl)(5-methyl-2-(2H-1,2,3-triazol-2-yl)phenyl)methanone |
| 40 | | | 5000 | 1203 | (±)-2-(((4,6-dimethylpyrimidin-2-yl)oxy)methyl)-7-azabicyclo[2.2.1]heptan-7-yl)(3-methyl-5-phenylisoxazol-4-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 41 | | | 35 | 22 | (±)-(2-(((4,6-dimethylpyrimidin-2-yl)oxy)methyl)-7-azabicyclo[2.2.1]heptan-7-yl)(2-ethoxynaphthalen-1-yl)methanone |
| 42 | | | 1277 | 253 | (±)-(2-(((4,6-dimethylpyrimidin-2-yl)oxy)methyl)-7-azabicyclo[2.2.1]heptan-7-yl)(2-ethoxyphenyl)methanone) |
| 43 | | | 222 | 92 | (±)-(2-(((4,6-dimethylpyrimidin-2-yl)oxy)methyl)-7-azabicyclo[2.2.1]heptan-7-yl)(2-fluoro-6-(pyrimidin-2-yl)phenyl)methanone |
| 44 | | | 400 | 104 | (±)-(2-(((4,6-dimethylpyrimidin-2-yl)oxy)methyl)-7-azabicyclo[2.2.1]heptan-7-yl)(5-fluoro-2-(pyrimidin-2-yl)phenyl)methanone |
| 45 | | | 79 | 59 | (±)-(2-(((4,6-dimethylpyrimidin-2-yl)oxy)methyl)-7-azabicyclo[2.2.1]heptan-7-yl)(5-methyl-2-(pyrimidin-2-yl)phenyl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 46 | | | 82 | 10 | (±)-(2-(((4,6-dimethylpyrimidin-2-yl)oxy)methyl)-7-azabicyclo[2.2.1]heptan-7-yl)(2-(thiophen-2-yl)phenyl)methanone |
| 47 | | | 460 | 418 | (±)-(6-methyl-2-(2H-1,2,3-triazol-2-yl)pyridin-2-yl)(2-(((5-(trifluoromethyl)pyridin-2-yl)oxy)methyl)-7-azabicyclo[2.2.1]heptan-7-yl)methanone |
| 48 | | | 3900 | 4700 | (±)-(3-ethoxy-6-methylpyridin-2-yl)(2-(((5-(trifluoromethyl)pyridin-2-yl)oxy)methyl)-7-azabicyclo[2.2.1]heptan-7-yl)methanone |
| 49 | | 81 | 69 | 192 | (±)-(2-(((5-bromopyridin-2-yl)oxy)methyl)-7-azabicyclo[2.2.1]heptan-7-yl)(6-methyl-3-(2H-1,2,3-triazol-2-yl)pyridin-2-yl)methanone |
| 50 | | | 460 | 4399 | (±)-(2-(((5-bromopyridin-2-yl)oxy)methyl)-7-azabicyclo[2.2.1]heptan-7-yl)(3-fluoro-2-methoxyphenyl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 51 | | | 974 | 1800 | (±)-(2-(((5-bromopyridin-2-yl)oxy)methyl)-7-azabicyclo[2.2.1]heptan-7-yl)(3-ethoxy-6-methylpyridin-2-yl)methanone |
| 52 | | | 350 | 2300 | (±)-(3-fluoro-2-(pyrimidin-2-yl)phenyl)(2-((pyridin-2-yloxy)methyl)-7-azabicyclo[2.2.1]heptan-7-yl)methanone |
| 53 | | | 2200 | >10000 | (±)-(6-methyl-3-(2H-1,2,3-triazol-2-yl)pyridin-2-yl)(2-((pyridazin-3-yloxy)methyl)-7-azabicyclo[2.2.1]heptan-7-yl)methanone |
| 54 | | | 3500 | 2200 | (±)-(6-methyl-3-(2H-1,2,3-triazol-2-yl)pyridin-2-yl)(2-(((2-methylpyridin-3-yl)oxy)methyl)-7-azabicyclo[2.2.1]heptan-7-yl)methanone |
| 55 | | 119 | 150 | 202 | (±)-(6-methyl-3-(2H-1,2,3-triazol-2-yl)pyridin-2-yl)(2-(((3-methylpyridin-2-yl)oxy)methyl)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 56 | | >10000 | | >10000 | (±)-(2-(((1-methyl-1H-pyrazol-5-yl)oxy)methyl)-7-azabicyclo[2.2.1]heptan-7-yl)(6-methyl-3-(2H-1,2,3-triazol-2-yl)pyridin-2-yl)methanone |
| 57 | | 1000 | | 7300 | (±)-(6-methyl-3-(2H-1,2,3-triazol-2-yl)pyridin-2-yl)(2-((pyridin-4-yloxy)methyl)-7-azabicyclo[2.2.1]heptan-7-yl)methanone |
| 58 | | 88 | 117 | 2400 | (±)-(6-methyl-3-(2H-1,2,3-triazol-2-yl)pyridin-2-yl)(2-((pyridin-3-yloxy)methyl)-7-azabicyclo[2.2.1]heptan-7-yl)methanone |
| 59 | | 2600 | | 4900 | (±)-(6-methyl-3-(2H-1,2,3-triazol-2-yl)pyridin-2-yl)(2-((pyrimidin-2-yloxy)methyl)-7-azabicyclo[2.2.1]heptan-7-yl)methanone |
| 60 | | 7800 | | >10000 | (±)-(6-methyl-3-(2H-1,2,3-triazol-2-yl)pyridin-2-yl)(2-((pyrazin-2-yloxy)methyl)-7-azabicyclo[2.2.1]heptan-7-yl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 61 | | 2800 | | >10000 | (±)-(6-methyl-3-(2H-1,2,3-triazol-2-yl)pyridin-2-yl)(2-((pyrimidin-4-yloxy)methyl)-7-azabicyclo[2.2.1]heptan-7-yl)methanone |
| 62 | | 74 | 46 | 188 | (±)-(6-methyl-3-(2H-1,2,3-triazol-2-yl)pyridin-2-yl)(2-(((6-methylpyridin-2-yl)oxy)methyl)-7-azabicyclo[2.2.1]heptan-7-yl)methanone |
| 63 | | 25 | 25 | 339 | (±)-(2-(((5-fluoropyridin-2-yl)oxy)methyl)-7-azabicyclo[2.2.1]heptan-7-yl)(6-methyl-3-(oxazol-2-yl)pyridin-2-yl)methanone |
| 64 | | 18 | 24 | 81 | (±)-(2-(((5-fluoropyridin-2-yl)oxy)methyl)-7-azabicyclo[2.2.1]heptan-7-yl)(6-methyl-3-(pyrimidin-2-yl)pyridin-2-yl)methanone |
| 65 | | 1440 | | 6200 | (±)-(3,6'-dimethyl-[2,3'-bipyridin]-2'-yl)(2-(((5-fluoropyridin-2-yl)oxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 66 | | 197 | 293 | 620 | (±)-(2-(((5-fluoropyridin-2-yl)oxy)methyl)-7-azabicyclo[2.2.1]heptan-7-yl)(6-methyl-3-(3-methyl-1,2,4-oxadiazol-5-yl)pyridin-2-yl)methanone |
| 67 | | 48 | 69 | 258 | (±)-(2-(((5-fluoropyridin-2-yl)oxy)methyl)-7-azabicyclo[2.2.1]heptan-7-yl)(6-methyl-3-(3-methyl-1H-pyrazol-1-yl)pyridin-2-yl)methanone |
| 68 | | 27 | 22 | 576 | (±)-(2-(((5-fluoropyridin-2-yl)oxy)methyl)-7-azabicyclo[2.2.1]heptan-7-yl)(6-methyl-3-(pyrrolidin-1-yl)pyridin-2-yl)methanone |
| 69 | | 40 | 64 | 174 | (±)-(2-(((5-fluoropyridin-2-yl)oxy)methyl)-7-azabicyclo[2.2.1]heptan-7-yl)(6-methyl-3-(3-methylisoxazol-5-yl)pyridin-2-yl)methanone |
| 70 | | 88 | 62 | 624 | (±)-(2-(((5-fluoropyridin-2-yl)oxy)methyl)-7-azabicyclo[2.2.1]heptan-7-yl)(6-methyl-3-(1H-pyrazol-1-yl)pyridin-2-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 71 | | | 1200 | 3700 | (±)-(5-methyl-3-(2H-1,2,3-triazol-2-yl)pyridin-2-yl)(2-((pyridin-2-yloxy)methyl)-7-azabicyclo[2.2.1]heptan-7-yl)methanone |
| 72 | | 137 | 162 | 2400 | (±)-(4-methyl-3-(2H-1,2,3-triazol-2-yl)pyridin-2-yl)(2-((pyridin-2-yloxy)methyl)-7-azabicyclo[2.2.1]heptan-7-yl)methanone |
| 73 | | | 278 | 7900 | (±)-(3-(dimethylamino)-6-methylpyridin-2-yl)(2-((pyridin-2-yloxy)methyl)-7-azabicyclo[2.2.1]heptan-7-yl)methanone |
| 74 | | | 359 | 1700 | (±)-(3-(2H-1,2,3-triazol-2-yl)quinolin-2-yl)(2-((pyridin-2-yloxy)methyl)-7-azabicyclo[2.2.1]heptan-7-yl)methanone |
| 75 | | 18 | 7 | 220 | (±)-(7-ethoxyquinolin-8-yl)(2-((pyridin-2-yloxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 76 | | | >10000 | >10000 | (±)-(3,6-dimethylimidazo[1,2-a]pyridin-5-yl)(2-((pyridin-2-yloxy)methyl)-7-azabicyclo[2.2.1]heptan-7-yl)methanone |
| 77 | | | 103 | 66 | 867 (±)-(1-methyl-4-phenyl-1H-pyrazol-3-yl)((1S,2R,4R)-2-((pyridin-2-yloxy)methyl)-7-azabicyclo[2.2.1]heptan-7-yl)methanone |
| 78 | | | 418 | | 3100 (±)-(1-methyl-3-phenyl-1H-pyrazol-4-yl)((1S,2R,4R)-2-((pyridin-2-yloxy)methyl)-7-azabicyclo[2.2.1]heptan-7-yl)methanone |
| 79 | | | 2400 | | 8500 (±)-((3,7-dimethylimidazo[1,2-a]pyridin-8-yl)(2-((pyridin-2-yloxy)methyl)-7-azabicyclo[2.2.1]heptan-7-yl)methanone |
| 80 | | | 1100 | | >10000 (±)-(7-methylimidazo[1,2-a]pyridin-8-yl)(2-((pyridin-2-yloxy)methyl)-7-azabicyclo[2.2.1]heptan-7-yl)methanone |

-continued

| Ex. No. | Compound | rOX1 K<sub>i</sub> (nm) | hOX1 K<sub>i</sub> (nm) | hOX2 K<sub>i</sub> (nm) | Compound Name |
|---|---|---|---|---|---|
| 81 | | | 916 | 2900 | (±)-(1-methyl-4-phenyl-1H-pyrazol-5-yl)(2-((pyridin-2-yloxy)methyl)-7-azabicyclo[2.2.1]heptan-7-yl)methanone |
| 82 | | | >10000 | >10000 | (±)-((6-methylimidazo[1,2-a]pyridin-5-yl)(2-((pyridin-2-yloxy)methyl)-7-azabicyclo[2.2.1]heptan-7-yl)methanone |
| 83 | | 17 | 12 | 271 | (±)-(3-ethoxyisoquinolin-4-yl)(2-((pyridin-2-yloxy)methyl)-7-azabicyclo[2.2.1]heptan-7-yl)methanone |
| 84 | | | 2600 | 9701 | (±)-(1-methyl-5-phenyl-1H-pyrazol-4-yl)(-2-((pyridin-2-yloxy)methyl)-7-azabicyclo[2.2.1]heptan-7-yl)methanone |
| 85 | | | >10000 | >10000 | (±)-(6-methyl-3-(4-methylpiperazin-1-yl)pyridin-2-yl)(2-((pyridin-2-yloxy)methyl)-7-azabicyclo[2.2.1]heptan-7-yl)methanone |

-continued

| Ex. No. | Compound | rOX1 K_i (nm) | hOX1 K_i (nm) | hOX2 K_i (nm) | Compound Name |
|---|---|---|---|---|---|
| 86 | | | >10000 | >10000 | (±)-(6-methyl-3-(piperazin-1-yl)pyridin-2-yl)(2-((pyridin-2-yloxy)methyl)-7-azabicyclo[2.2.1]heptan-7-yl)methanone |
| 87 | | 4200 | | >10000 | (±)-(6-methyl-3-morpholinopyridin-2-yl)((1S,2R,4R)-2-((pyridin-2-yloxy)methyl)-7-azabicyclo[2.2.1]heptan-7-yl)methanone |
| 88 | | 47 | 49 | 690 | (±)-(7-methoxyquinolin-8-yl)(2-((pyridin-2-yloxy)methyl)-7-azabicyclo[2.2.1]heptan-7-yl)methanone |
| 89 | | 11 | 10 | 38 | (±)-(2-ethoxynaphthalen-1-yl)(2-((pyridin-2-yloxy)methyl)-7-azabicyclo[2.2.1]heptan-7-yl)methanone |
| 90 | | 3000 | | >10000 | (±)-(3,6'-dimethyl-[2,3'-bipyridin]-2'-yl)(2-((pyridin-2-yloxy)methyl)-7-azabicyclo[2.2.1]heptan-7-yl)methanone |

| Ex. No. | Compound | rOX1 K_i (nm) | hOX1 K_i (nm) | hOX2 K_i (nm) | Compound Name |
|---|---|---|---|---|---|
| 91 | | | 624 | 3300 | (±)-(3-(2H-1,2,3-triazol-2-yl)pyridin-2-yl)(2-((pyridin-2-yloxy)methyl)-7-azabicyclo[2.2.1]heptan-7-yl)methanone |
| 92 | | 20 | 11 | 218 | (±)-(2-methyl-5-phenylthiazol-4-yl)(2-((pyridin-2-yloxy)methyl)-7-azabicyclo[2.2.1]heptan-7-yl)methanone |
| 93 | | 40 | 73 | 836 | (±)-(6-methyl-3-(oxazol-2-yl)pyridin-2-yl)(2-((pyridin-2-yloxy)methyl)-7-azabicyclo[2.2.1]heptan-7-yl)methanone |
| 94 | | 170 | 200 | 2100 | (±)-(6-methyl-3-(3-methylisoxazol-5-yl)pyridin-2-yl)(2-((pyridin-2-yloxy)methyl)-7-azabicyclo[2.2.1]heptan-7-yl)methanone |
| 95 | | | 247 | 3700 | (±)-(6-methyl-3-(1H-pyrazol-1-yl)pyridin-2-yl)(2-((pyridin-2-yloxy)methyl)-7-azabicyclo[2.2.1]heptan-7-yl)methanone |

-continued

| Ex. No. | Compound | rOX1 K_i (nm) | hOX1 K_i (nm) | hOX2 K_i (nm) | Compound Name |
|---|---|---|---|---|---|
| 96 | 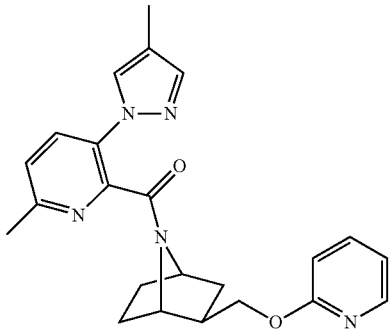 [SMILES: Cc1cnn(-c2ccc(C)nc2C(=O)N2C3CCC2C(COc2ccccn2)C3)c1] | | 70 | 76 | 950 | (±)-(6-methyl-3-(4-methyl-1H-pyrazol-1-yl)pyridin-2-yl)(2-((pyridin-2-yloxy)methyl)-7-azabicyclo[2.2.1]heptan-7-yl)methanone |
| 97 | 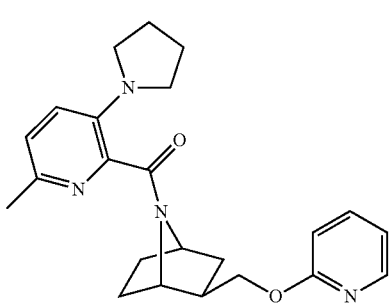 [SMILES: Cc1ccc(N2CCCC2)c(C(=O)N2C3CCC2C(COc2ccccn2)C3)n1] | | 35 | 32 | 840 | (±)-(6-methyl-3-(pyrrolidin-1-yl)pyridin-2-yl)(2-((pyridin-2-yloxy)methyl)-7-azabicyclo[2.2.1]heptan-7-yl)methanone |
| 98 | 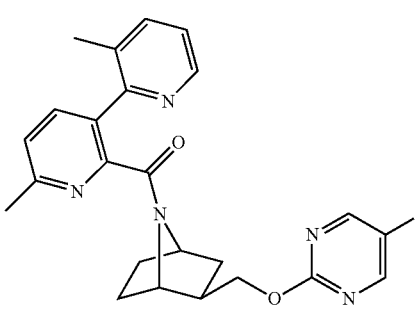 | | >10000 | | >10000 | (±)-(3,6'-dimethyl-[2,3'-bipyridin]-2'-yl)(2-(((5-fluoropyrimidin-2-yl)oxy)methyl)-7-azabicyclo[2.2.1]heptan-7-yl)methanone |
| 99 | 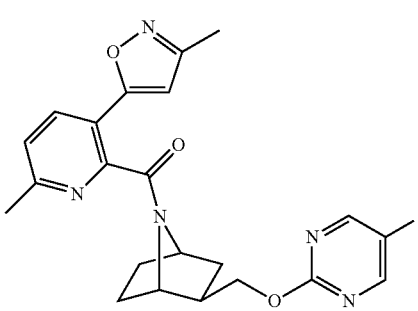 | | 1500 | | 2900 | (±)-(2-(((5-fluoropyrimidin-2-yl)oxy)methyl)-7-azabicyclo[2.2.1]heptan-7-yl)(6-methyl-3-(3-methylisoxazol-5-yl)pyridin-2-yl)methanone |
| 100 | 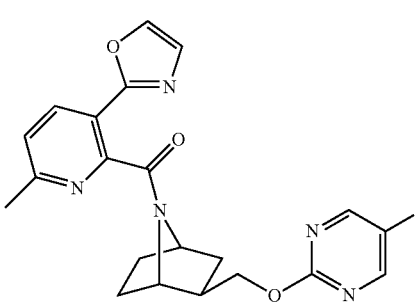 | | 950 | | 1800 | (±)-(2-(((5-fluoropyrimidin-2-yl)oxy)methyl)-7-azabicyclo[2.2.1]heptan-7-yl)(6-methyl-3-(oxazol-2-yl)pyridin-2-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 101 | | | 650 | 1200 | (±)-(2-(((5-fluoropyrimidin-2-yl)oxy)methyl)-7-azabicyclo[2.2.1]heptan-7-yl)(6-methyl-3-(pyrrolidin-1-yl)pyridin-2-yl)methanone |
| 102 | | | | | (±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone |
| 103 | | | 1700 | 3600 | (±)-(2-(((5-fluoropyrimidin-2-yl)oxy)methyl)-7-azabicyclo[2.2.1]heptan-7-yl)(6-methyl-3-(4-methyl-1H-pyrazol-1-yl)pyridin-2-yl)methanone |
| 104 | | | 1100 | 4600 | (±)-(2-(((5-fluoropyrimidin-2-yl)oxy)methyl)-7-azabicyclo[2.2.1]heptan-7-yl)(6-methyl-3-(1H-pyrazol-1-yl)pyridin-2-yl)methanone |
| 105 | | | | | (±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 106 | | | 300 | 154 | (±)-(2,6-dimethoxyphenyl)(2-(((5-fluoropyridin-2-yl)oxy)methyl)-7-azabicyclo[2.2.1]heptan-7-yl)methanone |
| 107 | | | 440 | 2200 | (±)-((3-fluoro-2-methoxyphenyl)(2-(((5-fluoropyridin-2-yl)oxy)methyl)-7-azabicyclo[2.2.1]heptan-7-yl)methanone |
| 108 | | 10 | 12 | 12 | (±)-(2-(((5-fluoropyridin-2-yl)oxy)methyl)-7-azabicyclo[2.2.1]heptan-7-yl)(2-methoxy-6-(2H-1,2,3-triazol-2-yl)phenyl)methanone |
| 109 | | 29 | 20 | 99 | (±)-(5-fluoro-2-(1H-pyrazol-5-yl)phenyl)(2-(((5-fluoropyridin-2-yl)oxy)methyl)-7-azabicyclo[2.2.1]heptan-7-yl)methanone |
| 110 | | 54 | 67 | 94 | (±)-(2-(((5-fluoropyridin-2-yl)oxy)methyl)-7-azabicyclo[2.2.1]heptan-7-yl)(2-methyl-6-(2H-1,2,3-triazol-2-yl)phenyl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 111 | | | 19 | 198 | (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 112 | | | 480 | 1000 | (±)-(5-chloro-3-(2H-1,2,3-triazol-2-yl)pyridin-2-yl)(2-(((5-fluoropyridin-2-yl)oxy)methyl)-7-azabicyclo[2.2.1]heptan-7-yl)methanone |
| 113 | | | 3400 | 4800 | (±)-(2-(((5-fluoropyridin-2-yl)oxy)methyl)-7-azabicyclo[2.2.1]heptan-7-yl)(5-methoxy-3-(2H-1,2,3-triazol-2-yl)pyridin-2-yl)methanone |
| 114 | | 20 | 48 | 73 | (±)-(2-(((5-fluoropyridin-2-yl)oxy)methyl)-7-azabicyclo[2.2.1]heptan-7-yl)(5-methoxy-2-(2H-1,2,3-triazol-2-yl)phenyl)methanone |
| 115 | | 57 | 78 | 108 | (±)-(2-fluoro-6-(2H-1,2,3-triazol-2-yl)phenyl)(2-(((5-fluoropyridin-2-yl)oxy)methyl)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 116 | | 142 | 250 | 315 | (±)-(4-fluoro-2-(2H-1,2,3-triazol-2-yl)phenyl)(2-(((5-fluoropyridin-2-yl)oxy)methyl)-7-azabicyclo[2.2.1]heptan-7-yl)methanone |
| 117 | | 62 | 82 | 245 | (±)-(3-fluoro-2-(2H-1,2,3-triazol-2-yl)phenyl)(2-(((5-fluoropyridin-2-yl)oxy)methyl)-7-azabicyclo[2.2.1]heptan-7-yl)methanone |
| 118 | | | 440 | 2200 | (±)-(3-ethoxy-6-methylpyridin-2-yl)(2-(((5-fluoropyridin-2-yl)oxy)methyl)-7-azabicyclo[2.2.1]heptan-7-yl)methanone |
| 119 | | | 500 | 1300 | (±)-(2-(((5-fluoropyridin-2-yl)oxy)methyl)-7-azabicyclo[2.2.1]heptan-7-yl)(4-methoxy-2-(2H-1,2,3-triazol-2-yl)phenyl)methanone |
| 120 | | 15 | 14 | 124 | (±)-(5-chloro-2-(2H-1,2,3-triazol-2-yl)phenyl)(2-(((5-fluoropyridin-2-yl)oxy)methyl)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 121 | 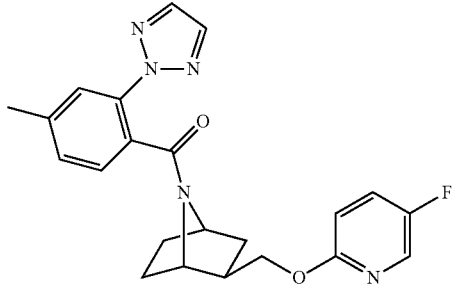 [SMILES: Cc1ccc(C(=O)N2C3CCC2C(COc2ccc(F)cn2)C3)c(-n2nccn2)c1] | 78 | 68 | 340 | (±)-(2-(((5-fluoropyridin-2-yl)oxy)methyl)-7-azabicyclo[2.2.1]heptan-7-yl)(4-methyl-2-(2H-1,2,3-triazol-2-yl)phenyl)methanone |
| 122 | 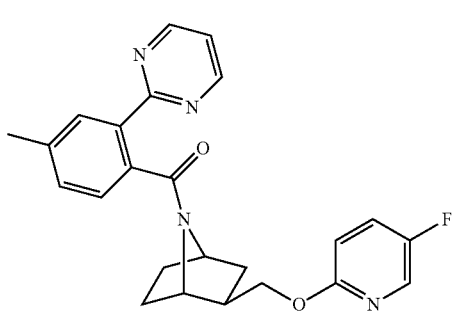 [SMILES: Cc1ccc(C(=O)N2C3CCC2C(COc2ccc(F)cn2)C3)c(-c2ncccn2)c1] | 118 | 154 | 1000 | (±)-(2-(((5-fluoropyridin-2-yl)oxy)methyl)-7-azabicyclo[2.2.1]heptan-7-yl)(4-methyl-2-(pyrimidin-2-yl)phenyl)methanone |
| 123 | 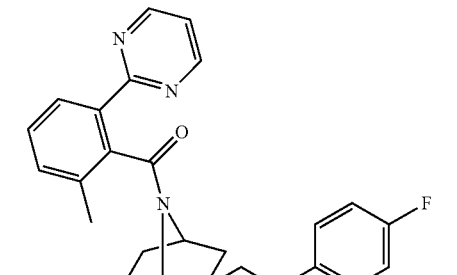 |  | 400 | 286 | (±)-(2-(((5-fluoropyridin-2-yl)oxy)methyl)-7-azabicyclo[2.2.1]heptan-7-yl)(2-methyl-6-(pyrimidin-2-yl)phenyl)methanone |
| 124 | 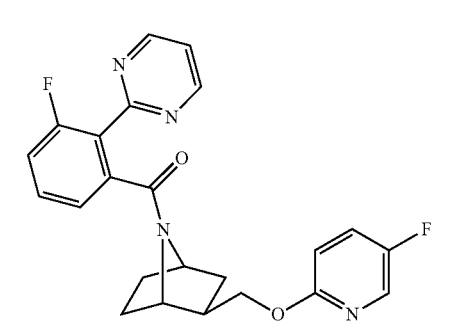 [SMILES: O=C(c1cccc(F)c1-c1ncccn1)N1C2CCC1C(COc1ccc(F)cn1)C2] | 83 | 52 | 355 | (±)-(3-fluoro-2-(pyrimidin-2-yl)phenyl)(-2-(((5-fluoropyridin-2-yl)oxy)methyl)-7-azabicyclo[2.2.1]heptan-7-yl)methanone |
| 125 | 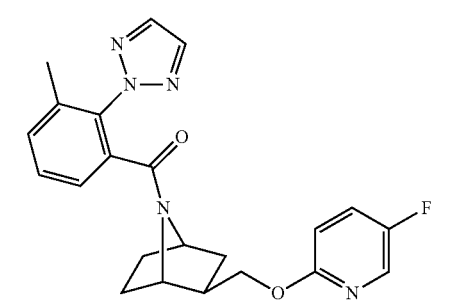 [SMILES: Cc1cccc(C(=O)N2C3CCC2C(COc2ccc(F)cn2)C3)c1-n1nccn1] | 47 | 29 | 132 | (±)-(2-(((5-fluoropyridin-2-yl)oxy)methyl)-7-azabicyclo[2.2.1]heptan-7-yl)(3-methyl-2-(2H-1,2,3-triazol-2-yl)phenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 126 | | 23 | 27 | 231 | (±)-(2-(((5-fluoropyridin-2-yl)oxy)methyl)-7-azabicyclo[2.2.1]heptan-7-yl)(5-(hydroxymethyl)-2-(2H-1,2,3-triazol-2-yl)phenyl)methanone |
| 127 | | | 190 | 1100 | (±)-(2-(3-methyl-1,2,4-oxadiazol-5-yl)phenyl)(2-((pyridin-2-yloxy)methyl)-7-azabicyclo[2.2.1]heptan-7-yl)methanone |
| 128 | | | 5700 | 10000 | (±)-(6-methyl-2-(2H-1,2,3-triazol-2-yl)pyridin-3-yl)(2-((pyridin-2-yloxy)methyl)-7-azabicyclo[2.2.1]heptan-7-yl)methanone |
| 129 | | | 190 | 1000 | (±)-(3-fluoro-2-(2H-1,2,3-triazol-2-yl)phenyl)(2-((pyridin-2-yloxy)methyl)-7-azabicyclo[2.2.1]heptan-7-yl)methanone |
| 130 | | | 3700 | 7199 | (±)-(6-methyl-2-(1H-1,2,3-triazol-1-yl)pyridin-3-yl)(2-((pyridin-2-yloxy)methyl)-7-azabicyclo[2.2.1]heptan-7-yl)methanone |

-continued

| Ex. No. | Compound | rOX1 $K_i$ (nm) | hOX1 $K_i$ (nm) | hOX2 $K_i$ (nm) | Compound Name |
|---|---|---|---|---|---|
| 131 | | | 10000 | 10000 | (±)-(6-methyl-2-(2H-1,2,3-triazol-2-yl)pyridin-3-yl)(2-(((4-(trifluoromethyl)pyrimidin-2-yl)oxy)methyl)-7-azabicyclo[2.2.1]heptan-7-yl)methanone |
| 132 | | | 10000 | 7399 | (±)-(6-methyl-2-(1H-1,2,3-triazol-1-yl)pyridin-3-yl)(2-(((4-(trifluoromethyl)pyrimidin-2-yl)oxy)methyl)-7-azabicyclo[2.2.1]heptan-7-yl)methanone |
| 133 | | | 1400 | 950 | (±)-(2-(3-methyl-1,2,4-oxadiazol-5-yl)phenyl)(2-(((4-(trifluoromethyl)pyrimidin-2-yl)oxy)methyl)-7-azabicyclo[2.2.1]heptan-7-yl)methanone |
| 134 | | | 1500 | 690 | (±)-(3-fluoro-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 135 | 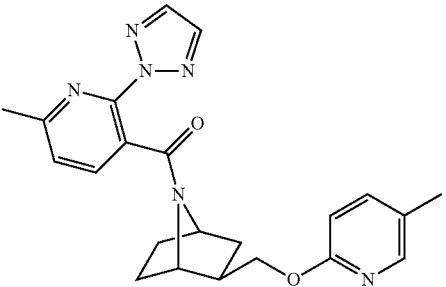 | | 5400 | 3900 | (±)-(6-methyl-2-(2H-1,2,3-triazol-2-yl)pyridin-3-yl)(2-(((5-methylpyridin-2-yl)oxy)methyl)-7-azabicyclo[2.2.1]heptan-7-yl)methanone |
| 136 | 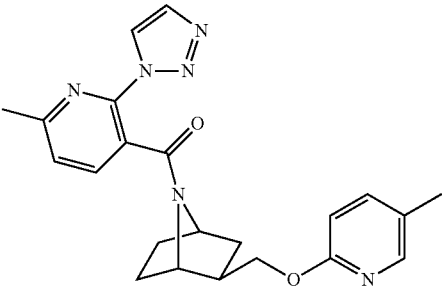 | | 6800 | 1200 | (±)-(6-methyl-2-(1H-1,2,3-triazol-1-yl)pyridin-3-yl)(2-(((5-methylpyridin-2-yl)oxy)methyl)-7-azabicyclo[2.2.1]heptan-7-yl)methanone |
| 137 | 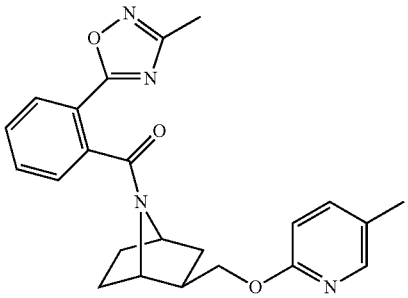 [SMILES: Cc1ccc(OCC2CC3CCC2N3C(=O)c2ccccc2-c2nc(C)no2)nc1] | | 950 | 425 | (±)-(2-(3-methyl-1,2,4-oxadiazol-5-yl)phenyl)(2-(((5-methylpyridin-2-yl)oxy)methyl)-7-azabicyclo[2.2.1]heptan-7-yl)methanone |
| 138 | 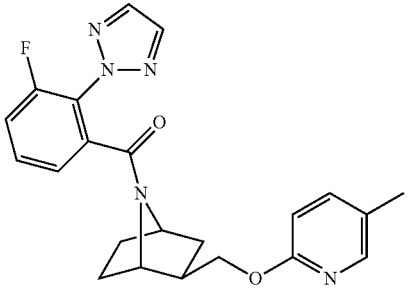 [SMILES: Cc1ccc(OCC2CC3CCC2N3C(=O)c2cccc(F)c2-n2nccn2)nc1] | | 606 | 250 | (±)-(3-fluoro-2-(2H-1,2,3-triazol-2-yl)phenyl)(2-(((5-methylpyridin-2-yl)oxy)methyl)-7-azabicyclo[2.2.1]heptan-7-yl)methanone |
| 139 | 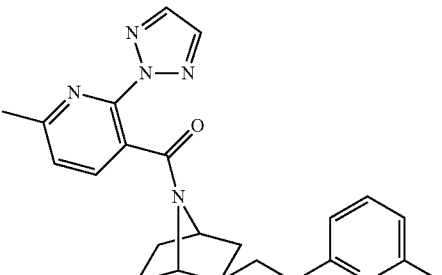 | | 4399 | 6500 | (±)-(6-methyl-2-(2H-1,2,3-triazol-2-yl)pyridin-3-yl)(2-(((6-methylpyridin-2-yl)oxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 140 | 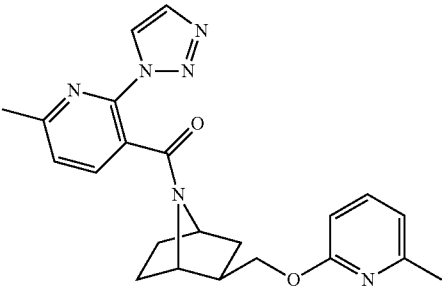 | | 3100 | 2300 | (±)-(6-methyl-2-(1H-1,2,3-triazol-1-yl)pyridin-3-yl)(2-(((6-methylpyridin-2-yl)oxy)methyl)-7-azabicyclo[2.2.1]heptan-7-yl)methanone |
| 141 | 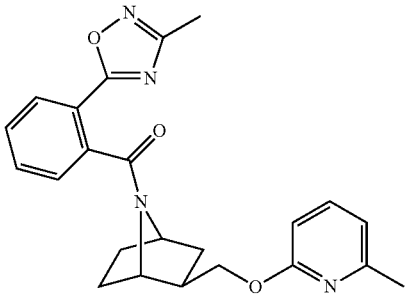 [SMILES: Cc1cccc(OCC2CC3CCC2N3C(=O)c2ccccc2-c2nc(C)no2)n1] | | 280 | 300 | (±)-(2-(3-methyl-1,2,4-oxadiazol-5-yl)phenyl)(2-(((6-methylpyridin-2-yl)oxy)methyl)-7-azabicyclo[2.2.1]heptan-7-yl)methanone |
| 142 | 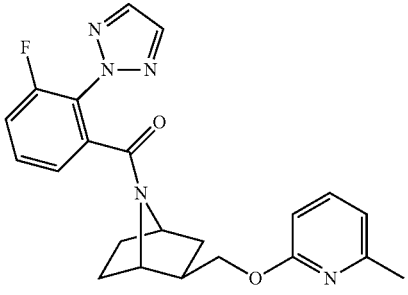 [SMILES: Cc1cccc(OCC2CC3CCC2N3C(=O)c2cccc(F)c2-n2nccn2)n1] | | 207 | 300 | (±)-(3-fluoro-2-(2H-1,2,3-triazol-2-yl)phenyl)(2-(((6-methylpyridin-2-yl)oxy)methyl)-7-azabicyclo[2.2.1]heptan-7-yl)methanone |
| 143 | 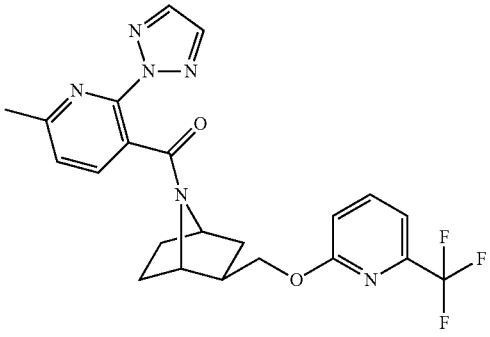 [SMILES: Cc1ccc(C(=O)N2C3CCC2C(COc2cccc(C(F)(F)F)n2)C3)c(-n2nccn2)n1] | | 3900 | 4600 | (±)-(6-methyl-2-(2H-1,2,3-triazol-2-yl)pyridin-3-yl)(2-(((6-(trifluoromethyl)pyridin-2-yl)oxy)methyl)-7-azabicyclo[2.2.1]heptan-7-yl)methanone |
| 144 | 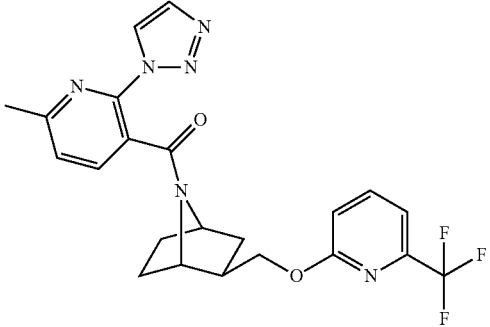 | | 3600 | 3200 | (±)-(6-methyl-2-(1H-1,2,3-triazol-1-yl)pyridin-3-yl)(2-(((6-(trifluoromethyl)pyridin-2-yl)oxy)methyl)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 145 | | | 340 | 330 | (±)-(2-(3-methyl-1,2,4-oxadiazol-5-yl)phenyl)(2-(((6-(trifluoromethyl)pyridin-2-yl)oxy)methyl)-7-azabicyclo[2.2.1]heptan-7-yl)methanone |
| 146 | | | 180 | 196 | (±)-(3-fluoro-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone |
| 147 | | | | | (±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone |
| 148 | | | 6299 | 3200 | (±)-(6-methyl-2-(1H-1,2,3-triazol-1-yl)pyridin-3-yl)(2-((quinoxalin-2-yloxy)methyl)-7-azabicyclo[2.2.1]heptan-7-yl)methanone |

| Ex. No. | Compound | rOX1 K_i (nm) | hOX1 K_i (nm) | hOX2 K_i (nm) | Compound Name |
|---|---|---|---|---|---|
| 149 | | | 220 | 2000 | (±)-(2-(3-methyl-1,2,4-oxadiazol-5-yl)phenyl)(2-((quinoxalin-2-yloxy)methyl)-7-azabicyclo[2.2.1]heptan-7-yl)methanone |
| 150 | | | 180 | 990 | (±)-(3-fluoro-2-(2H-1,2,3-triazol-2-yl)phenyl)(2-((quinoxalin-2-yloxy)methyl)-7-azabicyclo[2.2.1]heptan-7-yl)methanone |
| 151 | | | 10000 | 10000 | (±)-(2-(((4,6-dimethylpyrimidin-2-yl)oxy)methyl)-7-azabicyclo[2.2.1]heptan-7-yl)(6-methyl-2-(2H-1,2,3-triazol-2-yl)pyridin-3-yl)methanone |
| 152 | | | 10000 | 5899 | (±)-(2-(((4,6-dimethylpyrimidin-2-yl)oxy)methyl)-7-azabicyclo[2.2.1]heptan-7-yl)(6-methyl-2-(1H-1,2,3-triazol-1-yl)pyridin-3-yl)methanone |
| 153 | | | 1100 | 440 | (±)-(2-(((4,6-dimethylpyrimidin-2-yl)oxy)methyl)-7-azabicyclo[2.2.1]heptan-7-yl)(2-(3-methyl-1,2,4-oxadiazol-5-yl)phenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 154 | | | 690 | 300 | (±)-(2-(((4,6-dimethylpyrimidin-2-yl)oxy)methyl)-7-azabicyclo[2.2.1]heptan-7-yl)(3-fluoro-2-(2H-1,2,3-triazol-2-yl)phenyl)methanone |
| 155 | | | 1570 | 3600 | (±)-(2-ethoxy-4-methylpyridin-3-yl)(2-((pyridin-2-yloxy)methyl)-7-azabicyclo[2.2.1]heptan-7-yl)methanone |
| 156 | | | >10000 | >10000 | (±)-(6-methylimidazo[2,1-b]thiazol-5-yl)(2-((pyridin-2-yloxy)methyl)-7-azabicyclo[2.2.1]heptan-7-yl)methanone |
| 157 | | 94 | 134 | 537 | (±)-(5-bromo-2-ethoxypyridin-3-yl)(2-((pyridin-2-yloxy)methyl)-7-azabicyclo[2.2.1]heptan-7-yl)methanone |
| 158 | | | 2930 | 1780 | (±)-(2-ethoxy-6-methylpyridin-3-yl)(2-((pyridin-2-yloxy)methyl)-7-azabicyclo[2.2.1]heptan-7-yl)methanone |

-continued

| Ex. No. | Compound | rOX1 $K_i$ (nm) | hOX1 $K_i$ (nm) | hOX2 $K_i$ (nm) | Compound Name |
|---|---|---|---|---|---|
| 159 | 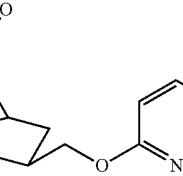 | | 262 | 786 | (±)-(7-hydroxyquinolin-8-yl)(2-((pyridin-2-yloxy)methyl)-7-azabicyclo[2.2.1]heptan-7-yl)methanone |
| 160 | 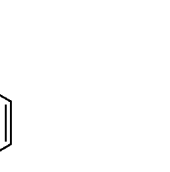 | | 8700 | >10000 | (±)-(2-ethoxy-5-phenylpyridin-3-yl)(2-((pyridin-2-yloxy)methyl)-7-azabicyclo[2.2.1]heptan-7-yl)methanone |
| 161 | 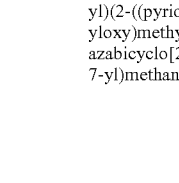 | | 478 | 1450 | (±)-(4-bromo-2-ethoxypyridin-3-yl)(2-((pyridin-2-yloxy)methyl)-7-azabicyclo[2.2.1]heptan-7-yl)methanone |
| 162 | 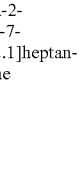 | | 8500 | >10000 | (±)-(2-chloro-4-ethoxypyridin-3-yl)(2-((pyridin-2-yloxy)methyl)-7-azabicyclo[2.2.1]heptan-7-yl)methanone |
| 163 |  | 150 | 153 | 150 | (±)-(2,4-diethoxypyridin-3-yl)(2-((pyridin-2-yloxy)methyl)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 164 | | | 9 | 7 | 195 | (3-ethoxyisoquinolin-4-yl)((1S,2R,4R)-2-((pyridin-2-yloxy)methyl)-7-azabicyclo[2.2.1]heptan-7-yl)methanone |
| 165 | | | | 409 | 550 | (±)-(2-ethoxyphenyl)(2-(((5-fluoropyridin-2-yl)oxy)methyl)-7-azabicyclo[2.2.1]heptan-7-yl)methanone |
| 166 | | | | 106 | 1141 | (±)-(5-fluoro-2-(2H-1,2,3-triazol-2-yl)phenyl)(2-((quinoxalin-2-yloxy)methyl)-7-azabicyclo[2.2.1]heptan-7-yl)methanone |
| 167 | | | | 9 | 14 | (±)-5-methyl-2-(2H-1,2,3-triazol-2-yl)phenyl)(2-(((5-methylpyridin-2-yl)oxy)methyl)-7-azabicyclo[2.2.1]heptan-7-yl)methanone |
| 168 | | | | 2300 | 7300 | (±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 169 | | | 8999 | 2526 | (±)-(5-fluoro-2-(2H-1,2,3-triazol-2-yl)phenyl)(2-(((pyridin-2-ylamino)methyl)-7-azabicyclo[2.2.1]heptan-7-yl)methanone |
| 170 | | | 1965 | 512 | (±)-(2-(((4,6-dimethylpyrimidin-2-yl)amino)methyl)-7-azabicyclo[2.2.1]heptan-7-yl)(5-fluoro-2-(2H-1,2,3-triazol-2-yl)phenyl)methanone |
| 171 | | | | 1935 | (±)-(5-fluoro-2-(2H-1,2,3-triazol-2-yl)phenyl)(2-(((4-(trifluoromethyl)pyrimidin-2-yl)amino)methyl)-7-azabicyclo[2.2.1]heptan-7-yl)methanone |
| 172 | | | | 686 | (±)-(5-fluoro-2-(2H-1,2,3-triazol-2-yl)phenyl)(2-(((6-(trifluoromethyl)pyridin-2-yl)amino)methyl)-7-azabicyclo[2.2.1]heptan-7-yl)methanone |
| 173 | | | 1260 | 3000 | (±)-(3-fluoro-2-methoxyphenyl)(2-(((5-fluoropyridin-2-yl)oxy)methyl)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 174 | 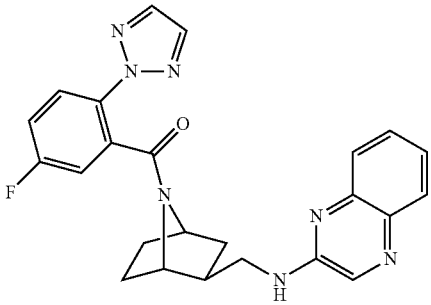 [SMILES: O=C(c1cc(F)ccc1-n1nccn1)N1C2CCC1C(CNc1cnc3ccccc3n1)C2] | | 373 | 1000 | (±)-(5-fluoro-2-(2H-1,2,3-triazol-2-yl)phenyl)(2-((quinoxalin-2-ylamino)methyl)-7-azabicyclo[2.2.1]heptan-7-yl)methanone |
| 175 | 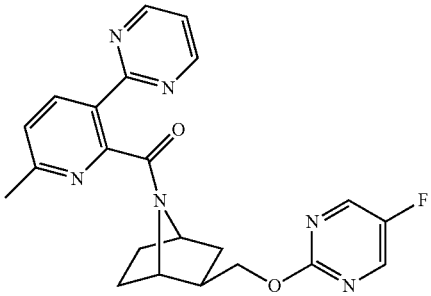 [SMILES: Cc1ccc(-c2ncccn2)c(C(=O)N2C3CCC2C(COc2ncc(F)cn2)C3)n1] | | 2500 | 4000 | (±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone |
| 176 | 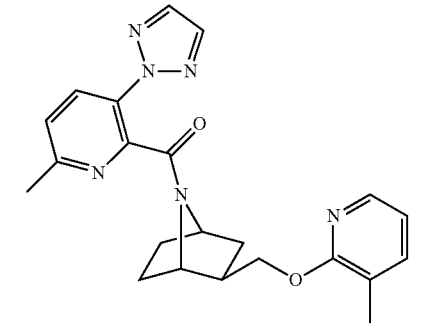 [SMILES: Cc1ccc(-n2nccn2)c(C(=O)N2C3CCC2C(COc2ncccc2C)C3)n1] | 119 | 150 | 202 | (±)-(6-methyl-3-(2H-1,2,3-triazol-2-yl)pyridin-2-yl)(2-(((3-methylpyridin-2-yl)oxy)methyl)-7-azabicyclo[2.2.1]heptan-7-yl)methanone |
| 177 | 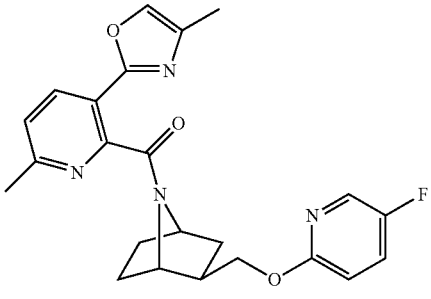 [SMILES: Cc1coc(-c2ccc(C)nc2C(=O)N2C3CCC2C(COc2ccc(F)cn2)C3)n1] | | 535 | 4000 | (±)-(2-(((5-fluoropyridin-2-yl)oxy)methyl)-7-azabicyclo[2.2.1]heptan-7-yl)(6-methyl-3-(4-methyloxazol-2-yl)pyridin-2-yl)methanone |
| 178 | 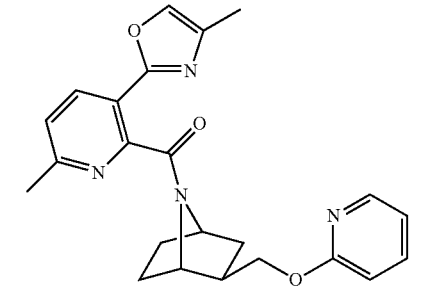 [SMILES: Cc1coc(-c2ccc(C)nc2C(=O)N2C3CCC2C(COc2ccccn2)C3)n1] | | 964 | >10000 | (6-methyl-3-(4-methyloxazol-2-yl)pyridin-2-yl)((1S,2R,4R)-2-((pyridin-2-yloxy)methyl)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 179 | 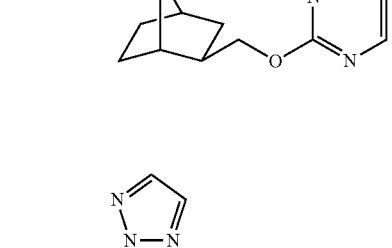 | | | | ((1S,2R,4R)-2-(((5-fluoropyrimidin-2-yl)oxy)methyl)-7-azabicyclo[2.2.1]heptan-7-yl)(6-methyl-3-(4-methyloxazol-2-yl)pyridin-2-yl)methanone |
| 180 | 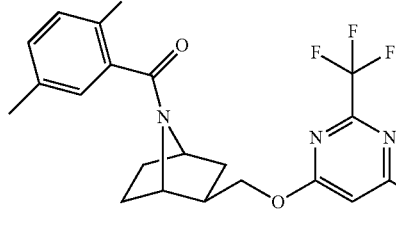 | | 33 | 32 | (±)-(5-methyl-2-(2H-1,2,3-triazol-2-yl)phenyl)(2-(((6-methyl-2-(trifluoromethyl)pyrimidin-4-yl)oxy)methyl)-7-azabicyclo[2.2.1]heptan-7-yl)methanone |
| 181 | 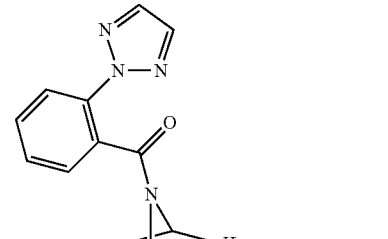 | 34 | 28 | 700 | (2-(2H-1,2,3-triazol-2-yl)phenyl)(1S,2R,4R)-2-((5-(trifluoromethyl)pyrazin-2-yl)amino)-7-azabicyclo[2.2.1]heptan-7-yl)methanone |
| 182 | 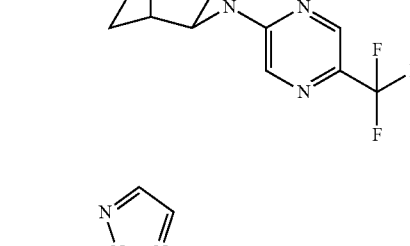 | 47 | 38 | 1100 | (±)-((2-(2H-1,2,3-triazol-2-yl)phenyl)(2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 183a | | | >10000 | >10000 | (2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 183b | | | 34 | 28 | 700 (2-(2H-1,2,3-triazol-2-yl)phenyl)((1R,2S,4S)-2-((5-(trifluoromethyl)pyrazin-2-yl)amino)-7-azabicyclo[2.2.1]heptan-7-yl)methanone |
| 184 | | | 189 | 349 | 4100 (±)-(5-methyl-3-(2H-1,2,3-triazol-2-yl)pyridin-2-yl)(2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 185 | 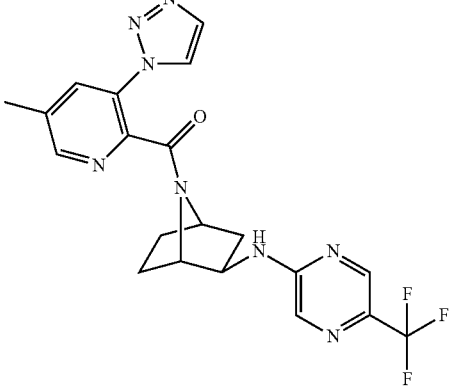 | | 1500 | 2700 | (±)-(5-methyl-3-(1H-1,2,3-triazol-1-yl)pyridin-2-yl)(2-((5-(trifluoromethyl)pyrazin-2-yl)amino)-7-azabicyclo[2.2.1]heptan-7-yl)methanone |
| 186 | 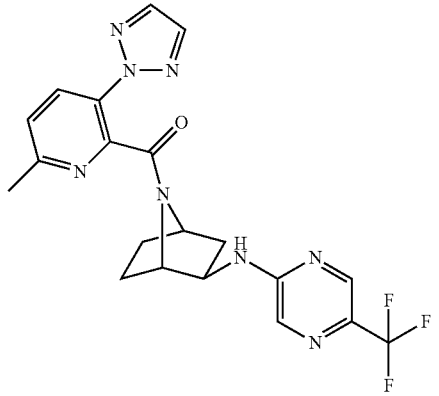 [SMILES: Cc1ccc(-n2nccn2)c(C(=O)N2C3CCC2C(Nc2cnc(C(F)(F)F)cn2)C3)n1] | 134 | 164 | 1200 | (±)-(6-methyl-3-(2H-1,2,3-triazol-2-yl)pyridin-2-yl)(2-((5-(trifluoromethyl)pyrazin-2-yl)amino)-7-azabicyclo[2.2.1]heptan-7-yl)methanone |
| 187 | 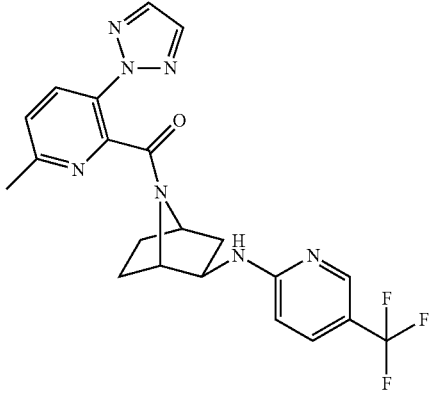 [SMILES: Cc1ccc(-n2nccn2)c(C(=O)N2C3CCC2C(Nc2ccc(C(F)(F)F)cn2)C3)n1] | 81 | 48 | 620 | (±)-(6-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 188 | | | 295 | 1500 | (±)-(5-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone |
| 189 | | | 766 | 1500 | (±)-(6-methyl-2-(2H-1,2,3-triazol-2-yl)pyridin-3-yl)(2-((5-(trifluoromethyl)pyridin-2-yl)amino)-7-azabicyclo[2.2.1]heptan-7-yl)methanone |
| 190 | | | 589 | 1200 | (±)-(6-methyl-2-(1H-1,2,3-triazol-1-yl)pyridin-3-yl)(2-((5-(trifluoromethyl)pyridin-2-yl)amino)-7-azabicyclo[2.2.1]heptan-7-yl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 191 | 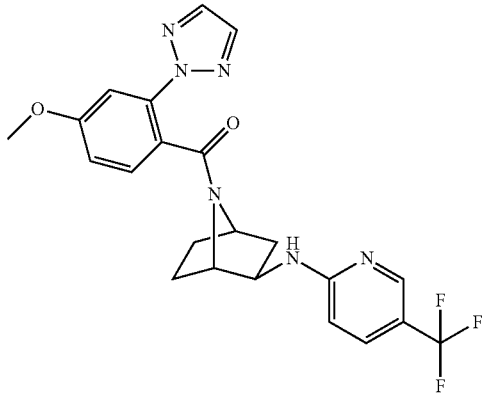 [SMILES: COc1ccc(C(=O)N2C3CCC2C(Nc2ccc(C(F)(F)F)cn2)C3)c(-n2nccn2)c1] | | 257 | 8800 | (±)-(4-methoxy-2-(2H-1,2,3-triazol-2-yl)phenyl)(2-((5-(trifluoromethyl)pyridin-2-yl)amino)-7-azabicyclo[2.2.1]heptan-7-yl)methanone |
| 192 | 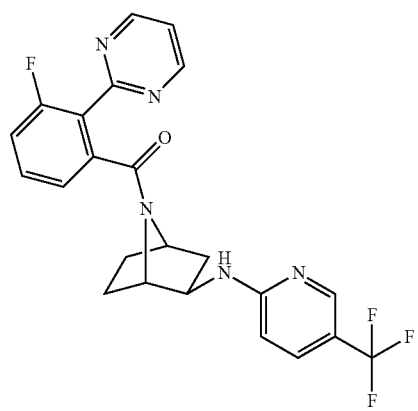 [SMILES: O=C(c1cccc(F)c1-c1ncccn1)N1C2CCC1C(Nc1ccc(C(F)(F)F)cn1)C2] | 60 | 52 | 1500 | (±)-(3-fluoro-2-(pyrimidin-2-yl)phenyl)(2-((5-(trifluoromethyl)pyridin-2-yl)amino)-7-azabicyclo[2.2.1]heptan-7-yl)methanone |
| 193 | 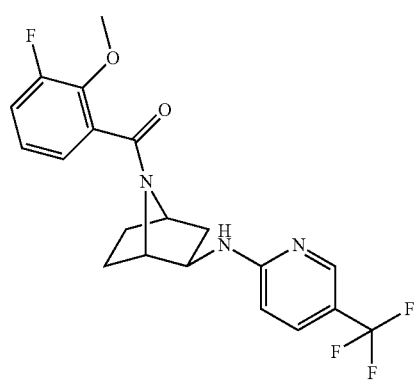 [SMILES: COc1c(F)cccc1C(=O)N1C2CCC1C(Nc1ccc(C(F)(F)F)cn1)C2] | | 2900 | >10000 | (±)-((3-fluoro-2-methoxyphenyl)(2-((5-(trifluoromethyl)pyridin-2-yl)amino)-7-azabicyclo[2.2.1]heptan-7-yl)methanone |

-continued
| Ex. No. | Compound | rOX1 K$_i$ (nm) | hOX1 K$_i$ (nm) | hOX2 K$_i$ (nm) | Compound Name |
|---|---|---|---|---|---|
| 194 | 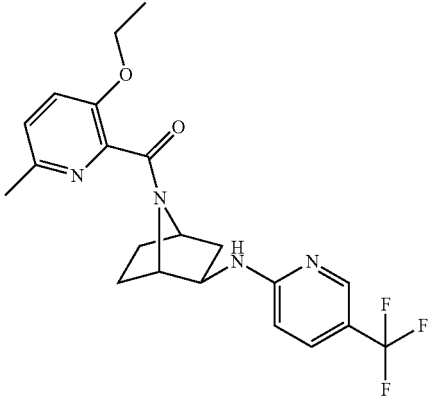 [SMILES: CCOc1ccc(C)nc1C(=O)N1C2CCC1C(Nc1ccc(C(F)(F)F)cn1)C2] | | 450 | 800 | (±)-(3-ethoxy-6-methylpyridin-2-yl)(2-((5-(trifluoromethyl)pyridin-2-yl)amino)-7-azabicyclo[2.2.1]heptan-7-yl)methanone |
| 195 | 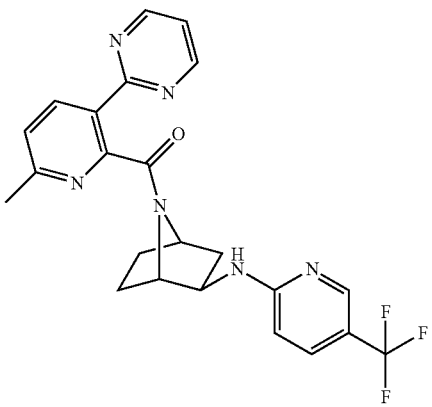 [SMILES: Cc1ccc(-c2ncccn2)c(C(=O)N2C3CCC2C(Nc2ccc(C(F)(F)F)cn2)C3)n1] | 57 | 37 | 325 | (±)-(6-methyl-3-(pyrimidin-2-yl)pyridin-2-yl)(2-((5-(trifluoromethyl)pyridin-2-yl)amino)-7-azabicyclo[2.2.1]heptan-7-yl)methanone |
| 196 | 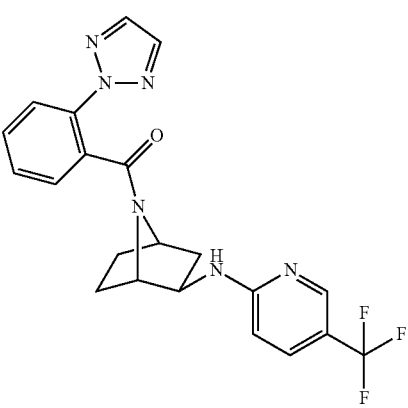 [SMILES: O=C(c1ccccc1-n1nccn1)N1C2CCC1C(Nc1ccc(C(F)(F)F)cn1)C2] | 59 | 61 | 1500 | (±)-(2-(2H-1,2,3-triazol-2-yl)phenyl)(2-((5-(trifluoromethyl)pyridin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 197 | | | 8999 | 862 | (±)-(2-((4,6-dimethylpyrimidin-2-yl)amino)-7-azabicyclo[2.2.1]heptan-7-yl)(5-fluoro-2-(2H-1,2,3-triazol-2-yl)phenyl)methanone |
| 198 | | | 1411 | 704 | (±)-(2-((4,6-dimethylpyrimidin-2-yl)amino)-7-azabicyclo[2.2.1]heptan-7-yl)(2-fluoro-6-(2H-1,2,3-triazol-2-yl)phenyl)methanone |
| 199 | | | 1634 | 553 | (±)-(2-((4,6-dimethylpyrimidin-2-yl)amino)-7-azabicyclo[2.2.1]heptan-7-yl)(4-fluoro-2-(2H-1,2,3-triazol-2-yl)phenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 200 | | | 1100 | 552 | (±)-(2-((4,6-dimethylpyrimidin-2-yl)amino)-7-azabicyclo[2.2.1]heptan-7-yl)(6-methyl-3-(pyrimidin-2-yl)pyridin-2-yl)methanone |
| 201 | | 3700 | | 1100 | (±)-(2-((4,6-dimethylpyrimidin-2-yl)amino)-7-azabicyclo[2.2.1]heptan-7-yl)(6-methyl-3-(2H-1,2,3-triazol-2-yl)pyridin-2-yl)methanone |
| 202 | | | 760 | 444 | (±)-(2-(2H-1,2,3-triazol-2-yl)phenyl)(2-((4,6-dimethylpyrimidin-2-yl)amino)-7-azabicyclo[2.2.1]heptan-7-yl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 203 | | | >10000 | 490 | (±)-(2-((4,6-dimethylpyrimidin-2-yl)amino)-7-azabicyclo[2.2.1]heptan-7-yl)(3-ethoxy-6-methylpyridin-2-yl)methanone |
| 204 | | 33 | 25 | 220 | (±)-(2-(2H-1,2,3-triazol-2-yl)phenyl)(2-(quinoxalin-2-ylamino)-7-azabicyclo[2.2.1]heptan-7-yl)methanone |
| 205 | | 79 | 50 | 168 | (±)-(6-methyl-3-(2H-1,2,3-triazol-2-yl)pyridin-2-yl)(2-(quinoxalin-2-ylamino)-7-azabicyclo[2.2.1]heptan-7-yl)methanone |
| 206 | | | 1200 | 1500 | (±)-(3-fluoro-2-methoxyphenyl)(2-(quinoxalin-2-ylamino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 207 | | | 120 | 95 | 64 | (±)-(3-ethoxy-6-methylpyridin-2-yl)(2-(quinoxalin-2-ylamino)-7-azabicyclo[2.2.1]heptan-7-yl)methanone |
| 208 | | | 26 | 30 | 90 | (±)-(6-methyl-3-(pyrimidin-2-yl)pyridin-2-yl)(2-(quinoxalin-2-ylamino)-7-azabicyclo[2.2.1]heptan-7-yl)methanone |
| 209 | | | | 1100 | 736 | (±)-(2-(2H-1,2,3-triazol-2-yl)phenyl)(2-((6-(trifluoromethyl)pyridin-2-yl)amino)-7-azabicyclo[2.2.1]heptan-7-yl)methanone |
| 210 | | | | 211 | 128 | (±)-((2-(2H-1,2,3-triazol-2-yl)phenyl)(2-((4-(trifluoromethyl)pyridin-2-yl)amino)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 211 | | | 110 | 55 | 1800 | (±)-(2-(2H-1,2,3-triazol-2-yl)phenyl)(2-((5-chloropyridin-2-yl)amino)-7-azabicyclo[2.2.1]heptan-7-yl)methanone |
| 212 | | | 734 | | 4900 | (±)-(2-(2H-1,2,3-triazol-2-yl)phenyl)(2-((6-(trifluoromethyl)pyridazin-3-yl)amino)-7-azabicyclo[2.2.1]heptan-7-yl)methanone |
| 213 | | | 2800 | | 7501 | (±)-(2-(2H-1,2,3-triazol-2-yl)phenyl)(2-((5-methoxypyridin-2-yl)amino)-7-azabicyclo[2.2.1]heptan-7-yl)methanone |
| 214 | | | 500 | | 3100 | (±)-(2-(2H-1,2,3-triazol-2-yl)phenyl)(2-((5-methylpyridin-2-yl)amino)-7-azabicyclo[2.2.1]heptan-7-yl)methanone |

-continued

| Ex. No. | Compound | rOX1 K_i (nm) | hOX1 K_i (nm) | hOX2 K_i (nm) | Compound Name |
|---|---|---|---|---|---|
| 215 | | | 1700 | 8999 | (±)-(2-(2H-1,2,3-triazol-2-yl)phenyl)(2-(pyridin-2-ylamino)-7-azabicyclo[2.2.1]heptan-7-yl)methanone |
| 216 | | 99 | 71 | 475 | (±)-(2-(2H-1,2,3-triazol-2-yl)phenyl)(2-((5-chlorobenzo[d]oxazol-2-yl)amino)-7-azabicyclo[2.2.1]heptan-7-yl)methanone |
| 217 | | 59 | 40 | 770 | (±)-(2-((5-bromopyridin-2-yl)amino)-7-azabicyclo[2.2.1]heptan-7-yl)(6-methyl-3-(pyrimidin-2-yl)pyridin-2-yl)methanone |
| 218 | | | 2700 | 6700 | (±)-(2-((5-bromopyridin-2-yl)amino)-7-azabicyclo[2.2.1]heptan-7-yl)(3-fluoro-2-methoxyphenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 219 | | | 257 | 1700 | (±)-(2-((5-bromopyridin-2-yl)amino)-7-azabicyclo[2.2.1]heptan-7-yl)(3-ethoxy-6-methylpyridin-2-yl)methanone |
| 220 | | 38 | 26 | 1100 | (±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone |
| 221 | | 172 | 200 | 3300 | (±)-(2-(2H-1,2,3-triazol-2-yl)phenyl)(2-((5-(trifluoromethyl)pyrimidin-2-yl)amino)-7-azabicyclo[2.2.1]heptan-7-yl)methanone |
| 222 | | 4800 | | >10000 | (±)-(3-fluoro-2-methoxyphenyl)(2-((5-(trifluoromethyl)pyrimidin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 223 | | | 550 | 4000 | (±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone |
| 224 | | | 2500 | 7399 | (±)-(3-ethoxy-6-methylpyridin-2-yl)(2-((5-(trifluoromethyl)pyrimidin-2-yl)amino)-7-azabicyclo[2.2.1]heptan-7-yl)methanone |
| 225 | | | 530 | 3300 | (±)-(6-methyl-3-(pyrimidin-2-yl)pyridin-2-yl)(2-((5-(trifluoromethyl)pyrimidin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 226 | | | >10000 | >10000 | (±)-(3-fluoro-2-methoxyphenyl)(2-((5-(trifluoromethyl)pyrimidin-2-yl)amino)-7-azabicyclo[2.2.1]heptan-7-yl)methanone |
| 227 | | | >10000 | >10000 | (±)-(3-ethoxy-6-methylpyridin-2-yl)(2-((5-(trifluoromethyl)pyrimidin-2-yl)amino)-7-azabicyclo[2.2.1]heptan-7-yl)methanone |
| 228 | | | >10000 | >10000 | (±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone |

-continued

| Ex. No. | Compound | rOX1 $K_i$ (nm) | hOX1 $K_i$ (nm) | hOX2 $K_i$ (nm) | Compound Name |
|---|---|---|---|---|---|
| 229 | | | >10000 | >10000 | (±)-(3-ethoxy-6-methylpyridin-2-yl)(2-(quinoxalin-2-ylamino)-7-azabicyclo[2.2.1]heptan-7-yl)methanone |
| 230 | | | >10000 | >10000 | (±)-(6-methyl-3-(2H-1,2,3-triazol-2-yl)pyridin-2-yl)(2-(quinoxalin-2-ylamino)-7-azabicyclo[2.2.1]heptan-7-yl)methanone |
| 231 | | | >10000 | >10000 | (±)-(3-fluoro-2-methoxyphenyl)(2-(quinoxalin-2-ylamino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 232 | | | | | (±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone |
| 233 | | | | | (±)-(2-((5-bromopyridin-2-yl)amino)-7-azabicyclo[2.2.1]heptan-7-yl)(3-ethoxy-6-methylpyridin-2-yl)methanone |
| 234 | | | | | (±)-(2-((5-bromopyridin-2-yl)amino)-7-azabicyclo[2.2.1]heptan-7-yl)(3-fluoro-2-methoxyphenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 235 | | | >10000 | >10000 | (±)-((2-(2H-1,2,3-triazol-2-yl)phenyl)(2-((4-(trifluoromethyl)pyridin-2-yl)amino)-7-azabicyclo[2.2.1]heptan-7-yl)methanone |
| 236 | | | >10000 | >10000 | (±)-(2-((5-fluoropyridin-2-yl)amino)-7-azabicyclo[2.2.1]heptan-7-yl)(6-methyl-3-(2H-1,2,3-triazol-2-yl)pyridin-2-yl)methanone |
| 237 | | | >10000 | >10000 | (±)-(3-fluoro-2-methoxyphenyl)(2-((5-fluoropyridin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 238 | | 16 | 16 | 955 | (3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 239 | | 22 | 19 | 490 | (2-ethoxynaphthalen-1-yl)((1S,2R,4R)-2-((5-(trifluoromethyl)pyrazin-2-yl)amino)-7-azabicyclo[2.2.1]heptan-7-yl)methanone |
| 240 | | | 400 | 2100 | isoquinolin-4-yl((1S,2R,4R)-2-((5-(trifluoromethyl)pyrazin-2-yl)amino)-7-azabicyclo[2.2.1]heptan-7-yl)methanone |
| 241 | | 134 | 159 | 5064 | (4-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 242 | | 31 | 41 | 239 | (2-methoxy-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 243 | | 34 | 45 | 723 | (5-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 244 | | 74 | 46 | 235 | (5-(4-fluorophenyl)-2-methylthiazol-4-yl)((1S,2R,4R)-2-((5-(trifluoromethyl)pyrazin-2-yl)amino)-7-azabicyclo[2.2.1]heptan-7-yl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 245 | | 10 | 7 | 288 | (3-methyl-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 246 | | 29 | 17 | 1022 | (3-ethoxyisoquinolin-4-yl)((1S,2R,4R)-2-((5-(trifluoromethyl)pyrazin-2-yl)amino)-7-azabicyclo[2.2.1]heptan-7-yl)methanone |
| 247 | | | 420 | 1130 | (6-methyl-2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 248 | | | 153 | 119 | >10000 | (6-methyl-2-(1H-1,2,3-triazol-1-yl)pyridin-3-yl)((1S,2R,4R)-2-((5-(trifluoromethyl)pyrazin-2-yl)amino)-7-azabicyclo[2.2.1]heptan-7-yl)methanone |
| 249 | | | 57 | 54 | 5600 | (4-methoxy-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 250 | | | | 5649 | >10000 | (1H-benzo[d]imidazol-2-yl)((1S,2R,4R)-2-((5-(trifluoromethyl)pyrazin-2-yl)amino)-7-azabicyclo[2.2.1]heptan-7-yl)methanone |
| 251 | | | | 520 | 5300 | (1-methyl-1H-benzo[d]imidazol-2-yl)((1S,2R,4R)-2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 252 | | 45 | 27 | 1230 | (3-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 253 | | 155 | 152 | 9601 | (4-(difluoromethoxy)-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 254 | | 23 | 20 | 377 | (3-fluoro-2-(3-methyl-1,2,4-oxadiazol-5-yl)phenyl)((1S,2R,4R)-2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 255 | | 32 | 29 | 265 | (5-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 256 | | 84 | 60 | 1100 | (5-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 257 | | 85 | 102 | 3200 | (4-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 258 | | | 42 | 48 | 690 | (2-fluoro-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 259 | | | >10000 | | >10000 | (6-methylimidazo[2,1-b]thiazol-5-yl)((1S,2R,4R)-2-((5-(trifluoromethyl)pyrazin-2-yl)amino)-7-azabicyclo[2.2.1]heptan-7-yl)methanone |
| 260 | | | 14 | 10 | 519 | (3-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone |
| 261 | | | >10000 | | 5000 | (2-((4,6-dimethylpyrimidin-2-yl)amino)-7-azabicyclo[2.2.1]heptan-7-yl)(3-fluoro-2-methoxyphenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 262 | | 106 | 175 | 4200 | (3-fluoro-2-(pyridazin-3-yl)phenyl)((1S,2R,4R)-2-((5-(trifluoromethyl)pyrazin-2-yl)amino)-7-azabicyclo[2.2.1]heptan-7-yl)methanone |
| 263 | | 44 | 41 | 1100 | (3-methyl-2-(pyridazin-3-yl)phenyl)((1S,2R,4R)-2-((5-(trifluoromethyl)pyrazin-2-yl)amino)-7-azabicyclo[2.2.1]heptan-7-yl)methanone |
| 264 | | | 1400 | >10000 | (3-fluoro-2-(pyridazin-4-yl)phenyl)((1S,2R,4R)-2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 265 | | 20 | 23 | 188 | (3-fluoro-2-(pyrazin-2-yl)phenyl)((1S,2R,4R)-2-((5-(trifluoromethyl)pyrazin-2-yl)amino)-7-azabicyclo[2.2.1]heptan-7-yl)methanone |
| 266 | | 5 | 7 | 121 | (3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone |
| 267 | | 33 | 61 | 1700 | (4-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 268 | | | 450 | 3700 | (3-fluoro-2-(pyridin-4-yl)phenyl)((1S,2R,4R)-2-((5-(trifluoromethyl)pyrazin-2-yl)amino)-7-azabicyclo[2.2.1]heptan-7-yl)methanone |
| 269 | | 48 | 111 | 1700 | (3-fluoro-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone |
| 270 | | | 325 | 145 | ((1S,2R,4R)-2-((3-bromoimidazo[1,2-a]pyrazin-8-yl)amino)-7-azabicyclo[2.2.1]heptan-7-yl)(3-fluoro-2-(pyrimidin-2-yl)phenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 271 | | 41 | 42 | 2300 | (3-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone |
| 272 | | 21 | 26 | 742 | (3-methyl-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone |
| 273 | | 17 | 12 | 328 | (3-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 274 | 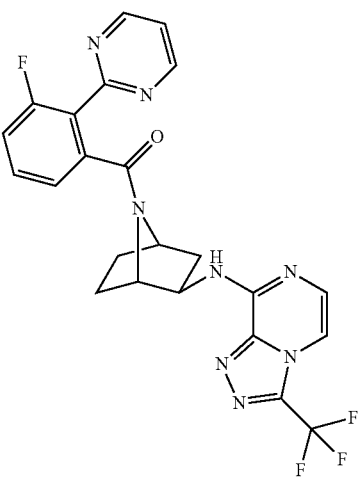 [SMILES: O=C(c1cccc(F)c1-c1ncccn1)N1C2CCC1C(Nc1nccn3c(C(F)(F)F)nnc13)C2] | | >10000 | 2560 | (3-fluoro-2-(pyrimidin-2-yl)phenyl)((1S,2R,4R)-2-((3-(trifluoromethyl)-[1,2,4]triazolo[4,3-a]pyrazin-8-yl)amino)-7-azabicyclo[2.2.1]heptan-7-yl)methanone |
| 275 | 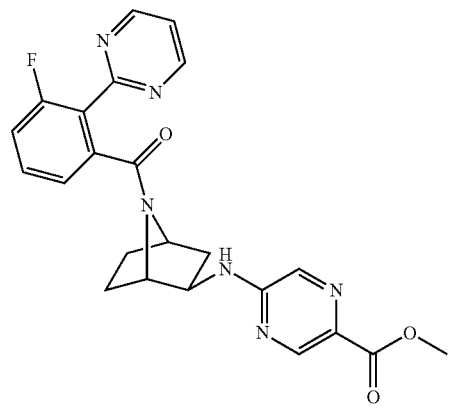 [SMILES: COC(=O)c1cnc(NC2CC3CCC2N3C(=O)c2cccc(F)c2-c2ncccn2)cn1] | | >10000 | >10000 | methyl 5-(((1S,2R,4R)-7-(3-fluoro-2-(pyrimidin-2-yl)benzoyl)-7-azabicyclo[2.2.1]heptan-2-yl)amino)pyrazine-2-carboxylate |
| 276 | 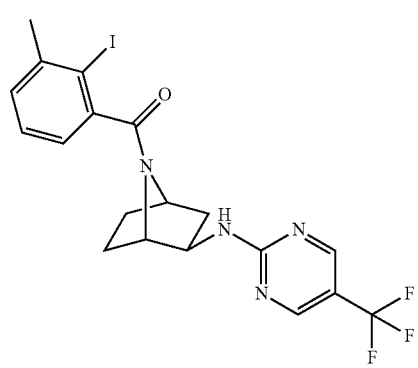 [SMILES: Cc1cccc(C(=O)N2C3CCC2C(Nc2ncc(C(F)(F)F)cn2)C3)c1I] | 133 | 97 | 2500 | (2-iodo-3-methylphenyl)((1S,2R,4R)-2-((5-(trifluoromethyl)pyrimidin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 277 | | | 457 | 7399 | (3-fluoro-2-iodophenyl)((1S,2R,4R)-2-((5-(trifluoromethyl)pyrimidin-2-yl)amino)-7-azabicyclo[2.2.1]heptan-7-yl)methanone |
| 278 | | 87 | 77 | 934 | (3-fluoro-2-(pyrimidin-2-yl)phenyl)((1S,2R,4R)-2-((5-methylpyrazin-2-yl)amino)-7-azabicyclo[2.2.1]heptan-7-yl)methanone |
| 279 | | 15 | 8 | 1100 | (3-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone |
| 280 | | 39 | 37 | 1300 | (4-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 281 | | | 21 | 17 | 1200 | (3-methyl-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone |
| 282 | | | | 486 | >10000 | (3-fluoro-2-(pyrimidin-2-yl)phenyl)((1S,2R,4R)-2-(methyl(5-(trifluoromethyl)pyrazin-2-yl)amino)-7-azabicyclo[2.2.1]heptan-7-yl)methanone |
| 283 | | | 14 | 9 | 417 | (3-methyl-2-(oxazol-2-yl)phenyl)((1S,2R,4R)-2-((5-(trifluoromethyl)pyrimidin-2-yl)amino)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 284 | 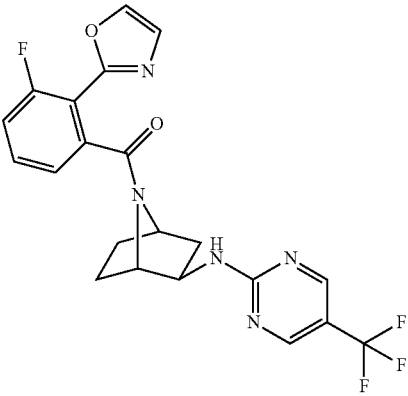 [SMILES: O=C(c1cccc(F)c1-c1ncco1)N1C2CCC1C(Nc1ncc(C(F)(F)F)cn1)C2] | | 29 | 27 | 1700 | (3-fluoro-2-(oxazol-2-yl)phenyl)((1S,2R,4R)-2-((5-(trifluoromethyl)pyrimidin-2-yl)amino)-7-azabicyclo[2.2.1]heptan-7-yl)methanone |
| 285 | 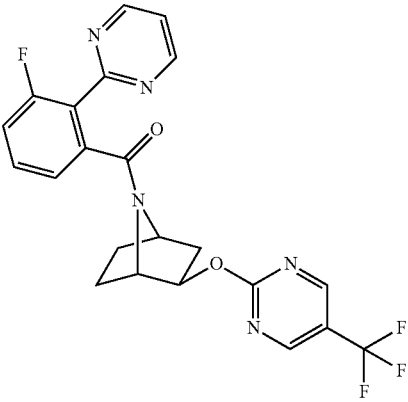 [SMILES: O=C(c1cccc(F)c1-c1ncccn1)N1C2CCC1C(Oc1ncc(C(F)(F)F)cn1)C2] | | 720 | >10000 | (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone |
| 286 | 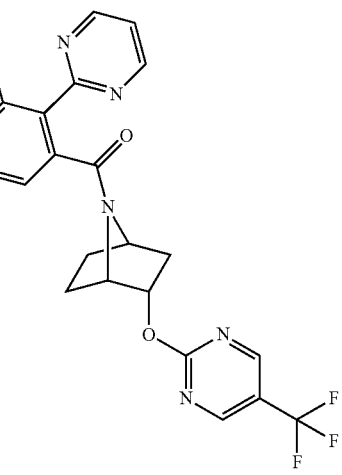 | | >10000 | >10000 | (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 287 | | | 472 | 767 | (3-ethoxy-6-methylpyridin-2-yl)((1S,2R,4R)-2-((5-(trifluoromethyl)pyrazin-2-yl)amino)-7-azabicyclo[2.2.1]heptan-7-yl)methanone |
| 288 | | 94 | 128 | 1900 | (3-(2H-1,2,3-triazol-2-yl)pyridin-2-yl)((1S,2R,4R)-2-((5-(trifluoromethyl)pyrazin-2-yl)amino)-7-azabicyclo[2.2.1]heptan-7-yl)methanone |
| 289 | | 13 | 32 | 173 | (2-methoxy-6-(pyrimidin-2-yl)phenyl)((1S,2R,4R)-2-((5-(trifluoromethyl)pyrazin-2-yl)amino)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 290 | | 21 | 19 | 558 | (2-fluoro-6-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 291 | | 15 | 35 | 425 | (7-ethoxyquinolin-8-yl)((1S,2R,4R)-2-((5-(trifluoromethyl)pyrazin-2-yl)amino)-7-azabicyclo[2.2.1]heptan-7-yl)methanone |
| 292 | | | >10000 | >10000 | (2-(1,4-dimethyl-1H-pyrazol-5-yl)-6-methoxyphenyl)((1S,2R,4R)-2-((5-(trifluoromethyl)pyrazin-2-yl)amino)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 293 | | 23 | 37 | 1100 | (3-methyl-2-(pyridin-2-yl)phenyl)((1S,2R,4R)-2-((5-(trifluoromethyl)pyrimidin-2-yl)amino)-7-azabicyclo[2.2.1]heptan-7-yl)methanone |
| 294 | | 21 | 15 | 1200 | (3-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |
| 295 | | 9 | 8 | 257 | (3-methyl-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 296 | 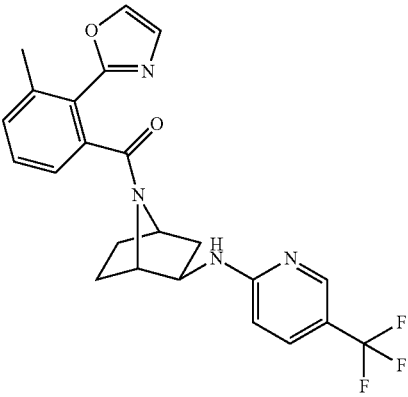 [SMILES: Cc1cccc(C(=O)N2C3CCC2C(Nc2ccc(C(F)(F)F)cn2)C3)c1-c1ncco1] | | 5 | 6 | 114 | (3-methyl-2-(oxazol-2-yl)phenyl)((1S,2R,4R)-2-((5-(trifluoromethyl)pyridin-2-yl)amino)-7-azabicyclo[2.2.1]heptan-7-yl)methanone |
| 297 | 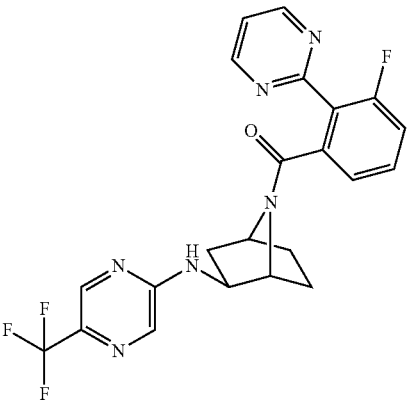 [SMILES: O=C(c1cccc(F)c1-c1ncccn1)N1C2CCC1C(Nc1cnc(C(F)(F)F)cn1)C2] | | >10000 | >10000 | | (3-fluoro-2-(pyrimidin-2-yl)phenyl)((1R,2S,4S)-2-((5-(trifluoromethyl)pyrazin-2-yl)amino)-7-azabicyclo[2.2.1]heptan-7-yl)methanone |
| 298 | 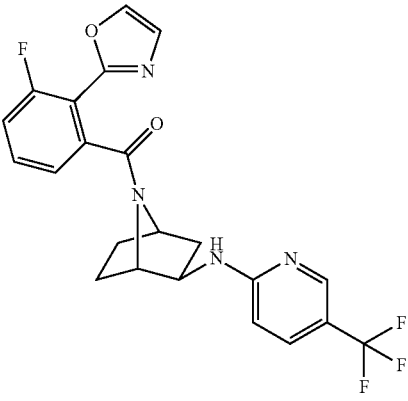 [SMILES: O=C(c1cccc(F)c1-c1ncco1)N1C2CCC1C(Nc1ccc(C(F)(F)F)cn1)C2] | | | | | (3-fluoro-2-(oxazol-2-yl)phenyl)((1S,2R,4R)-2-((5-(trifluoromethyl)pyridin-2-yl)amino)-7-azabicyclo[2.2.1]heptan-7-yl)methanone |

-continued

| Ex. No. | Compound | rOX1 K_i (nm) | hOX1 K_i (nm) | hOX2 K_i (nm) | Compound Name |
|---|---|---|---|---|---|
| 299 | 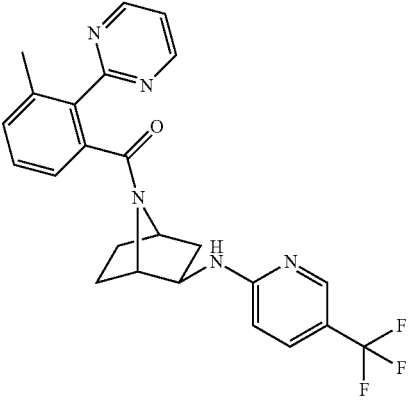 | | | | (3-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone |
| 300 | 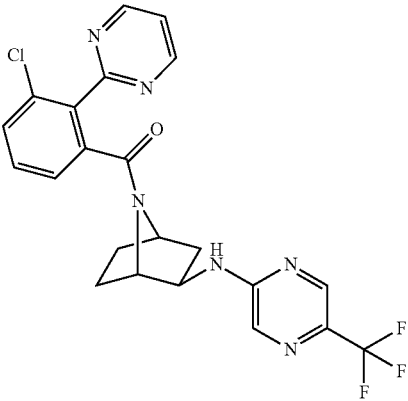 [SMILES: O=C(c1cccc(Cl)c1-c1ncccn1)N1C2CCC1C(Nc1cnc(C(F)(F)F)cn1)C2] | | | | (3-chloro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 301 | 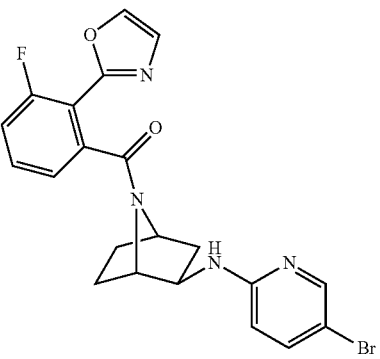 | | | | ((1S,2R,4R)-2-((5-bromopyridin-2-yl)amino)-7-azabicyclo[2.2.1]heptan-7-yl)(3-fluoro-2-(oxazol-2-yl)phenyl)methanone |
| 302 | 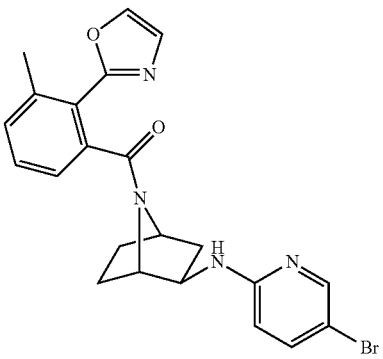 | | | | ((1S,2R,4R)-2-((5-bromopyridin-2-yl)amino)-7-azabicyclo[2.2.1]heptan-7-yl)(3-methyl-2-(oxazol-2-yl)phenyl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 303 | | | | | ((1S,2R,4R)-2-((5-bromopyridin-2-yl)amino)-7-azabicyclo[2.2.1]heptan-7-yl)(3-fluoro-2-(pyrimidin-2-yl)phenyl)methanone |
| 304 | | | | | (((1S,2R,4R)-2-((5-bromopyridin-2-yl)amino)-7-azabicyclo[2.2.1]heptan-7-yl)(3-methyl-2-(pyrimidin-2-yl)phenyl)methanone |
| 305 | | | | | (((1S,2R,4R)-2-((5-bromopyridin-2-yl)amino)-7-azabicyclo[2.2.1]heptan-7-yl)(3-fluoro-2-(2H-1,2,3-triazol-2-yl)phenyl)methanone |
| 306 | | | | | ((1S,2R,4R)-2-((5-bromopyridin-2-yl)amino)-7-azabicyclo[2.2.1]heptan-7-yl)(3-methyl-2-(2H-1,2,3-triazol-2-yl)phenyl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 307 | | | | | ((1S,2R,4R)-2-((5-bromopyrazin-2-yl)amino)-7-azabicyclo[2.2.1]heptan-7-yl)(3-fluoro-2-(oxazol-2-yl)phenyl)methanone |
| 308 | | | | | ((1S,2R,4R)-2-((5-bromopyrazin-2-yl)amino)-7-azabicyclo[2.2.1]heptan-7-yl)(3-methyl-2-(oxazol-2-yl)phenyl)methanone |
| 309 | | | | | ((1S,2R,4R)-2-((5-bromopyrazin-2-yl)amino)-7-azabicyclo[2.2.1]heptan-7-yl)(3-fluoro-2-(pyrimidin-2-yl)phenyl)methanone |
| 310 | | | | | ((1S,2R,4R)-2-((5-bromopyrazin-2-yl)amino)-7-azabicyclo[2.2.1]heptan-7-yl)(3-methyl-2-(pyrimidin-2-yl)phenyl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 311 | | | | | ((1S,2R,4R)-2-((5-bromopyrazin-2-yl)amino)-7-azabicyclo[2.2.1]heptan-7-yl)(3-fluoro-2-(2H-1,2,3-triazol-2-yl)phenyl)methanone |
| 312 | | | | | ((1S,2R,4R)-2-((5-bromopyrazin-2-yl)amino)-7-azabicyclo[2.2.1]heptan-7-yl)(3-methyl-2-(2H-1,2,3-triazol-2-yl)phenyl)methanone |
| 313 | | | | | ((1S,2R,4R)-2-((5-bromopyrimidin-2-yl)amino)-7-azabicyclo[2.2.1]heptan-7-yl)(3-fluoro-2-(oxazol-2-yl)phenyl)methanone |
| 314 | | | | | ((1S,2R,4R)-2-((5-bromopyrimidin-2-yl)amino)-7-azabicyclo[2.2.1]heptan-7-yl)(3-methyl-2-(oxazol-2-yl)phenyl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 315 | | | | | ((1S,2R,4R)-2-((5-bromopyrimidin-2-yl)amino)-7-azabicyclo[2.2.1]heptan-7-yl)(3-fluoro-2-(pyrimidin-2-yl)phenyl)methanone |
| 316 | | | | | ((1S,2R,4R)-2-((5-bromopyrimidin-2-yl)amino)-7-azabicyclo[2.2.1]heptan-7-yl)(3-methyl-2-(pyrimidin-2-yl)phenyl)methanone |
| 317 | | | | | ((1S,2R,4R)-2-((5-bromopyrimidin-2-yl)amino)-7-azabicyclo[2.2.1]heptan-7-yl)(3-fluoro-2-(2H-1,2,3-triazol-2-yl)phenyl)methanone |
| 318 | | | | | ((1S,2R,4R)-2-((5-bromopyrimidin-2-yl)amino)-7-azabicyclo[2.2.1]heptan-7-yl)(3-methyl-2-(2H-1,2,3-triazol-2-yl)phenyl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 319 | | | | | (3-methyl-2-(pyridin-2-yl)phenyl)((1S,2R,4R)-2-((5-(trifluoromethyl)pyridin-2-yl)amino)-7-azabicyclo[2.2.1]heptan-7-yl)methanone |
| 320 | | | | | (3-fluoro-2-(pyridin-2-yl)phenyl)((1S,2R,4R)-2-((5-(trifluoromethyl)pyridin-2-yl)amino)-7-azabicyclo[2.2.1]heptan-7-yl)methanone |
| 321 | | | | | (3-fluoro-2-(pyridin-2-yl)phenyl)((1S,2R,4R)-2-((5-(trifluoromethyl)pyrimidin-2-yl)amino)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 322 | | | | | (3-methyl-2-(pyridin-2-yl)phenyl)((1S,2R,4R)-2-((5-(trifluoromethyl)pyrazin-2-yl)amino)-7-azabicyclo[2.2.1]heptan-7-yl)methanone |
| 323 | | | | | (3-fluoro-2-(pyridin-2-yl)phenyl)((2S)-2-((5-(trifluoromethyl)pyrazin-2-yl)amino)-7-azabicyclo[2.2.1]heptan-7-yl)methanone |
| 324 | | | | | (3-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 325 | | | | | (2-methoxy-6-(pyrimidin-2-yl)phenyl)((1S,2R,4R)-2-((5-(trifluoromethyl)pyridin-2-yl)oxy)-7-azabicyclo[2.2.1]heptan-7-yl)methanone |
| 326 | | | | | (5-fluoro-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |
| 327 | | | | | (4-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 328 | | | | | (3-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |
| 329 | | | | | (5-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone |
| 330 | | | | | (2-fluoro-6-(pyrimidin-2-yl)phenyl)((1S,2R,4R)-2-((5-(trifluoromethyl)pyridin-2-yl)oxy)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 331 | | | | | (2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |
| 332 | | | | | (6-methyl-3-(2H-1,2,3-triazol-2-yl)pyridin-2-yl)((1S,2R,4R)-2-((5-(trifluoromethyl)pyridin-2-yl)oxy)-7-azabicyclo[2.2.1]heptan-7-yl)methanone |
| 333 | | | | | (3-methyl-2-(oxazol-2-yl)phenyl)((1S,2R,4R)-2-((5-(trifluoromethyl)pyridin-2-yl)oxy)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 334 | | | | | (3-methyl-2-(pyridin-2-yl)phenyl)((1S,2R,4R)-2-((5-(trifluoromethyl)pyridin-2-yl)oxy)-7-azabicyclo[2.2.1]heptan-7-yl)methanone |
| 335 | | | | | (2-(5-fluoropyrimidin-2-yl)phenyl)((1S,2R,4R)-2-((5-(trifluoromethyl)pyridin-2-yl)oxy)-7-azabicyclo[2.2.1]heptan-7-yl)methanone |
| 336 | | | | | (2-fluoro-6-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 337 | | | | | (5-methyl-3-(2H-1,2,3-triazol-2-yl)pyridin-2-yl)((1S,2R,4R)-2-((5-(trifluoromethyl)pyridin-2-yl)oxy)-7-azabicyclo[2.2.1]heptan-7-yl)methanone |
| 338 | | | | | (2-bromo-3-fluorophenyl)((1S,2R,4R)-2-((5-(trifluoromethyl)pyridin-2-yl)oxy)-7-azabicyclo[2.2.1]heptan-7-yl)methanone |
| 339 | | | | | (3-fluoro-2-(pyrimidin-2-yl)phenyl)((1S,2R,4R)-2-((5-(trifluoromethyl)pyrazin-2-yl)oxy)-7-azabicyclo[2.2.1]heptan-7-yl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 340 | | | | | (2-methoxy-6-(pyrimidin-2-yl)phenyl)((1S,2R,4R)-2-((5-(trifluoromethyl)pyrazin-2-yl)oxy)-7-azabicyclo[2.2.1]heptan-7-yl)methanone |
| 341 | | | | | (5-fluoro-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |
| 342 | | | | | (4-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 343 | | | | | (3-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |
| 344 | | | | | (5-fluoro-2-(pyrimidin-2-yl)phenyl)((1S,2R,4R)-2-((5-(trifluoromethyl)pyrazin-2-yl)oxy)-7-azabicyclo[2.2.1]heptan-7-yl)methanone |
| 345 | | | | | (2-fluoro-6-(pyrimidin-2-yl)phenyl)((1S,2R,4R)-2-((5-(trifluoromethyl)pyrazin-2-yl)oxy)-7-azabicyclo[2.2.1]heptan-7-yl)methanone |

| Ex. No. | Compound | rOX1 $K_i$ (nm) | hOX1 $K_i$ (nm) | hOX2 $K_i$ (nm) | Compound Name |
|---|---|---|---|---|---|
| 346 | | | | | (2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |
| 347 | | | | | (6-methyl-3-(2H-1,2,3-triazol-2-yl)pyridin-2-yl)((1S,2R,4R)-2-((5-(trifluoromethyl)pyrazin-2-yl)oxy)-7-azabicyclo[2.2.1]heptan-7-yl)methanone |
| 348 | | | | | (3-methyl-2-(oxazol-2-yl)phenyl)((1S,2R,4R)-2-((5-(trifluoromethyl)pyrazin-2-yl)oxy)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 349 | | | | | (3-methyl-2-(pyridin-2-yl)phenyl)((1S,2R,4R)-2-((5-(trifluoromethyl)pyrazin-2-yl)oxy)-7-azabicyclo[2.2.1]heptan-7-yl)methanone |
| 350 | | | | | (2-(5-fluoropyrimidin-2-yl)phenyl)((1S,2R,4R)-2-((5-(trifluoromethyl)pyrazin-2-yl)oxy)-7-azabicyclo[2.2.1]heptan-7-yl)methanone |
| 351 | | | | | (2-fluoro-6-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 352 | | | | | (5-methyl-3-(2H-1,2,3-triazol-2-yl)pyridin-2-yl)((1S,2R,4R)-2-((5-(trifluoromethyl)pyrazin-2-yl)oxy)-7-azabicyclo[2.2.1]heptan-7-yl)methanone |
| 353 | | | | | (2-bromo-3-fluorophenyl)((1S,2R,4R)-2-((5-(trifluoromethyl)pyrazin-2-yl)oxy)-7-azabicyclo[2.2.1]heptan-7-yl)methanone |
| 354 | | | | | (2-methoxy-6-(pyrimidin-2-yl)phenyl)((1S,2R,4R)-2-((5-(trifluoromethyl)pyrimidin-2-yl)oxy)-7-azabicyclo[2.2.1]heptan-7-yl)methanone |
| 355 | | | | | (5-fluoro-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 356 | | | | | (4-methyl-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |
| 357 | | | | | (3-methyl-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |
| 358 | | | | | (5-fluoro-2-(pyrimidin-2-yl)phenyl)((1S,2R,4R)-2-((5-(trifluoromethyl)pyrimidin-2-yl)oxy)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 359 | | | | | (2-fluoro-6-(pyrimidin-2-yl)phenyl)((1S,2R,4R)-2-((5-(trifluoromethyl)pyrimidin-2-yl)oxy)-7-azabicyclo[2.2.1]heptan-7-yl)methanone |
| 360 | | | | | (2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |
| 361 | | | | | (6-methyl-3-(2H-1,2,3-triazol-2-yl)pyridin-2-yl)((1S,2R,4R)-2-((5-(trifluoromethyl)pyrimidin-2-yl)oxy)-7-azabicyclo[2.2.1]heptan-7-yl)methanone |

| Ex. No. | Compound | rOX1 K$_i$ (nm) | hOX1 K$_i$ (nm) | hOX2 K$_i$ (nm) | Compound Name |
|---|---|---|---|---|---|
| 362 | 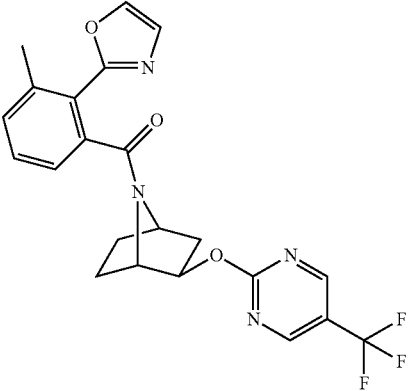 | | | | (3-methyl-2-(oxazol-2-yl)phenyl)((1S,2R,4R)-2-((5-(trifluoromethyl)pyrimidin-2-yl)oxy)-7-azabicyclo[2.2.1]heptan-7-yl)methanone |
| 363 | 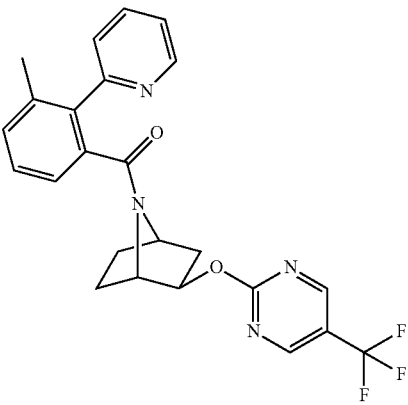 [SMILES: Cc1cccc(C(=O)N2C3CCC2C(Oc2ccc(C(F)(F)F)cn2)C3)c1-c1ccccn1] | | | | (3-methyl-2-(pyridin-2-yl)phenyl)((1S,2R,4R)-2-((5-(trifluoromethyl)pyrimidin-2-yl)oxy)-7-azabicyclo[2.2.1]heptan-7-yl)methanone |
| 364 | 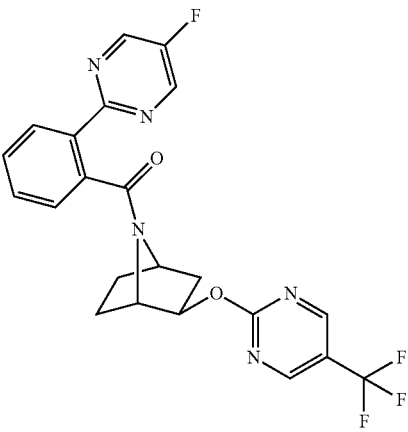 [SMILES: O=C(c1ccccc1-c1ncc(F)cn1)N1C2CCC1C(Oc1ncc(C(F)(F)F)cn1)C2] | | | | (2-(5-fluoropyrimidin-2-yl)phenyl)((1S,2R,4R)-2-((5-(trifluoromethyl)pyrimidin-2-yl)oxy)-7-azabicyclo[2.2.1]heptan-7-yl)methanone |

-continued

| Ex. No. | Compound | rOX1 K$_i$ (nm) | hOX1 K$_i$ (nm) | hOX2 K$_i$ (nm) | Compound Name |
|---|---|---|---|---|---|
| 365 | | | | | (2-fluoro-6-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |
| 366 | | | | | (5-methyl-3-(2H-1,2,3-triazol-2-yl)pyridin-2-yl)((1S,2R,4R)-2-((5-(trifluoromethyl)pyrimidin-2-yl)oxy)-7-azabicyclo[2.2.1]heptan-7-yl)methanone |
| 367 | | | | | (2-bromo-3-fluorophenyl)((1S,2R,4R)-2-((5-(trifluoromethyl)pyrimidin-2-yl)oxy)-7-azabicyclo[2.2.1]heptan-7-yl)methanone |

What is claimed:

1. A compound of the Formula (I):

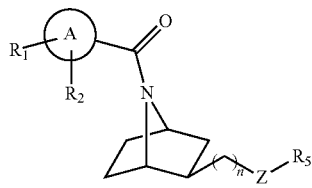

(I)

or an enantiomer, diastereomer, tautomer, or isotopic variant thereof;
or a pharmaceutically acceptable salt or solvate thereof;
wherein:
 $R_1$ is H;
 $R_2$ is H;
 ring A is:

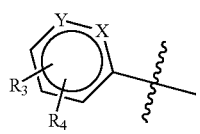

X is $CR_6$ and Y is $CR_7$;
$R_6$ is H or pyrimidinyl;
$R_7$ is H or halo;
$R_3$ is H or pyrimidinyl;
$R_4$ is H or halo;
Z is NH;
$R_5$ is optionally substituted pyrazinyl.

2. The compound of claim 1, wherein n is 1.
3. The compound of claim 1, wherein $R_6$ is H.
4. The compound of claim 1, wherein $R_6$ is pyrimidinyl.
5. The compound of claim 1, wherein $R_7$ is H.
6. The compound of claim 1, wherein $R_7$ is halo.
7. The compound of claim 6, wherein $R_7$ is F, Cl, or Br.
8. The compound of claim 1, wherein $R_3$ is H.
9. The compound of claim 1, wherein $R_3$ is pyrimidinyl.
10. The compound of claim 1, wherein $R_4$ is H.
11. The compound of claim 1, wherein $R_4$ is halo.
12. The compound of claim 11, wherein $R_4$ is F, Cl, or Br.
13. The compound of claim 12, wherein R4 is F.
14. The compound of claim 1, wherein $R_5$ is substituted with one trihaloalkyl.
15. The compound of claim 14, wherein $R_5$ is substituted with one trifluoromethyl.
16. A pharmaceutical composition comprising a therapeutically effective amount of a compound according to claim 1 and at least one pharmaceutically acceptable excipient.
17. A method of treating a disease, disorder, or medical condition, wherein the disease, disorder, or medical condition is a sleep disorder, a metabolic disorder, a neurological disorder, an arrhythmia, acute heart failure, an ulcer, irritable bowel syndrome, diarrhea, gastroesophageal reflux, a mood disorder, post-traumatic stress disorder, a panic disorder, attention deficit disorder, cognitive deficiency, or substance abuse, comprising administering a compound of claim 1 to a patient in need thereof.
18. The method of claim 17, wherein the disease, disorder, or medical condition is a mood disorder, post-traumatic stress disorder, panic disorder, attention deficit disorder, cognitive deficiency, or substance abuse.
19. The method of claim 17, wherein the disease, disorder, or medical condition is post-traumatic stress disorder or a panic disorder.
20. The method of claim 17, wherein the sleep disorder is a sleep-wake transition disorder, insomnia, restless legs syndrome, jet-lag, disturbed sleep, or a sleep disorder secondary to neurological disorders.
21. The method of claim 17, wherein the metabolic disorder is overweight, obesity, insulin resistance, type II diabetes, hyperlipidemia, a gallstone, angina, hypertension, breathlessness, tachycardia, infertility, sleep apnea, back and joint pain, a varicose vein, or osteoarthritis.
22. The method of claim 17, wherein the neurological disorder is Parkinson's disease, Alzheimer's disease, Tourette's syndrome, catatonia, anxiety, delirium, or dementia.

* * * * *